US011430544B2

(12) United States Patent
Erlander et al.

(10) Patent No.: US 11,430,544 B2
(45) Date of Patent: *Aug. 30, 2022

(54) IDENTIFICATION OF TUMORS AND TISSUES

(71) Applicant: BIOTHERANOSTICS, INC., San Diego, CA (US)

(72) Inventors: Mark G. Erlander, Encinitas, CA (US); Xiao-Jun Ma, San Diego, CA (US)

(73) Assignee: BIOTHERANOSTICS, INC., San Diego, CA (US)

( * ) Notice: Subject to any disclaimer, the term of this patent is extended or adjusted under 35 U.S.C. 154(b) by 1164 days.

This patent is subject to a terminal disclaimer.

(21) Appl. No.: 15/368,446

(22) Filed: Dec. 2, 2016

(65) Prior Publication Data

US 2017/0286596 A1 Oct. 5, 2017

Related U.S. Application Data

(63) Continuation of application No. 11/422,059, filed on Jun. 2, 2006, now abandoned.

(Continued)

(51) Int. Cl.

*G16B 40/20* (2019.01)
*G16B 40/00* (2019.01)

(Continued)

(52) U.S. Cl.

CPC ........... *G16B 40/20* (2019.02); *C12Q 1/6886* (2013.01); *G16B 25/10* (2019.02); *G16B 40/00* (2019.02); *C12Q 2600/112* (2013.01); *G16B 25/00* (2019.02); *G16B 40/10* (2019.02); *G16B 40/30* (2019.02)

(58) Field of Classification Search

CPC ........ C12Q 2537/143; C12Q 2535/122; C12Q 2563/179; C12Q 1/6806; C12Q 1/6809; C12Q 1/6886; C12Q 1/6851; C12Q 1/6874; C12Q 2531/113; C12Q 1/6883; C12Q 2545/114; C12Q 2600/158; C12Q 1/6811; C12Q 2537/165; C12Q 2600/112; C12Q 1/68; C12Q 1/686; C12Q 1/6876; C12Q 2600/118; C12Q 1/6881; C12Q 2539/00; C12Q 1/6844; C12Q 2545/101; C12Q 2600/16; C12Q 2525/207; C12Q 2600/166; C12N 15/1075; G16B 30/00; G16B 20/00; G16B 20/20; G16B 40/00; G16B 25/00; G16B 25/10; G16B 30/10; G16B 40/20; G16B 40/30; G16B 5/00; G16B 45/00; G16B 50/30; G16B 35/00; G16B 35/20; G16B 50/00; G16B 30/20; G16B 20/10; G16B 35/10; G16B 10/00; G16B 20/30; G16B 20/40; G16B 25/20; G16B 40/10; G16B 5/20; G16B 99/00; G16B 50/20; G16B 5/30; G16B 50/10; G01N 33/57484; G01N 33/574; G01N 2800/50; G01N 2800/56; G01N 33/5044; G01N 2800/60; G01N 2800/7028; G01N 2800/52; G01N 33/57407; G16H 10/40; G16H 50/30; G16H 50/70; G16H 50/20; G16H 70/60; G16H 10/60; G16H 50/50; G16H 20/00; G16H 10/20; G16H 20/10; G16H 20/40; G16H 40/63; G16H 15/00; G16H 70/40; G16H 70/20; G16H 70/00; G06F 17/18; G06F 17/10; G06F 17/11; G06F 16/285; G06F 17/15; G06F 16/2264; G06F 16/31; G06F 30/27; G06N 20/00; G06N 5/003; G06N 7/005; G06N 3/04; G06N 3/08; G06N 3/0445; G06N 3/088; G06N 20/20; G06N 3/02; G06N 5/025; G06N 3/0472; G06T 2207/20084; G06T 2207/20081; G06T 2207/30096; G06T 5/50; G06K 9/6267; G06K 9/00147; G06K 9/4628; G06K 9/6256; G06K 9/6277; G06K 9/628; G06K 9/6231; C12P 19/34; C40B 40/08; C40B 40/06; C40B 50/10; C40B 60/12; C40B 60/14; G16C 20/70; G16C 20/20; Y10T 436/143333

See application file for complete search history.

(56) References Cited

U.S. PATENT DOCUMENTS

| | | | |
|---|---|---|---|
| 5,871,697 | A | 2/1999 | Rothberg et al. |
| 6,328,709 | B1 | 12/2001 | Hung et al. |

(Continued)

FOREIGN PATENT DOCUMENTS

| | | |
|---|---|---|
| WO | WO 2001/094629 | 12/2001 |
| WO | WO 2002/103320 | 12/2002 |

(Continued)

OTHER PUBLICATIONS

Dudoit et al. Comparison of discrimination methods for the classification of tumors using gene expression data. Mar. 2002 Journal of the American Statistical Association, vol. 97, No. 457 pp. 77-87.*

(Continued)

*Primary Examiner* — Mary K Zeman

(74) *Attorney, Agent, or Firm* — Finnegan, Henderson, Farabow, Garrett & Dunner, LLP

(57) ABSTRACT

The invention provides methods for the use of gene expression measurements to classify or identify tumors in samples obtained from a subject in a clinical setting, such as in cases of formalin fixed, paraffin embedded (FFPE) samples.

8 Claims, 13 Drawing Sheets

Specification includes a Sequence Listing.

Related U.S. Application Data

(60) Provisional application No. 60/687,174, filed on Jun. 3, 2005.

(51) Int. Cl.

| | |
|---|---|
| ***C12Q 1/6886*** | (2018.01) |
| ***G16B 25/10*** | (2019.01) |
| ***G16B 25/00*** | (2019.01) |
| ***G16B 40/10*** | (2019.01) |
| ***G16B 40/30*** | (2019.01) |

(56) References Cited

U.S. PATENT DOCUMENTS

| | | | | |
|---|---|---|---|---|
| 6,794,141 | B2 | 9/2004 | Erlander et al. | |
| 7,364,846 | B2 | 4/2008 | Erlander et al. | |
| 7,504,214 | B2 | 3/2009 | Erlander et al. | |
| 7,514,209 | B2 | 4/2009 | Dai et al. | |
| 7,930,105 | B2 * | 4/2011 | Ma | C12Q 1/6886 702/19 |
| 9,447,470 | B2 * | 9/2016 | Erlander | C12Q 1/6886 |
| 9,670,553 | B2 * | 6/2017 | Erlander | C12Q 1/6886 |
| 9,856,533 | B2 | 1/2018 | Erlander et al. | |
| 10,329,624 | B2 * | 6/2019 | Ma | G01N 33/57492 |
| 10,538,816 | B2 * | 1/2020 | Erlander | C12Q 1/6886 |
| 2002/0110820 | A1 | 8/2002 | Ramaswamy et al. | |
| 2002/0172965 | A1 * | 11/2002 | Kamb | C12Q 1/6809 435/5 |
| 2003/0017481 | A1 | 1/2003 | Golub et al. | |
| 2003/0138793 | A1 | 7/2003 | Su et al. | |
| 2003/0148295 | A1 | 8/2003 | Wan et al. | |
| 2003/0219767 | A1 | 11/2003 | Ayers et al. | |
| 2003/0224374 | A1 | 12/2003 | Dai et al. | |
| 2003/0225526 | A1 | 12/2003 | Golub et al. | |
| 2003/0225528 | A1 | 12/2003 | Baker et al. | |
| 2004/0002067 | A1 | 1/2004 | Erlander et al. | |
| 2004/0063120 | A1 * | 4/2004 | Beer | G01N 33/57423 435/6.14 |
| 2004/0076984 | A1 | 4/2004 | Eils et al. | |
| 2004/0098367 | A1 | 5/2004 | Tamayo et al. | |
| 2004/0241728 | A1 * | 12/2004 | Liew | C12Q 1/6809 435/6.13 |
| 2004/0253606 | A1 | 12/2004 | Aziz et al. | |
| 2005/0003341 | A1 | 1/2005 | Polansky | |
| 2005/0143334 | A1 * | 6/2005 | Tarin | G01N 33/57415 514/44 R |
| 2005/0208500 | A1 | 9/2005 | Erlander et al. | |
| 2005/0260572 | A1 | 11/2005 | Kato et al. | |
| 2005/0272061 | A1 | 12/2005 | Petroziello et al. | |
| 2006/0094035 | A1 | 5/2006 | Eriander et al. | |
| 2006/0265138 | A1 | 11/2006 | Bowtell et al. | |
| 2006/0292572 | A1 | 12/2006 | Stuart et al. | |
| 2007/0020655 | A1 | 1/2007 | Erlander et al. | |
| 2009/0157326 | A1 | 6/2009 | Dai et al. | |
| 2010/0178653 | A1 | 7/2010 | Aharonov et al. | |
| 2010/0273172 | A1 | 10/2010 | Rosenfeld et al. | |
| 2010/0323903 | A1 | 12/2010 | Rosenwald et al. | |
| 2011/0077168 | A1 | 3/2011 | Rosenwald et al. | |
| 2011/0097756 | A1 | 4/2011 | Hagmann et al. | |
| 2013/0023441 | A1 | 1/2013 | Erlander et al. | |
| 2017/0286596 | A1 * | 10/2017 | Erlander | G16B 25/10 |
| 2018/0073085 | A1 | 3/2018 | Erlander et al. | |

FOREIGN PATENT DOCUMENTS

| | | | |
|---|---|---|---|
| WO | 2003041562 | A2 | 5/2003 |
| WO | 2005059109 | A2 | 6/2005 |
| WO | WO 2005/118879 | | 12/2005 |
| WO | WO 2006/080597 | | 8/2006 |
| WO | WO 2006/132971 | | 12/2006 |
| WO | WO 2007/137366 | | 12/2007 |
| WO | WO 2010/108638 | | 9/2010 |
| WO | WO 2013/002750 | | 1/2013 |

OTHER PUBLICATIONS

Dudoit S., Fridly J. (2003) Introduction to Classification in Microarray Experiments. In: Berrar D.P., Dubitzky W., Granzow M. (eds) A Practical Approach to Microarray Data Analysis. Springer, Boston, MA.*

Nutt et al. Gene-expression based classification of malignant gliomas correlates better with survival than histological classification. 2003. Cancer Research vol. 63 pp. 1602-1607.*

Li et al. A comparative study of feature selection and multiclass classification methods for tissue classification based on gene expression 2004. Bioinformatics vol. 20 No. 15 pp. 2429-2437.*

Tschentscher et al. Tumor classification based on gene expression profiling shows that uveal melanomas with and without monosomy 3 represent two distinct entities. 2003. Cancer research vol. 63 pp. 2578-2584.*

Smirnov et al. Global gene expression profiling of circulating tumor cells. Jun. 15, 2005. Cancer Research vol. 65 No. 12 pp. 4993-4997.*

Affymetrix, "Affymetrix GeneChip Human Genome U133 Array Set HG-U133A", GEO, (2002).

Bloom et al., "Multi-platform, multi-site, microarray-based human tumor classification", Am J Pathol., 164(1):9-16 (2004).

Bridgewater et al., "Gene expression profiling may improve diagnosis in patients with carcinoma of unknown primary", Br J Cancer., 98(8):1425-1430 (2008).

Buckhaults et al., "Identifying tumor origin using a gene expression-based classification map", Cancer Res., 63(14):4144-4149 (2003).

Cole et al., "The genetics of cancer—a 3D model", Nat Genet., 21(1 Suppl):38-41 (1999).

Dennis et al., "Identification from public data of molecular markers of adenocarcinoma characteristic of the site of origin", Cancer Res., 62(21):5999-6005 (2002).

Dirisi et al., "Use of a cDNA microarray to analyse gene expression patterns in human cancer", Nat Genet., 14(4):457-460 (1996).

Feng et al., "Molecular biomarkers for cancer detection in blood and bodily fluids", Crit Rev Clin Lab Sci., 43(5-6):497-560 (2006).

Giordana et al., "Organ-specific molecular classification of primary lung, colon, and ovarian adenocarcinomas using gene expression profiles", Am J Pathol., 159(41:1231-1238 (2001).

Golub et al., "Molecular classification of cancer: class discovery and class prediction by gene expression monitoring", Science, 286(5439):531-537 (1999).

Lockhart et al., "Genomics, gene expression and DNA arrays", Nature., 405(6788):827-836 (2000).

Ramaswamy et al., "Multiclass cancer diagnosis using tumor gene expression signatures", Proc Natl Acad Sci U S A., 98(26):15149-15154 (2001).

Shedden et al., "Accurate molecular classification of human cancers based on gene expression using a simple classifier with a pathological tree-based framework", Am J Pathol., 163(5):1985-1995 (2003).

Srinivas et al., "Trends in biomarker research for cancer detection", Lancet Oncol., 2(11):698-704 (2001).

Su et al., "Molecular Classification of Human Carcinomas by Use of Gene Expression Signatures", Cancer Research, 61:7388-7393 (2001).

Tamayo et al., "Interpreting patterns of gene expression with self-organizing maps: methods and application to hematopoietic differentiation", Proc Natl Acad Sci U S A., 96(6):2907-2912 (1999).

Tothill et al., "An expression-based site of origin diagnostic method designed for clinical application to cancer of unknown origin", Cancer Res., 65(10):4031-4040 (2005).

"Affymetrix Genechip Human Genome U133 plus 2.0 Array," GEO, abstract, XP002343693 (2003).

Altschul et al., "Basid Local Alignment Search Tool," *J. Mol. Biol.*, 215:403-410 (1990).

Barden et al., "Classification of follicular thyroid tumors by molecular signature: results of gene profiling," *Clin. Cancer Res.*, 9(5):1792-1800 (2003).

(56) References Cited

OTHER PUBLICATIONS

Bhattacharjee et al., "Classification of human lung carcinomas by mRNA expression profiling reveals distinct adenocarcinoma subclasses," *Proc Natl Acad Sci USA*, 98(24):13790-13795 (2001).
Brachtel et al., "Molecular classification of cancer with the 92-gene assay in cytology and limited tissue samples," *Oncotarget*, 7(19):27220-27231 (2016).
CancerConnect.com, Pathology Tests, attached, available at http://news.cancerconnect.com/testingcenter/Pathologytests (accessed Aug. 16, 2016).
Dash et al., "Distance Based Feature Selection for Clustering Microarray Data," *Database Systems for Advanced Applications*, Eds. Tsuji, Jin, Higuchi, pp. 512-519 (2008).
Epstein et al., "Microarray technology—enhanced versatility, persistent challenge," *Curr Opin Biotechnol.*, 11(1):36-41 (2000).
Erlander et al., "Performance and clinical evaluation of the 92-gene real-time PCR assay for tumor classification," *J Mol Diagn.*, 13(5):493-503 (2011).
Glinsky et al., "Classification of human breast cancer using gene expression profiling as a component of the survival predictor algorithm," *Clin Cancer Res.*, 10(7):2272-2283 (2004).
International Search Report and Written Opinion for PCT/US2005/019736 dated Feb. 28, 2006 (14 pages).
Iwao et al., "Molecular classification of primary breast tumors possessing distinct prognostic properties," *Hum Mol Genet.*, 11(2):199-206 (2002).
Kerr et al., "Multisite validation study to determine performance characteristics of a 92-gene molecular cancer classifier," *Clin Cancer Res.*, 18(14):3952-3960 (2012).
Khan et al., "Classification and diagnostic prediction of cancers using gene expression profiling and artificial neural networks," *Nat Med.*, 7(6):673-679 (2001).
Lopez-Encuentra et al., "Comparison between clinical and pathologic staging in 2,994 cases of lung cancer," *Ann Thorac Surg.*, 79(3):974-979 (2005).
Ma et al., "Gene expression signatures associated with clinical outcome in breast cancer via laser capture microdissection," *Breast Cancer Research and Treatment*, 82(Suppl 1):S15.
Ma et al., "Molecular classification of human cancers using a 92-gene real-time qu antitative polymerase chain reaction assay," *Arch Pathol Lab Med.*, 130(4):465-473 (2006).
Martin et al., "Linking gene expression patterns to therapeutic groups in breast cancer," *Cancer Res.*, 60(8):2232-2238 (2000).
Nielsen et al., "Tissue microarray validation of epidermal growth factor receptor and SALL2 in synovial sarcoma with comparison to tumors of similar histology," *Am J Pathol.*, 163(4):1449-1456 (2003).
Noonan et al., "Characterization of the homeodomain gene EMX2: sequence conservation, expression analysis, and a search for mutations in endometrial cancers," *Genomics*, 76(1-3):37-44 (2001).
Okada et al., "Analysis of gene-expression profiles in testicular seminomas using a genome-wide cDNA microarray," *Int J Oncol.*, 23(6):1615-1635 (2003).
Osoegawa et al., "A bacterial artificial chromosome library for sequencing the complete human genome," *Genome Res.*, 11(3):483-496 (2001).
Perou et al., "Distinctive gene expression patterns in human mammary epithelial cells and breast cancers," *Proc Natl Acad Sci USA*, 96(16):9212-9217 (1999).
Ramaswamy et al., "A molecular signature of metastasis in primary solid tumors," *Nat Genet.*, 33(1):49-54 (2003).
Schena et al., "Quantitative monitoring of gene expression patterns with a complementary DNA microarray," *Science*, 270(5235):467-470 (1995).
Sgroi et al., "In vivo gene expression profile analysis of human breast cancer progression," *Cancer Res.*, 59(22):5656-5661 (1999).
Sgroi et al., "In vivo gene expression profiling of human breast cancer," Laboratory Investigation, United States and Canadian Academy of Pathology, 82(1):51A (2002).
Takahashi et al., "Gene expression profiling of clear cell renal cell carcinoma: gene identification and prognostic classification," *Proc Natl Acad Sci USA*, 98(17):9754-9759 (2001).
Van'T Veer et al., "Gene expression profiling predicts clinical outcome of breast cancer," *Nature*, 415(6871):530-536 (2002).
Welford et al., "Detection of differentially expressed genes in primary tumor tissues using representational differences analysis coupled to microarray hybridization," *Nucleic Acids Res.*, 26(12):3059-3065 (1998).
Winston, "Small Cell Lung Cancer", Medscape, accessed Feb. 17, 2015 http://emedicine.medscape.com/article/280104-overview.
Yeung et al., "Multiclass classification of microarray data with repeated measurements: application to cancer," *Genome Biol.*, 4(12):R83 (2003).
Giordano et al., "Distinct transcriptional profiles of adrenocortical tumors uncovered by DNA microarray analysis," *Am. J. Pathol.*, 162(2):521-531 (2003).
Kim et al., "Microarray applications in cancer research," *Cancer Res. Treat.*, 36(4):207-213 (2004).

* cited by examiner

IDENTIFICATION OF TUMORS AND TISSUES

RELATED APPLICATIONS

This application is a continuation of U.S. patent application Ser. No. 11/422,056, filed Jun. 2, 2006, which claims benefit of priority to U.S. Provisional Patent Application 60/687,174, filed Jun. 3, 2005, the content of each of which is hereby incorporated by reference as if fully set forth.

FIELD OF THE INVENTION

This invention relates to the use of gene expression to classify human tumors. The classification is performed by use of gene expression profiles, or patterns, of about 5 to 49 expressed sequences that are correlated with tumors arising from certain tissues as well as being correlated with certain tumor types. The invention also provides for the use of about 5 to 49 specific gene sequences, the expression of which are correlated with tissue source and tumor type in various cancers. The gene expression profiles, whether embodied in nucleic acid expression, protein expression, or other expression formats, may be used to determine a cell containing sample as containing tumor cells of a tissue type or from a tissue origin to permit a more accurate identification of the cancer and thus treatment thereof as well as the prognosis of the subject from whom the sample was obtained.

SUMMARY OF THE INVENTION

This invention relates to the use of gene expression measurements to classify or identify tumors in cell containing samples obtained from a subject in a clinical setting, such as in cases of formalin fixed, paraffin embedded (FFPE) samples as well as fresh samples, that have undergone none to little or minimal treatment (such as simply storage at a reduced, non-freezing, temperature), and frozen samples. The invention thus provides the ability to classify tumors in the real-world conditions faced by hospital and other laboratories which conduct testing on clinical FFPE samples. The samples may be of a primary tumor sample or of a tumor that has resulted from a metastasis of another tumor. Alternatively, the sample may be a cytological sample, such as, but not limited to, cells in a blood sample. In some cases of a tumor sample, the tumors may not have undergone classification by traditional pathology techniques, may have been initially classified but confirmation is desired, or have been classified as a "carcinoma of unknown primary" (CUP) or "tumor of unknown origin" (TUO) or "unknown primary tumor". The need for confirmation is particularly relevant in light of the estimates of 5 to 10% misclassification using standard techniques. Thus the invention may be viewed as providing means for cancer identification, or CID.

In a first aspect of the invention, the classification is performed by use of gene expression profiles, or patterns, of about 5 to 49 expressed sequences. The gene expression profiles, whether embodied in nucleic acid expression, protein expression, or other markers of gene expression, may be used to determine a cell containing sample as containing tumor cells of a tissue type or from a tissue origin to permit a more accurate identification of the cancer and thus treatment thereof as well as the prognosis of the subject from whom the sample was obtained.

In some embodiments, the invention is used to classify among at least 34 or at least 39 tumor types with significant accuracy in a clinicalsetting. The invention is based in part on the surprising and unexpected discovery that about 5 to 49 expressed sequences in the human genome are capable of classifying among at least 34, or at least 39, tumor types, as well as subsets of those tumor types, in a meaningful manner. Stated differently, the invention is based in part on the discovery that it is not necessary to use supervised learning to identify gene sequences which are expressed in correlation with different tumor types. Thus the invention is based in part on the recognition that any about 5 to 49 expressed sequences, even a random collection of expressed sequences, has the capability to classify, and so may be used to classify, a cell as being a tumor cell of a tissue or tissue origin. Moreover, relatively few expressed sequences are needed to classify among different tumor types. The ratio of expressed sequences to the number of tumor types that can be classified, based on the expression levels of the sequences, ranges from about 1:2 to about 5:2 or higher as demonstrated herein.

In another aspect, the invention provides for the classifying of a cell containing sample as containing a tumor cell of a tissue type or origin by determining the expression levels of about 5 to 49 transcribed sequences and then classifying the cell containing sample as containing a tumor cell of a plurality (two or more) of tumor types. To classify among 34 to 39 tumor types, and subsets thereof, as few as about any 5 expressed sequences may be used to provide classification in a meaningful manner. It was discovered that the expressed sequences need not be those the expression levels of which are evidently or highly correlated (directly, or indirectly through correlation with another expressed sequence) with any of the tumor types. Thus the invention provides, in yet another embodiment for the use of the expression levels of genes, the expression levels of which are not strongly correlated with the actual classification of the particular tumor sample, as one of the about 5 to 49 transcribed sequences. All of the genes selected may be such non-correlates, or only a portion of the genes may be non-correlates, typically at least 90%, 85%, 75%, 50% or 25%, as well as portions falling within the ranges created by using any two of the foregoing point examples as endpoints of a range.

The invention is practiced by determining the expression levels of gene sequences where the sequences need not have been selected based on a correlation of their expression levels with the tumor types to be classified. Thus as a non-limiting example, the gene sequences need not be selected based on their correlation values with tumor types or a ranking based on the correlation values. Additionally, the invention may be practice with use of gene expression levels which are not necessarily correlated to one or more other gene expression level(s) used for classification. Thus m some embodiments, the ability for the expression level of one expressed sequence to function in classification is not redundant with (is independent of) the ability of at least one other gene expression level used for classification.

The invention may be applied to identify the origin of a cancer in a patient in a wide variety of cases including, but not limited to, identification of the origin of a cancer in a clinical setting. In some embodiments, the identification is made by classification of a cell containing sample known to contain cancer cells, but the origin of those cells is unknown. In other embodiments, the identification is made by classification of a cell containing sample as containing one or more cancer cells followed by identification of the origin(s) of those cancer cell(s). In further embodiments, the invention is practiced with a sample from a subject with a previous history of cancer, and identification is made by classification of a cell as either being cancer from a previous origin of cancer or a new origin. Additional embodiments include those where multiple cancers found in the same organ or tissue and the invention is used to determine the origin of each cancer, as well as whether the cancers are of the same origin.

The invention is also based in part on the discovery that the expression levels of particular gene sequences can be used to classify among tumor types with greater accuracy than the expression levels of a random group of gene sequences. In one embodiment, the invention provides for the use of expression levels of about 5 to 49 expressed sequences from a first set of 74 expressed sequences in the human genome to classify among at least 39 tumor types with significant accuracy. The invention thus provides for the identification and use of gene expression patterns (or profiles or "signatures") based on the about 5 to 49 expressed sequences as correlated with at least the 39 tumor types. The invention also provides for the use of about 5 to 49 of the 74 of these expressed sequences to classify among subsets of the 39 tumor types. The ratio of expressed sequences to the number of tumor types, from 2 to 39, that can be classified based on the expression levels of the sequences ranges from about 1:2 to about 5:2 with greater accuracy than the use of a random group of expressed sequences. Depending on the number of tumor types, accuracies ranging from over 75% to 95% may be achieved readily.

In another embodiment, the invention provides for the use of expression levels of about 5 to 49 expressed sequences of a second set of 90 expressed sequences in the human genome to classify among at least 39 tumor types, or subsets thereof, with significant accuracy. 38 of the sequences in this second set are present in the first set of 74 sequences. The expression levels of the about 5 to 49 sequences in the second set may be used in the same manner as described for the first set of 74 sequences. Depending on the number of tumor types, accuracies ranging from about 75% to about 95% may be achieved.

The invention is also based in part upon the discovery that use of about 5 to 49 expressed sequences to classify among 53 tumor types, which include (but is not limited to) the 34 and 39 types described herein, was limited by the number of available samples of some tumor types. As noted hereinbelow, accuracy is linked to the number of available samples of each tumor type such that the ability to classify additional tumor types is readily achieved by the application of increased numbers of each tumor type. Thus while the invention is exemplified by use in classifying among 34 or 39 tumor types as well as subsets of the 34 or 39, about 5 to 49 expressed sequences can also be used to classify among all tumor types with the inclusion of samples of the additional tumor types. Thus the invention also provides for the classification of a tumor as being a type beyond the 34 or 39 types described herein.

The invention is based upon the expression levels of the gene sequences in a set of known tumor cells from different tissues and of different tumor types. These gene expression profiles (of gene sequences in the different known tumor cells/types), whether embodied in nucleic acid expression, protein expression, or other expression formats, may be compared to the expression levels of the same sequences in an unknown tumor sample to identify the sample as containing a tumor of a particular type and/or a particular origin or cell type. The invention provides, such as in a clinical setting, the advantages of a more accurate identification of a cancer and thus the treatment thereof as well as the prognosis, including survival and/or likelihood of cancer recurrence following treatment, of the subject from whom the sample was obtained.

The invention is further based in part on the discovery that use of about 5 to 49 expressed sequences as described herein as capable of classifying among two or more tumor types necessarily and effectively eliminates one or more tumor types from consideration during classification. This reflects the lack of a need to select genes with expression levels that are highly correlated with all tumor types within the range of the classification system. Stated differently, the invention may be practiced with a plurality of genes the expression levels of which are not highly correlated with any of the individual tumor types or multiple types in the group of tumor types being classified. This is in contrast to other approaches based upon the selection and use of highly correlated genes, which likely do not "rule out" other tumor types as opposed to "rule in" a tumor type based on the positive correlation.

The classification of a tumor sample as being one of the possible tumor types described herein to the exclusion of other tumor types is of course made based upon a level of confidence as described below. Where the level of confidence is low, or an increase in the level of confidence is preferred, the classification can simply be made at the level of a particular tissue origin or cell type for the tumor in the sample. Alternatively, and where a tumor sample is not readily classified as a single tumor type, the invention permits the classification of the sample as one of a few possible tumor types described herein. This advantageously provides for the ability to reduce the number of possible tissue types, cell types, and tumor types from which to consider for selection and administration of therapy to the patient from whom the sample was obtained.

The invention thus provides a non-subjective means for the identification of the tissue source and/or tumor type of one or more cancers of an afflicted subject. Where subjective interpretation may have been previously used to determine the tissue source and/or tumor type, as well as the prognosis and/or treatment of the cancer based on that determination, the present invention provides objective gene expression patterns, which may used alone or in combination with subjective criteria to provide a more accurate identification of cancer classification. The invention is particularly advantageously applied to samples of secondary or metastasized tumors, but any cell containing sample (including a primary tumor sample) for which the tissue source and/or tumor type is preferably determined by objective criteria may also be used with the invention. Of course the ultimate determination of class may be made based upon a combination of objective and non-objective (or subjective/partially subjective) criteria.

The invention includes its use as part of the clinical or medical care of a patient. Thus in addition to using an expression profile of genes as described herein to assay a cell containing sample from a subject afflicted with cancer to determine the tissue source and/or tumor type of the cancer, the profile may also be used as part of a method to determine the prognosis of the cancer in the subject. The classification of the tumor/cancer and/or the prognosis may be used to select or determine or alter the therapeutic treatment for said subject. Thus the classification methods of the invention may be directed toward the treatment of disease, which is diagnosed in whole or in part based upon the classification. Given the diagnosis, administration of an appropriate anti-tumor agent or therapy, or the withholding or alternation of an anti-tumor agent or therapy may be used to treat the cancer.

Other clinical methods include those involved in the providing of medical care to a patient based on a classification as described herein. In some embodiments, the methods relate to providing diagnostic services based on expression levels of gene sequences, with or without inclusion of an interpretation of levels for classifying cells of a sample. In some embodiments, the method of providing a diagnostic service of the invention is preceded by a determination of a need for the service. In other embodiments, the method includes acts in the monitoring of the performance of the service as well as acts in the request or receipt of reimbursement for the performance of the service.

The details of one or more embodiments of the invention are set forth in the accompanying drawing and the description below. Other features, objects, and advantages of the invention will be apparent from the drawing and detailed description, and from the claims.

Definitions

As used herein, a "gene" is a polynucleotide that encodes a discrete product, whether RNA or proteinaceous in nature. It is appreciated that more than one polynucleotide may be capable of encoding a discrete product. The term includes alleles and polymorphisms of a gene that encodes the same product, or a functionally associated (including gain, loss, or modulation of function) analog thereof, based upon chromosomal location and ability to recombine during normal mitosis.

A "sequence" or "gene sequence" as used herein is a nucleic acid molecule or polynucleotide composed of a discrete order of nucleotide bases. The term includes the ordering of bases that encodes a discrete product (i.e. "coding region"), whether RNA or proteinaceous in nature. It is appreciated that more than one polynucleotide may be capable of encoding a discrete product. It is also appreciated that alleles and polymorphisms of the human gene sequences may exist and may be used in the practice of the invention to identify the expression level(s) of the gene sequences or an allele or polymorphism thereof. Identification of an allele or polymorphism depends in part upon chromosomal location and ability to recombine during mitosis.

The terms "correlate" or "correlation" or equivalents thereof refer to an association between expression of one or more genes and another event, such as, but not limited to, physiological phenotype or characteristic, such as tumor type.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), as well as unmodified forms of the polynucleotide.

The term "amplify" is used in the broad sense to mean creating an amplification product can be made enzymatically with DNA or RNA polymerases. "Amplification," as used herein, generally refers to the process of producing multiple copies of a desired sequence, particularly those of a sample. "Multiple copies" mean at least 2 copies. A "copy" does not necessarily mean perfect sequence complementarity or identity to the template sequence. Methods for amplifying mRNA are generally known in the art, and include reverse transcription PCR (RT-PCR) and quantitative PCR (or Q-PCR) or real time PCR. Alternatively, RNA may be directly labeled as the corresponding cDNA by methods known in the art.

By "corresponding", it is meant that a nucleic acid molecule shares a substantial amount of sequence identity with another nucleic acid molecule. Substantial amount means at least 95%, usually at least 98% and more usually at least 99%, and sequence identity is determined using the BLAST algorithm, as described in Altschul et al. (1990). J. Mol. Biol. 215:403-410 (using the published default setting, i.e. parameters w=4, t=17).

A "microarray" is a linear or two-dimensional or three dimensional (and solid phase) army of discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, such as of at least about $50/cm^2$, at least about $100/cm^2$, or at least about $500/cm^2$, up to about $1,000/cm^2$ or higher. The arrays may contain less than about 500, about 1000, about 1500, about 2000, about 2500, or about 3000 immobilized polynucleotides in total. As used herein, a DNA microarray is an army of oligonucleotide or polynucleotide probes placed on a chip or other surfaces used to hybridize to amplified or cloned polynucleotides from a sample. Since the position of each particular group of probes in the array is known, the identities of a sample polynucleotides can be determined based on their binding to a particular position in the microarray. As an alternative to the use of a microarray, an array of any size may be used in the practice of the invention, including an arrangement of one or more position of a two-dimensional or three dimensional arrangement in a solid phase to detect expression of a single gene sequence. In some embodiments, a microarray for use with the present invention may be prepared by photolithographic techniques (such as synthesis of nucleic acid probes on the surface from the 3' end) or by nucleic synthesis followed by deposition on a solid surface.

Because the invention relies upon the identification of gene expression, some embodiments of the invention determine expression by hybridization of mRNA, or an amplified or cloned version thereof, of a sample cell to a polynucleotide that is unique to a particular gene sequence. Polynucleotides of this type contain at least about 16, at least about 18, at least about 20, at least about 22, at least about 24, at least about 26, at least about 28, at least about 30, or at least about 32 consecutive basepairs of a gene sequence that is not found in other gene sequences. The term "about" as used in the previous sentence refers to an increase or decrease of 1 from the stated numerical value. Other embodiments are polynucleotides of at least or about 50, at least or about 100, at least about or 150, at least or about 200, at least or about 250, at least or about 300, at least or about 350, at least or about 400, at least or about 450, or at least or about 500 consecutive bases of a sequence that is not found in other gene sequences. The term "about" as used in the preceding sentence refers to an increase or decrease of 10% from the stated numerical value. Longer polynucleotides may of course contain minor mismatches (e.g. via the presence of mutations) which do not affect hybridization to the nucleic acids of a sample. Such polynucleotides may also be referred to as polynucleotide probes that are capable of hybridizing to sequences of the genes, or unique portions thereof, described herein. Such polynucleotides may be labeled to assist in their detection. The sequences may be those of mRNA encoded by the genes, the corresponding cDNA to such mRNAs, and/or amplified versions of such sequences. In some embodiments of the invention, the polynucleotide probes are immobilized on an array, other solid support devices, or in individual spots that localize the probes.

In other embodiments of the invention, all or part of a gene sequence may be amplified and detected by methods such as the polymerase chain reaction (PCR) and variations thereof, such as, but not limited to, quantitative PCR (Q-PCR), reverse transcription PCR (RT-PCR), and real-time PCR (including as a means of measuring the initial amounts of mRNA copies for each sequence in a sample), optionally real-time RT-PCR or real-time Q-PCR. Such methods would utilize one or two primers that are complementary to portions of a gene sequence, where the primers are used to prime nucleic acid synthesis. The newly synthesized nucleic acids are optionally labeled and may be detected directly or by hybridization to a polynucleotide of the invention. The newly synthesized nucleic acids may be contacted with polynucleotides (containing sequences) of the invention under conditions which allow for their hybridization. Additional methods to detect the expression of expressed nucleic acids include RNAse protection assays, including liquid phase hybridizations, and in situ hybridization of cells.

Alternatively, and in further embodiments of the invention, gene expression may be determined by analysis of expressed protein in a cell sample of interest by use of one or more antibodies specific for one or more epitopes of individual gene products (proteins), or proteolytic fragments thereof, in said cell sample or in a bodily fluid of a subject. The cell sample may be one of breast cancer epithelial cells enriched from the blood of a subject, such as by use of labeled antibodies against cell surface markers followed by fluorescence activated cell sorting (FACS). Such antibodies may be labeled to permit their detection after binding to the gene product. Detection methodologies suitable for use in the practice of the invention include, but are not limited to, immunohistochemistry of cell containing samples or tissue, enzyme linked immunosorbent assays (ELISAs) including antibody sandwich assays of cell containing tissues or blood samples, mass spectroscopy, and immuno-PCR.

The terms "label" or "labeled" refer to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

"Expression" and "gene expression" include transcription and/or translation of nucleic acid material.

As used herein, the term"comprising" and its cognates are used in their inclusive sense: that is, equivalent to the term"including" and its corresponding cognates.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in the sequence of a gene disclosed herein interest in comparison to a reference sequence. A sequence mutation includes single nucleotide changes, or alterations of more than one nucleotide in a sequence, due to mechanisms such as substitution, deletion or insertion. Single nucleotide polymorphism (SNP) is also a sequence mutation as used herein. Because the present invention is based on the relative level of gene expression, mutations in non-coding regions of genes as disclosed herein may also be assayed in the practice of the invention.

"Detection" or "detecting" includes any means of detecting, including direct and indirect determination of the level of gene expression and changes therein.

Unless defined otherwise all technical and scientific terms used herein have the same meaning as commonly understood to one of ordinary skill in the art to which this invention belongs.

Figure 1:
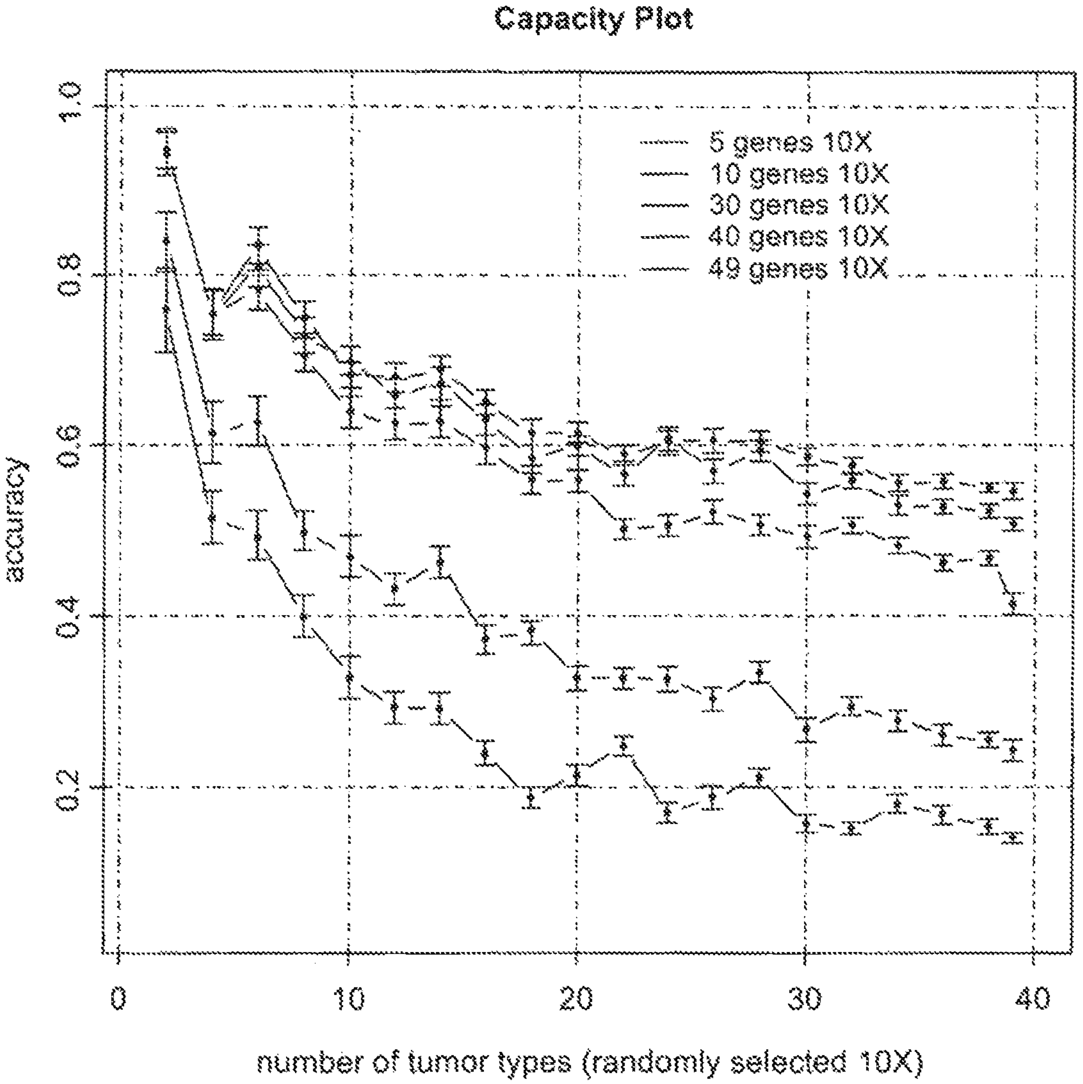
FIG. 1 shows a capacity plot for the ability to use the expression levels of subsets of a set of 100 expressed gene sequences to classify among 39 tumor types and subsets thereof. Expression levels of random combinations of 5, 10, 15, 20, 25, 30, 35, 40, 45, and 49 (each sampled times) of the 100 sequences were used with data from tumor types and then used to predict test random sets of tumor samples (each sampled 10 times) ranging from 2 to 39 types. A plot of numbers of tumor types (x-axis) versus prediction accuracies (y-axis) for results using from 5 to 49 genes are shown as non-limiting examples. The data from using 5 genes results in a curve closest to the x-axis 9 while the data from using 49 genes results in a curve farthest from the x-axis. Generally, accuracy improves with higher numbers of gene sequences, where from 30 to 49 gene sequences (the three curves farthest from the x-axis) provides about the same level of accuracy.

If the tumor is of a non-germ cell origin, then it is either of a epithelial or non-epithelial origin. If it is the former, then it is either squamous or non-squamous origin. Squamous origin tumors are of cervix, esophagus, larynx, lung, or skin in origin. Non-squamous origin tumors are of urinary bladder, breast, carcinoid-intestine, cholangiocarcinoma, digestive, kidney, liver, lung, prostate, reproductive system, skin-basal cell, or thyroid-follicular-papillary origin. Among those of digestive origin, the tumors are of small and large bowel, stomach-adenocarcinoma, bile duct, esophagus, gall bladder, and pancreas in origin. The esophagus origin tumors may be of either Barrett's esophagus or adenocarcinoma types. Of the reproductive system origin tumors, they may be of cervix adenocarcinoma type, endometrial tumor, or ovarian origin. Ovarian origin tumors are of the clear, serous, mucinous, and endometroid types.

If the tumor is of non-epithelial origin, then it is of adrenal gland, brain, GIST (gastrointestinal stromal tumor), lymphoma, meningioma, mesothelioma, sarcoma, skin melanoma, or thyroid-medullary origin. Of the lymphomas, they are B cell, Hodgkin's, or T cell type. Of the sarcomas, they are leiomyosarcoma, osteosarcoma, soft-tissue sarcoma, soft tissue MFH (malignant fibrous histiocytoma), soft tissue sarcoma synovial, soft tissue Ewing's sarcoma, soft tissue fibrosarcoma, and soft tissue rhabdomyosarcoma types.

DETAILED DESCRIPTION OF MODES OF PRACTICING THE INVENTION

This invention provides methods for the use of gene expression information to classify tumors in a more objective manner than possible with conventional pathology techniques. Thus in a first aspect, the invention provides a method of classifying a cell containing sample as including a tumor cell of (or from) a type of tissue or a tissue origin. The method comprises determining or measuring the expression levels of about five to 49 transcribed sequences from cells in a cell containing sample obtained from a subject, and classifying the sample as containing tumor cells of a type of tissue from a plurality of tumor types based on the expression levels of said sequences.

As used herein, "a plurality" refers to the state of two or more.

The classifying is based upon a comparison of the expression levels of the about 5 to 49 transcribed sequences in the cells of the sample to their expression levels in known tumor samples and/or known non-tumor samples. Alternatively, the classifying is based upon a comparison of the expression levels of the about 5 to 49 transcribed sequences to the expression of reference sequences in the same samples, relative to, or based on, the same comparison in known tumor samples and/or known non-tumor samples. Thus as a non-linuting example, the expression levels of the gene sequences may be determined in a set of known tumor samples to provide a database against which the expression levels detected or determined in a cell containing sample from a subject is compared. The expression level(s) of gene sequence(s) in a sample also may be compared to the expression level(s) of said sequence(s) in normal or non-cancerous cells, preferably from the same sample or subject. As described below and in embodiments of the invention utilizing Q-PCR or real time Q-PCR, the expression levels may be compared to expression levels of reference genes in the same sample or a ratio of expression levels may be used.

In practice, the method utilizes a ratio, of transcribed sequences to the number of tumor types classified, ranging from about 1:2 to about 5:2 or higher. Stated differently, the ratio of the number of expression levels needed to the number of tumor types that may be classified based upon those levels, ranges from about 1:2 to about 1:1 to about 3:2 to about 2:1 to about 5:2 or higher. This is reflected by the ability to use as few as about 20 expression levels to classify among 39 tumor types (see FIG. 6). Thus, and based on data as shown in FIGS. 1-9, the invention may be practiced with about 5 to 49 gene sequences within the ratio of genes assessed to tumors classified.

The selection of about 5 to 49 gene sequences to use may be random, or by selection based on various criteria. As one non-limiting example, the gene sequences may be selected based upon unsupervised learning, including clustering techniques. As another non-limiting example, selection may be to reduce or remove redundancy with respect to their ability to classify tumor type. For example, gene sequences are selected based upon the lack of correlation between their expression and the expression of one or more other gene sequences used for classifying. This is accomplished by assessing the expression level of each gene sequence in the expression data set for correlation, across the plurality of samples, with the expression level of each other gene in the data set to produce a correlation matrix of correlation coefficients. These correlation determinations may be performed directly, between expression of each pair of gene sequences, or indirectly, without direct comparison between the expression values of each pair of gene sequences.

A variety of correlation methodologies may be used in the correlation of expression data of individual gene sequences within the data set. Non-limiting examples include parametric and non-parametric methods as well as methodologies based on mutual information and non-linear approaches. Non-limiting examples of parametric approaches include Pearson correlation (or Pearson r, also referred to as linear or product-moment correlation) and cosine correlation. Non-limiting examples of non-parametric methods include Spearman's R (or rank-order) correlation, Kendall's Tau correlation, and the Gamma statistic. Each correlation methodology can be used to determine the level of correlation between the expressions of individual gene sequences in the data set. The correlation of all sequences with all other sequences is most readily considered as a matrix. Using Pearson's correlation as a non-limiting example, the correlation coefficient r in the method is used as the indicator of the level of correlation. When other correlation methods are used, the correlation coefficient analogous to r may be used, along with the recognition of equivalent levels of correlation corresponding to r being at or about 0.25 to being at or about 0.5.

The correlation coefficient may be selected as desired to reduce the number of correlated gene sequences to various numbers. In some embodiments of the invention using r, the selected coefficient value may be of about 0.25 or higher, about 0.3 or higher, about 0.35 or higher, about 0.4 or higher, about 0.45 or higher, or about 0.5 or higher. The selection of a coefficient value means that where expression between gene sequences in the data set is correlated at that value or higher, they are possibly not included in a subset of the invention. Thus in some embodiments, the method comprises excluding or removing (not using for classification) one or more gene sequences that are expressed in correlation, above a desired correlation coefficient, with another gene sequence in the tumor type data set. It is pointed out, however, that there can be situations of gene sequences that are not correlated with any other gene sequences, in which case they are not necessarily removed from use in classification.

Thus the expression levels of gene sequences, where more than about 10%, more than about 20%, more than about 30%, more than about 40%, more than about 50%, more than about 60%, more than about 70%, more than about 80%, or more than about 90% of the levels are not correlated with that of another one of the gene sequences used, may be used in the practice of the invention. Correlation between expression levels may be based upon a value below about 0.9, about 0.8, about 0.7, about 0.6, about 0.5, about 0.4, about 0.3, or about 0.2. The ability to classify among classes with exclusion of the expression levels of some gene sequences is present because expression of the gene sequences in the subset is correlated with expression of the gene sequences excluded from the subset. So no information was lost because information based on the expression of the excluded gene sequences is still represented by sequences retained in the subset. Therefore, expression of the gene sequences of the subset has information content relevant to properties and/or characteristics (or phenotype) of a cell. This has application and relevance to the classification of additional tumor type classes not included as part of the original gene expression data set which can be classified by use of a subset of the invention because based on the redundancy of information between expression of sequences in the subset and sequences expressed in those additional classes. Thus the invention may be used to classify cells as being a tumor type beyond the plurality of known classes used to generate the original gene expression data set.

Selection of gene sequences based upon reducing correlation of expression to a particular tumor type may also be used. This also reflects a discovery of the present invention, based upon the observation that expression levels that were most highly correlated with one or more tumor types was not necessarily of greatest value in classification among different tumor types. This is reflected both by the ability to use randomly selected gene sequences for classification as well as the use of particular sequences, as described herein, which are not expressed with the most significant correlation with one or more tumor types. Thus the invention may be practiced without selection of gene sequences based upon the most significant P values or a ranking based upon correlation of gene expression and one or more tumor types. Thus the invention may be practiced without the use of ranking based methodologies, such as the Kruskal-Wallis H-test.

The gene sequences used in the practice of the invention may include those which have been observed to be expressed in correlation with particular tumor types, such as expression of the estrogen receptor, which has been observed to be expressed in correlation with some breast and ovarian cancers. In some embodiments of the invention, however, the invention is practiced with use of the expression level of at least one gene sequence that has not been previously identified as being associated with any of the tumor types being classified. Thus the invention may be practiced without all of the gene sequences having previously been associated or correlated with expression in the 2 or more (up to 39 or more) tumor types to which a cell containing sample may be classified.

While the invention is described mainly with respect to human subjects, samples from other subjects may also be used. All that is necessary is the ability to assess the expression levels of gene sequences in a plurality of known tumor samples such that the expression levels in an unknown or test sample may be compared. Thus the invention may be applied to samples from any organism for which a plurality of expressed sequences, and a plurality of known tumor samples, are available. One non-limiting example is application of the invention to mouse samples, based upon the availability of the mouse genome to permit detection of expressed murine sequences and the availability of known mouse tumor samples or the ability to obtain known samples. Thus, the invention is contemplated for use with other samples, including those of mammals, primates, and animals used in clinical testing (such as rats, mice, rabbits, dogs, cats, and chimpanzees) as non-limiting examples.

While the invention is readily practiced with the use of cell containing samples, any nucleic acid containing sample which may be assayed for gene expression levels may be used in the practice of the invention. Without limiting the invention, a sample of the invention may be one that is suspected or known to contain tumor cells. Alternatively, a sample of the invention may be a "tumor sample" or "tumor containing sample" or "tumor cell containing sample" of tissue or fluid isolated from an individual suspected of being afflicted with, or at risk of developing, cancer. Non-limiting examples of samples for use with the invention include a clinical sample, such as, but not limited to, a fixed sample, a fresh sample, or a frozen sample. The sample may be an aspirate, a cytological sample (including blood or other bodily fluid), or a tissue specimen, which includes at least some information regarding the in situ context of cells in the specimen, so long as appropriate cells or nucleic acids are available for determination of gene expression levels. The invention is based in part on the discovery that results obtained with frozen tissue sections can be validly applied to the situation with fixed tissue or cell samples and extended to fresh samples.

Non-limiting examples of fixed samples include those that are fixed with formalin or formaldehyde (including FFPE samples), with Boudin's, glutaldehyde, acetone, alcohols, or any other fixative, such as those used to fix cell or tissue samples for immunohistochemistry (IHC). Other examples include fixatives that precipitate cell associated nucleic acids and proteins. Given possible complications in handling frozen tissue specimens, such as the need to maintain its frozen state, the invention may be practiced with non-frozen samples, such as fixed samples, fresh samples, including cells from blood or other bodily fluid or tissue, and minimally treated samples. In some applications of the invention, the sample has not been classified using standard pathology techniques, such as, but not limited to, immunohistochemistry based assays.

In some embodiments of the invention, the sample is classified as containing a tumor cell of a type selected from the following 53, and subsets thereof: Adenocarcinoma of Breast, Adenocarcinoma of Cervix, Adenocarcinoma of Esophagus, Adenocarcinoma of Gall Bladder, Adenocarcinoma of Lung, Adenocarcinoma of Pancreas, Adenocarcinoma of Small-Large Bowel, Adenocarcinoma of Stomach, Astrocytoma, Basal Cell Carcinoma of Skin, Cholangiocarcinoma of Liver, Clear Cell Adenocarcinoma of Ovary, Diffuse Large B-Cell Lymphoma, Embryonal Carcinoma of Testes, Endometrioid Carcinoma of Uterus, Ewings Sarcoma, Follicular Carcinoma of Thyroid, Gastrointestinal Stromal Tumor, Germ Cen Tumor of Ovary, Germ Cell Tumor of Testes, Glioblastoma Multiforme, Hepatocellular Carcinoma of Liver, Hodgkin's Lymphoma, Large Cell Carcinoma of Lung, Leiomyosarcoma, Liposarcoma. Lobular Carcinoma of Breast, Malignant Fibrous Histiocytoma, Medulary Carcinoma of Thyroid, Melanoma, Meningioma, Mesothelioma of Lung, Mucinous Adenocarcinoma of Ovary, Myofibrosarcoma, Neuroendocrine Tumor of Bowel, Oligodendroglioma, Osteosarcoma, Papillary Carcinoma of Thyroid, Pheochromocytoma, Renal Cell Carcinoma of Kidney, Rhabdomyosarcoma, Seminoma of Testes, Serous Adenocarcinoma of Ovary, Small Cell Carcinoma of Lung, Squamous Cell Carcinoma of Cervix, Squamous Cell Carcinoma of Esophagus, Squamous Cell Carcinoma of Larynx, Squamous Cell Carcinoma of Lung, Squamous Cell Carcinoma of Skin, Synovial Sarcoma, T-Cell Lymphoma, and transitional Cell Carcinoma of Bladder.

In other embodiments of the invention, the sample is classified as containing a tumor cell of a type selected from the following 34, and subsets thereof: adrenal, brain, breast, carcinoid-intestine, cervix (squamous cell), cholangiocarcinoma, endometrium, germ-cell, GIST (gastrointestinal stromal tumor), kidney, leiomyosarcoma, liver, lung (adenocarcinoma, large cell), lung (small cell), lung (squamous), lymphoma (B cell), Lymphoma (Hodgkins), meningioma, mesothelioma, osteosarcoma, ovary (clear cell), ovary (serous cell), pancreas, prostate, skin (basal cell), skin (melanoma), small and large bowel; soft tissue (liposarcoma); soft tissue (MFH or Malignant Fibrous Histiocytoma), soft tissue (Sarcoma-synovial), testis (seminoma), thyroid (follicular-papillary), thyroid (medullary carcinoma), and urinary bladder.

In further embodiments of the invention, the sample is classified as containing a tumor cell of a type selected from the following 39, and subsets thereof: adrenal gland, brain, breast, carcinoid-intestine, cervix-adenocarcinoma, cervix-squamous, endometrium, gall bladder, germ cell-ovary, GIST, kidney, leiomyosarcoma, liver, lung-adenocarcinoma-large cell, lung-small cell, lung-squamous, lymphoma-B cell, lymphoma-Hodgkin's, lymphoma-T cell, meningioma, mesothelioma, osteosarcoma, ovary-clear cell, ovary-serous, pancreas, prostate, skin-basal cell, skin-melanoma, skin-squamous, small and large bowel, soft tissue-liposarcoma, soft tissue-MFH, soft tissue-sarcoma-synovial, stomach-adenocarcinoma, testis-other (or non-seminoma), testis-seminoma, thyroid-follicular-papillary, thyroid-medullary, and urinary bladder.

The methods of the invention may also be applied to classify a cell containing sample as containing a tumor cell of a tumor of a subset of any of the above sets. The size of the subset will usually be small, composed of two, three, four, five, six, seven, eight, nine, or ten of the tumor types described above. Alternatively, the size of the subset may be any integral number up to the full size of the set. Thus embodiments of the invention include classification among 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 of the above types. In some embodiments, the subset will be composed of tumor types that are of the same tissue or organ type. Alternatively, the subset will be composed of tumor types of different tissues or organs. In some embodiments, the subset will include one or more types selected from adrenal gland, brain, carcinoid-intestine, cervix-adenocarcinoma, cervix-squamous, gall bladder, germ cell-ovary, GIST, leiomyosarcoma, liver, meningioma, osteosarcoma, skin-basal cell, skin-squamous, soft tissue-liposarcoma, soft tissue-MFH, soft tissue-sarcoma-synovial, testis-other (or non-seminoma), testis-seminoma, thyroid-follicular-papillary, and thyroid-medullary.

Classification among subsets of the above tumor types is demonstrated by the results shown in FIGS. 1-9, where the expression levels of as few as about 5 or more genes sequences can be used to classify among random samples of 2 tumor types among those in the set of 39 listed above. Expression levels of as few as about 20 to 49 can be used to classify among all 39 tumor types with varying degrees of accuracy. The invention may be practiced with the expression levels of about 10 or more, about 15 or more, about 20 or more, about 25 or more, about 30 or more, about 35 or more, about 40 or more, or about 45 or more to 49 transcribed sequences as found in the human "transcriptome" (transcribed portion of the genome). The invention may also be practiced with expression levels of about 10-20 or more, about 20-30 or more, about 30-40 or more, about 40-50 or more, or 49 transcribed sequences. In some embodiments of the invention, the transcribed genes may be randomly picked or include all or some of the specific genes sequences disclosed herein. As demonstrated herein, classification with accuracies of about 55%, about 60%, about 65%, about 70%, about 75%, about 80%, about 85%, about 90%, or about 95% or higher can be performed by use of the instant invention.

In other embodiments, the gene expression levels of other gene sequences may be determined along with the above described determinations of expression levels for use in classification. One non-limiting example of this is seen in the case of a microarray based platform to determine gene expression, where the expression of other gene sequences is also measured. Where those other expression levels are not used in classification, they may be considered the results of “excess” transcribed sequences and not critical to the practice of the invention. Alternatively, and where those other expression levels are used in classification, they are within the scope of the invention, where the description of using particular numbers of sequences does not necessarily exclude the use of expression levels of additional sequences. In some embodiments, the invention includes the use of expression level(s) from one or more “excess” gene sequences, such as those which may provide information redundant to one or more other gene sequences used in a method of the invention.

Because classification of a sample as containing cells of one of the above tumor types inherently also classifies the tissue or organ site origin of the sample, the methods of the invention may be applied to classification of a tumor sample as being of a particular tissue or organ site of the patient. This application of the invention is particularly useful in cases where the sample is of a tumor that is the result of metastasis by another tumor. In some embodiments of the invention, the tumor sample is classified as being one of the following 24: Adrenal, Bladder, Bone, Brain, Breast, Cervix, Endometrium, Esophagus, Gall Bladder, Kidney, Larynx, Liver, Lung, Lymph Node, Ovary, Pancreas, Prostate, Skin, Soft Tissue, Small/Large Bowel, Stomach, Testes, Thyroid, and Uterus.

While the invention also provides for classification as one of the above tumor types based upon comparisons to the expression levels of sequences in the 39 tumor types, it is possible that a higher level of confidence in the classification is desired. If an increase in the confidence of the classification is preferred, the classification can be adjusted to identify the tumor sample as being of a particular origin or cell type as shown in FIG. 10. Thus an increase in confidence can be made in exchange for a decrease in specificity as to tumor type by identification of origin or cell type.

The classification of a cell containing sample as having a tumor cell of one of the 39 tumor types above inherently also classifies the tissue or organ site origin of the sample. For example, the identification of a sample as being cervix-squamous necessarily classifies the tumor as being of cervical origin, squamous cell type (and thus epithelial rather than non-epithelial in origin) as shown in FIG. 10. It also means that the tumor was necessarily not germ cell in origin. Thus, the methods of the invention may be applied to classification of a tumor sample as being of a particular tissue or organ site of a subject or patient. This application of the invention is particularly useful in cases where the sample is of a tumor that is the result of metastasis by another tumor.

The practice of the invention to classify a cell containing sample as having a tumor cell of one of the above types is by use of an appropriate classification algorithm that utilizes supervised learning to accept 1) the levels of expression of the gene sequences in a plurality of known tumor types as a training set and 2) the levels of expression of the same genes in one or more cells of a sample to classify the sample as having cells of one of the tumor types. Further discussion of this is provided in the Example section herein. The levels of expression may be provided based upon the signals in any format, including nucleic acid expression or protein expression as described herein.

As would be evident to the skilled practitioner, the range of classification is affected by the number of tumor types as well as the number of samples for each tumor type. But given adequate samples of the full range of human tumors as provided herein, the invention is readily applied to the classification of those tumor types as well as additional types.

Non-limiting examples of classification algorithms that may be used in the practice of the invention include supervised learning algorithms, machine learning algorithms, linear discriminant analysis, attribute selection algorithms, and artificial neural networks (ANN). In preferred embodiments of the invention, a distance-based classification algorithm, such as the k-nearest neighbor (KNN) algorithm, or support vector machine (SVM) are used.

The use of KNN is in some embodiments of the invention and is discussed further as a non-limiting representative example. KNN can be used to analyze the expression data of the genes in a “training set” of known tumor samples including all 39 of the tumor types described herein. The training data set can then be compared to the expression data for the same genes in a cell containing sample. The expression levels of the genes in the sample are then compared to the training data set via KNN to identify those tumor samples with the most similar expression patterns. As a non-limiting example, the five “nearest neighbors” may be identified and the tumor types thereof used to classify the unknown tumor sample. Of course other numbers of “nearest neighbors” may be used. Non-limiting examples include less than 5, about 7, about 9, or about 11 or more “nearest neighbors”.

As a hypothetical example, if the five “nearest neighbors” of an unknown sample are four B cell lymphomas and one T cell lymphoma, then the classification of the sample as being of a B cell lymphoma can be made with great accuracy. This has been used with 84% or greater accuracy, such as 90%, as described in the Examples.

The classification ability may be combined with the inherent nature of the classification scheme to provide a means to increase the confidence of tumor classification in certain situations. For example, if the five “nearest neighbors” of a sample are three ovary clear cell and two ovary serous tumors, confidence can be improved by simply treating the tumors as being of ovarian origin and treating the subject or patient (from whom the sample was obtained) accordingly. See FIG. 10. This is an example of trading off specificity in favor of increased confidence. This provides the added benefit of addressing the possibility that the unknown sample was a mucinous or endometroid tumor. Of course the skilled practitioner is free to treat the tumor as one or both of these two most likely possibilities and proceeding in accordance with that determination.

Because the developmental lineage of tumor cells in certain tumor types (e.g., germ cells) can be complex and involve multiple cell types, FIG. 10 may appear to be oversimplified. However, it serves as a good basis to relate known histopathology and to serve as a “guide tree” for analyzing and relating tumor-associated gene expression signatures.

The inherent nature of the classification scheme also provides a means to increase the confidence of tumor classification in cases wherein the “nearest neighbors” are ambiguous. For example, if the five “nearest neighbors” were one urinary bladder, one breast, one kidney, one liver, and one prostate, the classification can simply be that of a non-squamous cell tumor. Such a determination can be made with significant confidence and the subject or patient from whom the sample was obtained can be treated accordingly. Without being bound by theory, and offered solely to improve the understanding of the invention, the last two examples reflect the similarities in gene expression of cells of a similar cell type and/or tissue origin.

Embodiments of the invention include use of the methods and materials described herein to identify the origin of a cancer from a patient. Thus given a sample containing tumor cells, the tissue origin of the tumor cells is identified by use of the present invention. One non-limiting example is in the case of a subject with an inflamed lymph node containing cancer cells. The cells may be from a tissue or organ that drains into the lymph node or it may be from another tissue source. The present invention may be used to classify the cells as being of a particular tumor tissue type (or origin) which allows the identification of the source of the cancer cells. In an alternative non-limiting example, the sample (such as that from a lymph node) contains cells, which are first assayed by use of the invention to classify at least one cell as being a tumor cell of a tissue type or origin. This is then used to identify the source of the cancer cells in the sample. Both of these are examples of the advantageous use of the invention to save time, effort, and cost in the use of other cancer diagnostic tests.

In further embodiments, the invention is practiced with a sample from a subject with a previous history of cancer. As a non-limiting example, a cell containing sample (from the lymph node or elsewhere) of the subject may be found to contain cancer cells such that the present invention may be used to determine whether the cells are from the same or a different tissue from that of the previous cancer. This application of the invention may also be used to identify a new primary tumor, such as the case where new cancer cells are found in the liver of a subject who previously had breast cancer. The invention may be used to identify the new cancer cells as being the result of metastasis from the previous breast cancer (or from another tumor type, whether previously identified or not) or as a new primary occurrence of liver cancer. The invention may also be applied to samples of a tissue or organ where multiple cancers are found to determine the origin of each cancer, as well as whether the cancers are of the same origin.

While the invention may be practiced with the use of expression levels of a random group of expressed gene sequences, the invention also provides exemplary gene sequences for use in the practice of the invention. The invention includes a first group of 74 gene sequences from which about 5 to 49 may be used in the practice of the invention. The 5 to 49 gene sequences may be used along with the determination of expression levels of additional sequences so long as the expression levels of gene sequences from the set of 74 are used in classifying. A non-limiting example of such embodiments of the invention is where the expression of from about 5 to 49 of the 74 gene sequences is measured along with the expression levels of a plurality of other sequences, such as by use of a microarray based platform used to perform the invention. Where those other expression levels are not used in classification, they may be considered the results of "excess" transcribed sequences and not critical to the practice of the invention. Alternatively, and where those other expression levels are used in classification, they are within the scope of the invention, where the use of the above described sequences does not necessarily exclude the use of expression levels of additional sequences. mRNA sequences corresponding to a set of 74 gene sequences for use in the practice of the invention are provided in Example 6 (Sequence Listing) below along with additional identifying information. The listing of the identifying information, including accession numbers and other information, is provided by the following.

---

>Hs.73995_mRNA_1 gi|190403|gb|M60502.1|HUMPROFILE Human profilaggrin mRNA, 3' end polyA=1
>Hs.75236_mRNA_4 gi|14280328|gb|AY033998.1| *Homo sapiens* polyA=3
>Hs.299867_mRNA_1 gi|4758533|ref|NM_004496.1| *Homo sapiens* hepatocyte nuclear factor 3, alpha (HNF3A), mRNA polyA=3
>Hs.285401_contig1
AI147926|AI880620|AA768316|AA761543|AA279147|AI216016|AI738663|N79248|AI684
489|AA960845|AI718599|AI379138|N29366|BF002507|AW044269|R34339|R66326|H0464
8|R67467|AI523112|BF941500 polyA=2 polyA=3
>Hs.182507_mRNA_1 gi|15431324|ref|NM_002283.2| *Homo sapiens* keratin, hair, basic, 5 (KRTHB5), mRNA polyA=3
>Hs.292653_contig1
AI200660|AW014007|AI341199|AI692279|AI393765|AI378686|AI695373|AW292108|T10
352|R44346|AW470408|AI380925|BF938983|AW003704|H08077|F03856|H08075|F08895|
AW468398|AI865976|H22568|AI858374|AI216499 polyA=2 polyA=3
>Hs.97616_mRNA_3 gi|12654852|gb|BC001270.1|BC001270 *Homo sapiens* clone MGC:5069 IMAGE:3458016 polyA=3
>Hs.123078_mRNA_3 gi|14328043|gb|BC009237.1|BC009237 *Homo sapiens* clone MGC:2216 IMAGE:2989823 polyA=3
>Hs.285508_contig1 AW194680|BF939744|BF516467 polyA=1 polyA=1
>Hs.183274_contig1
BF437393|BF064008|BF509951|AW134603|AI277015|AI803254|AA887915|BF054958|AI0
04413|AI393911|AI278517|AW612644|AI492162|AI309226|AI863671|AA448864|AI6401
65|AA479926|AA461188|AA780161|BF591180|AI918020|AI758226|AI291375|BF001845|
BF003064|AI337393|AI522206|BE856784|BF001760|AI280300 FLAG=1 polyA=2 WARN polyA=3
>Hs.334841_mRNA_3 gi|14290606|gb|BC009084.1|BC009084 *Homo sapiens* clone MGC:9270 IMAGE:3853674 polyA=3
>Hs.3321_contig1
AI804745|AI492375|AA594799|BE672611|AA814147|AA722404|AW170088|D11718|BG153
444|AI680648|AA063561|BE219054|AI590287|R55185|AI479167|AI796872|AI018324|A
I701122|BE218203|AA905336|AI681917|BI084742|AI480008|AI217994|AI401468
polyA=2 polyA=3
>Hs.306216_singlet1 AW083022 polyA=1 polyA=2
>Hs.99235_contig1 AA456140|AI167259|AA450056 polyA=2 polyA=3
>Hs.169172_mRNA_2 gi|2274961|emb|AJ000388.1|HSCANPX *Homo sapiens* mRNA for calpain-like protease CANPX polyA=3

-continued

>Hs.351486_mRNA_1 gi|16549178|dbj|AK054605.1|AK054605 *Homo sapiens* cDNA FLJ30043 fis, clone 3NB692001548 polyA=0
>Hs.153504_contig2
BE962007|AW016349|AW016358|AW139144|AA932969|AI025620|AI688744|AI865632|AA854291|AA932970|AU156702|AI634439|AA152496|AI539557|AI123490|AI613215|AI318363|AW105672|AA843483|AI366889|AW181938|AI813801|AI433695|AA934772|N72230|AI760632|BE858965|AW058302|AI760087|AI682077|AA886672|AI350384|AW243848|AW300574|BE466359|AI859529|AI921588|BF062899|BE855597|BE617708 polyA=2 polyA=3
>Hs.199354_singlet1 AI669760 polyA=1 polyA=2
>Hs.162020_contig1 AW291189|AA505872 polyA=2 polyA=3
>Hs.30743_mRNA_3 gi|18201906|ref|NM_006115.2| *Homo sapiens* preferentially expressed antigen in melanoma (PRAME), mRNA polyA=3
>Hs.271580_contig1
AI632869|AW338882|AW338875|AW613773|AI982899|AW193151|BE206353|BE208200|AI811548|AW264021 polyA=2 polyA=3
>Hs.69360_mRNA_2 gi|14250609|gb|BC008764.1|BC008764 *Homo sapiens* clone MGC:1266 IMAGE:3347571 polyA=3
>Hs.30827_contig1 H07885|N39347|W85913|AA583408|W86449 polyA=2 polyA=3
>Hs.211593_contig2
BF592799|AI570478|AA234440|R40214|BE501078|AW593784|AI184050|AI284161|W72149|AW780437|AI247981|AW241273|H60824 polyA=2 polyA=3
>Hs.155097_mRNA_1 gi|15080385|gb|BC011949.1|BC011949 *Homo sapiens* clone MGC:9006 IMAGE:3863603 polyA=3
>Hs.5163_mRNA_1 gi|15990433|gb|BC015582.1|BC015582 *Homo sapiens* clone MGC:23280 IMAGE:4637504 polyA=3
>Hs.55150_mRNA_1 gi|17068414|gb|BC017586.1|BC017586 *Homo sapiens* clone MGC:26610 IMAGE:4837506 polyA=3
>Hs.170177_contig3
AI620495|AW291989|AA780896|AA976262|AI298326|BF111862|AW591523|AI922518|AI480280|BF589437|AA600354|AI886238|AA035599|H90049|BF112011|N52601|AI570965|AI565367|AW768847|H90073|BE504361|N45292|AI632075|AA679729|AW168052|AI978827|AI968410|AI669255|N45300|AI651256|AI698970|AI521256|AW078614|AI802070|AI885947|AI342534|AI653624|AW243936|T16586|R15989|AI289789|AI871636|AI718785|AW148847 polyA=2 polyA=3
>Hs.184601_mRNA_5 gi|4426639|gb|AF104032.1|AF104032 *Homo sapiens* polyA=2
>Hs.351972_singlet1 AA865917 polyA=2 polyA=3
>Hs.5366_mRNA_2 gi|15277845|gb|BC012926.1|BC012926 *Homo sapiens* clone MGC:16817 IMAGE:3853503 polyA=3
>Hs.18140_contig1
AI685931|AA410954|T97707|AA706873|AI911572|AW614616|AA548520|AW027764|BF511251|AI914294|AW151688 polyA=1 polyA=1
>Hs.133196_contig2
BF224381|BE467992|AW137689|AI695045|AW207361|BF445141|AA405473 polyA=2 WARN polyA=3
>Hs.63325_mRNA_5 gi|15451939|ref|NM_019894.1| *Homo sapiens* transmembrane protease, serine 4 (TMPRSS4), mRNA polyA=3
>Hs.250692_mRNA_2 gi|184223|gb|M95585.1|HUMHLF Human hepatic leukemia factor (HLF) mRNA, complete cds polyA=3
>Hs.250726_singlet4 AW298545 polyA=2 polyA=3
>Hs.79217_mRNA_2 gi|16306657|gb|BC001504.1|BC001504 *Homo sapiens* clone MGC:2273 IMAGE:3505512 polyA=3
>Hs.47986_mRNA_1 gi|13279253|gb|BC004331.1|BC004331 *Homo sapiens* clone MGC:10940 IMAGE:3630835 polyA=3
>Hs.94367_mRNA_1 gi|10440200|dbj|AK027147.1|AK027147 *Homo sapiens* cDNA: FLJ23494 fis, clone LNG01885 polyA=3
>Hs.49215_contig1
BI493248|N66529|AA452255|BI492877|AW196683|AI963900|BF478125|AI421654|BE466675 polyA=1 polyA=1
>Hs.281587_contig2
R61469|R15891|AA007214|R61471|AI014624|N69765|AW592075|H09780|AA709038|AI335898|AI559229|F09750|R49594|H11055|T72573|AA935558|AA988654|AA826438|AI002431|AI299721 polyA=1 polyA=2
>Hs.79378_mRNA_1 gi|16306528|ref|NM_003914.2| *Homo sapiens* cyclin A1 (CCNA1), mRNA polyA=3
>Hs.156469_contig2
AI341378|AI670817|AI701687|AI335022|AW235883|AI948598|AA446356 polyA=2 polyA=3
>Hs.6631_mRNA_1 gi|7020430|dbj|AK000380.1|AK000380 *Homo sapiens* cDNA FLJ20373 fis, clone HEP19740 polyA=3
>Hs.155977_contig1 AI309080|AI313045 polyA=1 WARN polyA=1
>Hs.95197_mRNA_4 gi|5817138|emb|AL110274.1|HSM800829 *Homo sapiens* mRNA; cDNA DKFZp564I0272 (from clone DKFZp564I0272) polyA=3
>Hs.48956_contig1 N64339|AI569513|AI694073 polyA=1 polyA=1
>Hs.118825_mRNA_10 gi|1495484|emb|X96757.1|HSSAPKK3 *H. sapiens* mRNA for MAP kinase kinase polyA=3
>Hs.135118_contig3
AI683181|AI082848|AW770198|AI333188|AI873435|AW169942|AI806302|AW340718|BF196955|AA909720 polyA=1 polyA=2

-continued

>Hs.171857_mRNA_1 gi|13161080|gb|AF332224.1|AF332224 *Homo sapiens* testis protein mRNA, partial cds polyA=3
>Hs.18910_mRNA_3 gi|12804464|gb|BC001639.1|BC001639 *Homo sapiens* clone MGC:1944 IMAGE:2959372 polyA=3
>Hs.194774_mRNA_1 gi|16306633|gb|BC001492.1|BC001492 *Homo sapiens* clone MGC:1774 IMAGE:3510004 polyA=3
>Hs.127428_mRNA_2 gi|16306818|gb|BC006537.1|BC006537 *Homo sapiens* clone MGC:1934 IMAGE:2987903 polyA=3
>Hs.126852_contig1 AI802118|BF197404|BF224434|AA931964|AW236083|AI253119|AW614335|AI671372|AI793240|AW006851|AI953604|AI640505|AI633982|AW195809|AI493069|AW058576|AW293622 polyA=2 polyA=3
>Hs.28149_mRNA_1 gi|14714936|gb|BC010626.1|BC010626 *Homo sapiens* clone MGC:17687 IMAGE:3865868 polyA=3
>Hs.35453_mRNA_3 gi|7018494|emb|AL157475.1|HSM802461 *Homo sapiens* mRNA; cDNA DKFZp761G151 (from clone DKFZp761G151); partial cds polyA=3
>Hs.180570_contig1 R08175|AA707224|AA699986|R11209|W89099|T98002|AA494546 polyA=2 polyA=3
>Hs.196270_mRNA_1 gi|11545416|gb|AF283645.1|AF283645 *Homo sapiens* chromosome 8 map 8q21 polyA=3
>Hs.9030_mRNA_3 gi|12652600|gb|BC000045.1|BC000045 *Homo sapiens* clone MGC:2032 IMAGE:3504527 polyA=3
>Hs.1282_mRNA_3 gi|4559405|ref|NM_000065.1| *Homo sapiens* complement component 6 (C6), mRNA polyA=1
>Hs.268562_mRNA_2 gi|15341874|gb|BC013117.1|BC013117 *Homo sapiens* clone MGC:8711 IMAGE:3882749 polyA=3
>Hs.151301_mRNA_3 gi|16041747|gb|BC015754.1|BC015754 *Homo sapiens* clone MGC:23085 IMAGE:4862492 polyA=3
>Hs.111_contig1 AA946776|AW242338|H24274|AI078616 polyA=1 polyA=2
>Hs.150753_contig1 AI123582|AI288234 polyA=0 polyA=0
>Hs.82109_mRNA_1 gi|14250611|gb|BC008765.1|BC008765 *Homo sapiens* clone MGC:1622 IMAGE:3347793 polyA=3
>Hs.44276_mRNA_2 gi|12654896|gb|BC001293.1|BC001293 *Homo sapiens* clone MGC:5259 IMAGE:3458115 polyA=3
>Hs.2142_mRNA_4 gi|13325274|gb|BC004453.1|BC004453 *Homo sapiens* clone MGC:4303 IMAGE:2819400 polyA=3
>Hs.180908_contig1 AA846824|AW611680|AA846182|AA846342|AA846360 polyA=2 polyA=3
>Hs.89436_mRNA_1 gi|16507959|ref|NM_004063.2| *Homo sapiens* cadherin 17, LI cadherin (liver-intestine) (CDH17), mRNA polyA=1
>Hs.151544_mRNA_8 gi|3153107|emb|AL023657.1|HSDSHP *Homo sapiens* SH2D1A cDNA, formerly known as DSHP polyA=3
>Hs.1657_contig4 AW473119|AA164586|AI540656|AI758480|AI810941|AI978964|AI675862|AI784397|AW591562|AW514102|AI888116|AI983175|AI634735|AI669577|AI202659|AI910598|AI961352|AI565481|AI886254|AI538838|AA291749|AW571455|AI370308|AI274727|AW473925|AW514787|AI273871|AW470552|AI524356|AI888281|AW089672|AI952766|AW440601|AI654044|AW438839|AI972926 polyA=2 polyA=3
>Hs.35984_mRNA_1 gi|6049161|gb|AF133587.1|AF133587 *Homo sapiens* chromosome 22 map 22q11.2 polyA=3
>Hs.334534_mRNA_2 gi|17389403|gb|BC017742.1|BC017742 *Homo sapiens*, clone IMAGE:4391536, mRNA polyA=3
>Hs.60162_mRNA_1 gi|10437644|dbj|AK025181.1|AK025181 *Homo sapiens* cDNA: FLJ21528 fis, clone COL05977 polyA=3

As would be understood by the skilled person, detection of expression of any of the above identified sequences, or the sequences provided in Example 6 (Sequence Listing) below may be performed by the detection of expression of any appropriate portion or fragment of these sequences. Preferably, the portions are sufficiently large to contain unique sequences relative to other sequences expressed in a cell containing sample. Moreover, the skilled person would recognize that the disclosed sequences represent one strand of a double stranded molecule and that either strand may be detected as an indicator of expression of the disclosed sequences. This follows because the disclosed sequences are expressed as RNA molecules in cells which are preferably converted to cDNA molecules for ease of manipulation and detection. The resultant cDNA molecules may have the sequences of the expressed RNA as well as those of the complementary strand thereto. Thus either the RNA sequence strand or the complementary strand may be detected. Of course is it also possible to detect the expressed RNA without conversion to cDNA.

In some embodiments of the invention, the expression levels of gene sequences is measured by detection of expressed sequences in a cell containing sample as hybridizing to the following oligonucleosides, which correspond to the above sequences as indicated by the accession numbers provided.

```
>AF133587
CCCGGATCGCCATCAGTGTCATCGAGTTCAAACCCTGAGCCCTTCATTCA
CCTCTGTGAG

>BC017742
TGCCCTTGCTCTGTGTCATCTCAGTCATTTGACTTAGAAAGTGCCCTTCA
AAAGGACCCT

>BF437393
GGAGGGAGGGCTAATTATATATTTTGTTGTTCCTCTATACTTTGTTCTGT
TGTCTGCGCC
```

-continued

>AI620495
CAGTTTGGATTGTATAATAACGCCAAGCCCAGTTGTAGTCGTTTGAGTGC
AGTAATGAAA

>AK000380
AAATCAGAGTAACCCTTTCTGTATTGAGTGCAGTGTTTTTACTCTTTTC
TCATGCACAT

>BC009237
TGCCTGGCACAAAGAAGGAAGAATATAAATGATAGTTCGACTCGTCTGTG
GAAGAACTTA

>BC008765
AGTCTTTTGCTTTTGGCAAAACTCTACTTAATCCAATGGGTTTTTCCCTG
TACAGTAGAT

>BC001504
GGTTACTGTGGGTGGAATAGTGGAGGCCTTCAACTGATTAGACAAGGCCC
GCCCACATCT

>NM_019894
TAAAATGCACTGCCCTACTGTTGGTATGACTACCGTTACCTACTGTTGTC
ATTGTTATTA

>BF224381
TTCTCTTTTGGGGGCAAACACTATGTCCTTTTCTTTTTCTAGATACAGTT
AATTCCTGGA

>AL157475
AAGACCCACACCCTGTAGCAATACCAAGTGCTATTACATAATCAATGGAC
GATTTATACT

>AY033998
AGTGTTGCAAGTTTCCTTTAAAACCAACAAAGCCCACAAGTCCTGAATTT
CCCATTCTTA

>H07885
GTCACTGTCATAGCAGCTGTGATTTCACAAGGAAGGGTGCTGCAGGGGGA
CCTGGTTGAT

>NM_004496
TTTCATCCAGTGTTATGCACTTTCCACAGTTGGTGTTAGTATAGCCAGAG
GGTTTCATTA

>AA846824
GGGAAGTAGGGATTATTCGTTTAAATTCAATCGCGAGCACCAAGTCGGAC
TGGCCGGGGA

>BC017586
GGGACCAGGCCCTGGGACAGCCATGTGGCTCCAAATGACTAAATGTCAGC
TCAAAAACCA

>AA456140
TCCGTTTATGGAGGCAATTCCATATCCTTTCTTGAACGCACATTCAGCTT
ACCCCAGAGA

>NM_002283
AGAGTTAAGCCACTTCCTGGGTCTCCTTCTTATGACTGTCTATGGGTGCA
TTGCCTTCTG

>AL023657
GTGGCCTGAGTAATGCATTATGGGTGGTTTACCATTTCTTGAGGTAAAAG
CATCACATGA

>BC001639
ACACATGCATGTGTCTGTGTATGTGTGAATGTGAGAGAGACACAGCCCTC
CTTTCAGAAG

>BC015754
TCTGTAACTGCACAACCCTGGGGTTTGCTGCAGAGCTATTTCTTTCCATG
TAAAGTAGTG

>AF332224
AAACACTCTTTCCGACTCCAGAGGAGAAGCTGGCAGCTCTCTGTAAGAAA
TATGCTGATC

>BC001270
GCTTCCTCTATCGCCCAATGCAAAATCGATGAAATGGGGAGTTCTCTGGG
CCAGGCCACA

-continued

>AI147926
GTAGAATCCTCTGTTCATAATGAACAAGATGAACCAATGTGGATTAGAAA
GAAGTCCGAG

>AW298545
CTGTTTTAAAACTGAATGGCACGAAATTGTTTTCCTCAACTCGGAGATTC
CTGTATGGAG

>AI802118
AATAAATAGTAGCTCTGCTGATGATGACGTTGATAACCAAACTGTTCTGT
GGTCTTAAGT

>AI683181
CAAACAGCCCGGTCTTGATGCAGGAGAGTCTGGAAAAGGAAGAAAATGGT
TTCAGTTTCA

>M95585
AACATGGACCATCCAAATTTATGGCCGTATCAAATGGTAGCTGAAAAAAC
TATATTTGAG

>AK027147
TTGTAATCATGCCAATTCCAGATCAATAACTGCATGTCTGTTCTTTGGTA
GAAATAGCTT

>AW291189
AAAGATTATTAACCCAAATCACCTTTCTTGCTTACTCCAGATGCCTCAGC
CTCTGATATA

>AI632869
GACTTCCTTTAGGATCTCAGGCTTCTGCAGTTCTCATGACTCCTACTTTT
CATCCTAGTC

>BC006537
CTGTATATTTTGCAATAGTTACCTCAAGGCCTACTGACCAAATTGTTGTG
TTGAGATGAT

>R61469
TGTTCAAACAGACTTTAACCTCTGCATCATACTTAACCCTGCGACATGCG
TACAGTATGC

>BC009084
TGAGTCATATACATTTACTGACCACTGTTGCTTGTTGCTCACTGTGCTGC
TTTTCCATGA

>N64339
CTGAAATGTGGATGTGATTGCCTCAATAAAGCTCGTCCCCATTGCTTAAG
CCTTCAAAAA

>AI200660
ATCAAGAAAACCTAATCTTCTGACTCCCAGGCCAGGATGTTTTATTTCTC
ACATCATGTC

>AK054605
TTCATTTCCAAACATCATCTTTAAGACTCCAAGGATTTTTCCAGGCACAG
TGGCTCATAC

>NM_006115
AGTTAGAAATAGAATCTGAATTTCTAAAGGGAGATTCTGGCTTGGGAAGT
ACATGTAGGA

>X96757
CAATTTTCTTTTTACTCCCCCTCTTAAGGGGGCCTTGGAATCTATAGTAT
AGAATGAACT

>AI804745
GGGTGGAGTTTCAGTGAGAATAAACGTGTCTGCCTTTGTGTGTGTGTATA
TATACAGAGA

>AJ000388
CTCGCTCATTTTTTACCATGTTTTCCAGTCTGTTTAACTTCTGCAGTGCC
TTCACTACAC

>BC008764
CTTTGGGCCGAGCACTGAATGTCTTGTACTTTAAAAAAATGTTTCTGAGA
CCTCTTTCTA

>AI309080
CTGGACCCTTGGAGCAGTGTTGTGTGAACTTGCCTAGAACTCTGCCTTCT
CCGTTGTCAA

-continued

>AA865917
CCACCTCCTTCGACCTCCACTGCGCCCCACCTCCCTGCCTGTGTGTGTTA
TTTCAAAGGA

>AA946776
TCTGGCTGGTGGCCTGCGCGAGGGTGCAGTCTTACTTAAAAGACTTTCAG
TTAATTCTCA

>AF104032
AGATGCTGTCGGCACCATGTTTATTTATTTCCAGTGGTCATGCTCAGCCT
TGCTGCTCTG

>AW194680
TCCTTCCTCTTCGGTGAATGCAGGTTATTTAAACTTTGGGAAATGTACTT
TTAGTCTGTC

>BC001293
GTCCTGTCCCTGTCTGGGAGTTGTGTTATTTAAAGATATTCTGTATGTTG
TATCTTTTGC

>BE962007
ATTATATTTCAGGTGTCCTGAACAGGTCACTAGACTCTACATTGGGCAGC
CTTTAAATAT

>BI493248
AGGAATGGTACTACCGTTCCAGATTTTCTGTAATTGCTTCTGCAAAGTAA
TAGGCTTCTT

>AF283645
CTGTACCCAAAGGATGCCAGAATACTAGTATTTTTATTTATCGTAAACAT
CCACGAGTGC

>AI669760
ATTGCCCCCCTAACCAATCATGCAAACTTTTCCCCCCCTGGGGTAATTCA
CCAGTTAAAA

>BC001492
CCCACAGTATTTAATGCCCTGTCAGTCCCTTCTAGTCTGACTCAATGGTA
ACTTGCTGTA

>BC004453
AAAACCAACTCTCTACTACACAGGCCTGATAACTCTGTACGAGGCTTCTC
TAACCCCTAG

>BC010626
CTCAGACTGGGCTCCACACTCTTGGGCTTCAGTCTGCCCATCTGCTGAAT
GGAGACAGCA

>BC013117
CCTAATGGGGATTCCTCTGGTTGTTCACTGCCAAAACTGTGGCATTTTCA
TTACAGGAGA

>BC011949
CACTCACAATTGTTGACTAAAATGCTGCCTTTAAAACATAGGAAAGTAGA
ATGGTTGAGT

>AW083022
CTTTGAAGGGCTGCTGCACATTGTTGAATCCATCGACCTTTAGCTGCAAT
GGGATCTCTA

>R08175
TGCCTCATCGATATTATAGGGGTCCATCACAACCCAACTGTGTGGCCGGA
TCCTGAGTCT

>NM_000065
AAAACAGACAAAAGCCTTTGCCTTCATGAAGCATACATTCATTCAGGGGT
AGACACACAA

>AK025181
TAACAAACAAAGGCAGTAGCTCATCACTTGGGTAGCAGGTACCCATTTTA
GGACCCTACA

>NM_003914
ATATCAGAAGTGCCAATAATCGTCATAGGCTTCTGCACGTTGGATCAACT
AATGTTGTTT

>AI123582
ATCATAGCCCAACCATGTGAGAAGAAGGAGAAGGCCCCCCTTTCTTCATT
AATCTGAAAA

-continued

>BC004331
GCAGACCATTCTATCATACCTGGCAGGGCTTCTGTTTTATTTTGTAGGCT
GGATGCTACC

>AI341378
ACTACAAGCCTCTTGTTTTTCACCAAAACCCTACATCTCAGGCTTACTAA
TTTTTGTGAT

>NM_004063
GCCATGCATACATGCTGCGCATGTTTTCTTCATTCGTATGTTAGTAAAGT
TTTGGTTATT

>BC012926
CACCTATTTATTTTACCTCTTTCCCAAACCTGGAGCATTTATGCCTAGGC
TTGTCAAGAA

>AL110274
GTGGACATAGCCACTAACCAACTAGTTACCTTTGGACTGCAACAAAAAAT
GTGAAAATGA

>AW473119
ACTTGTAAACCTCTTTTGCACTTTGAAAAAGAATCCAGCGGGATGCTCGA
GCACCTGTAA

>AI685931
AATTCTCTATAAACGGTTCACCAGCAAACCACCAATACATTCCATTGTTT
GCCTAGAGAG

>BF592799
AATGGCCCATGCATGCTGTTTGCAGCAGTCAATTGAGTTGAATTAGAATT
CCAACCATAC

>BC000045
GAGCTCAGTACTTGCCCTGTGAAAATCCCAGAAGCCCCCGCTGTCAATGT
TCCCCATCCA

>BC015582
ATGAAGCGGAATTAGGCTCCCGAGCTAAGGGACTCGCCTAGGGTCTCACA
GTGAGTAGGA

>M60502
AGTGGCTATATCAACATCAGGGCTAGCACATCTTTCTCTATTATCCTTCT
ATTGGAATTC

The invention also provides a second group of 90 gene sequences from which about 5 to 49 may be used in the practice of the invention. The about 5 to 49 gene sequences may be used along with the determination of expression levels of additional sequences so long as the expression levels of gene sequences from the set of 90 are used in classifying. A non-limiting example of such embodiments of the invention is where the expression of about 5 to 49 of the 90 gene sequences is measured along with the expression levels of a plurality of other sequences, such as by use of a microarray based platform used to perform the invention. Where those other expression levels are not used in classification, they may be considered the results of “excess” transcribed sequences and not critical to the practice of the invention. Alternatively, and where those other expression levels are used in classification, they are within the scope of the invention, where the use of the above described sequences does not necessarily exclude the use of expression levels of additional sequences.

38 members of the set of 90 are included in the first set of 74 described above. The accession numbers of these members in common between the two sets are AA456140, AA846824, AA946776, AF332224, AI620495, AI632869, AI802118, AI804745, AJ000388, AK025181, AK027147, AL157475, AW194680, AW291189, AW298545, AW473119, BC000045, BC001293, BC001504, BC004453, BC006537, BC008765, BC009084, BC011949, BC012926, BC013117, BC015754, BE962007, BF224381, BF437393, BI493248, M60502, NM_000065, NM_003914, NM_004063, NM 004496, NM 006115, and R61469.

mRNA sequences corresponding to members of the set of 90 that are not present in the set of 74 gene sequences are also provided in Example 6 (Sequence Listing) along with additional identifying information. The listing of the identifying information for these 52 unique members by accession numbers, as well as corresponding oligonucleotide sequences which may be used in the practice of the invention, is provided by the following.

>R15881
ACTTCTGGTGATGATAAAAATGGTTTTATCACCCAGATGTGAAAGAAGCT
GCCTGTTTAC

>AI041545
GTGGTTCTGTAAAAACGCAGAGGAAAAGAGCCAGAAGGTTTCTGTTTAAT
GCATCTTGCC

>NM_024423
TTTATAAGGAAGCAGCTGTCTAAAATGCAGTGGGGTTTGTTTTGCAATGT
TTTAAACAGA

>AB038160
CTTATGAAGCTGGCCGGGCCACTCACGTTCAATGGTACATCTGGGTCTCT
ATGTGGTTCT

>AK026790
GTGAGCCAGCATTTCCCATAGCTAACCCTATTCTCTTAGTCTTTCAAAAT
GTAGAATGGG

>BC012727
CTTTACACCTGATAAAATATTTTGCGAAGAGAGGTGTTCTTTTTCCTTAC
TGGTGCTGAA

>BC016451
GCATACATCTCATCCACAGGGGAAGATAAAGATGGTCACACAAACAGTTT
CCATAAAGAT

>H09748
TGAGTTCAGCATGTGTCTGTCCATTTCATTTGTACGCTTGTTCAAAACCA
AGTTTGTTCT

>NM_006142
AAGACCGAGACTGAGGGAAAGCATGTCTGCTGGGTGTGACCATGTTTCCT
CTCAATAAAG

>AF191770
GGCATCTGGCCCCTGGTAGCCAGCTCTCCAGAATTACTTGTAGGTAATTC
CTCTCTTCAT

>NM_006378
TGGATGTTTGTGCGCGTGTGTGGACAGTCTTATCTTCCAGCATGATAGGA
TTTGACCATT

>BC006819
TCCTGGCAGAGCCATGGTCCCAGGCTTCCCAAAAGTGTTTGTGGCAATTA
TTCCCCTAGG

>X79676
TTTGATGATAGCAGACATTGTTACAAGGACATGGTGAGTCTATTTTTAAT
GCACCAATCT

>BC006811
TTCTTCCAGTTGCACTATTCTGAGGGAAAATCTGACACCTAAGAAATTTA
CTGTGAAAAA

>NM_000198
GAACAATTGTGGTCTCTCTTAACTTGAGGTTCTCTTTTGACTAATAGAGC
TCCATTTCCC

>AF301598
GTTAAGTGTGGCCAAGCGCACGGCGGCAAGTTTTCAAGCACTGAGTTTCT
ATTCCAAGAT

>NM_002847
CGGCCTACTGAGCGGACAGAATGATGCCAAAATATTGCTTATGTCTCTAC
ATGGTATTGT

-continued

>NM_004062
CAGGGTGTTTGCCCAATAATAAAGCCCCAGAGAACTGGGCTGGGCCCTAT
GGGATTGGTA

>AW118445
TGTACAGTTTGGTTGTTGCTGTAAATATGGTAGCGTTTTGTTGTTGTTGT
TTTTTCATGC

>BC002551
TACCAAACTGGGACTCACAGCTTTATTGGGCTTTCTTTGTGTCTTGTGTG
TTTCTTTTAT

>AA765597
CATTGAGGTTTGGATGGTGGCAGGTAAAACAGAAAGGCAAGATGTCATCT
GACATTAGGC

>AL137761
AGTTCAGCACTGTGGTTATCATTGGTGATGCCAGAAAACATTAGTAGACT
TAGACAATTG

>X78202
TAAAATTTCTTGATTGTGACTATGTGGTCATATGCCCGTGTTTGTCACTT
ACAAAAATGT

>AK025615
AGCCATCTGGTGTGAAGAACTCTATATTTGTATGTTGAGAGGGCATGGAA
TAATTGTATT

>BC001665
CTTATTGTCACTGGTTAAGAACTTGGCGAGATTGAAGGGCTTTTGTTATT
GTTGTTGGAT

>AI985118
CTTTCTAGTGAGCTAACCGTAACAGAGAGCCTACAGGATACACGTGAGAT
AATGTCACGT

>AL039118
TTGTCTTAAAATTTCTTGATTGTGATACTGTGGTCATATGCCCGTGTTTG
TCACTTACAA

>AA782845
CCTGGGGGAAAGGGGCATTCATGACCTGAACTTTTTAGCAAATTATTATT
CTCAGTTTCC

>BC016340
TTCATTAACAGTACTAAGTGGAAGGGATCTGCAGATTCCAAATTGGAATA
AGCTCTATCA

>AA745593
CCAATGCAGAAGAGTATTAAGAAAGATGCTCAAGTCCCATGGCACAGAGC
AAGGCGGGCA

>NM_004967
CAAGGCTACGATGGCTATGATGGTCAGAATTACTACCACCACCAGTGAAG
CTCCAGCCTG

>BF510316
AGCTCACAGCTGGACAGGTGTTGTATATAGAGTGGAATCTCTTGGATGCA
GCTTCAAGAA

>AA993639
TCCAAAGTAGAAAGGGTTCTTTTAGAAAACTTGAAGAATGTGCCTCCTCT
TAGCATCTGT

>AV656862
GATGCATTTTTCAGTCCCTTTTCAGAGCAAATGCTTTTGCAATGGTAGTA
ATGTTTAGTT

>X69699
CCTGTGGGGCTTCTCTCCTTGATGCTTCTTTCTTTTTTTAAAGACAACCT
GCCATTACCA

>BC013282
TTGCACTAAGTCATGCTGTTTCCTCAAAGAAGCTTTGTTTTTTGTTAACG
TATTACTCAG

>AI457360
CTGGATCCCAGGCCCTGGCACCCCTCAGGAAATACAAGAAAAAGAATATT
CACATCTGTT

-continued

>AW445220
TTAGAGGGGCCACCTATCAACTCATCAGTGTTCAAAGAATATGCTGGGAG
CATGGGTGAG

>AF038191
GGCCCATTTATGTCCCTCATGTCTCTAGATTTTCTCGTCACCCAGCCTCA
AAAATATATG

>X05615
TCCCCAAAAACCTCACCCGAGGCTGCCCACTATGGTCATCTTTTTCTCTA
AAATAGTTAC

>BC005364
GAAATTCCTCACACCTTGCACCTTCCCTACTTTTCTGAATTGCTATGACT
ACTCCTTGTT

>AK025701
TGTCTGTCCACCACGAGATGGGAGGAGGAGAAAAAGCGGTACGATGCCTT
CCTGACCTCA

>BF446419
GTCTTATCTCTCAGGGGGGGTTTAAGTGCCGTTTGCAATAATGTCGTCTT
ATTTATTTAG

>AK025470
CCGAGTAGTATGGGTCTCTGTGTGAGAAACCAGGAGATATTTTCATCTTG
TTCGGAAATA

>BE552004
TTGTGCAAAAGTCCCACAACCTTTCTGGATTGATAGTTTGTGGTGAAATA
AACAATTTTA

>H05388
TCCAGTATTCTGCAGGGCCAGTCAGTTGTACAGAAGTTGGAATATTCTGT
TCCAGAATTA

>NM_033229
GTCTCGAACAGCGGTTGTTTTTACTTTATTTATCTTAGGCCCTCAGCTCC
CTGACGTCCT

>BC010437
AGTGAATCTTTTCCTCTTGGTAGCATCAACACTGGGGATAAATCAGAACC
ATTCTGTGGA

>AI952953
TGAGAGCCCAGAACAAGAAGGAGCAGAAGGGCACTTTGACCTTCATTATT
ATGAAAATCA

>R45389
GGAAGAACTGATGCTTGCTGCTAACTAAAGTTTTGGATGTATCGATTTAG
AGAACCAATT

>NM_001337
GAATGAGAGAATAAGTCATGTTCCTTCAAGATCATGTACCCCAATTTACT
TGCCATTACT

>AI499593
TACGGAAAGGAAACAGGTTATACTCTTAGATTTAAAAAGTGAAAGAAACT
GCAGGCGCCT

In some embodiments of the invention, the expression levels of gene sequences is measured by detection of expressed sequences in a cell containing sample as hybridizing to the above oligonucleotides, which correspond to sequences in Example 6 (Sequence Listing) as indicated by the accession numbers provided.

In additional embodiments, the invention provides for use of any number of the gene sequences of the set of 74 or the set of 90 in the methods of the invention. Thus anywhere from 1 to all of the 49 gene sequences used in the invention may be from either or both of the above sets. So from one, two, three, four, or five, or more of the about 5 to 49 sequences may be from the set of 74 or the set of 90. Similarly, and where from 10 to 49 sequences are used, six, seven, eight, nine, or ten of the sequences may be from one of these sets.

As used herein, a "tumor sample" or "tumor containing sample" or "tumor cell containing sample" or variations thereof, refer to cell containing samples of tissue or fluid isolated from an individual suspected of being afflicted with, or at risk of developing, cancer. The samples may contain tumor cells which may be isolated by known methods or other appropriate methods as deemed desirable by the skilled practitioner. These include, but are not limited to, microdissection, laser capture microdissection (LCM), or laser microdissection (LMD) before use in the instant invention. Alternatively, undissected cells within a "section" of tissue may be used. Non-limiting examples of such samples include primary isolates (in contrast to cultured cells) and may be collected by any non-invasive or minimally invasive means, including, but not limited to, ductal lavage, fine needle aspiration, needle biopsy, the devices and methods described in U.S. Pat. No. 6,328,709, or any other suitable means recognized in the art. Alternatively, the sample may be collected by an invasive method, including, but not limited to, surgical biopsy.

The detection and measurement of transcribed sequences may be accomplished by a variety of means known in the art or as deemed appropriate by the skilled practitioner. Essentially, any assay method may be used as long as the assay reflects, quantitatively or qualitatively, expression of the transcribed sequence being detected.

The ability to classify tumor samples is provided by the recognition of the relevance of the level of expression of the gene sequences (whether randomly selected or specific) and not by the form of the assay used to determine the actual level of expression. An assay of the invention may utilize any identifying feature of a individual gene sequence as disclosed herein as long as the assay reflects, quantitatively or qualitatively, expression of the gene in the "transcriptome" (the transcribed fraction of genes in a genome) or the "proteome" (the translated fraction of expressed genes in a genome). Additional assays include those based on the detection of polypeptide fragments of the relevant member or members of the proteome. Non-limiting examples of the latter include detection of proteolytic fragments found in a biological fluid, such as blood or serum. Identifying features include, but are not limited to, unique nucleic acid sequences used to encode (DNA), or express (RNA), said gene or epitopes specific to, or activities of, a protein encoded by a gene sequence.

Additional means include detection of nucleic acid amplification as indicative of increased expression levels and nucleic acid inactivation, deletion, or methylation, as indicative of decreased expression levels. Stated differently, the invention may be practiced by assaying one or more aspect of the DNA template(s) underlying the expression of each gene sequence, of the RNA used as an intermediate to express the sequence, or of the proteinaceous product expressed by the sequence, as well as proteolytic fragments of such products. As such, the detection of the presence of, amount of, stability of, or degradation (including rate) of, such DNA, RNA and proteinaceous molecules may be used in the practice of the invention.

In some embodiments, all or part of a gene sequence may be amplified and detected by methods such as the polymerase chain reaction (PCR) and variations thereof, such as, but not limited to, quantitative PCR (Q-PCR), reverse transcription PCR (RT-PCR), and real-time PCR (including as a means of measuring the initial amounts of mRNA copies for each sequence in a sample), optionally real-time RT-PCR or real-time Q-PCR. Such methods would utilize one or two primers that are complementary to portions of a gene sequence, where the primers are used to prime nucleic acid synthesis. The newly synthesized nucleic acids are optionally labeled and may be detected directly or by hybridization to a polynucleotide of the invention. The newly synthesized nucleic acids may be contacted with polynucleotides (containing gene sequences) of the invention under conditions which allow for their hybridization. Additional methods to detect the expression of expressed nucleic acids include RNAse protection assays, including liquid phase hybridizations, and in situ hybridization of cells.

Alternatively, the expression of gene sequences in FFPE samples may be detected as disclosed in U.S. applications 60/504,087, filed Sep. 19, 2003, 10/727,100, filed Dec. 2, 2003, and U.S. Pat. No. 10,773,761, filed Feb. 6, 2004 (all three of which are hereby incorporated by reference as if fully set forth). Briefly, the expression of all or part of an expressed gene sequence or transcript may be detected by use of hybridization mediated detection (such as, but not limited to, microarray, bead, or particle based technology) or quantitative PCR mediated detection (such as, but not limited to, real time PCR and reverse transcriptase PCR) as non-limiting examples. The expression of all or part of an expressed polypeptide may be detected by use of immunohistochemistry techniques or other antibody mediated detection (such as, but not limited to, use of labeled antibodies that bind specifically to at least part of the polypeptide relative to other polypeptides) as non-limiting examples. Additional means for analysis of gene expression are available, including detection of expression within an assay for global, or near global, gene expression in a sample (e.g. as part of a gene expression profiling analysis such as on a microarray). Non-limiting examples linear RNA amplification and those described in U.S. patent application Ser. No. 10/062,857 (filed on Oct. 25, 2001), as well as U.S. Provisional Patent Applications 60/298,847 (filed Jun. 15, 2001) and 60/257,801 (filed Dec. 22, 2000), all of which are hereby incorporated by reference in their entireties as if fully set forth.

In embodiments using a nucleic acid based assay to determine expression includes immobilization of one or more gene sequences on a solid support, including, but not limited to, a solid substrate as an array or to beads or bead based technology as known in the art. Alternatively, solution based expression assays known in the art may also be used. The immobilized gene sequence(s) may be in the form of polynucleotides that are unique or otherwise specific to the gene(s) such that the polynucleotides would be capable of hybridizing to the DNA or RNA of said gene(s). These polynucleotides may be the full length of the gene(s) or be short sequences of the genes (up to one nucleotide shorter than the full length sequence known in the art by deletion from the 5' or 3' end of the sequence) that are optionally minimally interrupted (such as by mismatches or inserted non-complementary basepairs) such that hybridization with a DNA or RNA corresponding to the genes is not affected. In some embodiments, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal. Thus the practice of the present invention is unaffected by the presence of minor mismatches between the disclosed sequences and those expressed by cells of a subject's sample. A non-limiting example of the existence of such mismatches are seen in cases of sequence polymorphisms between individuals of a species, such as individual human patients within *Homo sapiens*.

As will be appreciated by those skilled in the art, some gene sequences include 3' poly A (or poly T on the complementary strand) stretches that do not contribute to the uniqueness of the disclosed sequences. The invention may thus be practiced with gene sequences lacking the 3' poly A (or poly T) stretches. The uniqueness of the disclosed sequences refers to the portions or entireties of the sequences which are found only in nucleic acids, including unique sequences found at the 3' untranslated portion thereof. Some unique sequences for the practice of the invention are those which contribute to the consensus sequences for the genes such that the unique sequences will be useful in detecting expression in a variety of individuals rather than being specific for a polymorphism present in some individuals. Alternatively, sequences unique to an individual or a subpopulation may be used. The unique sequences may be the lengths of polynucleotides of the invention as described herein.

In additional embodiments of the invention, polynucleotides having sequences present in the 3' untranslated and/or non-coding regions of gene sequences are used to detect expression levels in cell containing samples of the invention. Such polynucleotides may optionally contain sequences found in the 3' portions of the coding regions of gene sequences. Polynucleotides containing a combination of sequences from the coding and 3' non-coding regions preferably have the sequences arranged contiguously, with no intervening heterologous sequence(s).

Alternatively, the invention may be practiced with polynucleotides having sequences present in the 5' untranslated and/or non-coding regions of gene sequences to detect the level of expression in cells and samples of the invention. Such polynucleotides may optionally contain sequences found in the 5' portions of the coding regions. Polynucleotides containing a combination of sequences from the coding and 5' non-coding regions may have the sequences arranged contiguously, with no intervening heterologous sequence(s). The invention may also be practiced with sequences present in the coding regions of gene sequences.

The polynucleotides of some embodiments contain sequences from 3' or 5' untranslated and/or non-coding regions of at least about 16, at least about 18, at least about 20, at least about 22, at least about 24, at least about 26, at least about 28, at least about 30, at least about 32, at least about 34, at least about 36, at least about 38, at least about 40, at least about 42, at least about 44, or at least about 46 consecutive nucleotides. The term "about" as used in the previous sentence refers to an increase or decrease of 1 from the stated numerical value. Other embodiments use polynucleotides containing sequences of at least or about 50, at least or about 100, at least about or 150, at least or about 200, at least or about 250, at least or about 300, at least or about 350, or at least or about 400 consecutive nucleotides. The term "about" as used in the preceding sentence refers to an increase or decrease of 10% from the stated numerical value.

Sequences from the 3' or 5' end of gene coding regions as found in polynucleotides of the invention are of the same lengths as those described above, except that they would naturally be limited by the length of the coding region. The 3' end of a coding region may include sequences up to the 3' half of the coding region. Conversely, the 5' end of a coding region may include sequences up the 5' half of the coding region. Of course the above described sequences, or the coding regions and polynucleotides containing portions thereof, may be used in their entireties.

In another embodiment of the invention, polynucleotides containing deletions of nucleotides from the 5' and/or 3' end of gene sequences may be used. The deletions are preferably of 1-5, 5-10, 10-15, 15-20, 20-25, 25-30, 30-35, 35-40, 40-45, 45-50, 50-60, 60-70, 70-80, 80-90, 90-100, 100-125, 125-150, 150-175, or 175-200 nucleotides from the 5' and/or 3' end, although the extent of the deletions would naturally be limited by the length of the sequences and the need to be able to use the polynucleotides for the detection of expression levels.

Other polynucleotides of the invention from the 3' end of gene sequences include those of primers and optional probes for quantitative PCR. Preferably, the primers and probes are those which amplify a region less than about 750, less than about 700, less than about 650, less than about 6000, less than about 550, less than about 500, less than about 450, less than about 400, less than about 350, less than about 300, less than about 250, less than about 200, less than about 150, less than about 100, or less than about 50 nucleotides from the from the polyadenylation signal or polyadenylation site of a gene or expressed sequence. The size of a PCR amplicon of the invention may be of any size, including at least or about 50, at least or about 100, at least about or 150, at least or about 200, at least or about 250, at least or about 300, at least or about 350, or at least or about 400 consecutive nucleotides, all with inclusion of the portion complementary to the PCR primers used.

Other polynucleotides for use in the practice of the invention include those that have sufficient homology to gene sequences to detect their expression by use of hybridization techniques. Such polynucleotides preferably have about or 95%, about or 96%, about or 97%, about or 98%, or about or 99% identity with the gene sequences to be used. Identity is determined using the BLAST algorithm, as described above. The other polynucleotides for use in the practice of the invention may also be described on the basis of the ability to hybridize to polynucleotides of the invention under stringent conditions of about 30% v/v to about 50% formamide and from about 0.01M to about 0.15M salt for hybridization and from about 0.01M to about 0.15M salt for wash conditions at about 55 to about 65° C. or higher, or conditions equivalent thereto.

In a further embodiment of the invention, a population of single stranded nucleic acid molecules comprising one or both strands of a human gene sequence is provided as a probe such that at least a portion of said population may be hybridized to one or both strands of a nucleic acid molecule quantitatively amplified from RNA of a cell or sample of the invention. The population may be only the antisense strand of a human gene sequence such that a sense strand of a molecule from, or amplified from, a cell may be hybridized to a portion of said population. The population preferably comprises a sufficiently excess amount of said one or both strands of a human gene sequence in comparison to the amount of expressed (or amplified) nucleic acid molecules containing a complementary gene sequence.

The invention further provides a method of classifying a human tumor sample by detecting the expression levels of about 5 to 49 transcribed sequences in a nucleic acid or cell containing sample obtained from a human subject, and classifying the sample as containing a tumor cell of a tumor type found in humans to the exclusion of one or more other human tumor types. In some embodiments, the method may be used to classify a sample as being, or having cells of one of the 53 tumor types listed above to the exclusion of one or more of the other 52. In other embodiments, the method is used to classify a sample as being, or having cells of, one of the 34 tumor types listed above to the exclusion of one or more of the other 33 tumor types. In further embodiments, the method is used to classify a sample as being, or having cells of, one of the 39 tumor types listed above to the exclusion of one or more of the other 38 tumor types.

The invention also provides a method for classifying tumor samples as being one of a subset of the possible tumor types described herein by detecting the expression levels of 50 or more transcribed sequences in a nucleic acid containing tumor sample obtained from a human subject, and classifying the sample as being one of a number of tumor types found in humans to the exclusion of one or more other human tumor types. In some embodiments of the invention, the number of other tumor types is from 1 to about 3, more preferably from 1 to about 5, from 1 to about 7, or from 1 to about 9 or about 10. In other embodiments, the number of tumor types are all of the same tissue or organ origin such as those listed above. This aspect of the invention is related to the above discussion of FIG. 10 and of trading off specificity in favor of increased confidence, and may be advantageously applied to situations where the classification of a sample as a single tumor type is at a level of accuracy or performance that can be improved by classifying the sample as one of a subset of possible tumor types.

In additional embodiments, the invention may be practiced by analyzing gene expression from single cells or homogenous cell populations which have been dissected away from, or otherwise isolated or purified from, contaminating cells of a sample as present in a simple biopsy. One advantage provided by these embodiments is that contaminating, non-tumor cells (such as infiltrating lymphocytes or other immune system cells) may be removed as so be absent from affecting the genes identified or the subsequent analysis of gene expression levels as provided herein. Such contamination is present where a biopsy is used to generate gene expression profiles.

In further embodiments of the invention utilizing Q-PCR or reverse transcriptase Q-PCR as the assay platform, the expression levels of gene sequences of the invention may be compared to expression levels of reference genes in the same sample or a ratio of expression levels may be used. This provides a means to "normalize" the expression data for comparison of data on a plurality of known tumor types and a cell containing sample to be assayed. While a variety of reference genes may be used, the invention may also be practiced with the use of S particular reference gene sequences that were identified for use with the set of 39 tumor types. Moreover, the Q-PCR may be performed in whole or in part with use of a multiplex format.

mRNA sequences corresponding to the 8 reference sequences are provided in Example 6 (Sequence Listing) along with additional identifying information. The listing of the identifying information, including accession numbers and other information, is provided by the following.

>Hs.77031_mRNA_1 gi|16741772|gb|BC016680.1|BC016680 *Homo sapiens* clone MGC:21349 IMAGE:4338754 polyA=3

>Hs.77541_mRNA_1 gi|12804364|gb|BC003043.1|BC003043 *Homo sapiens* clone MGC:4370 IMAGE:2822973 polyA=3

-continued

>Hs.7001_mRNA_1 gi|6808256|emb|AL137727.1|HSM802274 *Homo sapiens* mRNA; cDNA DKFZp434M0519 (from clone DKFZp434M0519); partial cds polyA=3
>Hs.302144_mRNA_1 gi|11493400|gb|AF130047.1|AF130047 *Homo sapiens* clone FLB3020 polyA=0
>Hs.26510_mRNA_2 gi|11345385|gb|AF308803.1|AF308803 *Homo sapiens* chromosome 15 map 15q26 polyA=3
>Hs.324709_mRNA_2 gi|12655026|gb|BC001361.1|BC001361 *Homo sapiens* clone MGC:2474 IMAGE:3050694 polyA=2
>Hs.65756_mRNA_3 gi|3641494|gb|AF035154.1|AF035154 *Homo sapiens* chromosome 16 map 16p13.3 polyA=3
>Hs.165743_mRNA_2 gi|13543889|gb|BC006091.1|BC006091 *Homo sapiens* clone MGC:12673 IMAGE:3677524 polyA=3

Detection of expression of any of the above reference sequences may be by the same or different methodology as for the other gene sequences described above. In some embodiments of the invention, the expression levels of gene sequences is measured by detection of expressed sequences in a cell containing sample as hybridizing to the following oligonucleotides, which correspond to the above sequences as indicated by the accession numbers provided.

>BC006091
TCATCTTCACCAAACCAGTCCGAGGGGTCGAAGCCAGACACGAGAGGAAG
AGGGTCCTGG

>BC003043
CTCTGCTCCTGCTCCTGCCTGCATGTTCTCTCTGTTGTTGGAGCCTGGAG
CCTTGCTCTC

>AF130047
TGCTCCCGGCTGTCCTCCTCTCCTCTTCCCTAGTGAGTGGTTAATGAGTG
TTAATGCCTA

>AF035154
CCCCATCTCTAAAACCAGTAAATCAGCCAGCGAATACCCGGAAGCAAGAT
GCACAGGCGG

>BC001361
CCAGAAACAAGGAAGAGGAAAGACAAAGGGAAGGGACGGGAGCCCTGGAG
AAGCCCGACC

>AF308803
AAGTACAACCCATGCTGCTAAGATGCGAGCAGGAAGAGGCATCCTTTGCT
AAATCCTGTT

>BC016680
ACCTCACCCCTGCCCGGCCCAAGCTCTACTTGTGTACAGTGTATATTGTA
TAATAGACAA

>AL137727
TTCCCTTAATTCCTCCTCCCGACCTTTTTTACCCCCCCAGTTGCAGTATT
TAACTGGGCT

In an additional aspect, the methods provided by the present invention may also be automated in whole or in part. This includes the embodiment of the invention in software. Non-limiting examples include processor executable instructions on one or more computer readable storage devices wherein said instructions direct the classification of tumor samples based upon gene expression levels as described herein. Additional processor executable instructions on one or more computer readable storage devices are contemplated wherein said instructions cause representation and/or manipulation, via a computer output device, of the process or results of a classification method.

The invention includes software and hardware embodiments wherein the gene expression data of a set of gene sequences in a plurality of known tumor types is embodied as a data set. In some embodiments, the gene expression data set is used for the practice of a method of the invention. The invention also provides computer related means and systems for performing the methods disclosed herein. In some embodiments, an apparatus for classifying a cell containing sample is provided. Such an apparatus may comprise a query input configured to receive a query storage configured to store a gene expression data set, as described herein, received from a query input; and a module for accessing and using data from the storage in a classification algorithm as described herein. The apparatus may further comprise a string storage for the results of the classification algorithm, optionally with a module for accessing and using data from the string storage in an output algorithm as described herein.

The steps of a method, process, or algorithm described in connection with the embodiments disclosed herein may be embodied directly in hardware, in a software module executed by a processor, or in a combination of the two. The various steps or acts in a method or process may be performed in the order shown, or may be performed in another order. Additionally, one or more process or method steps may be omitted or one or more process or method steps may be added to the methods and processes. An additional step, block, or action may be added in the beginning, end, or intervening existing elements of the methods and processes.

A further aspect of the invention provides for the use of the present invention in relation to clinical activities. In some embodiments, the determination or measurement of gene expression as described herein is performed as part of providing medical care to a patient, including the providing of diagnostic services in support of providing medical care. Thus the invention includes a method in the medical care of a patient, the method comprising determining or measuring expression levels of gene sequences in a cell containing sample obtained from a patient as described herein. The method may further comprise the classifying of the sample, based on the determination/measurement, as including a tumor cell of a tumor type or tissue origin in a manner as described herein. The determination and/or classification may be for use in relation to any aspect or embodiment of the invention as described herein.

The determination or measurement of expression levels may be preceded by a variety of related actions. In some embodiments, the measurement is preceded by a determination or diagnosis of a human subject as in need of said measurement. The measurement may be preceded by a determination of a need for the measurement, such as that by a medical doctor, nurse or other health care provider or professional, or those working under their instruction, or personnel of a health insurance or maintenance organization in approving the performance of the measurement as a basis to request reimbursement or payment for the performance.

The measurement may also be preceded by preparatory acts necessary to the actual measuring. Non-limiting examples include the actual obtaining of a cell containing sample from a human subject; or receipt of a cell containing sample; or sectioning a cell containing sample; or isolating cells from a cell containing sample; or obtaining RNA from cells of a cell containing sample; or reverse transcribing RNA from cells of a cell containing sample. The sample may be any as described herein for the practice of the invention.

In additional embodiments, the invention provides for a method of ordering, or receiving an order for, the performance of a method in the medical care of a patient or other method of the invention. The ordering may be made by a medical doctor, a nurse, or other health care provider, or those working under their instruction, while the receiving, directly or indirectly, may be made by any person who performs the method(s). The ordering may be by any means of communication, including communication that is written, oral, electronic, digital, analog, telephonic, in person, by facsimile, by mail, or otherwise passes through a jurisdiction within the United States.

The invention further provides methods in the processing of reimbursement or payment for a test, such as the above method in the medical care of a patient or other method of the invention. A method in the processing of reimbursement or payment may comprise indicating that 1) payment has been received, or 2) payment will be made by another payer, or 3) payment remains unpaid on paper or in a database after performance of an expression level detection, determination or measurement method of the invention. The database may be in any form, with electronic forms such as a computer implemented database included within the scope of the invention. The indicating may be in the form of a code (such as a CPT code) on paper or in the database. The "another payer" may be any person or entity beyond that to whom a previous request for reimbursement or payment was made.

Alternative, the method may comprise receiving reimbursement or payment for the technical or actual performance of the above method in the medical care of a patient; for the interpretation of the results from said method; or for any other method of the invention. Of course the invention also includes embodiments comprising instructing another person or party to receive the reimbursement or payment. The ordering may be by any communication means, including those described above. The receipt may be from any entity, including an insurance company, health maintenance organization, governmental health agency, or a patient as non-limiting examples. The payment may be in whole or in part. In the case of a patient, the payment may be in the form of a partial payment known as a co-pay.

In yet another embodiment, the method may comprise forwarding or having forwarded a reimbursement or payment request to an insurance company, health maintenance organization, governmental health agency, or to a patient for the performance of the above method in the medical care of a patient or other method of the invention. The request may be by any communication means, including those described above.

In a further embodiment, the method may comprise receiving indication of approval for payment, or denial of payment, for performance of the above method in the medical care of a patient or other method of the invention. Such an indication may come from any person or party to whom a request for reimbursement or payment was made. Non-limiting examples include an insurance company, health maintenance organization, or a governmental health agency, like Medicare or Medicaid as non-limiting examples. The indication may be by any communication means, including those described above.

An additional embodiment is where the method comprises sending a request for reimbursement for performance of the above method in the medical care of a patient or other method of the invention. Such a request may be made by any communication means, including those described above. The request may have been made to an insurance company, health maintenance organization, federal health agency, or the patient for whom the method was performed.

A further method comprises indicating the need for reimbursement or payment on a form or into a database for performance of the above method in the medical care of a patient or other method of the invention. Alternatively, the method may simply indicate the performance of the method. The database may be in any form, with electronic forms such as a computer implemented database included within the scope of the invention. The indicating may be in the form of a code (such as a CPT code) on paper or in the database.

In the above methods in the medical care of a patient or other method of the invention, the method may comprise reporting the results of the method, optionally to a health care facility, a health care provider or professional, a doctor, a nurse, or personnel working therefor. The reporting may also be directly or indirectly to the patient. The reporting may be by any means of communication, including those described above.

The invention further provides kits for the determination or measurement of gene expression levels in a cell containing sample as described herein. A kit will typically comprise one or more reagents to detect gene expression as described herein for the practice of the present invention. Non-limiting examples include polynucleotide probes or primers for the detection of expression levels, one or more enzymes used in the methods of the invention, and one or more tubes for use in the practice of the invention. In some embodiments, the kit will include an array, or solid media capable of being assembled into an array, for the detection of gene expression as described herein. In other embodiments, the kit may comprise one or more antibodies that is immunoreactive with epitopes present on a polypeptide which indicates expression of a gene sequence. In some embodiments, the antibody will be an antibody fragment.

A kit of the invention may also include instructional materials disclosing or describing the use of the kit or a primer or probe of the present invention in a method of the invention as provided herein. A kit may also include additional components to facilitate the particular application for which the kit is designed. Thus, for example, a kit may additionally contain means of detecting the label (e.g. enzyme substrates for enzymatic labels, filter sets to detect fluorescent labels, appropriate secondary labels such as a sheep anti-mouse-HRP, or the like). A kit may additionally include buffers and other reagents recognized for use in a method of the invention.

Having now generally described the invention, the same will be more readily understood through reference to the following examples which are provided by way of illustration, and are not intended to be limiting of the present invention, unless specified.

EXAMPLES

Example 1: Information Capacity of Random Gene Sets

Figure 2:
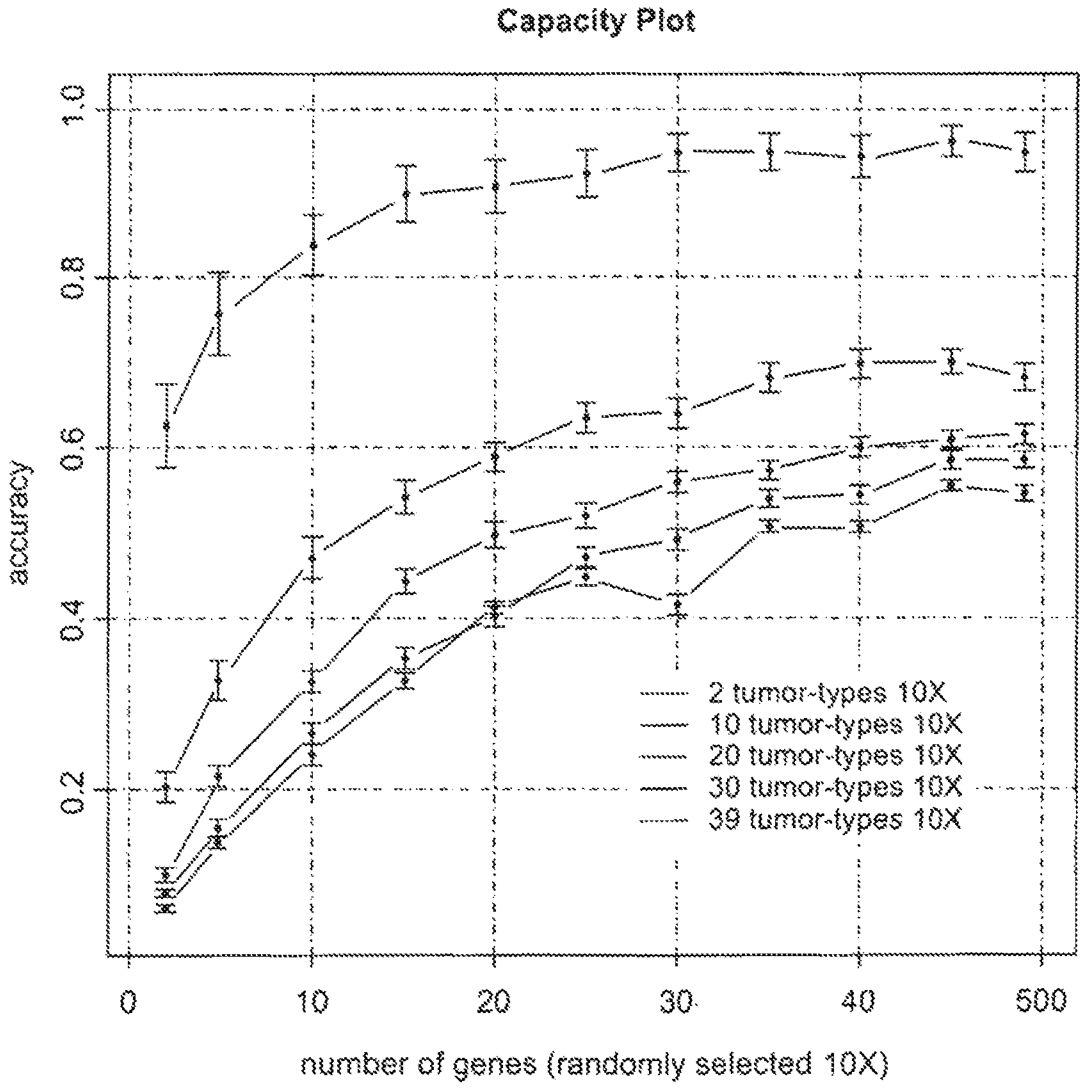
FIG. 2 shows an alternative presentation of the data used with respect to FIG. 1. A plot of numbers of gene sequences used, ranging from 5-49 (and in the x-axis), versus prediction accuracies (y-axis) for various representative numbers of tumor types is shown. The plotted lines, from top to bottom, are of the results from 2, 10, 20, 30, and 39 tumor types, respectively.
Figure 3:
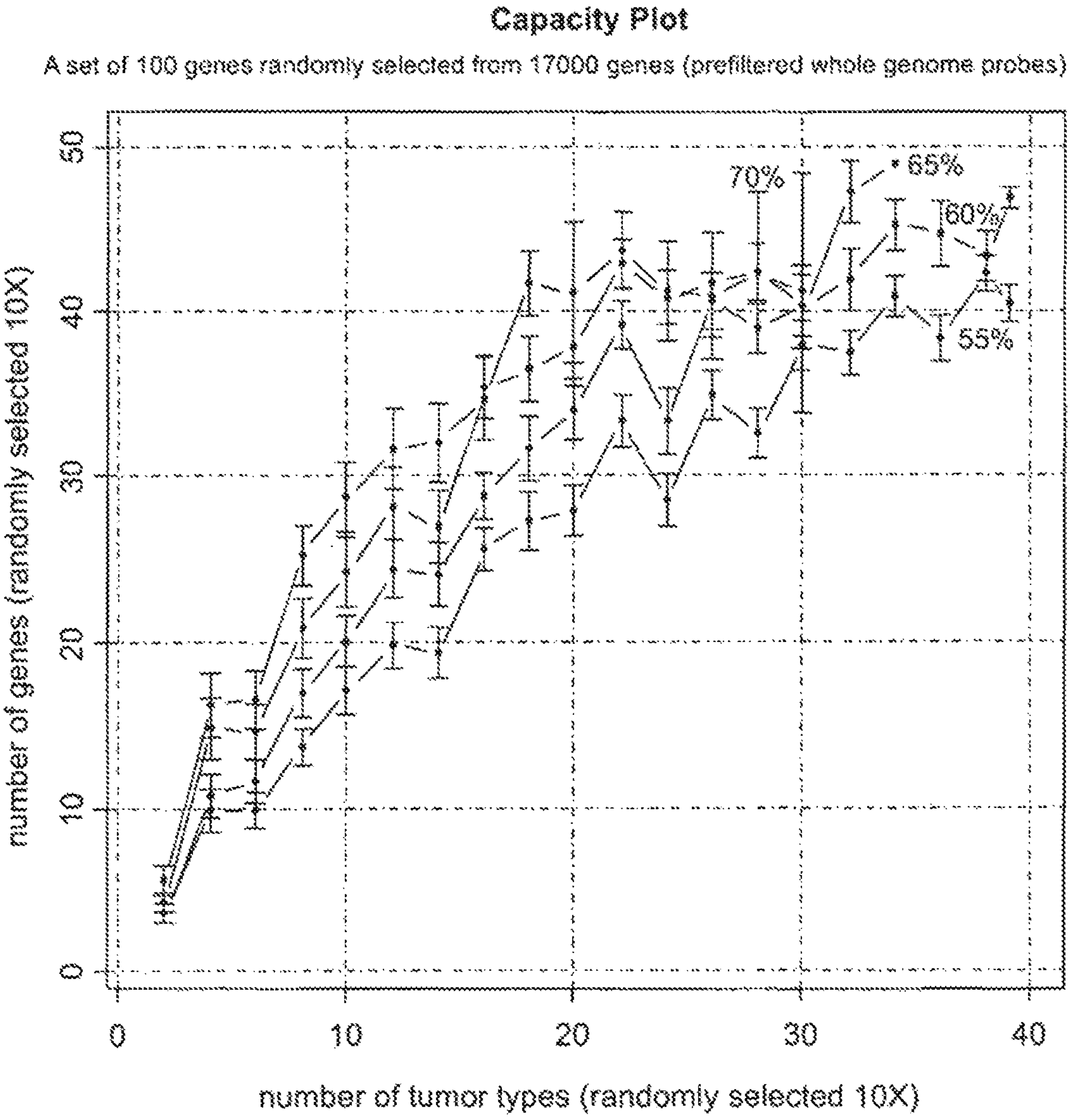
FIG. 3 provides a further analysis of the ability to use the expression levels of subsets of a set of 100 randomly selected expressed gene sequences to classify among 39 tumor types. The data used with FIGS. 1 and 2 is presented in a plot of the number of tumor types versus the number of gene sequences used at prediction accuracies from 55-70% are shown as non-limiting examples. Generally, accuracy improves with higher numbers of gene sequences.

Subsets of 100 randomly selected expressed gene sequences used to classify among 39 tumor types were tested for their ability to classify among subsets of the 39 tumor types. The expression levels of random combinations of 5, 10, 15, 20, 25, 30, 35, 40, 45, and 49 (each combination sampled 10 times) of the 100 expressed sequences were used with data from tumor types and then used to predict test random sets of tumor samples (each sampled 10 times) ranging from 2 to all 39 types. FIG. 1 shows the classification capability of various gene sets are shown relative to the number of tumor types classified. As expected, a higher number of gene sequences are needed to classify tumor types with higher accuracies. FIG. 2 shows the classification performance for various numbers of tumor types relative to the number of gene sequences used.

The GenBank accession numbers of the 100 gene sequences are AF269223, BC006286, AK025501, AJ002367, AI469140, AW013883, NM 001238, A1476350, BC006546, AI041212, BF724944, AI376951, R56211, BC006393, X13274, BC001133, N62397, BC000885, AK001588, AK057901, AF146760, AI951287, AK025604, BC007581, BC015025, R43102, AW449550, A1922539, AI684144, A1277662, BC015999, AW444656. BC011612, BC015401, BF447279, BC009956, AL050163, BC001248, BE672684, AL137353, BC001340, U45975, BE856598, BC009060, AL137728, AA713797, AL583913, AK054617, A1028262, AI753041, BG939593, AL080179, AA814915, AF131798, AI961568, BC009849, AK021603, BC012561, AI570494, BC006973, AW294857, BC004952, AK026535, AI923614, AW082090, A1005513, AF339768, AK023167, AF169693, AF076249, BC007662, BC015520, A1814187, AI565381, AW271626, AK024120, AF139065, BC014075, AM887245, AF257081, AI767898, AF070634, AF155132, X69804, U65579, NM_004933, AI655104, AW131780, AI650407, AF131774, AA814057, AJ311123, BC009702, AF264036, AL161961, AJ010857. AF106912, AK023542, AF073518, and D83032. They were indexed from 1 to 100, and representative random sets used in the invention are as follows:

For 2 genes, genes 33 and 63, genes 17 and 72, genes 64 and 21, genes 48 and 25, genes 88 and 54, genes 80 and 32, genes 24 and 99, genes 14 and 31, genes 80 and 23, and genes 18 and 34 were used as the 10 random sets.

For 5 genes, set 1, genes 27, 97, 56, 88, and 50 were used. In set 2, genes 24, 26, 35, 48, and 83 were used. In set 3, genes 46, 62, 75, 91, and 2 were used. In set 4, genes 19, 61, 34, 87, and 13 were used. In set 5, genes 56, 32, 66, 20, and 55 were used. In set 6, genes 90, 21, 6, 78, and 66 were used. In set 7, genes 73, 47, 3, 82, and 86 were used. In set 8, genes 74, 39, 13, 7, and 67 were used. In set 9, genes 34, 1, 24, 85, and 62 were used. In set 10, genes 23, 89, 15, 54, and 98 were used.

For 10 genes, set 1, genes 11, 58, 90, 40, 20, 44, 10, 78, 72, and 74 were used. In set 2, genes 79, 71, 42, 48, 93, 56, 55, 14, 92, and 52 were used. In set 3, genes 62, 53, 52, 19, 98, 26, 76, 65, 33, and 40 were used. In set 4, genes 94, 8, 16, 99, 58, 19, 97, 92, 76, and 86 were used. In set 5, genes 18, 97, 16, 94, 84, 52, 11, 24, 89, and 92 were used. In set 6, genes 12, 42, 45, 51, 2, 75, 63, 28, 13, and 58 were used. In set 7, genes 67, 98, 55, 32, 82, 42, 2, 45, 37, and 23 were used. In set 8, genes 40, 43, 69, 68, 13, 97, 35, 3, 44, and 42 were used. In set 9, genes 69, 47, 96, 80, 100, 50, 42, 26, 65, and 17 were used. In set 10, genes 83, 84, 69, 67, 19, 85, 35, 11, 70, and 64 were used.

For 15 genes, set 1, genes 98, 81, 43, 63, 18, 56, 19, 97, 47, 13, 48, 99, 75, 45, and 83 were used. In set 2, genes 5, 72, 31, 59, 81, 40, 92, 3, 23, 50, 57, 74, 62, 21, and 93 were used. In set 3, genes 11, 69, 91, 100, 38, 1, 73, 64, 90, 26, 62, 2, 37, 23, and 18 were used. In set 4, genes 76, 9, 53, 4, 11, 41, 77, 44, 87, 51, 54, 49, 43, 56, and 67 were used. In set 5, genes 55, 34, 13, 89, 52, 74, 96, 80, 48, 22, 31, 39, 43, 91, and 54 were used. In set 6, genes 59, 88, 15, 90, 4, 73, 93, 7, 10, 18, 98, 83, 43, 3, and 5 were used. Inset 7, genes 68, 91, 77, 33, 88, 94, 95, 41, 46, 27, 36, 51, 97, 7, and 2 were used. Inset 8, genes 7, 10, 78, 40, 70, 84, 55, 1, 98, 22, 99, 91, 8, 17, and 89 were used. Inset 9, genes 65, 10, 38, 8, 77, 98, 37, 43, 93, 99, 86, 16, 82, 27, and 9 were used. In set 10, genes 97, 27, 78, 38, 24, 19, 55, 47, 77, 13, 45, 25, 43, 70, and 68 were used.

For 20 genes, set 1, genes 41, 94, 38, 76, 35, 65, 92, 26, 49, 7, 85, 54, 77, 66, 98, 15, 86, 69, 70, and 67 were used. In set 2, genes 43, 87, 1, 81, 7, 14, 94, 28, 25, 55, 100, 41, 18, 47, 96, 89, 26, 53, 29, and 32 were used. In set 3, genes 48, 80, 90, 99, 50, 98, 36, 91, 6, 41, 61, 96, 74, 66, 9, 5, 16, 18, 20, and 1 were used. In set 4, genes 49, 58, 73, 24, 94, 22, 41, 52, 18, 19, 63, 91, 74, 37, 59, 95, 53, 87, 72, and 13 were used. In set 5, genes 67, 74, 2, 98, 46, 69, 5, 42, 22, 66, 60, 20, 100, 80, 24, 76, 63, 9, 39, and 15 were used. In set 6, genes 10, 74, 50, 92, 69, 68, 52, 56, 63, 71, 11, 17, 29, 64, 88, 59, 25, 94, 35, and 57 were used. In set 7, genes 97, 72, 16, 19, 14, 42, 70, 31, 29, 13, 22, 37, 95, 69, 87, 39, 18, 81, 58, and 100 were used. In set 8, genes 5, 3, 18, 91, 77, 19, 82, 31, 92, 22, 93, 45, 76, 84, 46, 100, 53, 99, 89, and 42 were used. In ret 9, genes 62, 3, 85, 37, 34, 93, 52, 40, 74, 25, 86, 57, 33, 60, 20, 77, 78, 17, 28, and 13 were used. In set 10, genes 22, 26, 23, 39, 35, 10, 43, 32, 65, 38, 54, 45, 8, 17, 90, 20, 83, 60, 6, and 58 were used.

For 25 genes, set 1, genes 21, 28, 50, 27, 8, 48, 74, 80, 38, 96, 71, 15, 89, 84, 32, 26, 55, 36, 29, 68, 13, 7, 18, 63, and 72 were used. In set 2, genes 61, 38, 59, 92, 3, 80, 33, 68, 79, 70, 44, 26, 95, 63, 85, 27, 60, 43, 75, 96, 42, 99, 58, 48, and 91 were used. In set 3, genes 75, 83, 78, 5, 99, 56, 26, 36, 57, 23, 37, 28, 88, 16, 63, 2, 72, 59, 9, 80, 52, 91, 62, 3, and 27 were used. In set 4, genes 48, 75, 84, 83, 88, 29, 13, 9, 98, 6, 31, 63, 45, 5, 51, 52, 39, 22, 100, 91, 74, 12, 94, 21, and 8 were used. In set 5, genes 79, 84, 47, 43, 26, 37, 46, 19, 85, 91, 2, 10, 81, 89, 38, 71, 17, 57, 7, 93, 31, 87, 29, 78, and 73 were used. In set 6, genes 62, 93, 83, 42, 97, 96, 78, 98, 47, 22, 67, 48, 89, 95, 24, 81, 16, 45, 8, 90, 66, 64, 2, 3, and 58 were used. Inset 7, genes 100, 34, 58, 28, 104, 35, 88, 76, 6, 30, 83, 81, 67, 36, 39, 87, 66, 45, 20, 15, 86, 56, 55, and 95 were used. In set 8, genes 17, 43, 50, 63, 47, 58, 95, 32, 79, 60, 16, 91, 86, 22, 97, 21, 9, 55, 72, 78, 77, 45, 100, 14, and 30 were used. In set 9, genes 24, 67, 60, 94, 59, 14, 70, 84, 8, 89, 63, 23, 39, 11, 81, 42, 33, 3, 12, 93, 54, 35, 78, 73, and 90 were used. In set 10, genes 11, 2, 19, 62, 13, 51, 30, 80, 81, 82, 52, 34, 67, 57, 25, 95, 93, 39, 26, 48, 44, 89, 61, 17, and 18 were used.

For 30 genes, set 1, genes 30, 97, 54, 21, 34, 9, 56, 71, 62, 14, 24, 23, 89, 61, 76, 41, 29, 67, 94, 22, 88, 4, 40, 33, 38, 78, 82, 66, 84, and 100 were used. Inset 2, genes 89, 41, 56, 43, 98, 44, 35, 26, 19, 86, 15, 67, 8, 69, 3, 76, 48, 17, 55, 31, 25, 91, 72, 36, 18, 82, 37, 50, 9, and 75 were used. In set 3, genes 28, 39, 78, 15, 65, 93, 66, 29, 88, 35, 49, 69, 50, 9, 53, 80, 81, 95, 76, 44, 48, 64, 83, 11, 70, 33, 73, 96, 56, and 92 were used. Inset 4, genes 4, 2, 19, 6, 11, 84, 94, 44, 60, 37, 29, 97, 53, 83, 98, 45, 65, 9, 85, 35, 20, 89, 10, 17, 23, 74, 70, 41, 18, and 76 were used. In set 5, genes 27, 4, 43, 1, 10, 95, 88, 74, 77, 47, 63, 81, 31, 9, 41, 100, 87, 57, 8, 79, 24, 6, 26, 20, 55, 61, 34, 42, 25, and 39 were used. Inset 6, genes 47, 67, 98, 56, 37, 44, 5, 70, 48, 12, 20, 86, 83, 89, 27, 59, 19, 54, 69, 97, 43, 71, 58, 82, 8, 50, 51, 10, 25, and 72 were used. In set 7, genes 100, 99, 37, 58, 44, 60, 39, 3, 59, 96, 50, 68, 94, 69, 83, 90, 17, 4, 5, 67, 88, 56, 29, 79, 23, 1, 38, 25, 49, and 74 were used. In set 8, genes 26, 23, 58, 47, 6, 68, 41, 31, 16, 64, 19, 75, 36, 32, 87, 2, 12, 97, 73, 21, 53, 78, 15, 94, 1, 20, 79, 81, 70, and 7 were used. In set 9, genes 61, 48, 78, 75, 12, 36, 37, 66, 91, 2, 92, 32, 8, 26, 6, 82, 14, 68, 4, 88, 39, 89, 43, 41, 40, 87, 69, 74, 42, and 9 were used. Inset 10, genes 58, 99, 60, 39, 50, 25, 22, 57, 48, 85, 24, 10, 97, 68, 36, 38, 93, 62, 52, 56, 34, 18, 32, 64, 95, 81, 74, 88, 61, and 96 were used.

For 35 genes, set 1, genes 52, 68, 22, 92, 43, 75, 20, 62, 15, 76, 99, 61, 64, 36, 12, 66, 24, 21, 31, 88, 25, 6, 93, 91, 55, 74, 69, 90, 23, 4, 80, 72, 97, 58, and 1 were used. In set 2, genes 48, 21, 68, 16, 96, 10, 1, 69, 36, 20, 3, 14, 59, 53, 12, 84, 90, 17, 9, 65, 4, 32, 75, 81, 88, 37, 38, 5, 94, 60, 64, 45, 7, 43, and 55 were used. In set 3, genes 33, 95, 59, 86, 83, 76, 36, 55, 90, 22, 62, 98, 34, 46, 4, 87, 5, 66, 38, 78, 97, 100, 71, 25, 30, 2, 21, 99, 12, 54, 9, 14, 81, 32, and 52 were used. In set 4, genes 27, 64, 40, 59, 63, 100, 50, 19, 1, 10, 96, 2, 34, 28, 67, 26, 87, 41, 15, 57, 33, 11, 94, 66, 82, 6, 52, 55, 84, 47, 97, 83, 80, 62, and 5 were used. Inset 5, genes 99, 86, 92, 72, 83, 48, 79, 46, 91, 2, 90, 9, 23, 44, 85, 31, 38, 81, 76, 54, 71, 14, 3, 13, 62, 11, 39, 4, 95, 36, 20, 30, 75, 63, and 51 were used. Inset 6, genes 41, 89, 81, 29, 86, 95, 34, 42, 50, 9, 45, 21, 64, 84, 74, 91, 69, 98, 57, 79, 39, 87, 93, 63, 26, 82, 2, 59, 30, 71, 83, 38, 77, 24, and 73 were used. In set 7, genes 87, 60, 59, 98, 43, 38, 28, 64, 29, 92, 22, 27, 40, 33, 69, 71, 73, 79, 15, 70, 32, 90, 76, 93, 6, 50, 55, 9, 49, 54, 36, 5, 48, 19, and 10 were used. In set 8, genes 100, 70, 98, 79, 91, 23, 37, 29, 73, 65, 78, 31, 3, 11, 30, 51, 16, 40, 95, 94, 62, 38, 67, 39, 82, 72, 22, 5, 87, 57, 6, 75, 35, 99, and 46 were used. In set 9, genes 46, 61, 59, 86, 29, 74, 56, 89, 52, 26, 54, 20, 84, 97, 33, 71, 14, 36, 38, 49, 28, 60, 19, 90, 11, 42, 87, 92, 82, 21, 94, 3, 22, 2, and 39 were used. In set 10, genes 31, 76, 77, 27, 72, 38, 42, 36, 53, 82, 61, 39, 98, 81, 34, 80, 22, 100, 8, 32, 17, 21, 28, 56, 59, 29, 55, 5, 62, 40, 90, 87, 24, 68, and 37 were used.

For 40 genes, set 1, genes 64, 50, 46, 22, 51, 6, 47, 12, 2, 30, 45, 7, 63, 55, 91, 90, 80, 49, 71, 8, 79, 82, 77, 76, 97, 5, 95, 11, 32, 70, 20, 62, 38, 26, 41, 58, 44, 87, 35, and 23 were used. In set 2, genes 44, 26, 16, 12, 30, 45, 71, 90, 37, 68, 32, 70, 58, 43, 51, 6, 62, 92, 87, 20, 56, 5, 47, 48, 86, 29, 98, 22, 59, 76, 8, 79, 64, 14, 50, 3, 54, 83, 96, and 80 were used. In set 3, genes 20, 34, 57, 70, 39, 15, 25, 33, 78, 51, 87, 46, 67, 80, 28, 52, 66, 72, 22, 88, 97, 3, 90, 6, 82, 42, 41, 94, 85, 61, 54, 84, 14, 9, 81, 19, 7, 91, 23, and 40 were used. In set 4, genes 61, 46, 64, 71, 35, 58, 100, 23, 95, 17, 87, 68, 54, 8, 50, 4, 27, 49, 47, 52, 53, 28, 24, 34, 45, 2, 89, 48, 3, 65, 42, 9, 92, 36, 6, 84, 51, 60, 77, and 94 were used. In set 5, genes 28, 97, 21, 43, 22, 89, 94, 87, 99, 5, 4, 20, 13, 61, 37, 42, 72, 62, 7, 12, 31, 23, 60, 98, 48, 38, 53, 56, 29, 69, 26, 82, 24, 74, 86, 10, 67, 2, 47, and 46 were used. In set 6, genes 12, 74, 96, 77, 78, 72, 53, 87, 47, 29, 40, 98, 52, 22, 69, 3, 58, 97, 60, 48, 55, 80, 57, 39, 50, 89, 71, 9, 63, 51, 21, 23, 73, 32, 20, 19, 25, 5, 38, and 46 were used. In set 7, genes 88, 79, 54, 44, 37, 36, 32, 91, 47, 50, 60, 92, 82, 80, 46, 19, 98, 20, 76, 29, 9, 95, 2, 77, 97, 74, 90, 73, 100, 1, 34, 85, 24, 71, 57, 99, 68, 13, 43, and 53 were used. In set 8, genes 23, 39, 7, 64, 20, 27, 69, 43, 38, 89, 50, 3, 16, 79, 83, 72, 65, 66, 32, 30, 100, 82, 28, 22, 54, 84, 53, 75, 59, 37, 34, 49, 12, 86, 71, 97, 26, 88, 70, and 57 were used. In set 9, genes 74, 96, 80, 39, 40, 82, 38, 56, 35, 93, 55, 73, 44, 17, 81, 27, 2, 83, 65, 89, 76, 8, 18, 45, 58, 77, 14, 49, 21, 6, 4, 92, 33, 13, 12, 88, 98, 24, 84, and 36 were used. In set 10, genes 35, 77, 48, 62, 26, 12, 41, 68, 81, 5, 37, 70, 28, 72, 50, 83, 64, 99, 74, 57, 84, 76, 52, 14, 87, 97, 3, 31, 73, 58, 44, 24, 15, 66, 45, 91, 4, 32, 46, and 49 were used.

For 45 genes, set 1, genes 52, 97, 84, 72, 96, 34, 18, 38, 88, 80, 91, 49, 71, 64, 93, 26, 62, 40, 68, 29, 67, 39, 60, 9, 13, 74, 95, 99, 27, 47, 25, 45, 31, 8, 69, 17, 75, 53, 51, 12, 23, 1, 6, 30, and 50 were used. In set 2, genes 97, 80, 55, 32, 94, 84, 28, 3, 6, 48, 17, 41, 65, 37, 79, 34, 61, 83, 35, 49, 27, 38, 43, 2, 24, 77, 25, 71, 58, 14, 8, 30, 46, 98, 82, 75, 22, 72, 26, 74, 93, 66, 73, 1, and 53 were used. In set 3, genes 64, 45, 38, 92, 23, 74, 66, 60, 100, 3, 82, 20, 54, 11, 19, 16, 80, 86, 14, 75, 62, 10, 52, 47, 13, 31, 35, 53, 41, 9, 79, 39, 17, 22, 99, 58, 46, 83, 43, 40, 44, 90, 95, 12, and 81 were used. In set 4, genes 20, 66, 9, 24, 16, 76, 99, 42, 86, 58, 15, 93, 48, 28, 26, 50, 68, 12, 2, 37, 82, 36, 27, 57, 45, 41, 32, 1, 52, 54, 30, 39, 7, 100, 59, 23, 94, 75, 8, 60, 55, 34, 38, 29, and 87 were used. In set 5, genes 66, 88, 73, 53, 51, 69, 36, 87, 78, 40, 58, 76, 31, 65, 56, 42, 100, 68, 5, 18, 17, 91, 45, 22, 74, 82, 1, 44, 67, 43, 10, 63, 79, 92, 6, 72, 80, 75, 9, 30, 19, 61, 99, 3, and 38 were used. In set 6, genes 75, 66, 84, 59, 9, 70, 100, 27, 79, 41, 73, 67, 23, 39, 28, 68, 21, 69, 38, 72, 86, 82, 36, 46, 77, 34, 47, 54, 13, 16, 7, 88, 22, 26, 4, 89, 55, 24, 61, 12, 35, 50, 95, 92, and 80 were used. In set 7, genes 59, 86, 10, 29, 53, 88, 43, 64, 11, 13, 19, 17, 36, 65, 73, 94, 20, 51, 80, 24, 66, 83, 44, 47, 21, 6, 52, 82, 69, 54, 100, 28, 18, 34, 35, 30, 74, 91, 49, 46, 60, 5, 38, 71, and 2 were used. In set 8, genes 77, 32, 55, 44, 6, 98, 94, 19, 10, 71, 72, 85, 67, 75, 78, 88, 90, 58, 89, 27, 69, 42, 31, 47, 1, 37, 52, 7, 57, 45, 11, 83, 49, 46, 34, 64, 14, 24, 87, 9, 56, 8, 20, 36, and 15 were used. In set 9, genes 4, 27, 83, 61, 46, 15, 35, 26, 51, 54, 23, 38, 100, 7, 42, 58, 44, 8, 22, 37, 20, 89, 56, 91, 70, 29, 11, 19, 87, 99, 21, 65, 72, 75, 49, 40, 45, 30, 43, 48, 63, 3, 18, 74, and 1 were used. In set 10, genes 68, 19, 90, 52, 55, 23, 17, 53, 3, 2, 74, 82, 26, 88, 48, 6, 8, 43, 15, 73, 57, 67, 85, 91, 13, 44, 81, 1, 75, 33, 51, 21, 4, 41, 77, 86, 40, 18, 31, 78, 92, 10, 64, 99, and 69 were used.

Classification of subsets of the 39 tumor types was performed with use of random selections of tumor types from the group of 39. The expression levels of gene sequence sets as described herein were used to classify random combinations of tumor types. Different random sets of tumor types were used with each of the sets of 100, 74, and 90 gene sequences as described in these examples. Representative, and non-limiting, examples of random sets of from 2 to 20 tumor types used are as follows, where the set of 39 tumor types were indexed from 1 to 39.

For 2 tumor types, set 1 used types 26 and 16. Set 2 used types 8 and 5. Set 3 used types 39 and 8. Set 4 used types 27 and 23. Set 5 used types 8 and 19. Set 6 used 12 and 21. Set 7 used types 30 and 15. Set 8 used types 30 and 5. Set 9 used types 18 and 22. Set 10 used types 27 and 26.

For 4 tumor types, set 1 used types 20, 35, 15 and 7. Set 2 used types 36, 1, 28 and 19. Set 3 used types 13, 4, 12 and 21. Set 4 used types 12, 33, 14 and 28. Set 5 used types 6, 28, 5 and 37. Set 6 used types 5, 25, 36 and 15. Set 7 used types 12, 26, 21 and 19. Set 8 used types 19, 3, and 17. Set 9 used types 18, 10, 8 and 9. Set 10 used types 28, 20, 2 and 22.

For 6 tumor types, set 1 used types 27, 3, 10, 39, 11 and 20. Set 2 used types 33, 10, 20, 32, 13 and 19. Set 3 used types 31, 27, 18, 39, 8 and 16. Set 4 used types 25, 28, 10, 12, 7 and 39. Set 5 used types 14, 13, 28, 24, 30 and 36. Set 6 used types 9, 24, 8, 17, 36 and 26. Set 7 used types 20, 1, 34, 26, 6 and 19. Set 8 used types 12, 13, 3, 17, 34 and 22. Set 9 used types 7, 1, 17, 13, 20 and 34. Set 10 used types 5, 11, 25, 29, 28 and 35.

For 8 tumor type, set 1 used types 34, 33, 28, 3, 23, 25, 9 and 29. Set 2 used types 27, 8, 38, 28, 20, 14, 12 and 9. Set 3 used types 29, 21, 19, 13, 26, 11 and 31. Set 4 used types 25, 17, 7, 20, 34, 8, 28 and 10. Set 5 used types 36, 28, 35, 26, 2, 8, 29 and 7. Set 6 used types 10, 23, 2, 27, 33, 21, 25 and 35. Set 7 used types 10, 18, 38, 2, 6, 7, 19 and 32. Set 8 used types 11, 37, 6, 28, 3, 9, 2 and 16. Set 9 used types 22, 2, 10, 8, 17, 19 and 33. Set 10 used types 35, 39, 8, 10, 37, 4, 36 and 6.

For 10 tumor types, set 1 used types 25, 10, 26, 2, 32, 31, 39, 23, 22 and 18. Set 2 used types 12, 35, 6, 16, 20, 3, 39, 36, 11 and 2. Set 3 used types 34, 1, 15, 29, 5, 39, 2, 12, 25 and 18. Set 4 used types 10, 8, 14, 18, 31, 19, 23, 20, 32 and 33. Set 5 used types 10, 18, 37, 15, 4, 35, 33, 24, 39 and 20. Set 6 used types 22, 16, 4, 3, 18, 21, 1, 25, 37 and 13. Set 7 used types 14, 6, 28, 18, 11, 13, 2, 32, 33 and 19. Set 8 used types 39, 2, 38, 4, 34, 8, 25, 6, 32 and 35. Set 9 used types 3, 10, 11, 16, 6, 15, 18, 14, 12 and 26. Set 10 used types 24, 25, 21, 9, 36, 29, 20, 39, 10 and 37.

For 12 tumor types, set 1 used types 26, 20, 4, 12, 2, 31, 38, 18, 16, 39, 3 and 33. Set 2 used types 25, 16, 4, 9, 29, 27, 14, 24, 21, 7, 23 and 2. Set 3 used types 31, 18, 23, 13, 25, 1, 29, 21, 35, 10, 32 and 39. Set 4 used types 8, 34, 23, 9, 35, 14, 25, 21, 2, 33, 18 and 28. Set 5 used types 6, 11, 21, 8, 5, 7, 19, 32, 3, 13, 36 and 9. Set 6 used types 12, 33, 14, 26, 27, 15, 2, 21, 36, 35, 9 and 39. Set 7 used types 26, 29, 32, 17, 31, 19, 6, 5, 20, 34, 2 and 24. Set 8 used types 17, 12, 8, 22, 28, 9, 27, 29, 14, 35, 4 and 32. Set 9 used types 29, 9, 36, 23, 33, 18, 21, 35, 3, 6, 2 and 1. Set 10 used types 1, 3, 35, 29, 22, 27, 8, 23, 2, 36, 14 and 19.

For 14 tumor types, set 1 used types 9, 26, 38, 25, 31, 3, 15, 14, 17, 33, 12, 35, 39 and 16. Set 2 used types 1, 26, 16, 25, 20, 12, 14, 37, 38, 24, 23, 33, 27 and 35. Set 3 used types 11, 21, 35, 38, 32, 34, 27, 39, 16, 15, 4, 5, 13 and 18. Set 4 used types 27, 5, 13, 28, 18, 17, 15, 20, 29, 37, 21, 36, 25 and 14. Set 5 used types 5, 12, 17, 9, 25, 21, 33, 37, 8, 15, 24, 3, 34 and 28. Set 6 used types 11, 19, 34, 26, 9, 6, 32, 14, 27, 29, 30, 16, 24 and 17. Set 7 used types 31, 26, 11, 18, 19, 20, 9, 8, 5, 36, 12, 6, 27 and 38. Set 8 used types 20, 17, 11, 5, 15, 9, 2, 39, 34, 24, 27, 26, 35 and 10. Set 9 used types 1, 14, 39, 30, 17, 6, 10, 35, 31, 33, 15, 29, 32 and 7. Set 10 used types 1, 19, 24, 28, 34, 12, 13, 18, 32, 11, 14, 21, 22 and 25.

For 16 tumor types, set 1 used types 27, 15, 8, 12, 6, 20, 26, 19, 25, 2, 37, 38, 7, 39, 4 and 33. Set 2 used types 17, 18, 28, 5, 6, 31, 25, 13, 8, 20, 37, 36, 35, 9, 23 and 27. Set 3 used types 23, 37, 34, 14, 16, 27, 32, 33, 21, 38, 4, 30, 24, 22, 17 and 25. Set 4 used types 7, 37, 38, 21, 34, 31, 32, 25, 10, 36, 19, 11, 6, 26, 18 and 35. Set 5 used types 9, 32, 12, 24, 20, 13, 38, 21, 39, 23, 36, 18, 37, 22, 5 and 3. Set 6 used types 14, 21, 5, 17, 6, 20, 18, 35, 22, 10, 3, 23, 13, 2, 34 and 26. Set 7 used types 1, 8, 19, 6, 9, 39, 28, 18, 13, 31, 14, 16, 37, 12, 3 and 25. Set 8 used types 32, 36, 28, 38, 9, 33, 2, 5, 4, 11, 19, 18, 13, 8, 12 and 3. Set 9 used types 9, 14, 10, 5, 28, 32, 23, 6, 39, 3, 17, 8, 19, 1, 31 and 12. Set 10 used types 4, 34, 11, 6, 38, 19, 7, 20, 23, 3, 25, 37, 26, 1, 15 and 12.

For 18 tumor types, set 1 used types 15, 24, 39, 35, 7, 30, 16, 13, 20, 3, 26, 4, 12, 10, 34, 25, 21 and 28. Set 2 used types 21, 23, 29, 11, 10, 19, 13, 28, 4, 20, 17, 24, 30, 12, 39, 34, 31 and 9. Set 3 used types 7, 17, 27, 6, 30, 8, 22, 2, 32, 26, 21, 14, 4, 38, 1, 35, 16 and 28. Set 4 used types 17, 13, 20, 33, 10, 3, 16, 22, 1, 38, 2, 9, 28, 5, 6, 19, 12 and 11. Set 5 used types 4, 35, 21, 25, 18, 17, 8, 14, 31, 30, 9, 1, 2, 23, 36, 29, 32 and 37. Set 6 used types 17, 34, 2, 18, 19, 15, 16, 13, 4, 24, 5, 35, 6, 22, 28, 37, 38 and 1. Set 7 used types 34, 26, 12, 25, 27, 3, 17, 7, 2, 32, 9, 36, 21, 19, 22, 8, 20 and 29. Set 8 used types 12, 34, 38, 25, 17, 22, 14, 39, 10, 7, 31, 2, 3, 11, 29, 30, 16 and 24. Set 9 used types 13, 26, 27, 14, 5, 10, 8, 7, 16, 30, 37, 4, 6, 35, 28, 1, 36 and 20. Set 10 used types 15, 2, 17, 23, 26, 28, 36, 38, 12, 6, 19, 37, 20, 14, 9, 39, 11 and 21.

For 20 tumor types, set 1 used types 25, 13, 21, 15, 37, 20, 12, 28, 9, 10, 26, 22, 14, 24, 16, 7, 39, 34, 33 and 4. Set 2 used types 20, 17, 10, 27, 19, 28, 5, 1, 23, 21, 38, 7, 13, 22, 32, 31, 9, 4, 3 and 24. Set 3 used types 17, 13, 7, 20, 11, 38, 34, 3, 15, 12, 5, 39, 9, 10, 4, 35, 27, 6, 21 and 33. Set 4 used types 6, 13, 17, 26, 1, 7, 33, 5, 10, 32, 3, 23, 35, 4, 14, 28, 12, 38, 8 and 27. Set 5 used types 10, 23, 9, 38, 5, 29, 12, 27, 25, 6, 7, 26, 37, 31, 24, 36, 19, 15, 16 and 11. Set 6 used types 30, 24, 21, 11, 23, 25, 8, 9, 7, 31, 27, 5, 14, 29, 1, 19, 16, 12, 22 and 17. Set 7 used types 26, 13, 23, 19, 22, 11, 25, 21, 33, 20, 6, 17, 2, 10, 31, 34, 27, 37, 7 and 9. Set 8 used types 30, 1, 38, 7, 31, 37, 11, 25, 6, 19, 28, 33, 17, 29, 10, 27, 16, 3, 14 and 15. Set 9 used types 15, 19, 26, 24, 5, 33, 11, 2, 13, 18, 31, 22, 32, 20, 23, 6, 10, 25, 36 and 3. Set 10 used types 24, 25, 21, 29, 14, 18, 31, 2, 20, 39, 23, 9, 38, 12, 6, 32, 22, 26, 33 and 7.

Example 4: Specified Gene Sets

A first set of 74 genes and a second set of 90 genes, where the two sets have 38 members in common, were used in the practice of the invention.

Figure 4:
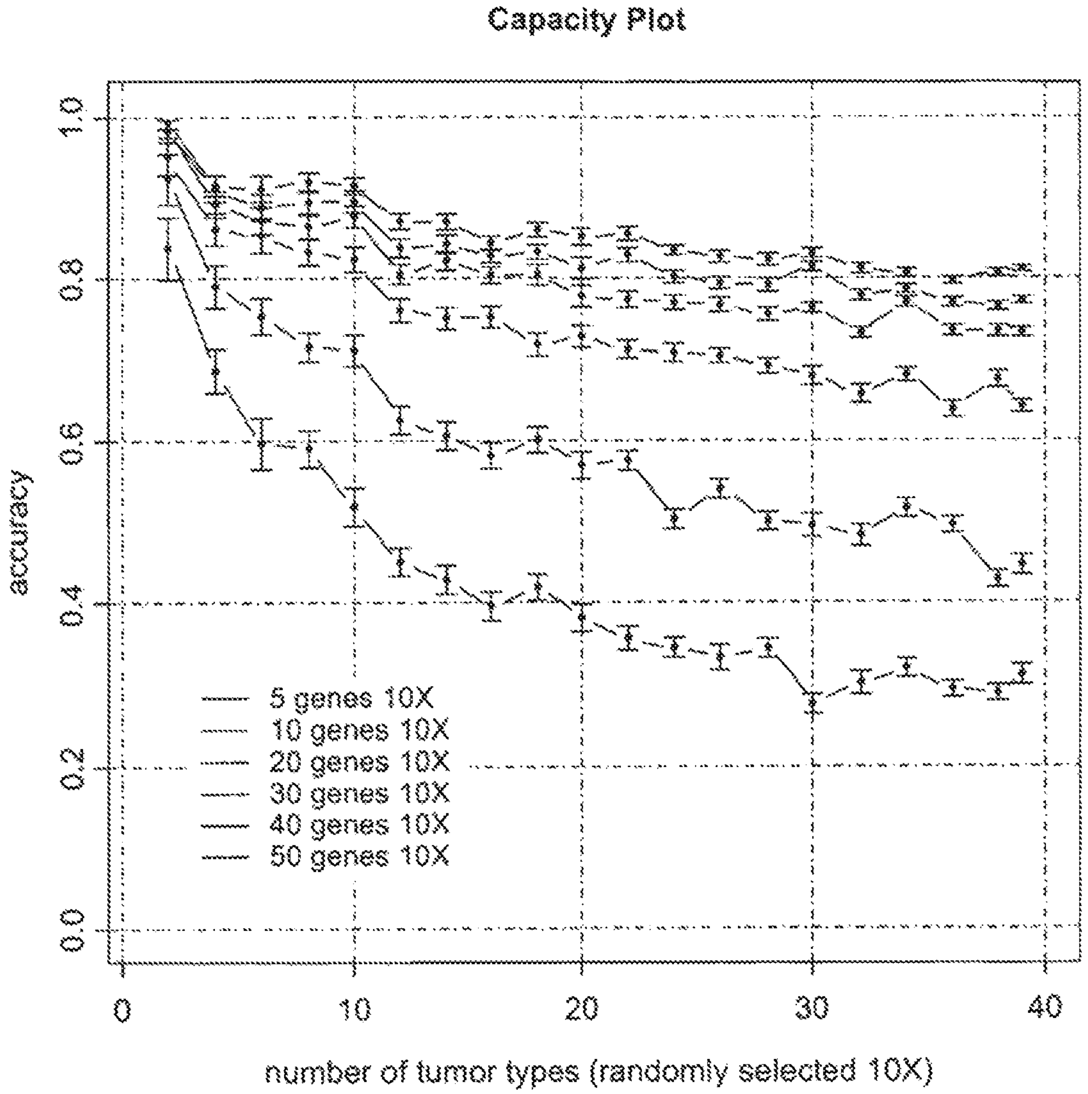
FIG. 4 shows a capacity plot for the ability to use the expression levels of portions of a first set of 74 expressed gene sequences to classify among 39 tumor types and subsets thereof. Expression levels of random combinations of 5, 10, 15, 20, 25, 30, 35, 40, 45, and 49 (each sampled 10 times) of the 74 sequences were used with data from tumor types and then used to predict test random sets of tumor samples (each sampled 10 times) ranging from 2 to 39 types. A plot of numbers of tumor types versus prediction accuracies for results using from 5 to 49 genes are shown as non-limiting examples. The plotted lines, from top to bottom, are of the results from 49, 40, 30, 20, 10, and gene sequences, respectively.
Figure 5:
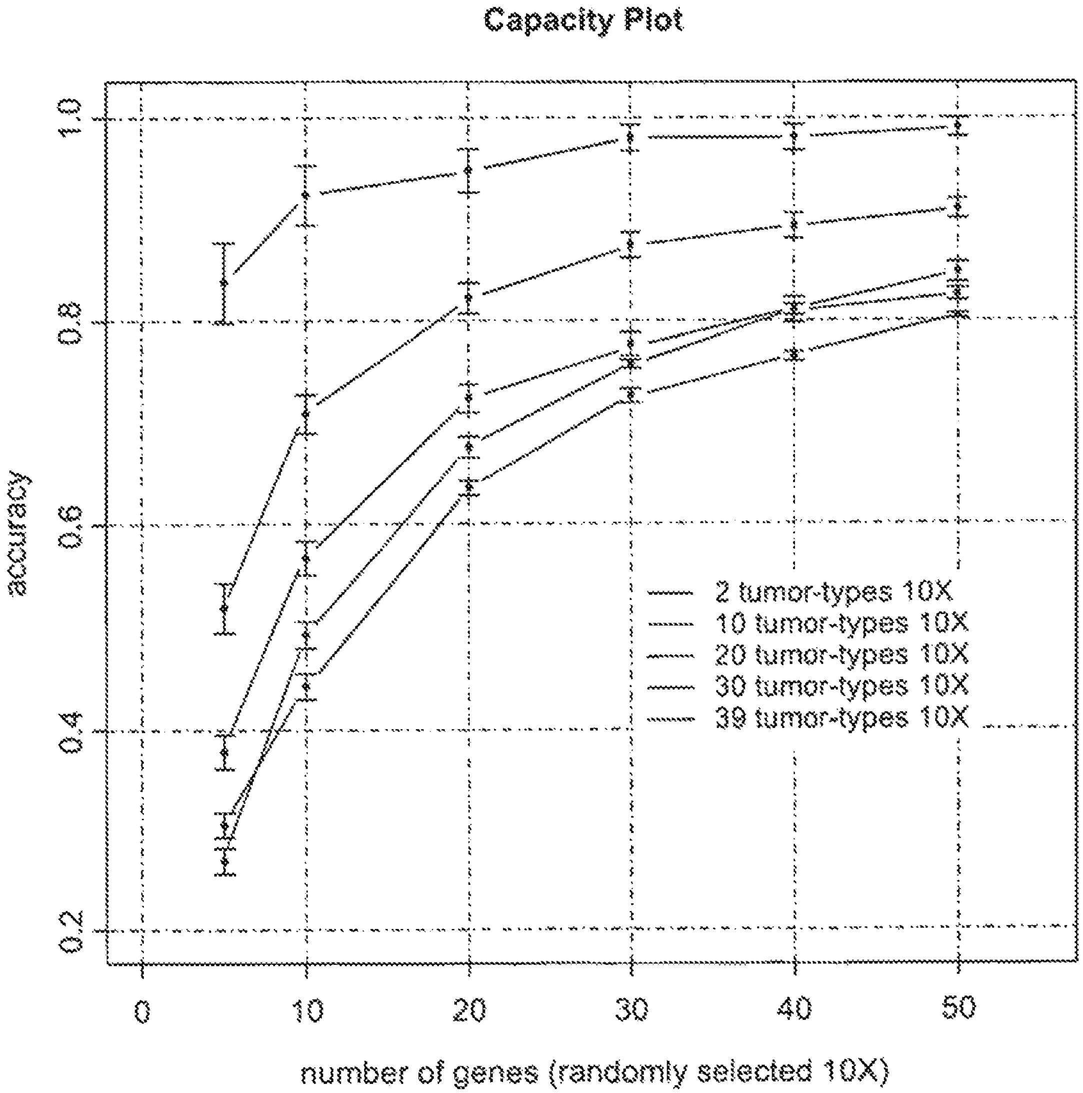
FIG. 5 shows an alternative presentation of the data used with respect to FIG. 4. A plot of number a of gene sequences used, ranging from 5-49, versus prediction accuracies for various representative numbers of tumor types is shown. The plotted lines, from top to bottom, are of the results from 2, 10, 20, 30, and 39 tumor types, respectively.
Figure 6:
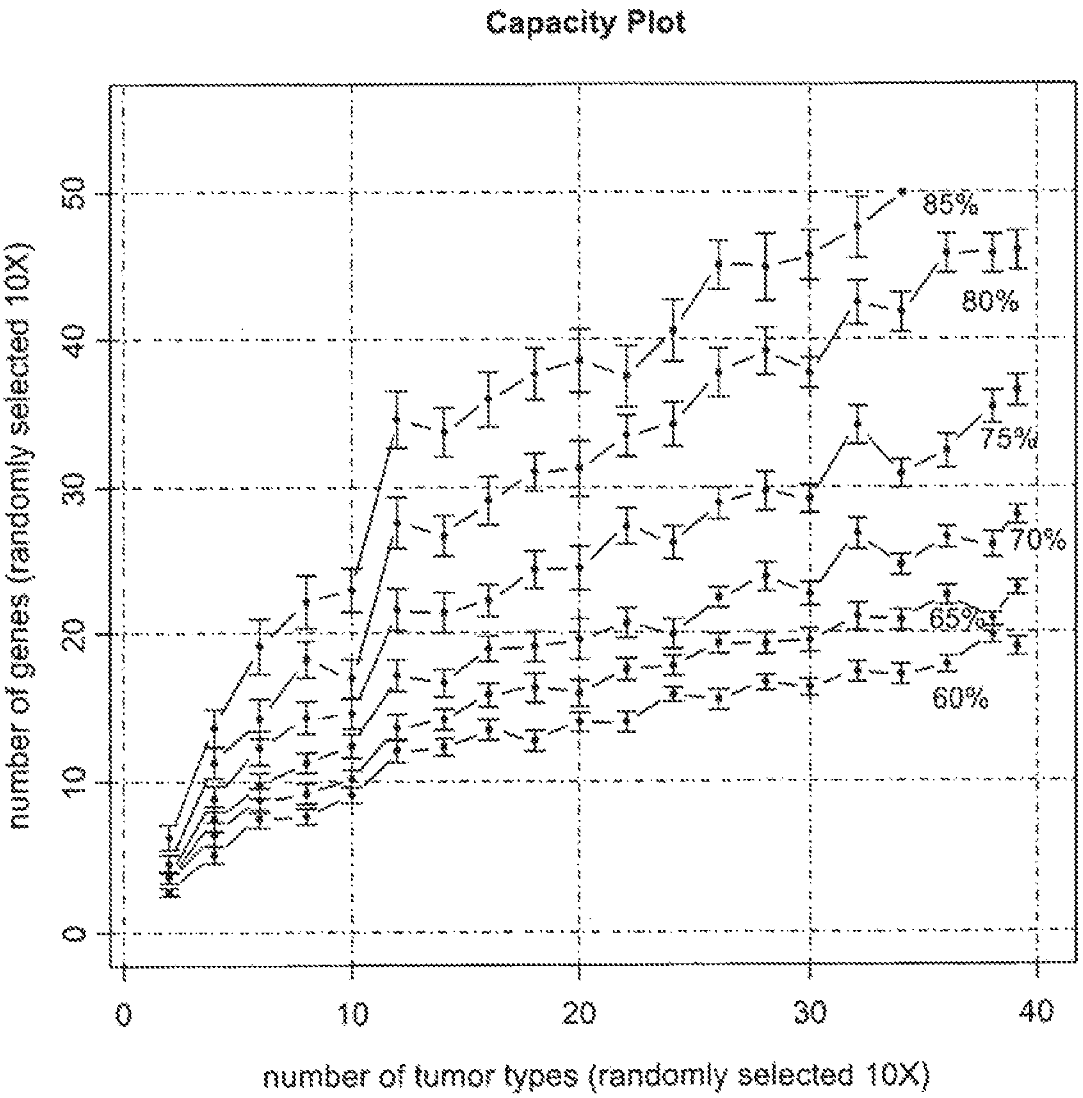
FIG. 6 is analogous to FIG. 3 except with presentation of the data used with FIGS. 4 and 5.

Random subsets of about 5 to 49 members of the set of 74 expressed gene sequences were evaluated in a manner analogous to that described in Example 3. Again, the expression levels of random combinations of 5, 10, 15, 20, 25, 30, 35, 40, 45, and 49 (each combination sampled 10 times) of the 74 expressed sequences were used with data from tumor types and then used to predict test random sets of tumor samples (each sampled 10 times) ranging from 2 to all 39 types. The resulting data are shown in FIGS. 4-6.

The members of the 74 gene sequences were indexed fin 1 to 74, and representative random sets used in the invention are as follows:

For 2 genes, set 1, genes 64 and 6 were used. For set 2, genes 64 and 13 were used. For set 3, genes 67 and 51 were used. For set 4, genes 51 and 29 were used. For set 5, genes 46 and 12 were used. For set 6, genes 68 and 65 were used. For set 7, genes 6 and 28 were used. For set 8, genes 9 and 55 were used. For set 9, genes 55 and 71 were used. For set 10, genes 63 and 39 were used.

For 5 genes, set 1, genes 8, 64, 50, 54, and 4 were used. Inset 2, genes 39, 17, 45, 34, and 15 were used. In set 3, genes 10, 4, 61, 21, and 55 were used. In set 4, genes 59, 37, 21, 23, and 64 were used. In set 5, genes 69, 8, 25, 59, and 63 were used. In set 6, genes 45, 71, 19, 59, and 38 were used. In set 7, genes 21, 43, 14, 48, and 30 were used. In set 8, genes 73, 35, 36, 10, and 9 were used. Inset 9, genes 62, 28, 11, 70, and 64 were used. Inset 10, genes 8, 16, 70, 18, and 59 were used.

For 10 genes, set 1, genes 49, 72, 38, 68, 52, 21, 1, 10, 2, and 40 were used. In set 2, genes 54, 70, 28, 64, 68, 41, 44, 20, 7, and 2 were used. In set 3, genes 71, 49, 51, 11, 18, 53, 8, 42, 36, and 58 were used. Inset 4, genes 72, 15, 35, 3, 23, 8, 2, 48, 22, and 65 were used. In set 5, genes 44, 19, 6, 22, 38, 5, 37, 9, 30, and 14 were used. In set 6, genes 15, 27, 3, 10, 31, 19, 44, 39, 48, and 46 were used. Inset 7, genes 70, 30, 9, 33, 63, 71, 32, 34, 20, and 7 were used. In set 8, genes 45, 29, 54, 58, 15, 21, 68, 5, 42, and 62 were used. In set 9, genes 74, 17, 66, 46, 10, 8, 63, 5, 24, and 2 were used. In set 10, genes 33, 2, 34, 19, 60, 71, 42, 51, 70, and 66 were used.

For 15 genes, set 1, genes 13, 22, 26, 67, 64, 40, 68, 71, 4, 28, 24, 33, 46, 69, and 41 were used. Inset 2, genes 10, 1, 14, 70, 71, 64, 46, 67, 45, 48, 65, 74, 34, 49, and 37 were used. In set 3, genes 58, 30, 44, 40, 51, 36, 33, 60, 39, 21, 54, 64, 25, 13, and 35 were used. In set 4, genes 63, 70, 60, 32, 31, 16, 49, 65, 38, 5, 72, 47, 40, 2, and 46 were used. Inset 5, genes 43, 6, 40, 13, 39, 72, 68, 41, 27, 73, 36, 25, 33, 34, and 1 were used. In set 6, genes 68, 67, 71, 59, 73, 62, 31, 43, 7, 44, 21, 48, 54, 58, and 6 were used. In set 7, genes 16, 50, 61, 62, 27, 2, 21, 1, 41, 28, 68, 35, 17, 47, and 46 were used. Inset 8, genes 27, 18, 44, 66, 2, 20, 53, 64, 46, 70, 57, 7, 51, 10, and 45 were used. In set 9, genes 65, 8, 43, 23, 50, 46, 21, 41, 44, 3, 31, 17, 7, 66, and 70 were used. Inset 10, genes 16, 14, 61, 51, 39, 33, 43, 31, 53, 65, 74, 42, 29, 9, and 11 were used.

For 20 genes, set 1, genes 14, 60, 6, 71, 74, 16, 62, 39, 56, 44, 32, 72, 18, 42, 66, 49, 1, 9, 69, and 21 were used. In set 2, genes 23, 1, 7, 27, 26, 71, 12, 4, 22, 69, 62, 44, 6, 25, 57, 28, 33, 9, 21, and 51 were used. In set 3, genes 46, 48, 29, 54, 55, 69, 73, 47, 6, 27, 24, 21, 15, 43, 45, 7, 62, 25, 22, and 74 were used. In set 4, genes 12, 65, 24, 73, 45, 57, 49, 63, 61, 1, 58, 10, 2, 18, 8, 51, 67, 69, 59, and 13 were used. In set 5, genes 33, 43, 9, 52, 54, 38, 8, 16, 48, 1, 39, 60, 17, 6, 15, 66, 68, 63, 37, and 42 were used. Inset 6, genes 43, 19, 44, 28, 56, 34, 66, 42, 73, 40, 65, 38, 54, 20, 51, 37, 30, 35, 53, and 61 were used. In set 7, genes 61, 6, 20, 4, 34, 53, 70, 38, 35, 46, 36, 16, 1, 23, 68, 12, 59, 71, 65, and 14 were used. In set 8, genes 25, 68, 69, 3, 33, 49, 19, 56, 54, 4, 32, 6, 45, 16, 67, 52, 65, 14, 12, and 40 were used. In set 9, genes 47, 7, 36, 32, 61, 74, 14, 45, 26, 51, 69, 12, 41, 42, 64, 25, 27, 57, 23, and 58 were used. In set 10, genes 27, 13, 3, 17, 51, 7, 37, 43, 20, 12, 52, 21, 25, 2, 5, 32, 62, 47, 4, and 26 were used.

For 25 genes, set 1, genes 57, 61, 31, 38, 3, 7, 72, 43, 32, 23, 28, 71, 48, 17, 2, 49, 10, 30, 66, 12, 69, 41, 20, 63, and 68 were used. In set 2, genes 18, 54, 47, 57, 24, 42, 66, 46, 16, 58, 37, 60, 62, 9, 2, 27, 36, 52, 13, 32, 45, 6, 43, 21, and 56 were used. Inset 3, genes 47, 48, 52, 16, 56, 54, 42, 37, 17, 41, 35, 21, 6, 9, 63, 10, 49, 68, 23, 25, 70, 3, 58, 2, and 31 were used. In set 4, genes 50, 10, 25, 16, 68, 15, 29, 73, 27, 63, 3, 17, 28, 66, 19, 13, 4, 9, 36, 48, 23, 57, 59, 26, and 14 were used. In set 5, genes 40, 39, 43, 49, 66, 15, 14, 29, 36, 21, 19, 44, 72, 58, 69, 12, 11, 9, 37, 46, 32, 51, 3, 24, and 6 were used. In set 6, genes 42, 49, 44, 32, 46, 35, 70, 40, 3, 21, 11, 67, 25, 56, 37, 43, 60, 55, 16, 27, 30, 53, 63, 23, and 33 were used. In set 7, genes 70, 27, 68, 17, 64, 65, 18, 69, 10, 67, 42, 23, 48, 14, 31, 11, 55, 25, 52, 34, 13, 45, 12, 29, and 47 were used. In set 8, genes 48, 10, 17, 27, 25, 55, 12. 62, 30, 65, 15, 49, 70, 14, 54, 24, 33, 26, 50, 60, 6, 40, 67, 11, and 2 were used. In set 9, genes 41, $4^7$, 24, 59, 7, 44, 2, 67, 12, 19, 13, 17, 35, 56, 28, 14, 61, 15, 60, 58, 1, 64, 31, 45, and 23 were used. In set 10, genes 42, 72, 41, 38, 57, 27, 4, 13, 9, 43, 34, 28, 8, 62, 64, 46, 12, 70, 21, 66, 16, 7, 48, 3, and 54 were used.

For 30 genes, set 1, genes 16, 47, 67, 9, 22, 10, 64, 72, 46, 6, 60, 74, 3, 68, 57, 63, 14, 54, 58, 30, 28, 18, 70, 73, 52, 39, 34, 61, 12, 21 were used. In set 2, genes 18, 1, 44, 24, 68, 26, 62, 10, 47, 67, 37, 55, 32, 35, 34, 14, 49, 30, 17, 16, 51, 45, 74, 31, 9, 57, 66, 39, 53, and 8 were used. In set 3, genes 58, 45, 55, 39, 22, 32, 9, 49, 31, 13, 51, 56, 28, 12, 3, 59, 74, 35, 42, 67, 69, 47, 66, 18, 52, 57, 43, 5, 26, and 4 were used. In set 4, genes 45, 1, 74, 12, 18, 23, 59, 27, 38, 40, 72, 56, 50, 20, 52, 32, 5, 16, 9, 21, 60, 64, 49, 70, 30, 61, 6, 10, 31, and 24 were used. Inset 5, genes 60, 53, 7, 32, 73, 25, 69, 48, 17, 45, 16, 3, 14, 9, 37, 41, 72, 43, 68, 39, 20, 51, 59, 23, 6, 15, 74, 19, 31, and 66 were used. Inset 6, genes 47, 54, 9, 38, 60, 33, 40, 12, 57, 45, 26, 56, 11, 27, 67, 25, 69, 59, 68, 7, 61, 72, 23, 21, 28, 48, 29, 65, 37, and 15 were used. In set 7, genes 21, 42, 30, 57, 65, 59, 53, 74, 45, 66, 68, 41, 19, 24, 8, 10, 61, 43, 38, 67, 37, 47, 40, 22, 63, 35, 70, 72, 5, and 6 were used. In set 8, genes 58, 11, 28, 36, 24, 34, 53, 9, 44, 23, 51, 70, 22, 17, 15, 59, 5, 60, 1, 64, 21, 50, 35, 52, 31, 43, 38, 39, 32, and 62 were used. In set 9, genes 43, 30, 63, 7, 60, 40, 39, 1, 48, 17, 69, 57, 6, 62, 19, 38, 36, 13, 66, 64, 25, 31, 65, 47, 27, 16, 53, 68, 37, and 41 were used. In set 10, genes 22, 17, 4, 2, 37, 16, 49, 7, 63, 64, 14, 15, 74, 43, 25, 54, 46, 50, 53, 67, 39, 62, 59, 10, 55, 72, 65, 52, 58, and 19 were used.

For 35 genes, set 1, genes 4, 43, 55, 49, 13, 26, 32, 21, 18, 50, 14, 20, 65, 7, 24, 52, 58, 8, 30, 37, 54, 71, 2, 31, 44, 61, 66, 67, 28, 39, 10, 70, 17, 19, and 45 were used. In set 2, genes 14, 13, 67, 21, 48, 28, 69, 47, 50, 3, 68, 63, 22, 41, 60, 61, 5, 44, 56, 65, 7, 66, 15, 6, 45, 2, 36, 5, 30, 72, 34, 46, 24, 29, and 12 were used. In set 3, genes 67, 25, 58, 11, 17, 16, 3, 69, 21, 1, 59, 26, 72, 41, 47, 2, 34, 24, 10, 19, 33, 5, 50, 9, 71, 20, 62, 8, 68, 61, 23, 37, 35, 60, and 32 were used. In set 4, genes 5, 30, 14, 1, 59, 27, 28, 51, 55, 61, 18, 37, 17, 73, 6, 44, 67, 12, 35, 11, 53, 72, 70, 25, 21, 7, 34, 13, 74, 43, 52, 39, 54, 2, and 19 were used. Inset 5, genes 56, 64, 58, 35, 1, 23, 43, 4, 73, 28, 54, 6, 51, 68, 49, 37, 16, 71, 3, 21, 48, 69, 70, 10, 26, 22, 50, 44, 2, 60, 38, 40, 66, 63, and 65 were used. In set 6, genes 72, 49, 51, 44, 19, 28, 1, 11, 3, 40, 33, 41, 70, 29, 48, 62, 50, 4, 47, 60, 68, 10, 61, 32, 20, 13, 22, 59, 65, 64, 67, 21, 35, 39, and 24 were used. In set 7, genes 14, 35, 31, 20, 8, 59, 50, 15, 52, 62, 19, 30, 71, 68, 72, 47, 38, 74, 36, 49, 73, 22, 41, 25, 69, 16, 32, 24, 51, 43, 65, 3, 6, 53, and 29 were used. In set 8, genes 22, 44, 23, 9, 26, 56, 72, 59, 35, 61, 51, 69, 64, 30, 53, 27, 11, 55, 39, 67, 48, 28, 14, 10, 8, 12, 40, 24, 57, 34, 50, 32, 42, 41, and 38 were used. In set 9, genes 15, 7, 27, 6, 67, 9, 26, 57, 30, 37, 58, 23, 42, 11, 36, 52, 32, 29, 62, 21, 41, 61, 64, 18, 40, 35, 66, 1, 2, 56, 16, 3, 55, 10, and 51 were used. Inset 10, genes 9, 14, 71, 25, 44, 37, 49, 46, 66, 53, 7, 33, 22, 12, 73, 50, 27, 24, 13, 5, 41, 51, 61, 16, 28, 56, 23, 20, 10, 8, 70, 48, 42, 52, and 34 were used.

For 40 genes, set 1, genes 26, 36, 43, 30, 62, 19, 20, 51, 41, 71, 1, 63, 10, 56, 65, 17, 15, 50, 5, 35, 4, 54, 12, 70, 48, 31, 47, 37, 34, 8, 3, 69, 40, 44, 46, 59, 61, 74, 23, 27 were used. In set 4?2, genes 1, 4, 38, 24, 37, 69, 21, 52, 13, 2, 63, 51, 30, 16, 27, 58, 74, 20, 32, 53, 59, 31, 50, 10, 42, 8, 54, 36, 5, 47, 70, 41, 12, 46, 28, 19, 35, 9, 61, and 48 were used. In set 3, genes 35, 48, 40, 47, 20, 67, 57, 72, 15, 17, 46, 37, 9, 2, 60, 30, 65, 49, 29, 64, 16, 21, 7, 74, 61, 11, 58, 71, 62, 23, 24, 55, 3, 53, 52, 27, 18, 50, 25, and 66 were used. Inset 4, genes 35, 10, 59, 19, 27, 40, 30, 4, 9, 52, 2, 29, 26, 41, 55, 17, 13, 53, 71, 63, 58, 44, 45, 62, 70, 16, 64, 48, 43, 8, 38, 72, 49, 37, 18, 36, 74, 42, 46, and 54 were used. Inset 5, genes 16, 61, 1, 10, 20, 51, 22, 6, 43, 65, 66, 24, 30, 9, 14, 40, 32, 74, 18, 71, 15, 28, 52, 31, 56, 55, 23, 4, 58, 36, 60, 54, 25, 63, 27, 64, 50, 29, 44, and 45 were used. In set 6, genes 15, 30, 3, 50, 61, 47, 13, 48, 45, 17, 46, 10, 28, 37, 8, 54, 9, 5, 63, 18, 39, 49, 34, 68, 14, 23, 43, 11, 1, 51, 56, 67, 20, 57, 6, 19, 25, 31, 21, and 12 were used. In set 7, genes 45, 73, 53, 29, 35, 56, 70, 51, 30, 59, 49, 22, 6, 43, 28, 31, 40, 4, 66, 25, 37, 19, 12, 65, 26, 74, 46, 50, 23, 62, 17, 69, 36, 41, 34, 27, 67, 7, 24, and 13 were used. In set 8, genes 62, 30, 38, 41, 18, 13, 49, 71, 68, 47, 50, 70, 66, 5, 23, 33, 27, 56, 6, 7, 34, 28, 26, 58, 53, 46, 16, 52, 72, 42, 10, 54, 67, 64, 12, 8, 19, 57, 73, and 17 were used. In set 9, genes 11, 32, 48, 54, 42, 67, 13, 53, 21, 44, 57, 22, 40, 12, 5, 29, 69, 37, 17, 39, 45, 73, 60, 26, 14, 72, 4, 59, 24, 46, 18, 51, 36, 61, 35, 9, 19, 16, 38, and 28 were used. In set 10, genes 58, 1, 55, 59, 11, 63, 3, 26, 49, 69, 34, 47, 65, 46, 14, 39, 5, 67, 16, 66, 64, 38, 44, 32, 15, 22, 19, 71, 23, 52, 45, 53, 48, 8, 60, 73, 9, 30, 25, and 37 were used.

For 45 genes, set 1, genes 26, 21, 17, 34, 19, 27, 6, 61, 24, 42, 3, 60, 70, 43, 54, 13, 9, 20, 28, 58, 12, 23, 33, 4, 63, 56, 67, 1, 11, 68, 41, 59, 45, 5, 48, 32, 10, 44, 16, 65, 51, 62, 22, 38, and 74 were used. In set 2, genes 21, 41, 67, 5, 51, 53, 28, 25, 31, 60, 52, 17, 50, 11, 29, 45, 2, 32, 71, 13, 68, 22, 74, 33, 48, 56, 62, 42, 26, 14, 61, 23, 9, 46, 66, 10, 64, 59, 54, 69, 27, 47, 44, 34, and 40 were used. In set 3, genes 68, 48, 43, 74, 17, 4, 49, 34, 38, 60, 12, 42, 18, 5, 51, 32, 1, 57, 9, 11, 30, 13, 37, 15, 29, 33, 44, 20, 55, 70, 45, 41, 24, 56, 35, 52, 59, 7, 25, 2, 31, 64, 71, 22, and 39 were used. In set 4, genes 44, 61, 51, 69, 65, 72, 29, 57, 40, 62, 66, 63, 67, 55, 74, 14, 56, 11, 16, 58, 1, 15, 3, 48, 42, 7, 8, 30, 18, 19, 23, 60, 4, 10, 21, 43, 12, 37, 32, 25, 22, 50, 34, 59, and 2 were used. In set 5, genes 67, 54, 33, 41, 5, 61, 3, 10, 2, 71, 73, 53, 25, 42, 44, 23, 9, 38, 45, 62, 32, 46, 40, 8, 66, 49, 16, 24, 68, 69, 21, 52, 20, 6, 48, 11, 57, 39, 22, 31, 63, 36, 34, 35, and 17 were used. In set 6, genes 43, 45, 19, 17, 4, 58, 37, 7, 42, 52, 2, 62, 25, 66, 24, 15, 22, 74, 68, 67, 8, 1, 33, 70, 31, 50, 64, 14, 61, 51, 6, 38, 35, 39, 72, 5, 27, 36, 11, 18, 12, 48, 46, 54, and 71 were used. In set 7, genes 41, 45, 58, 11, 66, 26, 53, 13, 60, 4, 65, 18, 67, 73, 28, 55, 56, 57, 29, 68, 23, 19, 42, 17, 22, 62, 61, 10, 43, 64, 38, 71, 7, 40, 16, 34, 74, 12, 37, 8, 63, 44, 49, 47, and 3 were used. In set 8, genes 47, 40, 59, 14, 50, 71, 1, 57, 19, 28, 6, 34, 68, 4, 30, 20, 31, 33, 38, 39, 17, 41, 24, 65, 70, 61, 3, 35, 45, 11, 9, 8, 73, 42, 26, 23, 46, 72, 25, 64, 16, 53, 62, 18, and 7 were used. In set 9, genes 61, 5, 69, 22, 7, 17, 26, 13, 2, 30, 55, 33, 47, 14, 59, 32, 9, 44, 23, 45, 42, 25, 15, 57, 48, 50, 1, 68, 18, 72, 46, 73, 67, 36, 63, 60, 28, 21, 20, 8, 29, 35, 37, 38, and 71 were used. In set 10, genes 22, 31, 58, 50, 64, 11, 17, 67, 41, 2, 21, 4, 61, 70, 54, 3, 71, 25, 40, 43, 69, 38, 9, 73, 45, 16, 34, 10, 7, 52, 35, 19, 66, 24, 5, 60, 18, 14, 59, 32, 68, 15, 56, 63, and 65 were used.

Figure 7:
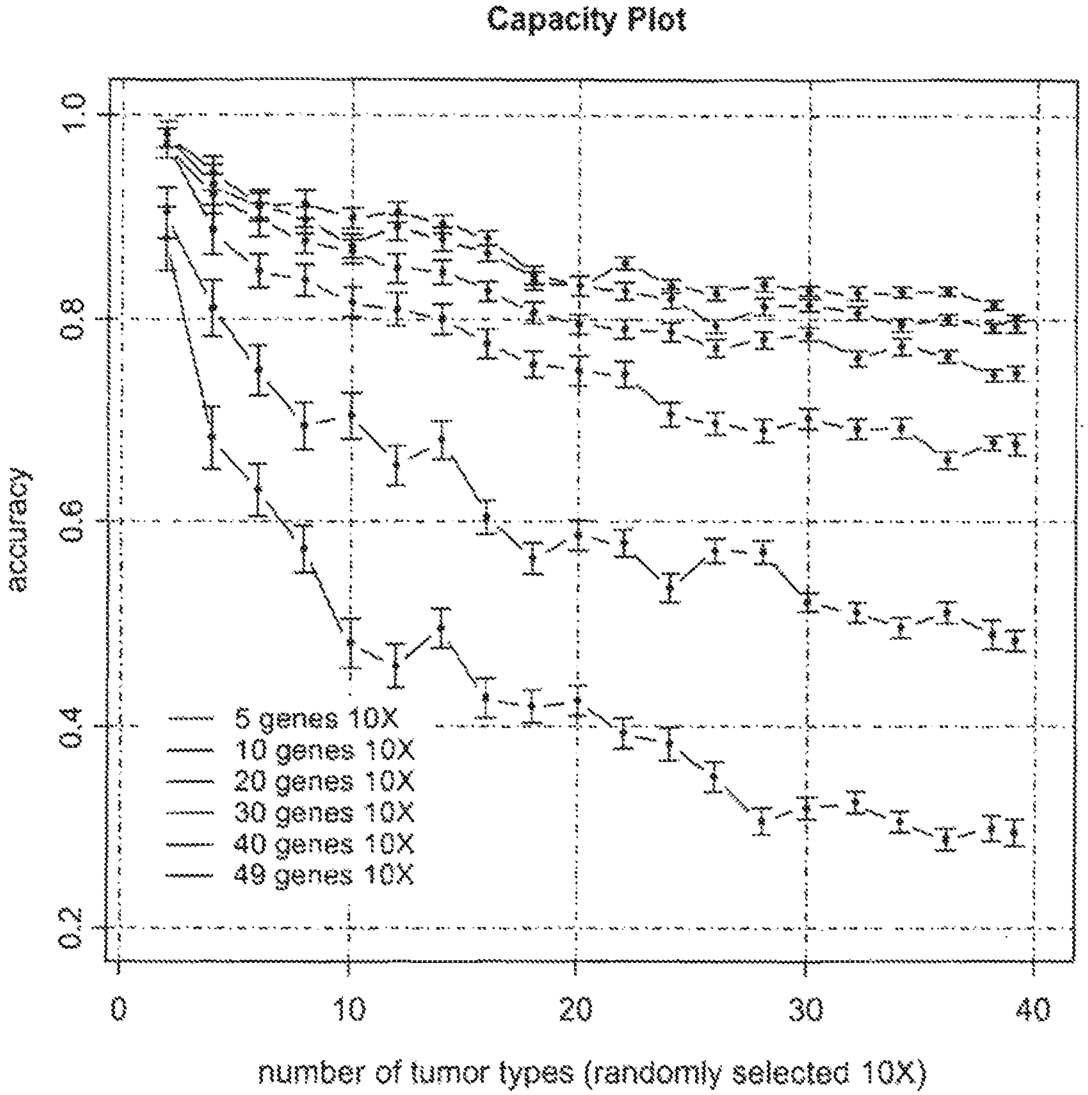
FIG. 7 shows a capacity plot for the ability to use the expression levels of subsets of a set of 90 expressed gene sequences to classify among 39 tumor types and subsets thereof. Expression levels of random combinations of 5, 10, 15, 20, 25, 30, 35, 40, 45, and 49 (each sampled times) of the 90 sequences were used with data from tumor types and then used to predict test random sets of tumor samples (each sampled 10 times) ranging from 2 to 39 types. A plot of numbers of tumor types versus prediction accuracies for results using fim 5 to 49 genes are shown as non-limiting examples. The plotted lines, from top to bottom, are of the results from 49, 40, 30, 20, 10, and gene sequences, respectively.
Figure 8:
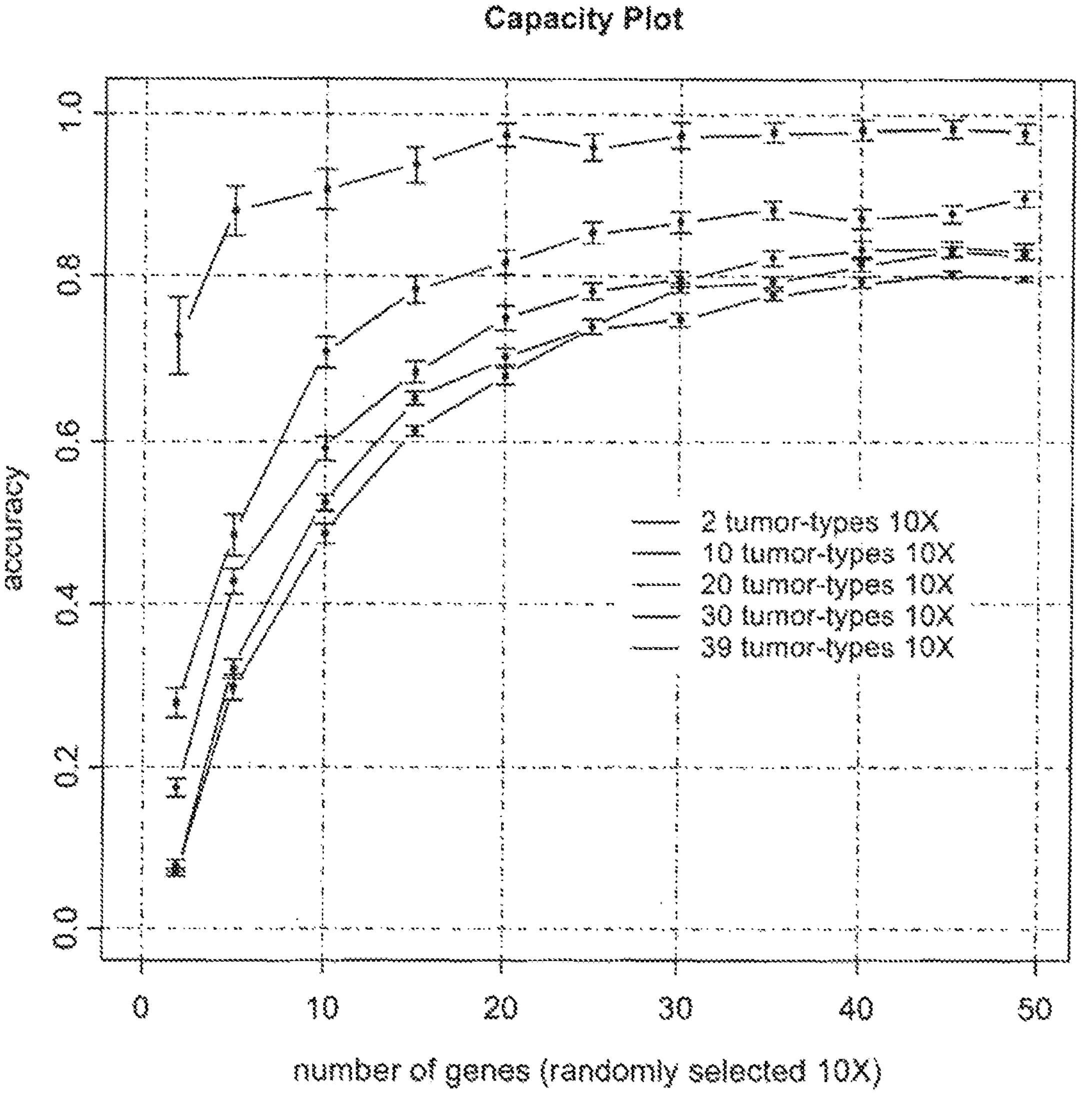
FIG. 8 shows an alternative presentation of the data used with respect to FIG. 7. A plot of numbers of gene sequences used, ranging from 5-49, versus prediction accuracies for various representative numbers of tumor types is shown. The plotted lines, from top to bottom, are of the results from 2, 10, 20, 30, and 39 tumor types, respectively.
Figure 9:
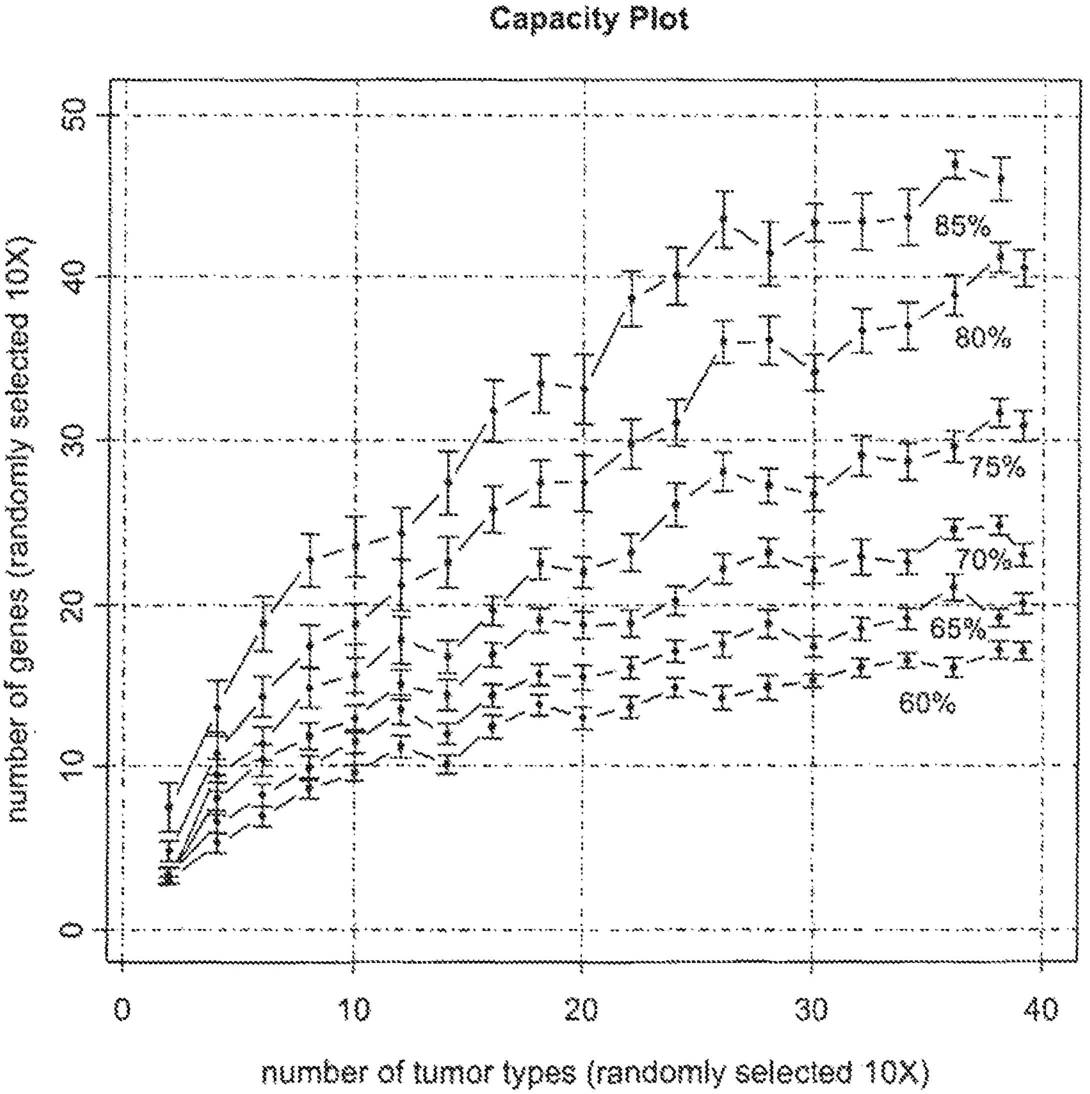
FIG. 9 is analogous to FIGS. 3 and 6 except with presentation of the data used with FIGS. 7 and 8.
Figure 10A:
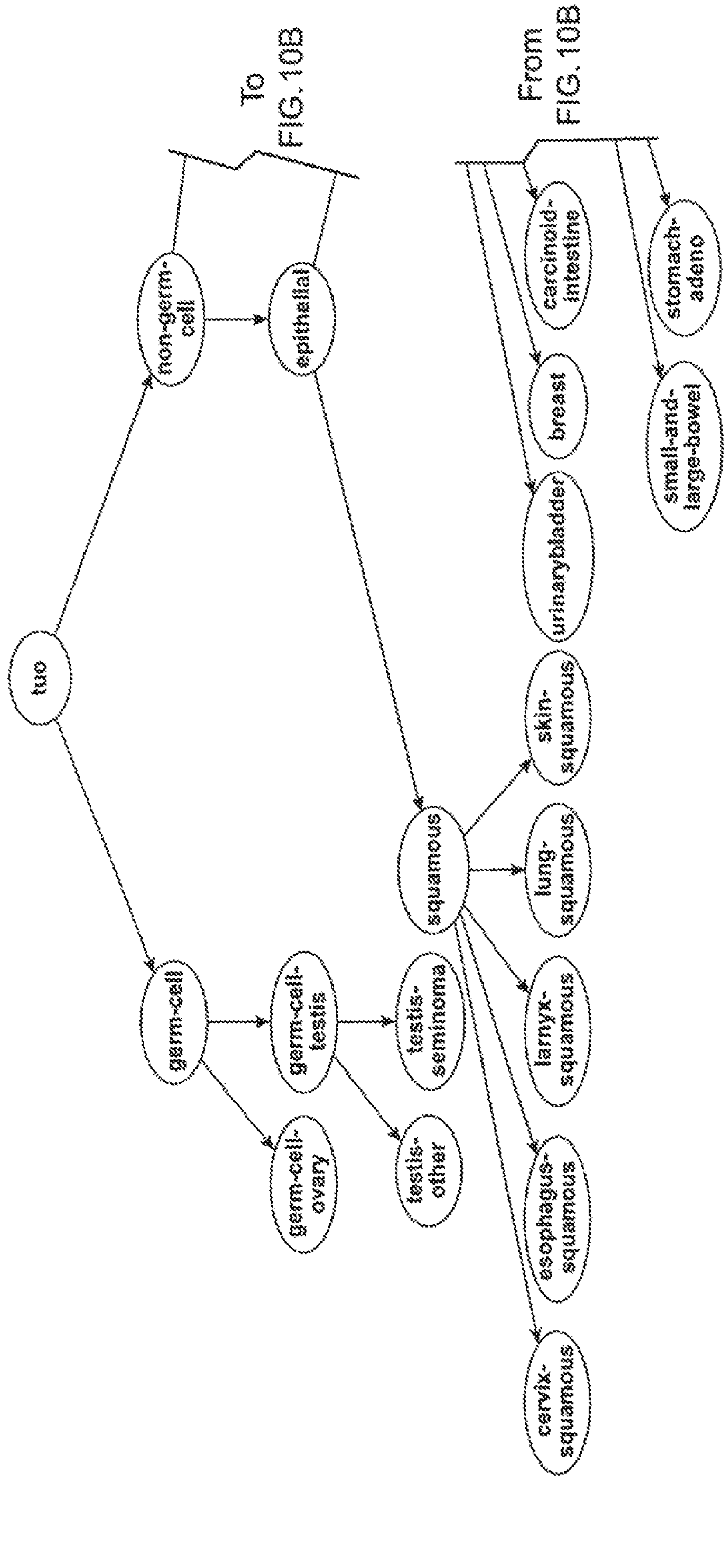
FIGS. 10A-10D show a "tree" that classifies tumor types covered herein as well as additional known tumor types. It was constructed mainly according to "Cancer, Principles and Practice of Oncology, (DeVito, Hellman and Rosenberg), $6^{th}$ edition". Thus beginning with a "tumor of unknown origin" (or "tuo"), the first possibilities are that it is either of a germ cell or non-germ cell origin. If it is the farmer, then it may be of ovary or testes origin. Within those of testes origin, the tumor may be of seminoma origin or an "other" origin.
Figure 10B:
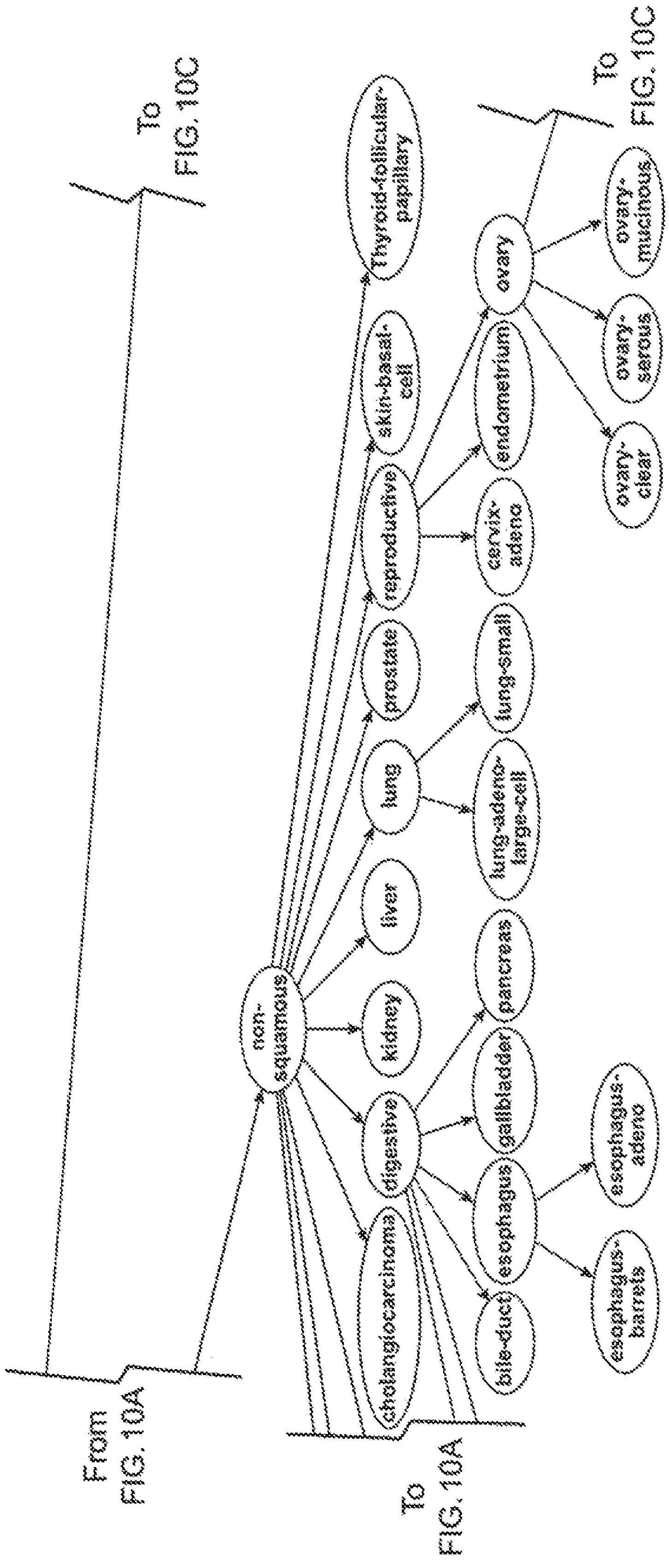
Figure 10C:
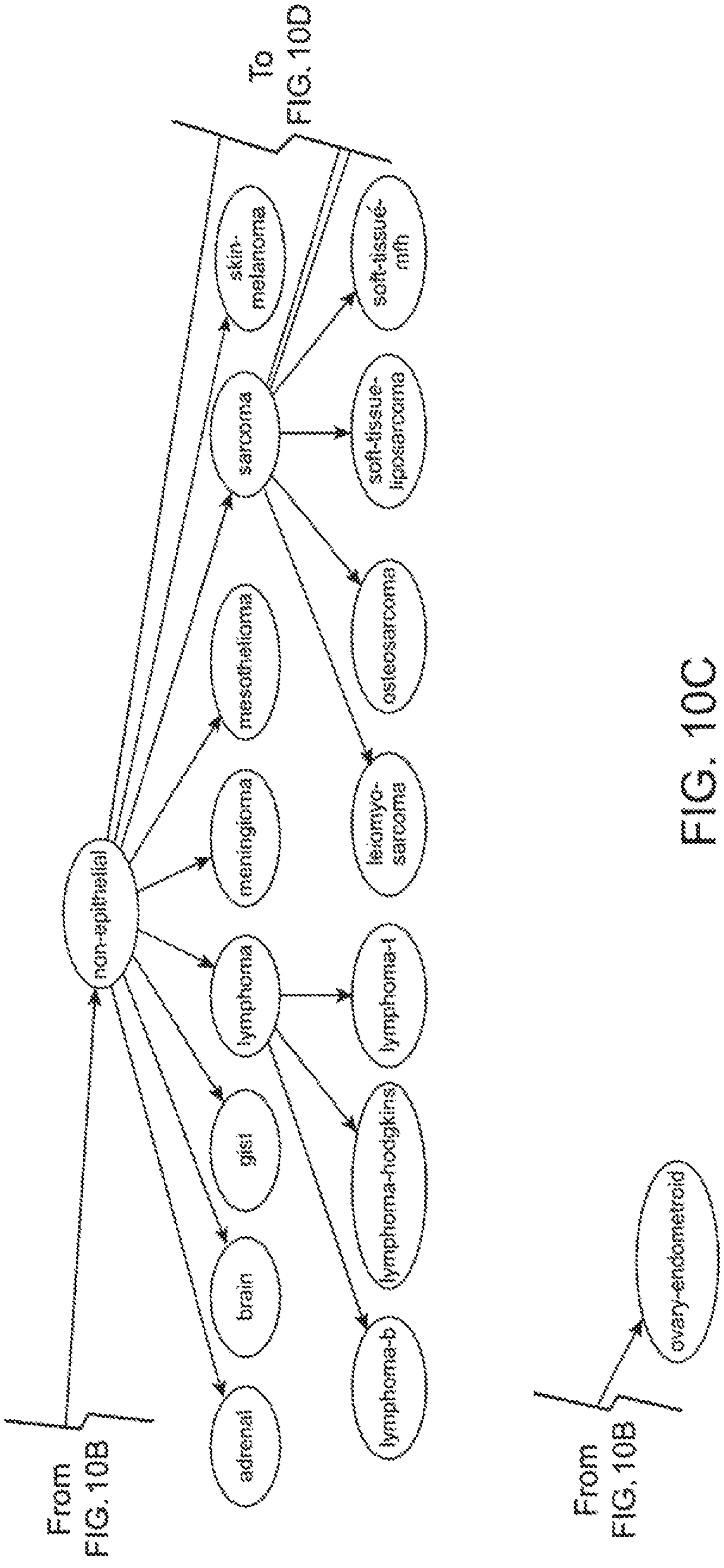
Figure 10D:
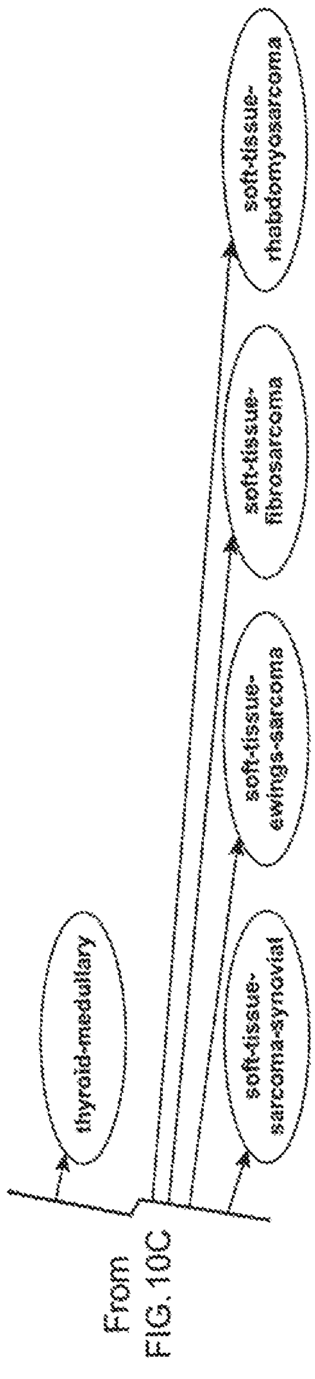

A similar experiment was performed with random subsets of about 5 to 49 members of the set of 90 expressed gene sequences. Again, the expression levels of random combinations of 5, 10, 15, 20, 25, 30, 35, 40, 45, and 49 (each combination sampled 10 times) of the 90 expressed sequences were used with data from tumor types and then used to predict test random sets of tumor samples (each sampled 10 times) ranging from 2 to all 39 types. The resulting data are shown in FIGS. 7-9.

The members of the 90 gene sequences were indexed from 1 to 90, and representative random sets used in the invention are as follows:

For 2 genes, set 1, genes 30 and 72 were used. For set 2, genes 65 and 88 were used. For set 3, genes 76 and 88 were used. For set 4, genes 5 and 86 were used. For set 5, genes and 32 were used. For set 6, genes 6 and 59 were used. For set 7, genes 57 and 2 were used. For set 8, genes 49 and 28 were used. For set 9, genes 37 and 35 were used. For set 10, genes 34 and 18 were used.

For 5 genes set 1, genes 1, 83, 59, 36, 66, and 88 were used. In set 2, genes 58, 13, 59, 22, and 64 were used. In set 3, genes 46, 72, 51, 88, and 14 were used. In set 4, genes 23, 74, 22, 27, and 20 were used. Inset 5, genes 58, 54, 78, 87, and 50 were used. Inset 6, genes 59, 6, 56, 78, and 9 were used. Inset 7, genes 30, 78, 69, 83, and 21 were used. Inset 8, genes 5, 39, 54, 56, and 55 were used. In set 9, genes 9, 70, 54, 67, and 43 were used. In set 10, genes 80, 81, 63, 90, and 53 were used.

For 10 genes, set 1, genes 70, 17, 45, 5, 2, 37, 6, 76, 39, and 14 were used. In set 2, genes 54, 16, 80, 26, 15, 45, 50, 8, 73, and 48 were used. In set 3, genes 66, 87, 31, 74, 37, 45, 19, 1, 70, and 7 were used. In set 4, genes 85, 17, 78, 61, 23, 59, 27, 18, 58, and 24 were used. In set 5, genes 44, 89, 36, 76, 49, 3, 21, 24, 38, and 69 were used. In set 6, genes 32, 72, 55, 2, 86, 81, 53, 45, 17, and 74 were used. In set 7, genes 27, 55, 62, 33, 32, 84, 21, 45, 23, and 7 were used. In set 8, genes 62, 45, 68, 31, 69, 39, 33, 63, 19, and 22 were used. In set 9, genes 71, 39, 11, 56, 88, 80, 37, 77, 62, and 35 were used. Inset 10, genes 38, 83, 41, 47, 66, 87, 10, 4, 88, and 22 were used.

For 15 genes, set 1, genes 61, 17, 64, 14, 1, 41, 72, 47, 69, 48, 49, 70, 12, 20, and 35 were used. Inset 2, genes 26, 49, 69, 31, 84, 42, 24, 56, 82, 12, 29, 2, 21, 15, and 71 were used. In set 3, genes 54, 62, 8, 32, 58, 65, 39, 44, 35, 22, 34, 77, 43, 83, and 75 were used. In set 4, genes 62, 50, 57, 80, 28, 83, 32, 56, 14, 2, 3, 48, 67, 79, and 72 were used. In set 5, genes 55, 58, 77, 68, 90, 76, 17, 72, 85, 34, 43, 33, 62, 6, and 64 were used. In set 6, genes 41, 63, 90, 9, 25, 35, 2, 14, 65, 87, 11, 36, 10, 79, and 17 were used. In set 7, genes 69, 89, 77, 33, 71, 4, 6, 46, 72, 13, 68, 81, 31, 50, and 32 were used. In set 8, genes 29, 69, 34, 47, 32, 52, 63, 73, 23, 25, 33, 10, 37, 17, and 55 were used. In set 9, genes 24, 13, 45, 17, 51, 48, 20, 30, 29, 40, 53, 19, 88, 76, and 28 were used. In set 10, genes 86, 33, 19, 4, 84, 25, 78, 29, 88, 10, 7, 67, 85, 45, and 8 were used.

For 20 genes, set 1, genes 57, 78, 43, 50, 14, 71, 56, 25, 80, 31, 88, 4, 49, 13, 3, 38, 32, 8, 52, and 75 were used. In set 2, genes 84, 46, 23, 85, 55, 82, 56, 83, 48, 89, 8, 60, 21, 40, 20, 17, 87, 24, 34, and 39 were used. In set 3, genes 72, 88, 53, 46, 82, 9, 34, 21, 76, 24, 14, 35, 90, 31, 58, 30, 15, 41, 7, and 28 were used. Inset 4, genes 22, 62, 21, 3, 45, 50, 58, 72, 69, 82, 49, 42, 47, 9, 15, 59, 17, 24, 40, and 52 were used. In set 5, genes 71, 18, 74, 53, 43, 75, 76, 54, 63, 64, 10, 5, 90, 51, 31, 58, 28, 35, 70, and 23 were used. In set 6, genes 7, 30, 77, 25, 17, 16, 35, 68, 56, 37, 78, 87, 45, 8, 42, 82, 72, 23, 58, and 54 were used. In set 7, genes 3, 58, 67, 5, 87, 62, 56, 88, 73, 50, 22, 52, 10, 60, 57, 42, 46, 26, 7, and 82 were used. In set 8, genes 63, 19, 22, 13, 82, 12, 44, 52, 8, 90, 35, 81, 79, 15, 83, 76, 51, 27, 45, and 56 were used. In set 9, genes 65, 34, 76, 81, 58, 86, 83, 46, 40, 55, 48, 42, 57, 70, 21, 72, 71, 17, 22, and 24 were used. In set 10, genes 34, 74, 2, 53, 76, 73, 19, 72, 88, 87, 44, 70, 40, 39, 22, 45, 83, 77, 30, and 46 were used.

For 25 genes, set 1, genes 13, 77, 22, 85, 58, 8, 23, 2, 40, 81, 50, 31, 14, 41, 21, 52, 6, 74, 11, 17, 83, 7, 9, 19, 18 were used. In set 2, genes 3, 12, 8, 87, 34, 75, 31, 88, 77, 39, 40, 60, 54, 9, 37, 5, 51, 53, 32, 35, 66, 4, 26, 59, and 29 were used. Inset 3, genes 29, 41, 44, 56, 88, 72, 90, 6, 19, 63, 42, 24, 49, 70, 39, 17, 82, 13, 9, 4, 51, 40, 22, 71, and 25 were used. In set 4, genes 70, 82, 55, 43, 40, 32, 16, 13, 22, 41, 7, 85, 46, 42, 73, 76, 14, 60, 50, 72, 5, 81, 67, 57, and 83 were used. In set 5, genes 88, 83, 53, 26, 29, 4, 38, 71, 11, 66, 14, 89, 39, 34, 84, 41, 7, 64, 87, 3, 67, 43, 50, 79, and 6 were used. In set 6, genes 88, 16, 83, 4, 7, 39, 56, 82, 10, 20, 87, 79, 3, 35, 76, 49, 43, 11, 74, 13, 48, 22, 64, 34, and 89 were used. In set 7, genes 6, 64, 39, 50, 44, 46, 61, 28, 79, 43, 35, 85, 48, 9, 59, 47, 57, 5, 24, 33, 80, 11, 42, 20, and 26 were used. In set 8, genes 59, 24, 46, 33, 50, 71, 53, 21, 86, 10, 75, 23, 74, 60, 43, 22, 16, 62, 85, 79, 81, 34, 73, 2, and 1 were used. In set 9, genes 68, 11, 64, 54, 37, 28, 44, 73, 83, 89, 2, 41, 59, 75, 21, 23, 88, 71, 34, 29, 1, 47, 84, 60, and 72 were used. In set 10, genes 5, 12, 60, 84, 32, 58, 70, 2, 38, 42, 24, 13, 85, 10, 49, 90, 55, 81, 39, 27, 65, 56, 31, 34, and 57 were used.

For 30 genes, set 1, genes 24, 88, 10, 69, 64, 8, 19, 54, 80, 70, 11, 9, 29, 56, 36, 79, 30, 65, 2, 58, 23, 74, 41, 16, 77, 4, 78, 14, 85, and 32 were used. In set 2, genes 73, 27, 19, 52, 87, 51, 63, 4, 76, 64, 90, 81, 42, 47, 9, 62, 40, 65, 83, 30, 39, 59, 10, 11, 54, 44, 43, 6, 86, and 41 were used. In set 3, genes 28, 47, 41, 8, 24, 54, 26, 49, 61, 17, 46, 64, 20, 16, 1, 33, 82, 79, 85, 5, 86, 69, 31, 65, 83, 7, 67, 35, 48, and 57 were used. In set 4, genes 13, 21, 83, 35, 47, 57, 8, 66, 75, 17, 38, 70, 39, 23, 9, 1, 2, 28, 68, 81, 36, 80, 52, 22, 44, 37, 85, 15, 72, and 86 were used. In set 5, genes 81, 20, 36, 89, 13, 14, 46, 58, 59, 62, 28, 7, 1, 25, 35, 83, 26, 50, 51, 15, 16, 56, 71, 5, 47, 6, 78, 80, 85, and 84 were used. In set 6, genes 68, 74, 73, 89, 38, 72, 33, 35, 15, 79, 3, 37, 23, 67, 10, 62, 64, 77, 44, 60, 75, 7, 51, 12, 46, 76, 81, 26, 42, and 6 were used. Inset 7, genes 34, 55, 62, 40, 78, 35, 76, 30, 21, 77, 46, 71, 66, 69, 63, 81, 51, 38, 84, 53, 82, 89, 29, 14, 36, 45, 60, 7, 52, and 27 were used. In set 8, genes 56, 12, 35, 79, 57, 4, 16, 9, 24, 58, 40, 72, 80, 67, 23, 76, 88, 69, 52, 78, 32, 47, 14, 46, 64, 83, 17, 59, 81, and 20 were used. In set 9, genes 73, 27, 12, 58, 54, 62, 48, 43, 16, 41, 49, 84, 9, 75, 13, 50, 19, 3, 76, 78, 56, 68, 71, 25, 24, 60, 18, 35, 45, and 51 were used. In set 10, genes 82, 21, 24, 85, 51, 18, 72, 28, 89, 22, 34, 4, 53, 75, 83, 23, 50, 5, 42, 13, 88, 63, 40, 64, 38, 35, 39, 44, 59, and 70 were used.

For 35 genes, set 1, genes 2, 69, 70, 89, 9, 11, 5, 17, 63, 18, 12, 59, 58, 85, 26, 71, 61, 10, 3, 1, 22, 79, 84, 30, 48, 82, 38, 44, 56, 42, 88, 6, 60, 14, and 28 were used. In set 2, genes 84, 81, 88, 46, 12, 50, 38, 78, 62, 48, 19, 43, 26, 66, 4, 20, 40, 58, 9, 52, 87, 47, 6, 55, 21, 75, 31, 77, 57, 53, 45, 34, 30, 32, and 39 were used. Inset 3, genes 6, 3, 22, 89, 8, 78, 87, 71, 42, 63, 18, 40, 68, 77, 64, 88, 5, 58, 43, 72, 80, 10, 21, 56, 11, 59, 61, 2, 19, 76, 30, 20, 14, 69, and 35 were used. In set 4, genes 55, 42, 89, 41, 56, 33, 24, 28, 15, 61, 63, 18, 90, 60, 35, 76, 70, 52, 8, 1, 64, 23, 13, 39, 71, 31, 3, 81, 10, 34, 66, 44, 16, 7, and 78 were used. In set 5, genes 59, 58, 12, 50, 47, 42, 28, 22, 76, 54, 1, 18, 7, 53, 68, 73, 20, 67, 14, 72, 23, 13, 39, 10, 70, 55, 45, 17, 31, 51, 80, 3, 24, 30, and 46 were used. Inset 6, genes 53, 66, 26, 3, 73, 47, 61, 63, 51, 41, 29, 5, 19, 10, 57, 22, 64, 11, 34, 89, 43, 24, 31, 60, 27, 76, 17, 86, 70, 81, 50, 46, 36, 14, and 45 were used. In set 7, genes 18, 88, 90, 13, 73, 81, 64, 56, 84, 2, 4, 22, 3, 25, 35, 54, 89, 86, 27, 41, 6, 34, 38, 14, 74, 36, 59, 8, 40, 55, 42, 83, 39, 44, and 60 were used. In set 8, genes 46, 32, 22, 15, 67, 89, 14, 5, 70, 39, 49, 9, 84, 71, 12, 78, 27, 86, 26, 57, 20, 43, 58, 87, 42, 8, 31, 1, 54, 62, 69, 40, 29, 52, and 64 were used. Inset 9, genes 3, 39, 55, 25, 90, 10, 9, 77, 62, 78, 18, 12, 58, 51, 22, 67, 7, 61, 59, 35, 52, 4, 65, 38, 32, 71, 87, 88, 63, 50, 73, 70, 44, 45, and 84 were used. Inset 10, genes 65, 54, 51, 38, 40, 5, 43, 71, 34, 30, 22, 6, 36, 64, 63, 13, 70, 85, 21, 88, 77, 86, 79, 66, 25, 18, 26, 19, 76, 56, 23, 60, 75, 2, and 49 were used.

For 40 genes, set 1, genes 81, 80, 68, 77, 17, 71, 34, 33, 48, 88, 90, 32, 23, 2, 38, 59, 75, 82, 50, 56, 12, 36, 6, 87, 72, 37, 26, 15, 35, 66, 13, 76, 55, 3, 78, 18, 52, 47, 73, and 20 were used. In set 2, genes 11, 65, 27, 44, 88, 49, 55, 57, 1, 72, 9, 28, 56, 67, 13, 58, 42, 36, 8, 31, 40, 14, 26, 35, 62, 22, 19, 84, 78, 21, 2, 41, 74, 71, 52, 30, 25, 76, 85, and 63 were used. In set 3, genes 50, 22, 10, 54, 9, 51, 15, 34, 29, 35, 76, 89, 33, 6, 88, 56, 36, 70, 87, 40, 83, 62, 1, 42, 25, 78, 30, 26, 44, 60, 69, 47, 49, 31, 18, 59, 37, 52, 61, and 17 were used. Inset 4, genes 27, 33, 7, 89, 36, 59, 48, 42, 66, 39, 90, 52, 2, 14, 30, 80, 9, 56, 21, 87, 65, 67, 41, 73, 82, 20, 4, 46, 5, 84, 88, 15, 44, 58, 78, 85, 3, 64, 6, and 8 were used. In set 5, genes 43, 24, 86, 29, 46, 90, 40, 1, 71, 57, 12, 84, 69, 19, 42, 62, 28, 35, 5, 63, 52, 17, 39, 4, 67, 81, 50, 47, 61, 54, 87, 70, 77, 6, 10, 38, 37, 79, 31, and 36 were used. In set 6, genes 28, 5, 78, 85, 16, 20, 36, 52, 43, 29, 67, 83, 12, 79, 84, 8, 81, 46, 11, 3, 54, 86, 10, 60, 71, 51, 39, 53, 59, 69, 44, 61, 7, 56, 27, 50, 66, 70, 1, and 25 were used. Inset 7, genes 39, 47, 48, 24, 25, 3, 41, 16, 65, 73, 63, 14, 70, 57, 12, 64, 90, 23, 27, 38, 66, 71, 54, 21, 83, 28, 72, 53, 11, 30, 80, 15, 6, 88, 89, 85, 81, 61, 78, and 34 were used. Inset 8, genes 61, 8, 57, 16, 24, 64, 48, 36, 58, 28, 27, 40, 70, 77, 25, 76, 52, 35, 62, 4, 60, 7, 54, 37, 11, 20, 72, 34, 56, 78, 10, 86, 51, 29, 84, 47, 30, 21, 59, and 67 were used. In set 9, genes 67, 3, 83, 33, 35, 26, 25, 79, 68, 19, 18, 84, 14, 58, 66, 57, 1, 2, 27, 64, 23, 24, 76, 81, 17, 37, 38, 30, 45, 75, 49, 39, 5, 53, 43, 15, 51, 40, 69, and 12 were used. In set 10, genes 39, 77, 29, 70, 85, 45, 54, 79, 31, 43, 15, 11, 47, 83, 76, 21, 67, 14, 4, 19, 49, 42, 18, 13, 12, 7, 88, 8, 3, 35, 81, 55, 71, 60, 72, 57, 46, 40, 56, and 32 were used.

For 45 genes, set 1, genes 7, 63, 45, 87, 19, 55, 36, 42, 9, 4, 79, 68, 46, 35, 40, 80, 59, 58, 38, 17, 50, 30, 13, 39, 33, 84, 34, 64, 2, 57, 24, 88, 65, 16, 53, 18, 28, 8, 60, 15, 43, 73, 77, 20, and 78 were used. In set 2, genes 70, 19, 81, 68, 38, 35, 48, 9, 53, 11, 73, 42, 54, 28, 32, 40, 60, 88, 25, 7, 67, 17, 36, 51, 44, 46, 10, 89, 14, 80, 39, 41, 27, 8, 75, 47, 61, 57, 59, 76, 86, 65, 63, 74, and 77 were used. In set 3, genes 55, 24, 63, 17, 32, 81, 2, 67, 51, 85, 27, 46, 60, 90, 25, 35, 58, 11, 47, 33, 73, 3, 74, 52, 15, 86, 6, 78, 36, 66, 57, 13, 49, 28, 75, 70, 4, 77, 43, 26, 61, 64, 20, 1, and 23 were used. In set 4, genes 49, 72, 13, 51, 55, 11, 29, 5, 43, 44, 40, 6, 38, 67, 47, 35, 36, 28, 81, 24, 80, 32, 16, 88, 63, 87, 86, 79, 21, 1, 30, 10, 62, 58, 23, 12, 78, 26, 69, 56, 85, 42, 17, 84, and 39 were used. In set 5, genes 53, 33, 18, 65, 22, 83, 50, 88, 76, 40, 82, 68, 85, 5, 63, 45, 78, 16, 42, 54, 27, 66, 70, 74, 7, 51, 89, 64, 49, 37, 84, 86, 34, 39, 80, 31, 61, 87, 69, 4, 81, 30, 14, 41, and 29 were used. In set 6, genes 7, 60, 38, 14, 73, 9, 79, 81, 22, 10, 85, 51, 40, 87, 3, 26, 57, 56, 12, 72, 39, 59, 63, 28, 64, 71, 69, 21, 67, 48, 50, 66, 46, 88, 11, 13, 24, 8, 58, 75, 2, 41, 5, 44, and 55 were used. In set 7, genes 15, 65, 31, 19, 11, 38, 2, 9, 64, 66, 22, 35, 49, 3, 77, 43, 32, 56, 39, 54, 80, 21, 6, 40, 27, 86, 10, 16, 70, 30, 85, 23, 26, 4, 55, 73, 42, 13, 41, 68, 29, 57, 28, 72, and 58 were used. In set 8, genes 83, 27, 9, 62, 84, 78, 13, 5, 74, 55, 12, 34, 58, 3, 67, 57, 24, 45, 42, 47, 75, 25, 29, 44, 46, 61, 56, 70, 86, 37, 14, 49, 60, 89, 28, 72, 59, 38, 2, 81, 50, 7, 6, 21, and 82 were used. Inset 9, genes 7, 10, 35, 14, 79, 66, 33, 52, 16, 55, 68, 59, 57, 19, 11, 47, 22, 38, 61, 30, 71, 50, 63, 88, 53, 80, 6, 54, 77, 21, 37, 84, 9, 65, 12, 49, 40, 73, 76, 2, 28, 29, 3, 72, and 18 were used. Inset 10, genes 12, 19, 9, 80, 84, 15, 7, 2, 39, 21, 48, 40, 51, 69, 74, 83, 5, 66, 27, 26, 89, 60, 4, 86, 41, 44, 35, 10, 76, 53, 63, 16, 37, 79, 11, 42, 68, 3, 59, 82, 77, 73, 85, 67, and 14 were used.

For 49 genes, set 1, genes 84, 47, 56, 1, 18, 21, 57, 54, 27, 89, 44, 85, 64, 10, 77, 34, 65, 66, 80, 70, 46, 23, 53, 61, 24, 81, 43, 35, 30, 74, 83, 51, 20, 17, 72, 4, 49, 68, 60, 28, 67, 19, 42, 55, 73, 36, 7, 39, and 33 were used. Inset 2, genes 47, 29, 58, 36, 21, 53, 40, 7, 83, 77, 24, 89, 71, 64, 60, 4, 37, 86, 27, 57, 62, 63, 72, 1, 88, 78, 68, 17, 51, 16, 82, 42, 81, 18, 32, 49, 55, 10, 11, 66, 35, 23, 70, 20, 61, 25, 48, 43, and 54 were used. Inset 3, genes 54, 2, 62, 67, 44, 25, 8, 53, 86, 33, 75, 32, 45, 76, 43, 65, 59, 58, 42, 64, 47, 78, 3, 57, 71, 88, 14, 23, 51, 83, 1, 41, 7, 56, 40, 20, 39, 72, 70, 19, 5, 35, 50, 82, 37, 48, 15, 31, and 16 were used. Inset 4, genes 35, 65, 48, 43, 69, 62, 64, 74, 82, 39, 37, 1, 88, 45, 66, 12, 79, 55, 38, 84, 17, 30, 25, 26, 89, 56, 28, 57, 59, 34, 85, 14, 47, 44, 41, 19, 60, 20, 73, 2, 63, 75, 49, 80, 58, 77, 27, 54, and 29 were used. In set 5, genes 64, 51, 36, 12, 84, 24, 65, 47, 88, 26, 10, 19, 73, 90, 35, 53, 18, 55, 80, 70, 79, 82, 87, 77, 15, 85, 83, 7, 72, 1, 6, 57, 38, 45, 74, 33, 62, 86, 31, 69, 27, 14, 4, 29, 54, 44, 63, 78, and 42 were used. In set 6, genes 24, 39, 85, 42, 88, 32, 65, 23, 6, 75, 53, 77, 64, 90, 13, 82, 47, 31, 48, 8, 78, 67, 63, 44, 26, 40, 14, 34, 18, 59, 2, 17, 20, 56, 83, 68, 86, 9, 38, 73, 89, 55, 29, 69, 72, 16, 28, 51, and 81 were used. In set 7, genes 32, 70, 57, 67, 1, 73, 52, 38, 65, 83, 5, 40, 49, 31, 66, 85, 6, 82, 12, 48, 89, 3, 19, 41, 62, 16, 46, 61, 24, 18, 55, 30, 33, 56, 68, 20, 81, 10, 86, 9, 15, 63, 78, 22, 75, 14, 13, 43, and 77 were used. In set 8, genes 17, 30, 47, 85, 7, 3, 6, 35, 76, 77, 25, 86, 36, 75, 44, 29, 69, 60, 63, 64, 82, 51, 19, 68, 41, 28, 73, 18, 10, 26, 42, 78, 67, 12, 80, 33, 13, 57, 38, 87, 49, 59, 74, 50, 90, 46, 8, 81, and 4 were used. In set 9, genes 20, 76, 42, 36, 66, 21, 8, 28, 22, 15, 56, 5, 2, 86, 17, 62, 23, 1, 80, 73, 52, 83, 32, 65, 44, 82, 35, 60, 47, 90, 74, 9, 84, 50, 4, 77, 55, 57, 19, 71, 25, 48, 81, 53, 34, 38, 3, 37, and 16 were used. Inset 10, genes 84, 87, 3, 41, 36, 71, 33, 57, 85, 26, 53, 22, 82, 31, 2, 45, 24, 18, 37, 35, 77, 20, 63, 25, 6, 17, 58, 7, 9, 49, 28, 76, 79, 67, 13, 80, 66, 5, 43, 4, 74, 75, 21, 86, 23, 39, 42, 27, and 54 were used.

Example 5: PCR Based Detection

As noted above, the determination or measurement of gene expression may be performed by PCR, such as the use of quantitative PCR. Detecting expression of about 5 to 49 expressed sequences in the human genome may be used in such embodiments of the invention. Additionally, expression levels of about 5 to 49 gene sequences in the set of 74, the set of 90, or a combination set of the two (with a total of 126 gene sequences given the presence of 38 gene sequences in common between the two sets) may also be used. The invention contemplates the use of quantitative PCR to measure expression levels, as described above, of about 5 to 49 of 87 gene sequences, all of which are present in either the set of 74 or the set of 90. Of the 87 gene sequences, 60 are present in the set of 74, and 63 are present in the set of 90. The identifiers/accession numbers of the 87 gene sequences are AA456140, AA745593, AA765597, AA782845, AA865917, AA946776, AA993639, AB038160, AF104032, AF133587, AF301598, AF332224. A1041545, A1147926, A1309080, A1341378, A1457360, A1620495, A1632869, A1683181, A1685931, A1802118, A1804745, A1952953, A1985118, AJ000388, AK025181, AK027147, AK054605, AL023657, AL039118, AL110274, AL157475, AW118445, AW194680, AW291189, AW298545, AW445220, AW473119, AY033998, BC000045, BC001293, BC001504, BC001639, BC002551, BC004331, BC004453, BC005364, BC006537, BC006811, BC006819, BC008764, BC008765, BC009084, BC009237, BC010626, BC011949, BC012926, BC013117. BC015754, BC017586, BE552004, BE962007, BF224381, BF437393, BF446419, BF592799. B1493248, H05388, H07885, H09748, M95585, N64339, NM_000065, NM 001337, NM_003914, NM 004062, NM 004063, NM_0044%, NM_006115, NM 019894, NM_033229. R15881, R45389, R61469, X69699, and X96757.

The use of from about 5 to 49 of these sequences in the practice of the invention may include the use of expression levels measured for reference gene sequences as described herein. In some embodiments, the reference gene sequences are one or more of the 8 disclosed herein. The invention contemplates the use of one or more of the reference sequences identified by AF308803, AL137727, BC003043, BC006091, and BC016680 in PCR or QPCR based embodiments of the invention. Of course all 5 of these reference sequences may also be used in combination.

Example 6: mRNA Sequences (Sequence Listing)

```
>Hs.73995_mRNA_1 gi|190403|gb|M60502.1|HUMPROFILE Human profilaggrin mRNA,
3' end polyA = 1
GGCCACTCTGCAGACAGCTCCAGACAATCAGGCACTCGTCACACAGAGTCTTCCTCTCGT
GGACAGGCTGCGTCATCCCATGAACAGGCAAGATCAAGTGCAGGAGAAAGACATGGATCC
CACCACCAGCAGTCAGCAGACAGCTCCAGACACGCAGGCATTGGGCACGGACAAGCTTCA
TCTGCAGTCAGAGACAGTGGACACCGAGGGTACAGAGGTAGTCAGGCCACTGACAGTGAG
GGACATTCAGAAGACTCAGACACACAGTCAGTGTCAGCACAGGGACAAGCTGGGCCCCAT
CAGCAGAGCCACCAAGAGTCCGCACGTGGCCAGTCAGGGGAAAGCTCTGGACGTTCAGGG
TCTTTCCTCTACCAGGTGAGCACTCATGAACAGTCTGAGTCCACCCATGGACAGTCTGTG
CCCAGCACTGGAGGAAGACAAGGATCCCACCATGATCAGGCACAAGACAGCTCCAGGCAC
TCAGCATCCCAAGAGGGTCAGGACACCATTCGTGGACACCCGGGGCCAAGCAGAGGAGGA
AGACAGGGGTCCCACCACGAGCAATCGGTAGATAGGTCTGGACACTCAGGGTCCCATCAC
AGCCACACCACATCCCAGGGAAGGTCTGATGCCTCCCGTGGGCAGTCAGGATCCAGAAGT
GCAAGCAGACAAACACATGACCAGGAACAATCAGGAGACGGCTCTAGGCACTCAGGGTCG
CGTCATCAGGAAGCTTCCTCTTGGGCCGACAGCTCTAGACACTCACAGGCAGTCCAGGGA
CAATCAGAGGGGTCCAGGACAAGCAGGCGCCAGGGATCCAGTGTTAGCCAGGACAGTGAC
AGTCAGGGACACTCAGAAGACTCTGAGAGGCGGTCTGGGTCTGCTTCCAGAAACCATCGT
GGATCTGCTCAGGAGCAGTCAAGAGATGGCTCCAGACACCCCAGGTCCCATCACGAAGAC
AGAGCCGGTCACGGGGACTCTGCAGAGAGCTCCAGACAATCAGGCACTCATCATGCAGAG
AATTCCTCTGGTGGACAGGCTGCATCATCCCATGAACAGGCAAGATCAAGTGCAGGAGAG
AGACATGGATCCCACTACCAGCAGTCAGCAGACAGCTCCAGACACTCAGGCATTGGGCAC
GGACAAGCTTCATCTGCAGTCAGAGACAGTGGACACCGAGGGTCCAGTGGTAGTCAGGCC
AGTGACAATGAGGGACATTCAGAAGACTCAGACACACAGTCAGTGTCAGCCCACCGACAG
GCTGGGCGCCATCACGAGAGCCACCAAGAGTCCACACGTGGCCGGTCACGAGGAAGGTCT
GGACGTTCAGGGTCTTTCCTCTACCAGGTGAGCACTCATGAACAGTCTGAGTCTGCCCAT
GGACGGGCTGGGCCCAGTACTGGAGGAAGACAAGGATCCCGCCACGAGCAGGCACGAGAC
AGCTCCAGGCACTCAGCGTCCCAAGAGGGTCAGGACACCATTCGTGGACACCCGGGGTCA
AGGAGAGGAGGAAGACAGGGATCCTACCACGAGCAATCGGTAGATAGGTCTGGACACTCA
GGGTCCCATCACAGCCACACCACATCCCAGGGAAGGTCTGATGCCTCCCATGGGCAGTCA
GGATCCAGAAGTGCAAGCAGAGAAACACGTAATGAGGAACAGTCAGGAGACGGCTCCAGG
CACTCAGGGTCGCGTCACCATGAAGCTTCCACTCAGGCTGACAGCTCTAGACACTCACAG
TCCGGCCAGGGTGAATCAGCGGGGTCCAGGAGAAGCAGGCGCCAGGGATCCAGTGTTAGC
CAGGACAGTGACAGTGAGGCATACCCAGAGGACTCTGAGAGGCGATCTGAGTCTGCTTCC
AGAAACCATCATGGATCTTCTCGGGAGCAGTCAAGAGATGGCTCCAGACACCCCGGATCC
TCTCACCGCGATACAGCCAGTCATGTACAGTCTTCACCTGTACAGTCAGACTCTAGTACC
GCTAAGGAACATGGTCACTTTAGTAGTCTTTCACAAGATTCTGCGTATCACTCAGGAATA
CAGTCACGTGGCAGTCCTCACAGTTCTAGTTCTTATCATTATCAATCTGAGGGCACTGAA
AGGCAAAAAGGTCAATCAGGTTTAGTTTGGAGACATGGCAGCTATGGTAGTGCAGATTAT
GATTATGGTGAATCCGGGTTTAGACACTCTCAGCACGGAAGTGTTAGTTACAATTCCAAT
CCTGTTCTTTTCAAGGAAAGATCTGATATCTGTAAAGCAAGTGCGTTTGGTAAAGATCAT
CCAAGGTATTATGCAACGTATATTAATAAGGACCCAGGTTTATGTGGCCATTCTAGTGAT
ATATCGAAACAACTGGGATTTAGTCAGTCACAGAGATACTATTACTATGAGTAAGAAATT
AATGGCAAAGGAATTAATCCAAGAATAGAAGAATGAAGCAAGTTCACTTTCAATCAAGAA
ACTTCATAATACTTTCAGGGAAGTTATCTTTTCCTGTCAATCTGTTTAAAATATGCTATA
GTATTTCATTAGTTTGGTGGTAACTTATTTTTATTGTGTAATGATCTTTAAACGCTATAT
TTCAGAAATATTAAATGGAAGAAATCAATATCATGGAGAGCTAACTTTAGAAAACTAGCT
```

-continued

GGAGTATTTTAGGAGATTCTGGGTCAAGTAATGTTTTATGTTTTTGAAAGTTTAAGTTTT
AGACACTCCCCAAATTTCTAAATTAATCTTTTTCAGAAATATCGAAGGAGCCAAAAATAT
AAAACAGTTCTGATATCCAAAGTGGCTATATCAACATCAGGGCTAGCACATCTTTCTCTA
TTATCCTTCTATTGGAATTCTAGTATTCTGTATTCAAAAAATCATCTTGGACATAATTAA
TATTTTAGTAAGCTGCATCTAAATTAAAAATAAACTATTCATCATATAAT

>Hs.75236_mRNA_4 gi|14280328|gb|AY033998.1| *Homo sapiens* polyA = 3
TAGAATCGGGGGTTTCAGCTCACTGCTCCTTTTCTTTTTTTTCTTTCTCTCCCCCGCCCA
CCCCCCCAAAAATAATTGATTTGCTTTACAATCATCCACACTGTGTTTTGTGGATCTTTA
ATTATATATAACAATAGTAGTCATTTTAAATATATATTCTGAAATCTTTGCAAATTTTAA
CAGAAGAGTCGAAGCTCTGCGAGACCCAATATTTGCCAATAAGAATGGTTATGATAATTA
GCACCATGGAGCCTCAGGTGTCAAATGGTCCGACATCCAATACAAGCAATGGACCCTCCA
GCAACAACAGAAACTGTCCTTCTCCCATGCAAACAGGGGCAACCACAGATGACAGCAAAA
CCAACCTCATCGTCAACTATTTACCCCAGAATATGACCCAAGAAGAATTCAGGAGTCTCT
TCGGGAGCATTGGTGAAATAGAATCCTGCAAACTTGTGAGAGACAAAATTACAGGACAGA
GTTTAGGGTATGGATTTGTTAACTATATTGATCCAAAGGATGCAGAGAAAGCCATCAACA
CTTTAAATGGACTCAGACTCCAGACCAAAACCATAAAGGTCTCATATGCCCGTCCGAGCT
CTGCCTCAATCAGGGATGCTAACCTCTATGTTAGCGGCCTTCCCAAAACCATGACCCAGA
AGGAACTGGAGCAACTTTTCTCGCAATACGGCCGTATCATCACCTCACGAATCCTGGTTG
ATCAAGTCACAGGAGTGTCCAGAGGGGTGGGATTCATCCGCTTTGATAAGAGGATTGAGG
CAGAAGAAGCCATCAAAGGGCTGAATGGCCAGAAGCCCAGCGGTGCTACGGAACCGATTA
CTGTGAAGTTTGCCAACAACCCCAGCCAGAAGTCCAGCCAGGCCCTGCTCTCCCAGCTCT
ACCAGTCCCCTAACCGGCGCTACCCAGGTCCACTTCACCACCAGGCTCAGAGGTTCAGGC
TGGACAATTTGCTTAATATGGCCTATGGCGTAAAGAGACTGATGTCTGGACCAGTCCCCC
CTTCTGCTTGTTCCCCCAGGTTCTCCCCAATTACCATTGATGGAATGACAAGCCTTGTGG
GAATGAACATCCCTGGTCACACAGGAACTGGGTGGTGCATCTTTGTCTACAACCTGTCCC
CCGATTCCGATGAGAGTGTCCTCTGGCAGCTCTTTGGCCCCTTTGGAGCAGTGAACAACG
TAAAGGTGATTCGTGACTTCAACACCAACAAGTGCAAGGGATTCGGCTTTGTCACCATGA
CCAACTATGATGAGGCGGCCATGGCCATCGCCAGCCTCAACGGGTACCGCCTGGGAGACA
GAGTGTTGCAAGTTTCCTTTAAAACCAACAAAGCCCACAAGTCCTGAATTTCCCATTCTT
ACTTACTAAAATATATATAGAAATATATACGAACAAAACACACGCGCGCACACACACACA
TACACGAAAGAGAGAGAAACAAACTTTTCAAGGCTTATATTCAACCATGGACTTTATAAG
CCAGTGTTGCCTAAGTATTAAAACATTGGATTATCCTGAGGTGTACCAGGAAAGGATTTT
ATATGCTTAGAAAAAAPAAAAAAAA >Hs.299867_mRNA_1 gi|4758533|ref|NM_004496.1| *Homo sapiens* hepatocyte
nuclear factor 3, alpha (HNF3A), mRNA polyA = 3
TCCAGGAATCGATAGTGCATTCGTGCGCGCGGCCGCCCGTCGCTTCGCACAGGGCTGGAT
GGTTGTATTGGGCAGGGTGGCTCCAGGATGTTAGGAACTGTGAAGATGGAAGGGCATGAA
ACCAGCGACTGGAACAGCTACTACGCAGACACGCAGGAGGCCTACTCCTCGGTCCCGGTC
AGCAACATGAACTCAGGCCTGGGCTCCATGAACTCCATGAACACCTACATGACCATGAAC
ACCATGACTACGAGCGGCAACATGACCCCGGCGTCCTTCAACATGTCCTATGCCAACCCG
GCCTTAGGGGCCGGCCTGAGTCCCGGCGCAGTAGCCGGCATGCCGGGGGGCTCGGCGGGC
GCCATGAACAGCATGACTGCGGCCGGCGTGACGGCCATGGGTACGGCGCTGAGCCCGAGC
GGCATGGGCGCCATGGGTGCGCAGCAGGCGGCCTCCATGATGAATGGCCTGGGCCCCTAC
GCGGCCGCCATGAACCCGTGCATGAGCCCCATGGCGTACGCGCCGTCCAACCTGGGCCGC
AGCCGCGCGGGCGGCGGCGGCGACGCCAAGACGTTCAAGCGCAGTTACCCGCACGCCAAG
CCGCCCTACTCGTACATCTCGCTCATCACCATGGCCATCCAGCGGGCGCCCAGCAAGATG
CTCACGCTGAGCGAGATCTACCAGTGGATCATGGACCTCTTCCCCTATTACCGGCAGAAC
CAGCAGCGCTGGCAGAACTCCATCCGCCACTCGCTGTCCTTCAATGACTGCTTCGTCAAG
GTGGCACGCTCCCCGGACAAGCCGGGCAAGGGCTCCTACTGGACGCTGCACCCGGACTCC
GGCAACATGTTCGAGAACGGCTGCTACTTGCGCCGCCAGAAGCGCTTCAAGTGCGAGAAG
CAGCCGGGGGCCGGCGGCGGGGGCGGGAGCGGAAGCGGGGGCAGCGGCGCCAAGGGCGG
CCTGAGAGCCGCAAGGACCCCTCTGGCGCCTCTAACCCCAGCGCCGACTCGCCCCTCCAT
CGGGGTGTGCACGGGAAGACCGGCCAGCTAGAGGGCGCGCCGGCCCCGGGCCCGGCCGCC
AGCCCCCAGACTCTGGACCACAGTGGGGCGACGGCGACAGGGGGCGCCTCGGAGTTGAAG
ACTCCAGCCTCCTCAACTGCGCCCCCCATAAGCTCCGGGCCCGGGGCGCTGGCCTCTGTG
CCCGCCTCTCACCCGGCACACGGCTTGGCACCCCACGAGTCCCAGCTGCACCTGAAAGGG
GACCCCCACTACTCCTTCAACCACCCGTTCTCCATCAACAACCTCATGTCCTCCTCGGAG
CAGCAGCATAAGCTGGACTTCAAGGCATACGAACAGGCACTGCAATACTCGCCTTACGGC
TCTACGTTGCCCGCCAGCCTGCCTCTAGGCAGCGCCTCGGTGACCACCAGGAGCCCCATC
GAGCCCTCAGCCCTGGAGCCGGCGTACTACCAAGGTGTGTATTCCAGACCCGTCCTAAAC
ACTTCCTAGCTCCCGGGACTGGGGGGTTTGTCTGGCATAGCCATGCTGGTAGCAAGAGAG
AAAAAATCAACAGCAAACAAAACCACACAAACCAAACCGTCAACAGCATAATAAAATCCA
ACAACTATTTTTATTTCATTTTTCATGCACAACCTTGCCCCCAGTGCAAAAGACTGTTAC
TTTATTATTGTATTCAAAATTCATTGTGTATATTACTACAAAGACGGCCCCAAACCAATT
TTTTTCCTGCGAAGTTTAATGATCCACAAGTGTATATATGAAATTCTCCTCCTTCCTTGC
CCCCCTCTCTTTCTTCCCTCTTGGCCCTCCAGACATTCTAGTTTGTGGAGGGTTATTTAA
AAAACAAAAAGGAAGATGGTCAAGTTTGTAAAATATTTGTTTGTGCTTTTCCCCCCTCCT
TACCTGACCCCCTACGAGTTTACAGGCTTGTGGCAATACTCTTAACCATAAGAATTGAAA
TGGTGAAGAAACAAGTATACACTAGAGGCTCTTAAAAGTATTGAAAAGACAATACTGCTG
TTATATAGCAAGACATAAACAGATTATAAACATCAGAGCCATTTGCTTCTCAGTTTACAT
TTCTGATACATGCAGATAGCAGATGTCTTTAAATGAAATACATGTATATTGTGTATGGAC
TTAATTATGCACATGCTCAGATGTGTAGACATCCTCCGTATATTTACATAACATATAGAG
GTAATAGATAGGTGATATACGTGATACGTTCTCAAGAGTTGCTTGACCGAAAGTTACAAG
GACCCCAACCCCTTTGCTCTCTACCCACAGATGGCCCTGGGAACAATCCTCAGGAATTGC
CCTCAAGAACTCGCTTCTTTGCTTTGAGAGTGCCATGGTCATGTCATTCTGAGGTACATA
ACACATAAATTAGTTTCTATGAGTGTATACCATTTAAAGATTTTTTCAGTAAAGGGAATA
TTACATGTTGGGAGGAGGAGATAAGTTATAGGGAGCTGGATTTCAAACGGTGGTCCAAGA
TTCAAAAATCCTATTGATAGTGGCCATTTTAATCATTGCCATCGTGTGCTTGTTTCATCC
AGTGTTATGCACTTTCCACAGTTGGTGTTAGTATAGCCAGAGGGTTTCATTATTATTTCT -continued CTTTGCTTTCTCAATGTTAATTTATTGCATGGTTTATTCTTTTTCTTTACAGCTGAAATT
GCTTTAAATGATGGTTAAAATTACAAATTAAATTGGGAATTTTTATCAATGTGATTGTAA
TTAAAAATATTTTGATTTAAATAACAAAAATAATACCAGATTTTAAGCCGCGGAAAATGT
TCTTGATCATTTGCAGTTAAGGACTTTAAATAAATCAAATGTTAACAAAAAA >Hs.285401_contig1
AI147926|AI880620|AA768316|AA761543|AA279147|AI216016|AI738663|N79248|
AI684489|AA960845|AI718599|AI379138|N29366|BF002507|AW044269|R34339|R66326|
H04648|R67467|AI523112|BF941500 polyA = 2 polyA = 3
TGTTTTTCTAGTTCATTTTGTGTTTCCAACTTTTCATGTAAAATTTTAATTATTTTTGAA
TGTGTGGATGTGAGACTGAGGTGCCTTTTGGTACTGAAATTCTTTTTCCATGTACCTGAA
GTGTTACTTTTGTGATATAGGAAATCCTTGTATATATACTTTATTGGTCCCTAGGCTTCC
TATTTTGTTACCTTGCTTTCTCTATGGCATCCACCATTTTGATTGTTCTACTTTTATGAT
ATGTTTTCATAAGTGGTTAAGCAAGTATTCTCGTTACTTTTGCTCTTAAATCCCTATTCA
TTACAGCAATGTTGGTGGTCAAAGAAAATGATAAACAACTTGAATGTTCAATGGTCCTGA
AATACATAACAACATTTTAGTACATTGTAAAGTAGAATCCTCTGTTCATAATGAACAAGA
TGAACCAATGTGGATTAGAAAGAAGTCCGAGATATTAATTCCAAAATATCCAGACATTGT
TAAAGGGAAATTGCAATAAATATTTGTAACATAAAAAAAAAAAAAAA >Hs.182507_mRNA_1 gi|15431324|ref|NM_002283.2| *Homo sapiens* keratin, hair, basic, 5 (KRTHB5), mRNA polyA = 3
AGCTCTCCCCACCAATAAAAGGACCAGGGAGGATCAGAGAGAGCAGAAGGATCCTGAGCC
TCGCACTCTGCCGCCCGCACCACCTTCCGCTGCCTCTCAGACTCTGCTCAGCCTCACACG
ATGTCGTGCCGCTCCTACAGGATCAGCTCAGGATGCGGGGTCACCAGGAACTTCAGCTCC
TGCTCAGCTGTGGCCCCCAAAACTGGCAACCGCTGCTGCATCAGCGCCGCCCCCTACCGA
GGGGTGTCCTGCTACCGAGGGCTGACGGGCTTCGGCAGCCGCAGCCTCTGCAACCTGGGC
TCCTGCGGGCCCCGGATAGCTGTAGGTGGCTTCCGAGCCGGCTCCTGCGGACGCAGCTTC
GGCTACCGCTCCGGGGGCGTGTGCGGACCCAGCCCCCCATGCATCACTACCGTGTCGGTC
AACGAGAGCCTCCTCACGCCCCTCAACCTGGAGATCGACCCCAACGCACAGTGCGTGAAG
CAGGAGGAGAAGGAGCAGATCAAGTCCCTCAACAGCAGGTTCGCGGCCTTCATCGACAAG
GTGCGCTTCCTGGAGCAGCAGAACAAGCTGCTGGAGACCAAGTGGCAGTTCTACCAGAAC
CAGCGCTGCTGCGAGAGCAACCTGGAGCCACTGTTCAGTGGCTACATCGAGACTCTGCGG
CGGGAGGCCGAGTGCGTGGAGGCCGACAGCGGGAGGCTGGCCTCAGAGCTCAACCATGTG
CAGGAGGTGCTGGAGGGCTACAAGAAGAAGTATGAAGAGGAGGTGGCCCTGAGAGCCACA
GCAGAGAATGAGTTTGTCGTTCTAAAGAAGGACGTGGACTGTGCCTACCTGCGGAAATCA
GACCTGGAGGCCAATGTGGAGGCCCTGGTGGAGGAGTCTAGCTTCCTGAGGCGCCTCTAT
GAAGAGGAGATCCGCGTTCTCCAAGCCCACATCTCAGACACCTCGGTCATAGTCAAGATG
GACAACAGCCGAGACCTGAACATGGACTGCATCATCGCTGAGATCAAGGCTCAGTATGAC
GATGTTGCCAGCCGCAGCCGGGCCGAGGCTGAGTCCTGGTACCGTAGCAAGTGTGAGGAG
ATGAAGGCCACGGTGATCAGGCATGGGGAGACCCTGCGCCGCACCAAGGAGGAGATCAAC
GAGCTGAACCGCATGATCCAGAGGCTGACGGCCGAGATTGAGAATGCCAAGTGCCAGCGT
GCCAAGCTGGAGGCTGCTGTGGCTGAGGCAGAGCAGCAGGGTGAGGCGGCCCTCAGCGAT
GCCCGCTGCAAGCTGGCTGAGCTGGAGGGCGCCCTGCAGAAGGCCAAGCAGGACATGGCC
TGCCTGCTCAAGGAGTACCAGGAGGTGATGAACTCCAAGCTGGGCCTGGACATCGAGATC
GCCACCTACAGGCGCCTGCTGGAGGGCGAGGAACACAGGCTGTGTGAAGGTGTGGGCTCT
GTGAATGTCTGTGTCAGCAGCTCCCGTGGTGGAGTCTCCTGTGGGGGCCTCTCCTACAGC
ACCACCCCAGGGCGCCAGATCACTTCTGGCCCCTCAGCCATAGGCGGCAGCATCACGGTG
GTGGCCCCTGACTCCTGTGCCCCCTGCCAGCCTCGTTCCTCCAGCTTCAGCTGCGGGAGT
AGCCGGTCGGTCCGCTTTGCCTAGTAGAGTCATGGAGCCAGGGCTTCCTGCCAAGCACCT
GCCTGCCTGCATCACTGCACTGAATGGCATGTGAATGGAAAATGTGTGCTTGCTTCCAGA
ATCTTCTGGATGTTCCTACAGAGGGAAAGACCTACAGAGGGAAAGACCCTCGGGCCGCTC
CCCTGCGCCTTTTCATGCTAGGGAGATGCATCCTAGTTGTCCTCCTGGCAGCTGTTTTCA
GAGGCATTCCCAGCCCTTCACTTAACTCCTACTTAGCTCCAAAATACCTGTATCCAATTT
GTATTATTCCCCCAGCTCTCAGGGACAAGACCAGTCCCCCAGCGTGGTGGTCAGCACGGA
AGCTCCACCTTCTGGGTGGAGGCGCCATCCTAACCATCCAGCCAGGCCACCCACAACCCG
AGAATCAGGGAGAAAGTCCCTCCCCAGCAGCCCCCTCCTCCTGGCTGGGAAGAATGGTCC
CCCAGCAAGCACTTGCCTGTTCATTCCCGTTCATGTTTTGCTTCTCTCTCAGACTGCCTT
CCTGCTTCTGGGCTAACCTGTTCCAGCCAGGCTCCTCATGTGACCTCGCAGTTGAGAAGC
CCATTATCGTGGGGCATCCTTTTGCCTACAGCCCCTGGTTAGGGCACTTTGGACAGGTCT
TGCTATTCAGTGAACCTTTGTACATTTCAAAGAAGACTCCATGGCTGCTCCAGATGCCCC
CTTGCTGGGTGCAGGTGGGGACTGTCCAATGCAGAGCTGGCGGGACAGAGAGTTAAGCCA
CTTCCTGGGTCTCCTTCTTATGACTGTCTATGGGTGCATTGCCTTCTGGGTTGTCTCGAT
CTGTGTTTCAATAAATGCCGCTGCAATGCAAAAAAAAAAAAAAAAAAA >Hs.292653_contig1
AI200660|AW014007|AI341199|AI692279|AI393765|AI378686|AI695373|AW292108|
T10352|R44346|AW470408|AI380925|BF938983|AW003704|H08077|F03856|H08075|
F08895|AW468398|AI865976|H22568|AI858374|AI216499 polyA = 2 polyA = 3
CAATCAGTGAAAATTCTATATTCCTTTGGCATTTTTGTGACATATTCAATTCAGTTNTAT
GTTCCAGCAGAGATCATTATCCCTGGGATCACATCCAAATTTCATACTAAATGGAAGCAA
ATCTGTGAATTTGGGATAAGATCCTTCTTGGTTAGTATTACTTGCGCCGGAGCAATGTCT
TATTCCTCGTTTAGACATTGTGATTTCCTTCGTTGGAGCTGTGAGCAGCAGCACATTGGC
CCTAATCCTGCCACCTTTGGTTGAAATTCTTACATTTTCGAAGGAACATTATAATATATG
GATGGTCCTGAAAAATATTTCTATAGCATTCACTGGAGTTGTTGGCTTCTTATTAGGTAC
ATATATAACTGTTGAAGAAATTATTTATCCTACTCCCAAAGTTGTAGCTGGCACTCCACA
GAGTCCTTTTCTAAATTTGAATTCAACATGCTTAACATCTGGTTTGAAATAGTAAAAGCA
GAATCATGAGTCTTCTATTTTTGTCCCATTTCTGAAAATTATCAAGATAACTAGTAAAAT
ACATTGCTATATACATAAAAAATGGTAACAAACTCTGTTTTCTTTGGCACGATATTAATAT
TTTGGAAGTAATCATAACTCTTTACCAGTAGTGGTAAACCTATGAAAAATCCTTGCTTTT
AAGTGTTAGCAATAGTTCAAAAAATTAAGTTCTGAAAATTGAAAAAATTAAAATGTAAAA
AAATTAAAGAATAAAAATACTTCTATTATTCTTTTATCTCAGTAAGAAATACCTTAACCA -continued AGATATCTCTCTTTTATGCTACTCTTTTGCCACTCACTTGAGAACAGAATAGGATTTCAA
CAATAAGAGAATAAAATAAGAACATGTATAACAAAAAGCTCTCTCCAGATCATCCCTGTG
AATGCCAAAGTAAACTTTATGTACAGTGTAAAAAAAAAAAAAATCTCAGTTATGTTTTTAT
TAGCCAAATTCTAATGATTGGCTCCTGGAAGTATAGAAAACTCCCATTAACATAATATAA
GCATCAGAAAATTGCAAACACTAGAATTAATTTTACACTCTAATGGTAGTTGATCTTCAT
AGTCAAGAGGCACTGTTCAAGATCATGACTTAGTGTTTCAATGAAATTTGAAAAGGGACT
TTAAAACTTATCCAGTGCAACTCCCTTGTTTTTCGTCAGAGGAAAAGGAGGCCTAGAAAG
GTTAAGTAACTTGGTCGAGACCACTCAGCCTTGAGATCAAGAAAACCTAATCTTCTGACT
CCCAGGCCAGGATGTTTTATTTCTCACATCATGTCCAAGAAAAAGAATAAATTATGTTCA
GCTTAAAAAAAAAAAAAAAAAAAAAAAAA >Hs.97616 mRNA_3 gi|12654852|gb|BC001270.1|BC001270 *Homo sapiens* clone MGC:5069 IMAGE:3456016 polyA = 3
CGGAGGCGGCGCCGACGGGGACTGCTGAGGCGCGCAGAGGGTCGGCGGCGCCCGGGAGCC
TGTCGCTGGCGCGGTCCGGGCGGGAGGCTCGGCGGCGGGCGGCAGCATGTCGGTGGCGGG
GCTGAAGAAGCAGTTCTACAAGGCGAGCCAGCTGGTCAGTGAGAAGGTCGGAGGGGCCGA
GGGGACCAAGCTGGATGATGACTTCAAAGAGATGGAGAAGAAGGTGGATGTCACCAGCAA
GGCGGTGACAGAAGTGCTGGCCAGGACCATCGAGTACCTGCAGCCCAACCCAGCCTCGCG
GGCTAAGCTGACCATGCTCAACACGGTGTCCAAGATCCGGGGCCAGGTGAAGAACCCCGG
CTACCCGCAGTCGGAGGGGCTTCTGGGCGAGTGCATGATCCGCCACGGGAAGGAGCTGGG
CGGCGAGTCCAACTTTGGTGACGCATTGCTGGATGCCGGCGAGTCCATGAAGCGCCTGGC
AGAGGTGAAGGACTCCCTGGACATCGAGGTCAAGCAGAACTTCATTGACCCCCTCCAGAA
CCTGTGCGAGAAAGACCTGAAGGAGATCCAGCACCACCTGAAGAAACTGGAGGGCCGCCG
CCTGGACTTTGACTACAAGAAGAAGCGGCAGGGCAAGATCCCCGATGAGGAGCTACGCCA
GGCGCTGGAGAAGTTCGAGGAGTCCAAGGAGGTGGCAGAAACCAGCATGCACAACCTCCT
GGAGACTGACATCGAGCAGGTGAGTCAGCTCTCGGCCCTGGTGGATGCACAGCTGGACTA
CCACCGGCAGGCCGTGCAGATCCTGGACGAGCTGGCGGAGAAGCTCAAGCGCAGGATGCG
GGAAGCTTCCTCACGCCCTAAGCGGGAGTATAAGCCGAAGCCCCGGGAGCCCTTTGACCT
TGGAGAGCCTGAGCAGTCCAACGGGGGCTTCCCCTGCACCACAGCCCCCAAGATCGCAGC
TTCATCGTCTTTCCGATCTTCCGACAAGCCCATCCGGACCCCTAGCCGGAGCATGCCGCC
CCTGGACCAGCCGAGCTGCAAGGCGCTGTACGACTTCGAGCCCGAGAACGACGGGGAGCT
GGGCTTCCATGAGGGCGACGTCATCACGCTGACCAACCAGATCGATGAGAACTGGTACGA
GGGCATGCTGGACGGCCAGTCGGGCTTCTTCCCGCTCAGCTACGTGGAGGTGCTTGTGCC
CCTGCCGCAGTGACTCACCCGTGTCCCCGCCCCGCCCCTCCGTCCACACTGGCCGGCACC
CCCTGCTGGGTCTCCTGCATTCCACGGAGCCCCTGCTGCCAGGGCGGTGTCTGAGCCTGC
CGGCGCCACCTGGGCCCCGGCCCTTGAGGTACTCCCTGAGCAGGACCCCACACTTGGGTG
GGGGGGCTTATCTGGGTGGGTGGGGATGCCTGTTTACACTAGCGCTGACTCCCAACGGTG
ACGGCTCCCTTCCCCACTCCATGGCGCCAGCCTCTCCCCCGCTCCCCAACTTCTCGCCC
AGCTGGCCGAGGCGGGGCAACACTAAGGTGCTCTTAGAAACACTAATGTTCCTCTGGGGC
AGCCCCCACCTCCGTCCTGACCCGACGGGGGCCCGGCCCACTGCCTACCCTCGAGTCCCG
CAGCCTTAACAGGATGGGATCGAGGGTCCCCATGGGGTGGCTCAGAGATAGGACCCTGGT
TTTAAATCCCTCCCAGCCTGGTGCTGGTGATGGGCCCTGGCCCTACTCCAGGGCCAATGC
ACCCCCGCCTCACACACGCACTCCTTCTCCTCAAGGCCAGGGCAGAGGGCCTCACCGCCT
CCCGGGCCTGCTGTCAGCTTGCAGCCCGGGGACAGAGGCCAGCTGGGATCTGCCTGAGGA
CAGAGAACATGGTCTCCTGCAGGGCCCTGCCTCCCAAGCCCCGCCCTCAGAAAGCCAAGT
ACCTTTTCAGCTTTTTAACTGCCCCCATCCCAACCCAGGGAGGCCTGTGTCACTCTGGCA
CAAGCTGCCACCACCAGCCACCCACACCCACCCCAGCACACCTCACACGGGACCACAGCC
GCGCTGCCGAGGGCCAAGCACAAAGGTTCCAGTGAGCGCATGTCCCAGCCCCTGGTGGCC
AGGCTCCCCTTGCTGAGCCGCTGCCACTTCACCCTGTGGGAAGTGGCCCCAGCCATCTCC
TCTAGACCAAGGCAGGCAGCCCCGACATCTGCTTCCTCTATCGCCCAATGCAAAATCGAT
GAAATGGGGAGTTCTCTGGGCCAGGCCACATTCACATTCCCCTCCCCCTGTGGTCCAGTG
AAGCCTCCGGACCCCAGGCTCTGCTCTGCCCTGCCCTGCACCCCCCTCGTCAGAAGTACA
TGAGGGGCGCAGAGATGAGCACACAGCTTTGGGCACGGTCCAGGGCAAACTGAAATGTAC
GCCTGAATTTTGTAAACAGAAGTATTAAATGTCTCTTTCTAC >Hs.123078 mRNA_3 gi|14328043|gb|BC009237.1|BC009237 *Homo sapiens* clone MGC:2216 IMAGE:5989823 polyA = 3
GGCACGAGGGAGGTGCAGAGCTGAGAATGAGGCGATTTCGGAGGATGGAGAAATAGCCCC
GAGTCCCGTGGAAAATGAGGCCGGCGGACTTGCTGCAGCTGGTGCTGCTGCTCGACCTGC
CCAGGGACCTGGGCGGAATGGGGTGTTCGTCTCCACCCTGCGAGTGCCATCAGGAGGAGG
ACTTCAGAGTCACCTGCAAGGATATTCAACGCArCCCCAGCTTACCGCCCAGTACGCAGA
CTCTGAAGCTTATTGAGACTCACCTGAGAACTATTCCAAGTCATGCATTTTCTAATCTGC
CCAATATTTCCAGAATCTACGTATCTATAGATGTGACTCTGCAGCAGCTGGAATCACACT
CCTTCTACAATTTGAGTAAAGTGACTCACATAGAAATTCGGAATACCAGGAACTTAACTT
ACATAGACCCTGATGCCCTCAAAGAGCTCCCCCTCCTAAAGTTCCTTGGCATTTTCAACA
CTGGACTTAAAATGTTCCCTGACCTGACCAAAGTTTATTCCACTGATATATTCTTTATAC
TTGAAATTACAGACAACCCTTACATGACGTCAATCCCTGTGAATGCTTTTCAGGGACTAT
GCAATGAAACCTTGACACTGAAGCTGTACAACAATGGCTTTACTTCAGTCCAAGGATATG
CTTTCAATGGGACAAAGCTGGATGCTGTTTACCTAAACAAGAATAAATACCTGACAGTTA
TTGACAAAGATGCATTTGGAGGAGTATACAGTGGACCAAGCTTGCTGCTGCCTCTTGGAA
GAAAGTCCTTGTCCTTTGAGACTCAGAAGGCCCCAAGCTCCAGTATGCCATCATGATGCC
TGCTAAGGCAGCCACCTTGGTGTACATGCTCACAGAGGCTCTGTTCATGGAGCAGCTGCT
GTTTGAAAAAATTTTGAAATGCAAGATCCACAACTAGATGGAAGGCACTCTAGTCTTTGCA
GAAAAAAATGTACCTGAATGTACATTGCACAATGCCTGGCACAAAGAAGGAAGAATATAA
ATGATAGTTCGACTCGTCTGTGGAAGAACTTACAATCATGGGGAAAGATGGAATAAAAAC
ATTTTTTAAACAGCAAAAAPAAAAAAAAA >Hs.285508 contig1 AW194680|BF939744|BF516467 polyA = 1 polyA = 1
CCCCAGCCCCTCTCACCCACCCTCCTTCCCACCAGCCTGCTCTCCGCAGGCCCACTGTCT
TTGGGTTTAATGACGTCTCTTCTCTGTGGAACTTCACGATTCCTTCCCACGGTCAACTCG
GGACCTCCCAGCGACCACTGCAGCCTGCGGACGAGGCCGGGACTTGGCCGAGCGGATCCT -continued AATAAGGGGAAAATGGTAAATGCAAACGTCCCGTTACAATTTTACCGCCAGTGTGCTGTC
GTTCCCCCTCCCCCTCTCCGAGTCCTCGTGGGGACACGGCGGGGTCTGTAGGAAGTTGGG
CCGGGTTGGGGGTTGCTAGAAGGCGCTGGTGTTTTGCTCTGAGTTTTAAGAGATCCCTTC
CTTCCTCTTCGGTGAATGCAGGTTATTTAAACTTTGGGAAATGTACTTTTAGTCTGTCAT
ATCAAGGCATGAGTCACTGTCTTTTTTTGTGTGAATAAATGGTTTCTAGTACAATGGA >Hs.183274 contig1
BF437393|BF064008|BF509951|AW134603|AI277015|AI803254|AA887915|BF054958|
AI004413|AI393911|AI278517|AW612644|AI492162|AI309226|AI863671|AA448864|
AI640165|AA479926|AA461188|AA780161|BF591180|AI918020|AI758226|AI291375|
BF001845|BF003064|AI337393|AI522206|BE856784|BF001760|AI280300
FLAG = 1 polyA = 2 WARN polyA = 3
GCGGCCGCCCGCACGTCCGCGGGTCCCGGCCGCGCCGCCGCCGCGCGCCCCTGCCCGAGA
GAGCTCTGGCCCCGCTAGCGGGGCCAGGAGCCGGGCCTCCCACCGCAGCGTCCCCCGCCG
CGCCAGTCCCCGCTAGTGGTAGTATCTCGTAATAGCTTCTGTGTGTGAGCTACCGTGGAT
CTCCTTCCCTTCTCTTGGGGGCCGGGGGGAAAGAAAAGGATTTAAGCAAAGGCTCCCTCG
CCCTGTGAGGGCGAGCGGCAAAGGCCCGGCTGAGCCCCCCATGCCCCTCCCCTCCCCGTG
TAAAAAGCCTCCTTGTGCAATTGTCTTTTTTTTCCTTTGAACGTGCTTCTTTGTAATGAC
CAAGGTACCGATTTCTGCTAAGTTCTCCCAACAACATGAAACTGCCTATTCACGCCGTAA
TTCTTTCTGTCTCCCTTCTCTCTCTCTCTCGCTCGCTCGCTCTCGCTCTCGCTCTCTC
TCGCTGCGTCCTCATTTCCCCTCCCAATCCTCTCTCCCCTCTGCAACCCCCCAGCTCGCT
GGCTTTCTCTCTGGCTTCTCTCTTTTCCTCCTCCACCCACCCCCTTTGGTTTGACAATTT
TGTCTTAAGTGTTTCTCAAAAGAGGTTACTTTAGTTAGCATGCGCGCTGTGGGCAATTGT
TACAAGTGTTCTTAGGTTTACTGTGAAGAGAATGTATTCTGTATCCGTGAATTGCTTTAT
GGGGGGGAGGGAGGGCTAATTATATATTTGTTGTTCCTCTATACTTTGTTCTGTTGTCT
GCGCCTGAAAAGGGCGGAAGAGTTACAATAAAGTTTACAAGCGAGAACCCGAAAAAAAAA
AAAA >Hs.334841_mRNA_3 gi|14290606|gb|BC009084.1|BC009084 *Homo sapiens* clone
MGC:9270 IMAGE:3853674 polyA = 3
CACCAGCACAGCAAACCCGCCGGGATCAAAGTGTACCAGTCGGCAGCATGGCTACGAAAT
GTGGGAATTGTGGACCCGGCTACTCCACCCCTCTGGAGGCCATGAAAGGACCCAGGGAAG
AGATCGTCTACCTGCCCTGCATTTACCGAAACACAGGCACTGAGGCCCCAGATTATCTGG
CCACTGTGGATGTTGACCCCAAGTCTCCCCAGTATTGCCAGGTCATCCACCGGCTGCCCA
TGCCCAACCTGAAGGACGAGCTGCATCACTCAGGATGGAACACCTGCAGCAGCTGCTTCG
GTGATAGCACCAAGTCGCGCACCAAGCTGGTGCTGCCCAGTCTCATCTCCTCTCGCATCT
ATGTGGTGGACGTGGGCTCTGAGCCCCGGGCCCCAAAGCTGCACAAGGTCATTGAGCCCA
AGGACATCCATGCCAAGTGCGAACTGGCCTTTCTCCACACCAGCCACTGCCTGGCCAGCG
GGGAAGTGATGATCAGCTCCCTGGGAGACGTCAAGGGCAATGGCAAAGGGGGTTTTGTGC
TGCTGGATGGGGAGACGTTCGAGGTGAAGGGGACATGGGAGAGACCTGGGGGTGCTGCAC
CGTTGGGCTATGACTTCTGGTACCAGCCTCGACACAATGTCATGATCAGCACTGAGTGGG
CAGCTCCCAATGTCTTACGAGATGGCTTCAACCCCGCTGATGTGGAGGCTGGACTGTACG
GGAGCCACTTATATGTATGGGACTGGCAGCGCCATGAGATTGTGCAGACCCTGTCTCTAA
AAGATGGGCTTATTCCCTTGGAGATCCGCTTCCTGCACAACCCAGACGCTGCCCAAGGCT
TTGTGGGCTGCGCACTCAGCTCCACCATCCAGCGCTTCTACAAGAACGAGGGAGGTACAT
GGTCAGTGGAGAAGGTGATCCAGGTGCCCCCCAAGAAAGTGAAGGGCTGGCTGCTGCCCG
AAATGCCAGGCCTGATCACCGACATCCTGCTCTCCCTGGACGACCGCTTCCTCTACTTCA
GCAACTGGCTGCATGGGGACCTGAGGCAGTATGACATCTCTGACCCACAGAGACCCCGCC
TCACAGGACAGCTCTTCCTCGGAGGCAGCATTGTTAAGGGAGGCCCTGTGCAAGTGCTGG
AGGACGAGGAACTAAAGTCCCAGCCAGAGCCCCTAGTGGTCAAGGGAAAACGGGTGGCTG
GAGGCCCTCAGATGATCCAGCTCAGCCTGGATGGGAAGCGCCTCTACATCACCACGTCGC
TGTACAGTGCCTGGGACAAGCAGTTTTACCCTGATCTCATCAGGGAAGGCTCTGTGATGC
TGCAGGTTGATGTAGACACAGTAAAAGGAGGGCTGAAGTTGAACCCCAACTTCCTGGTGG
ACTTCGGGAAGGAGCCCCTTGGCCCAGCCCTTGCCCATGAGCTCCGCTACCCTGGGGGCG
ATTGTAGCTCTGACATCTGGATTTGAACTCCACCCTCATCACCCACACTCCCTATTTTGG
GCCCTCACTTCCTTGGGGACCTGGCTTCATTCTGCTCTCTCTTGGCACCCGACCCTTGGC
AGCATGTACCACACAGCCAAGCTGAGACTGTGGCAATGTGTTGAGTCATATACATTTACT
GACCACTGTTGCTTGTTGCTCACTGTGCTGCTTTTCCATGAGCTCTTGGAGGCACCAAGA
AATAAACTCGTAACCCTGTCCTTCAAAAAAAAAAAAAAA >Hs.3321_contig1
AI804745|AI492375|AA594799|BE672611|AA814147|AA722404|AW170088|D11718|
BG153444|AI680648|AA063561|BE219054|AI590287|R55185|AI479167|AI796872|
AI018324|AI701122|BE218203|AA905336|AI681917|BI084742|AI480008|AI217994|
AI401468 polyA = 2 polyA = 3
CCGGAGATAACTTGAGGGCTATAGAGGACCGGCTAATACTGGTCCTGAATTTGGCTTCAG
GCCTCACCAACCAAGTGGCCGTGGCCTTGCCGTCTTGCCCGTCGGCCCCCGGTGAGGCCT
GGACCCCTGGGGTCCCGGCACCAGGCCCCGGCTTCCGACCCTGGCAGAAGCCCAAGATCT
GGTCCCTCGCGGAGACTGCCACAAGCCCCGGACACCCGCGCCGGCTCGCCTCCCGGCGCG
GGGGGGTCTCCACCGGGGGGCAACGGTCGCGCCTTTCCGCCCTGCAGCTCTCTCCGGGCC
GCCGCCGCCGCCGCCGCTCACAGACTGGTCTCAGCGCCGCTGGGCAAGTTCCCGGCTTGG
ACCAACCGGCCGTTTCCAGGCCCACCGCCCGGCCCCCGCCCGCACCCGCTCTCCCTGCTG
GGCTCTGCCCCTCCGCACCTGCTGGGACTTCCCGGAGCCGCGGGCCACCCGGCTGCCGCC
GCCGCCTTCGCTCGGCCAGCGGAGCCCGAAGGCGGAACAGATCGCTGTAGTGCCTTGGAA
GTGGAGAAAAAGTTACTCAAGACAGCTTTCCATCCCGTGCCCAGGCGGCCCCAGAACCAT
CTGGACGCCGCCCTGGTCTTATCGGCTCTCTCCTCATCCTAGTTCTTTAAAAAAAAACAA
AAAAACAAAAAAAACTTTTTTTAATCGTTGTAATAATTGTATAAAAAAAATCGCTCTGTA
TAGTTACAACTTGTAAGCATGTCCGTGTATAAATACCTAAAAGCAAAACTAAACAAAGAA
AGTAAGAAAAAGAAATAAAACCAGTCCTCCTCAGCCCTCCCCAAGTCGCTTCTGTGGCAC
CCCGCATTCGCTGTGAGGTTTGTTTGTCCGGTTGATTTTGGGGGGTGGAGTTTCAGTGAG
AATAAACGTGTCTGCCTTTGTGTGTGTGTATATATACAGAGAAATGTACATATGTGTGAA -continued CCAAATTGTACGAGAAAGTATCTATTTTTGGCTAAATAAATGAGCTGCTGCCACTTTGAC
TATAAAAAAAPAAAAAAAAAAAAAAAAAA >Hs.306216_singlet1 AW083022 polyA = 1 polyA = 2
TATGAGCACCTTCACATGGATCCACTTGAGGAAAGAAGGTGGACCGAATTTGTAAACGGT
GTGCAGCAATATATATCAATTCGTTCTGAGATAATCGCCACTTACGCTCTCTGTGGTTTT
GCCAATATCGGGTCCCTAGGAATCGTGATCGGCGGACTCACATCCATGGCTCCTTCCAGA
AAGCGTGATATCGCCTCGGGGGCAGTGAGAGCTCTGATTGCGGGGACCGTGGCCTGCTTC
ATGACAGCCTGCATCGCAGGCATACTCTCCAGCACTCCTGTGGACATCAACTGCCATCAC
GTTTTAGAGAATGCCTTCAACTCCACTTTCCCTGGAACCCCAACCAAGGGTGATAGCTTG
TTGCCAAAGTCTGTTGAGCAGCCCTGTTGCCCAGGGTCCTGGTGAAGTCATCCCAGGAGG
AAACCCCAGTCTGTATTCTTTGAAGGGCTGCTGCACATTGTTGAATCCATCGACCTTTAG
CTGCAATGGGATCTCTAATACATTTTGAGGTCAGCCACTTCTCCAGTGGAACTCTGAAGT
ACAGATGCTGAATTTTCTGCTTTGGAAAGAAAAAAAA >Hs.99235_contig1 AA456140|AI167259|AA450056 polyA = 2 polyA = 3
ACTCGGCATGTGATGAACACCCATAGTTAAGAAACCATGGAGCAAGAAAGCTTGTGGAAA
GTCTCTCTCCTTCCTCATAAGACATGCACACTAATACACATACACACCAAAAAATTACAC
ATTTTAAAACTGCTAAGCTTGGATTTAACTGAATCATATATCTTTTATCATGTTATCCTA
AAAGTGAGAAGACATAACCAAGACATGGAAATAAATGTGAAAGCTGGAGCCGAAGAGTCA
AAGAGCTAAAAAATTAAGTCTAGAACATTCTATGAGGATAGTATAAATAAAAAGAAATAC
AGTCTAGACATGCTGCAAGGAAAGAAGATTCTAAAGTCCGTTTATGGAGGCAATTCCATA
TCCTTTCTTGAACGCACATTCAGCTTACCCCAGAGAGCAAGTGAGGCAATCTGGCAAAAG
ATTAATAAAGATGTAAACCCCTGGAAAAAAAAAAAA >Hs.169172_mRNA_2 gi|2274961|emb|AJ000388.1|HSCANPX I mRNA for calpain-like protease CANPX polyA = 3
GAATTCGGCACGAGATAGTTTTCAGGTTAAGAAAGCCAGAATCTTTGTTCAGCCACACTG
ACTGAACAGACTTTTAGTGGGGTTACCTGGCTAACAGCAGCAGCGGCAACGGCAGCAGCA
GCAGCAGCAGCAGCAGCAGCAGCAGCAGGGCTCCTGGGATAACTCAGGCATAGTTCAACA
CTATGGGTCCTCCTCTGAAGCTCTTCAAAAACCAGAAATACCAGGAACTGAAGCAGGAAT
GCATCAAAGACAGCAGACTTTTCTGTGATCCAACATTTCTGCCTGAGAATGATTCTCTTT
TCTACTTCCGACTGCTTCCTGGAAAGGTGGTGTGGAAACGTCCCCAGGACATCTGTGATG
ACCCCCATCTGATTGTGGGCAACATTAGCAACCACCAGCTGACCCAAGGGAGACTGGGGC
ACAAGCCAATGGTTTCTGCATTTTCCTGTTTGGCTGTTCAGGAGTCTCATTGGACAAAGA
CAATTCCCAACCATAAGGAACAGGAATGGGACCCTCAAAAAACAGAAAAATACGCTGGGA
TATTTCACTTTCGTTTCTGGCATTTTGGAGAATGGACTGAAGTGGTGATTGATGACTTGT
TGCCCACCATTAACGGAGATCTGGTCTTCTCTTTCTCCACTTCCATGAATGAGTTTTGGA
ATGCTCTGCTGGAAAAAGCTTATGCAAAGCTGCTAGGCTGTTATGAGGCCCTGGATGGTT
TGACCATCACTGATATTATTGTGGACTTCACGGGCACATTGGCTGAAACTGTTGACATGC
AGAAAGGAAGATACACTGAGCTTGTTGAGGAGAAGTACAAGCTATTCGGAGAACTGTACA
AAACATTTACCAAAGGTGGTCTGATCTGCTGTTCCATTGAGTCTCCCAATCAGGAGGAGC
AAGAAGTTGAAACTGATTGGGGTCTGCTGAAGGGCCATACCTATACCATGACTGATATTC
GCAAAATTCGTCTTGGAGAGAGACTTGTGGAAGTCTTCAGTGCTGAGAAGGTGTATATGG
TTCGCCTGAGAAACCCCTTGGGAAGACAGGAATGGAGTGGCCCCTGGAGTGAAATTTCTG
AAGAGTGGCAGCAACTGACTGCATCAGATCGCAAGAACCTGGGGCTTGTTATGTCTGATG
ATGGAGAGTTTTGGATGAGCTTGGAGGACTTTTGCCGCAACTTTCACAAACTGAATGTCT
GCCGCAATGTGAACAACCCTATTTTTGGCCGAAAGGAGCTGGAATCGGTGTTGGGATGCT
GGACTGTGGATGATGATCCCCTGATGAACCGCTCAGGAGGCTGCTATAACAACCGTGATA
CCTTCCTGCAGAATCCCCAGTACATCTTCACTGTGCCTGAGGATGGGCACAAGGTCATTA
TGTCACTGCAGCAGAAGGACCTGCGCACTTACCGCCGAATGGGAAGACCTGACAATTACA
TCATTGGCTTTGAGCTCTTCAAGGTGGAGATGAACCGCAAATTCCGCCTCCACCACCTCT
ACATCCAGGAGCGTGCTGGGACTTCCACCTATATTGACACCCGCACAGTGTTTCTGAGCA
AGTACCTGAAGAAGGGCAACTATGTGCTTGTCCCAACCATGTTCCAGCATGGTCGCACCA
GCGAGTTTCTCCTGAGAATCTTCTCTGAAGTGCCTGTCCAGCTCAGGGAACTGACTCTGG
ACATGCCCAAAATGTCCTGCTGGAACCTGGCTCGTGGCTACCCGAAAGTAGTTACTCAGA
TCACTGTTCACAGTGCTGAGGACCTGGAGAAGAAGTATGCCAATGAAACTGTAAACCCAT
ATTTGGTCATCAAATGTGGAAAGGAGGAAGTCCGTTCTCCTGTCCAGAAGAATACAGTTC
ATGCCATTTTTGACACCCAGGCCATTTTCTACAGAAGGACCACTGACATTCCTATTATAG
TACAGGTCTGGAACAGCCGAAAATTCTGTGATCAGTTCTTGGGGCAGGTTACTCTGGATG
CTGACCCCAGCGACTGCCGTGATCTGAAGTCTCTGTACCTGCGTAAGAAGGGTGGTCCAA
CTGCCAAAGTCAAGCAAGGCCACATCAGCTTCAAGGTTATTTCCAGCGATGATCTCACTG
AGCTCTAAATCTGCAATCCCAGAGAATCCTGACAAAGCGTGCCACCCTTTTATTTTCCGT
CAGGTGCCAGGTCTTAGTTAAGATTCACAATCTTTAGAAAGAATGAGATTCACAATAATT
AACTCTTCCTCTCTTCTGATAAATTCCCCATACCTCCCAATCCAAGTAGCATCTGTAGCT
ACATAACCTATATACCTCCAGCAGCTGGACATGGGGAGCGACAGTCCTATCTAGACATCA
TACACATTTGCCAAGAAAGGATCTCTGGGGCTTCCGGGGGTGAGATTCAAGCAGGACAAT
AACAAGAGGCTGGACACCCTACAGATGTCTTTGATGTTTTCAGTTGTTTGATATATCTCC
CCTGTAGGGCATGTTGAGGAAGGAGGAGGGCTGATCAAGGCCAAGCTGGTCTAGCCTGAC
ATCCTAGCTCCTGACTGAACACTATAGACTTCCCAGCAGCATTTTCACCCAGCAGCCAGA
GCCGGCTTTAAGTCCCCAACCCTTACAGACACCACTGCCACCACCACCAACCACGACCAC
CACCACCACCACCACTCACCACCATCATCACCTCCGGAAAGTGTAGTCCTGCCCTAACCC
TAACCCCAAGTCACCCCCCACAGTAAATTTTACCTTCATGTTGAGAAAGCTTCCTGGTGC
TTAATCAAGAGCTGGAGTTCAATGAGTCCTAGACAGTGAGAGGGGCCTGAGCTTCAGCTC
AATGGAAGCCTGCTGTGTGCTCACAAGACGGAAAAGTGGAAGAAGCTGCAGTGGGAGACA
AAGCCTCGGTCCCCCACCCATCCACACACACCTACACTCACACACGCGCACATGGGCGCG
CAACGGAACTACCATTTCAGGCAGTCAGTGGGCAAGAGGAAAGATAAGTAAGTACCATAC
ACACCTTAAAAGATGAGGAGAATTCATCCAGACATATTACAGCCAGTTTGGGGCCCCTGA
CTTGCAATGTGAAACCTCTTCGCTTGCTGCTAGGTTTACAAACAAGCCCATTGTTCCTGT
GCCTCCTAATATTCATTTGTTACTGAAGGACCCCATCTGGGGACTTGAGACTTTGGTCCC
AGCCCAGACGCCTCAGACTGGTCTCAAAGTCAAGCAAGGCTTCACATCAGCTGCAAGTGT -continued
TAGTTTGCCAGCGCATGATCTCACTGAGCTTCTACAGAATCTGCAATCCCAGAGTCAATC
ATGACGAAATGTACGTCCCACCATCTTAACCTATCAACTTTCTGCCCCTCCTTCAAGGCC
CAGTATAAATGCCACCTCCTCCATGAAGCCTTCCCTAATTCCACCCCAAACCCCCACCTT
CAACAATATTTCAACGCTTCTGCAATGATGAAAAAGAAACATAGTTGTAGTACTTAGCCT
ACCTAGACCAGCAAGCATTCATTTTTAGCTCGCTCATTTTTTACCATGTTTTCCAGTCTG
TTTAACTTCTGCAGTGCCTTCACTACACTGCCTTACATAAACCAAATCACAATAAAGTTC
ATATTCAGTACAATTAAAAAAAAAAAAA >Hs.351486_mRNA_1 gi|16549178|dbj|AK054605.1|AK054605 *Homo sapiens* cDNA
FLJ30043 fis, clone 3NB692001548 polyA = 0
TATGCAAGTGTTTAACAGATGCTTCACTATTAAAATATTTTCCCCCCAAGTCTCAAATAT
TGAAGAATCTCTAACCAGGGACACCAGTCCCTACGAAGACCTTGGGCGATTTTGAAGTGC
GGGCACCTCGATTCCCCGAATCTGTAGTGTGGCTGGTATCGGTGTTCCCCTGGTTTAACT
AGCCTGTTTGAAGGCACAGATCATTCATGGGGAAGTATAACCGAATCCAGTCCTCTCCAC
CGCCTGGGGATCTTCACTTTCGCAGTCTACGACTGCCTGTGACTCCAGAAAGACAAACTG
CAGATTGGCCAAGATGGGGAAATTGAGGCAGAGAAGCCAAGACATGTGCTAAAGGTCATG
CAGGCTATGAATGGAGCTGGAATGTGAACGCAGGCCATATGACCCCAGAGCCCATGTTCT
TGAACCCTTAGAAAGACAGCAGCAACACACCTGGTGCAGCAGCTGCTTAGTTGGAGTGGC
TGACAAGGAGAGAATGATTTCCAGGAAGAGCGGAACACATATGGAAGGCCTTAGCTTATC
TTTAGCGCCTCATACACCCGTTCTGGACTTCAGAAAGGCCAGTGAGTGGGATTAGGCCTC
AGAGATAGGATGTCAGTCCCAGTGAGGGATGGCCTAGAGCATTCTTTAATTCTTTCCTTT
GGGTCACACATAAGAAACAATTTTCCAGCACTGATGAGTGTTATTAACAATGAGATGGGA
TAGAATTTAGTTTTCCCTATGGCTGTGCTTCAAAAATAGAAAAGCTGTCTTTTCTCTGGA
ATGATTGAATGAAGCTCTGGGGAGGAAAAGGTGGATTGGCAGATCTCTTAAAGGAAGCTT
CTCCTTCTAGGCACTATTCTAAGGCTTAATATTTTAACTCCCTATATTAACCTAGTTCAA
CTAAACAGTGATCTGAGTAATTTTATTTTTATTAAAGCTCAGATCAAAATGCCATTAACA
TTGATTGAGAAAATCAAAGGAATCTTTGATGTGAGTGGTTAAATTGCTGAATTATTTCAG
TCCCATACCCTCACAGCATGAGTACCTGATCTGATAGACTTCTTTGGAATTCCTTTTTTG
TTTGAGACAGAGTCTTGCTCTGTCGCCCAGGCTGGAGTGCAGCGGTGTGATCTCAACCAT
TGCAACCTCCACCTCCCAGGTTCAGGTGATTCTCATGCCTCAGCCTCCTGAGTAGCTGGG
ATTACAGATGTGCACCACCATGCCCGGCTAATTATTTTGTATCTTTAGTAGAGATGAAGT
TTTGCCATGTGGGCCAGGCTGTTCTCAAACTACTGGCCTCAAGTGATCTGCCCGCCTCGG
CCTCCCAGACTGCTGGGATTACAGGCGTGAGGCACCGTGCCTGGCTGGGATTCCATAATA
AATCCCTCTGTGTCTATTTCTTTTTTCAAATATAATTTTCTTCATTTCCAAACATCATCT
TTAAGACTCCAAGGATTTTTCCAGGCACAGTGGCTCATACCTGTAATCCCATTGCTTGGA
GAGGCCAAGGTGGAAGTTCATTTGAGGCCAGGAGTTCGAGACCAGGTGGGCAACATAGTG
AAACCTTGTCTCTACAACAT >Hs.153504_contig2
BE962007|AW016349|AW016358|AW139144|AA932969|AI025620|AI688744|AI865632|
AA854291|AA932970|AU156702|AI634439|AAI52496|AI539557|AI123490|AI613215|
AI318363|AW105672|AA843483|AI366889|AW181938|AI813801|AI433695|AA934772|
N72230|AI760632|BE858965|AW058302|AI760087|AI682077|AA886672|AI350384|
AW243848|AW300574|BE466359|AI859529|AI921588|BF062899|BE855597|BE617708
polyA = 2 polyA = 3
TGTTTATATAACTGTGTTCGTTTTTGTTGTTCCGTCCCGTCGTCCTTGTAGACTCTCATC
CTCGTGTGTTTTGGACCCTCCAGGGGTGACATCGGGTCTTGTGTTCAGCTCTCCTGGACT
GTTATTCCTTGTCCGCGTGTTCGTGTTAGACATTGTCCACGATCTGTATCATGCCTATGT
CTCACTTTGGTCTCTTATTTCAGCGTGAACACTATAGTTCCAAGTTTGTTCGGATAATTC
TGATTCTTGTCACCAGCGTGAGATTTCAACAGAACTTGTTTGGAACAAATACTCACTTAA
AACTTCAGCAGAAGAAAAATTACTTAGTCCTTAGGCCAACCAATTTAACTGCAGTGTCAT
GTTTCACAGGCCTTCCTACATTTAGAAATCGTCACACAGCTGTGATAAGAGTAGATTATT
TTACTATGAAATAATTCTGAATAGATGAAAGCATAAAATGTGAGAAACTGAATGTATTAT
TCAGGAAGAATACTGAGTGCCTTCATTTAACTAAAGTTGAATGTAAAAGTCAATTTGCAC
TTCTTTATAATCCTCTGGTTTAGAATTATAAATTGTTAAAACCTTGATAATTGTCATTTA
ATTATATTTCAGGTGTCCTGAACAGGTCACTAGACTCTACATTGGGCAGCCTTTAAATAT
GATTCTTTGTAATGCTAAATAGCCTTTTTTTCTCTTTTTACTGCAACTTAATATTTCTAT
TTAGAACACAGAAAATGAAAATATTTAGAATAAGTTGTACATTTGATGACAAATAAATCA
CTATTAAAATAAAAAAAAAAAAAAAAA >Hs.199354_singlet1 AI669760 polyA = 1 polyA = 2
AGGAACCCCTGTGGGAAAGGTTTAAACCTAAAACAGTGCCCCCTTTGGCTCCTCCTCCCT
TGGCGGAATGGGTTCCTGGACCATGTGCATTTCANTGGGCCATGGGATTTACATTTCCTT
GCATCCCCAGGTGGTTTGATCCCTGCCAGGGCCCCTTCCTTCCTGCTCATGGTTTTCAGG
GGGCCTGATCATGGAAAGTAAGGGGGTTGGGCCTTCCCTTTTGGGGGTGAACCCTGACTC
CATCCCCCTATTGCCCCCCTAACCAATCATGCAAACTTTTCCCCCCCTGGGGTAATTCAC
CAGTTAAAAAAAGCTTTTTTTAAATGTTTTGTTTTGGGGGGGGGGCAGGGCCCCCTTTTT
GTTTTTTTAAGGAGTTGGTTTTGGTTTTTGGCTGATGTTTTGTTTTTTAACATGCCCCCA
GTTTGTAAGGCCAAAGGTAAAAAAAAAAAAAAAAAAAAAAAAAAAAAAAAAAAAAAAAAA
AAAAAAAA >Hs.162020_contig1 AW291189|AA505872 polyA = 2 polyA = 3
TAAGCTTTAAAGGCTCTGTGTTAGGGCATAGTCTAGAAACATGGGGCCCAAGGGCACCGG
GAAAACTTACAAAGGGAAGAGATGGAACTGGGAGGGTTCAAGCTACCAGTTCCATCTCTC
CATGTTTTAGAGAATTGGGGCACTAAGTCAGCCAGGTAAGGTCAGGTCAGAGGAGGGCCC
GGATGAAGCATGAGATGCAGAGGGACAGTGCGTGAATGGAGACCTTGGGTAGCACCAACG
TGTAGCGGCAGAGGTGGGGTGGATGTGGCTGATGTCAGGGAGAGAATGGGGAGCATGCAC
AGGGCTCAGTCTTATACATACATTGAAAATCCTTTAGCCTTTCAAAGATTATTAACCCAA
ATCACCTTTCTTGCTTACTCCAGATGCCTCAGCCTCTGATATAATTGCTAAGTATCTGCC
GTGTTAAAAATAAACATTTGAGAATCAAAAAAAAAAAAAAAA -continued >Hs.30743_mRNA_3 gi|18201906|ref|NM_006115.2| *Homo sapiens* preferentially expressed antigen in melanoma (PRAME), mRNA polyA = 3
GCTTCAGGGTACAGCTCCCCCGCAGCCAGAAGCCGGGCCTGCAGCGCCTCAGCACCGCTC
CGGGACACCCCACCCGCTTCCCAGGCGTGACCTGTCAACAGCAACTTCGCGGTGTGGTGA
ACTCTCTGAGGAAAAACCATTTTGATTATTACTCTCAGACGTGCGTGGCAACAAGTGACT
GAGACCTAGAAATCCAAGCGTTGGAGGTCCTGAGGCCAGCCTAAGTCGCTTCAAAATGGA
ACGAAGGCGTTTGTGGGGTTCCATTCAGAGCCGATACATCAGCATGAGTGTGTGGACAAG
CCCACGGAGACTTGTGGAGCTGGCAGGGCAGAGCCTGCTGAAGGATGAGGCCCTGGCCAT
TGCCGCCCTGGAGTTGCTGCCCAGGGAGCTCTTCCCGCCACTCTTCATGGCAGCCTTTGA
CGGGAGACACAGCCAGACCCTGAAGGCAATGGTGCAGGCCTGGCCCTTCACCTGCCTCCC
TCTGGGAGTGCTGATGAAGGGACAACATCTTCACCTGGAGACCTTCAAAGCTGTGCTTGA
TGGACTTGATGTGCTCCTTGCCCAGGAGGTTCGCCCCAGGAGGTGGAAACTTCAAGTGCT
GGATTTACGGAAGAACTCTCATCAGGACTTCTGGACTGTATGGTCTGGAAACAGGGCCAG
TCTGTACTCATTTCCAGAGCCAGAAGCAGCTCAGCCCATGACAAAGAAGCGAAAAGTAGA
TGGTTTGAGCACAGAGGCAGAGCAGCCCTTCATTCCAGTAGAGGTGCTCGTAGACCTGTT
CCTCAAGGAAGGTGCCTGTGATGAATTGTTCTCCTACCTCATTGAGAAAGTGAAGCGAAA
GAAAAATGTACTACGCCTGTGCTGTAAGAAGCTGAAGATTTTTGCAATGCCCATGCAGGA
TATCAAGATGATCCTGAAAATGGTGCAGCTGGACTCTATTGAAGATTTGGAAGTGACTTG
TACCTGGAAGCTACCCACCTTGGCGAAATTTTCTCCTTACCTGGGCCAGATGATTAATCT
GCGTAGACTCCTCCTCTCCCACATCCATGCATCTTCCTACATTTCCCCGGAGAAGGAAGA
GCAGTATATCGCCCAGTTCACCTCTCAGTTCCTCAGTCTGCAGTGCCTGCAGGCTCTCTA
TGTGGACTCTTTATTTTTCCTTAGAGGCCGCCTGGATCAGTTGCTCAGGCACGTGATGAA
CCCCTTGGAAACCCTCTCAATAACTAACTGCCGGCTTTCGGAAGGGGATGTGATGCATCT
GTCCCAGAGTCCCAGCGTCAGTCAGCTAAGTGTCCTGAGTCTAAGTGGGGTCATGCTGAC
CGATGTAAGTCCCGAGCCCCTCCAAGCTCTGCTGGAGAGAGCCTCTGCCACCCTCCAGGA
CCTGGTCTTTGATGAGTGTGGGATCACGGATGATCAGCTCCTTGCCCTCCTGCCTTCCCT
GAGCCACTGCTCCCAGCTTACAACCTTAAGCTTCTACGGGAATTCCATCTCCATATCTGC
CTTGCAGAGTCTCCTGCAGCACCTCATCGGGCTGAGCAATCTGACCCACGTGCTGTATCC
TGTCCCCCTGGAGAGTTATGAGGACATCCATGGTACCCTCCACCTGGAGAGGCTTGCCTA
TCTGCATGCCAGGCTCAGGGAGTTGCTGTGTGAGTTGGGGCGGCCCAGCATGGTCTGGCT
TAGTGCCAACCCCTGTCCTCACTGTGGGGACAGAACCTTCTATGACCCGGAGCCCATCCT
GTGCCCCTGTTTCATGCCTAACTAGCTGGGTGCACATATCAAATGCTTCATTCTGCATAC
TTGGACACTAAAGCCAGGATGTGCATGCATCTTGAAGCAACAAAGCAGCCACAGTTTCAG
ACAAATGTTCAGTGTGAGTGAGGAAAACATGTTCAGTGAGGAAAAAACATTCAGACAAAT
GTTCAGTGAGGAAAAAAAGGGGAAGTTGGGGATAGGCAGATGTTGACTTGAGGAGTTAAT
GTGATCTTTGGGGAGATACATCTTATAGAGTTAGAAATAGAATCTGAATTTCTAAAGGGA
GATTCTGGCTTGGGAAGTACATGTAGGAGTTAATCCCTGTGTAGACTGTTGTAAAGAAAC
TGTTGAAAATAAAGAGAAGCAATGTGAAGCAAAPAAAAAAAA >Hs.271580_contig1
AI632869|AW338882|AW338875|AW613773|AI982899|AW193151|BE206353|BE208200|
AI811548|AW264021 polyA = 2 polyA = 3
AACACAGCCCTACCAANCAATGATGACCAGTGGAAAACAATGAAGTCACCAAACCCTGGA
CAGGGCTCATGCTCCAGGACAANTTGCTGTGGCGTAAATGGTCCATCAGACTGGCAAAAA
TACACATCTGCCTTCCGGACTGAGAATAATGATGCTGACTATCCCTGGCCTCGTCAATGC
TGTGTTATGAACAATCTTAAAGAACCTCTCAACCTGGAGGCTTGTAAACTAGGCGTGCCT
GGTTTTTATCACAATCAGGGCTGCTATGAACTGATCTCTGGTCCAATGAACCGACACGCC
TGGGGGGTTGCCTGGTTTGGATTTGCCATTCTCTGCTGGACTTTTTGGGTTCTCCTGGGT
ACCATGTTCTACTGGAGCAGAATTGAATATTAAGCATAAAGTGTTGCCACCATACCTCCT
TCCCCGAGTGACTCTGGATTTGGTGCTGGAACCAGCTCTCTCCTAATATTCCACGTTTGT
GCCCCACACTAACGTGTGTGTCTTACATTGCCAAGTCAGATGGTACGGACTTCCTTTAGG
ATCTCAGGCTTCTGCAGTTCTCATGACTCCTACTTTTCATCCTAGTCTAGCATTCTGCAA
CATTTATATAGACTGTTGAAAGGAGAATtTGAAAAATGCATAATAACTACTTCCATCCCT
GCTTATTTTTAATTTGGGAAAATAAATACATTCGAAGGAAAAAAAAA >Hs.69360_mRNA_2 gi|14250609|gb|BC008764.1|BC008764 *Homo sapiens* clone MGC:1266 IMAGE:3347571 polyA = 3
GGCACGAGGGCGAAATTGAGGTTTCTTGGTATTGCGCGTTTCTCTTCCTTGCTGACTCTC
CGAATGGCCATGGACTCGTCGCTTCAGGCCCGCCTGTTTCCCGGTCTCGCTATCAAGATC
CAACGCAGTAATGGTTTAATTCACAGTGCCAATGTAAGGACTGTGAACTTGGAGAAATCC
TGTGTTTCAGTGGAATGGGCAGAAGGAGGTGCCACAAAGGGCAAAGAGATTGATTTTGAT
GATGTGGCTGCAATAAACCCAGAACTCTTACAGCTTCTTCCCTTACATCCGAAGGACAAT
CTGCCCTTGCAGGAAAATGTAACAATCCAGAAACAAAAACGGAGATCCGTCAACTCCAAA
ATTCCTGCTCCAAAAGAAAGTCTTCGAAGCCGCTCCACTCGCATGTCCACTGTCTCAGAG
CTTCGCATCACGGCTCAGGAGAATGACATGGAGGTGGAGCTGCCTGCAGCTGCAAACTCC
CGCAAGCAGTTTTCAGTTCCTCCTGCCCCCACTAGGCCTTCCTGCCCTGCAGTGGCTGAA
ATACCATTGAGGATGGTCAGCGAGGAGATGGAAGAGCAAGTCCATTCCATCCGAGGCAGC
TCTTCTGCAAACCCTGTGAACTCAGTTCGGAGGAAATCATGTCTTGTGAAGGAAGTGGAA
AAAATGAAGAACAAGCGAGAAGAGAAGAAGGCCCAGAACTCTGAAATGAGAATGAAGAGA
GCTCAGGAGTATGACAGTAGTTTTCCAAACTGGGAATTTGCCCGAATGATTAAAGAATTT
CGGGCTACTTTGGAATGTCATCCACTTACTATGACTGATCCTATCGAAGAGCACAGAATA
TGTGTCTGTGTTAGGAAACGCCCACTGAATAAGCAAGAATTGGCCAAGAAAGAAATTGAT
GTGATTTCCATTCCTAGCAAGTGTCTCCTCTTGGTACATGAACCCAAGTTGAAAGTGGAC
TTAACAAAGTATCTGGAGAACCAAGCATTCTGCTTTGACTTTGCATTTGATGAAACAGCT
TCGAATGAAGTTGTCTACAGGTTCACAGCAAGGCCACTGGTACAGACAATCTTTGAAGGT
GGAAAAGCAACTTGTTTTGCATATGGCCAGACAGGAAGTGGCAAGACACATACTATGGGC
GGAGACCTCTCTGGGAAAGCCCAGAATGCATCCAAAGGGATCTATGCCATGGCCTCCCGG
GACGTCTTCCTCCTGAAGAATCAACCCTGCTACCGGAAGTTGGGCCTGGAAGTCTATGTG
ACATTCTTCGAGATCTACAATGGGAAGCTGTTTGACCTGCTCAACAAGAAGGCCAAGCTG
CGCGTGCTGGAGGACGGCAAGCAACAGGTGCAAGTGGTGGGGCTGCAGGAGCATCTGGTT
AACTCTGCTGATGATGTCATCAAGATGATCGACATGGGCAGCGCCTGCAGAACCTCTGGG -continued CAGACATTTGCCAACTCCAATTCCTCCCGCTCCCACGCGTGCTTCCAAATTATTCTTCGA
GCTAAAGGGAGAATGCATGGCAAGTTCTCTTTGGTAGATCTGGCAGGGAATGAGCGAGGC
GCGGACACTTCCAGTGCTGACCGGCAGACCCGCATGGAGGGCGCAGAAATCAACAAGAGT
CTCTTAGCCCTGAAGGAGTGCATCAGGGCCCTGGGACAGAACAAGGCTCACACCCCGTTC
CGTGAGAGCAAGCTGACACAGGTGCTGAGGGACTCCTTCATTGGGGAGAACTCTAGGACT
TGCATGATTGCCACGATCTCACCAGGCATAAGCTCCTGTGAATATACTTTAAACACCCTG
AGATATGCAGACAGGGTCAAGGAGCTGAGCCCCCACAGTGGGCCCAGTGGAGAGCAGTTG
ATTCAAATGGAAACAGAAGAGATGGAAGCCTGCTCTAACGGGGCGCTGATTCCAGGCAAT
TTATCCAAGGAAGAGGAGGAACTGTCTTCCCAGATGTCCAGCTTTAACGAAGCCATGACT
CAGATCAGGGAGCTGGAGGAGAAGGCTATGGAAGAGCTCAAGGAGATCATACAGCAAGGA
CCAGACTGGCTTGAGCTCTCTGAGATGACCGAGCAGCCAGACTATGACCTGGAGACCTTT
GTGAACAAAGCGGAATCTGCTCTGGCCCAGCAAGCCAAGCATTTCTCAGCCCTGCCAGAT
GTCATCAAGGCCTTGCGCCTGGCCATGCAGCTGGAAGAGCAGGCTAGCAGACAAATAAGC
AGCAAGAAACGGCCCCAGTGACGACTGCAAATAAAAATCTGTTTGGTTTGACACCCAGCC
TCTTCCCTGGCCCTCCCCAGAGAACTTTGGGTACCTGGTGGGTCTAGGCAGGGTCTGAGC
TGGGACAGGTTCTGGTAAATGCCAAGTATGGGGGCATCTGGGCCCAGGGCAGCTGGGGAG
GGGGTCAGAGTGACATGGGACACTCCTTTTCTGTTCCTCAGTTGTCGCCCTCACGAGAGG
AAGGAGCTCTTAGTTACCCTTTTGTGTTGCCCTTCTTTCCATCAAGGGGAATGTTCTCAG
CATAGAGCTTTCTCCGCAGCATCCTGCCTGCGTGGACTGGCTGCTAATGGAGAGCTCCCT
GGGGTTGTCCTGGCTCTGGGGAGAGAGACGGAGCCTTTAGTACAGCTATCTGCTGGCTCT
AAACCTTCTACGCCTTTGGGCCGAGCACTGAATGTCTTGTACTTTAAAAAAATGTTTCTG
AGACCTCTTTCTACTTTACTGTCTCCCTAGAGATCCTAGAGGATCCCTACTGTTTTCTGT
TTTATGTGTTTATACATTGTATGTAACAATAAAGAGAAAAAATAAAAAAAAAAAAAAAAA
AAAAAAAAAAAA >Hs.30827_contig1 H07885|N39347|W85913|AA583408|W86449 polyA = 2 polyA = 3
ATCGGACTTCGGTNAACTNTGGCAAGGATTGGACAGNCTAGGTAGGCTAAATGTGTGCTC
TGTCCCTGTTTGCTTCAACAGAGGAGCAAGCCTCAGCTGAGAAGGAGGGCACNTGGAACA
CCTAGCTCCTCCCGTGATTCCCCAAACCCATAACATTCTTCCATAGGGCTGGAACCAGTG
CCCCGTCCTGACAGGGATGAAAAGTGAACCCCTCAGGTCAGGAGAGGCCAGAGTTGAGGT
TCTGCCACTTCCTGTCCCTGGGGAGCCACTCAAGTTACCAGGGCTACCGGCTGAAATAAA
TCTTTTCCGGGTAGGGTCAAGGGCAGTGTGTTCCAAGGCAACTGATGTAGGCCAGTTGCG
TGACTCCAGGTTTGTCCTGGTACTCAGTGGGTCCAATCACCTGGCATTGATCACCTGGCA
TTGATCAGCACCCACCCCACCCCTGAGGCTTGCCCAGCCCCCAGGCCCTCAGATCCCTGC
TCTTCCTGCCTTTCCTGCCCATGTGTCACCCAGCACCCAAGGTTCAGTGACACAGGGTGG
TTTGGAGCTGGTCACTGTCATAGCAGCTGTGATTTCACAAGGAAGGGTGCTGCAGGGGGA
CCTGGTTGATGGGGAGTGGGAAGGGGAAGGAATAAAGAGATCTTCCTCAGGTAAAAAAAA
AAAAAAAAAA >Hs.211593_contig2
BF592799|AI570478|AA234440|R40214|BE501078|AW593784|AI184050|AI284161|
W72149|AW780437|AI247981|AW241273|H60824 polyA = 2 polyA = 3
ACCTCGTTTGCTCCCAGTTACTTCTTATCTGGAGCAGTAATGTAGTCCACTTCACTCATG
CCTACCCCGCGTGTCTCGTCTCCTGACATGTCTCACAGACGCTCCTGAAGTTAGGTCATT
ACCTAACCCATAGTTATTTACCTTGAAAGATGGGTCTCCGCACTTGGAAAGGTTTCAAGA
CTTGATACTGCAATAAATTATGGCTCTTCACCTGGGCGCCAACTGCTGATCAACGAAATG
CTTGTTGAATCAGGGGCAAACGGAGTACAGACGTCTCAAGACTGAAACGGCCCCATTGCC
TGGTCTAGTAGCGGATCTCACTCAGCCGCAGACAAGTAATCACTAACCCGTTTTATTCTA
TTCCTATCTGTGGATGTGTAAATGGCTGGGGGGCCAGCCCTGGATAGGTTTTTATGGGAA
TTCTTTACAATAAACATAGCTTGTAACTTGAGATCTACAAATCCATTCATCCTGATTGGG
CATGAAATCCATGGTCAAGAGGACAAGTGGAAAGTGAGAGGGAAGGTTTGCTAGACACCT
TCGCTTGTTATCTTGTCAAGATAGAAAAGATAGTATCATTTCACCCTTGCCAGTAAAAAC
CTTTCCATCCACCCATTCTCAGCAGACTCCAGTATTGGCACAGTCACTCACTGCCATTCT
CACACTATAACAAGAAAAGAAATGAAGTGCATAAGTCTCCTGGGAAAAGAACCTTAACCC
CTTCTCGTGCCATGACTGGTGATTTCATGACTCATAAGCCCCTCCGTAGGCATCATTCAA
GATCAATGGCCCATGCATGCTGTTTGCAGCAGTCAATTGAGTTGAATTAGAATTCCAACC
ATACATTTTAAAGGTATTTGTGCTGTGTGTATATTTTGATAAAATGTTGTGACTTCATGG
CAAACAGGTGGATGTGTAAAAATGGAATAAAAAAAAAAAAAAGAGTCAAAAAAAAAAAAA
AATT >Hs.155097_mRNA_1 gi|15080385|gb|BC011949.1|BC011949 *Homo sapiens* clone
MGC:9006 IMAGE:3863603 polyA = 3
GGCGCCCAAGCCGCCGCCGCCAGATCGGTGCCGATTCCTGCCCTGCCCCGACCGCCAGCG
CGACCATGTCCCATCACTGGGGGTACGGCAAACACAACGGACCTGAGCACTGGCATAAGG
ACTTCCCCATTGCCAAGGGAGAGCGCCAGTCCCCTGTTGACATCGACACTCATACAGCCA
AGTATGACCCTTCCCTGAAGCCCCTGTCTGTTTCCTATGATCAAGCAACTTCCCTGAGGA
TCCTCAACAATGGTCATGCTTTCAACGTGGAGTTTGATGACTCTCAGGACAAAGCAGTGC
TCAAGGGAGGACCCCTGGATGGCACTTACAGATTGATTCAGTTTCACTTTCACTGGGGTT
CACTTGATGGACAAGGTTCAGAGCATACTGTGGATAAAAAGAAATATGCTGCAGAACTTC
ACTTGGTTCACTGGAACACCAAATATGGGGATTTTGGGAAAGCTGTGCAGCAACCTGATG
GACTGGCCGTTCTAGGTATTTTTTTGAAGGTTGGCAGCGCTAAACCGGGCCTTCAGAAAG
TTGTTGATGTGCTGGATTCCATTAAAACAAAGGGCAAGAGTGCTGACTTCACAAACTTTG
CAGCTCGTGGCCTCCTTCCTGAATCCCTGGATTACTGGACCTACCCAGGCTCACTGACCA
CCCCTCCTCTTCTGGAATGTGTGACCTGGATTGTGCTCAAGGAACCCATCAGCGTCAGCA
GCGAGCAGGTGTTGAAATTCCGTAAACTTAACTTCAATGGGGAGGGTGAACCCGAAGAAC
TGATGGTGGACAACTGGCGCCCAGCTCAGCCACTGAAGAACAGGCAAATCAAAGCTTCCT
TCAAATAAGATGGTCCCATAGTCTGTATCCAAATAATGAATCTTCGGGTGTTTCCCTTTA
GCTAAGCACAGATCTACCTTGGTGATTTGGACCCTGGTTGCTTTGTGTCTAGTTTTCTAG
ACCCTTCATCTCTTACTTGATAGACTTACTAATAAAATGTGAAGACTAGACCAATTGTCA
TGCTTGACACAACTGCTGTGGCTGGTTGGTGCTTTGTTTATGGTAGTAGTTTTTCTGTAA
CACAGAATATAGGATAAGAAATAAGAATAAAGTACCTTGACTTTGTTCACAGCATGTAGG -continued GTGATGAGCACTCACAATTGTTGACTAAAATGCTGCCTTTAAAACATAGGAAAGTAGAAT
GGTTGAGTGCAAATCCATAGCACAAGATAAATTGAGCTAGTTAAGGCAAATCAGGTAAAA
TAGTCATGATTCTATGTAATGTAAACCAGAAAAAATAAATGTTCATGATTTCAAGATGTT
ATATTAAAGAAAAACTTTAAAAATTATTATATATTTATAGCAAAGTTATCTTAAATATGA
ATTCTGTTGTAATTTAATGACTTTTGAATTACAGAGATATAAATGAAGTATTATCTGTAA
AAATTGTTATAATTAGAGTTGTGATACAGAGTATATTTCCATTCAGACAATATATCATAA
CTTAATAAATATTGTATTTTAGATATATTCTCTAATAAAATTCAGAATTCTAAAAAAAAA
AAAAAAAA >Hs.5163_mRNA_1 gi|15990433|gb|BC015582.1|BC015582 *Homo sapiens* clone
MGC:23280 IMAGE:4637504 polyA = 3
GGCACGAGGCATGGAGGCGCTGCTGCTGGGCGCGGGGTTGCTGCTGGGCGCTTACGTGCT
TGTCTACTACAACCTGGTGAAGGCCCCGCCGTGCGGCGGCATGGGCAACCTGCGGGGCCG
CACGGCCGTGGTCACGGGTGAGTGCGGAGGCGGGTGAGTGCGAGCTGGCGGGGCGCGCGG
AGAGGAGGCCGGGCCGGCGGTAGCAGCGGCCCGCCGGGCTCAGCTCAGCTCGGCTCCCGC
CCGCGGTCCGCAGGCGCCAACAGCGGCATCGGAAAGATGACGGCGCTGGAGCTGGCGCGC
CGGGGAGCGCGCGTGGTGCTGGCCTGCCGCAGCCAGGAGCGCGGGGAGGCGGCTGCCTTC
GACCTCCGCCAGGAGAGTGGGAACAATGAGGTCATCTTCATGGCCTTGGACTTGGCCAGT
CTGGCCTCGGTGCGGGCCTTTGCCACTGCCTTTCTGAGCTCTGAGCCACGGTTGGACATC
CTCATCCACAATGCCGGTATCAGTTCCTGTGGCCGGACCCGTGAGGCGTTTAACCTGCTG
CTTCGGGTGAACCATATCGGTCCCTTTCTGCTGACACATCTGCTGCTGCCTTGCCTGAAG
GCATGTGCCCCTAGCCGCGTGGTGGTGGTAGCCTCAGCTGCCCACTGTCGGGGACGTCTT
GACTTCAAACGCCTGGACCGCCCAGTGGTGGGCTGGCGGCAGGAGCTGCGGGCATATGCT
GACACTAAGCTGGCTAATGTACTGTTTGCCCGGGAGCTCGCCAACCAGCTTGAGGCCACT
GGCGTCACCTGCTATGCAGCCCACCCAGGGCCTGTGAACTCGGAGCTGTTCCTGCGCCAT
GTTCCTGGATGGCTGCGCCCACTTTTGCGCCCATTGGCTTGGCTGGTGCTCCGGGCACCA
AGAGGGGGTGCCCAGACACCCCTGTATTGTGCTCTACAAGAGGGCATCGAGCCCCTCAGT
GGGAGATATTTTGCCAACTGCCATGTGGAAGAGGTGCCTCCAGCTGCCCGAGACGACCGG
GCAGCCCATCGGCTATGGGAGGCCAGCAAGAGGCTGGCAGGGCTTGGGCCTGGGGAGGAT
GCTGAACCCGATGAAGACCCCCAGTCTGAGGACTCAGAGGCCCCATCTTCTCTAAGCACC
CCCCACCCTGAGGAGCCCACAGTTTCTCAACCTTACCCCAGCCCTCAGAGCTCACCAGAT
TTGTCTAAGATGACGCACCGAATTCAGGCTAAAGTTGAGCCTGAGATCCAGCTCTCCTAA
CCCTCAGGCCAGGATGCTTGCCATGGCACTTCATGGTCCTTGAAAACCTCGGATGTGTGC
GAGGCCATGCCCTGGACACTGACGGGTTTGTGATCTTGACCTCCGTGGTTACTTTCTGGG
GCCCCAAGCTGTGCCCTGGACATCTCTTTTCCTGGTTGAAGGAATAATGGGTGATTATTT
CTTCCTGAGAGTGACAGTAACCCCAGATGGAGAGATAGGGGTATGCTAGACACTGTGCTT
CTCGGAAATTTGGATGTAGTATTTTCAGGCCCCACCCTTATTGATTCTGATCAGCTCTGG
AGCAGAGGCAGGGAGTTTGCAATGTGATGCACTGCCAACATTGAGAATTAGTGAACTGAT
CCCTTTGCAACCGTCTAGCTAGGTAGTTAAATTACCCCCATGTTAATGAAGCGGAATTAG
GCTCCCGAGCTAAGGGACTCGCCTAGGGTCTCACAGTGAGTAGGAGGAGGGCCTGGGATC
TGAACCCAAGGGTCTGAGGCCAGGGCCGACTGCCGTAAGATGGGTGCTGAGAAGTGAGTC
AGGGCAGGGCAGCTGGTATCGAGGTGCCCCATGGGAGTAAGGGGACGCCTTCCGGGCGGA
TGCAGGGCTGGGGTCATCTGTATCTGAAGCCCCTCGGAATAAAGCGCGTTGACCGCCAAA
AAAAAAAAAAAAAAAAAAAAAAAAAAAAAAAAAAAAAAAAAAA >Hs.55150_mRNA_1 gi|17068414|gb|BC017586.1|BC017586 *Homo sapiens* clone
MGC:26610 IMAGE:4837506 polyA = 3
AGCGGTGGAGAAAAGGCAGAACCAGAGTAGAGATTGACAGTGAGCTGAGCCAATCAGGCT
GTGAATCTGCAGCAGTGATCCCAGGTCCTCCAATTAATACTAAGAGAGTGGACCAGGGCC
CCTGAGGAAGACAGATGGCAGGGACAGCGCGCCATGACCGAGAGATGGCGATCCAGGCCA
AGAAAAAGCTCACCACGGCCACCAACCCCATTGAAAGACTCCGACTGCAGTGCCTGGCCA
GGGGCTCTGCTGGGATCAAAGGACTTGGCAGAGTGTTTAGAATTATGGATGACGATAATA
ATCGAACCCTTGATTTTAAAGAATTTATGAAAGGGTTAAATGATTATGCTGTGGTCATGG
AAAAAGAAGAGGTGGAAGAACTTTTCCGGAGGTTTGATAAAGATGGAAATGGAACAATAG
ACTTCAATGAATTTCTTCTCACATTAAGACCTCCAATGTCCAGAGCCAGAAAAGAGGTAA
TCATGCAAGCTTTTAGAAAGTTAGACAAGACTGGAGATGGTGTTATAACAATCGAAGACC
TTCGTGAAGTATATAATGCAAAACACCACCCAAAGTACCAGAATGGGGAATGGAGTGAGG
AACAAGTATTTAGGAAATTTCTGGATAACTTTGATTCACCCTATGACAAAGATGGATTGG
TGACCCCTGAGGAGTTCATGAACTACTATGCAGGTGTGAGCGCATCCATTGACACTGATG
TGTACTTCATCATCATGATGAGAACCGCCTGGAAGCTTTAAGCACATGACCTGGGGACCA
GGCCCTGGGACAGCCATGTGGCTCCAAATGACTAAATGTCAGCTCAAAAACCAGAATCGT
ATTTGATTTCACACTCATCCTAATGTTTTTTTCTGTGTCAAAATATTGCATTTTCTGGGG
CCAAAAAACAGGCAGAAATAAAAGACATTGAGTAGTCAAAAAAAAAAAAAAA >Hs.170177_contig3
AI620495|AW291989|AA780896|AA976262|AI298326|BF111862|AW591523|AI922518|
AI4802801|BF589437|AA600354|AI886238|AA035599|H90049|BF112011|N52601|
AI570965|AI565367|AW768847|H90073|BE504361|N45292|AI632075|AA679729|AW168052|
AI978827|AI968410|AI669255|N45300|AI651256|AI698970|AI521256|AW078614|
AI802070|AI885947|AI342534|AI653624|AW243936|T16586|R15989|AI289789|AI871636|
AI718785|AW148847 polyA = 2 polyA = 3
TAGAGCATTAAAATAACTATCAGGCAGAAGAATCTTTCTTCTCGCCTAGGATTTCAGCCA
TGCGCGCGCTCTCTCTCTTTCTCTCTCTTTTCCTCTCTCTCCCTCTTTCTAGCCTGGGGC
TTGAATTTGCATGTCTAATTCATTTACTCACCATATTTGAATTGGCCTGAACAGATGTAA
ATCGGGAAGGATGGGAAAAACTGCAGTCATCAACAATGATTAATCAGCTGTTGCAGGCAG
TGTCTTAAGGAGACTGGTAGGAGGAGGCATGGAAACCAAAAGGCCGTGTGTTTAGAAGCC
TAATTGTCACATCAAGCATCATTGTCCCCATGCAACAACCACCACCTTATACATCACTTC
CTGTTTTAAGCAGCTCTAAAACATAGACTGAAGATTTATTTTTAATATGTTGACTTTATT
TCTGAGCAAAGCATCGGTCATGTGTGTATTTTTTCATAGTCCCACCTTGGAGCATTTATG
TAGACATTGTAAATAAATTTTGTGCAAAAAGGACTGGAAAAATGAACTGTATTATTGCAA
TTTTTTTTTGTAAAAGTAGCAGTTTGGTATGAGTTGGCATGCATACAAGATTTACTAAGT -continued GGGATAAGCTAATTATACTTTTTGTTGTGGATAAACAAATGCTTGTTGATAGCCTTTTTC
TATCAAGAAACCAAGGAGCTAATTATTAATAACAATCATTGCACACTGAGTCTTAGCGTT
TCTGATGGAAACAGTTTGGATTGTATAATAACGCCAAGCCCAGTTGTAGTCGTTTGAGTG
CAGTAATGAAATCTGAATCTAAAATAAAAACAAGATTATTTTTGTCAAAAAAAAAAAAAA
AAAAAAAAAA >Hs.184601_mRNA_5 gi|4426639|gb|AF104032.1|AF104032 *Homo sapiens* polyA = 2
GCGGCGCGCACACTGCTCGCTGGGCCGCGGCTCCCGGGTGTCCCAGGCCCGGCCGGTGCG
CAGAGCATGGCGGGTGCGGGCCCGAAGCGGCGCGCGCTAGCGGCGCCGGCGGCCGAGGAG
AAGGAAGAGGCGCGGGAGAAGATGCTGGCCGCCAAGAGCGCGGACGGCTCGGCGCCGGCA
GGCGAGGGCGAGGGCGTGACCCTGCAGCGGAACATCACGCTGCTCAACGGCGTGGCCATC
ATCGTGGGGACCATTATCGGCTCGGGCATCTTCGTGACGCCCACGGGCGTGCTCAAGGAG
GCAGGCTCGCCGGGGCTGGCGCTGGTGGTGTGGGCCGCGTGCGGCGTCTTCTCCATCGTG
GGCGCGCTCTGCTACGCGGAGCTCGGCACCACCATCTCCAAATCGGGCGGCGACTACGCC
TACATGCTGGAGGTCTACGGCTCGCTGCCCGCCTTCCTCAAGCTCTGGATCGAGCTGCTC
ATCATCCGGCCTTCATCGCAGTACATCGTGGCCCTGGTCTTCGCCACCTACCTGCTCAAG
CCGCTCTTCCCCACCTGCCCGGTGCCCGAGGAGGCAGCCAAGCTCGTGGCCTGCCTCTGC
GTGCTGCTGCTCACGGCCGTGAACTGCTACAGCOTGAAGGCCGCCACCCGGGTCCAGGAT
GCCTTTGCCGCCGCCAAGCTCCTGGCCCTGGCCCTGATCATCCTGCTGGGCTTCGTCCAG
ATCGGGAAGGGTGATGTGTCCAATCTAGATCCCAACTTCTCATTTGAAGGCACCAAACTG
GATGTGGGGAACATTGTGCTGGCATTATACAGCGGCCTCTTTGCCTATGGAGGATGGAAT
TACTTGAATTTCGTCACAGAGGAAATGATCAACCCCTACAGAAACCTGCCCCTGGCCATC
ATCATCTCCCTGCCCATCGTGACGCTGGTGTACGTGCTGACCAACCTGGCCTACTTCACC
ACCCTGTCCACCGAGCAGATGCTGTCGTCCGAGGCCGTGGCCGTGGACTTCGGGAACTAT
CACCTGGGCGTCATGTCCTGGATCATCCCCGTCTTCGTGGGCCTGTCCTGCTTCGGCTCC
GTCAATGGGTCCCTGTTCACATCCTCCAGGCTCTTCTTCGTGGGGTCCCGGGAAGGCCAC
CTGCCCTCCATCCTCTCCATGATCCACCCACAGCTCCTCACCCCCGTGCCGTCCCTCGTG
TTCACGTGTGTGATGACGCTGCTCTACGCCTTCTCCAAGGACATCTTCTCCGTCATCAAC
TTCTTCAGCTTCTTCAACTGGCTCTGCGTGGCCCTGGCCATCATCGGCATGATCTGGCTG
CGCCACAGAAAGCCTGAGCTTGAGCGGCCCATCAAGGTGAACCTGGCCCTGCCTGTGTTC
TTCATCCTGGCCTGCCTCTTCCTGATCGCCGTCTCCTTCTGGAAGACACCCGTGGAGTGT
GGCATCGGCTTCACCATCATCCTCAGCGGGCTGCCCGTCTACTTCTTCGGGGTCTGGTGG
AAAAACAAGCCCAAGTGGCTCCTCCAGGGCATCTTCTCCACGACCGTCCTGTGTCAGAAG
CTCATGCAGGTGGTCCCCCAGGAGACATAGCCAGGAGGCCGAGTGGCTGCCGGAGGAGCA
TGCGCAGAGGCCAGTTAAAGTAGATCACCTCCTCGAACCCACTCCGGTTCCCCGCAACCC
ACAGCTCAGCTGCCCATCCCAGTCCCTCGCCGTCCCTCCCAGGTCGGGCAGTGGAGGCTG
CTGTGAAAACTCTGGTACGAATCTCATCCCTCAACTGAGGGCCAGGGACCCAGGTGTGCC
TGTGCTCCTGCCCAGGAGCAGCTTTTGGTCTCCTTGGGCCCTTTTTCCCTTCCCTCCTTT
GTTTACTTATATATATATTTTTTTTAAACTTAAATTTTGGGTCAACTTGACACCACTAAG
ATGATTTTTTAAGGAGCTGGGGGAAGGCAGGAGCCTTCCTTTCTCCTGCCCCAAGGGCCC
AGACCCTGGGCAAACAGAGCTACTGAGACTTGGAACCTCATTGCTACGACAGACTTGCAC
TGAAGCCGGACAGCTGCCCAGACACATGGGCTTGTGACATTCGTGAAAACCAACCCTGTG
GGCTTATGTCTCTGCCTTAGGGTTTGCAGAGTGGAAACTCAGCCGTAGGGTGGCACTGGG
AGGGGGTGGGGGATCTGGGCAAGGTGGGTGATTCCTCTCAGGAGGTGCTTGAGGCCCCGA
TGGACTCCTGACCATAATCCTAGCCCTGAGACACCATCCTGAGCCAGGGAACAGCCCCAG
GGTTGGGGGGTGCCGGCATCTCCCCTAGCTCACCAGGCCTGGCCTCTGGGCAGTGTGGCC
TCTTGGCTATTTCTGTGTCCAGTTTTGGAGGCTGAGTTCTGGTTCATGCAGACAAAGCCC
TGTCCTTCAGTCTTCTAGAAACAGAGACAAGAAAGGCAGACACACCGCGGCCAGGCACCC
ATGTGGGCGCCCACCCTGGGCTCCACACAGCAGTGTCCCCTGCCCCAGAGGTCGCAGCTA
CCCTCAGCCTCCAATGCATTGGCCTCTGTACCGCCCGGCAGCCCCTTCTGGCCGGTGCTG
GGTTCCCACTCCCGGCCTAGGCACCTCCCCGCTCTCCCTGTCACGCTCATGTCCTGTCCT
GGTCCTGATGCCCGTTGTCTAGGAGACAGAGCCAAGCACTGCTCACGTCTCTGCCGCCTG
CGTTTGGAGGCCCCTGGGCTCTCACCCAGTCCCCACCCGCCTGCAGAGAGGGAACTAGGG
CACCCCTTGTTTCTGTTGTTCCCGTGAATTTTTTTCGCTATGGGAGGCAGCCGAGGCCTG
GCCAATGCGGCCCACTTTCCTGAGCTGTCGCTGCCTCCATGGCAGCAGCCAAGGACCCCC
AGAACAAGAAGACCCCCCCGCAGGATCCCTCCTGAGCTCGGGGGGCTCTGCCTTCTCAGG
CCCCGGGCTTCCCTTCTCCCCAGCCAGAGGTGGAGCCAAGTGGTCCAGCGTCACTCCAGT
GCTCAGCTGTGGCTGGAGGAGCTGGCCTGTGGCACAGCCCTGAGTGTCCCAAGCCGGGAG
CCAACGAAGCCGGACACGGCTTCACTGACCAGCGGCTGCTCAAGCCGCAAGCTCTCAGCA
AGTGCCCAGCGGAGCCTGCCGCCCCCACCTGGGCACCGGGACCCCCTCACCATCCAGTGG
GCCCGGAGAAACCTGATGAACAGTTTGGGGACTCAGGACCAGATGTCCGTCTCTCTTGCT
TGAGGAATGAAGACCTTTATTCACCCCTGCCCCGTTGCTTCCCGCTGCACATGGACAGAC
TTCACAGCGTCTGCTCATAGGACCTGCATCCTTCCTGGGGACGAATTCCACTCGTCCAAG
GGACAGCCCACGGTCTGGAGGCCGAGGACCACCAGCAGGCAGGTGGACTGACTGTGTTGG
GCAAGACCTCTTCCCTCTGGGCCTGTTCTCTTGGCTGCAAATAAGGACAGCAGCTGGTGC
CCCACCTGCCTGGTGCATTGCTGTGTGAATCCAGGAGGCAGTGGACATCGTAGGCAGCCA
CGGCCCCGGGTCCAGGAGAAGTGCTCCCTGGAGGCACGCACCACTGCTTCCCACTGGGGC
CGGCGGGGCCCACGCACGACGTCAGCCTCTTACCTTCCCGCCTCGGCTAGGGGTCCTCGG
GATGCCGTTCTGTTCCAACCTCCTGCTCTGGGACGTGGACATGCCTCAAGGATACAGGGA
GCCGGCGGCCTCTCGACGGCACGCACTTGCCTGTTGGCTGCTGCGGCTGTGGGCGAGCAT
GGGGGCTGCCAGCGTCTGTTGTGGAAAGTAGCTGCTAGTGAAATGGCTGGGGCCGCTGGG
GTCCGTCTTCACACTGCGCAGGTCTCTTCTGGGCGTCTGAGCTGGGGTGGGAGCTCCTCC
GCAGAAGGTTGGTGGGGGGTCCAGTCTGTGATCCTTGGTGCTGTGTGCCCCACTCCAGCC
TGGGGACCCCACTTCAGAAGGTAGGGGCCGTGTCCCGCGGTGCTGACTGAGGCCTGCTTC
CCCCTCCCCCTCCTGCTGTGCTGGAATTCCACAGGGACCAGGGCCACCGCAGGGGACTGT
CTCAGAAGACTTGATTTTTCCGTCCCTTTTTCTCCACACTCCACTGACAAACGTCCCCAG
CGGTTTCCACTTGTGGGCTTCAGGTGTTTTCAAGCACAACCCACCACAACAAGCAAGTGC
ATTTTCAGTCGTTGTGCTTTTTTGTTTTGTGCTAACGTCTTACTAATTTAAAGATGCTGT
CGGCACCATGTTTATTTATTTCCAGTGGTCATGCTCAGCCTTGCTGCTCTGCGTGGCGCA
GGTGCCATGCCTGCTCCCTGTCTGTGTCCCAGCCACGCAGGGCCATCCACTGTGACGTCG
GCCGACCAGGCTGGACACCCTCTGCCGAGTAATGACGTGTGTGGCTGGGACCTTCTTTAT -continued TCTGTGTTAATGGCTAACCTGTTACACTGGGCTGGGTTGGGTAGGGTGTTCTGGCTTTTT
TGTGGGGTTTTTATTTTTAGAAACACTCAATCATCCTAAAAAAAAAAAAAAAAAAAAAAA
AAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAA >Hs.351972_singlet1 AA865917 polyA = 2 polyA = 3
GGGACTTGGAAAGGGGAACTGGGATTTGGGGAGGGGCTGGAGGACTTCCGCACGCTTCCA
CCTCCTTCGACCTCCACTGCGCCCCACCTCCCTGCCTGTGTGTGTTATTTCAAAGGAAAA
GAACAAAAGGAATAAATTTTCTAAGCTCTTT AAAAAAAAAAAAAAAAAAAAAAA >Hs.5366_mRNA_2 gi|15277845|gb|BC012926.1|BC012926 *Homo sapiens* clone
MGC:16817 IMAGE:3853503 polyA = 3
GCAGGCTCTGCCTGTGGCCACTAGCAGAGAAGCTGCTGTCCTTCCACCACCAGCACCGGA
CCACCTGCTCCAAGACCAGCCTCCTGGGGGGACCAGGCACCCGGCCTTCACTGGCACCCA
GGGAGCCGTCCTCAGCAGCGTCAACATGTCAAGGCCCAGCAGCAGAGCCATTTACTTGCA
CCGGAAGGAGTACTCCCAGAACCTCACCTCAGAGCCCACCCTCCTGCAGCACAGGGTGGA
GCACTTGATGACATGCAAGCAGGGGAGTCAGAGAGTCCAGGGGCCCGAGGATGCCTTGCA
GAAGCTGTTCGAGATGGATGCACAGGGCCGGGTGTGGAGCCAAGACTTGATCCTGCAGGT
CAGGGACGGCTGGCTGCAGCTGCTGGACATTGAGACCAAGGAGGAGCTGGACTCTTACCG
CCTAGACAGCATCCAGGCCATGAATGTGGCGCTCAACACATGTTCCTACAACTCCATCCT
GTCCATCACCGTGCAGGAGCCGGGCCTGCCAGGCACTAGCACTCTGCTCTTCCAGTGCCA
GGAAGTGGGGGCAGAGCGACTGAAGACCAGCCTGCAGAAGGCTCTGGAGGAAGAGCTGGA
GCAAAGCAGACCTCGACTTGGAGGCCTTCAGCCAGGCCAGGACAGATGGAGGGGGCCTGC
TATGGAAAGGCCGCTCCCTATGGAGCAGGCACGCTATCTGGAGCCGGGGATCCCTCCAGA
ACAGCCCCACCAGAGGACCCTAGAGCACAGCCTCCCACCATCCCCAAGGCCCCTGCCACG
CCACACCAGTGCCCGAGAACCAAGTGCCTTTACTCTGCCTCCTCCAAGGCGGTCCTCTTC
CCCCGAGGACCCAGAGAGGGACGAGGAAGTGCTGAACCATGTCCTAAGGGACATTGAGCT
GTTCATGGGAAAGCTGGAGAAGGCCCAGGCAAAGACCAGCAGGAAGAAGAAATTTGGGAA
AAAAAACAAGGACCAGGGAGGTCTCACCCAGGCACAGTACATTGACTGCTTCCAGAAGAT
CAAGTACAGCTTCAACCTCCTGGGAAGGCTGGCCACCTGGCTGAAGGAGACAAGTGCCCC
TGAGCTCGTACACATCCTCTTCAAGTCCCTGAACTTCATCCTGGCCAGGTGCCCTGAGGC
TGGCCTAGCAGCCCAAGTGATCTCACCCCTCCTCACCCCTAAAGCTATCAACCTGCTACA
GTCCTGTCTAAGCCCACCTGAGAGTAACCTTTGGATGGGGTTGGGCCCAGCCTGGACCAC
TAGCCGGGCCGACTGGACAGGCGATGAGCCCCTGCCCTACCAACCCCACATTCTCGGATGA
CTGGCAACTTCCAGAGCCCTCCAGCCAAGCACCCTTAGGATACCAGGACCCTGTTTCCCT
TCGGCGGGGAAGTCATAGGTTAGGGAGCACCTCACACTTTCCTCAGGAGAAGACACACAA
CCATGACCCTCAGCCTGGGGACCCCAACTCCAGGCCCTCCAGCCCCAAACCTGCCCAGCC
AGCCCTGAAAATGCAAGTCTTGTACGAGTTTGAAGCTAGGAACCCACGGGAACTGACTGT
GGTCCAGGGAGAGAAGCTGGAGGTTCTGGACCACAGCAAGCGGTGGTGGCTGGTGAAGAA
TGAGGCGGGACGGAGCGGCTACATTCCAAGCAACATCCTGGAGCCCCTACAGCCGGGGAC
CCCTGGGACCCAGGGCCAGTCACCCTCTCGGGTTCCAATGCTTCGACTTAGCTCGAGGCC
TGAAGAGGTCACAGACTGGCTGCAGGCAGAGAACTTCTCCACTGCCACGGTGAGGACACT
TGGGTCCCTGACGGGGAGCCAGCTACTTCGCATAAGACCTGGGGAGCTACAGATGCTATG
TCCACAGGAGGCCCCACGAATCCTGTCCCGGCTGGAGGCTGTCAGAAGGATGCTGGGGAT
AAGCCCTTAGGCACCAGCTTAGACACCTCCAAGAACCAGGCCCCGCTGATGCAAGATGGC
AGATCTGATACCCATTAGAGCCCCGAGAATTCCTCTTCTGGATCCCAGTTTGCAGCAAAC
CCCACACCCCAGCTCACACAGCAAAAACAATGGACAGGCCCAGAGGGTGAAGCAAACAGT
GTCCCTTCTGGCTGTGTTGGAGCCTCCCCAGTAACCACCTATTTATTTTACCTCTTTCCC
AAACCTGGAGCATTTATGCCTAGGCTTGTCAAGAATCTGTTCAGTCCCTCTCCTTCTCAA
TAAAAGCATCTTCAAGCTTGAAAAAAAAAAAAAAA >Hs.18140_contig1
AI685931|AA410954|T97707|AA706873|AI911572|AW614616|AA548520|AW027764|
BF511251|AI914294|AW151688 polyA = 1 polyA = 1
CCTTCCATTGAATTCCACCAGACACATTCAGGTTANCTTCGTAATGTCTTCATATGAGTA
TCAATCAACACCTTCCCCAACTCAATTGTACTAGGTTGTAGAGCACAAGGATGGTCTCGT
GCTGCTCTGTGGCACCTGTGCCTACACTGCTCTGAGCTTTGAGGAGGCTGCTCTCTTTGC
TGACCCCATGATCTTTTCTGCCCTTCTGTTAAGGGCATTGGCCACAGCAACGGGGCAAAT
GCCCCAAGCTGGCTGTAAGTGACCCATCCCTTTGGCTCCCATGATTAGACCAAGGAGAGG
CATGGGGTCCAGCTGAGCCATTCAGAACCATTCCTTAGCATTTTCCACTCAAAGGTTAGA
GATGAGATTTTCTCTTCCCAAGGCTACCTCTGGCCATGGTTCCAGCTTCATGGGGGCAAT
GGGATTAGGAAAATGAGGTCAACCTGCAAAGGAAAGCAGATGCAAGAGATGGAGACAGAA
TGGGGGTGTCCTGGGGATCTTGGAGCCTGAATTCATTGGCACAAAAGGCAGCAGCATCCT
CACTGTATCTGCAGTCCATTTGGACTCAATAAAAACTTTGAAAGTCACATGTGTTATGGA
ATTCCTTCTCAGTGACACATTCATCTGTGCTCAGTTGTCCCAGCAAGGGTCAGCCCCTCA
TACCCCTGCAGCATCCGCTGCTATGAAGCAGAGCTGTAAACGCCCTCCCTGTGTATAGGA
AAAGCTACATGGAGCAAATCCTCCTGCCTGAAGAAGTGCATCTCAGCATCACTTCAGCTG
TCGGGGCATTTGTGGGGAGAACCAGACCACCTCTGCGGAAGGCAGCAGACCCTCTTCCAG
CCATGGATGGAGTTGAATTCTCTATAAACGGTTCACCAGCAAACCACCAATACATTCCAT
TGTTTGCCTAGAGAGAAATTTAAAAATAAATAAATGTTCACTTAT >Hs.133196_contig2
BF224381|BE467992|AW137689|AI695045|AW207361|BF445141|AA405473 polyA = 2
WARN polyA = 3
TGCGGCCGCGGCATGAAAGGCGGCGAGGAGAGGCAGCACTGCTGCTCTTGACTTCTGAGC
AGGGCTTAGAGAGCCTGCCCCGGCTTAAGCCGAGCTGCTGGTGCTGACCCTGAGCGCCGA
GTCCGCGAGCTCTGAGTCCGGAGCCTCCCAGCCGTGGAGCCGTGGGATGAGGGGGGCGTT
GGGGGACAGGGCAAAGTCGATCTTGGTTGTACAGCCGCCCGATCCTAGCGCGGAGCTGCG
AGCCTGACCGGCCGCGTCTGGCATGGTCAGAGAAAGAATTTTCTTTTCCCAACTCCGGCT
TTTGGTTTTGTGTGTCCACCTTGCGCAACTCCGGAGCCAGCCGACCCCACATGGATTCTC
AACAGGTGGCCGGCACATCTTCTGAGCCTCGCTCTCTCATCTGAAAGTGGAGTGTAAGTC -continued CAAGAAGATTCATTTAGACAAAGAAGGTGGAAAAAAAGGACTTTCTGGGCCAGCAAGTCG
GATGACCACCCTCCAAGGGGCAGAGGAGGGCCCATTTTGTGAAGAAGAAATCAACTACCC
GGAAAACGCCACAGGAGGACATGTTTCTGCAGATGTAGTTGCCCTAGAAACAGAAGAGTA
TGGGGGTGTGAATGTCTTCTCTTTTGGGGGCAAACACTATGTCCTTTTCTTTTTCTAGAT
ACAGTTAATTCCTGGAAATTTTAGCGAGTTTGTTCTTGTGGATATTTTGAACAATAAAGA
GTGAAAATCAAAAAAA >Hs.63325_mRNA5 gi|15451939|ref|NM_019894.11 *Homo sapiens* transmembrane
protease, serine 4 (TMPRSS4), mRNA polyA = 3
CCCAATCACTCCTGGAATACACAGAGAGAGGCAGCAGCTTGCTCAGCGGACAAGGATGCT
GGGCGTGAGGGACCAAGGCCTGCCCTGCACTCGGGCCTCCTCCAGCCAGTGCTGACCAGG
GACTTCTGACCTGCTGGCCAGCCAGGACCTGTGTGGGGAGGCCCTCCTGCTGCCTTGGGG
TGACAATCTCAGCTCCAGGCTACAGGGAGACCGGGAGGATCACAGAGCCAGCATGTTACA
GGATCCTGACAGTGATCAACCTCTGAACAGCCTCGATGTCAAACCCCTGCGCAAACCCCG
TATCCCCATGGAGACCTTCAGAAAGGTGGGGATCCCCATCATCATAGCACTACTGAGCCT
GGCGAGTATCATCATTGTGGTTGTCCTCATCAAGGTGATTCTGGATAAATACTACTTCCT
CTGCGGGCAGCCTCTCCACTTCATCCCGAGGAAGCAGCTGTGTGACGGAGAGCTGGACTG
TCCCTTGGGGGAGGACGAGGAGCACTGTGTCAAGAGCTTCCCCGAAGGGCCTGCAGTGGC
AGTCCGCCTCTCCAAGGACCGATCCACACTGCAGGTGCTGGACTCGGCCACAGGGAACTG
GTTCTCTGCCTGTTTCGACAACTTCACAGAAGCTCTCGCTGAGACAGCCTGTAGGCAGAT
GGGCTACAGCAGCAAACCCACTTTCAGAGCTGTGGAGATTGGCCCAGACCAGGATCTGGA
TGTTGTTGAAATCACAGAAAACAGCCAGGAGCTTCGCATGCGGAACTCAAGTGGGCCCTG
TCTCTCAGGCTCCCTGGTCTCCCTGCACTGTCTTGCCTGTGGGAAGAGCCTGAAGACCCC
CCGTGTGGTGGGTGGGGAGGAGGCCTCTGTGGATTCTTGGCCTTGGCAGGTCAGCATCCA
GTACGACAAACAGCACGTCTGTGGAGGGAGCATCCTGGACCCCCACTGGGTCCTCACGGC
AGCCCACTGCTTCAGGAAACATACCGATGTGTTCAACTGGAAGGTGCGGGCAGGCTCAGA
CAAACTGGGCAGCTTCCCATCCCTGGCTGTGGCCAAGATCATCATCATTGAATTCAACCC
CATGTACCCCAAAGACAATGACATCGCCCTCATGAAGCTGCAGTTCCCACTCACTTTCTC
AGGCACAGTCAGGCCCATCTGTCTGCCCTTCTTTGATGAGGAGCTCACTCCAGCCACCCC
ACTCTGGATCATTGGATGGGGCTTTACGAAGCAGAATGGAGGGAAGATGTCTGACATACT
GCTGCAGGCGTCAGTCCAGGTCATTGACAGCACACGGTGCAATGCAGACGATGCGTACCA
GGGGGAAGTCACCGAGAAGATGATGTGTGCAGGCATCCCGGAAGGGGGTGTGGACACCTG
CCAGGGTGACAGTGGTGGGCCCCTGATGTACCAATCTGACCAGTGGCATGTGGTGGGCAT
CGTTAGCTGGGGCTATGGCTGCGGGGGCCCGAGCACCCCAGGAGTATACACCAAGGTCTC
AGCCTATCTCAACTGGATCTACAATGTCTGGAAGGCTGAGCTGTAATGCTGCTGCCCCTT
TGCAGTGCTGGGAGCCGCTTCCTTCCTGCCCTGCCCACCTGGGGATCCCCCAAAGTCAGA
CACAGAGCAAGAGTCCCCTTGGGTACACCCCTCTGCCCACAGCCTCAGCATTTCTTGGAG
CAGCAAAGGGCCTCAATTCCTGTAAGAGACCCTCGCAGCCCAGAGGCGCCCAGAGGAAGT
CAGCAGCCCTAGCTCGGCCACACTTGGTGCTCCCAGCATCCCAGGGAGAGACACAGCCCA
CTGAACAAGGTCTCAGGGGTATTGCTAAGCCAAGAAGGAACTTTCCCACACTACTGAATG
GAAGCAGGCTGTCTTGTAAAAGCCCAGATCACTGTGGGCTGGAGAGGAGAAGGAAAGGGT
CTGCGCCAGCCCTGTCCGTCTTCACCCATCCCCAAGCCTACTAGAGCAAGAAACCAGTTG
TAATATAAAATGCACTGCCCTACTGTTGGTATGACTACCGTTACCTACTGTTGTCATTGT
TATTACAGCTATGGCCACTATTATTAAAGAGCTGTGTAACATCAAAAAAAAAAAAAAAAA
AAAA >Hs.250692_mRNA_2 gi|184223|gb|M95585.1|HUMHLF Human hepatic leukemia
factor (HLF) mRNA, complete cds polyA = 1
TTTTTCAATTTTGAACATTTTGCAAAACGAGGGGTTCGAGGCAGGTGAGAGCATCCTGCA
CGTCGCCGGGGAGCCCGCGGGCACTTGGCGCGCTCTCCTGGGACCGTCTGCACTGGAAAC
CCGAAAGTTTTTTTTTAATATATATATTTTTATGCAGATGTATTTATAAAGATATAAGTAAT
TTTTTTCTTCCCTTTTCTCCACCGCCTTGAGAGCGAGTACTTTTGGCAAAGGACGGAGGA
AAAGCTCAGCAACATTTTAGGGGGCGGTTGTTTCTTTCTTTCTTATTTCTTTTTTAAGGG
GAAAAAATTTGAGTGCATCGCGATGGAGAAAATGTCCCGACCGCTCCCCCTGAATCCCAC
CTTTATCCCGCCTCCCTACGGCGTGCTCAGGTCCCTGCTGGAGAACCCGCTGAAGCTCCC
CCTTCACCACGAAGACGCATTTAGTAAAGATAAAGACAAAGAAAAGAAGCTGGATGATGA
GAGTAACAGCCCGACGGTCCCCCAGTCGGCATTCCTGGGGCCTACCTTATGGGACAAAAC
CCTTCCCTATGACGGAGATACTTTCCAGTTGGAATACATGGACCTGGAGGAGTTTTTGTC
AGAAAATGGCATTCCCCCCAGCCCATCTCAGCATGACCACAGCCCTCACCCTCCTGGGCT
GCAGCCAGCTTCCTCGGCTGCCCCCTCGGTCATGGACCTCAGCAGCCGGGCCTCTGCACC
CCTTCACCCTGGCATCCCATCTCCGAACTGTATGCAGAGCCCCATCAGACCAGGTCAGCT
GTTGCCAGCAAACCGCAATACACCAAGTCCCATTGATCCTGACACCATCCAGGTCCCAGT
GGGTTATGAGCCAGACCCAGCAGATCTTGCCCTTTCCAGCATCCCTGGCCAGGAAATGTT
TGACCCTCGCAAACGCAAGTTCTCTGAGGAAGAACTGAAGCCACAGCCCATGATCAAGAA
AGCTCGCAAAGTCTTCATCCCTGATGACCTGAAGGATGACAAGTACTGGGCAAGGCGCAG
AAAGAACAACATGGCAGCCAAGCGCTCCCGCGACGCCCGGAGGCTGAAAGAGAACCAGAT
CGCCATCCGGGCCTCGTTCCTGGAGAAGGAGAACTCGGCCCTCCGCCAGGAGGTGGCTGA
CTTGAGGAAGGAGCTGGGCAAATGCAAGAACATACTTGCCAAGTATGAGGCCAGGCACGG
GCCCCTGTAGGATGGCATTTTTGCAGGCTGGCTTTGGAATAGATGGACAGTTTGTTTCCT
GTCTGATAGCACCACACGCAAACCAACCTTTCTGACATCAGCACTTTACCAGAGGCATAA
ACACAACTGACTCCCATTTTGGTGTGCATCTGTGTGTGTGTGCGTGTATATGTGCTTGTG
CTCATGTGTGTGGTCAGCGGTATGTGCGTGTGCGTGTTCCTTTGCTCTTGCCATTTTAAG
GTAGCCCTCTCATCGTCTTTTAGTTCCAACAAAGAAAGGTGCCATGTCTTTACTAGACTG
AGGAGCCCTCTCGCGGGTCTCCCATCCCCTCCCTCCTTCACTCCTGCCTCCTCAGCTTTG
CTTCATGTTCGAGCTTACCTACTCTTCCAGGACTCTCTGCTTGGATTCACTAAAAAGGGC
CCTGGTAAAATAGTGGATCTCAGTTTTTAAGAGTACAAGCTCTTGTTTCTGTTTAGTCCG
TAAGTTACCATGCTAATGAGGTGCACACAATAACTTAGCACTACTCCGCAGCTCTAGTCC
TTTATAAGTTGCTTTCCTCTTACTTTCAGTTTTGGTGATAATCGTCTTCAAATTAAAGTG
CTGTTTAGATTTATTAGATCCCATATTTACTTACTGCTATCTACTAAGTTTCCTTTTAAT
TCTACCAACCCCAGATAAGTAAGAGTACTATTAATAGAACACAGAGTGTGTTTTTGCACT
GTCTGTACCTAAAGCAATAATCCTATTGTACGCTAGAGCATGCTGCCTGAGTATTACTAG -continued TGGACGTAGGATATTTTCCCTACCTAAGAATTTCACTGTCTTTTAAAAAACAAAAAGTAA
AGTAATGCATTTGAGCATGGCCAGACTATTCCCTAGGACAAGGAAGCAGAGGGAAATGGG
AGGTCTAAGGATGAGGGGTTAATTTATCAGTACATGAGCCAAAAACTGCGTCTTGGATTA
GCCTTTGACATTGATGTGTTCGGTTTTGTTGTTCCCCTTCCCTCACACCCTGCCTCGCCC
CCACTTTTCTAGTTAACTTTTTCCATATCCCTCTTGACATTCAAAACAGTTACTTAAGAT
TCAGTTTTCCCACTTTTTGGTAATATATATATATTTTTGTGAATTATACTTTGTTGTTTTTA
AAAAGAAAATCAGTTGATTAAGTTAATAAGTTGATGTTTTCTAAGGCCCTTTTTCCTAGT
GGTGTCATTTTTGAATGCCTCATAAATTAATGATTCTGAAGCTTATGTTTCTTATTCTCT
GTTTGCTTTTGAACGTATGTGCTCTTATAAAGTGGACTTCTGAAAAATGAATGTAAAAGA
CACTGGTGTATCTCAGAAGGGGATGGTGTTGTCACAAACTGTGGTTAATCCAATCAATTT
AAATGTTTACTATAGACCAAAAGGAGAGATTATTAAATCGTTTAATGTTTATACAGAGTA
ATTATAGGAAGTTCTTTTTTGTACAGTATTTTTCAGATATAAATACTGACAATGTATTTT
GGAAGACATATATTATATATATAGAAAAGAGGAGAGGAAAACTATTCCATGTTTTAAAATTA
TATAGCAAAGATATATATTCACCAATGTTGTACAGAGAAGAAGTGCTTGGGGGTTTTTGA
AGTCTTTAATATTTTAAGCCCTATCACTGACACATCAGCATGTTTTCTGCTTTAAATTAA
AATTTTATGACAGTATCGAGGCTTGTGATGACGAATCCTGCTCTAAAATACACAAGGAGC
TTTCTTGTTTCTTATTAGGCCTCAGAAAGAAGTCAGTTAACGTCACCCAAAAGCACAAAA
TGGATTTTAGTCAAATATTTATTGGATGATACAGTGTTTTTTAGGAAAAGCATCTGCCAC
AAAAATGTTCACTTCGAAATTCTGAGTTCCTGGAATGGCACGTTGCTGCCAGTGCCCCAG
ACAGTTCTTTTCTACCCTGCGGGCCCGCACGTTTTATGAGGTTGATATCGGTGCTATGTG
TTTGGTTTATAATTTGATAGATGTTTGACTTTAAAGATGATTGTTCTTTTGTTTCATTAA
GTTGTAAAATGTCAAGAAATTCTGCTGTTACGACAAAGAAACATTTTACGCTAGATTAAA
ATATCCTTTCATCAATGGGATTTTCTAGTTTCCTGCCTTCAGAGTATCTAATCCTTTAAT
GATCTGGTGGTCTCCTCGTCAATCCATCAGCAATGCTTCTCTCATAGTGTCATAGACTTG
GGAAACCCAACCAGTAGGATATTTCTACAAGGTGTTCATTTTGTCACAAGCTGTAGATAA
CAGCAAGAGATGGGGGTGTATTGGAATTGCAATACATTGTTCAGGTGAATAATAAAATCA
AAAACTTTTGCAATCTTAAGCAGAGATAAATAAAAGATAGCAATATGAGACACAGGTGGA
CGTAGAGTTGGCCTTTTTACAGGCAAAGAGGCGAATTGTAGAATTGTTAGATGGCAATAG
TCATTAAAAACATAGAAAAATGATGTCTTTAAGTGGAGAATTGTGGAAGGATTGTAACAT
GGACCATCCAAATTTATGGCCGTATCAAATGGTAGCTGAAAAAACTATATTTGAGCACTG
GTCTCTCTTGGAATTAGATGTTTATATCAAATGAGCATCTCAAATGTTTTCTGCAGAAAA
AAATAAAAAGATTCTAATAAAAAAA >Hs.250726_singlet4 AW298545 polyA = 2 polyA = 3
TTCCTTCCCTCCCTCCNTTCCTCAGGAGCCGCCAGTCCCCAAGTTGGCTGTGGTTGGGCA
CCTGGTTTGGGTCCTGCAGAGCTGGGCTCAGGCCCTGGGCTCTGAACCTGTGAACCCTTG
CTGTGTTACGAAACTTTCCTTCCTCTGAGGGCCTTGAACCCTCTCCTTTTCTTCTTTTGG
GGGTGGGGGTTAACTTTATTTTCTCTTCCCTGTATCTGCCTCTCCCTTCCCTCAATTTCC
TGTTTTAAAACTGAATGGCACGAAATTGTTTTCCTCAACTCGGAGATTCCTGTATGGAGA
GAATCAATTTCTATATTTGCAATAAATTTCTTATTTAAAGCTAAAAAAAAAAAAAAAA >Hs.79217_mRNA_2 gi|16306657|gb|BC001504.1|BC001504 *Homo sapiens* clone
MGC:2273 IMAGE:3505512 polyA = 3
GGCACGAGGGCCATCTGTGGGGGCTTTGGGCCAGGGGTCTCCGGACAGCATGAGCGTGGG
CTTCATCGGCGCTGGCCAGCTGGCTTTTGCCCTGGCCAAGGGCTTCACAGCAGCAGGCGT
CTTGGCTGCCCACAAGATAATGGCTAGCTCCCCAGACATGGACCTGGCCACAGTTTCTGC
TCTCAGGAAGATGGGGGTGAAGTTGACACCCCACAACAAGGAGACGGTGCAGCACAGTGA
TGTGCTCTTCCTGGCTGTGAAGCCACACATCATCCCCTTCATCCTGGATGAAATAGGCGC
CGACATTGAGGACAGACACATTGTGGTGTCCTGCGCGGCCGGCGTCACCATCAGCTCCAT
TGAGAAGAAGCTGTCAGCGTTTCGGCCAGCCCCCAGGGTCATCCGCTGCATGACCAACAC
TCCAGTCGTGGTGCGGGAGGGGGCCACCGTGTATGCCACAGGCACGCACGCCCAGGTGGA
GGACGGGAGGCTCATGGAGCAGCTGCTGAGCAGCGTGGGCTTCTGCACGGAGGTGGAAGA
GGACCTGATTGATGCCGTCACGGGGCTCAGTGGCAGCGGCCCCGCCTACGCATTCACAGC
CCTGGATGCCCTGGCTGATGGGGGCGTGAAGATGGGACTTCCAAGGCGCCTGGCAGTCCG
CCTCGGGGCCCAGGCCCTCCTGGGGGCTGCCAAGATGCTGCTGCACTCAGAACAGCACCC
AGGCCAGCTCAAGGACAACGTCAGCTCTCCTGGTGGGGCCACCATCCATGCCTTGCATGT
GCTGGAGAGTGGGGGCTTCCGCTCCCTGCTCATCAACGCTGTGGAGGCCTCCTGCATCCG
CACACGGGAGCTGCAGTCCATGGCTGACCAGGAGCAGGTGTCACCAGCCGCCATCAAGAA
GACCATCCTGGACAAGGTGAAGCTGGACTCCCCTGCAGGGACCGCTCTGTCGCCTTCTGG
CCACACCAAGCTGCTCCCCCGCAGCCTGGCCCCAGCGGGCAAGGATTGACACGTCCTGCC
TGACCACCATCCTGCCACCACCTTCTCTTCTCTTGTCACTAGGGGGACTAGGGGGTCCCC
AAAGTGGCCCACTTTCTGTGGCTCTGATCAGCGCAGGGGCCAGCCAGGGACATAGCCAGG
GAGGGGCCACATCACTTCCCACTGGAAATCTCTGTGGTCTGCAAGTGCTTCCCAGCCCAG
AACAGGGGTGGATTCCCCAACCTCAACCTCCTTTCTTCTCTGCTCCCAAACCATGTCAGG
ACCACCTTCCTCTAGAGCTCGGGAGCCCGGAGGGTCTTCACCCACTCCTACTCCAGTATC
AGCTGGCACGGGCTCCTTCCTGAGAGCAAAGGTCAAGGACCCCCTCTGTGAAGGCTCAGC
AGAGGTGGGATCCCACGCCCCTCCCGGCCCCTCCCTGCCCTCCATTCAGGGAGAAACCT
CTCCTTCCCGTGTGAGAAGGGCCAGAGGGTCCAGGCATCCCAAGTCCAGCGTGAAGGGCC
ACAGCCCCTCTTGGCTGCCAAGCACGCAGATCCCATGGACATTTGGGGAAAGGGCTCCTT
GGGCTGCTGGTGAACTTCTGTGGCCACCACCTCCTGCTCCTGACCTCCCTGGGAGGGTGC
TATCAGTTCTGTCCTGGCCCTTTCAGTTTTATAAGTTGGTTTCCAGCCCCCAGTGTCCTG
ACTTCTGTCTGCCACATGAGGAGGGAGGCCCTGCCTGTGTGGGAGGGTGGTTACTGTGGG
TGGAATAGTGGAGGCCTTCAACTGATTAGACAAGGCCCGCCCACATCTTGGAGGGCATCT
GCCTTACTGATTAAAATGTCAATGTAATCTAAAAAAAAAAAAAAAAA >Hs.47986_mRNA_1 gi|13279253|gb|BC004331.1|BC00433| *Homo sapiens* clone
MGC:10940 IMAGE:3630835 polyA = 3
GATAAATGCGGAGGGACGGTCCAGCTTTAGCTCTCTGCTCGCCGCCGCCGCTGTCGCCGC
CACCTCCTCTGATCTACGAAAGTCATGTTACCCAACACCGGGAGGCTGGCAGGATGTACA
GTTTTTATCACAGGTGCAAGCCGTGGCATTGGCAAAGCTATTGCATTGAAAGCAGCAAAG -continued GATGGAGCAAATATTGTTATTGCTGCAAAGACCGCCCAGCCACATCCAAAACTTCTAGGC
ACAATCTATACTGCTGCTGAAGAAATTGAAGCAGTTGGAGGAAAGGCCTTGCCATGTATT
GTTGATGTGAGAGATGAACAGCAGATCAGTGCTGCAGTGGAGAAAGCCATCAAGAAATTT
GGAGCTTATACCATTGCTAAGTATGGTATGTCTATGTATGTGCTTGGAATGGCAGAAGAA
TTTAAAGGTGAAATTGCAGTCAATGCATTATGGCCTAAAACAGCCATACACACTGCTGCT
ATGGATATGCTGGGAGGACCTGGTATCGAAAGCCAGTGTAGAAAAGTTGATATCATTGCA
GATGCAGCATATTCCATTTTCCAAAAGCCAAAAAGTTTTACTGGCAACTTTGTCATTGAT
GAAAATATCTTAAAAGAAGAAGGAATAGAAAATTTTGACGTTTATGCAATTAAACCAGGT
CATCCTTTGCAACCAGATTTCTTCTTAGATGAATACCCAGAAGCAGTTAGCAAGAAAGTG
GAATCAACTGGTGCTGTTCCAGAATTCAAAGAAGAGAAACTGCAGCTGCAACCAAAACCA
CGTTCTGGAGCTGTGGAAGAAACATTTAGAATTGTTAAGGACTCTCTCAGTGATGATGTT
GTTAAAGCCACTCAAGCAATCTATCTGTTTGAACTCTCCGGTGAAGATGGTGGCACGTGG
TTTCTTGATCTGAAAAGCAAGGGTGGGAATGTCGGATATGGAGAGCCTTCTGATCAGGCA
GATGTGGTGATGAGTATGACTACTGATGACTTTGTAAAAATGTTTTCAGGGAAACTAAAA
CCAACAATGGCATTCATGTCAGGGAAATTGAAGATTAAAGGTAACATGGCCCTAGCAATC
AAATTGGAGAAGCTAATGAATCAGATGAATGCCAGACTGTGAAGGAAAATATAAAAAAA
AGTCGACTGCTATGCTCAAAAGTAAAAAAGCTCAACAGTTAAAATCTAATGTTTGTTT
TCTTTCCTGTTATATTATAAGGATATGCACGTTTGTTCTGGAAAAGATAGAATTTGTCTC
TAAAAGACTTGAAATTGTAATTAAAATGGCAAGCTAATCAAACATAAGCTTCATTAAGTG
GGATTCTAAGACAGTCTGTGTTTTTATATTTCAAGGGTTTAACCCTTTGAGCCTTACATC
TCATTCACTGTCTTTCTCCAAGAAAAGTATTTTGGGCGGACAGTCAGATCAAGCAGTAAA
ATTAGCTCTTTCAAATCTTCTTGTCATGTAAAATGAAGCTAGTCTGTTTTAAAATTTTTA
GTTTTGGATTGTATACTAATGAAAATCTTAATGATGTTTTTGATTTTTATATACTTATTT
TAAAGAAAATCTTATATAGTACATTTTACAAAAATTATAAAAAATGAATTAGTACTGGCG
AGGACTAAATGAAACAATAATTTTTCATTTTGATAACTAGCTTTCCAGGTGGACTTAGCC
ATAGGAAAATATTACTAATGTAATTTAACAAATTGCTGCATGTATTCCATTTAAAAATAT
GTTTAAATTGTCCTAAAACAAAATAATTTTCTCCCTAGGAGTATGCATTTGGCTACAGTG
TTTTGAAACAGAAACCTTAGAATAGGTCATTGGTATGGGCTGAACTGTGTATCCCCCAAT
TCATTTGTTGAGGTCCTAACTCCCATTTCTTTTGAATGTGACTGTTCGGAGATGAGGCCT
TTAAAGAGGTGACTTAAGTTCAAAGGAGGCTGTTAGTCTAATCCAACATGGTGTCCTTTG
GACATAAGAGATACCAGCAATGTGTGCACAGAACAAAGACCAGGAGAGGACACAGTGAGA
AGGCAGTTATCTGCAAGCAAAGAGAGAGGCTTCAGAAGAAACAAAATCACCAGCACCTTG
ATCTTTGACTTCTAATCTCCAGAATAGTGAGAAATAAATTTCTGTTGTTAAGCCGTCCAC
TGTGGGAGGCCGACGCAGGAGGATTGCTTGAGGCCAGGAGTTCAAGGCCAGCCTGGACAA
CATAGTAAGACCCTATCTCTACCCCCCTAATAAATTAATTTAAAAAGCCCCCCAATCTGT
GGTATTTTATTATGGCAGCCCTAGCAAGCTAATACAGTGGTTTGAGAGGCTGGGAGGGTT
GAGGGGAAGATAAACTTTTAAAAAGCTCTTATCTTTCATTTCAATCAGTTAAAAATACTT
GCTCAGTGTAACAATTTTGCTTCTCAGCTTCCACTCTAATATTGTTGTGCCATTAAGCAA
TTTAGCTAATCCTGACATTTCTTAGATTCATAATGTTAGGAGCATTTAATCTGTATTTTA
CAAGTTAGGAAGCAGAGGATCAGAGATGGGAAAGGACTAGCCCAAGGCCAACATTAACAA
GCCCTCTAACAAAAACTTTACAATACATTTATGTTGAATGGAACTCCAAGATCTCACCTC
TCCATCCAGGAATGGAGTCCATGTAATCAAAGTGAACTTAAAAATAGGACAGTTTCAACA
AGTCAGGAGATTCACAGCAACTGATCAAAGGGAGTCCAGTCAACGTGAGCAAGCGTGATT
ATGATGAGGAAGCCCCCTCTGCTTTAATCCACACAAGGAACGTAACCTGAAGTAACCTGA
TGTTAACCAATCTGCTGTGTCTACTATGCTGTTTCCTTGTTCCTGCTAGTGCTGCTTTAC
AAATGCAGACCATTCTATCATACCTGGCAGGGCTTCTGTTTTATTTTGTAGGCTGGATGC
TACCCAGTTCATGAATCGCTATAAGCCAATTAGATCTTTAAAAAAAAAAAAAAAAAAAAA
AAA >Hs.94367 mRNA_1 gi|10440200|dbj|AK027147.1|AK027147 *Homo sapiens* cDNA:
FLJ23494 fis, clone LNG01885 polyA = 3

TATTAAAAGTACCCCATGGATGGACCTCCAAATGAGTTTAGGGTAATTGCGCTTAAAATA
TTAGGACCAAAGTACATTTATTTTATAGATGGAGGAGGCGAGGAGACGAGTGGGGACCAG
CTTGACATCCAGTCTTCACCTGGACATATGGAAAGAACAAATGTGCGATCTGCTCGTTCC
CTCTGAAGGTCTCTGTTACGTATTTCCTCCTCTCCTCCAGAGCATAATAACCAATGACTG
CTCTCAGAAAGGTACTGTGACCACCACTTGCTTGGCTCTCCAACTTCCTCCCCCATTTCC
CTCTTGACTCCTGTTTGCCATAACACCTTCTGTCCCCTAGCCTTGCCTCAGGTCCCCGAC
GAATCCTGCCCTTAATCTGTGGGGGTGGTAGGTGGCACTGGTTTGAAGAGCTTACTGGAT
CTCCCTCAGTGAGTCAGCCTGGAGTTGTGTTTGAAAACCACAGGCCCTGACTGTGGCTGT
AAGACCTCCCAGACACCACCTGCTGCTGCCTATCATCATCTTCAGGTGCTGGGCTCCCCT
GTGGGCCTCGTCTGCCCGCCCTCTGCTGCAGCTGTCCCATGGGCGCCCGCCCTCTCTGAC
ACCACAAGAGAGCCCATCTAGATTCCAGGAAAAAACTCATCTTTATTTGCCTTCTTCCCA
CTGAAGGTAAAAGCAACATTAATAACCACAACAAATACTTAGTGAGTGCTTACTATTATT
CATTTAATTGTAGGCCCTTCCATCCCTGGCCATGATGAGAGACATGCCATAGCTTACTCC
TAAAGAGACCTGAGGACACACGTGCACAAACATATTGGGCATATCATCAATGGCATCAAA
ACTGATTTTCCCTGTCTACCCAGAACAGGCCTGAGGGAGAGGGAAAAGCGGATACCCACC
TGTGTCGCTGTTTGCGTGCCAAGTCCAGGAACAGTCCATACAGCCCTGCTGCATCCCACG
ACGCTGTCACAAAGCAGGAGTTCATCCGAGGCCAAGGTATGGAGAAACTGAGGCCCAGAA
ATTGATGTCCAGAATGCTTTGCTCTTAGCCACTGTACTATTATGGCATATTTTATCTTTA
TGTATTGCATCATTTCATGGATTCAAGTTTATCAATGTCCTTTGACAAGTTTAAAAATCT
GTCTGCTAAAATCTATCAAATACATTAAGGAAAAGTCCCACTTGGCACATCTCCCACACC
AGATGTTAATTATTCATACTGCATGACTGAGGATTTTGGAGGCAGAGAGAGATTCATCTG
CAATATTTGGAACACCAATGGAGGTCTATGTCAACACAGAATTTATACAGCAGCTGGTGC
TAGTCAGAGCTAATGACAGAATTTCAGTTTAATAAAAAGACCCCCAACTGAGCACACCAT
CTTGAAAAAAGTATACTTATCAAACAGCTTTCAATCAGTTCAAGAGAGACACCTTAATTG
GGGAGAGGAAGAATTGCAGAGTAGTTTGTAATCATGCCAATTCCAGATCAATAACTGCAT
GTCTGTTCTTTGGTAGAAATAGCTTTTGCTTTATATTAAGTAATCACATATATATTCTCT
CTATTTGGATAAGGAAACCTTCGCTTTATTTGACAATGTATAATGATATACTCTTCTAAT
TCACCTCTGTGTCTTCACAATAAACATGAGTAAAATTTAGACAAGTGATGGTAAAGGTCA

-continued

ATATAATTATTTATTTTTAAAATAAATTTTGTATCTAACAGGAAAGCAGTTCTTATGAAA
TTTTTATATTTTCAAAAATTGTTTTGTTCAAATAAAATTTTATGAGTAAAGTTAAAAAAA
AAAAAAAAAAAAAAAAAAAAAAAA

>Hs.49215 contig1
BI493248|R66529|AA452255|BI492877|AW196683|AI963900|BF478125|AI421654|
BE466675 polyA = 1 polyA = 1
GGGTACCTGGTGGGGCCAATCACCGAGCCATGAACATCAGTAACGTACTCTAAAGACCAA
GGCTACGATGGCTATGATGGTCAGAATTACTACCACCACCAGTGAAGCTCCAGCCTGGGA
TGAATTCATCCATTCTGGCTTTGCATCCGGCTACCATTTTCGAAGTTCAACTCAGGAAGG
TGCAATATAACAAATGTGCATATTATAATGAGGAATGGTACTACCGTTCCAGATTTTCTG
TAATTGCTTCTGCAAAGTAATAGGCTTCTTGTCCCTTTTTTTTCTGGCATGTTATGGAAT
GATCATTGTAAATCAGGACCATTTATCAAGCAGTACACCAACTCATAAGATCAAATTTCA
TTGAATGGTTTGAGGTTGTAGCTCTATAAATAGTAGTTTTTAACATGCCTGTAGTATTGC
TAACTGCAAAAACATACTCTTTGTACAAGAAGTGCTTCTAAGAATTTCATTGACATTAAT
GACACTGTATACAATAAATGTGTAGTTTCTTAATCGCACTACCTATGCAACACTGTGTAT
TAGGTTTATCATCCTCATGTATTTTTATGTGACCTGTATGTATATTCTAATCTACGAGTT
TTATCACAAATAAAAATGCAATCCTTCAAA >Hs.281587 contig2
R61469|R1591|AA007214|R61471|AI014624|N69765|AW592075|H09780|AA709038|
AI335898|AI559229|F09750|R49594|H11055|T72573|AA935558|AA988654|AA826438|
AI002431|AI29972| polyA = 1 polyA = 2
AAGGTGGGCTTTCATTGTGATTTTTGTTCTGTTGCAGTAATATAGGAGCACATTTTGGCC
ATTGTAATTACAGGGAACAAAGGGATTGCGGACACATATCTGGACTTCTTTTCCTCCCTT
ATTGTTGTGGAAGAGACACTAGAAATGCTCAAACACCTGCAATATACAGAATATACACAA
TTTTATTCCAGTATTTCCCTAACATATGGTTTAAAATTATTCCAGGTATACAGTGTATGC
AATTCTGCATTATCACAGAGGAACAACTTCTTTTTTAAAAAATAAATAGGTCAGCCATTT
TTATTAACGTGCAAAAACTTTATCACTCTAACATGCTCTAGGTAGTTGAGGAAAAGAGGT
CTGATCACTGTTTGTATTTTATTTTCTTTGTGGGAACATTTCACCTGCTGAGTGTACATG
AATTTGCTTTCTATAAAAGGCTTTTATGAGTTTACAGTAGAATCAGTGGAAGGAAGAGTT
AATAAGGGCTGTTTTTAAAAAAACAAACAAACAAACAAAACAAATAATTAAAAAAAAATT
TTACATTCCTTCCTATTCTCTAACTACACTTGGGAAGTGCACTTCAGATAAGTTTGCAGT
GTGACTGAGAGATGAAGGAAATCCATAGAAAAGGTCCTCTTAGTGAACAAAATTTAGTTA
TTAACTTTATAGCTATGAAATTTCCCCGGGCATTTGTTTTTGTTCAAACAGACTTTAACC
TCTGCATCATACTTAACCCTGCGACATGCGTACAGTATGCATATTTTGTTTTGAAAAAAA
ATGTTTCGTTCCAGTCTGTTAAGAATATTCAAAAATAATAAAGGTATTGCTTAATAAAAT
TGCTAGAATTGTTTAGCAGTACATGCACAATATTTTACTAGATTCTTTGTTTTAATAGTG
TTTTGTTGAGACTGAAAATCTTAAAATGGTCTGCGCAAATACAAAAAAAAAGAAAACACC
AAAAAAAAAA >Hs.79378_mRNA_1 gi|16306528|ref|NM_003914.2| *Homo sapiens* cyclin A1
(CCNA1), mRNA polyA = 3
GGTGTTGTTCCGGACACATAGAAAGATAACGACGGGAAGAGCGGGGCCCGCTTTGGGGTC
CAGGCAGGTTTTGGGGCCTCCTGTCTGGTGGGAGGAGGCCGCAGCGCAGCACCCTGCTCG
TCACTTGGGATGGAGACCGGCTTTCCCGCAATCATGTACCCTGGATCTTTTATTGGGGGC
TGGGGAGAAGAGTATCTCAGCTGGGAAGGACCGGGGCTCCCAGATTTCGTCTTCCAGCAG
CAGCCCGTGGAGTCTGAAGCAATGCACTGCAGCAACCCCAAGAGTGGAGTTGTGCTGGCT
ACAGTGGCCCGAGGTCCCGATGCTTGTCAGATACTCACCAGAGCCCCGCTGGGCCAGGAT
CCCCCGCAGAGGACAGTGCTAGGGCTGCTAACTGCAAATGGGCAGTACAGGAGGACCTGT
GGCCAGGGGATCACAAGAATCAGGTGTTATTCTGGATCAGAAAATGCCTTCCCTCCAGCT
GGAAAGAAAGCACTCCCTGACTGTGGGGTCCAAGAGCCCCCCAAGCAAGGGTTTGACATC
TACATGGATGAACTAGAGCAGGGGGACAGAGACAGCTGCTCGGTCAGAGAGGGGATGGCA
TTTGAGGATGTGTATGAAGTAGACACCGGCACACTCAAGTCAGACCTGCACTTCCTGCTG
GATTTCAACACAGTTTCCCCTATGCTGGTAGATTCATCTCTCCTCTCCCAGTCTGAAGAT
ATATCCAGTCTTGGCACAGATGTGATAAATGTGACTGAATATGCTGAAGAAATTTATCAG
TACCTTAGGGAAGCTGAAATAAGGCACAGACCCAAAGCACACTACATGAAGAAGCAGCCA
GACATCACGGAAGGCATGCGCACGATTCTGGTGGACTGGCTGGTGGAGGTTGGGGAAGAA
TATAAACTTCGAGCAGAGACCCTGTATCTGGCTGTCAACTTCCTGGACAGGTTCCTTTCA
TGTATGTCTGTTCTGAGAGGGAAACTGCAGCTCGTAGGAACAGCAGCTATGCTTTTGGCT
TCGAAATATGAAGAGATATATCCTCCTGAAGTAGACGAGTTTGTCTATATCACCGATGAT
ACATACACAAAACGACAACTGTTAAAAATGGAACACTTGCTTCTGAAAGTTCTAGCTTTT
GATCTGACAGTACCAACCACCAACCAGTTTCTCCTTCAGTACTTGAGGCGACAAGGAGTG
TGCGTCAGGACTGAGAACCTGGCTAAGTACGTAGCAGAGCTGAGTCTACTTGAAGCAGAT
CCATTCTTGAAATATCTTCCTTCACTGATAGCTGCAGCAGCTTTTTGCCTGGCAAACTAT
ACTGTGAACAAGCACTTTTGGCCAGAAACCCTTGCTGCATTTACAGGGTATTCATTAAGT
GAAATTGTGCCTTGCCTGAGTGAGCTTCATAAAGCGTACCTTGATATACCCCATCGACCT
CAGCAAGCAATTAGGGAGAAGTACAAGGCTTCAAAGTACCTGTGTGTGTCCCTCATGGAG
CCACCTGCAGTTCTTCTTCTACAATAAGTTTCTGAATGGAAGCACTTCCAGAACTTCACC
TCCATATCAGAAGTGCCAATAATCGTCATAGGCTTCTGCACGTTGGATCAACTAATGTTG
TTTACAATATAGATGACATTTTAAAAATGTAAATGAATTTAGTTTCCCTTAGACTTTAGT
AGTTTGTAATATAGTCCAACATTTTTTAAACAATAAACTGCTTGTCTTATGACAAAAAAA
AAA >Hs.156469_contig2
AI341378|AI670817|AI701687|AI335022|AW235883|AI948598|AA446356 polyA = 2
polyA = 3
TCCAAGCCATTAAGGACTGTGGAACTTGCTATGATCATGGACGTGCTGTATGGTGGCGTT
TGTTATGCAGGAATTGATACAGATCCTGAGCTAAAATACCCAAAAGGTGCTGGGCGAGTT
GCTTTCTCCAATCAGCAGAGCTATATTGCTGCCATTAGTGCTCGGTTTGTTCAGCTTCAG
CATGGTGATATTGATAAACGTGTGGAGGTAAAGCCATATGTGCTAGATGACCAGATGTGT -continued GATGAATGCCAGGGCGCACGCTGTGGTGGAAAATTTGCTCCCTTTTTTTGTGCCAATGTC
ACTTGCCTGCAGTATTACTGTGAGTTTTGTTGGGCAAATATCCACTCTCGTGCTGGACGT
GAGTTCCATAAGCCATTGGTAAAGGAAGGTGCTGATCGCCCACGTCAGATCCACTTCCGC
TGGAACTAAGAATAGCAAACTGGCCTCTGTTTAACAAGGAAAGAAAGGGTGCATGTGGCT
TACTGTGTCTGAAGATACTGACATGCAGAAGAAATAAGTGCATTCTTCTGCTTTTCACCC
CAGCTATCAATACATGCATCTTTATCAGCAGCCAAAACACTACAAGCCTCTTGTTTTTCA
CCAAAACCCTACATCTCAGGCTTACTAATTTTTGTGATATTTCATGTTCAAATAAAATG
TTTTTTTGTATTTCAAAAAAAAAAAAAAAAAAAAAA >Hs.6631_mRNA_1 gi|7020430|dbj|AK000380.1|AK000380 *Homo sapiens* cDNA FLJ20373 fis, clone HEP19740 polyA = 3
CTCGATGTAGAGGGGTTGGTAGCAGACAGGTGGTTACATTAGAATAGTCACACAAACTGT
TCAGTGTTGCAGGAACCTTTTCTTGGGGGTGGGGGAGTTTCCCTTTTCTAAAAATGCAAT
GCACTAAAACTATTTTAAGAATGTAGTTAATTCTGCTTATTCATAAAGTGGGCATCTTCT
GTGTTTTAGGTGTAATATCGAAGTCCTGGCTTTTCTCGTTTTCTCACTTGCTCTCTTGTT
CTCTGTTTTTTTAAACCAATTTTACTTTATGAATATATTCATGACATTTGTAATAAATGT
CTTGAGAAAGAATTTGTTTCATGGCTTCATGGTCATCACTCAAGCTCCCGTAAGGATATT
ACCGTCTCAGGAAAGGATCAGGACTCCATGTCACAGTCCTGCCATCTTACTTTCCTCTTG
TCGAGTTCTGAGTGGAAATAACTGCATTATGGCTGCTTTAACCTCAGTCATCAAAAGAAA
CTTGCTGTTTTTTAGGCTTGATCTTTTTCCTTTGTGGTTAATTTTCCTGTATATTGTGAA
AATGGGGGATTTTCCCTCTGCTCCCACCCACCTAAACACAGCAGCCATTTGTACCTGTTT
GCTTCCCATCCCACTTGGCACCCACTCTGACCTCTTGTCAGTTTCCTGTTCCTGGTTCCA
TCTTTTTGAAAAAGGCCCTCCTTTGAGCTACAAACATCTGGTAAGACAAGTACATCCACT
CATGAATGCAGACACAGCAGCTGGTGGTTTTGTGTATACCTGTAAAGACAAGCTGAGAGG
CTTACTTTTTGGGGAAGTAAAAGAAGATGGAAATGGATGTTTCATTTGTATGAGTTTGGA
GCAGTGCTGAAGGCCAAAGCCGCCTACTGGTTTGTAGTTAACCTAGAGAAGGTTGAAAAA
TTAATCCTACCTTTAAAGGGATTTGAGGTAGGCTGGATTCCATCGCCACAGGACTTTAGT
TAGAATTAAATTCCTGCTTGTAATTTATATCCATGTTTAGGCTTTTCATAAGATGAAACA
TGCCACAGTGAACACACTCGTGTACATATCAAGAGAAGAAGGAAAGGCACAGGTGGAGAA
CAGTAAAAGGTGGGCAGATGTCTTTGAAGAAATGCTCAATGTCTGATGCTAAGTGGGAGA
AGGCAGAGAACAAAGGATGTGGCATAATGGTCTTAACATTATCCAAAGACTTGAAGCTCC
ATGTCTGTAAGTCAAATGTTACACAAAAAAAAAATGCAAATGGTGTTTCATTGGAATTACC
AAGTGCTTAGAACTTGCTGGCTTTCCCATAGGTGGTAAAGGGGTCTGAGCTCACACCGAG
TTGTGCTTGGCTTGCTTGTGCAGCTCCAGGCACCCGGTGGGCACTCTGGTGGTGTTTGTG
GTGAACTGAATTGAATCCATTGTTGGGCTTAAGTTACTGAAATTGGAACACCCCTTTGTCC
TTCTCGGCGGGGGCTTCCTGGTCTGTGCTTTACTTGGCTTTTTTCCTTCCCGTCTTAGCC
TCACCCCCTTGTCAACCAGATTGAGTTGCTATAGCTTGATGCAGGGACCCAGTGAAGTTT
CTCCGTTAAAGATTGGGAGTCGTCGAAATGTTTAGATTCTTTTAGGAAAGGAATTATTTT
CCCCCCTTTTACAGGGTAGTAACTTCTCCACAGAAGTGCCAATATGGCAAAATTACACAA
GAAAACAGTATTGCAATGACACCATTACATAAGGAACATTGAACTGTTAGAGGAGTGCTC
TTCCAAACAAAACAAAAATGTCTCTAGGTTTAGTCAGAGCTTTCACAAGTAATAACCTTT
CTGTATTAAAATCAGAGTAACCCTTTCTGTATTGAGTGCAGTGTTTTTTACTCTTTTCTC
ATGCACATGTTACGTTGGAGAAAATGTTTACAAAAATGGTTTTGTTACACTAATGCGCAC
CACATATTTATGGTATATTTTAAGTGACTTTTTATGGGTTATTTAGGTTTTCGTCTTAGT
TGTAGCACACTTACCCTAATTTTGCCAATTATTAATTTGCTAAATAGTAATACAAATGAC
AACTGCATTAAATTTACTAATTATAAAAGCTGCAAGCAGACTGGTGGCAAGTACACAGCC
CTTTTTTTTGCAGTGCTAACTTGTCTACTGTGTATTATGAAAATTACTGTTGTCCCCCCA
CCCTTTTTTCCTTAAATAAGTAAAATGACACCCTAAAAAAAAAAAAAAAAAAAAAAAAAA
AAAAAAA >Hs.155977_cOntig1 AI309080|AI313045 polyA = 1 WARN polyA = 1
TATACGGCTGCTAGAAGACGACAGAAGGTGGCTTGGGGGTGGATATCTTTGGGTTGCTGG
AAAAGGTGTGGGAAGGTTCAGGATGGTGGGAGGGACTGAGGTCCCTGAGGTGAAGAGGCC
CTTGGTCCTGACGGGTTTGACCCGTGCCTGGACCCTTGGAGCAGTGTTGTGTGAACTTGC
CTAGAACTCTGCCTTCTCCGTTGTCAATAAAGCCTCCCCCTCATGACCTAAAAAAAAAAA
AAAAAAAAAAAAAAAAAGTCGTATCGA >Hs.95197_mRNA_4 gi|5817138|emb|AL110274.1|HSM800829 *Homo sapiens* mRNA; cDNA DKFZp564I0272 (from clone DKFZp564I0272) polyA = 3
GAGCAGGAAAATATATACCCTAAACAGAAACTCTTACTTGTTTTATGAGCAAGTCTGAGT
GAGTCCTAAAATGGCTGGCGAAGAGCTACCAATACTGACTGACAGGTCACCTTAAAGCCT
CTAGGTGTGCCAAGTTTGATTTATCTTAGGGACTAGAACCTAGTCTTCTAAATGTGATTT
TGCCTTGCTGTTTCGTCCTGATGTGAAGGTAACCACACAGAGAGATTGGGCTGCATCAGT
AATGATATGCATACCTTTCGTGCATCAGTGAGCTTCTTCCCTGTTAACTGTATGACCACA
AAATTTAGCTGGAGTAAATAAATATGCGACAGAAATCCTGGAACAAGATGGTGAAATTGC
TTAAGAATCGAGACTTCAGGGCTCAATGACCTCTGAGCATGTTTCCCAAAGTGTGACCCA
CATGACCATCTGTCTCTCAGTCTCCTGGTCCCTCCGTAGAGCTTCTGAAACTGAATCTTT
GTGGGGTGGGGGTAGCGTTCAAGAATCAAAAGTTGAACCAAGCTCTTTGGGTGATACTTA
TGTATACTGAGGTTCAGGAACTGCTGGAGAGATGACTGGGCACCAAGAGGATGACAGTGA
CTCAGCTGGCATCCCTTAGCTGGTTCATGGCAGAGCTGAGTGGGCACTCCTGTCTCTGAC
CCCAGCTTCAGTGCTCTTTATCTCCTCCATGCCTCCTCAGTCGTGCTGCTCTAAGACTGC
TTACTGGCTTTCCTTCATGTCCTGGGCACAGAGCAGTTCTTTTGGTAGCAGATTTGAGTC
CACTTCCCCCGTGCACAGATCACTGCTCAGGACCCAGAGAGGAGCAGCTCTGCTCCAGCA
GGGTTTTCCATTGCATCACACACCCAAACGGTAGGATCCAACAGTCACACTTGAAAGCAA
CCATAATTGTGAGGTTTCTGATGCTGTAGACTTCCTTACATTTCTCACAACCTAGTTAGA
GAGTCACATGGGGGTGAAGTGTGGCTCGCGACCTGCCCCAACAAGTGCGTGCAGAAGCCA
GGAAACAAAGGAGTAAATTCACTTCAAATGGGATGCACATGGTGTCCGTGATGAAGAGAC
ACATTCAGAATTGCCCAAGGACAGGAAAATGACCAGAGAGAGCCAGAGCTGAGCTGGTAA
TAAAGAGACTCCGAGACTGAGTGGAGTTAATGAGGGAAGCATGCAACGAGTGGGGCAATT
TCAGTTGGTTTCTCTCATTGCTTTAAGCGAAATGAACTATACGGACAGGAGAACAGCCTG
CTTGCCCCAGTCTCTCCTTGGCCGCCCTCTGTTGTCCCTGTCAACTCAGGTGCCCACGGT -continued GCTCAGAGGAGGTGCTGGCAAAGCCCCTGGAGCCTTATGTAGGCCATGGGGGCTCCTAAA
AGGAACCTGAATGAATCATTTACAGCAGGTCTCTCTTGTAAAGCCCAGCCACAGTAACTC
GTACACTGACTGTTTCAAAAGACAGCCTTTCTTAATCATTTAATTGTTTCATATTCAAAT
ATATCTCCTAATTGTTTTTATTTTTTCCTGATCTAGAAGATATGACAACAGGGTAGAACT
TGGGAAGAGGGAATAGGAAGCTCGCCCTTCCTCCTTCCCTCCTCCCCTCTCTACTTTCCT
TCCTTCCTTGGTCATCAGGTACCTTCTTTGTGCCTGCTGTTGTAGGCTACACCCTATGTT
TGGTGGAAGGCAAAAGAAAAATCAGTAGGATACAACTCAGTAGGGAAGACAGAGATATT
CAAGCCCCTTGTCCTCCCAGTGTGATAAGTGTGGTGGTTGAGGTGTGAACAAGGGGCTCT
GTGAACAGAGAGGACGAAAGAGGAGCTCCTCCTGAGGCTGTTGGGAAAAGCATCACTGAA
GAGTGACTTTCAGAAGAAGAGAAGAAAAAGAGGAGAACATGCGTGATTTTATAATGAAAT
AGATTAGATAAGGGGAAAAAAGGCATTTAAACAAGGCAAAAAGAACAGGAGAATAGAGAA
GAGATGTGGAGGAGAAGGAGCACTGTAGTAAACACGCAGAAGGACAGGAACACTTAGACA
TGCAACCCACTCCCACCCTCCGTCTTGGGGGAGGAAAGCACACTACTGTCCCAAAGAACT
AATACTGAACCAGTGCTGCCTTGTGGAGAGAGGCATGGCCAAGGCGTTCAGAGACCTGGG
CCTGGTCCCACCGCTGCCCACAGCACTCAGCCTCTGAGCACAGCCTGGGGTCATCTGTGT
GCCCTCTGGCCAAGGCTGATGGTAGTTCTCTGAGTAATTGAGAGTCATTGCCTGTCTGTG
CAGTATTGTGAAAACAAGTCACCTTTTAACTTTAAAACTACTTTAAAAAACTTTAAAGTT
TTAAAAAAACTTCTTTAAAAACTACTCATGAGATGACAGTTTCTCTGACCCTCAGAGGAA
GGCTGGGCTGCGCATACGTGAGGAATTTTTACATGAACATCCCAGGACTTGCTGTTCGCA
GGTGATAAACTGCACCTCCCCAGGACTCCCGCTGCACTCACATGCAGCTCCCTGGACTTC
TGGTATCTGACCCGGCCCATTTCTGTGTTTCAGGGGAGAATTTGGCTTGCGGGAGTACTC
AGAAGTTAAGACGGTGACAGTAAAGATCCCCCAGAAGAACTCCTAAGAAGGCCAAGAAGG
AGGATGAAGCCCAGCCTGCACGTCTGTCCCTCTCTGCTTTCTCTGTAGGGCCCAGCTCTC
AGGAATACAAAGTTGAGCCACGGTCCTTACTTAAAGATTGAAAAGATAACATGTAGGCCA
GGCAGGTCACTGCACAACTAAAGCAAACCAGCTGGGTACAGTTTCTTGGCACTCTGTAAG
GGGCCACCTTAATCATACCAAATATTGGGGAAAGTGGGATAAAGGGAGGAGGAGGAGCTA
GCAGACACATCCAGTATCTCCTTCTGGAGCACAGGATGAAATAAGGGAGCTGTATTATTT
CATGTCTTTGTCACAAAGAACTTTCCTCTCAAGGAAAGGTGACCTTTCTCCTGTCTTCAT
TTTCCTCCTTCCAGGCCCTCCTCGCTCACCCACCCCTCCCTCTCTTCCAAGGAGATGTCA
GCTGAGCTCATTCTGGGGCAGATGTTTGGGCCGGGAACAATTTTTCAAGGTTGTAAAGCC
AAATTATCATTTCATGTTATCCATTTCTTCAAAGCAAAACATGAAATGGTTTTAGCTAGA
GTCAGACCAGAATGAAAATGCCAGGAGCTGGTACACTACAGATGTAGTAAGAACCTGGGA
TATTCCTGACCCAATCTGGTTTTCTTTTACCCATAAATAACATGAATGAAAAAAGATTGG
GACAATAGAGACTGGAAGTCATCATGTGCAGTTCACCGCTTCTGAGCTTGCTGCAGTTTT
GGGGTGTGTGTGTATTAGATTCCTTCTCAGTTATTCTGGAATAAGGCAAGGAGTGGGTTG
TTTTTCATAGCTAGATAAGATCTTTTCCAAAGTTTTTCTTAGAACCAACCAAAAAACAAT
CCGAGTAGGCCCGAGAATTTGATAATGCTGGATGCCTTGCAGACATCATTCAGTTTCTAA
TATTGGGCAACAATTATTATTAAATGAATTATTTCTGTAGTTGGAATCTGTACCTTCTGA
ACCTCTACACCAATAACTGCTGCAGGTGTGATTTTGGTCTGTCACACTGTACATCTATCA
TAATGTGCCCTGTATCTATTGGCAGTGACCTTGGAAAATCTGGCCAAGCCTAGGGGTTTC
CTTTTCCATTTGCCAAGTTCCATTGTGCCAGGACTGCCGTGCTCCACTGAGCTCCTCTGT
CACACCCCATTCTTGCCCCTCACTGGGCAGGCCATGGCCTACAGCTTGCAGGGAGTAAAG
CAGGCCCGCCTCCCTTTCTTCCCATCCACATACTCCTCTTCTGCTTTCCAGTGACTCCAC
CAGTTTGATGTGGGAAGTGTTAGCTTCCTTTCCTTCTTCCATCCCTTCTTCCATCTTTCC
AGCTGTCAAATCCAATCCAGTCTCTAACCTAAATGCAGATCATTTATTTAAAAGTACCAA
ACATAACCCAGAGTATGTGGAATATGGGCAACATATATATAGCCTTCTGTATTTAACGAT
CTTCTGCTTCTTAACCGTACCAGTTTTCTATTTATAACTCTTATCTATCCATGATGTTTT
AAAGTCTCCACTTGCTGTTATTTACAAACGACAGTGCATTCAGCAGCCCAGTGCCGTGAG
CCCTGACAGATGCCGTATTTCTGAGTGCTTCCATGTGAATGCTGCCCTCCTGTAGCATGT
GTCCAAGTGGACATAGCCACTAACCAACTAGTTACCTTTGGACTGCAACAAAAAATGTGA
AAATGAAGATTTATTTCTTTTAATTTACTTAAAAAGAAACCTCTGTGCTAGCAATAAAGC
ATTTATATTGTGCAAAAAAAAAAAAAAAAAAAAAC >Hs.48956_contig1 N64339|AI569513|AI694073 polyA = 1 polyA = 1
TGAAAATTTATATAACTGTTGTTGATAAGGAACATTATCCAGGAATTGATACGTTTATTA
GGAAAAGATATTTTTATAGGCTTGGATGTTTTTAGTTCTGACTTTGAATTTATATAAAGT
ATTTTTATAATGACTGGTCTTCCTTACCTGGAAAAACATGCGATGTTAGTTTTAGAATTA
CACCACAAGTATCTAAATTTGGAACTTACAAAGGGTCTATCTTGTAAATATTGTTTTGCA
TTGTCTGTTGGCAAATTTGTGAACTGTCATGATACGCTTAAGGTGGAAAGTGTTCATTGC
ACAATATATTTTTACTGCTTTCTGAATGTAGACGGAACAGTGTGGAAGCAGAAGGCTTTT
TTAACTCATCCGTTTGCCAATCATTGCAAACAACTGAAATGTGGATGTGATTGCCTCAAT
AAAGCTCGTCCCCATTGCTTAAGCCTTCAAAAA >Hs.118825_mRNA_10 gi|1495484|emb|X96757.1|HSSAPKK3 *H.sapiens* mRNA for MAP kinase kinase polyA = 3
CTTTTAGCTGCCAGCCCTGGCCCATCATGTAGCTGCAGCACAGCCTTCCCTAACGTTGCA
ACTGGGGGAAAAATCACTTTCCAGTCTGTTTTGCAAGGTGTGCATTTCCATCTTGATTCC
CTGAAAGTCCATCTGCTGCATCGGTCAAGAGAAACTCCACTTGCATGAAGATTGCACGCC
TGCAGCTTGCATCTTTGTTGCAAAACTAGCTACAGAAGAGAAGCAAGGCAAAGTCTTTTG
TGCTCCCCTCCCCCATCAAAGGAAAGGGGAAAATGTCTCAGTCGAAAGGCAAGAAGCGAA
ACCCTGGCCTTAAAATTCCAAAAGAAGCATTTGAACAACCTCAGACCAGTTCCACACCAC
CTAGAGATTTAGACTCCAAGGCTTGCATTTCTATTGGAAATCAGAACTTTGAGGTGAAGG
CAGATGACCTGGAGCCTATAATGGAACTGGGACGAGGTGCGTACGGGGTGGTGGAGAAGA
TGCGGCACGTGCCCAGCGGGCAGATCATGGCAGTGAAGCGGATCCGAGCCACAGTAAATA
GCCAGGAACAGAAACGGCTACTGATGGATTTGGATATTTCCATGAGGACGGTGGACTGTC
CATTCACTGTCACCTTTTATGGCGCACTGTTTCGGGAGGGTGATGTGTGGATCTGCATGG
AGCTCATGGATACATCACTAGATAAATTCTACAAACAAGTTATTGATAAAGGCCAGACAA
TTCCAGAGGACATCTTAGGGAAAATAGCAGTTTCTATTGTAAAAGCATTAGAACATTTAC
ATAGTAAGCTGTCTGTCATTCACAGAGACGTCAAGCCTTCTAATGTACTCATCAATGCTC
TCGGTCAAGTGAAGATGTGCGATTTTGGAATCAGTGGCTACTTGGTGGACTCTGTTGCTA
AAACAATTGATGCAGGTTGCAAACCATACATGGCCCCTGAAGAATAAACCCAGAGCTCA -continued ACCAGAAGGGATACAGTGTGAAGTCTGACATTTGGAGTCTGGGCATCACGATGATTGAGT
TGGCCATCCTTCGATTTCCCTATGATTCATGGGGAACTCCATTTCAGCAGCTCAAACAGG
TGGTAGAGGAGCCATCGCCACAACTCCCAGCAGACAAGTTCTCTGCAGAGTTTGTTGACT
TTACCTCACAGTGCTTAAAGAAGAATTCCAAAGAACGGCCTACATACCCAGAGCTAATGC
AACATCCATTTTTCACCCTACATGAATCCAAAGGAACAGATGTGGCATCTTTTGTAAAAC
TGATTCTTGGAGACTAAAAAGCAGTGGACTTAATCGGTTGACCCTACTGTGGATTGGTGG
GTTTCGGGGTGAAGCAAGTTCACTACAGCATCAATAGAAAGTCATCTTTGAGATAATTTA
ACCCTGCCTCTCAGAGGGTTTTCTCTCCCAATTTTCTTTTTACTCCCCCTCTTAAGGGGG
CCTTGGAATCTATAGTATAGAATGAACTGTCTAGATGGATGAATTATGATAAAGGCTTAG
GACTTCAAAAGGTGATTAAATATTTAATGATGTGTCATATGAAAAAAAAAAAAAAAAAAA
AAAAAAAAAAAAAAAAAAAAAAAAAA >Hs.135118_contig3
AI683181|AI082848|AW770198|AI333188|AI873435|AW169942|AI806302|AW340718|
BF196955|AA909720 polyA = 1 polyA = 2
CAGTCCCACCATGTATTTTGCTTTGTTTCTAAAAAGCTTTTTAAAAACTGTTATTTAATA
CCAAAGGGAGGAATCGTATGGGTTCTTCTGCCCACCGTTGTGACTAAGAATGCACAGGGA
CTTGGTTCTCGTTGCACCTTTTTTAGTAACATGTTTCATGGGGACCCACTGTACAGCCC
TTCATTCTGCTGTGTCAGTTTGGCCTGGCCTGACACTGGCTGCCCCAGCGGGGACCACGG
AAGCAGAGTGAGAGCCTTCGCTGAGTCAATGCTACCTTCAGCCCCAGACGCATCCCATTT
CCATGTCTTCCATGCTCACTGCTCATGCACTTTTTACACGGTTTCTTCCAAACAGCCCGG
TCTTGATGCAGGAGAGTCTGGAAAAGGAAGAAAATGGTTTCAGTTTCAAAATTCAAAGGA
AAAAGTTGAGGACTTATTTTGTCCTGTCAAGATTGCAAGAACATGTAAAATGTACGGAGC
TTCATAATACGTTATATTGTTCCGAAGCAGCTCGTTGAGAAACATTTGTTTTCAATAACA
TTTTAGCTTAAAAAAAAA >Hs.171857_mRNA_1 gi|13161080|gb|AF332224.1|AF332224 *Homo sapiens* testis
protein mRNA, partial cds polyA = 3
TCACCTCGTGGCGTAGGGGAGAGGTAACACCGAGAAGAGGCAGCGGCGGTGGCNCAGAGA
CGATTGGTGCCAAACAGGGCAGAACGCAACTCAGCTCTGGGTTTGTGAATAGCACAATGG
AAGAAGCTGGACTTTGTGGGTTAAGAGAGAAAGCAGATATGTTGTGTAACTCTGAATCAC
ATGATATTCTTCAACATCAAGACTCAAATTGCAGTGCCACAAGTAATAAACATTTATTGG
AAGATGAAGAAGGCCGTGACTTTATAACAAAGAACAGGAGTTGGGTGAGCCCAGTGCACT
GCACACAAGAGTCAAGAAGGGAGCTTCCTGAGCAAGAAGTAGCCCCTCCGTCTGGTCAGC
AAGCTTTACAATTGCAACAGGAACAAAGAAAAAGTCTTAGGAAAAGAAGTTTTATTATTG
ATGCAAGCCCTAAACACTCTTTCCGACTCCAGAGGAGAAGCTGGCAGCTCTCTGTAAGAA
ATATGCTGATCTTGGAAATTCACCTCTTCTATAGAAGAGTTTGTTTTGAACTATACGATT
TGAAACAAAATTCTTTTTTTGGAGACTATGGAAACATTCTCAACAGGGAAACCCTACTAG
ACTTTGTAAAGCAAATAATGGAAAAGATACAGAACTTTTTGAAGAATCATGGGAAATTTT
TATAATTAAATAAATGCTAAAATTCTGTTTTGTGAAACATTTATGGGAATTATCACTGAC
AGTTTTTGTACACTTTCAAATAGTGTTAAAGCAGCAACTCCATGTTGTAAATGCACAAAA
CAAATATTTAGTTAATAATCAACTCCAAGAATAAAGCTGTAACAATAATAGTTAAAAAAA
A >Hs.18910_mRNA_3 gi|12804464|gb|BC001639.1|BC001639 *Homo sapiens* clone
MGC:1944 IMAGE:2959372 polyA = 3
GGCACGAGGGTCAGCAGCCGCCAGACTTCCTGCCGAAGTCCGAGCCCCCTCCCGGGGCTG
GAGGGGGGCAAGCGGGTTCCGAGGTGCAAAGCCTGGTGCCCCGAGCCCTGCGGAGCTCGG
GGCCAGCATGGCCCCCACGCTGCAACAGGCGTACCGGAGGCGCTGGTGGATGGCCTGCAC
GGCTGTGCTGGAGAACCTCTTCTTCTCTGCTGTACTCCTGGGCTGGGGCTCCCTGTTGAT
CATTCTGAAGAACGAGGGCTTCTATTCCAGCACGTGCCCAGCTGAGAGCAGCACCAACAC
CACCCAGGATGAGCAGCGCAGGTGGCCAGGCTGTGACCAGCAGGACGAGATGCTCAACCT
GGGCTTCACCATTGGTTCCTTCGTGCTCAGCGCCACCACCCTGCCACTGGGGATCCTCAT
GGACCGCTTTGGCCCCCGACCCGTGCGGCTGGTTGGCAGTGCCTGCTTCACTGCGTCCTG
CACCCTCATGGCCCTGGCCTCCCGGGACGTGGAAGCTCTGTCTCCGTTGATATTCCTGGC
GCTGTCCCTGAATGGCTTTGGTGGCATCTGCCTAACGTTCACTTCACTCACGCTGCCCAA
CATGTTTGGGAACCTGCGCTCCACGTTAATGGCCCTCATGATTGGCTCTTACGCCTCTTC
TGCCATTACGTTCCCAGGAATCAAGCTGATCTACGATGCCGGTGTGGCCTTCGTGGTCAT
CATGTTCACCTGGTCTGGCCTGGCCTGCCTTATCTTTCTGAACTGCACCCTCAACTGGCC
CATCGAAGCCTTTCCTGCCCCTGAGGAAGTCAATTACACGAAGAAGATCAAGCTGAGTGG
GCTGGCCCTGGACCACAAGGTGACAGGTGACCTCTTCTACACCCATGTGACCACCATGGG
CCAGAGGCTCAGCCAGAAGGCCCCCAGCCTGGAGGACGGTTCGGATGCCTTCATGTCACC
CCAGGATGTTCGGGGCACCTCAGAAAACCTTCCTGAGAGGTCTGTCCCCTTACGCAAGAG
CCTCTGCTCCCCCACTTTCCTGTGGAGCCTCCTCACCATGGGCATGACCCAGCTGCGGAT
CATCTTCTACATGGCTGCTGTGAACAAGATGCTGGAGTACCTTGTGACTGGTGGCCAGGA
GCATGAGACAAATGAACAGCAACAAAAGGTGGCAGAGACAGTTGGGTTCTACTCCTCCGT
CTTCGGGGCCATGCAGCTGTTGTGCCTTCTCACCTGCCCCCTCATTGGCTACATCATGGA
CTGGCGGATCAAGGACTGCGTGGACGCCCCAACTCAGGGCACTGTCCTCGGAGATGCCAG
GGACGGGGTTGCTACCAAATCCATCAGACCACGCTACTGCAAGATCCAAAAGCTCACCAA
TGCCATCAGTGCCTTCACCCTGACCAACCTGCTGCTTGTGGGTTTTGGCATCACCTGTCT
CATCAACAACTTACACCTCCAGTTTGTGACCTTTGTCCTGCACACCATTGTTCGAGGTTT
CTTCCACTCAGCCTGTGGGAGTCTCTATGCTGCAGTGTTCCCATCCAACCACTTTGGGAC
GCTGACAGGCCTGCAGTCCCTCATCAGTGCTGTGTTCGCCTTGCTTCAGCAGCCACTTTT
CATGGCGATGGTGGGACCCCTGAAAGGAGAGCCCTTCTGGGTGAATCTGGGCCTCCTGCT
ATTCTCACTCCTGGGATTCCTGTTGCCTTCCTACCTCTTCTATTACCGTGCCCGGCTCCA
GCAGGAGTACGCCGCCAATGGGATGGGCCCACTGAAGGTGCTTAGCGGCTCTGAGGTGAC
CGCATAGACTTCTCAGACCAAGGGACCTGGATGACAGGCAATCAAGGCCTGAGCAACCAA
AAGGAGTGCCCCATATGGCTTTTCTACCTGTAACATGCACATAGAGCCATGGCCGTAGAT
TTATAAATACCAAGAGAAGTTCTATTTTTGTAAAGACTGCAAAAAGGAGGAAAAAAAACC
TTCAAAAACGCCCCCTAAGTCAACGCTCCATTGACTGAAGACAGTCCCTATCCTAGAGGG
GTTGAGCTTTCTTCCTCCTTGGGTTGGAGGAGACCAGGGTGCCTCTTATCTCCTTCTAGC -continued GGTCTGCCTCCTGGTACCTCTTGGGGGGATCGGCAAACAGGCTACCCCTGAGGTCCCATG
TGCCATGAGTGTGCACACATGCATGTGTCTGTGTATGTGTGAATGTGAGAGAGACACAGC
CCTCCTTTCAGAAGGAAAGGGGCCTGAGGTGCCAGCTGTGTCCTGGGTTAGGGGTTGGGG
GTCGGCCCCTTCCAGGGCCAGGAGGGCAGGTTCCCTCTCTGGTGCTGCTGCTTGCAAGTC
TTAGAGGAAATAAAAAGGGAAGTGAGAAAAAAAAAAAAAAAAAA >Hs.194774 mRNA_1 gi|16306633|gb|BC001492.1|BC001492 *Homo sapiens* clone
MGC:1774 IMAGE:3510004 polyA = 3
GGCACGAGGGAGGCGGCGGCTCCAGCCGGCGCGGCGCGAGGCTCGGCGGTGGGATCCGGC
GGGCGGTGCTAGCTCCGCGCTCCCTGCCTCGCTCGCTGCCGGGGGCGGTCGGAAGGCGCG
GCGCGAAGCCCGGGTGGCCCGAGGGCGCGATGGCTGCTCCTGTCCCGTGGGCCTGCTGTG
CTGTGCTTGCCGCCGCCGCCGCAGTTGTCTACGCCCAGAGACACAGTCCACAGGAGGCAC
CCCATGTGCAGTACGAGCGCCTGGGCTCTGACGTGACACTGCCATGTGGGACAGCAAACT
GGGATGCTGCGGTGACGTGGCGGGTAAATGGGACAGACCTGGCCCCTGACCTGCTCAACG
GCTCTCAGCTGGTGCTCCATGGCCTGGAACTGGGCCACAGTGGCCTCTACGCCTGCTTCC
ACCGTGACTCCTGGCACCTGCGCCACCAAGTCCTGCTGCATGTGGGCTTGCCGCCGCGGG
AGCCTGTGCTCAGCTGCCGCTCCAACACTTACCCCAAGGGCTTCTACTGCAGCTGGCATC
TGCCCACCCCCACCTACATTCCCAACACCTTCAATGTGACTGTGCTGCATGGCTCCAAAA
TTATGGTCTGTGAGAAGGACCCAGCCCTCAAGAACCGCTGCCACATTCGCTACATGCACC
TGTTCTCCACCATCAAGTACAAGGTCTCCATAAGTGTCAGCAATGCCCTGGGCCACAATG
CCACAGCTATCACCTTTGACGAGTTCACCATTGTGAAGCCTGATCCTCCAGAAAATGTGG
TAGCCCGGCCAGTGCCCAGCAACCCTCGCCGGCTGGAGGTGACGTGGCAGACCCCCTCGA
CCTGGCCTGACCCTGAGTCTTTTCCTCTCAAGTTCTTTCTGCGCTACCGACCCCTCATCC
TGGACCAGTGGCAGCATGTGGAGCTGTCCGACGGCACAGCACACACCATCACAGATGCCT
ACGCCGGGAAGGAGTACATTATCCAGGTGGCAGCCAAGGACAATGAGATTGGGACATGGA
GTGACTGGAGCGTAGCCGCCCACGCTACGCCCTGGACTGAGGAACCGCGACACCTCACCA
CGGAGGCCCAGGCTGCGGAGACCACGACCAGCACCACCAGCTCCCTGGCACCCCCACCTA
CCACGAAGATCTGTGACCCTGGGGAGCTGGGCAGCGGCGGGGGACCCTCGGCACCCTTCT
TGGTCAGCGTCCCCATCACTCTGGCCCTGGCTGCCGCTGCCGCCACTGCCAGCAGTCTCT
TGATCTGAGCCCGGCACCCCATGAGGACATGCAGAGCACCTGCAGAGGAGCAGGAGGCCG
GAGCTGAGCCTGCAGACCCCGGTTTCTATTTTGCACACGGGCAGGAGGACCTTTTGCATT
CTCTTCAGACACAATTTGTGGAGACCCCGGCGGGCCCGGGCCTGCCGCCCCCCAGCCCTG
CCGCACCAAGCTGGCCCTCCTTCCTCCCTCAGGGGAGGTGGGCCATGCAGCTAACCCACC
CACCAAAGACCCCCTCACCCTGGCCCCTTGGGCTGGACCCTCCAATGCCAGCGACTCCCA
GGAGCCCTTGGGGGACGTGAGGGGAGCCTCTCACATCCGATTTCTCCTCCTGCCCCAGCC
TCCTGTCTATCCCAGGGTCTCTGTTGCCACCATCAGATTATAAGCTCCTGATGCTGGGGG
GGCCCAGCCATCCCCCTCCCCCCAGCACCCACAATTTTCAGTCCCCTCCCCTCTGCCCTG
TTTTGTATACCCCTCCCCTGACCCTGCTCCTATCCCACAGTATTTAATGCCCTGTCAGTC
CCTTCTAGTCTGACTCAATGGTAACTTGCTGTATTTGAATTTTTTATAGATGTATATACA
GGGTGGGGGGAGTGGGCGGTTCTCATTAAACGTCACCATTTCATGAAAAAAAAAAAAAAA
AAA >Hs.127428 mRNA 2 gi|16306818|gb|BC006537.1|BC006537 *Homo sapiens* clone
MGC:1934 IMAGE:987903 polyA = 3
GGCACGAGGAGTTTCATAATTTCCGTGGGTCGGGCCGGGCGGGCCAGGCGCTGGGCACGG
TGATGGCCACCACTGGGGCCCTGGGCAACTACTACGTGGACTCGTTCCTGCTGGGCGCCG
ACGCCGCGGATGAGCTGAGCGTTGGCCGCTATGCGCCGGGGACCCTGGGCCAGCCTCCCC
GGCAGGCGGCGACGCTGGCCGAGCACCCCGACTTCAGCCCGTGCAGCTTCCAGTCCAAGG
CGACGGTGTTTGGCGCCTCGTGGAACCCAGTGCACGCGGCGGGCGCCAACGCTGTACCCG
CTGCGGTGTACCACCACCATCACCACCACCCCTACGTGCACCCCCAGGCGCCCGTGGCGG
CGGCGGCGCCGGACGGCAGGTACATGCGCTCCTGGCTGGAGCCCACGCCCGGTGCGCTCT
CCTTCGCGGGCTTGCCCTCCAGCCGGCCTTATGGCATTAAACCTGAACCGCTGTCGGCCA
GAAGGGGTGACTGTCCCACGCTTGACACTCACACTTTGTCCCTGACTGACTATGCTTGTG
GTTCTCCTCCAGTTGATAGAGAAAAACAACCCAGCGAAGGCGCCTTCTCTGAAAACAATG
CTGAGAATGAGAGCGGCGGAGACAAGCCCCCCATCGATCCCAATAACCCAGCAGCCAACT
GGCTTCATGCGCGCTCCACTCGGAAAAAGCGGTGCCCCTATACAAAACACCAGACCCTGG
AACTGGAGAAAGAGTTTCTGTTCAACATGTACCTCACCAGGGACCGCAGGTACGAGGTGG
CTCGACTGCTCAACCTCACCGAGAGGCAGGTCAAGATCTGGTTCCAGAACCGCAGGATGA
AAATGAAGAAAATCAACAAAGACCGAGCAAAAGACGAGTGATGCCATTTGGGCTTATTTA
GAAAAAAGGGTAAGCTAGAGAGAAAAAGAAAGAACTGTCCGTCCCCCTTCCGCCTTCTCC
CTTTTCTCACCCCCACCCTAGCCTCCACCATCCCCGCACAAAGCGGCTCTAAACCTCAGG
CCACATCTTTTCCAAGGCAAACCCTGTTCAGGCTGGCTCGTAGGCCTGCCGCTTTGATGG
AGGAGGTATTGTAAGCTTTCCATTTTCTATAAGAAAAAGGAAAAGTTGAGGGGGGGGCAT
TAGTGCTGATAGCTGTGTGTGTTAGCTTGTATATATATTTTTAAAAATCTACCTGTTCCT
GACTTAAAACAAAAGGAAAGAAACTACCTTTTTATAATGCACAACTGTTGATGGTAGGCT
GTATAGTTTTTAGTCTGTGTAGTTAATTTAATTTGCAGTTTGTGCGGCAGATTGCTCTGC
CAAGATACTTGAACACTGTGTTTTATTGTGGTAATTATGTTTTGTGATTCAAACTTCTGT
GTACTGGGTGATGCACCCATTGTGATTGTGGAAGATAGAATTCAATTTGAACTCAGGTTG
TTTATGAGGGGAAAAAAACAGTTGCATAGAGTATAGCTCTGTAGTGGAATATGTCTTCTG
TATAACTAGGCTGTTAACCTATGATTGTAAAGTAGCTGTAAGAATTTCCCAGTGAAATAA
AAAAAAATTTTAAGTGTTCTCGGGGATGCATAGATTCATCATTTTCTCCACCTTAAAAAT
GCGGGCATTTAAGTCTGTCCATTATCTATATAGTCCTGTCTTGTCTATTGTATATATAAT
CTATATGATTAAAGAAAATATGCATAATCAGACAAGCTTGAATATTGTTTTTGCACCAGA
CGAACAGTGAGGAAATTCGGAGCTATACATATGTGCAGAAGGTTACTACCTAGGGTTTAT
GCTTAATTTTAATCGGAGGAAATGAATGCTGATTGTAACGGAGTTAATTTTATTGATAAT
AAATTATACACTATGAAACCGCCATTGGGCTACTGTAGATTTGTATCCTTGATGAATCTG
GGGTTTCCATCAGACTGAACTTACACTGTATATTTTGCAATAGTTACCTCAAGGCCTACT
GACCAAATTGTTGTGTTGAGATGATATTTAACTTTTTGCCAAATAAAATATATTGATTCT
TTTCTAAAAAAAAAAAAAAAAAAAA -continued >Hs.126852_contig1
AI802118|EF197404|BF224434|AA931964|AW236083|AI253119|AW614335|AI671372|
AI793240|AW006851|AI953604|AI640505|AI633982|AW195809|AI493069|AW058576|
AW293622 polyA = 2 polyA = 3
AAACCAGTGTATCCAGTCATGGAAAAGAAGGAGGAAGATGGCACCCTGGAGCGGGGGCAC
TGGAACAACAAGATGGAGTTTGTGCTGTCAGTGGCTGGGGAGATCATTGGCTTAGGCAAC
GTCTGGAGGTTTCCCTATCTCTGCTACAAAAATGGGGGAGGTGAGATGAGAGCCCTTGTG
CCACCCCACCCACTCCTGGAAGGAGGATACTTCCATCTCCTGCACTTACGGCCCCTCTGG
GGAGTCCCATAGATGTATAGAATTCTGGAGGTAGGAGGACGCTTGGAGGTCATTAAGGAC
ACTCTGTAAGAGACTAAGACCTAGAAAGGTTACGTGACTATCCCAGGGCTCTTTCTATTA
TAACGTGGCATCGTAGAAATATGAGCACAAGCTGGAACCAGGTGGATGAGAGTTTGGATT
CTGGCTCTGCTACTTAACACTCTGTGTGATCTTGGACAAGTTACTTAAGCTCTCAGAGCA
TCAATTGCCGCTCCTGCAAATTGAGATAATAATGCCTGCCTTTCAAGGTCATTGTAAGGA
TTAGAGACAATGTGTGTAAAGCACTTAATAAATAGTAGCTCTGCTGATGATGACGTTGAT
AACCAAACTGTTCTGTGGTCTTAAGTAATAAATAGTAGCTCTGCTGATGATGACGTTGAT
AACCAAACTGTTCTGTGGTCTTAAGTAATAAGTAGTAGCTCTGTTGATGATGACGTTGAT
AACCAAACTGTTCTGTGGTCTTAAGTAATAAGTAGTAGCTCTGCTGATGATGACGTTGAT
AACCAAACTGTTCTGTGGTCTTAAGTAATAAATAGTAGCTCTGCTGATGATGATGTTGAT
AACCAAACTGTTCTGTGGTCTTAAGTAATAAATAGTAGCTCTGCTGATGATGACGTTGAT
AACCAAACTGTTCTGTGGTCTTAAGTAATAAATAGTAGCTCTGCTGATGATGACGTTGAT
AACCAAACTGTTCTGTGGTCTTAAGTAATAAATAGTAGCTCTGCTGATGATGACGTTGAT
AAAAAAAAAAAAAAAAAAAAAAAA >Hs.28149_mRNA_1 gi|14714936|gb|EC010626.1|BC010626 *Homo sapiens* clone
MGC:17687 IMAGE:3865868 polyA = 3
GGAAGACATCAGGATGTACCATCTGCCCTTCTGTCGGACCCCAGGGTACGTCCCATGAGC
GCGGCCGAGCTGCGTCGAGGGCAGCAGAGCGTGCTGCACTGCTCAGGGACCCGGACTCTG
CAGTTTCTCCTGCACTGTTTTCACCTTTGGCCAGACGGGCTCTGGGAAGACCTACACCCT
GACTGGACCCCCTCCCCAGGGGGAGGGGGTGCCTGTACCCCCCAGCCTGGCTGGCATCAT
GCAGAGGACCTTCGCCTGGCTGTTGGACCGCGTGCAGCACCTGGGTGCCCCTGTCACCCT
TCGCGCCTCTTATCTGGAGATCTACAATGAGCAGGTTCGGGACTTGCTGAGCCTGGGGTC
TCCCCGGCCCCTCCCTGTTCGCTGGAACAAGACTCGGGGCTTCTATGTGGAGCAGCTGCG
GGTGGTGGAATTTGGGAGTCTGGAGGCCCTGATGGAACTTTTGCAAACGGGTCTCAGCCG
TCGAAGGAACTCAGCCCACACCCTGAACCAGGCCTCCAGCCGAAGCCATGCCCTGCTCAC
CCTTTACATCAGCCGTCAAACTGCCCAGCAGATGCCTTCTGTGGACCCTGGGGAGCCCCC
TGTTGGTGGGAAGCTGTGCTTTGTGGACCTGGCAGGCAGTGAGAAGGTAGCAGCCACGGG
ATCCCGTGGGGAGCTGATGCTTGAGGCTAACAGCATCAACCGAAGCCTGCTGGCCCTGGG
TCACTGCATCTCCCTGCTGCTGGACCCACAGCGGAAGCAGAGCCACATCCCTTTCCGGGA
CAGCAAGCTCACCAAGTTGCTGGCAGACTCACTGGGAGGGCGCGGGGTCACCCTCATGGT
GGCCTGCGTGTCCCCCTCAGCCCAGTGCCTTCCTGAGACTCTCAGCACCCTGCGATATGC
AAGCCGAGCTCAGCGGGTCACCACCCGACCACAGGCCCCCAAGTCTCCTGTGGCAAAGCA
GCCCCAGCGTTTGGAGACAGAGATGCTGCAGCTCCAGGAGGAGAACCGTCGCCTGCAGTT
CCAGCTGGACCAAATGGACTGCAAGGCCTCAGGGCTCAGTGGAGCCCGGGTGGCCTGGGC
CCAGCGGAACCTGTACGGGATGCTACAGGAGTTCATGCTAGAGAATGAGAGGCTCAGGAA
AGAAAAGAGCCAGCTGCAGAATAGCCGAGACCTGGCCCAGAATGAGCAGCGCATCCTGGC
CCAGCAGGTCCATGCACTAGAGAGGCGTCTCCTCTCTGCCTGCTACCATCACCAGCAGGG
TCCTGGCCTGACCCCACCGTGTCCCTGCTTGATGGCCCCAGCTCCCCCTTGCCATGCACT
GCCACCCCTCTACTCCTGCCCCTGCTGCCACATCTGCCCACTGTGTCGAGTGCCCCTGGC
CCACTGGGCCTGCCTGCCAGGGGAGCACCACCTGCCCCAGGTGTTGGACCCTGAGGCCTC
AGGTGGCAGGCCCCCATCTGCCCGGCCCCCACCCTGGGCACCCCCATGCAGCCCTGGCTC
TGCCAAGTGCCCAAGAGAGAGGAGTCACAGTGACTGGACTCAGACCCGAGTCCTGGCAGA
GATGTTGACGGAGGAGGAGGTGGTACCTTCTGCACCTCCCCTGCCTGTGAGGCCCCCGAA
GACATCACCAGGGCTCAGAGGTGGGGCCGGGGTTCCAAACCTGGCCCAGAGACTGGAGGC
CCTCAGAGACCAGATTGGCAGCTCCCTGCGACGTGGCCGCAGCCAGCCACCCTGCAGTGA
GGGCGCACGGAGCCCAGGCCAAGTCCTCCCTCCCCATTGAAGGCCAAGTGGGAACCCAGG
AGACTGCTGTGTGACCTCAGACTGGGCTCCACACTCTTGGGCTTCAGTCTGCCCATCTGC
TGAATGGAGACAGCAGCTGCTACTCCACCTGCAGCTGGGCTAGGGGCGGGGACTGGGGGT
GCTATTTAGGGGAACAAGGGGATTCAGGAGAAACCAGGCAGCAGGGGATGAAATACATGA
ATAAAGAGAGGCATCAGCTCCAAAAAAAAAAAAAAAAAAAAAA >Hs.35453_mRNA_3 gi|7018494|emb|AL157475.1|HSM802461 *Homo sapiens* mRNA;
cDNA DKFZp761G151 (from clone DKFZp761G151); partial cds polyA = 3
CTCCCCCTGAGAGAGGCTGGGCAGCACCCCCCTTCTGCCAGGAGTGCCAGCCAAGGTGCC
AGACCCCTGTCCAGTGGCAAGCTGGAAGGCTTTCAGAGCATCGATGAAGCTATAGCCTGG
CTCAGGAAGGAACTGACGGAGATGCGGCTGCAGGACCAGCAACTGGCCAGACAGCTCATG
CGCCTGCGTGGCGACATCAACAAGCTGAAAATCGAACACACCTGCCGCCTCCACAGGAGG
ATGCTCAACGATGCCACCTACGAGCTGGAGGAGCGGGATGAGCTGGCCGACCTCTTCTGT
GACTCCCCTCTTGCCTCCTCCTTCAGCCTCTCCACACCACTCAAGCTTATTGGCGTGACC
AAGATGAACATCAACTCTCGGAGGTTCTCTCTCTGCTGAGGAGCCCTCAGACTGGGCGGA
GGGGCTGGAGCGGAGGGCTTGGGCTGGAGGGGTGTCAGAGGAAGCTGAGGCCAAGTTACT
CCAGTGGGTCTCCCGGAGGCAGGGGTCCCTGGGACTGGCGACTCAAGGGCCCCAGGACCT
ATTCAGTGGTGCTCTCCCACCCAGGGGCCCTGGGTGTGGATGCCAGTGTCTCTGTGACTG
GCTCTTGCTTACTACCCAAAGAGCTCTGCAGAAGGGCCGCTCCAACCAAGATGTTAAAGG
AGACCTGGGTTCCCACCATAATCCATCCCTCCACGGTCACGTTCCTGTTTCCTGGAATCA
CTGGTGCTATGAACTGGGATTCCCAAAGGGAGGCCCCCCAACAAAGCTGTCATTTTTGCA
GAAGGCTGTCCCGCAAGGGCCTTGGGGGAAATTAGGCATGTCAGATGTGCCTGTCTCACG
TGCTGTTGCTGTCCTCTAAGTATTGTCTCAAATTCACCCTAAGTACATGACTCAGCAACA
TTGACAGGGAGCTACTAGGAAGGGAAAATCGAAAGGCATGACAAATGGGCACTTGGGGAC
GCAGCCCCAGTGGCTGGCAGCCAGTGTCTCTGGTGAGCCTGACACTACAAGGCTGTGTAA
ATTGTAAATTCTGGCGTGTGCTGGGACATGTGATGGGGGCACTAGCGTAGCTTGGGTGCA -continued ACAAGCACAGATGTCCCCATTGTCTCCCCTGGCCACATGCATCTCCAAAGAGCCTCTTCA
CTGCCACCCACACCCCAGGGTGACAGCCTGGGAGACCACTGGTGACTGAACCAGGCAGGT
CCTGAAAGCATTTTCCATAACTGAATTCTCCTGCAGGGGCGTGACCGGGGCCTCCTGGTG
GATTCTGGTGGTGTCACCTTACTGCCCTCTCTGGAAAGACAATCTAGGGAGCCCAGAGGC
CCATCCTGAGCCTCCTCTGAGATTTTGTGCCTGACCTAAACAACTAGTTTTAATAAGACT
GTTACTGATGTGTTGTTCACTTGTTAGTAACTGATTTTTGTCCAAATGCGGAAGCCACTT
GTGTAGGTCAACTACAGTGCGTAGGATTTGATTTTAAGAGTTTCTCCCTCCCAACAGGCT
TGAGGATCAGCAAGTTAAGACCCCAGCAGGTTAGGGAGGTCAGTCTGGGGTCATACGGCA
TGGCAGGGGTCCCTCGGCCAGACCCGTAGAATCCTGAGATAAGGAGTGTTTCTGACCTTT
GGTGTCATCTAGTCGAGTCCTCTCATTAGTAAAGGAGCAAAGTGAAACCTGGGGGAGGAG
AAGGACTTCCCTCAGGTTGCACAGCTGTTTAGGCTATAGAATATTGATGTGTGAAACCAT
TATTGATAATGCCTAGTAGATCACATGTCAATGAACTTGAACCCCAAAGATGGTCGTGAT
GCTTTGCCAAACCCGCACACTGCCAACCCCTCTACTCTCCACCTCAGCCCCCACCCACAT
CTCCCAGAGTATTGCAATTCAGAACATTTGGGTCAAGGTGGAGCAAGGCACTGACAGTGG
CCCCACAGGGCATGTGTCACTAATCACTGTCCCATGGTCTACGCACGGCATCTGGCTGCT
CTGTCTACTGTGACTTCTTCCTGTGTAATCTCAGTGGGGCCCGTGTCCACCCACACATCG
TGACCCACATAGGGGAGAGGTTGCTTTTCTTTTGTGGGCTGAGAGTAGGACAATGCAAAT
GAATGATCTCTAGTAGACAGAAAAGAACTTGGTCTCTTTTTTAAAATTTCAAAGAGCCAG
AAGTTCTATGCCTCCTTCAAAGTAGGCAGAACAACGCAGCCAAGATCTACTGTCTGCCAT
GCTCTGTGCAATGAAGTCTGCAGGCCTGAGGACCATGTACTGCTGTCCTTCCTCAGAGCT
CTGCACAAACACTGCCAAGTCCTGAAGACGCATTCCTTTCCTGCCAACCTCTTTCCAGAT
AAGCCCTTGAGGTCTCGGGCTGACCTACACACACACACACACACACACACACACACACAC
ACACCCCCACACACACACACACACGACAGAGAACATGCCATAAACATCCTTGAACCCATG
CAGGAAAGCCCATCCCATATTCTGAAAAAATGCCAAATTAGGTTTTTCTTTCTTTTTGGA
AATCAGTCATTACAGTAACCGAAACCATTGGGTTCAGCGAAAATGGAAAGATTTAGCTGA
ATGTAGTCAGTCCAATTAAGTTGGATGCAACTGAGTGATTTAGTTGCTTGGGTAACCCAG
TGCTTGCTTGCTTTCTTCATTCTCTGGGTGGAAACTAAGATCAAGACACATGTTTGGGGA
TAAGTTAAATGTCTGAGCTATTTTGCTCGGTTTATCCTAAGAGAACTTTATTATGGGATG
AGGAGGTGACCCAAGATGAGAAGTGGAGGGGGACAGCGATGTTTTCTAAACATCGTCCAG
TGTTGACTGGCTTCCTTACTTTGCACAGTGAACACAACTAACCACATTAATTCAGCTTTG
TGAAGTCCCTGCTCTCTGTGGGTTCTATGAGTCAGCAGCAACATTGGCCTAACCTCCGTC
CCAGCCTCCTGGCTCACCACATGTGTACAGTGCTGTTTGCAGTTGTACTCATTATCCATC
CATCTCTCTGCCATCCCCAAGCATCGCTGGGTGTAAAACGCAAACTCTCCACCGACACTG
CCATGCGTGGTCATGTCTTGATGCCTTCAGGGGCTCAGTAGCTATCAAAGAGGCCTGGAG
GGCCTGGGCAGGCTTGACGATGCCTGACCGAGTTCAAGACCCACACCCTGTAGCAATACC
AAGTGCTATTACATAATCAATGGACGATTTATACTTTTATTTTTTATGATTATTTGTTTC
TATATTGCTGTTAGAAAAAGTGAAATAAAAATACTTCAAAAGAAAAAAAAAAAAAAAAAA
AAAAAAAAAAAAAAGAAAAAAAAAAAAAAAAAAA >Hs.180570_contig1 R08175|AA707224|AA699986|R11209|W89099|T98002|AA494546
polyA = 2 polyA = 3
TGAAGGACCGCGATCCTAAAGAGATTGAATGGGACGACCTGGCCCAGCTGCCCTTCCTGA
CCATGTGCGTGAAGGAGAGCCTGAGGTTACATCCCCCAGCTCCCTTCATCTCCCGATGCT
GCACCCAGGACATTGTTCTCCCAGATGGCCGAGTCATCCCCAAGGGCATTACCTGCCTCA
TCGATATTATAGGGGTCCATCACAACCCAACTGTGTGGCCGGATCCTGAGTCTACGACCC
CTTCCGCTTTGACCCAGAGAACAGCAAGGGGAGGTCACCTCTGGCTTTTAATTCCCTTCT
CCGCAGGGCCCAGGAACTGCATCGGGCCAGCGTTTCCCATGGCGGAGATGAAAGTGGTTC
CTGGCGTTGATGCTGCTGCACTTCCGGTTCCTGCCAGACCACACTGAGCCCCGCAGGAAG
CTGGAACTGATCATTGCGGCCGAGGGCGGGCTTTGGCTGCGGGTGGAGCCCCTGAATGTA
GGCTTGCAGTGACTTTCTGACCCATCCACCTGTTTTTTTGCAGATTGTCATGAATAAAAC
GGTGCTGTCACCTCAAAAAAAAAAAANNNAAAA >Hs.196270_mRNA_1 gi|11545416|gb|AF283645.1|AF283645 *Homo sapiens*
chromosome 8 map 8q21 polyA = 3
GAGTCCTCTCGTTGGTCCCGGAGGTGGGGTTGCGCTCACAAGGGGCGACCGTCGCCACGG
TGGCGGCCACTGCATCGCGTCCCACCTCCGCGGCCCTGGGCGCCGTGGTGTCGACGGGCC
CCGAGCCTATGACGGGCCAGGGCCAGTCGGCGTCCGGGTCGTCGGCGTGGAGCACGGTAT
TCCGCCACGTCCGGTATGAGAACCTGATAGCGGGCGTGAGCGGCGGCGTCTTATCCAACC
TTGCGCTGCATCCGCTCGACCTCGTGAAGATCCGCTTCGCCGTGAGTGATGGATTGGAAC
TGAGACCGAAATATAATGGAATTTTACATTGCTTGACTACCATTTGGAAACTTGATGGAC
TACGGGGACTTTATCAAGGAGTAACCCCAAATATATGGGGTGCAGGTTTATCCTGGGGAC
TCTACTTTTTCTTTTACAATGCCATCAAGTCATATAAAACAGAAGGAAGAGCTGAACATT
TAGAGGCAACAGAATACCTTGTCTCAGCTGCTGAAGCTGGAGCCATGACCCTCTGCATTA
CAAACCCATTATGGGTAACAAAAACTCGCCTTATGTTACAGTATGATGCTGTTGTTAACT
CCCCACACCGACAATATAAAGGAATGTTTGATACACTTGTGAAAATATATAAGTATGAAG
GTGTGCGTGGATTATATAAGGGATTTGTTCCTGGGCTGTTTGGAACATCGCATGGTGCCC
TTCAGTTTATGGCATATGAATTGCTGAAGTTGAAGTACAACCAGCATATCAATAGATTAC
CAGAAGCCCAGTTGAGCACAGTAGAATATATATCTGTTGCAGCACTATCCAAAATATTTG
CTGTCGCAGCAACATACCCATATCAAGTCGTAAGAGCTCGTCTTCAGGATCAACACATGT
TTTACAGTGGTGTAATAGATGTAATCACAAAGACATGGAGGAAAGAAGGCGTCGGTGGAT
TTTACAAGGGAATTGCTCCTAATTTGATTAGAGTGACTCCAGCCTGCTGTATTACCTTTG
TGGTATATGAAAACGTCTCACATTTTTTACTTGACCTTAGAGAAAAGAGAAAGTAAGCTC
AAAGAGGACAATTCCAGTATATCTGCCCAAGGCAGCAACAAGCTCTTTTGTGTTTAAGGC
ATAAAAGAAGAATTCTGCATAGAAACATGGCTCATATTCGAAATTGCTCTATAGTCATTA
GAAGCCAGAGAACTGCTAAGTCTCCTGCAATGTTTTTCTTGCTTTTTGCCTTCCCCATAT
ATATGGAACTTGGCTACCTCTGCCTGAAATGGCTGCCATCAACACAATGTTAAAACTGAC
ACGAAGGATAGAGTTTCACAGATTTCTACGTTTTATTGGTGGAAGCTGATTTGCAACATT
TGCTAAATGGATTAGATGAATGTACTTCTTTTTGTGAGCTTACTTGCCTGGATTGCTTTA
AAATTAACCTTTGTGCAATACCAAGAAAATAGCTCTTTAAAAGAATGTCTTTGTATGTCT
CAAGGTAAATTAAGGATTTACTGAATAAGGTGTTGACCAAATCCAGACCATTTTATTTTA
TTTTTTTATTTATTTATTTTTTGAGATGGAGTCTTGCTTTGTCGCCCAGGCTGGAGTGCA -continued GTGGCGTGATCTCAGCTCACTGCAACCTCCACCTCCCGGGTTCACGCCATTCTCCTGCCT
CAGCCTCCTGAGTAGCTGGGACTACAGGCACCTGCCACCACGCCTGGCTAACTTTTTTT
ATATTTTGAGTAGAAATGGGGTTTCACCATGTTAGCCAGGATGGTCTCAATCTCCTGACC
TTGTGATCCGCCTGCCTTGGCCTCCCAAAGTGCTGGGATTACAGGCGTGAGCCACTGCGC
CTGGCCAGACCATTTTAGAATTGGGAAATTTTAGTGAGAAAAAATGCACTGTAAATATGC
TTTAGTTTTAATTCAGTTGGGATGCACTACCTAGCGAAAATTGAGAAACTATATACTTCT
CAGAGAAATATCTGACATCTATTGTCATTCCATTGCTATTTTTTTTCCCCAGAGACTTCC
ATAATTTAAAATAAAATCCTAGATCCAGTTCTTGTTTTTTGGCATAAATACTTAATCTAT
TTTAAATTTATAAAATCTGAGCTTCTAGGATCCAGCTGTGTCAACCTTTATTTAGCATAT
ATAACTATAAATCACTTATTACAGATGCTAAATAGATCACCTTTTACAGATGCTGAAATG
TTTGGGATATGTTTGTTGACAAGGTAAATGGAAATGAGAAACTTTATACTTCAGTTTTCA
GATATATGGATCTAGATCCCAAATAAATGATTAATCTTCATTGGTTTCTCAAATTCAGGT
TGAAATACAAATTAATAGCCTTTATTGATTTTACTTTTATGAGTCATTGTAGACATCTAT
AAATATAAAAGGGCCTGTACCCAAAGGATGCCAGAATACTAGTATTTTTATTTATCGTAA
ACATCCACGAGTGCTGTTGCACTACCATCTATTTGTTGTAAATAAAAGTGTTGTTTTCAA
AAAAAAAAAAAAAA >Hs.9030_mRNA_3 gi|12652600|gb|BC000045.1|BC000045 *Homo sapiens* clone
MGC:2032 IMAGE:3504527 polyA = 3
CTAGAGGGGCGGAAAGTAACAAGGAGGTGGGGGTACAAATCCTCAGCTCCTGCTTCCGCA
AGCACTAACCTGCTCTGAAGTGAGCCAGGCAGCTCTGGCCATCTTTTCCCAGCCACAGAA
TCAGGTGATGGTCCAGAATTAAGAGCTGTCACCTGTGTCATTCACTCACAATGGAAGAAA
TGAAGAAGACTGCCATCCGGCTGCCCAAAGGCAAACAGAAGCCTATAAAGACGGAATGGA
ATTCCCGGTGTGTCCTTTTCACCTACTTCCAAGGGGACATCAGCAGCGTAGTGGATGAAC
ACTTCTCCAGAGCTCTGAGCAATATCAAGAGCCCCCAGGAATTGACCCCCTCGAGTCAGA
GTGAAGGTGTGATGCTGAAAAACGATGATAGCATGTCTCCAAATCAGTGGCGTTACTCGT
CTCCATGGACAAAGCCACAACCAGAAGTACCTGTCACAAACCGTGCCGCCAACTGCAACT
TGCATGTGCCTGGTCCCATGGCTGTGAATCAGTTCTCACCGTCCCTGGCTAGGAGGGCCT
CTGTTCGGCCTGGGGAGCTGTGGCATTTCTCCTCCCTGGCGGGCACCAGCTCCTTAGAGC
CTGGCTACTCTCATCCCTTCCCCGCTCGGCACCTGGTTCCAGAGCCCCAGCCTGATGGGA
AACGTGAGCCTCTCCTAAGTCTCCTCCAGCAAGACAGATGCCTAGCCCGTCCTCAGGAAT
CTGCCGCCAGGGAGAATGGCAACCCTGGCCAGATAGCTGGAAGCACAGGGTTGCTCTTCA
ACCTGCCTCCCGGCTCAGTTCACTATAAGAAACTATATGTATCTCGTGGATCTGCCAGTA
CCAGCCTTCCAAATGAAACTCTTTCAGAGTTAGAGACACCTGGGAAATACTCACTTACAC
CACCAAACCACTGGGGCCACCCACATCGATACCTGCAGCATCTTTAGTCAAGTTGGAGGA
GAAAGACAACACTTGGTCTAAGACACGGCAGCAAGACATCCCTGCATATTGTTCCAGATA
AAAATGAAAGCTGCTCACACCCACTTGCCTCCCCAATCTGTTAAACAGCTTCGTGTCTAG
TATGAGCTCAGTACTTGCCCTGTGAAAATCCCAGAAGCCCCCGCTGTCAATGTTCCCCAT
CCACACCCTGCTTGCTCCTGTGTAACAGCTCAGATGATGAATAATAATAAAACTGTACTT
TTTTGGATGGTGAAAAAAAAAAAAAAAAAAAA >Hs.1282_mRNA_3 gi|4559405|ref|NM_000065.1| *Homo sapiens* complement
component 6 (C6), mRNA polyA = 1
TTGCCTTGTGTTAGCTAGCAATAAGAAAAGAAGCTTTGTTTGGATTAACATATATACCCT
CTTCATTCTGCATACCTATTTTTTCCCCAATAATTTGCAGCTTAGGTCCGAGGACACCAC
AAACTCTGCTTAAAGGGCCTGGAGGCTCTCAAGGCATGGCCAGACGCTCTGTCTTGTACT
TCATCCTGCTGAATGCTCTGATCAACAAGGGCCAAGCCTGCTTCTGTGATCACTATGCAT
GGACTCAGTGGACCAGCTGCTCAAAAACTTGCAATTCTGGAACCCAGAGCAGACACAGAC
AAATAGTAGTAGATAAGTACTACCAGGAAAACTTTTGTGAACAGATTTGCAGCAAGCAGG
AGACTAGAGAATGTAACTGGCAAAGATGCCCCATCAACTGCCTCCTGGGAGATTTTGGAC
CATGGTCAGACTGTGACCCTTGTATTGAAAAACAGTCTAAAGTTAGATCTGTCTTGCGTC
CCAGTCAGTTTGGGGGACAGCCATGCACTGAGCCTCTGGTAGCCTTTCAACCATGCATTC
CATCTAAGCTCTGCAAAATTGAAGAGGCTGACTGCAAGAATAAATTTCGCTGTGACAGTG
GCCGCTGCATTGCCAGAAAGTTAGAATGCAATGGAGAAAATGACTGTGGAGACAATTCAG
ATGAAAGGGACTGTGGGAGGACAAAGGCAGTATGCACACGGAAGTATAATCCCATCCCTA
GTGTACAGTTGATGGGCAATGGGTTTCATTTTCTGGCAGGAGAGCCCAGAGGAGAAGTCC
TTGATAACTCTTTCACTGGAGGAATATGTAAAACTGTCAAAAGCAGTAGGACAAGTAATC
CATACCGTGTTCCGGCCAATCTGGAAAATGTCGGCTTTGAGGTACAAACTGCAGAAGATG
ACTTGAAAACAGATTTCTACAAGGATTTAACTTCTCTTGGACACAATGAAAATCAACAAG
GCTCATTCTCAAGTCAGGGGGGGAGCTCTTTCAGTGTACCAATTTTTTATTCCTCAAAGA
GAAGTGAAAATATCAACCATAATTCTGCCTTCAAACAAGCCATTCAAGCCTCTCACAAAA
AGGATTCTAGTTTTATTAGGATCCATAAAGTGATGAAAGTCTTAAACTTCACAACGAAAG
CTAAAGATCTGCACCTTTCTGATGTCTTTTTGAAAGCACTTAACCATCTGCCTCTAGAAT
ACAACTCTGCTTTGTACAGCCGAATATTCGATGACTTTGGGACTCATTACTTCACCTCTG
GCTCCCTGGGAGGCGTGTATGACCTTCTCTATCAGTTTAGCAGTGAGGAACTAAAGAACT
CAGGTTTAACCGAGGAAGAAGCCAAACACTGTGTCAGGATTGAAACAAAGAAACGCGTTT
TATTTGCTAAGAAAACAAAAGTGGAACATAGGTGCACCACCAACAAGCTGTCAGAGAAAC
ATGAAGGTTCATTTATACAGGGAGCAGAGAAATCCATATCCCTGATTCGAGGTGGAAGGA
GTGAATATGGAGCAGCTTTGGCATGGGAGAAAGGGAGCTCTGGTCTGGAGGAGAAGACAT
TTTCTGAGTGGTTAGAATCAGTGAAGGAAAATCCTGCTGTGATTGACTTTGAGCTTGCCC
CCATCGTGGACTTGGTAAGAAACATCCCCTGTGCAGTGACAAAACGGAACAACCTCAGGA
AAGCTTTGCAAGAGTATGCAGCCAAGTTCGATCCTTGCCAGTGTGCTCCATGCCCTAATA
ATGGCCGACCCACCCTCTCAGGGACTGAATGTCTGTGTGTGTGTCAGAGTGGCACCTATG
GTGAGAACTGTGAGAAACAGTCTCCAGATTATAAATCCAATGCAGTAGACGGACAGTGGG
GTTGTTGGTCTTCCTGGAGTACCTGTGATGCTACTTATAAGAGATCGAGAACCCGAGAAT
GCAATAATCCTGCCCCCCAACGAGGAGGGAAACGCTGTGAGGGGGAGAAGCGACAAGAGG
AAGACTGCACATTTTCAATCATGGAAAACAATGGACAACCATGTATCAATGATGATGAAG
AAATGAAAGAGGTCGATCTTCCTGAGATAGAAGCAGATTCCGGGTGTCCTCAGCCAGTTC
CTCCAGAAAATGGATTTATCCGGAATGAAAAGCAACTATACTTGGTTGGAGAAGATGTTG
AAATTTCATGCCTTACTGGCTTTGAAACTGTTGGATACCAGTACTTCAGATGCTTACCAG
ACGGGACCTGGAGACAAGGGGATGTGGAATGCCAACGGACGGAGTGCATCAAGCCAGTTG -continued TGCAGGAAGTCCTGACAATTACACCATTTCAGAGATTGTATAGAATTGGTGAATCCATTG
AGCTAACTTGCCCCAAAGGCTTTGTTGTTGCTGGGCCATCAAGGTACACATGCCAGGGGA
ATTCCTGGACACCACCCATTTCAAACTCTCTCACCTGTGAAAAAGATACTCTAACAAAAT
TAAAAGGCCATTGTCAGCTGGGACAGAAACAATCAGGATCTGAATGCATTTGTATGTCTC
CAGAAGAAGACTGTAGCCATCATTCAGAAGATCTCTGTGTGTTTGACACAGACTCCAACG
ATTACTTTACTTCACCCGCTTGTAAGTTTTTGGCTGAGAAATGTTTAAATAATCAGCAAC
TCCATTTTCTACATATTGGTTCCTGCCAAGACGGCCGCCAGTTAGAATGGGGTCTTGAAA
GGACAAGACTTTCATCCAACAGCACAAAGAAAGAATCCTGTGGCTATGACACCTGCTATG
ACTGGGAAAAATGTTCAGCCTCCACTTCCAAATGTGTCTGCCTATTGCCCCCACAGTGCT
TCAAGGGTGGAAACCAACTCTACTGTGTCAAAATGGGATCATCAACAAGTGAGAAAACAT
TGAACATCTGTGAAGTGGGAACTATAAGATGTGCAAACAGGAAGATGGAAATACTGCATC
CTGGAAAGTGTTTGGCCTAGCACAATTACTGCTAGGCCCAGCACAATGAACAGATTTACC
ATCCCGAAGAACCAACTCCTACAAATGAGAATTCTTGCACAAACAGCAGACTGGCATGCT
CAAAGTTACTGACAAAAATTATTTTCTGTTAGTTTGAGATCATTATTCTCCCCTGACTCT
CCTGTTTGGGCATGTCTTATTCAGTTCCAGCTCATGACGCCCTGTAGCATACCCCTAGGT
ACCAACTTCCACAGCAGTCTCGTAAATTCTCCTGTTCACATTGTACAAAAATAATGTGAC
TTCTGAGGCCCTTATGTAGCCTGTGACATTAAGCATTCTCACAATTAGAAATAAGAATAA
AACCCATAATTTTCTTCAATGAGTTAATAAACAGAAATCTCCAGAACCTCTGAAACACAT
TCTTGAAGCCCAGCTTTCATATCTTCATTCAACAAATAATTTCTGAGTGTGTATACAGGA
TGTCAAGTACTGACCAAAGTCCTGAGAACTCGGCAGATAATAAAACAGACAAAAGCCTTT
GCCTTCATGAAGCATACATTCATTCAGGGGTAGACACACAAAAAATGAAATAAACAGGTA
AAATATGTAGC >Hs.268562_mRNA 2 gi|15341874|gb|BC013117.1|BC013117 *Homo sapiens* clone
MGC:8711 IMAGE:3882749 polyA = 3
CTCTCCTCGCCCGCTGGGTGCTGAAGTTGGGCGGATGGCAGCAAACCGGCTCCGCTAGAG
GACCGAGCCGCCCAGCCCCGCTCCCCCGGACCCATCGGCGCGCTGCCCACACCTCCAGGC
GACCGGCCAACTGGGTCCTGAAGTAGCTGAAATGCGAAAAAGGCAGCAGTCCCAAAATGA
AGGAACACCTGCCGTGTCTCAAGCTCCTGGAAACCAGAGGCCCAACAACACCTGTTGCTT
TTGTTGGTGCTGTTGTTGCAGCTGCTCCTGCCTCACTGTGAGGAATGAAGAAAGAGGGGA
AAATGCGGGAAGACCCACACACACTACAAAAATGGAGAGTATCCAGGTCCTAGAGGAATG
CCAAAACCCCACTGCAGAGGAAGTCTTGTCCTGGTCTCAAAATTTTGACAAGATGATGAA
GGCCCCAGCAGGAAGAAACCTTTTCAGAGAGTTCCTCCGAACAGAATACAGTGAAGAGAA
CCTACTTTTCTGGCTTGCTTGTGAAGACTTAAAGAAGGAGCAGAACAAAAAAGTAATTGA
AGAAAAGGCTAGGATGATATATGAAGATTACATTTCTATACTATCACCAAAAGAGGTCAG
TCTTGATTCTCGAGTTAGAGAGGTGATCAATAGAAATCTGTTGGATCCCAATCCTCACAT
GTATGAAGATGCCCAACTTCAGATATATACTTTAATGCACAGAGATTCTTTTCCAAGGTT
TTTGAACTCTCAAATTTATAAGTCATTTGTTGAAAGTACTGCTGGCTCTTCTTCTGAATC
TTAATGTTCATTTAAAAACAATCATTTTGGAGGGCTGAGATGGGAAATAAAAGTAGTTAA
ATAACATCAGAAACTGAGTTCCTGGAGAACTACAGTTTAGCATTCCTCAGGCTACTGTGA
AAACACAACCGTTATGGTCTTTGTCTCCATTTTTATCAAGGTTTTCCATGGTTAAGTTTG
GAGAAAATACCACACAAAACAATGAATTGCCAAATTGTTTGTTTTATTCAAGACTCATTC
TACTTGCAAGCAAAGTGTATTTGTAGTCCTATGAACAGTCTCCTCGTGTATCTCCAGAGA
CTGCATGTGCAAAGTAAAATGCTTCATTTGCCACATAGTTGTTGTAATATTTAATCCAGT
AGCATAACTTATATCTGTATTTAAGGACTTTTGTGCAATATGGTCTTAAGAAATAATTGC
CAAAAAAATCGGCCATGGTTCTGCATTTTTAACATAATCTAAGACAGAAAAAAAGCAATT
TTTACTATGTAACAATGGTATTCAACATTCTATATACTGTGTTTAGTACACTAATTTTGA
AGCCAATATTTCTGTACATGAAAAAGAGCTATTTATCTCTGTTTGTTGGAAAATCCTAAT
GGGGATTCCTCTGGTTGTTCACTGCCAAAACTGTGGCATTTTCATTACAGGAGAGTTTAC
TATGCTAAAAGCAAAAAACAAAAAAAAAAAAAAAGGGAAGAAGGAAAAAAGCAAAAAACA
ATTTGAAGATATCCTATCTCAATGACAAATCAAAAGAGTGATATTGCTTTTAACTGTAAT
AGAAGAAAATGAATTTATGTATATATCAGATGTCCAATACTGTAATTAATTTATTAAAGA
CTGGCTCTCCAGTTTTAAAAAAAAAAAAAAAAAAAAAAAAAAAAAAAAAAAA >Hs.151301_mRNA_3 gi|16041747|gb|BC015754.1|BC015754 *Homo sapiens* clone
MGC:23085 IMAGE:4862492 polyA = 3
AAAAGAACCAGGATTGCATTTGAAGTTAAGCTGCAAAAAACCAGTCGATCAACAGATTTT
CGAGTCCCACAGTCAATATGCACCATGTTTAATGTTATGGTTGATGCCAAAGCTCAATCA
ACAAAACTTTGCAGCATGGAAATGGGCCAAGAGTTTGCTAAAATGTGGCATCAATACCAT
TCAAAAATAGACGAACTAATTGAAGAAACTGTTAAAGAAATGATAACACTCTTGGTTGCA
AAGTTCGTTACTATCTTGGAAGGAGTGCTGGCAAAATTATCCAGATATGACGAAGGGACT
TTGTTTTCTTCTTTTCTGTCATTTACCGTGAAGGCAGCTTCCAAATATGTGGATGTACCT
AAACCCGGGATGGACGTGGCCGACGCCTACGTGACTTTCGTCCGCCATTCTCAGGATGTC
CTGCGTGATAAGGTCAATGAGGAGATGTACATAGAAAGGTTATTTGATCAATGGTACAAC
AGCTCCATGAACGTGATCTGCACCTGGTTGACGGACCGGATGGACTTACAGCTTCATATT
TATCAGTTGAAAACACTAATTAGGATGGTAAAGAAAACCTACAGAGATTTCCGATTGCAA
GGGGTCCTGGACTCCACCTTAAACAGCAAGACCTATGAAACGATCCGGAACCGTCTCACT
GTGGAGGAAGCCACAGCATCAGTGAGTGAAGGTGGGGGACTGCAGGGCATCAGCATGAAG
GACAGCGATGAGGAAGACGAAGAAGACGATTAGACCATTTGGTCCTAGAGTCTGCTGGGA
CAGAGTCCTGTAATCAGTGCATGTCCTTAGTCTGTTAGTTAAACCCATTAGGAATTTTCT
GTCAACTACCATGCCCATGAGATGTTTATCAATACAACTGCCATTTTAGCTATGTGGTAC
CAAGATTAGCAAATGACCTTCATATCCACTGATTTCCTGATGTCCATGTCTATATGTTTA
CAAGCAATATGGAGCACCATTCTTTAAATACTGTTCATGGAGAATACATAGTCTAACCAC
TAGGCGTGTCCCTGTTATCAGCAAAGATCAATGATGCTTCATTCATGTACTATGTATGCA
TTGGTGGTAAATGGATGTGAGGGCAAGTACATCAAGTACATTCACTCTGTTTCACGTATG
TGGATGCCAGTTAATTAAATGAGTACGTAAATAAATTAATTAAAACACATAGATCTGCTT
TGTGTTTTTATTTTTATTTTTTGAAAAACAAAAGGCAAGTCTCCAACAATTAACTTTTGA
TGCTTTCTGTTCCCCTAAAACCAAAAAATGAACCCCTTGTGTCGTTGTTAACCCATCCTT
TCATTTACTCATATAATTAGCCAAAAAAAAAAGGATGGCTACATACCAATGGATTGATTC
TCTTAATTGCCACGGCAAGGGGGCGATCCTATCATGACTTAACATCAAGCGCGCAGTTCA
AAACTACTGTCTTCTGTCAAAGTTTTCTCCTCTTAAATGTTATTTTGCTTTTACGTCTCA -continued ACTGTGTATGTAAAAAAAACGAATATTTAAATTACAACCCTAGACTAAAAATGTGTTTAT
AATAAGATGTGGATATTTCCTTCAGTAGATTGTAACCATAATTTAAATTATTTTGTTCCA
CACTGTTTTTTATATCTGTCATGTACATTGCATTTTGATCTGTAACTGCACAACCCTGGG
GTTTGCTGCAGAGCTATTTCTTTCCATGTAAAGTAGTGGATCCATCTTGCTTTTGCCTTA
TATAAAGCCTACAGTTATGGAAGTGTGGAAAACTGTGGCTTCTCAATAAATATTCAGATG
TCCTAAGAAAAAAAAAAAAAAAAAAAAAAAAAAAAAAAAAAAAAAAAAAAAAAAAAAAAA
AAAAAAA >Hs.111_contig1 AA946776|AW242338|H24274|AI078616 polyA = 1 polyA = 2
ACCTGAACTGTCTAAGATATTCTAAGCAAAGTTGACAAAGACAATTCTCCACTTGAGCCC
TTAAAAATGTAACCACTATAAAGGTTTCACGCGGTGGTTCTTATTGATTCGCTGTGTCAT
CACATCAGCTCCACTGTTGCCAAACTTTGTCGCATGCATAATGTATGATGGAGGCTTGGA
TGGGAATATGCTGATTTTGTTCTGCACTTAAAGGCTTCTCCTCCTGGAGGGCTGCCTAGG
GCCACTTGCTTGATTTATCATGAGAGAAGAGGAGAGAGAGAGAGACTGAGCGCTAGGAGT
GTGTGTATGTGTGTGTGTGTGTGTGTGTGTGTGTGTGTATGTGTGTAGCGGGAGATGTGG
GCGGAGCGAGAGCAAAAGGACTGCGGCCTGATGCATGCTGGAAAAAGACACGCTTTTCAT
TTCTGATCAGTTGTACTTCATCCTATATCAGCACAGCTGCCATACTTCGACTTATCAGGA
TTCTGGCTGGTGGCCTGCGCGAGGGTGCAGTCTTACTTAAAAGACTTTCAGTTAATTCTC
ACTGGTATCATCGCAGTGAACTTAAAGCAAAGACCTCTTAGTAAAAAATAAAAAAAATAA
A >Hs.150753 contigl AI123582|AI288234 polyA = 0 polyA = 0
GCTTCTCTTTT,AAATTGACCCAAGGCATGAGCCACTGCGCCTGGCCAGCAAATGCTTTTT
GTGCAGAATACACTTCTTTCAGGCATTGTCAGGTGCTGTTTTGTTTAAGCTCTAACTCAC
CCCTGGAATACAGGGGAATGATGACAACCAGCCCAGCCAGGCCTGACTCATCATGGTCAC
ATCCAGCCCCCACCCCCGGCCAACTAACCACTGCAGGCTCCTCTTCCAGACTCACCAGGG
GGCCTCGAGGCCCCGGCATCTCCCTTGGCCCTGGGTGTGGGTTTTACAAGACTGTGTCTT
TCATGACATCATAGCCCAACCATGTGAGAAGAAGGAGAAGGCCCCCCTTTCTTCATTAAT
CTGAAAA >Hs.82109_mRNA_1 gi|14250611|gb|BC008765.1|BC008765 *Homo sapiens* clone
MGC:1622 IMAGE:3347793 polyA = 3
GGCACGAGGAAGGGCCTGTGGGTTTATTATAAGGCGGAGCTCGGCGGGAGAGGTGCGGGC
CGAATCCGAGCCGAGCGGAGAGGAATCCGGCAGTAGAGAGCGGACTCCAGCCGGCGGACC
CTGCAGCCCTCGCCTGGGACAGCGGCGCGCTGGGCAGGCGCCCAAGAGAGCATCGAGCAG
CGGAACCCGCGAAGCCGGCCCGCAGCCGCGACCCGCGCAGCCTGCCGCTCTCCCGCCGCC
GGTCCGGGCAGCATGAGGCGCGCGGCGCTCTGGCTCTGGCTGTGCGCGCTGGCGCTGAGC
CTGCAGCCGGCCCTGCCGCAAATTGTGGCTACTAATTTGCCCCCTGAAGATCAAGATGGC
TCTGGGGATGACTCTGACAACTTCTCCGGCTCAGGTGCAGGTGCTTTGCAAGATATCACC
TTGTCACAGCAGACCCCCTCCACTTGGAAGGACACGCAGCTCCTGACGGCTATTCCCACG
TCTCCAGAACCCACCGGCCTGGAGGCTACAGCTGCCTCCACCTCCACCCTGCCGGCTGGA
GAGGGGCCCAAGGAGGGAGAGGCTGTAGTCCTGCCAGAAGTGGAGCCTGGCCTCACCGCC
CGGGAGCAGGAGGCCACCCCCCGACCCAGGGAGACCACACAGCTCCCGACCACTCATCAG
GCCTCAACGACCACAGCCACCACGGCCCAGGAGCCCGCCACCTCCCACCCCCACAGGGAC
ATGCAGCCTGGCCACCATGAGACCTCAACCCCTGCAGGACCCAGCCAAGCTGACCTTCAC
ACTCCCCACACAGAGGATGGAGGTCCTTCTGCCACCGAGAGGGCTGCTGAGGATGGAGCC
TCCAGTCAGCTCCCAGCAGCAGAGGGCTCTGGGGAGCAGGACTTCACCTTTGAAACCTCG
GGGGAGAATACGGCTGTAGTGGCCGTGGAGCCTGACCGCCGGAACCAGTCCCCAGTGGAT
CAGGGGGCCACGGGGGCCTCACAGGGCCTCCTGGACAGGAAAGAGGTGCTGGGAGGGGTC
ATTGCCGTAGGCCTCGTGGGGCTCATCTTTGCTGTGTGCCTGGTGGGTTTCATGCTGTAC
CGCATGAAGAAGAAGGACGAAGGCAGCTACTCCTTGGAGGAGCCGAAACAAGCCAACGGC
GGGGCCTACCAGAAGCCCACCAAACAGGAGGAATTCTATGCCTGACGCGGGAGCCATGCG
CCCCCTCCGCCCTGCCACTCACTAGGCCCCCACTTGCCTCTTCCTTGAAGAACTGCAGGC
CCTGGCCTCCCCTGCCACCAGGCCACCTCCCCAGCATTCCAGCCCCTCTGGTCGCTCCTG
CCCACGGAGTCGTGGGGTGTGCTGGGAGCTCCACTCTGCTTCTCTGACTTCTGCCTGGAG
ACTTAGGGCACCAGGGGTTTCTCGCATAGGACCTTTCCACCACAGCCAGCACCTGGCATC
GCACCATTCTGACTCGGTTTCTCCAAACTGAAGCAGCCTCTCCCCAGGTCCAGCTCTGGA
GGGGAGGGGGATCCGACTGCTTTGGACCTAAATGGCCTCATGTGGCTGGAAGATCCTGCG
GGTGGGGCTTGGGGCTCACACACCTGTAGCACTTACTGGTAGGACCAAGCATCTTGGGGG
GGTGGCCGCTGAGTGGCAGGGGACAGGAGTCCACTTTGTTTCGTGGGGAGGTCTAATCTA
GATATCGACTTGTTTTTGCACATGTTTCCTCTAGTTCTTTGTTCATAGCCCAGTAGACCT
TGTTACTTCTGAGGTAAGTTAAGTAAGTTGATTCGGTATCCCCCCATCTTGCTTCCCTAA
TCTATGGTCGGGAGACAGCATCAGGGTTAAGAAGACTTTTTTTTTTTTTTTTTTTAAACT
AGGAGAACCAAATCTGGAAGCCAAAATGTAGGCTTAGTTTGTGTGTTGTCTCTTGAGTTT
GTCGCTCATGTGTGCAACAGGGTATGGACTATCTGTCTGGTGGCCCCGTTTCTGGTGGTC
TGTTGGCAGGCTGGCCAGTCCAGGCTGCCGTGGGGCCGCCGCCTCTTTCAAGCAGTCGTG
CCTGTGTCCATGCGCTCAGGGCCATGCTGAGGCCTGGGCCGCTGCCACGTTGGAGAAGCC
CGTGTGAGAAGTGAATGCTGGGACTCAGCCTTCAGACAGAGAGGACTGTAGGGAGGGCGG
CAGGGGCCTGGAGATCCTCCTGCAGACCACGCCCGTCCTGCCTGTGGCGCCGTCTCCAGG
GGCTGCTTCCTCCTGGAAATTGACGAGGGGTGTCTTGGGCAGAGCTGGCTCTGAGCGCCT
CCATCCAAGGCCAGGTTCTCCGTTAGCTCCTGTGGCCCCACCCTGGGCCCTGGGCTGGAA
TCAGGAATATTTTCCAAAGAGTGATAGTCTTTTGCTTTTGGCAAAACTCTACTTAATCCA
ATGGGTTTTTCCCTGTACAGTAGATTTTCCAAATGTAATAAACTTTAATATAAAGTAAAA
AAAAAAAAAAAAAAAAAAAAAAAA >Hs.44276 mRNA_2 gi|12654896|gb|BC001293.1|BC001293 *Homo sapiens* clone
MGC:5259 IMAGE:3458115 polyA = 3
CGGATGGGGAAAAAAAAAGATGTCAGCTCCTCCGCTGTAGTATTGCTCCTTAAAAACCCC
TCTCTCTGAAAATGACATGCCCTCGCAATGTAACTCCGAACTCGTACGCGGAGCCCTTGG
CTGCGCCCGGCGGAGGAGAGCGCTATAGCCGGAGCGCAGGCATGTATATGCAGTCTGGGA
GTGACTTCAATTGCGGGGTGATGAGGGGCTGCGGGCTCGCGCCCTCGCTCTCCAAGAGGG -continued ACGAGGGCAGCAGCCCCAGCCTCGCCCTCAACACCTATCCGTCCTACCTCTCGCAGCTGG
ACTCCTGGGGCGACCCCAAAGCCGCCTATCGCCTGGAACAACCTGTTGGCAGGCCGCTGT
CCTCCTGCTCCTACCCACCTAGTGTCAAGGAGGAGAATGTCTGCTGCATGTACAGCGCAG
AGAAGCGGGCGAAAAGTGGCCCCGAGGCAGCTCTCTACTCCCACCCCTTGCCGGAGTCCT
GCCTTGGGGAGCACGAGGTACCCGTGCCCAGCTACTACCGCGCCAGCCCGAGCTACTCCG
CGCTGGACAAGACGCCCCACTGTTCTGGGGCCAACGACTTCGAAGCCCCTTTCGAGCAGC
GGGCCAGTCTCAACCCGCGCGCCGAACATCTGGAATCGCCTCAGCTGGGGGGCAAAGTGA
GTTTCCCTGAGACCCCCAAGTCCGACAGCCAGACCCCCAGCCCCAATGAAATCAAGACGG
AGCAGAGCCTGGCGGGCCCTAAAGGGAGCCCCTCGGAGAGCGAAAAGGAGAGGGCCAAAG
CTGCCGACTCCAGCCCAGACACCTCGGATAACGAAGCGAAAGAGGAGATAAAGGCAGAAA
ACACCACAGGAAATTGGCTGACAGCAAAGAGCGGAAGGAAGAAGAGGTGCCCCTATACTA
AACACCAGACGCTGGAATTGGAGAAAGAATTTCTGTTCAATATGTATTTGACGCGAGAGC
GCCGCCTGGAGATTAGCAAGACCATTAACCTTACAGACAGACAAGTCAAAATCTGGTTTC
AAAATCGCAGAATGAAACTCAAGAAAATGAACCGAGAGAATCGGATCCGGGAACTGACCT
CCAATTTTAATTTCACCTGAGAGCGCGGCCTCTCCTCCTCCCTTCCCGCTCCTTCCTCTC
CCCGCCCCTCCTCCCTTTGTGCCTGGTGATATATTTTTTTTTCCTCCCTGAGTATAAATG
CAATGCGACTGCAAAAAAGGCAAAGACCTCAGACTCTCCTTCCAAGGGACCTGTGGTTCG
TGCTGCGAAGATGCTTCCACTTAAAGCATGAGAAATGGGGTGCCGGGATGTGGGGTGTGG
TGTGTGCCCTCATAGATGGGGGTGGGAGTGTGGCTGGTGTGTGTGTCAAACCCTCACTCA
CCCACGCACTCACACACAGCATTCTGTTCTCCATGCAAAGTTAAGATCGAATCCATCCGC
TTGTAGGGGAAAAAAAGGAAAAAAATTAACCAGAGAGGGTCTGTAATCTCGCAGAGCACA
GGCAGAATCGTTCCTTCCTTGCTGCATTTCCTCCTTAGACTAATAGACGTTTTGGAAAGT
TCGGCTAGTGTTCGTGTGTTTGTCGTAGCACCCAGAGCCTCCACCAAACCCTCTCCATGT
CTTTACCTCCCAGTCGCTCTAAGAATCTGCTTGAAGTCTCGTATTTGTACTGCTTTCTGC
TTTTCTCCCACCCCTCCTAGCACCCCCACATCCCCCATCTAGTAACATCTCAGAAATTTC
ATCCAGAGGAACAAAAAAATTAAAAATAGAACATAGCAAAGCAAAGACAGAATGCCCCCC
CCCAAATATTGTCCTGTCCCTGTCTGGGAGTTGTGTTATTTAAAGATATTCTGTATGTTG
TATCTTTTGCATGTAGCTTCCTTAATGGAGAAAAAAAAATCCTAATAAATTTCCAGAATC
ATAATCCTCAAAAAAAAAAAAAAAAAAAAAAAAAAAAAAAAAAAAAAAAAAAAAAAAAAA
AAAAAAAAA >Hs.2142_mRNA_4 gi|13325274|gb|BC004453.1|BC004453 *Homo sapiens* clone
MGC:4303 IMAGE:2819400 polyA = 3
GCAGTGGCCACGAGAGGCAGGCTGGCTGGGACATGAGGTTGGCAGAGGGCAGGCAAGCTG
GCCCTTGGTGGGCCTCGTCCTGAGCACTCGGAGGCACTCCTATGCTTGGAAAGCTCGCTA
TGCTGCTGTGGGTCCAGCAGGCGCTGCTCGCCTTGCTCCTCCCCACACTCCTGGCACAGG
GAGAAGCCAGGAGGAGCCGAAACACCACCAGGCCCGCTCTGCTGAGGCTGTCGGATTACC
TTTTGACCAACTACAGGAAGGGTGTGCGCCCCGTGAGGGACTGGAGGAAGCCAACCACCG
TATCCATTGACGTCATTGTCTATGCCATCCTCAACGTGGATGAGAAGAATCAGGTGCTGA
CCACCTACATCTGGTACCGGCAGTACTGGACTCATGAGTTTCTCCAGTGGAACCCTGAGG
ACTTTGACAACATCACCAAGTTGTCCATCCCCACGGACAGCATCTGGGTCCCGGACATTC
TCATCAATGAGTTCGTGGATGTGGGGAAGTCTCCAAATATCCCGTACGTGTATATTCGGC
ATCAAGGCGAAGTTCAGAACTACAAGCCCCTTCAGGTGGTGACTGCCTGTAGCCTCGACA
TCTACAACTTCCCCTTCGATGTCCAGAACTGCTCGCTGACCTTCACCAGTTGGCTGCACA
CCATCCAGGACATCAACATCTCTTTGTGGCGCTTGCCAGAAAAGGTGAAATCCGACAGGA
GTGTCTTCATGAACCAGGGAGAGTGGGAGTTGCTGGGGGTGCTGCCCTACTTTCGGGAGT
TCAGCATGGAAAGCAGTAACTACTATGCAGAAATGAAGTTCTATGTGGTCATCCGCCGGC
GGCCCCTCTTCTATGTGGTCAGCCTGCTACTGCCCAGCATCTTCCTCATGGTCATGGACA
TCGTGGGCTTCTACCTGCCCCCCAACAGTGGCGAGAGGGTCTCTTTCAAGATTACACTCC
TCCTGGGCTACTCGGTCTTCCTGATCATCGTTTCTGACACGCTGCCGGCCACTGCCATCG
GCACTCCTCTCATTGGTGTCTACTTTGTGGTGTGCATGGCTCTGCTGGTGATAAGTTTGG
CCGAGACCATCTTCATTGTGCGGCTGGTGCACAAGCAAGACCTGCAGCAGCCCGTGCCTG
CTTGGCTGCGTCACCTGGTTCTGGAGAGAATCGCCTGGCTACTTTGCCTGAGGGAGCAGT
CAACTTCCCAGAGGCCCCCAGCCACCTCCCAAGCCACCAAGACTGATGACTGCTCAGCCA
TGGGAAACCACTGCAGCCACATGGGAGGACCCCAGGACTTCGAGAAGAGCCCGAGGGACA
GATGTAGCCCTCCCCCACCACCTCGGGAGGCCTCGCTGGCGGTGTGTGGGCTGCTGCAGG
AGCTGTCCTCCATCCGGCAATTCCTGGAAAAGCGGGATGAGATCCGAGAGGTGGCCCGAG
ACTGGCTGCGCGTGGGCTCCGTGCTGGACAAGCTGCTATTCCACATTTACCTGCTGGCGG
TGCTGGCCTACAGCATCACCCTGGTTATGCTCTGGTCCATCTGGCAGTACGCTTGAGTGG
GTACAGCCCAGTGGAGGAGGGGGTACAGTCCTGGTTAGGTGGGGACAGAGGATTTCTGCT
TAGGCCCCTCAGGACCCAGGGAATGCCAGGGACATTTTCAAGACACAGACAAAGTCCCGT
GCCCTGTTTCCAATGCCAATTCATCTCAGCAATCACAAGCCAAGGTCTGAACCCTTCCAC
CAAAAACTGGGTGTTCAAGGCCCTTACACCCTTGTCCCACCCCCAGCAGCTCACCATGGC
TTTAAAACATGCTCTCTTAGATCAGGAGAAACTCGGGCACTCCCTAAGTCCACTCTAGTT
GTGGACTTTTCCCCATTGACCCTCACCTGAATAAGGGACTTTGGAATTCTGCTTCTCTTT
CACAACTTTGCTTTTAGGTTGAAGGCAAAACCAACTCTCTACTACACAGGCCTGATAACT
CTGTACGAGGCTTCTCTAACCCCTAGTGTCTTTTTTTTTCTTCACCTCACTTGTGGCAGCT
TCCCTGAACACTCATCCCCCATCAGATGATGGGAGTGGGAAGAATAAAATGCAGTGAAAC
CCTAAAAAAAAAAAAAAAAAA >Hs.180908_cOntig1 AA846824|AW611680|AA846182|AA846342|AA846360 polyA = 2
polyA = 3
TCTTCGCTCCTCTACCCCATAAAATTCCCTACAAATGCAAAAATTCGAGATAGAAGAAGC
CGTCCCTGAAATTGCTGTCTAACATTCACCGGAAACCTCTCCATAAACAAGGAGAAACGA
ATGCACACGCATTTTTGCTAAGAAGCCCGGGATTAAGATTTAAGGATACAAGCTGAAAGA
AAAAATGAAAAATGCTTCTCCGCGCGTCAATCGAGGGGTGGATGCGCCACGCAGCTGAGC
CCAGCTCACAGCCACGCGTAAGACCAAAAGCTGCCATGGGTTCTGCGCGCGGAGACCTCA
GAGCCGAAGAGAGAAGTCCCCGCGTCAGAAACGCTGCGGATGCCAGGTCTTGAAAATGCT
GACTTCTGAGGCTAAGAATTATTTCAAAGACAAAAAGAAAPIGACTGGTGAGGAGGCCTTC -continued CGGTGCAAGGGCGCCTATCCGCTAATTTTGGATGGGGAAGTAGGGATTATTCGTTTAAAT
TCAATCGCGAGCACCAAGTCGGACTGGCCGGGGATGGAGAAGGGCAACCCCCACCTTTAG
AAAAATAAAAGATCTCGAAGGCCAAAAAAAAAAA >Hs.89436_mRNA_1 gi|16507959|ref|NM_004063.2| *Homo sapiens* cadherin 17, LI cadherin (liver-intestine) (CDH17), mRNA polyA = 1
AGGGAGTGTTCCCGGGGGAGATACTCCAGTCGTAGCAAGAGTCTCGACCACTGAATGGAA
GAAAAGGACTTTTAACCACCATTTTGTGACTTACAGAAAGGAATTTGAATAAAGAAAACT
ATGATACTTCAGGCCCATCTTCACTCCCTGTGTCTTCTTATGCTTTATTTGGCAACTGGA
TATGGCCAAGAGGGGAAGTTTAGTGGACCCCTGAAACCCATGACATTTTCTATTTATGAA
GGCCAAGAACCGAGTCAAATTATATTCCAGTTTAAGGCCAATCCTCCTGCTGTGACTTTT
GAACTAACTGGGGAGACAGACAACATATTTGTGATAGAACGGGAGGGACTTCTGTATTAC
AACAGAGCCTTGGACAGGGAAACAAGATCTACTCACAATCTCCAGGTTGCAGCCCTGGAC
GCTAATGGAATTATAGTGGAGGGTCCAGTCCCTATCACCATAGAAGTGAAGGACATCAAC
GACAATCGACCCACGTTTCTCCAGTCAAAGTACGAAGGCTCAGTAAGGCAGAACTCTCGC
CCAGGAAAGCCCTTCTTGTATGTCAATGCCACAGACCTGGATGATCCGGCCACTCCCAAT
GGCCAGCTTTATTACCAGATTGTCATCCAGCTTCCCATGATCAACAATGTCATGTACTTT
CAGATCAACAACAAAACGGGAGCCATCTCTCTTACCCGAGAGGGATCTCAGGAATTGAAT
CCTGCTAAGAATCCTTCCTATAATCTGGTGATCTCAGTGAAGGACATGGGAGGCCAGAGT
GAGAATTCCTTCAGTGATACCACATCTGTGGATATCATAGTGACAGAGAATATTTGGAAA
GCACCAAAACCTGTGGAGATGGTGGAAAACTCAACTGATCCTCACCCCATCAAAATCACT
CAGGTGCGGTGGAATGATCCCGGTGCACAATATTCCTTAGTTGACAAAGAGAAGCTGCCA
AGATTCCCATTTTCAATTGACCAGGAAGGAGATATTTACGTGACTCAGCCCTTGGACCGA
GAAGAAAAGGATGCATATGTTTTTTATGCAGTTGCAAAGGATGAGTACGGAAAACCACTT
TCATATCCGCTGGAAATTCATGTAAAAGTTAAAGATATTAATGATAATCCACCTACATGT
CCGTCACCAGTAACCGTATTTGAGGTCCAGGAGAATGAACGACTGGGTAACAGTATCGGG
ACCCTTACTGCACATGACAGGGATGAAGAAAATACTGCCAACAGTTTTCTAAACTACAGG
ATTGTGGAGCAAACTCCCAAACTTCCCATGGATGGACTCTTCCTAATCCAAACCTATGCT
GGAATGTTACAGTTAGCTAAACAGTCCTTGAAGAAGCAAGATACTCCTCAGTACAACTTA
ACGATAGAGGTGTCTGACAAAGATTTCAAGACCCTTTGTTTTGTGCAAATCAACGTTATT
GATATCAATGATCAGATCCCCATCTTTGAAAAATCAGATTATGGAAACCTGACTCTTGCT
GAAGACACAAACATTGGGTCCACCATCTTAACCATCCAGGCCACTGATGCTGATGAGCCA
TTTACTGGGAGTTCTAAAATTCTGTATCATATCATAAAGGGAGACAGTGAGGGACGCCTG
GGGGTTGACACAGATCCCCATACCAACACCGGATATGTCATAATTAAAAAGCCTCTTGAT
TTTGAAACAGCAGCTGTTTCCAACATTGTGTTCAAAGCAGAAAATCCTGAGCCTCTAGTG
TTTGGTGTGAAGTACAATGCAAGTTCTTTTGCCAAGTTCACGCTTATTGTGACAGATGTG
AATGAAGCACCTCAATTTTCCCAACACGTATTCCAAGCGAAAGTCAGTGAGGATGTAGCT
ATAGGCACTAAAGTGGGCAATGTGACTGCCAAGGATCCAGAAGGTCTGGACATAAGCTAT
TCACTGAGGGGAGACACAAGAGGTTGGCTTAAAATTGACCACGTGACTGGTGAGATCTTT
AGTGTGGCTCCATTGGACAGAGAAGCCGGAAGTCCATATCGGGTACAAGTGGTGGCCACA
GAAGTAGGGGGGTCTTCCTTGAGCTCTGTGTCAGAGTTCCACCTGATCCTTATGGATGTG
AATGACAACCCTCCCAGGCTAGCCAAGGACTACACGGGCTTGTTCTTCTGCCATCCCCTC
AGTGCACCTGGAAGTCTCATTTTCGAGGCTACTGATGATGATCAGCACTTATTTCGGGGT
CCCCATTTTACATTTTCCCTCGGCAGTGGAAGCTTACAAAACGACTGGGAAGTTTCCAAA
ATCAATGGTACTCATGCCCGACTGTCTACCAGGCACACAGAGTTTGAGGAGAGGGAGTAT
GTCGTCTTGATCCGCATCAATGATGGGGGTCGGCCACCCTTGGAAGGCATTGTTTCTTTA
CCAGTTACATTCTGCAGTTGTGTGGAAGGAAGTTGTTTCCGGCCAGCAGGTCACCAGACT
GGGATACCCACTGTGGGCATGGCAGTTGGTATACTGCTGACCACCCTTCTGGTGATTGGT
ATAATTTTAGCAGTTGTGTTTATCCGCATAAAGAAGGATAAAGGCAAAGATAATGTTGAA
AGTGCTCAAGCATCTGAAGTCAAACCTCTGAGAAGCTGAATTTGAAAAGGAATGTTTGAA
TTTATATAGCAAGTGCTATTTCAGCAACAACCATCTCATCCTATTACTTTTCATCTAACG
TGCATTATAATTTTTTAAACAGATATTCCCTCTTGTCCTTTAATATTTGCTAAATATTTC
TTTTTTGAGGTGGAGTCTTGCTCTGTCGCCCAGGCTGGAGTACAGTGGTGTGATCCCAGC
TCACTGCAACCTCCGCCTCCTGGGTTCACATGATTCTCCTGCCTCAGCTTCCTAAGTAGC
TGGGTTTACAGGCACCCACCACCATGCCCAGCTAATTTTTGTATTTTTAATAGAGACGGG
GTTTCGCCATTTGGCCAGGCTGGTCTTGAACTCCTGACGTCAAGTGATCTGCCTGCCTTG
GTCTCCCAATACAGGCATGAACCACTGCACCCACCTACTTAGATATTTCATGTGCTATAG
ACATTAGAGAGATTTTTCATTTTTCCATGACATTTTTCCTCTCTGCAAATGGCTTAGCTA
CTTGTGTTTTTCCCTTTTGGGGCAAGACAGACTCATTAAATATTCTGTACATTTTTTCTT
TATCAAGGAGATATATCAGTGTTGTCTCATAGAACTGCCTGGATTCCATTTATGTTTTTT
CTGATTCCATCCTGTGTCCCCTTCATCCTTGACTCCTTTGGTATTTCACTGAATTTCAAA
CATTTGTCAGAGAAGAAAAACGTGAGGACTCAGGAAAAAATAAATAAATAAAAGAACAGCC
TTTTCCCTTAGTATTAACAGAAATGTTTCTGTGTCATTAACCATCTTTAATCAATGTGAC
ATGTTGCTCTTTGGCTGAAATTCTTCAACTTGGAAATGACACAGACCCCACAGAAGGTGTT
CAAACACAACCTACTCTGCAAACCTTGGTAAAGGAACCAGTCAGCTGGCCAGATTTCCTC
ACTACCTGCCATGCATACATGCTGCGCATGTTTTCTTCATTCGTATGTTAGTAAAGTTTT
GGTTATTATATATTTAACATGTGGAAGAAAACAAGACATGAAAAGAGTGGTGACAAATCA
AGAATAAACACTGGTTGTAGTCAGTTTTGTTTGTTAA >Hs.151544_mRNA_8 gi|3153107|emb|AL023657.1|HSDSHP *Homo sapiens* SH2D1A cDNA, formerly known as DSHP polyA = 3
AAATCCTTCTTCCAATGTTCCTCCCCTCTCTGTATGAACCCTGTGTTGGGGGGCAGAAGA
TGGAAGCCCTTGGCAAGCTCGATCGAACCAAGCTACTAAATTGCTGAGCTCGTTTTAACT
GAAGTGTGAGAAGGAGGTTTAAGGCAAGTAGACAACATCCTGTTGTTGGGGTGCTTCTCT
CTTTTTTGCACATCTGGCTGAACTGGGAGTCAGGTGGTTGACTTGTGCCTGGCTGCAGTA
GCAGCGGCATCTCCCTTGCACAGTTCTCCTCCTCGGCCTGCCCAAGAGTCCACCAGGCCA
TGGACGCAGTGGCTGTGTATCATGGCAAAATCAGCAGGGAAACCGGCGAGAAGCTCCTGC
TTGCCACTGGGCTGGATGGCAGCTATTTGCTGAGGGACAGCGAGAGCGTGCCAGGCGTGT
ACTGCCTATGTGTGCTGTATCACGGTTACATTTATACATACCGAGTGTCCCAGACAGAAA
CAGGTTCTTGGAGTGCTGAGACAGCACCTGGGGTACATAAAAGATATTTCCGGAAAATAA
AAAATCTCATTTCAGCATTTCAGAAGCCAGATCAAGGCATTGTAATACCTCTGCAGTATC -continued CAGTTGAGAAGAAGTCCTCAGCTAGAAGTACACAAGGTACTACAGGGATAAGAGAAGATC
CTGATGTCTGCCTGAAAGCCCCATGAAGAAAAATAAAACACCTTGTACTTTATTTTCTAT
AATTTAAATATATGCTAAGTCTTATATATTGTAGATAATACAGTTCGGTGAGCTACAAAT
GCATTTCTAAAGCCATTGTAGTCCTGTAATGGAAGCATCTAGCATGTCGTCAAAGCTGAA
ATGGACTTTTGTACATAGTGAGGAGCTTTGAAACGAGGATTGGGAAAAAGTAATTCCGTA
GGTTATTTTCAGTTATTATATTTACAAATGGGAAACAAAAGGATAATGAATACTTTATAA
AGGATTAATGTCAATTCTTGCCAAATATAAATAAAAATAATCCTCAGTTTTTGTGAAAAG
CTCCATTTTTAGTGAAATATTATTTTATAGCTACTAATTTTAAAATGTCTTGCTTGATTG
TATGGTGGGAAGTTGGCTGGTGTCCCTTGTCTTTGCCAAGTTCTCCACTAGCTATGGTGT
CATAGGCTCTTTTGGGATTTTTGAAGCTGTATACTGTGTGCTAAAACAAGCACTAAACAA
AGAGTGAAGGATTTATGTTTAATTCTGAAAGCAACCTTCTTGCCTAGTGTTCTGATATTG
GACAGTAAAATCCACAGACCAACCTGGAGTTGAAAATCTTATAATTTAAAATATGCTCTA
AACATGTTTATCGTATTTGATGCTACAGGATTTGAAATTGTATTACAAATCCAATGAAAT
GAGTTTTTCTTTTCATTTACCTCTGCCCCAGTTGTTTCTACTACATGGAAGACCTCATTT
TGAAGGGAAATTTCAGCAGCTGCAGCTCATGAGTAACTGATTTGTAACAAGCCTCCTTTT
AAAGTAACCCTACAAAACCACTGGAAAGTTTATGGTTGTATTATTTTTTAAAAAAATTCC
AAGTGATTGAAACCTACACGAGATACAGAATTTTATGCGGCATTTTCTTCTCACATTTAT
ATTTTTGTGATTTTGTGATTGATTATATGTCACTTTGCTACAGGGCTCACAGAATTCATT
CACTCAACAAACATAATAGGGCGCTGAGGGCATAGAAGTAAAAACACCTGGTCCCTGCTC
TCAGTTCACTGTCTTGTTGGACGAGAAAAGAAACAATAACGATAAAAGACAGTGAAAGAA
AATAACGATAAAAGACAGTGAAAGAAAATAACAATAAAAGACAAGGAAAAAATAACAATG
AAAGTTGATAAGTACATGATAAGCGAGGTTCCCCGTGTGTAGGTAGATCTGGTCTTTAGA
GGCAGATAGATAGGTCAGTGCAAATACTCTGGTCCATGGGCCATATGAAAAGGCTAAGCT
TCACTGTAAAATAATAACTGGGAATTCTGGATTGTGTATGGGTGTTGGTGAACTTGGTTT
TAATTAGTGAACTGCTGAGAGACAGAGCTATTCTCCATCTACTGGCAAGACCTGATTTCT
GAGCATTTAATATGGATGCCGTGGGAGTACAAAAGTGGAGTGTGGCCTGAGTAATGCATT
ATGGGTGGTTTACCATTTCTTGAGGTAAAAGCATCACATGAACTTGTAAAGGAATTTAAA
AATCCTACTTTCATAATAAGTTGCATAGGTTTAATAATTTTTAATTATATGGCTTGAGTT
TAAATTGTAATAGGCGTAACTAATTTTAACTCTATAATGTGTTCATTCTGGAATAATCCT
AAACATATGAATTATGTTTGCATGTTCACTTCCAAGAGCCTTTTTTTGAAAAAAAGCTTT
TTTTGAATCATCAAGTCTTTCACATTTAAATAAAGTGTTTGAAAGCTTTATTTAAAAAAA
AAAAAAAAAAAAAAAAAAAAAAAAAAAAAAAAAAAAAAAAAAAAAAAAAAAAAAAAAAAA
AAGAAAAAAA >Hs.1657_contig4
AW473119|AAI64586|AI540656|AI758480|AI810941|AI978964|AI675862|AI784397|
AW591562|AW514102|AI888116|AI983175|AI634735|AI669577|AI202659|AI910598|
AI961352|AI565481|AI886254|AI538838|AA291749|AW571455|AI370308|AI274727|
AW473925|AW514787|AI273871|AW470552|AI524356|AI888281|AW089672|AI952766|
AW440601|AI654044|AW438839|AI972926 polyA = 2 poLyA = 3
AATTGTTTTCTAAGTAATTGCTGCCTCTATTATGGCACTTCATTTTTGCACTGTCTTTTG
AGATTCAAGAAAAATTTCTATTCTTTTTTTTGCATCCAATTGTGCCTGAACTTTTAAAAT
ATGTAAATGCTGCCATGTTCCAAACCCATCGTCAGTGTGTGTGTTTAGAGCTGTGCACCC
TAGAAACAACATATTGTCCCATGAGCAGGTGCCTGAGACACAGACCCCTTTGCATTCACA
GAGAGGTCATTGGTTATAGAGACTTGAATTAATAAGTGACATTATGCCAGTTTCTGTTCT
CTCACAGGTGATAAACAATGCTTTTTGTGCACTACATACTCTTCAGTGTAGAGCTCTTGT
TTTATGGGAAAAGGCTCAAATGCCAAATTGTGTTTGATGGATTAATATGCCCTTTTGCCG
ATGCATACTATTACTGATGTGACTCGGTTTTGTCGCAGCTTTGCTTTGTTTAATGAAACA
CACTTGTAAACCTCTTTTGCACTTTGAAAAAGAATCCAGCGGGATGCTCGAGCACCTGTA
AACAATTTTCTCAACCTATTTGATGTTCAAATAAAGAATTAAACTAAAAAAAAAAAAAAA
A >Hs.35984_mRNA_1 gi|6049161|gb|AF133587.1|AF133587 *Homo sapiens* chromosome
22 map 22q11.2 polyA = 3
GGCGCCGCGGACGCTGCTGGAGTCGCCTGGCAACGATGTCGCCTGGCAACTGAATAGGTT
GGCCAGTGGCGCGGGCTACTGGAAGCAGAAAGGGCTGCGGAGGCAGTGAGTGGTTTCTGC
AGAGCTTCATTTGGAAAGGCCTCTGTAGTTGGGGAAAGATGGCCCATTCCCAGAACTCCT
TGGAGCTTCCCATTAACATCAATGCCACCCAGATTACCACTGCCTATGGCCATCGGGCCC
TGCCCAAGCTGAAGGAGGAGCTGCAGTCAGAGGACCTCCAGACGAGGCAGAAAGCCCTCA
TGGCCCTGTGTGACCTCATGCATGACCCCGAGTGTATCTACAAGGCCATGAACATAGGCT
GTATGGAGAACCTGAAAGCTTTGCTGAAGGATAGCAACAGTATGGTGCGCATAAAGACCA
CCGAGGTGCTCCACATCACGGCAAGCCATAGCGTGGGCAGATACGCCTTTCTAGAGCACG
ACATCGTCCTTGCCCTGTCCTTCCTGCTGAATGACCCCAGCCCAGTCTGCCGGGGGAACC
TGTACAAGGCATACATGCAGCTGGTCCAGGTGCCTAGAGGGGCCCAAGAGATCATCAGCA
AAGGTCTGATTTCCTCACTGGTATGGAAGCTGCAGGTGGAGGTGGAGGAGGAGGAGTTCC
AGGAGTTCATCCTGGACACACTGGTCCTCTGCCTGCAGGAGGATGCCACCGAGGCCCTGG
GCAGCAATGTGGTGCTTGTCCTGAAGCAGAAGCTCCTCAGCGCCAACCAGAACATCCGCA
GCAAGGCCGCCCGTGCGCTCCTTAATGTCAGCATATCTCGAGAGGGCAAGAAACAGGTGT
GTCATTTTGACGTCATCCCCATCCTGGTCCATCTGCTGAAAGACCCAGTGGAGCATGTGA
AGTCTAACGCTGCCGGTGCCCTGATGTTCGCCACAGTGATCACTGAAGGGAAGTATGCGG
CCCTGGAGGCACAAGCCATCGGCCTGCTCCTGGAGCTGCTGCACTCCCCCATGACCATAG
CGCGCCTGAATGCCACCAAGGCCCTTACCATGCTGGCAGAGGCCCCCGAGGGCCGCAAGG
CCCTGCAGACGCACGTGCCCACTTTCCGTGCCATGGAGGTGGAGACTTACGAAAAGCCTC
AAGTGGCCGAAGCCTTACAGCGGGCAGCCCGGATCGCCATCAGTGTCATCGAGTTCAAAC
CCTGAGCCCTTCATTCACCTCTGTGAGTGAATAAATGTGCTAAGTCTCTTTAAAAAAAAA
AAAAAAAAAAAAAAAAAAAAAAAAA >Hs.334534_mRNA_2 gi|17389403|gb|BC017742.1|BC017742 *Homo sapiens*, clone
IMAGE:4391536, mRNA polyA = 3
AGAGCAGTAAGCTTGTGATAAAGGCCAATTCCAGGTAGCTCTTGAAGGTGATAGCCATCT
ACTTTCCAGTGGCTGCCAACCACAGGGAGTGCCAGTTAACACTGGAAGGATTAAGGCAAG -continued GTCCCTTCTCTTGAGACTCCCCTCTGAGATCTGAAAAATGAAGTGGCTTAGGAACATCAG
CAGTGAAGAACTGCCAAGAGTTGGTGAAGGTTGTCTCTTCCGAGGGCCTTCTGAAGACAG
GGCTCTTGAACAGACAAGTGGAAGGGCTGTACCAGGGATAAAGGAAAGAAGTGCCTGTCC
AGCAGGGAGCTTGAATTTAAGTTCCATGTATGAAGTCATTGGCTCTATCTGCATTTTTCT
GTCATTCTCTTCATTTGTTTTAAGGTGGAAAATTTTCTTACAGTTGATGCAAAGTATCAA
CTACTTTACCCTACCTTCTCCCCTTTTAGATGGGTTCTTCCTGAGTTTTGGAGTCTTGTA
TGATTATCAGTATTCCCCTGTCAAAATCAAATCTATTCAGGTTTCTTCACTGTTGAGAAC
ACCTAAATGTTTTTATTTTTGAGAAGTGGGGACAGAGTCTCACTATGTCACCCAGGCTGG
AGTGCAATGGCATGATCTCAGCTCACTGCAACCTTCGCCTCCTGGGTTCAAGCGATTCTC
CTGCCTCCGCCTCCTGAGTAGCTGGGATTATAGGCACGCACCACCACGCCCAGCTAATTT
TTTGTATTTTTAGTAGAGACAGAGTTTCACCATGTTGGCCAGGCTGGTCTTGAACTCCTG
ACCTTGTGATCCACCCACCTCGGCCTCCCAGAGTGCTGGGATTACAGGCATGAGCCACCA
CGCTTGGCTAAGAACACCTAAATTTTTATGTTTCTTGGCTCAAAAACCAGTTCCATTTCT
AATGTTGTCCTCACAAGAAGGCTAATTGGTGGTGAGACAGCAGGGGAGGAGGAAGAGCTG
TGGTTTGTAACTTGTTCAACTCAGGCAATAAGCGATTTTAGCTTTATTTAAAGTCTTCTG
TCCAGCTTTAAGCACTTTGTAAGACATGGCTGAAAGTAGCTTTTCTATCAGAATTGCAGA
TAGTCATGTTGGGCTAACAGTCAATTGGATATATTCCTTTACCTCACATGACCCCAGCAA
CTGTGGTGGTATCTAGAGGTGAAACAGGCAAGTGAAATGGACACCTCTGCTGTGAATGTT
TTAGAGAAGGAAATTCAAAAAATGTTGTAACTGAAAGCACTGTTGAATATGGGTATCGGC
TTTCTTTTTCACTTTGACTCTTAACATTATCAGTCAACTTCCACATTAATGAAAGTTGAC
CATAGTTATTTCCAAATAAAAAGAAACCAACTCTTACCAGGTCTTGGACTGTGATGTCAT
ATTATTCAGTTTTATGCTTGTTCCTGAGCAGAACTCATAAGAGTGACATAGTCAGCTGCT
GACGGCACCTCAGCCACGCCACTCTTACTCAGTTCAGTGGGTGTGCTTGCGTGGTAGGAT
GTGGTGCAGCCCTCTCTACGCTCTTCTATTTTTGGTATATTTCCTATCTAACCTTCAAAT
AGCTTCCAATTCTTTTTTTCTTGGACTGGCTTCATTCTGAATTTGTGCTAAAATAATCTT
TCATAAAGAGACCTCAGTTTATAGCGTAACAGACTACACAATGCACTGATGTTTTCATAA
TGTTTAAGGGACCCACTGCAAGAAGCTTGCTGCCTCCTTTTAATTGTATTCATTTAGATT
TTGATTTTCCATGTTAAGAAGGTGAGGTCCATGTTGGTGCCCTTCAGAGTAGAGAACCAT
GTAAACATTAGGAATGAACAGAGGCCTTAGGAATGAATAGAGAGTTTGCCTTATACAATT
TCCTGTTACAAAGCTCTCCCTCTCATGCAAAGTAGGGAACACCTTTTGAGCATCTTTGAA
TTTGACAAATGGTGCTGTTGCAAACACTTTTTTTTTGAGATGAAGTCTCGCGGTTGTCAC
CCGGGCTGGAGTGCAGTGGCGTGATCTCGGCTCACTGCAACTTCCACCTCCTGGGTTCCA
GCAGTTCTCCTGCCTCAGCCTCCCAAGTAGCTGAGATTACAGGCGCCTGCCACCCCACCT
GGCTGATTTTTGTAATTTTAGTAGAGACGGGGTTTCACCATGTTGGCCAGGCTGATTAAC
TCCTGACCTCAGGTGATCCACCTTTCTCGGCCTCCCAAAGTGCTGGGATTACGGGTGTGA
GCCACCGTGCCCGGCCTGCAAACACATTTTAATTGACAACACTAGGGCTGTTGTACAAAA
TAGTAATGATAGCCATGGAAGTTTTACCTTATTCTGTGAGAAGTGTTCTTAAACTTATTA
AGTGTCTAAACTAAGGTTTAGTGCTTTTTTAAAGGAAAGTTGTCCCAGGATTCATCCTAA
AGAAAGCAAAAGTTAATTCAACTGATCCACCAATGGAATTAGATGGGTAGAGTTGGGTTC
TTGAGTTTTACCACCACTTAGTTCCCACTGAATTTTGTAACTTCCTGTGTTTGCATCCTC
TGTTCCTATTCTGCCCTTGCTCTGTGTCATCTCAGTCATTTGACTTAGAAAGTGCCCTTC
AAAAGGACCCTGTTCACTGCTGCACTTTTCAATGAATTAAAATTTATTTCTGTTCTAAAA
AAAAAAAAAAA >Hs.60162_mRNA_1 gi|10437644|dbf|AK025181.1|AK025181 *Homo sapiens* cDNA:
FLJ21528 fis, clone COL05977 polyA = 3
TGATCAACAACTGTCAGCTCCCAGTCAGAGAGAAAGGGCCTCTTCAGTCTGTCTCAGGAG
ACTGGGAGAAACAGCATAAAGGACCCCACAAGGAAGGGAGAGGTACCCTGGGTCAGGCGC
TTGTGGAGAGAGGGCTTCGCATGTAAAGTGACGTCAGGGAAAATAGAACAGAAAAAAAGC
CAGGGCCAGCCCAGAGGCACCTGAGAAGAATCAGACCCACAGCTCAGCCCAGCCCTGGCA
CAGAGAAGAGACAGGCCTGGCAGCACCCAGGGACCCCCTTTCCTCAGCCTCCACCTGCAG
GACAGCAGGAGCACTGATGCGCTGAAGGTACGTTCTGGAGTCTGGAAGCAGCAGAACTGA
AGGAAGTAAACACGGGTGTCTGGGAAGACCCCTCAAGCTGCAGTAAAGCCCAGGACTGAA
TTGGCCACCTGAGGCCAAGGGTGGCACTCCAACCTCCTCCTAAAGGCTGGCTAGAGCCAC
AGGAAAGGGCCAGAAGCCAGAGAAAGGGCAAAGGTGGACCCCTGCCTCCAAACCTCCTCT
GGAGACTGACCTCCTCTTTCCTGTGCCTTATTGTTTCTCCCTCTTCTCTTGTTCGCCAC
TGGGCGGTGACCTCAGGGATCCTGGCCTAACCTGGTGATTGTGCAGGCAACTGTGTCCGA
GAAGACCCTTCTCTGGAAGATTGAACCCCAATTCAGCCATGGTGACTCCTTTGATGTCAA
ACTGGTAAGGGCTGAGCCGTGGGCACAGGATACCACTCCTTCCAGCTCTTCTGCTGTGAC
CTGCCCATGGAAGTCCCTGTGGACACGAAATCCTGTTTGGATCATCTAACTGGAGGCTCT
CTGTTCTTCACCTCCACGCGCCCTCTTGACCCCAGGAGGTTCAGGGGAGGAAGTACGCCA
CTCTCCACTGGCACCCTCCTTGGCCTACACAGAGTCACCCCTGAGCCCCTCAATGTGTGC
TGAGGTGGGCCCTGCTCTCTGCAGGGGTATGGAGAGAAATAGCTTGGGGTGCTGTGAGGC
CCCGAAGAAGCTGGGCCTGTCCTTCTCCATCGAGGCGATCCTAAAGAGGCCTGCCAGGAG
GAGTGATATGGACAGACCAGAAGGGCCAGGTGAAGAGGGCCCCGGAGAAGCTGCGGCCTC
AGGCTCTGGGCTAGAAAAGCCTCCAAAGGACCAGCCCCAGGAAGGAAGGAAGAGCAAGCG
GAGGGTTCGTACCACCTTCACCACTGAGCAGCTGCATGAGCTGGAGAAGATCTTCCACTT
TACCCACTACCCAGACGTTCACATCCGCAGCCAGCTGGCAGCCAGGATCAACCTCCCAGA
AGCTCGGGTGCAGATCTGGTTCCAGAATCAGCGAGCCAAGTGGCGGAAGCAGGAGAAGAT
TGGCAACCTGGGGGCTCCACAGCAGCTGAGTGAAGCCAGTGTGGTCCTGCCCACAAATCT
GGATGTGGCTGGGCCCACGTGGACATCCACTGCTCTGCGCAGGCTGGCTCCTCCCACGAG
CTGTTGTCCATCGGCTCAAGATCAGCTGGCCTCTGCCTGGTTCCCTGCCTGGATCACCCT
CCTCCCAGCGCACCCATGGGAAACACAGCCTGTCCCAGGTCTTCCCATCCATCAAACTTG
CATCCCTGTGCTATGCATCCTTCCACCTCCACACCCCAAATGGGGCAGCATCTGTGCTAC
TTCAACATAGAGATTGGACATGCTCTCCCCAAATGAGCCACTTTCCTCTCCAGGTGAAGG
CAGGTAGCAGATGTGCCCTGGGCCTCTGGGGAAATCGATCTCACAATCCAAAAATGGCCC
ACAGCCCAGGAAGCTACCCTGAACATGCCAGTTGGAAGGCTGCACCAGACTCAAAAGCAA
ACTAAACAATAAAGGACAGCTCTCTTCTCTCCTGGCTAAAGCTGCTCTCCTGGTTCAGAA
GACAGGCTGGATGAGATCTCAGGCCGAGCTCTGAAATAGGGAGGTAATCCTCCAGCACCT
GTGTTTCCTCTAACTTGCTGTGTGACCTCCAGCCGGTCACTCACCCTCTCTGGACCTCAT
CTGTAAGAGGAGCCAGCTGGATAAGATGATTTCTGAAGACGCTTCCATGGTGGGCACTGA -continued GGCACAGAGGAGGCCAAGGAGAGGTTGTTTGTTCATGCATGCATTCATCCGTGACACATG
AGTACCTACTGAGGACTCCATAAACAGAACGGGATACAGAGATAAACAATTTGGGTTCTG
TCCACGTTTGTCAAAAGGTGGTGCTGGCCCACCTCTGAAAGCAGAACACTTGCTCAACAA
CCTTGCTGTTGGCCCAAGTCTAACACATTCTTTATGACTGTGAGCATCTCAGAGTGAGAG
AAAAATGTAGAAAGTTTTTTAAATTCTAAACAGGATTTAGTGTCTTTAGTTATCTTGCTG
GATGGGAAAGGGATGTTGTCATTTCTGGCACAAATGAAAAGTAGGACGGAAAGCTCCTTT
CATTCAGTTTATCTTTCCAGGATATATGAAAAGGGACCAGCTGGAAGACTAGCCTCACTC
TGTCCTCGAAAGCCTGAGCTTTCATTCAACTCCCTATTTCCATGCAAAGACGCTGGGCAA
ACCACATGTTCTGTCTGAGCCTCAGTTTTCCTATCCATAAAATGAAGGTAGCCAGGCCTG
CCTCAAAGAGCATTCAGGAGGCTCTGAGAGGACATGAGAGTATTTTGCAAAGTGAGGGCA
AGGCCCAGTGTGGAGTGATATTGTTATTCCAAGATTCCACTGCAAAAGTGGCTGCTTTGG
ATGCCAGCCCAGGATGAGTAGTTCCTGTTCTCAGGGAGGTCATCCGCTGAGCATCCCTTC
TGCACAGATGTCTCTGATTCTTGTCCTTGCAGGTGGAGGACAGGGCCTGCTCCCCTAAGC
TGGGAAGCCTGGAATGACCTCTTGCACAAGCCTAAATTCCAGGAATCTTCCCCAAATCCC
AGATCCTCTGCAATCTACCTGCACCCCTGACCCACCCAGGAGTTGGACCGGGAGTTGGGA
AGCCTAGGTCTTAGTCCTACACTCCTTCTAATTTGCTGTGTAACCTTACCATTAATCTCT
CTGGGTCTCAGTTTTCTCATCTGTATTGGAGGTAGCAGTGCTAGCTCTGCCTTCAGGCAT
GCAATATGCCAGAACTACAGACAACAGCCCACAGGATGCAAAAGTGCTTTGCCATCTTAA
AAATGCCAGATCACTCAGAGCCTATGAATGTGGATATCAACACCAGGTCTCTAGCACCGC
TGGATGAAAGGAGAAGGCTAGAGGCTGAGGGAGGAAAGAGCAGTTAACAAACAAAGGCAG
TAGCTCATCACTTGGGTAGCAGGTACCCATTTTAGGACCCTACACTCAAATGTGCAAAAT
AAAATTTCTATCATTTTGCTATAAAAAAAAAAAAAAAAAAAAA >NM 004967
GAGTGAGTGAGAGGGCAGAGGAAATACTCAATCTGTGCCACTCACTGCCTTGAGCCTGCT
TCCTCACTCCAGGACTGCCAGAGGCTCACTCCCTTGAGCCTGCTTCCTCACTCCAGGACT
GCCAGAGGAAGCAATCACCAAAATGAAGACTGCTTTAATTTTGCTCAGCATTTTGGGAAT
GGCCTGTGCTTTCTCAATGAAAAATTTGCATCGAAGAGTCAAAATAGAGGATTCTGAAGA
AAATGGGGTCTTTAAGTACAGGCCACGATATTATCTTTACAAGCATGCCTACTTTTATCC
TCATTTAAAACGATTTCCAGTTCAGGGCAGTAGTGACTCATCCGAAGAAAATGGAGATGA
CAGTTCAGAAGAGGAGGAGGAAGAAGAGGAGACTTCAAATGAAGGAGAAAACAATGAAGA
ATCGAATGAAGATGAAGACTCTGAGGCTGAGAATACCACACTTTCTGCTACAACACTGGG
CTATGGAGAGGACGCCACGCCTGGCACAGGGTATACAGGGTTAGCTGCAATCCAGCTTCC
CAAGAAGGCTGGGGATATAACAAACAAAGCTACAAAAGAGAAGGAAAGTGATGAAGAAGA
AGAGGAGGAAGAGGAAGGAAATGAAAACGAAGAAAGCGAAGCAGAAGTGGATGAAAACGA
ACAAGGCATAAACGGCACCAGTACCAACAGCACAGAGGCAGAAAACGGCAACGGCAGCAG
CGGAGGAGACAATGGAGAAGAAGGGGAAGAAGAAAGTGTCACTGGAGCCAATGCAGAAGG
CACCACAGAGACCGGAGGGCAGGGCAAGGGCACCTCGAAGACAACAACCTCTCCAAATGG
TGGGTTTGAACCTACAACCCCACCACAAGTCTATAGAACCACTTCCCCACCTTTTGGGAA
AACCACCACCGTTGAATACGAGGGGGAGTACGAATACACGGGCGTCAATGAATACGACAA
TGGATATGAAATCTATGAAAGTGAGAACGGGGAACCTCGTGGGGACAATTACCGAGCCTA
TGAAGATGAGTACAGCTACTTTAAAGGACAAGGCTACGATGGCTATGATGGTCAGAATTA
CTACCACCACCAGTGAAGCTCCAGCCTG >NM_002847
GCCTCCCGCCGCCTCCCGCGCGGCCATGGACTGAGCGCCGCCGGCCAGGCCGCGGGGATG
GGGCCGCCGCTCCCGCTGCTGCTGCTGCTACTGCTGCTGCTGCCGCCACGCGTCCTGCCT
GCCGCCCCTTCGTCCGTCCCCCGCGGCCGGCAGCTCCCGGGGCGTCTGGGCTGCCTGCTC
GAGGAGGGCCTCTGCGGAGCGTCCGAGGCCTGTGTGAACGATGGAGTGTTTGGAAGGTGC
CAGAAGGTTCCGGCAATGGACTTTTACCGCTACGAGGTGTCGCCCGTGGCCCTGCAGCGC
CTGCGCGTGGCGTTGCAGAAGCTTTCCGGCACAGGTTTCACGTGGCAGGATGACTATACT
CAGTATGTGATGGACCAGGAACTTGCAGACCTCCCGAAAACCTACCTGAGGCGTCCTGAA
GCATCCAGCCCAGCCAGGCCCTCAAAACACAGCGTTGGCAGCGAGAGGAGGTACAGTCGG
GAGGGCGGTGCTGCCCTGGCCAACGCCCTCCGACGCCACCTGCCCTTCCTGGAGGCCCTG
TCCCAGGCCCCAGCCTCAGACGTGCTCGCCAGGACCCATACGGCGCAGGACAGACCCCCC
GCTGAGGGTGATGACCGCTTCTCCGAGAGCATCCTGACCTATGTGGCCCACACGTCTGCG
CTGACCTACCCTCCCGGGCCCCGGACCCAGCTCCGCGAGGACCTCCTGCCGCGGACCCTC
GGCCAGCTCCAGCCAGATGAGCTCAGCCCTAAGGTGGACAGTGGTGTGGACAGACACCAT
CTGATGGCGGCCCTCAGTGCCTATGCTGCCCAGAGGCCCCCAGCTCCCCCCGGGGAGGGC
AGCCTGGAGCCACAGTACCTTCTGCGTGCACCCTCAAGAATGCCCAGGCCTTTGCTGGCA
CCAGCCGCCCCCCAGAAGTGGCCTTCACCTCTGGGAGATTCCGAAGACCCCTCCAGCACA
GGCGATGGAGCACGGATTCATACCCTCCTGAAGGACCTGCAGAGGCAGCCGGCTGAGGTG
AGGGGCCTGAGTGGCCTGGAGCTGGACGGCATGGCTGAGCTGATGGCTGGCCTGATGCAA
GGCGTGGACCATGGAGTAGCTCGAGGCAGCCCTGGGAGAGCGGCCCTGGGAGAGTCTGGA
GAACAGGCGGATGGCCCCAAGGCCACCCTCCGTGGAGACAGCTTTCCAGATGACGGAGTG
CAGGACGACGATGATAGACTTTACCAAGAGGTCCATCGTCTGAGTGCCACACTCGGGGGC
CTCCTGCAGGACCACGGGTCTCGACTCTTACCTGGAGCCCTCCCCTTTGCAAGGCCCCTC
GACATGGAGAGGAAGAAGTCCGAGCACCCTGAGTCTTCCCTGTCTTCAGAAGAGGAGACT
GCCGGAGTGGAGAACGTCAAGAGCCAGACGTATTCCAAAGATCTGCTGGGGCAGCAGCCG
CATTCGGAGCCCGGGGCCGCTGCGTTTGGGGAGCTCCAAAACCAGATGCCTGGGCCCTCG
AAGGAGGAGCAGAGCCTTCCAGCGGGTGCTCAGGAGGCCCTCAGCGACGGCCTGCAATTG
GAGGTCCAGCCTTCCGAGGAAGAGGCGCGGGGCTACATCGTGACAGACAGAGACCCCCTG
CGCCCCGAGGAAGGAAGGCGGCTGGTGGAGGACGTCGCCCGCCTCCTGCAGGTGCCCAGC
AGTGCGTTCGCTGACGTGGAGGTTCTCGGACCAGCAGTGACCTTCAAAGTGAGCGCCAAT
GTCCAAAACGTGACCACTGAGGATGTGGAGAAGGCCACAGTTGACAACAAAGACAAACTG
GAGGAAACCTCTGGACTGAAAATTCTTCAAACCGGAGTCGGGTCGAAAAGCAAACTCAAG
TTCCTGCCTCCTCAGGCGGAGCAAGAAGACTCCACCAAGTTCATCGCGCTCACCCTGGTC
TCCCTCGCCTGCATCCTGGGCGTCCTCCTGGCCTCTGGCCTCATCTACTGCCTCCGCCAT
AGCTCTCAGCACAGGCTGAAGGAGAAGCTCTCGGGACTAGGGGGCGACCCAGGTGCAGAT
GCCACTGCCGCCTACCAGGAGCTGTGCCGCCAGCGTATGGCCACGCGGCCACCAGACCGA
CCTGAGGGCCCGCACACGTCACGCATCAGCAGCGTCTCATCCCAGTTCAGCGACGGGCCG -continued ATCCCCAGCCCCTCCGCACGCAGCAGCGCCTCATCCTGGTCCGAGGAGCCTGTGCAGTCC
AACATGGACATCTCCACCGGCCACATGATCCTGTCCTACATGGAGGACCACCTGAAGAAC
AAGAACCGGCTGGAGAAGGAGTGGGAAGCGCTGTGCGCCTACCAGGCGGAGCCCAACAGC
TCGTTCGTGGCCCAGAGGGAGGAGAACGTGCCCAAGAACCGCTCCCTGGCTGTGCTGACC
TATGACCACTCCCGGGTCCTGCTGAAGGCGGAGAACAGCCACAGCCACTCAGACTACATC
AACGCTAGCCCCATCATGGATCACGACCCGAGGAACCCCGCGTACATCGCCACCCAGGGA
CCGCTGCCCGCCACCGTGGCTGACTTTTGGCAGATGGTGTGGGAGAGCGGCTGCGTGGTG
ATCGTCATGCTGACACCCCTCGCGGAGAACGGCGTCCGGCAGTGCTACCACTACTGGCCG
GATGAAGGCTCCAATCTCTACCACATCTATGAGGTGAACCTGGTCTCCGAGCACATCTGG
TGTGAGGACTTCCTGGTGAGGAGCTTCTATCTGAAGAACCTGCAGACCAACGAGACGCGC
ACCGTGACGCAGTTCCACTTCCTGAGTTGGTATGACCGAGGAGTCCCTTCCTCCTCAAGG
TCCCTCCTGGACTTCCGCAGAAAAGTAAACAAGTGCTACAGGGGCCGTTCTTGTCCAATA
ATTGTTCATTGCAGTGACGGTGCAGGCCGGAGCGGCACCTACGTCCTGATCGACATGGTT
CTCAACAAGATGGCCAAAGGTGCTAAAGAGATTGATATCGCAGCGACCCTGGAGCACTTG
AGGGACCAGAGACCCGGCATGGTCCAGACGAAGGAGCAGTTTGAGTTCGCGCTGACAGCC
GTGGCTGAGGAGGTGAACGCCATCCTCAAGGCCCTTCCCCAGTGAGCGGCAGCCTCAGGG
GCCTCAGGGGAGCCCCCACCCCACGGATGTTGTCAGGAATCATGATCTGACTTTAATTGT
GTGTCTTCTATTATAACTGCATAGTAATAGGGCCCTTAGCTCTCCCGTAGTCAGCGCAGT
TTAGCAGTTAAAAGTGTATTTTTGTTTAATCAAACAATAATAAAGAGAGATTTGTGGAAA
AATCCAGTTACGGGTGGAGGGGAATCGGTTCATCAATTTTCACTTGCTTAAAAAAAATAC
TTTTTCTTAAAGCACCCGTTCACCTTCTTGGTTGAAGTTGTGTTAACAATGCAGTAGCCA
GCACGTTCGAGGCGGTTTCCAGGAAGAGTGTGCTTGTCATCTGCCACTTTCGGGAGGGTG
GATCCACTGTGCAGGAGTGGCCGGGGAAGCTGGCAGCACTCAGTGAGGCCGCCCGGCACA
CAAGGCACGTTTGGCATTTCTCTTTGAGAGAGTTTATCATTGGGAGAAGCCGCGGGGACA
GAACTGAACGTCCTGCAGCTTCGGGGCAAGTGAGACAATCACAGCTCCTCGCTGCGTCTC
CATCAACACTGCGCCGGGTACCATGGACGGCCCCGTCAGCCACACCTGTCAGCCCAAGCA
GAGTGATTCAGGGGCTCCCCGGGGGCAGACACCTGTGCACCCCATGAGTAGTGCCCACTT
GAGGCTGGCACTCCCCTGACCTCACCTTTGCAAAGTTACAGATGCACCCCAACATTGAGA
TGTGTTTTTAATGTTAAAATATTGATTTCTACGTTATGAAAACAGATGCCCCCGTGAATG
CTTACCTGTGAGATAACCACAACCAGGAAGAACAAATCTGGGCATTGAGCAAGCTATGAG
GGTCCCCGGGAGCACACGAACCCTGCCAGGCCCCCGCTGGCTCCTCCAGGCACGTCCCGG
ACCTGTGGGGCCCCAGAGAGGGGACATTTCCCTCCTGGGAGAGAAGGAGATCAGGGCAAC
TCGGAGAGGGCTGCGAGCATTTCCCTCCCGGGAGAGGAGATCAGGGCGACCTGCACGCAC
TGCGTAGAGCCTGGAAGGGAAGTGAGAAACCAGCCGACCGGCCCTGCCCCTCTTCCCGGG
ATCACTTAATGAACCACGTGTTTTGACATCATGTAAACCTAAGCACGTAGAGATGATTCG
GATTTGACAAAATAACATTTGAGTATCCGATTCGCCATCACCCCCTACCCCAGAAATAGG
ACAATTCACTTCATTGACCAGGATGATCACATGGAAGGCGGCGCAGAGGCAGCTGTGTGG
GCTGCAGATTTCCTGTGTGGGGTTCAGCGTAGAAAACGCACCTCCATCCCGCCCTTCCCA
CAGCATTCCTCCATCTTAGATAGATGGTACTCTCCAAAGGCCCTACCAGAGGGAACACGG
CCTACTGAGCGGACAGAATGATGCCAAAATATTGCTTATGTCTCTACATGGTATTGTAAT
GAATATCTGCTTTAATATAGCTATCATTTCTTTTCCAAAATTACTTCTCTCTATCTGGAA
TTTAATTAATCGAAATGAATTTATCTGAATATAGGAAGCATATGCCTACTTGTAATTTCT
AACTCCTTATGTTTGAAGAGAAACCTCCGGTGTGAGATATACAAATATATTTAATTGTGT
CATATTAAACTTCTGATTCAAAAAAAA >BC002551
GGCACGAGGCCACGAGCTGTTGTGCATCCAGAGGTGGAATTGGGGCCCGGCATTCCCTCC
TCGTCCCGGGCTGGCCCTTGCCCCCACCCTGCAACTCCTGGTTGAGATGGGCTCAGCCAA
GAGCGTCCCAGTCACACCAGCGCGGCCTCCGCCGCACAACAAGCATCTGGCTCGAGTGGC
GGACCCCCGTTCACCTAGTGCTGGCATCCTGCGCACTCCCATCCAGGTGGAGAGCTCTCC
ACAGCCAGGCCTACCAGCAGGGGAGCAACTGGAGGGTCTTAAACATGCCCAGGACTCAGA
TCCCCGCTCTCCTACTCTTGGTATTGCACGGACACCTATGAAGACCAGCAGTGGAGACCC
CCCAAGCCCACTGGTGAAACAGCTGAGTGAAGTATTTGAAACTGAAGACTCTAAATCAAA
TCTTCCCCCAGAGCCTGTTCTGCCCCCAGAGGCACCTTTATCTTCTGAATTGGACTTGCC
TCTGGGTACCCAGTTATCTGTTGAGGAACAGATGCCACCTTGGAACCAGACTGAGTTCCC
CTCCAAACAGGTGTTTTCCAAGGAGGAAGCAAGACAGCCCACAGAAACCCCTGTGGCCAG
CCAGAGCTCCGACAAGCCCTCAAGGGACCCTGAGACTCCCAGATCTTCAGGTTCTATGCG
CAATAGATGGAAACCAAACAGCAGCAAGGTACTAGGGAGATCCCCCCTCACCATCCTGCA
GGATGACAACTCCCCTGGCACCCTGACACTACGACAGGGTAAGCGGCCTTCACCCCTAAG
TGAAAATGTTAGTGAACTAAAGGAAGGAGCCATTCTTGGAACTGGACGACTTCTGAAAAC
TGGAGGACGAGCATGGGAGCAAGGCCAGGACCA’nACAAGGAAAATCAGCACTTTCCCTT
GGTGGAGAGCTAGGCCCTGCATGGCCCCAGCAATGCAGTCACCCAGGGCCTGGTGATATC
TGTGTCCTCTCACCCCTTCTTTCCCAGGGATACTGAGGAATGGCTTGTTTTCTTAGACTC
CTCCTCAGCTACCAAACTGGGACTCACAGCTTTATTGGGCTTTCTTTGTGTCTTGTGTGT
TTCTTTTATATTAAAGGAAGTAATTTTAAATGTTACTTTAAAAAGGTAAAAAAAAAAAAA
AAAAAAAA >AL039118
GCATTCGTAGTAAAGGTGCCCAAGAAATTATTTTGGCCATTTATTGTTTTGTCCTTTTCT
TTAAAGAACTGTTTTTTTTTCTTTTGTTTACTTTTAGACCAAAGATTGGGTTCTAGAAAA
TGCACTTGGTATACTAAGTATTAAAACAAACAAAAAGGAAAGTTGTTTCAGTTGGCAACA
CTGCCCATTCAATTGAATCAGAAGGGGACAAAATTAACGATTGCCTTCAGTTTGTGTTGT
GTATATTTTGATGTATGTGGTCACTAACAGGTCACTTTTATTTTTTCTAAATGTAGTGAA
ATGTTAATACCTATTGTACTTATAGGTAAACCTTGCAAATATGTAACCTGTGTTGCGCAA
ATGCCGCATAAATTTGAGTGATTGTTAATGTTGTCTTAAAATTTCTTGATTGTGATACTG
TGGTCATATGCCCGTGTTTGTCACTTACAAAAATGTTTACTATGAACACACAGAAATAAA
AATAGGCTAAATTCATATAAAAAAAAAAAAAAAAAAAAAAAAAAAAAAAAAAAAAAAA >NM_000198
GAGGCAGTAAGGACTTGGACTCCTCTGTCCAGCTTTTAACAATCTAAGTTACGGTTACCC
TCTTCTGGGTCACGCTAGAATCAGATCTGCTCTCCAGCATCTTCTGTTTCCTGGCAAGTG -continued TTTCCTGCTACTTTGGATTGGCCACGATGGGCTGGAGCTGCCTTGTGACAGGAGCAGGAG
GGCTTCTGGGTCAGAGGATCGTCCGCCTGTTGGTGGAAGAGAAGGAACTGAAGGAGATCA
GGGCCTTGGACAAGGCCTTCAGACCAGAATTGAGAGAGGAATTTTCTAAGCTCCAGAACA
GGACCAAGCTGACTGTACTTGAAGGAGACATTCTGGATGAGCCATTCCTGAAAAGAGCCT
GCCAGGACGTCTCGGTCGTCATCCACACCGCCTGTATCATTGATGTCTTTGGTGTCACTC
ACAGAGAGTCCATCATGAATGTCAATGTGAAAGGTACCCAGCTACTGTTGGAGGCCTGTG
TCCAAGCCAGTGTGCCAGTCTTCATCTACACCAGTAGCATAGAGGTAGCCGGGCCCAACT
CCTACAAGGAAATCATCCAGAACGGCCACGAAGAAGAGCCTCTGGAAAACACATGGCCCA
CTCCATACCCGTACAGCAAAAAGCTTGCTGAGAAGGCTGTGCTGGCGGCTAATGGGTGGA
ATCTAAAAAATGGTGATACCTTGTACACTTGTGCGTTAAGACCCACATATATCTATGGGG
AAGGAGGCCCATTCCTTTCTGCCAGTATAAATGAGGCCCTGAACAACAATGGGATCCTGT
CAAGTGTTGGAAAGTTCTCTACAGTCAACCCAGTCTATGTTGGCAACGTGGCCTGGGCCC
ACATTCTGGCCTTGAGGGCTCTGCGGGACCCCAAGAAGGCCCCAAGTGTCCGAGGTCAAT
TCTATTACATCTCAGATGACACGCCTCACCAAAGCTATGATAACCTTAATTACATCCTGA
GCAAAGAGTTTGGCCTCCGCCTTGATTCCAGATGGAGCCTTCCTTTAACCCTGATGTACT
GGATTGGCTTCCTGCTGGAAGTAGTGAGCTTCCTACTCAGCCCAATTTACTCCTATCAAC
CCCCCTTCAACCGCCACACAGTCACATTATCAAATAGTGTGTTCACCTTCTCTTACAAGA
AGGCTCAGCGAGATCTGGCGTATAAGCCACTCTACAGCTGGGAGGAAGCCAAGCAGAAAA
CCGTGGAGTGGGTTGGTTCCCTTGTGGACCGGCACAAGGAGACCCTGAAGTCCAAGACTC
AGTGATTTAAGGATGACAGAGATGTGCATGTGGGTATTGTTAGGAAATGTCATCAAACTC
CACCCACCTGGCTTCATACAGAAGGCAACAGGGGCACAAGCCCAGGTCCTGCTGCCTCTC
TTTCACACAATGCCCAACTTACTGTCTTCTTCATGTCATCAAAATCTGCACAGTCACTGG
CCCAACCAGAACTTTCTGTCCTAATCATACACCAGAAGACAAACAATATGATTTGCTGTT
ACCAAATCTCAGTGGCTGATTCTGAACAATTGTGGTCTCTCTTAACTTGAGGTTCTCTTT
TGACTAATAGAGCTCCATTTCCCCTCTTAAATGAGAAAGCATTTCTTTTCTCTTTAATCT
CCTATTCCTTCACACAGTTCAACATAAAGAGCAATAAATGTTTTAATGCTTAA >H05388
AAATTTTGACCCCATATAAAGAAATGTGTTATGTATGTTGTGCCTCCTTAGAGACATAAA
TTTAGTGTCAAAACATGGGAGATGGCTTACTCAGAAGCATACTCCACTTAACATACCATG
GCCTGAGCTAAGTACCATGTCCTGTTTGTGTCTTATTTTTAAATATTTTCTTTGTCCACA
TGGGCCGTTGACCTTAGAGTTAAGGCGGTTGCTTTTTTGAAGAAATCACCAAAGTTTCTG
GGAAACTATGTTCAAGGTTGAAATGGAGAGTAGATTTAATTTTATTTGTCTTGTAGGGAA
GAAATCTTCCTTTGAACCGCTTTTCTTGCTTTTTCCCTTTTTCCCAAACTAGGTTACAGG
TTCTTATCTGCAAGGTTCAAGTTGCTTAGACATTGTTTTCCAGTATTCTGCAGGGCCAGT
CAGTTGTACAGAAGTTGGAATATTCTGTTCCAGAATTAAAGAAGTTTTTAGATTATGAAA
TATTATGATAATAAAGCTATATTTCTGAAAAAAAAAAA >NN_004062
GAAGGAGCTCTCTTCTTGCTTGGCAGCTGGACCAAGGGAGCCAGTCTTGGGCGCTGGAGG
GCCTGTCCTGACCATGGTCCCTGCCTGGCTGTGGCTGCTTTGTGTCTCCGTCCCCCAGGC
TCTCCCCAAGGCCCAGCCTGCAGAGCTGTCTGTGGAAGTTCCAGAAAACTATGGTGGAAA
TTTCCCTTTATACCTGACCAAGTTGCCGCTGCCCCGTGAGGGGGCTGAAGGCCAGATCGT
GCTGTCAGGGGACTCAGGCAAGGCAACTGAGGGCCCATTTGCTATGGATCCAGATTCTGG
CTTCCTGCTGGTGACCAGGGCCCTGGACCGAGAGGAGCAGGCAGAGTACCAGCTACAGGT
CACCCTGGAGATGCAGGATGGACATGTCTTGTGGGGTCCACAGCCTGTGCTTGTGCACGT
GAAGGATGAGAATGACCAGGTGCCCCATTTCTCTCAAGCCATCTACAGAGCTCGGCTGAG
CCGGGGTACCAGGCCTGGCATCCCCTTCCTCTTCCTTGAGGCTTCAGACCGGGATGAGCC
AGGCACAGCCAACTCGGATCTTCGATTCCACATCCTGAGCCAGGCTCCAGCCCAGCCTTC
CCCAGACATGTTCCAGCTGGAGCCTCGGCTGGGGGCTCTGGCCCTCAGCCCCAAGGGGAG
CACCAGCCTTGACCACGCCCTGGAGAGGACCTACCAGCTGTTGGTACAGGTCAAGGACAT
GGGTGACCAGGCCTCAGGCCACCAGGCCACTGCCACCGTGGAAGTCTCCATCATAGAGAG
CACCTGGGTGTCCCTAGAGCCTATCCACCTGGCAGAGAATCTCAAAGTCCTATACCCGCA
CCACATGGCCCAGGTACACTGGAGTGGGGGTGATGTGCACTATCACCTGGAGAGCCATCC
CCCGGGACCCTTTGAAGTGAATGCAGAGGGAAACCTCTACGTGACCAGAGAGCTGGACAG
AGAAGCCCAGGCTGAGTACCTGCTCCAGGTGCGGGCTCAGAATTCCCATGGCGAGGACTA
TGCGGCCCCTCTGGAGCTGCACGTGCTGGTGATGGATGAGAATGACAACGTGCCTATCTG
CCCTCCCCGTGACCCCACAGTCAGCATCCCTGAGCTCAGTCCACCAGGTACTGAAGTGAC
TAGACTGTCAGCAGAGGATGCAGATGCCCCCGGCTCCCCCAATTCCCACGTTGTGTATCA
GCTCCTGAGCCCTGAGCCTGAGGATGGGGTAGAGGGGAGAGCCTTCCAGGTGGACCCCAC
TTCAGGCAGTGTGACGCTGGGGGTGCTCCCACTCCGAGCAGGCCAGAACATCCTGCTTCT
GGTGCTGGCCATGGACCTGGCAGGCGCAGAGGGTGGCTTCAGCAGCACGTGTGAAGTCGA
AGTCGCAGTCACAGATATCAATGATCACGCCCCTGAGTTCATCACTTCCCAGATTGGGCC
TATAAGCCTCCCTGAGGATGTGGAGCCCGGGACTCTGGTGGCCATGCTAACAGCCATTGA
TGCTGACCTCGAGCCCGCCTTCCGCCTCATGGATTTTGCCATTGAGAGGGGAGACACAGA
AGGGACTTTTGGCCTGGATTGGGAGCCAGACTCTGGGCATGTTAGACTCAGACTCTGCAA
GAACCTCAGTTATGAGGCAGCTCCAAGTCATGAGGTGGTGGTGGTGGTGCAGAGTGTGGC
GAAGCTGGTGGGGCCAGGCCCAGGCCCTGGAGCCACCGCCACGGTGACTGTGCTAGTGGA
GAGAGTGATGCCACCCCCCAAGTTGGACCAGGAGAGCTACGAGGCCAGTGTCCCCATCAG
TGCCCCAGCCGGCTCTTTCCTGCTGACCATCCAGCCCTCCGACCCCATCAGCCGAACCCT
CAGGTTCTCCCTAGTCAATGACTCAGAGGGCTGGCTCTGCATTGAGAAATTCTCCGGGGA
GGTGCACACCGCCCAGTCCCTGCAGGGCGCCCAGCCTGGGGACACCTACACGGTGCTTGT
GGAGGCCCAGGATACAGATGAGCCGAGACTGAGCGCTTCTGCACCCCTGGTGATCCACTT
CCTAAAGGCCCCTCCTGCCCCAGCCCTGACTCTTGCCCCTGTGCCCTCCCAATACCTCTG
CACACCCCGCCAAGACCATGGCTTGATCGTGAGTGGACCCAGCAAGGACCCCGATCTGGC
CAGTGGGCACGGTCCCTACAGCTTCACCCTTGGTCCCAACCCCACGGTGCAACGGGATTG
GCGCCTCCAGACTCTCAATGGTTCCCATGCCTACCTCACCTTGGCCCTGCATTGGGTGGA
GCCACGTGAACACATAATCCCCGTGGTGGTCAGCCACAATGCCCAGATGTGGCAGCTCCT
GGTTCGAGTGATCGTGTGTCGCTGCAACGTGGAGGGGCAGTGCATGCGCAAGGTGGGCCG
CATGAAGGGCATGCCCACGAAGCTGTCGGCAGTGGGCATCCTTGTAGGCACCCTGGTAGC
AATAGGAATCTTCCTCATCCTCATTTTCACCCACTGGACCATGTCAAGGAAGAAGGACCC -continued GGATCAACCAGCAGACAGCGTGCCCCTGAAGGCGACTGTCTGAATGGCCCAGGCAGCTCT
AGCTGGGAGCTTGGCCTCTGGCTCCATCTGAGTCCCCTGGGAGAGAGCCCAGCACCCAAG
ATCCAGCAGGGGACAGGACAGAGTAGAAGCCCCTCCATCTGCCCTGGGGTGGAGGCACCA
TCACCATCACCAGGCATGTCTGCAGAGCCTGGACACCAACTTTATGGACTGCCCATGGGA
GTGCTCCAAATGTCAGGGTGTTTGCCCAATAATAAAGCCCCAGAGAACTGGGCTGGGCCC
TATGGGATTGGTA >AA782845
TCTTTACCTATGTGAAGCGAGGTGACGTGATACGTCACTGGCGCCGTCTTATAATTTAGA
TGTAAAAATCTTTAGAAACAAATAAAACTCTCTATATATGTGTATGTCTGTGTACAAAAA
AATGACAGAGCTGATGGCCAGTGTATACAGAGCGTGGCCCGCGGTGTACAATACCCATAT
AAGGTACATTGTGCAGGAGGGGAATTGCTGGCTGCTTTTACTTCCTGACCAAGACTGAAA
AATTATTTACTGAAATCTGTAAACCTTTTTATGAAACTTTTAAGCACCAGGCTGTTTACT
TACACAATTTAGGTCTGCCAGAAAATTCTATCTGTGATAGATCTGTAAAGAGGGTCAGGG
GTTAGAGTTTACTATTTTTGAAGTTTACATTGTTACATATGAAATGGAAACATTATTTTG
AAACGTTGTCATAACCCAATGGTGCATTCTGTAACCATGGAGTCTTCTGTTTCCTGGGGG
AAAGGGGCATTCATGACCTGAACTTTTTAGCAAATTATTATTCTCAGTTTCCATTACCTG
TTTGGCCAAACAGATTAATAAAATATTTGAAAAAGAAGCAATAAAAAAAAAA >AI457360
CTGAGAAAGTCCGGTCCCTATAAGGGGACATCAGTGCGAGACCTGCTCCGTGCTGTGAGN
ACAAGAGGCACCATACAAGNAAGCTCCCAGTTGAGGTGCGACAGGCACTCGCCNAAGTCC
NTGATGGCTTCGTCCAGTACTCACAAAACGGCTCCCCCCGGCTGGTCCTTCACACGCACC
GAGCCATGAGGAGCTGGCGCCTCTGAGAGCCTCTTCCTGCCCTACTACCCGCCAGACTCA
GAGGCCAGGAGGCCATGCCCTGGGGCCACAGGGAGGTGAGGTGGGCTGGATGCCACACAG
ATGGTCTCCGTGCTGGCTCACTGAAGAGCTGAGCCTGTGGCTGGCCTCAGAATCAGGCTG
GGTGCAGTGGCTCACACCTGTAATCCCAGCATTTTGGGAGGCTGAGTGAGAGGATCACTT
GAGCTCAGGAGTTCGAGACCAGCCTGGCCAACATGGCAACACCCCATTTCTACAAAAAAT
TTGTAAAATTAGCCAGGCATGGTGGCGCACGCCTGTAGTCCCAGCTGCTTGGGAGGCTGA
GGTGGGAGAATCACTTGAGCCCAGGAGTTCGAGGCTGCAGTGAGCCAGGATCATGCCACT
GCACTCCAGCCTGGTCCACAGAGAGACACTGTCACCCCCTTTCCCCCACAAGACTGGCAG
AGGCTGGGCAGCCTGGGGCTGATGAAGCAGAGATGTTCGCTGGATCCCAGGCCCTGGCAC
CCCTCAGGAAATACAAGAAAAAGAATATTCACATCTGTTTAATGTGCATAAAGCCAAGGA
AAGGACAGTTCCGAATTC >BF446419
TTTTTTTTTTTTTTTTTAAATATTTAACTTATTTATTTAACAAAGTAGAAGGGAATCCAT
TGCTAGCTTTTCTGTGTTGGTGTCTAATATTTGGGTAGGGTGGGGGATCCCCAACAATCA
GGTCCCCTGAGATAGCTGGTCATTGGGCTGATCATTGCCAGAATCTTCTTCTCCTGGGGT
CTGGCCCCCCAAAATGCCTAACCCAGGACCTTGGGAATTCTACTCATCCCAAATGATAAT
TCCAAATGCTGTTACCCAAGGTTAGGGTGTTGAAGGAAGGTAGAGGGTGGGGCTTCAGGT
CTCAACGGCTTCCCTAACCACCCCTCTTCTCTTGGCCCAGCCTGGTTCCCCCCACTTCCA
CTCCCCTCTACTCTCTCTAGGACTGGGCTGATGAAGGCACTGCCCAAAATTTCCCCTACC
CCCAACTTTCCCCTACCCCCAACTTTCCCCACCAGCTCCACAACCCTGTTTGGAGCTACT
GCAGGACCAGAAGCACAAAGTGCGGTTTCCCAAGCCTTTGTCCATCTCAGCCCCCAGAGT
ATATCTGTGCTTGGGGAATCTCACACAGAAACTCAGGAGCACCCCCTGCCTGAGCTAAGG
GAGGTCTTATCTCTCAGGGGGGGTTTAAGTGCCGTTTGCAATAATGTCGTCTTATTTATT
TAGCGGGGTGAATATTTTATACTGTAAGTGAGCAATCAGAGTATAATGTTTATGGTGACA
AAATTAAAGGCTTTCTTATATGTTTAAAAAAA >BC006819
GCCTTATAAAGCACCAAGAGGCTGCCAGTGGGACATTTTCTCGGCCCTGCCAGCCCCCAG
GAGGAAGGTGGGTCTGAATCTAGCACCATGACGGAACTAGAGACAGCCATGGGCATGATC
ATAGACGTCTTTTCCCGATATTCGGGCAGCGAGGGCAGCACGCAGACCCTGACCAAGGGG
GAGCTCAAGGTGCTGATGGAGAAGGAGCTACCAGGCTTCCTGCAGAGTGGAAAAGACAAG
GATGCCGTGGATAAATTGCTCAAGGACCTGGACGCCAATGGAGATGCCCAGGTGGACTTC
AGTGAGTTCATCGTGTTCGTGGCTGCAATCACGTCTGCCTGTCACAAGTACTTTGAGAAG
GCAGGACTCAAATGATGCCCTGGAGATGTCACAGATTCCTGGCAGAGCCATGGTCCCAGG
CTTCCCAAAAGTGTTTGTGGCAATTATTCCCCTAGGCTGAGCCTGCTCATGTACCTCTGA
TTAATAAATGCTTATGAAATGAAAAAAAAAAAAAA >AA765597
CCAGCAAAGTCTCTTTTGACCACACGCTTTATCCGAGATGCTTAGAAGTATATTTGGCTG
TTTTATTTGCATCTTTGATTAAGATGTCTATCATTGTAAAAAGGTATTCAAAACAAAAGT
GTACTCTTTTATTATTATGAATCACATTGTACTGAGCTGTGAAGTCAGTGTTTTAAAAAT
GTAGAGTTTATTCATGGAGCATGCCATTGAGGTTTGGATGGTGGCAGGTAAAACAGAAAG
GCAAGATGTCATCTGACATTAGGCTACTTATAAATAAATGTTTATCTAGCTTTTATTTCA
TGCCCTAATGAATAAAACATGCTTCGAAAAAGAAAGTAAAAAAAAAAAACAAAA >X78202
GGCGAGAGAGACGCTCCCGCTCGCCGCCAGCTCTGATTGGCCCAGCGGTAGGAAAGGTTA
AACCAAAAATTTTTTTACAGCCCTAGTGTGCGCCTGTAGCTCGGAAAATTAATTGTGGCT
ATAGCCGCCTCGATCGCTGTCTCCCCAGCCTCGCCGCGGACGCTCCGGGACGCGCCCGCC
CGCCGCCCGGTTCTCCCCCCCTTTGGGCTGGTGCTGCTGCTGCTGTGACTGCTGCTGCGA
AAGGAGGAGGAGGAGGAGGAAGCAGCGGGGGGGGGAGCGGTGGGTGTGGGGAAACCAAG
AGTACAGTGGACGAGGACTCACCCCGGCGTGGTGTTCTTTTTTCTTCTTCTTTTTCTTTC
CTTTTTTTTTTTTTTTTCTAATTCCTGAGGGGTGGTTGCTGCTTTTGCTACATGACTTGC
CAGCGCCCGAGCCTGCGGTCCAACTGCGCTGCTGCCGGAGCGCTCAGTGCCGCCGCTGCC
GCCCGTGCCCCCCGCGCCCCGTTCGGCACCCACCGGTCGCCGCCCCGCCCGCGCGCCGCT
GTCCCGCTCCCGCGCCGCCGCCGCCGTTTCCCCCCGACGACTGGGTGATGCTGGACATGG
GAGATAGGAAAGAGGTGAAAATGATCCCCAAGTCCTCGTTCAGCATCAACAGCCTGGTGC -continued CCGAGGGCCTCCAGAACGACAACCACCACGCGAGCCACGGCCACCACAACAGCCACCACC
CCCAGCACCACCACCACCACCACCACCATCACCACCACCCGCCGCCGCCCGCCCCGCAAC
CGCCGCCGCCGCCGCAGCAGCAGCAGCCGCCGCCGCCGCCGAGACGCGGGGCCCGGCGCC
GACGACGACGAGGCCCCAGCAGTTGTTGTTCCGCCGCGCACGCACACGGCGCGCCTGAGG
GCCAACGGCAGCTGGCGCAAGGCGACCGGCGCGGCCGGGGGATCTGCCCCGTCGGGCCGG
ACGAGAAGGAGAAGGCCCGCGCCGGGGGGGAGGAGAAGAAGGGGGCGGGCGAGGGCGGCA
AGGACGGGGAGGGGGGCAAGGAGGGCGAGAAGAAGAACGGCAAGTACGAGAAGCCGCCGT
TCAGCTACAACGCGCTCATCATGATGGCCATGCGGCAGAGCCCCGAGAAGCGGCTCACGC
TCAACGGCATCTACGAGTTCATCATGAAGAACTTCCCTTACTACCGCGAGAACAAGCAGG
GCTGGCAGAACTCCATCCGCCACAATCTGTCCCTCAACAAGTGCTTCGTGAAGGTGCCGC
GCCACTACGACGACCCGGGCAAGGGCAACTACTGGATGCTGGACCCGTCGAGCGACGACG
TGTTCATCGGCGGCACCACGGGCAAGCTGCGGCGCTCCACCACCTCGCCGGCCAAGCCGG
CCTTCAAGCGCGGTGCCGCGCTCACCTCCACCGGCCTCACCTTCATGGACGCGCCGGCTC
CCTCTACTGGCCCATGTCGCCCTTCCTGTCCCTGCACCACCCCCGCCAGCAGCACTTTGA
GTTACAACGGGACCACGTCGGCCTACCCCAGCCACCCCATGCCCTACAGCTCCGTGTTGA
CTCAAAACTCGCTGGGCAACAACCACTCCTCCTCCACCGCCAACGGGCTGAGCGTGGACC
GGCTGGTCAACGGGGGAATCCCGTACGCCACGCACCACCTCACGGCCGCCGCGCTAACCG
CCTCGGTGCCCTGCGGCCTGCTGGTGCCCTGCTCTGGGACCTACTCCCTCAACCCCTGCT
CCGTCAACCTGCTCGCGGGCCAGACCAGTTACTTTTTCCCCCACGTCCCGCACCCGTCAA
TGACTTCGCAGAGCAGCACGTCCATGAGCGCCAGGGCCGCGTCCTCCTCCACGTCGCCGG
CAGGCCCCCCTCGACCCCTGCCCTGTGAGTCTTTAAGACCCTCTTTGCCAAGTTTTACGA
CGGGACTGTCTGGGGGACTGTCTGATTATTTCACACATCAAAATCAGGGGTCTTCTTCCA
ACCCTTTAATACATTAACATCCCTGGGACCAGACTGTAAGTGAACGTTTTACACACATTT
GCATTGTAAATGATAATTAAAAAAATAAGTCCAGGTATTTTTTATTAAGCCCCCCCCCTCC
CATTTCTGTACGTTTGTTCAGTCTCTAGGGTTGTTTATTATTCTAACAAGGTGTGGAGTG
TCAGCGAGGTGCAATGTGGGGAGAATACATTGTAGAATATAAGGTTTGGAAGTCAAATTA
TAGTAGAATGTGTATCTAAATAGTGACTGCTTTGCCATTTCATTCAAACCTGACAAGTCT
ATCTCTAAGAGCCGCCAGATTTCCATGTGTGCAGTATTATAAGTTATCATGGAACTATAT
GGTGGACGCAGACCTTGAGAACAACCTAAATTATGGGGAGAATTTTAAAATGTTAAACTG
TAATTTGTATTTAAAAAGCATTCGTAGTAAAGGTGCCCAAGAAATTATTTTGGCCATTTA
TTGTTTTCTCCTTTTCTTTAAAGAACTGTTTTTTTTTCTTTTGTTTACTTTTAGACCAAA
GATTGGGCGGTTCTAGAAAATGCGCCTTGGTATACTAAGTATTAAAACAAACAAAAAGGA
AAGTTGTTTCAGTTAACGCTGCCCATTCAATTGAATCAGAAGGGGACAAAATTAACGATT
GCCTTCAGTTTGTGTTGTGTATATTTTGATGTATGTGGTCACTAACAGGTCACTTTTATT
TTTTCTAAATGTAGTGAAATGTTAATACCTATTGTACTTATAGGTAAACCTTGCAAATAT
GTAACCTGTGTTGCGCAAATGCCGCATAAATTTGAGTGATTGTTAATGTTGTCTTAAAAT
TTCTTGATTGTGACTATGTGGTCATATGCCCGTGTTTGTCACTTACAAAAATGTTTACTA
TGAACACACATAAATAAAAAATAG >AK026790
AAAATGCTTACTCTTGTGGGCTACTTGTTGTGTGGAAAAAGGAAAACGGATTCATTTTCC
CATCGGCGACTTTATGACGACAGAAATGAACCAGTTCTGCGATTAGACAATGCACCGGAA
CCTTATGATGTGAGTTTTGGGAATTCTAGCTACTACAATCCAACTTTGAATGATTCAGCC
ATGCCAGAAAGTGAAGAAAATGCACGTGATGGCATTCCTATGGATGACATACCTCCACTT
CGTACTTCTGTATAGAACTAACAGCAAAAAGGCGTTAAACAGCAAGTGTCATCTACATCC
TAGCCTTTTGACAAATTCATCTTTCAAAAGGTTACACAAAATTACTGTCACGTTGGATTT
TGTCAAGGAGAATCATAAAAGCAGGAGACCAGTAGCAGAAATGTAGACAGGATGTATCAT
CCAAAGGTTTTCTTTCTTACAATTTTTGGCCATCCTGAGGCATTTACTAAGTAGCCTTAA
TTTGTATTTTAGTAGTATTTTCTTAGTAGAAAATATTTGTGGAATCAGATAAAACTAAAA
GATTTCACCATTACAGCCCTGCCTCATAACTAAATAATAAAAATTATTCCACCAAAAAAT
TCTAAAACAATGAAGATGACTCTTTACTGCTCTGCCTGAAGCCCTAGTACCATAATTCAA
GATTGCATTTTCTTAAATGAAAATTGAAAGGGTGCTTTTTAAAGAAAATTTGACTTAAAG
CTAAAAAGAGGACATAGCCCAGAGTTTCTGTTATTGGGAAATTGAGGCAATAGAAATGAC
AGACCTGTATTCTAGTACGTTATAATTTTCTAGATCAGCACACACATGATCAGCCCACTG
AGTTATGAAGCTGACAATGACTGCATTCAACGGGGCCATGGCAGGAAAGCTGACCCTACC
CAGGAAAGTAATAGCTTCTTTAAAAGTCTTCAAAGGTTTTGGGAATTTTAACTTGTCTTA
ATATATCTTAGGCTTCAATTATTTGGGTGCCTTAAAAACTCAATGAGAATCATGGTAAAA
AAAAAAAGTTAACCAAAGAATATACCTGTACATAATTTGTACAGTTTTAAGTTGTTAGAT
AGGAACTGGATTTCTTATGTATTAGACATTATTGCTCAATCATAATGGAATAGATTCTGC
ATCCCTAAATGTATGAACCATAAGGTTAAAAAGATGAATGGAAATATCAAACAACTTTT
CACTGAGCATCAGTTTCATAATCAATAATATAAGAAGATTAATTTGGATTCTAGTATGTT
TCAGTTTGTTTTTAATTACCACCTTCCTTTGGTAGAAAAAATATGTTCCTTGATGTAGGA
AAGTCTAGGTTTTAGAGATTAGAGGATGAGATCAAGAGTTAAATTCCTAAAGAAGCACTG
AATATATGAAGAGAGCAAACAAATCAAGTACCAACCTAGAGGCTTTATTTTTGAATTGAT
TCATGGTGTGTGTGTGTGTGTGTGTGTGTGTGTGTGTGTGTGTGTAACACAGAAACAGCT
TTCAGAAAATAAGGGATAGAAAGTAATGAAGAAAGTACTTACCCCATATTGCCATAAAAA
TAGCAAAGAAGACTGTCCCTCCATTATCGAACAAATATGTCACCTGAGTAGAAAACAAAC
AGAAATATTAGTCATGCAAATTGATTATATAATAAGCCAGTGAATACTGTTTGCACTCAGGT
ACTATGATTTTTTCTCAAATAGAATCATATTATTTTTATAGTACAGAAATATTATATATGA
ATTCCTTTCATGGGTCTTGCAACAATTTCACATGATTTTTCTCATGGGGAGAGGTGAAGA
AACAACATTAGCCCTCTTCTCTCCTCTCTTGATTCCCTTTATACCCCACCATCATTTCTG
ATTATAAATAATTCTACCATTCTATGGAAGTATTTGTGGGTCACAGATTGTCAAACTACT
TAATGAAAGTTGTATGAAATTAGTTTTTCAGGTGAGGCATTCCTAGTTGCAATTCCTGTT
AGCAAAACTTCTAGGAGTGGGGAAGTTGGAAAATGCAGGATTCTTCCAGTGAGCCAGCAT
TTCCCATAGCTAACCCTATTCTCTTAGTCTTTCAAAATGTAGAATGGGTCCAATAATGGC
TATAAGATGTAATAAATCCCATCTTAATTTGTTTTAAAAGTTTCATAAATCACTGAACAC
TTATGAAACAAAGTGTTTTTAATCAGATATCAACTGAAACTTCATAAAGGATGCATAGT
TTTATAATGTTATTGAATCAAATTTTAAGGCTTCTATTGTTTGATTTTAATAAAGTATAA
TCTCCTTTTTAAAAAAAAAAAAAAAAAAAAAAAAAAAAAAAAAAAAA -continued

```
>BC012727
GGCACGAGGCTGCCTGCCCCCCGGGTGGGGCTGCGGCTCTGGCCTCCCAGGCCCATCCTC
AACAGCTACCCCAGCCAACACCAAGGCCACAAGGGGACCCCGGCCTAGGAGGCAGGAAGC
CAAGGTACAGAGAGCAGCCTGGCCCTCACCAGTGCGCAAGCTGGGGCAGCAAGGCTGACA
GTTGCTGCATGCCCAGGGCAGGGTGTGGTACTGGCACCCAAGTTCAGCATGGCAGAGCTG
GCCAACAGCTTGTCCCCGATCTGCCTCCAGCCCCAAGATGCCTACAGCCCCCAGGCCCCT
TCGGCAGCACTGCCTCTGCCCACCTGCCTTTAAGAGACTCCAGGGCTGCTCCTGTCATGC
AGCGAAGGTTTTGTCTGTTTCAAAGTTCGAGACTCAACTTGAGGGACTGTTTTTGACAAT
CCCCGCTGACCTCCGCTCCTCGTGGCGCCCTGGCCCTACACCCAGCCTGGCCCAGGGCCG
GCTTTGCCTGGTGAGGCTGGAGGGAGCACCAGGACCTGCTGTCTGCTGTCAGCCCCTCCT
GGTGCTGGTGCCCTGATGCTGTGCCTTGTCACCCATTGAGCTGCAAGAGGGACCAAGAGG
GGGCCACGCAGCCAGCCAGATGCCTGGCCCTGTGCTGGGGCAGACAACGCTGCAGAGCCC
AGGGAGCCTGGCGCTAGGACGTGCGTCCTTGTGACACTGGCCTGTCTGAACTCACCTGGC
CTGGGAAGCACCGTCTGCCCGGGCCCAAGCCCTGCCCCTCCAGAGTCCAGAGCCAGGAAG
GGGCTGCTGAGGGCGAGCATCCTGCTGGGCTCTCTGCCCGGCCCACCCCTCCAAGGGGCT
GGCCTGTGAGCCTTGACTGGGATTCATGATGTGGAGGCCCCCAACTTCCAGAAGCAGCTG
GTACTCTGCTCACACAAGCGACTGGGCCGGCCGGCCCTGGACCCCTAGACCCCGAGCCGC
CTGCCGACTGCCTGCACAGGGAGAGCAGTTGAGGCCCGGGCAGGGCCCCCACACCAGACC
CCAACATAGCTTCCCCACCCAGGCACCCCCTCCCGGGGCAGCAGGCGTGGGAGTCAGGGC
TGCATGCTCCTCCCCTCCCACCTCACAGGCGGCCTTAGGCAAGTCATTTTCTGTCATCAC
AAGGTCGCCTCTGCCTAGTCAGGTCCTGGCGTCCAGAGTAAGGATGTGCGGCCCCCAGGC
CCCCGCACACCTCCCTCAGCACCAAGACCGGGACCCCCCCACCCACGTGTCTCATTGTGG
CTGCCTATGGACTCCCGGGCCTTGTGTGCAGGCCAGGCCCTTCCACTGATTTTTTAAAGT
GAACCATTGCTGGATCTCAGATTCTGTGGCATCTAAGGCCTAGCAGGGGTGGGCACACGG
GTCACCCGAGGCCCATACCAAGACTCTGTTCCTGCCCTAGGCCCAGTCTCAAAGGAAGCC
ACAAGGCGCGGGGGCCACTGAGGAAGGAAATGTTCATTTTCATTTGTCCAAAACCACCTT
AAGTTTTAAGTATATTAATCTTGATGCTTTTTAACTATTGCTTTTTAACTTGCTGAGATT
TAGAAATACTGTTATAAAAACTTTTTTAATTTCTGTATTTTTTTTCTGTATTGTATCTTC
ATGGGACATTAGGGGTTTTCTATGGTAAGCACACCTATGGTTTTGGTAAAAACATTATCA
AATATATATCCAGACGGTTCTTCCCTAGAAGAAAAACAAGTCTTTACACCTGATAAAATA
TTTTGCGAAGAGAGGTGTTCTTTTTCCTTACTGGTGCTGAAAGGAAGGATGGATAACGAG
GAGAAAATAAAACTGTGAGGCTCAAAAAAAAAAAAAAAAAA

>R45389
CCTGCCCTTCTCTATATGTACCATCTCCAAAAACCATGTACATCTCCAAAAACTGGAGTA
GAAAGTTAGATTGCTCAACTACAACTCCTCTAGAACTCTATAGCTCTGACATACAGATTC
ACACTCTCCTCTATTTGCTAAGTATGTAAAGAATGTTTTCTTTTAAAATGTTCTCTTTTG
AGAACAACTGCTTATTTGTTATAAAAGCATTTGGTTAAAATGATGTCATCATAAAGAACA
GTGGCTTTGTTTCAATACATATTTTTGAGATGATTATCTAGAAGCCAGATTAATAAAATC
AGCTTGTGACCTTGCTAAGCATATAAACTGGAAATTCAGATACATTCAAAATTATGGGTT
CATTTAAAAGTGTTCTACCTTTTGGGTATGAGACTAATATCACTAATTCCTCAATAGTTA
TCATGGCTCTATCTTAATTAATTAGAAAATATGTGTGTTTAATTCTTTGAGAATTAAAAT
AGAGAATATTAACAGAGGGTTAAAAACTGCTTCAACTCCAATAAGATAAAGGAAGCTCAA
AATCTATGAGCTGAGTGTTCAATTAGCTTTGCCTACTGAGTTCAATTTTATGTCAATACA
ACAGTGGATCAGACAGTACGACTTTGAACTGGTGAATGTAAACAATTGTTTTTCACCTAA
GCTGCTTTGGAAGAACTGATGCTTGCTGCTAACTAAAGTTTTGGATGTATCGATTTAGAG
AACCAATTAATACCTGCAAAATAAAGCATACTGTGGTACTTCTGTTTGATCTAGTATGTG
TGATTTTAGATTGATGGATTAAAAATTAATAAAGATCATACATTCCATACCAAAAAAAAA
AAAAAAAA

>BC006811
CCAGAAGCCTGCATTTCTGCATTCTGCTTAATTCCCTTTCCTTAGATTTGAAAGAAGCCA
ACACTAAACCACAAATATACAACAAGGCCATTTTCTCAAACGAGAGTCAGCCTTTAACGA
AATGACCATGGTTGACACAGAGATGCCATTCTGGCCCACCAACTTTGGGATCAGCTCCGT
GGATCTCTCCGTAATGGAAGACCACTCCCACTCCTTTGATATCAAGCCCTTCACTACTGT
TGACTTCTCCAGCATTTCTACTCCACATTACGAAGACATTCCATTCACAAGAACAGATCC
AGTGGTTGCAGATTACAAGTATGACCTGAAACTTCAAGAGTACCAAAGTGCAATCAAAGT
GGAGCCTGCATCTCCACCTTATTATTCTGAGAAGACTCAGCTCTACAATAAGCCTCATGA
AGAGCCTTCCAACTCCCTCATGGCAATTGAATGTCGTGTCTGTGGAGATAAAGCTTCTGG
ATTTCACTATGGAGTTCATGCTTGTGAAGGATGCAAGGGTTTCTTCCGGAGAACAATCAG
ATTGAAGCTTATCTATGACAGATGTGATCTTAACTGTCGGATCCACAAAAAAAGTAGAAA
TAAATGTCAGTACTGTCGGTTTCAGAAATGCCTTGCAGTGGGGATGTCTCATAATGCCAT
CAGGTTTGGGCGGATGCCACAGGCCGAGAAGGAGAAGCTGTTGGCGGAGATCTCCAGTGA
TATCGACCAGCTGAATCCAGAGTCCGCTGACCTCCGGGCCCTGGCAAAACATTTGTATGA
CTCATACATAAAGTCCTTCCCGCTGACCAAAGCAAAGGCGAGGGCGATCTTGACAGGAAA
GACAACAGACAAATCACCATTCGTTATCTATGACATGAATTCCTTAATGATGGGAGAAGA
TAAAATCAAGTTCAAACACATCACCCCCCTGCAGGAGCAGAGCAAAGAGGTGGCCATCCG
CATCTTTCAGGGCTGCCAGTTTCGCTCCGTGGAGGCTGTGCAGGAGATCACAGAGTATGC
CAAAAGCATTCCTGGTTTTGTAAATCTTGACTTGAACGACCAAGTAACTCTCCTCAAATA
TGGAGTCCACGAGATCATTTACACAATGCTGGCCTCCTTGATGAATAAAGATGGGGTTCT
CATATCCGAGGGCCAAGGCTTCATGACAAGGGAGTTTCTAAAGAGCCTGCGAAAGCCTTT
TGGTGACTTTATGGAGCCCAAGTTTGAGTTTGCTGTGAAGTTCAATGCACTGGAATTAGA
TGACAGCGACTTGGCAATATTTATTGCTGTCATTATTCTCAGTGGAGACCGCCCAGGTTT
GCTGAATGTGAAGCCCATTGAAGACATTCAAGACAACCTGCTACAAGCCCTGGAGCTCCA
GCTGAAGCTGAACCACCCTGAGTCCTCACAGCTGTTTGCCAAGCTGCTCCAGAAAATGAC
AGACCTCAGACAGATTGTCACGGAACACGTGCAGCTACTGCAGGTGATCAAGAAGACGGA
GACAGACATGAGTCTTCACCCGCTCCTGCAGGAGATCTACAAGGACTTGTACTAGCAGAG
AGTCCTGAGCCACTGCCAACATTTCCCTTCTTCCAGTTGCACTATTCTGAGGGAAAATCT
```

-continued

GACACCTAAGAAATTTACTGTGAAAAAGCATTTTAAAAAGAAAAGGTTTTAGAATATGAT
CTATTTTATGCATATTGTTTATAAAGACACATTTACAATTTACTTTTAATATTAAAAATT
ACCATATTATGAAAAAAAAAAAAAAAA

>X05615
GCAGTGGTTTCTCCTCCTTCCTCCCAGGAAGGGCCAGGAAAATGGCCCTGGTCCTGGAGA
TCTTCACCCTGCTGGCCTCCATCTGCTGGGTGTCGGCCAATATCTTCGAGTACCAGGTTG
ATGCCCAGCCCCTTCGTCCCTGTGAGCTGCAGAGGGAAACGGCCTTTCTGAAGCAAGCAG
ACTACGTGCCCCAGTGTGCAGAGGATGGCAGCTTCCAGACTGTCCAGTGCCAGAACGACG
GCCGCTCCTGCTGGTGTGTGGGTGCCAACGGCAGTGAAGTGCTGGGCAGCAGGCAGCCAG
GACGGCCTGTGGCTTGTCTGTCATTTTGTCAGCTACAGAAACAGCAGATCTTACTGAGTG
GCTACATTAACAGCACAGACACCTCCTACCTCCCTCAGTGTCAGGATTCAGGGGACTACG
CGCCTGTTCAGTGTGATGTGCAGCATGTCCAGTGCTGGTGTGTGGACGCAGAGGGGATGG
AGGTGTATGGGACCCGCCAGCTGGGGAGGCCAAAGCGATGTCCAAGGAGCTGTGAAATAA
GAAATCGTCGTCTTCTCCACGGGGTGGGAGATAAGTCACCACCCCAGTGTTCTGCGGAGG
GAGAGTTTATGCCTGTCCAGTGCAAATTTGTCAACACCACAGACATGATGATTTTTGATC
TGGTCCACAGCTACAACAGGTTTCCAGATGCATTTGTGACCTTCAGTTCCTTCCAGAGGA
GGTTCCCTGAGGTATCTGGGTATTGCCACTGTGCTGACAGCCAAGGGCGGGAACTGGCTG
AGACAGGTTTGGAGTTGTTACTGGATGAAATTTATGACACCATTTTTGCTGGCCTGGACC
TTCCTTCCACCTTCACTGAAACCACCCTGTACCGGATACTGCAGAGACGGTTCCTCGCAG
TTCAATCAGTCATCTCTGGCAGATTCCGATGCCCCACAAAATGTGAAGTGGAGCGGTTTA
CAGCAACCAGCTTTGGTCACCCCTATGTTCCAAGCTGCCGCCGAAATGGCGACTATCAGG
CGGTGCAGTGCCAGACGGAAGGGCCCTGCTGGTGTGTGGACGCCCAGGGGAAGGAAATGC
ATGGAACCCGGCAGCAAGGGGAGCCGCCATCTTGTGCTGAAGGCCAATCTTGTGCCTCCG
AAAGGCAGCAGGCCTTGTCCAGACTCTACTTTGGGACCTCAGGCTACTTCAGCCAGCACG
ACCTGTTCTCTTCCCCAGAGAAAAGATGGGCCTCTCCAAGAGTAGCCAGATTTGCCACAT
CCTGCCCACCCACGATCAAGGAGCTCTTTGTGGACTCTGGGCTTCTCCGCCCAATGGTGG
AGGGACAGAGCCAACAGTTTTCTGTCTCAGAAAATCTTCTCAAAGAAGCCATCCGAGCAA
TTTTTCCCTCCCGAGGGCTGGCTCGTCTTGCCCTTCAGTTTACCACCAACCCAAAGAGAC
TCCAGCAAAACCTTTTTGGAGGGAAATTTTTGGTGAATGTTGGCCAGTTTAACTTGTCTG
3AGCCCTTGGCACAAGAGGCACATTTAACTTCAGTCAATTTTTCCAGCAACTTGGTCTTG
CAAGCTTCTTGAATGGAGGGAGACAAGAAGATTTGGCCAAGCCACTCTCTGTGGGATTAG
ATTCAAATTCTTCCACAGGAACCCCTGAAGCTGCTAAGAAGGATGGTACTATGAATAAGC
CAACTGTGGGCAGCTTTGGCTTTGAAATTAACCTACAAGAGAACCAAAATGCCCTCAAAT
TCCTTGCTTCTCTCCTGGAGCTTCCAGAATTCCTTCTCTTCTTGCAACATGCTATCTCTG
TGCCAGAAGATGTGGCAAGAGATTTAGGTGATGTGATGGAAACGGTACTCGACTCCCAGA
CCTGTGAGCAGACACCTGAAAGGCTATTTGTCCCATCATGCACGACAGAAGGAAGCTATG
GGGATGTCCAATGCTTTTCCGGAGAGTGCTGGTGTGTGAATTCCTGGGGCAAAGAGCTTC
CAGGCTCAAGAGTCAGAGATGGACAGCCAAGGTGCCCCACAGACTGTGAAAAGCAAAGGG
CTCGCATGCAAAGCCTCATGGGCAGCCAGCCTGCTGGCTCCACCTTGTTTGTCCCTGCTT
3TACTAGTGAGGGACATTTCCTGCCTGTCCAGTGCTTCAACTCAGAGTGCTACTGTGTTG
ATGCTGAGGGTCAGGCCATTCCTGGAACTCGAAGTGCAATAGGGAAGCCCAAGAAATGCC
CCACGCCCTGTCAATTACAGTCTGAGCAAGCTTTCCTCAGGACGGTGCAGGCCCTGCTCT
CTAACTCCAGCATGCTACCCACCCTTTCCGACACCTACATCCCACAGTGCAGCACCGATG
GGCAGTGGAGACAAGTGCAATGCAATGGGCCTCCTGAGCAGGTCTTCGAGTTGTACCAAC
GATGGGAGGCTCAGAACAAGGGCCAGGATCTGACGCCTGCCAAGCTGCTAGTGAAGATCA
TGAGCTACAGAGAAGCAGCTTCCGGAAACTTCAGTCTCTTTATTCAAAGTCTGTATGAGG
CTGGCCAGCAAGATGTCTTCCCGGTGCTGTCACAATACCCTTCTCTGCAAGATGTCCCAC
TAGCAGCACTGGAAGGGAAACGGCCCCAGCCCAGGGAGAATATCCTCCTGGAGCCCTACC
TCTTCTGGCAGATCTTAAATGGCCAACTCAGCCAATACCCGGGGTCCTACTCAGACTTCA
GCACTCCTTTGGCACATTTTGATCTTCGGAACTGCTGGTGTGTGGATGAGGCTGGCCAAG
AACTGGAAGGAATGCGGTCTGAGCCAAGCAAGCTCCCAACGTGTCCTGGCTCCTGTGAGG
AAGCAAAGCTCCGTGTACTGCAGTTCATTAGGGAAACGGAAGAGATTGTTTCAGCTTCCA
ACAGTTCTCGGTTCCCTCTGGGGGAGAGTTTCCTGGTGGCCAAGGGAATCCGGCTGAGGA
ATGAGGACCTCGGCCTTCCTCCGCTCTTCCCGCCCCGGGAGGCTTTCGCGGAGTTTCTGC
GTGGGAGTGATTACGCCATTCGCCTGGCGGCTCAGTCTACCTTAAGCTTCTATCAGAGAC
GCCGCTTTTCCCCGGACGACTCGGCTGGAGCATCCGCCCTTCTGCGGTCGGGCCCCTACA
TGCCACAGTGTGATGCGTTTGGAAGTTGGGAGCCTGTGCAGTGCCACGCTGGGACTGGGC
ACTGCTGGTGTGTAGATGAGAAAGGAGGGTTCATCCCTGGCTCACTGACTGCCCGCTCTC
TGCAGATTCCACAGTGCCCGACAACCTGCGAGAAATCTCGAACCAGTGGGCTGCTTTCCA
GTTGGAAACAGGCTAGATCCCAAGAAAACCCATCTCCAAAAGACCTGTTCGTCCCAGCCT
GCCTAGAAACAGGAGAATATGCCAGGCTGCAGGCATCGGGGGCTGGCACCTGGTGTGTGG
ACCCTGCATCAGGAGAAGAGTTGCGGCCTGGCTCGAGCAGCAGTGCCCAGTGCCCAAGCC
TCTGCAATGTGCTCAAGAGTGGAGTCCTCTCTAGGAGAGTCAGCCCAGGCTATGTCCCAG
CCTGCAGGGCAGAGGATGGGGGCTTTTCCCCAGTGCAATGTGACCAGGCCCAGGGCAGCT
GCTGGTGTGTCATGGACAGCGGAGAAGAGGTGCCTGGGACGCGCGTGACCGGGGGCCAGC
CCGCCTGTGAGAGCCCGCGGTGTCCGCTGCCATTCAACGCGTCGGAGGTGGTTGGTGGAA
CAATCCTGTGTGAGACAATCTCGGGCCCCACAGGCTCTGCCATGCAGCAGTGCCAATTGC
TGTGCCGCCAAGGCTCCTGGAGCGTGTTTCCACCAGGGCCATTGATATGTAGCCTGGAGA
GCGGACGCTGGGAGTCACAGCTGCCTCAGCCCCGGGCCTGCCAACGGCCCCAGCTGTGGC
AGACCATCCAGACCCAAGGGCACTTTCAGCTCCAGCTCCCGCCGGGCAAGATGTGCAGTG
CTGACTACGCGGGTTTGCTGCAGACTTTCCAGGTTTTCATATTGGATGAGCTGACAGCCC
GCGGCTTCTGCCAGATCCAGGTGAAGACTTTTGGCACCCTGGTTTCCATTCCTGTCTGCA
ACAACTCCTCTGTGCAGGTGGGTTGTCTGACCAGGGAGCGTTTAGGAGTGAATGTTACAT
GGAAATCACGGCTTGAGGACATCCCAGTGGCTTCTCTTCCTGACTTACATGACATTGAGA
GAGCCTTGGTGGGCAAGGATCTCCTTGGGCGCTTCACAGATCTGATCCAGAGTGGCTCAT
TCCAGCTTCATCTGGACTCCAAGACGTTCCCAGCGGAAACCATCCGCTTCCTCCAAGGGG
ACCACTTTGGCACCTCTCCTAGGACACGGTTTGGGTGCTCGGAAGGATTCTACCAAGTCT
TGACAAGTGAGGCCAGTCAGGACGGACTGGGATGCGTTAAGTGCCATGAAGGAAGCTATT
CCCAAGATGAGGAATGCATTCCTTGTCCTGTTGGATTCTACCAAGAACAGGCAGGGAGCT
TGGCCTGTGTCCCATGTCCTGTGGGCAGAACGACCATTTCTGCCGGAGCTTTCAGCCAGA

-continued

CTCACTGTGTCACTGACTGTCAGAGGAACGAAGCAGGCCTGCAATGTGACCAGAATGGCC
AGTATCGAGCCAGCCAGAAGGACAGGGGCAGTGGGAAGGCCTTCTGTGTGGACGGCGAGG
GGCGGAGGCTGCCATGGTGGGAAACAGAGGCCCCTCTTGAGGACTCACAGTGTTTGATGA
TGCAGAAGTTTGAGAAGGTTCCAGAATCAAAGGTGATCTTCGACGCCAATGCTCCTGTGG
CTGTCAGATCCAAAGTTCCTGATTCTGAGTTCCCCGTGATGCAGTGCTTGACAGATTGCA
CAGAGGACGAGGCCTGCAGCTTCTTCACCGTGTCCACGACGGAGCCAGAGATTTCCTGTG
ATTTCTATGCTTGGACAAGTGACAATGTTGCCTGCATGACTTCTGACCAGAAACGAGATG
CACTGGGGAACTCAAAGGCCACCAGCTTTGGAAGTCTTCGCTGCCAGGTGAAAGTGAGGA
GCCATGGTCAAGATTCTCCAGCTGTGTATTTGAAAAAGGGCCAAGGATCCACCACAACAC
TTCAGAAACGCTTTGAACCCACTGGTTTCCAAAACATGCTTTCTGGATTGTACAACCCCA
TTGTGTTCTCAGCCTCAGGAGCCAATCTAACCGATGCTCACCTCTTCTGTCTTCTTGCAT
GCGACCGTGATCTGTGTTGCGATGGCTTCGTCCTCACACAGGTTCAAGGAGGTGCCATCA
TCTGTGGGTTGCTGAGCTCACCCAGTGTCCTGCTTTGTAATGTCAAAGACTGGATGGATC
CCTCTGAAGCCTGGGCTAATGCTACATGTCCTGGTGTGACATATGACCAGGAGAGCCACC
AGGTGATATTGCGTCTTGGAGACCAGGAGTTCATCAAGAGTCTGACACCCTTAGAAGGAA
CTCAAGACACCTTTACCAATTTTCAGCAGGTTTATCTCTGGAAAGATTCTGACATGGGGT
CTCGGCCTGAGTCTATGGGATGTAGAAAAAACACAGTGCCAAGGCCAGCATCTCCAACAG
AAGCAGGTTTGACAACAGAACTTTTCTCCCCTGTGGACCTCAACCAGGTCATTGTCAATG
GAAATCAATCACTATCCAGCCAGAAGCACTGGCTTTTCAAGCACCTGTTTTCAGCCCAGC
AGGCAAACCTATGGTGCCTTTCTCGTTGTGTGCAGGAGCACTCTTTCTGTCAGCTCGCAG
AGATAACAGAGAGTGCATCCTTGTACTTCACCTGCACCCTCTACCCAGAGGCACAGGTGT
GTGATGACATCATGGAGTCCAATACCCAGGGCTGCAGACTGATCCTGCCTCAGATGCCAA
AGGCCCTGTTCCGGAAGAAAGTTATACTGGAAGATAAAGTGAAGAACTTTTACACTCGCC
TGCCGTTCCAAAAACTGATGGGGATATCCATTAGAAATAAAGTGCCCATGTCTGAAAAAT
CTATTTCTAATGGGTTCTTTGAATGTGAACGACGGTGCGATGCGGACCCATGCTGCACTG
GCTTTGGATTTCTAAATGTTTCCCAGTTAAAAGGAGGAGAGGTGACATGTCTCACTCTGA
ACAGCTTGGGAATTCAGATGTGCAGTGAGGAGAATGGAGGAGCCTGGCGCATTTTGGACT
GTGGCTCTCCTGACATTGAAGTCCACACCTATCCCTTCGGATGGTACCAGAAGCCCATTG
CTCAAAATAATGCTCCCAGTTTTTGCCCTTTGGTTGTTCTGCCTTCCCTCACAGAGAAAG
TGTCTCTGGAATCGTGGCAGTCCCTGGCCCTCTCTTCAGTGGTTGTTGATCCATCCATTA
GGCACTTTGATGTTGCCCATGTCAGCACTGCTGCCACCAGCAATTTCTCTGCTGTCCGAG
ACCTCTGTTTGTCGGAATGTTCCCAACATGAGGCCTGTCTCATCACCACTCTGCAAACCC
AACTCGGGGCTGTGAGATGTATGTTCTATGCTGATACTCAAAGCTGCACACATAGTCTGC
AGGGTCGGAACTGCCGACTTCTGCTTCGTGAAGAGGCCACCCACATCTACCGGAAGCCAG
GAATCTCTCTGCTCAGCTATGAGGCATCTGTACCTTCTGTGCCCATTTCCACCCATGGCC
GGCTGCTGGGCAGGTCCCAGGCCATCCAGGTGGGTACCTCATGGAAGCAAGTGGACCAGT
TCCTTGGAGTTCCATATGCTGCCCCGCCCCTGGCAGAGAGGCACTTCCAGGCACCAGAGC
CCTTGAACTGGACAGGCTCCTGGGATGCCAGCAAGCCAAGGGCCAGCTGCTGGCAGCCAG
GCACCAGAACATCCACGTCTCCTGGAGTCAGTGAAGATTGTTTGTATCTCAATGTGTTCA
TCCCTCAGAATGTGGCCCCTAACGCGTCTGTGCTGGTGTTCTTCCACAACACCATGGACA
GGGAGGAGAGTGAAGGATGGCCGGCTATCGACGGCTCCTTCTTGGCTGCTGTTGGCAACC
TCATCGTGGTCACTGCCAGCTACCGAGTGGGTGTCTTCGGCTTCCTGAGTTCTGGATCCG
GAGAGGTGAGTGGCAACTGGGGGCTGCTGGACCAGGTGGCGGCTCTGACCTGGGTGCAGA
CCCACATCCGAGGATTTGGCGGGGACCCTCGGCGCGTGTCCCTGGCAGCAGACCGTGGCG
GGGCTGATGTGGCCAGCATCCACCTTCTCACGGCCAGGGCCACCAACTCCCAACTTTTCC
GGAGAGCTGTGCTGATGGGAGGCTCCGCACTCTCCCCGGCCGCCCGTCATCAGCCATGAGA
GGGCTCAGCAGCAGGCAATTGCTTTGGCAAAGGAGGTCAGTTGCCCCATGTCATCCAGCC
AAGAAGTGGTGTCCTGCCTCCGCCAGAAGCCTGCCAATGTCCTCAATGATGCCCAGACCA
AGCTCCTGGCCGTGAGTGGCCCTTTCCACTACTGGGGTCCTGTGATCGATGGCCACTTCC
TCCGTGAGCCTCCAGCCAGAGCACTGAAGAGGTCTTTATGGGTAGAGGTCGATCTGCTCA
TTGGGAGTTCTCAGGACGACGGGCTCATCAACAGAGCAAAGGCTGTGAAGCAATTTGAGG
AAAGTCGAGGCCGGACCAGTAGCAAAACAGCCTTTTACCAGGCACTGCAGAATTCTCTGG
GTGGCGAGGACTCAGATGCCCGCGTCGAGGCTGCTGCTACATGGTATTACTCTCTGGAGC
ACTCCACGGATGACTATGCCTCCTTCTCCCGGGCTCTGGAGAATGCCACCCGGGACTACT
TTATCATCTGCCCTATAATCGACATGGCCAGTGCCTGGGCAAAGAGGGCCCGAGGAAACG
TCTTCATGTACCATGCTCCTGAAAACTACGGCCATGGCAGCCTGGAGCTGCTGGCGGATG
TTCAGTTTGCCTTGGGGCTTCCCTTCTACCCAGCCTACGAGGGGCAGTTTTCTCTGGAGG
AGAAGAGCCTGTCGCTGAAAATCATGCAGTACTTTTCCCACTTCATCAGATCAGGAAATC
CCAACTACCCTTATGAGTTCTCACGGAAAGTACCCACATTTGCAACCCCCTGGCCTGACT
TTGTACCCCGTGCTGGTGGAGAGAACTACAAGGAGTTCAGTGAGCTGCTCCCCAATCGAC
AGGGCCTGAAGAAAGCCGACTGCTCCTTCTGGTCCAAGTACATCTCGTCTCTGAAGACAT
CTGCAGATGGAGCCAAGGGCGGGCAGTCAGCAGAGAGTGAAGAGGAGGAGTTGACGGCTG
GATCTGGGCTAAGAGAAGATCTCCTAAGCCTCCAGGAACCAGGCTCTAAGACCTACAGCA
AGTGACCAGCCCTTGAGCTCCCCAAAAACCTCACCCGAGGCTGCCCACTATGGTCATCTT
TTTCTCTAAAATAGTTACTTACCTTCAATAAAC4TATCTACATGCGGTG

>X79676
AGATCTCTCCAGATCACACTGTCACGTGTACCTAGCACATCTCGAGAACTCCTTTGGGCC
GTCTGGGGCCCGGGAAGGAAGCCTGAGTTCTCAAGATTCCAGGACTGAGAGTGCCAGCTT
GTCTCAAAGCCAGGTCAATGGTTTCTTTGCCAGCCATTTAGGTGACCAAACCTGGCAGGA
ATCACAGCATGGCAGCCCTTCCCCATCTGTAATATCCAAAGCCACCGAGAAAGAGACTTT
CACTGATAGTAACCAAAGCAAAACTAAAAAGCCAGGCATTTCTGATGTAACTGATTACTC
AGACCGTGGAGATTCAGACATGGATGAAGCCACTTACTCCAGCAGTCAGGATCATCAAAC
ACCAAAACAGGAATCTTCCTCTTCAGTGAATACATCCAACAAGATGAATTTTAAAACTTT
TCCTTCATCACCTCCTAGGTCTGGAGATATCTTTGAGGTTGAACTGGCTAAAAATGATAA
CAGCTTGGGGATAAGTGTCACGGGAGGTGTGAATACGAGTGTCAGACATGGTGGCATTTA
TGTGAAAGCTGTTATTCCCCAGGGAGCAGCAGAGTCTGATGGTAGAATTCACAAAGGTGA
TCGCGTCCTAGCTGTCAATGGAGTTAGTCTAGAAGGAGCCACCCATAAGCAAGCTGTGGA
AACACTGAGAAATACAGGACAGGTGGTTCATCTGTTATTAGAAAAGGGACAATCTCCAAC
ATCTAAAGAACATGTCCCGGTAACCCCACAGTGTACCCTTTCAGATCAGAATGCCCAAGG
TCAAGGCCCAGAAAAAGTGAAGAAAACAACTCAGGTCAAAGACTACAGCTTTGTCACTGA

-continued

AGAAAATACATTTGAGGTAAAATTATTTAAAAATAGCTCAGGTCTAGGATTCAGTTTTTC
TCGAGAAGATAATCTTATACCGGAGCAAATTAATGCCAGCATAGTAAGGGTTAAAAAGCT
CTTTCCTGGACAGCCAGCAGCAGAAAGTGGAAAAATTGATGTAGGAGATGTTATCTTGAA
AGTGAATGGAGCCTCTTTGAAAGGACTATCTCAGCAGGAAGTCATATCTGCTCTCAGGGG
AACTGCTCCAGAAGTATTCTTGCTTCTCTGCAGACCTCCACCTGGTGTGCTACCGGAAAT
TGATACTGCGCTTTTGACCCCACTTCAGTCTCCAGCACAAGTACTTCCAAACAGCAGTAA
AGACTCTTCTCAGCCATCATGTGTGGAGCAAAGCACCAGCTCAGATGAAAATGAAATGTC
AGACAAAAGCAAAAAACAGTGCAAGTCCCCATCCAGAAAAGACAGTTACAGTGACAGCAG
TGGGAGTGGAGAAGATGACTTAGTGACAGCTCCAGCAAACATATCAAATTCGACCTGGAG
TTCAGCTTTGCATCAGACTCTAAGCAACATGGTATCACAGGCACAGAGTCATCATGAAGC
ACCAAGAGTCAAGAAGATACCATTTGTACCATGTTTTACTATCCTCAGGAAAAGGCCCAA
TAAACCAGAGTTTGAGGACAGTAATCCTTCCCCTCTACCACCGGATATGGCTCCTGGGCA
GAGTTATCAACCCCAATCAGAATCTGCTTCCTCTAGTTCGATGGATAAGTATCATATACA
TCACATTTCTGAACCAACTAGACAAGAAAACTGGACACCTTTGAAAAATGACTTGGAAAA
TCACCTTGAAGACTTTGAACTGGAAGTAGAACTCCTCATTACCCTAATTAAATCAGAAAA
AGGAAGCCTGGGTTTTACAGTAACCAAAGGCAATCAGAGAATTGGTTGTTATGTTCATGA
TGTCATACAGGATCCAGCCAAAAGTGATGGAAGGCTAAAACCTGGGGACCGGCTCATAAA
GGTTAATGATACAGATGTTACTAATATGACTCATACAGATGCAGTTAATCTGCTCCGGGG
ATCCAAAACAGTCAGATTAGTTATTGGACGAGTTCTAGAATTACCCAGAATACCAATGTT
GCCTCATTTGCTACCGGACATAACACTAACGTGCAACAAAGAGGAGTTGGGTTTTTCCTT
ATGTGGAGGTCATGACAGCCTTTATCAAGTGGTATATATTAGTGATATTAATCCAAGGTC
CGTCGCAGCCATTGAGGGTAATCTCCAGCTATTAGATGTCATCCATTATGTGAACGGAGT
CAGCACACAAGGAATGACCTTGGAGGAAGTTAACAGAGCATTAGACATGTCACTTCCTTC
ATTGGTATTGAAAGCAACAAGAAATGATCTTCCAGTGGTCCCCAGCTCAAAGAGGTCTGC
TGTTTCAGCTCCAAAGTCAACCAAAGGCAATGGTTCCTACAGTGTGGGGTCTTGCAGCCA
GCCTGCCCTCACTCCTAATGATTCATTCTCCACGGTTGCTGGGGAAGAAATAAATGAAAT
ATCGTACCCCAAAGGAAAATGTTCTACTTATCAGATAAAGGGATCACCAAACTTGACTCT
GCCCAAAGAATCTTATATACAAGAAGATGACATTTATGATGATTCCCAAGAAGCTGAAGT
TATCCAGTCTCTGCTGGATGTTGTGGATGAGGAGTCCCAGAATCTTTTAAACGAAAATAA
TGCAGCAGGATACTCCTGTGGTCCAGGTACATTAAAGATGAATGGGAAGTTATCAGAAGA
GAGAACAGAAGATACAGACTGCGATGGTTCACCTTTACCTGAGTATTTTACTGAGGCCAC
CAAAATGAATGGCTGTGAAGAATATTGTGAAGAAAAAGTAAAAAGTGAAAGCTTAATTCA
GAAGCCACAAGAAAAGAAGACTGATGATGATGAAATAACATGGGGAAATGATGAGTTGCC
AATAGAGAGAACAAACCATGAAGATTCTGATAAAGATCATTCCTTTCTGACAAACGATGA
GCTCGCTGTACTCCCTGTCGTCAAAGTGCTTCCCTCTGGTAAATACACGGGCGCCAACTT
AAAATCAGTCATTCGAGTCCTGCGGGTTGCTAGATCAGGAATTCCTTCTAAGGAGCTGGA
GAATCTTCAAGAATTAAAACCTTTGGATCAGTGTCTAATTGGGCAAACTAAGGAAAACAG
AAGGAAGAACAGATATAAAAATATACTTCCCTATGATGCTACAAGAGTGCCTCTTGGAGA
TGAAGGTGGCTATATCAATGCCAGCTTCATTAAGATACCAGTTGGGAAAGAAGAGTTCGT
TTACATTGCCTGCCAAGGACCACTGCCTACAACTGTTGGAGACTTCTGGCAGATGATTTG
GGAGCAAAAATCCACAGTGATAGCCATGATGACTCAAGAAGTAGAAGGAGAAAAAATCAA
ATGCCAGCGCTATTGGCCCAACATCCTAGGCAAAACAACAATGGTCAGCAACAGACTTCG
ACTGGCTCTTGTGAGAATGCAGCAGCTGAAGGGCTTTGTGGTGAGGGCAATGACCCTTGA
AGATATTCAGACCAGAGAGGTGCGCCATATTTCTCATCTGAATTTCACTGCCTGGCCAGA
CCATGATACACCTTCTCAACCAGATGATCTGCTTACTTTTATCTCCTACATGAGACACAT
CCACAGATCAGGCCCAATCATTACGCACTGCAGTGCTGGCATTGGACGTTCAGGGACCCT
GATTTGCATAGATGTGGTTCTGGGATTAATCAGTCAGGATCTTGATTTTGACATCTCTGA
TTTGGTGCGCTGCATGAGACTACAAAGACACGGAATGGTTCAGACAGAGGATCAATATAT
TTTCTGCTATCAAGTCATCCTTTATGTCCTGACACGTCTTCAAGCAGAAGAAGAGCAAAA
ACAGCAGCCTCAGCTTCTGAAGTGACATGAAAAGAGCCTCTGGATGCATTTCCATTTCTC
TCCTTAACCTCCAGCAGACTCCTGCTCTCTATCCAAAATAAAGATCACAGAGCAGCAAGT
TCATACAACATGCATGTTCTCCTCTATCTTAGAGGGGTATTCTTCTTGAAAATAAAAAAT
ATTGAAATGCTGTATTTTTACAGCTACTTTAACCTATGATAATTATTTACAAAATTTTAA
CACTAACCAAACAATGCAGATCTTAGGGATGATTAAAGGCAGCATTTGATGATAGCAGAC
ATTGTTACAAGGACATGGTGAGTCTATTTTTAATGCACCAATCTTGTTTATAGCAAAAAT
GTTTTCCAATATTTTAATAAAGTAGTTATTTATAGGCATACTTGAAACCAGTATTTAAGC
TTTAAATGACAGTAATATTGGCATAGAAAAAAGTAGCAAATGTTTACTGTATCAATTTCT
AATGTTTACTATATAGAATTTCCTGTAATATATTTATATACTTTTTCATGAAAATGGAGT
TATCAGTTATCTGTTTGTTACTGCATCATCTGTTTGTAATCATTATCTCACTTTGTAAAT
AAAAACACACCTTAAAACATGAACAAGCCAAAAAAAAAAAAAAA

>NM_006142
CCAGGCAGCAGTTAGCCCGCCGCCCGCCTGTGTGTCCCCAGAGCCATGGAGAGAGCCAGT
CTGATCCAGAAGGCCAAGCTGGCAGAGCAGGCCGAACGCTATGAGGACATGGCAGCCTTC
CCAGGCAGCAGTTAGCCCGCCGCCCGCCTGTGTGTCCCCAGAGCCATGGAGAGAGCCAGT
CTGATCCAGAAGGCCAAGCTGGCAGAGCAGGCCGAACGCTATGAGGACATGGCAGCCTTC
ATGAAAGGCGCCGTGGAGAAGGGCGAGGAGCTCTCCTGCGAAGAGCGAAACCTGCTCTCA
GTAGCCTATAAGAACGTGGTGGGCGGCCAGAGGGCTGCCTGGAGGGTGCTGTCCAGTATT
GAGCAGAAAAGCAACGAGGAGGGCTCGGAGGAGAAGGGGCCCGAGGTGCGTGAGTACCGG
GAGAAGGTGGAGACTGAGCTCCAGGGCGTGTGCGACACCGTGCTGGGCCTGCTGGACAGC
CACCTCATCAAGGAGGCCGGGGACGCCGAGAGCCGGGTCTTCTACCTGAAGATGAAGGGT
GACTACTACCGCTACCTGGCCGAGGTGGCCACCGGTGACGACAAGAAGCGCATCATTGAC
TCAGCCCGGTCAGCCTACCAGGAGGCCATGGACATCAGCAAGAAGGAGATGCCGCCCACC
AACCCCATCCGCCTGGGCCTGGCCCTGAACTTTTCCGTCTTCCACTACGAGATCGCCAAC
AGCCCCGAGGAGGCCATCTCTCTGGCCAAGACCACTTTCGACGAGGCCATGGCTGATCTG
CACACCCTCAGCGAGGACTCCTACAAAGACAGCACCCTCATCATGCAGCTGCTGCGAGAC
AACCTGACACTGTGGACGGCCGACAACGCCGGGGAAGAGGGGGGCGAGGCTCCCCAGGAG
CCCCAGAGCTGAGTGTTGCCCGCCACCGCCCCGCCCTGCCCCCTCCAGTCCCCGCCCTGC
CGAGAGGACTAGTATGGGGTGGGAGGCCCCACCCTTCTCCCCTAGGCGCTGTTCTTGCTC
CAAAGGGCTCCGTGGAGAGGGACTGGCAGAGCTGAGGCCACCTGGGGCTGGGGATCCCAC
TCTTCTTGCAGCTGTTGAGCGCACCTAACCACTGGTCATGCCCCCACCCCTGCTCTCCGC

-continued

ACCCGCTTCCTCCCGACCCCAGGACCAGGCTACTTCTCCCCTCCTCTTGCCTCCCTCCTG
CCCCTGCTGCCTCTTGATTCGTAGGAATTGAGGAGTGTCTCCGCCTTGTGGCTGAGAACT
GGACAGTGGCAGGGGCTGGAGATGGGTGTGTGTGTGTGTGTGTGTGTGTGTGTGTGCGCG
CGCGCCAGTGCAAGACCGAGACTGAGGGAAAGCATGTCTGCTGGGTGTGACCATGTTTCC
TCTCAATAAAGTTCCCCTGTGACACTCAAAAAAAAAAAAAAAAAAAAAAAAAAAAAAAAA
AAAAAAAAAA

>AW445220
CGGCCGCGAGGCCCTGAGATGAGGCTCCAAAGACCCCGACAGGCCCCGGCGGGTGGGAGG
CGCGCGCCCCGGGGCGGGCGGGGCTCCCCCTACCGGCCAGACCCGGGGAGAGGCGCGCGG
AGGCTGCGAAGGTTCCAGAAGGGCGGGGAGGGGGCGCCGCGCGCTGACCCTCCCTGGGCA
CCGCTGGGGACGATGGCGCTGCTCGCCTTGCTGCTGGTCGTGGCCCTACCGCGGGTGTGG
ACAGACGCCAACCTGACTGCGAGACAACGAGATCCAGAGGACTCCCAGCGAACGGACGAG
GGTGACAATAGAGTGTGGTGTCATGTTTGTGAGAGAGAAAACACTTTCGAGTGCCAGAAC
CCAAGGAGGTGCAAATGGACAGAGCCATACTGCGTTATAGCGGCCGTGAAAATATTTCCA
CGTTTTTTCATGGTTGCGAAGCAGTGCTCCGCTGGTTGTGCAGCGATGGAGAGACCCAAG
CCAGAGGAGAAGCGGTTTCTCCTGGAAGAGCCCATGCCCTTCTTTTACCTCAAGTGTTGT
AAAATTCGCTACTGCAATTTAGAGGGGCCACCTATCAACTCATCAGTGTTCAAAGAATAT
GCTGGGAGCATGGGTGAGAGCTGTGGTGGGCTGTGGCTGGCCATCCTCCTGCTGCTGGCC
TCCATTGCAGCCGGCCTCAGCCTGTCTTGAGCCACGGGACTGCCACAGACTGAGCCTTCC
GGAGCATGGACTCGCTCCAGACCGTTGTCACCTGTTGCATTAAACTTGTTTTCTGTTGAT
TAAAAAAAAAAAAAAAAA

>AK025701
TTCAGCCGGAACGTTACTCCGTGTCCACCCGGATCGTGTGTGTGATCGAGGCTGCGGAGA
CGCCTTTCACGGGGGGTGTCGAGGTGGACGTCTTCGGGAAACTGGGCCGTTCGCCTCCCA
ATGTCCAGTTCACCTTCCAACAGCCCAAGCCTCTCAGTGTGGAGCCGCAGCAGGGACCGC
AGGCGGGCGGCACCACACTGACCATCCACGGCACCCACCTGGACACGGGCTCCCAGGAGG
ACGTGCGGGTGACCCTCAACGGCGTCCCGTGTAAAGTGACGAAGTTTGGGGCGCAGCTCC
AGTGTGTCACTGGCCCCCAGGCGACACGGGGCCAGATGCTTCTGGAGGTCTCCTACGGGG
GGTCCCCCGTGCCCAACCCCGGCATCTTCTTCACCTACCGCGAAAACCCCGTACTGCGAG
CCTTCGAGCCGCTACGAAGCTTTGCCAGTGGTGGCCGCAGCATCAACGTCACGGGTCAGG
GCTTCAGCCTGATCCAGAGGTTTGCCATGGTGGTCATCGCGGAGCCCCTGCAGTCCTGGC
AGCCGCCGCGGGAGGCTGAATCCCTGCAGCCCATGACGGTGGTGGGTACAGACTACGTGT
TCCACAATGACACCAAGGTCGTCTTCCTGTCCCCGGCTGTGCCTGAGGAGCCAGAGGTCT
ACAACCTCACGGTGCTGATCGAGATGGACGGGCACCGTGCCCTGCTCAGAACAGAGGCCG
GGGCCTTCGAGTACGTGCCTGACCCCACCCTTGAGAACTTCACAGGTGGCGTCAAGAAGC
AGGTCAACAAGCTCATCCACGCCCGGGGCACCAATCTGAACAAGGCGATGACGCTGCAGG
AGGCCGAGGCCTTCGTGGGTGCCGAGCGCTGCACCATGAAGACGCTGACGGAGACCGACC
TGTACTGTGAGCCCCCGGAGGTGCAGCCCCCGCCCAAGCGGCGGCAGAAACGAGACACCA
CACACAACCTGCCCGAGTTCATTGTGAAGTTCGGCTCTCGCGAGTGGGTGCTGGGCCGCG
TGGAGTACGACACACGGGTGAGCGACGTGCCGCTCAGCCTCATCTTGCCGCTGGTCATCG
TGCCCATGGTGGTCGTCATCGCGGTGTCTGTCTACTGCTACTGGAGGAAGAGCCAGCAGG
CCGAACGAGAGTATGAGAAGATCAAGTCCCAGCTGGAGGGCCTGGAGGAGAGCGTGCGGG
ACCGCTGCAAGAAGGAATTCACAGACCTGATGATCGAGATGGAGGACCAGACCAACGACG
TGCACGAGGCCGGCATCCCCGTGCTGGACTACAAGACCTACACCGACCGCGTCTTCTTCC
TGCCCTCCAAGGACGGCGACAAGGACGTGATGATCACCGGCAAGCTGGACATCCCCGAGC
CGCGGCGGCCGGTGGTGGAGCAGGCCCTCTACCAGTTCTCCAACCTGCTGAACAGCAAGT
CTTTCCTCATCAATTTCATCCACACCCTGGAGAACCAGCGGGAGTTCTCGGCCCGCGCCA
AGGTCTACTTCGCGTCCCTGCTGACGGTGGCGCTGCACGGGAAACTGGAGTACTACACGG
ACATCATGCACACGCTCTTCCTGGAGCTCCTGGAGCAGTACGTGGTGGCCAAGAACCCCA
AGCTGATGCTGCGCAGGTCTGAGACTGTGGTGGAGAGGATGCTGTCCAACTGGATGTCCA
TCTGCCTGTACCAGTACCTCAAGGACAGTGCCGGGGAGCCCCTGTACAAGCTCTTCAAGG
CCATCAAACATCAGGTGGAAAAGGGCCCGGTGGATGCGGTACAGAAGAAGGCCAAGTACA
CTCTCAACGACACGGGGCTGCTGGGGGATGATGTGGAGTACGCACCCCTGACGGTGAGCG
TGATCGTGCAGGACGAGGGAGTGGACGCCATCCCGGTGAAGGTCCTCAACTGTGACACCA
TCTCCCAGGTCAAGGAGAAGATCATTGACCAGGTGTACCGTGGGCAGCCCTGCTCCTGCT
GGCCCAGGCCAGACAGCGTGGTCCTGGAGTGGCGTCCGGGCTCCACAGCGCAGATCCTGT
CGGACCTGGACCTGACGTCACAGCGGGAGGGCCGGTGGAAGCGCGTCAACACCCTTATGC
ACTACAATGTCCGGGATGGAGCCACCCTCATCCTGTCCAAGGTGGGGGTCTCCCAGCAGC
CGGAGGACAGCCAGCAGGACCTGCCTGGGGAGCGCCATGCCCTCCTGGAGGAGGAGAACC
GGGTGTGGCACCTGGTGCGGCCGACCGACGAGGTGGACGAGGGCAAGTCCAAGAGAGGCA
GCGTGAAAGAGAAGGAGCGGACGAAGGCCATCACCGAGATCTACCTGACGCGGCTGCTCT
CAGTCAAGGGCACACTGCAGCAGTTTGTGGACAACTTCTTCCAGAGCGTGCTGGCGCCTG
GGCACGCGGTGCCACCTGCAGTCAAGTACTTCTTCGACTTCCTGGACGAGCAGGCAGAGA
AGCACAACATCCAGGATGAAGACACCATCCACATCTGGAAGACGAACAGTTTACCGCTCC
GGTTCTGGGTGAACATCCTCAAGAACCCCCACTTCATCTTTGACGTGCATGTCCACGAGG
TGGTGGACGCCTCGCTGTCAGTCATCGCGCAGACCTTCATGGATGCCTGCACGCGCACGG
AGCATAAGCTGAGCCGCGATTCTCCCAGCAACAAGCTGCTGTACGCCAAGGAGATCTCCA
CCTACAAGAAGATGGTGGAGGATTACTACAAGGGGATCCGGCAGATGGTGCAGGTCAGCG
ACCAGGACATGAACACACACCTGGCAGAGATTTCCCGGGCGCACACGGACTCCTTGAACA
CCCTCGTGGCACTCCACCAGCTCTACCAATACACGCAGAAGTACTATGACGAGATCATCA
ATGCCTTGGAGGAGGATCCTGCCGCCCAGAAGACGCAGCTGGCCTTCCGCCTGCAGCAGA
TTGCCGCTGCACTGGAGAACAAGGTCACTGACCTCTGACCTACAATCTCCAGTGCTGCCT
TGGGACATAGGTACCTGAGGTACCTGAGAGCCCCTCAGGGGAGGAGGCCGAGTGGCTGTG
GCTGAGGCCCCCACCCTCCCCTGGAACGCGCCCCAAGCCGGAGTGGGTGCAGCCGGAACC
CGCCCAGCGTCTAGACTGTAGCATCTTCCTCTGAGCAATACCGCCGGGCACCGCACCAGC
ACCAGCCCCAGCCCCAGCTCCCTCCGGCCGCAGAACCAGCATCGGGTGTTCACTGTCGAG
TCTCGAGTGATTTGAAAATGTGCCTTACGCTGCCACGCTGGGGGCAGCTGGCCTCCGCCT
CCGCCCACGCACCAGCAGCCGCCTCCATGCCCTAGGTTGGGCCCCTGGGGGATCTGAGGG
CCTGTGGCCCCCAGGGCAAGTTCCCAGATCCTATGTCTGTCTGTCCACCACGAGATGGGA

-continued

GGAGGAGAAAAAGCGGTACGATGCCTTCCTGACCTCACCGGCCTCCCCAAGGGTGCCGGC
ACTCTGGGTGGACTCACGGCTGCTGGGCCCCACGTCAAAGGTCAAGTGAGACGTAGGTCA
AGTCCTACGTCGGGGCCCAGACATCCTGGGGTCCTGGTCTGTCAGACAGGCTGCCCTAGA
GCCCCACCCAGTCCGGGGGGACTGGGAGCAGTTCCAAGACCACCCCACCCCTTTTTGTAA
ATCTTGTTCATTGTAAATCAAATACAGCGTCTTTTTCACTCCGAAAAAAAAAAAAAAAAA
AAAAAA

>NM_033229
GATGTGGGCACGCCTCAGAGCCAGAAGTTTATGGCTCCCACCTGCTCAATCTGACAGGAA
GCTTCTGCTCCCCAGTTCTCCCCAGCCACTGTGGTCTACAGATTCCAGGAAACCCATCCC
CCTGTGACCTCAGGGTGTGCTCTGTTCTCCACCCTAGGGACCAGAAGGAGCCAGGAGTAA
AGAACTGGCTTACTTGGCCGCCACTGGGAAATTCTGGGTAATTCGAGACGCCCTGGAATT
TGGACCCACTCCGCTGATAGGTGGTGGGCAGGGTTCTAGGGAACACAAGAGGCGGAGCCA
GGTGGCTTCCCTGTGCTGGCATTCTTGGCTCTCTCTCTCTCTCTTTCTCTCTCTCTGTCT
CTCTCTCTCTCTCTGTCTCTCAGCCTTGAAGCCGTTTCCCTCTGCGATTCATGTAAGTGT
GACTCGATTTCAGGGAAAGGGAACTCGCGTGGGCTGAGGAGACCGGAGTGGACGGGCTGG
GGAAGGCACCGTGATGCCCGCAACCCCGTCCCTGAAGGTGGTCCATGAGCTGCCTGCCTG
TACCCTCTGTGCGGGGCCGCTGGAGGATGCGGTGACCGTTCCCTGTGGACACACCTTCTG
CCGGCTCTGCCTCCCCGCGCTCTCCCAGATGGGGCCCAATCCTCGGGCAAGATCCTGCT
CTGCCCGCTCTGCCAAGAGGAGGAGCAGGCAGAGACTCCCATGGCCCCTGTGCCCCTGGG
CCCGCTGGGAGAAACTTACTGCGAGGAGCACGGCGAGAAGATCTACTTCTTCTGCGAGAA
CGATGCCGAGTTCCTCTGTGTGTTCTGCAGGGAGGGTCCCACGCACCAGGCGCACACCGT
GGGGTTCCTGGACGAGGCCATTCAGCCCTACCGGGATCGTCTCAGGAGTCGACTGGAAGC
TCTGAGCACGGAGAGAGATGAGATTGAGGATGTAAAGTGTCAAGAAGACCAGAAGCTTCA
AGTGCTGCTGACTCAGATCGAAAGCAAGAAGCATCAGGTGGAAACAGCTTTTGAGAGGCT
GCAGCAGGAGCTGGAGCAGCAGCGATGTCTCCTGCTGGCCAGGCTGAGGGAGCTGGAGCA
GCAGATTTGGAAGGAGAGGGATGAATATATCACAAAGGTCTCTGAGGAAGTCACCCGGCT
TGGAGCCCAGGTCAAGGAGCTGGAGGAGAAGTGTCAGCAGCCAGCAAGTGAGCTTCTACA
AGATGTCAGAGTCAACCAGAGCAGGTGTGAGATGAAGACTTTTGTGAGTCCTGAGGCCAT
TTCTCCTGACCTTGTCAAGAAGATCCGTGATTTCCACAGGAAAATACTCACCCTCCCAGA
GATGATGAGGATGTTCTCAGAAAACTTGGCGCATCATCTGGAAATAGATTCAGGGGTCAT
CACTCTGGACCCTCAGACCGCCAGCCGGAGCCTGGTTCTCTCGGAAGACAGGAAGTCAGT
GAGGTACACCCGGCAGAAGAAGAGCCTGCCAGACAGCCCCCTGCGCTTCGACGGCCTCCC
GGCGGTTCTGGGCTTCCCGGGCTTCTCCTCCGGGCGCCACCGCTGGCAGGTTGACCTGCA
GCTGGGCGACGGCGGCGGCTGCACGGTGGGGGTGGCCGGGGAGGGGGTGAGGAGGAAGGG
AGAGATGGGACTCAGCGCCGAGGACGGCGTCTGGGCCGTGATCATCTCGCACCAGCAGTG
CTGGGCCAGCACCTCCCCGGGCACCGACCTGCCGCTGAGCGAGATCCCGCGCGGCGTGAG
AGTCGCCCTGGACTACGAGGCGGGGCAGGTGACCCTCCACAACGCCCAGACCCAGGAGCC
CATCTTCACCTTCACTGCCTCTTTCTCCGGCAAAGTCTTCCCTTTCTTTGCCGTCTGGAA
AAAAGGTTCCTGCCTTACGCTGAAAGGCTGAAGTGGGGCGCGCGAAGGGCGGCGAAGCGG
AGACGGCGGCTCTCCGGGATCCAGCTCCGCCCCTGGCCAGTGTGCGGCCCGGGGGCTCCC
TGTGCCCGCGTGAGGCGAGAGAACAGGGGACTTGAGTCTCGAACAGCGGTTGTTTTTACT
TTATTTATCTTAGGCCCTCAGCTCCCTGACGTCCTGAGCCTCCCTGTGACGCTCTGGCCT
TCTCTGCACCTCAGAGTGCAGAACCACAGACGGCTTCGGCTGTGCCTAGGGCAACAGCCA
ACCTAGGAGCCAGCGGGCTTTCGGGGAAAAAAAAGAAAAAGACATCTAAAATAAAATGTT
TAAACTGTTTCAAAAT

>AV656862
TTTATACATTCTAAATCTCCCCAGTTTCTTTGGGGCTGGAAGATGCAACTTCCATTTAAT
AGAAACTTTGAAATCTTGGGGTAAGGGAGCAGTGGGGGGACTAGGGAGAAGGATAAGAAA
TAGAATTATTGAAAAGCCCCCACCAGGGACCTTCCTGGCCAGAATATGCAGAGTAATTCC
TGCTGGCTTCACCTTTGAAAGTCCCTCGAAACTATGCAGATGAAACTGAGTCTGTTTTTG
ATATTGTCAGATGTATTCTACCTTGGAAGTCCCAACACCTAAACTGGAATTCTTGTATTT
ACATCTCCTCCACTGTCCCCCACACCACCCCTCAATTCCTGCTGCCCCTGCTAATGTTAA
GCATTTTTCTCTTGTTATCATCAGGTTCACATTAAAAACAGATACTTACAAACTGACTTG
AAGCACAGATACTTTTACGAATGTGATAAAATATTTTCTTAAGAAAAGGAAAGAGGATGT
GGGTCAAATAAAACACCGCATGGATGTTGATTGGTGAATACTGGTGTAAGAAAAGGGAGC
TCAGGAATTTTTATTACTGTATTTGTAAATGAGTTTGAAGGAATTTGTAAATGCCACTGG
TACATTTTTAAGGTGACACATTTGCTCCTTATAAAGTTATTAAAAATTACAGGGTAAGCT
TAAATGACGTTTGCCAGTAGTTTTACTTTATATAATCAATATTGATATTGTTGCTGAACT
ATGTAACTTTATGATGCATTTTTCAGTCCCTTTTCAGAGCAAATGCTTTTGCAATGGTAG
TAATGTTTAGTTTAAATTGACTTAATAAATTATTACCTGAGCAAAAAAAAAAAAAAAAAA
AAAAAAAAAATAAAAAAAAAAAAAAAAAAAAAAAAAAAAAATAATAAAAAAAAAAAAAACA
AACAAATCAATAAAACTTAAACAAAAAAAAAAATAAAAAAAAA

>AI499593
GCAGAGATCGCCACATCGTCGGACAAGGTCAAGGACGGGGGCGGCGGGAACGAGGGCTCT
CCATGCCCACCGTGTCCCGGGCCCATAGCCGGGCAAGCCCTAGGAGGCAGCCGGGCGTCG
CCGGCCCCGGCGCCGTCACGCTCGCCCTCGGCGCAGTGTCCTTTTCCAGGCGGGACGGTG
CTGTCCCGGCCTCTCTACTACACCGCGCCCTTCTATCCCGGCTACACGAACTATGGCTCC
TTCGGACACCTTCATGGCCACCCGGGGCCGGGGCCGGCCCCCACACCCGGTCCGGGGTCT
CATTTCAATGGATTAAACCAGACCGTGTTGAACCGAGCGGACGCTTTGGCTAAAGACCCG
AAAATGTTGCGGAGCCAGTCTCAGCTAGACCTGTGCAAAGACTCTCCCTATGAATTGAAG
AAAGGTATGTCCGACATTTAACGCGGGCTGCGTCGGTCCCGGACTTTTCTAATTTATTAA
AAACATGGCCTTGGCAGTTATTTTTCCATCACCGAGAGAGAGAGACAGAGAGAGAAAATA
AACTACCCCTCCTATTCAGAAGTTTATAGTTTATGGAGATGGATGACATAAAAATGTAAA
CATCTCCACACACACAAAAAAATGTCTTAACCAACCGAAAAGAAAAATTAAAAAAGGATT
TGTATTAAATCTTATTCTGTATATTTAATGTAGCATTTTTGTATTTAAATTGATAATTCA
ATATCTTTGAAGTAAATTATGAAATCAAGACACCTGTACAGGCATTTAATGTTTTTTTGT
AATATAAATATATACATTTGTGTTTCCCCCAAAACTGTTTCATAGTTAAAAAATACAAGT
TTAATTTAATTTTTTACACCTATTGATTCTGCTGGGTATGAGCTAAAGTATTACGGAAAG

-continued

GAAACAGGTTATACTCTTAGATTTAAAAAGTGAAAGAAACTGCAGGCGCCTTTGTAAAAT
GCAAAATATTTAATTAAAAGAGATTTTAACATAATGAGAGCCACTCATTACTTTTTAGAA
GCCTCAATAAACTGTCCATTGCCTTGGTC

>AI952953
ATATCCAAGAAATTTGGACACCTATACCTACAGAATAATGAAATAGAAAAGATGAATCTN
ACAGTGATGTGTCCTTCTATTGACCCACTACATTACCACCATTTAACATACATTCGTGTG
GACCAAAATAAACTAAAAGAACCAATAAGCTCATACATCTTCTTCTGCTTCCCTCATATA
CACACTATTTATTATGGTGAACAACGAAGCACTAATGGTCAAACAATACAACTAAAGACC
CAAGTTTTCAGGAGATTTCCAGATGATGATGATGAAAGTGAAGATCACGATGATCCTGAC
AATGCTCATGAGAGCCCAGAACAAGAAGGAGCAGAAGGGCACTTTGACCTTCATTATTAT
GAAAATCAAGAATAGCAAGAAACTATATAGGTATACACTTACGACTTCACAAAACCTATA
CTTAATATAGTAAATCTAAGTAAACATGTATTACTCAAAGTAATATATTTAGAATTATGT
ATTAGTATAAGATCAGAATTGAATTTAAGTTGTTGGTGACATCTGCATCATTTCATAGGA
TTAGAACTTACTCAAAATAATGTAAATCTTTAAAAATATAAATTAGAATGACAAGTGGGA
ATCATAAATTAAACGTTAATGGTTTCTTATGCTCTTTTTAAATATAGAAATATCATGTTA
AAAAAAAA

>AK025470
ATGATTGCAACAGTGGATTTAAAAGTCAATGAATATGAGAAAAACCAAAAATGGCTTGAG
ATCCTAAATAAGATTGAAAACAAAACATACACGAAGCTCAAAAATGGACATGTGTTTAGG
AAGCAGGCACTGATGAGTGAAGAAAGGACTCTGTTATATGATGGCCTTGTTTACTGGAAA
ACTGCTACAGGTCGTTTCAAAGATATCCTAGCTCTACTTCTAACTGATGTGCTGCTCTTT
TTACAAGAAAAAGACCAGAAATACATCTTTGCAGCCGTTGATCAGAAGCCATCAGTTATT
TCCCTTCAAAAGCTTATTGCTAGAGAAGTTGCTAATGAGGAGAGAGGAATGTTTCTGATC
AGTGCTTCATCTGCTGGTCCTGAGATGTATGAAATTCACACCAATTCCAAGGAGGAACGC
AATAACTGGATGAGACGGATCCAGCAGGCTGTAGAAAGTTGTCCTGAAGAAAAAGGGGGA
AGGACAAGTGAATCTGATGAAGACAAGAGGAAAGCTGAAGCCAGAGTGGCCAAAATTCAG
CAATGTCAAGAAATACTCACTAACCAAGACCAACAAATTTGTGCGTATTTGGAGGAGAAG
CTGCATATCTATGCTGAACTTGGAGAACTGAGCGGATTTGAGGACGTCCATCTAGAGCCC
CACCTCCTTATTAAACCTGACCCAGGCGAGCCTCCCCAGGCAGCCTCATTACTGGCAGCA
GCACTGAAAGAAGCATTAGTCACAGGAGGGAGAGAAGGAAGAGGCTGTTCGGATGTGGAT
CCCGGGATCCAGGGTGTGGTAACCGACTTGGCCGTCTCTGATGCAGGGGAGAAGGTGGAA
TGTAGAAATTTTCCAGGTTCTTCACAATCAGAGATTATACAAGCCATACAGAATTTAACC
CGTCTCTTATACAGCCTTCAGGCCGCCTTGACCATTCAGGACAGCCACATTGAGATCCAC
AGGCTGGTTCTCCAGCAGCAGGAGGGCCTGTCTCTCGGCCACTCTATCCTCCGAGGCGGC
CCCTTGCAGGACCAGAAGTCTCGCGACGCGGACAGGCAGCATGAGGAGCTGGCCAATGTG
CACCAGCTTCAGCACCAGCTCCAGCAGGGGCAGCGGCGCTGGCTGCGCAGGTGTGAGCAG
CAGCAGCGGGCGCAGGCGACCAGGGAGAGCTGGCTGCAGGAGCGGGAGCGGGAGTGCCAG
TCGCAGGAGGAGCTGCTGCGGAGCCGGGGCGAGCTGGACCTCCAGCTCCAGGAGTAC
CAGCACAGCCTGGAGCGGCTGAGGGAGGGCCAGCGCCTGGTGGAGAGGGAGCAGGCGAGG
ATGCGGGCCCAGCAGAGCCTGCTGGGCCACTGGAAGCACGGCCGGCAGAGGAGCCTGTCC
GCGGTGCTCCTTCCGGGTGGCCCCGAGGTAATGGAACTTAATCGATCTGAGAGTTTATGT
CATGAAAACTCATTCTTCATCAATGAAGCTTTAGTACAAATGTCATTTAACACTTTCAAC
AAACTGAATCCATCAGTTATCCATCAGGATGCCACTTACCCTACAACTCAATCTCATTCT
GACTTGGTGAGGACTAGTGAACATCAAGTAGACCTCAAGGTGGACCCTTCTCAGCCTTCG
AATGTCAGTCACAAACTGTGGACAGCCGCTGGTTCCGGCCATCAGATACTTCCTTTCCAT
GAAAGCAGCAAGGATTCTTGTAAAAATGGCTCCAGTATGACAAAGTGCAGTTGTACGTTG
ACATCTCCCCCGGGACTGTGGACTGGAACCACATCTACTTTGAAGGATTTGGACACCTCC
CACACTGAGTCCCCAACCCCCATGACTCAAATTCACACCGCCCTCAACTGCAGGCGTTT
ATAACAGAAGCAAAGCTAAATCTACCGACAAGGACAATGACCAGACAAGATGGGGAAACT
GGAGATGGAGCCAAAGAAAATATTGTTTACCTCTAATTGTGTTGTCATTTTTCCAAACAA
AACAAAACACTGGCACTTTTGGGAGAAACTTTTTGTCTCCATTCCTTATGTATGTGTGAT
TGTCTGTGTCCAAATTGCTTTAAGAATAATATTTAATATTTCCTGGAAGCTCATTTTTTT
GGCATGAGTCTAATTAAATTATTGAAAGCCACCCTGTTTGTATAATCTTTAACTTATCAA
ATCTAATTTCAGATTTCTGGAGGAGAAACTAACTTGAATAAGCAGGACTATTTTAAAAGT
TGTTTTGACGCTAGAGTAAAATTCCATGTCACATTTTCTACCCAATCATCTGGATTTCAA
GATTCCTTTTAAGATCTCAATGAAGCAATTTGGATTTAAAGAGTGGTATTCACAAGGGGT
GAACTTTCACAGTCAGGGCAGTTGCCTCAGTGCCCACATAGGCAGAGGAGGATGTGGGAA
AGGGCTTTTCTCAGCTAGTTTTTGTGTGCTCATTTCTTCTGGGAGCATTAAAAGTGGTGA
TCTGTTACAGTCACTATTCAACTGGGCACGTGTTGTGATTGGTCAGTCACTGAGCCAGGG
ATACAGTCCGGACTTGCTTAGTACCTAAGCCTAATGCTGGTGGGGTTTCAAGACATGGTT
CAGCATCATCTTTTAACAAGGCCCAGAGGCCCAGAGCCCGCATCAAGTCATTTTGATGTA
AATAGTGAACTTTGTTAGAGCCCTCACTTCTATCAATCAGCTGTCCTGTCCCTGCCAGCA
CCTGGAGCACCAACTACCACTCCCTGGAAAGAACCCTTCCCTGCAGTTTTTTAAGGACAA
AACTGCCCACTCCTCATTAAGTTTGCTGCCTGGATACACTTTTCCACAAAGGAAAACTGG
CATATCCTGCCTTCCGAGTAGTATGGGTCTCTGTGTGAGAAACCAGGAGATATTTTCATC
TTGTTCGGAAATACTTGTATGTATTTTGGTGTCAATAAATATCTTGTACCTCATTAAAAA
AAAAAAAAAAAAA

>NM_006378
CTGAGCCGCATCTGCAATAGCACACTTGCCCGGCCACCTGCTGCCGTGAGCCTTTGCTGC
TGAAGCCCCTGGGGTCGCCTCTACCTGATGAGGATGTGCACCCCCATTAGGGGGCTGCTC
ATGGCCCTTGCAGTGATGTTTGGGACAGCGATGGCATTTGCACCCATACCCCGGATCACC
TGGGAGCACAGAGAGGTGCACCTGGTGCAGTTTCATGAGCCAGACATCTACAACTACTCA
GCCTTGCTGCTGAGCGAGGACAAGGACACCTTGTACATAGGTGCCCGGGAGGCGGTCTTC
GCTGTGAACGCACTCAACATCTCCGAGAAGCAGCATGAGGTGTATTGGAAGGTCTCAGAA
GACAAAAAAGCAAAATGTGCAGAAAAGGGGAAATCAAAACAGACAGAGTGCCTCAACTAC
ATCCGGGTGCTGCAGCCACTCAGCGCCACTTCCCTTTACGTGTGTGGGACCAACGCATTC
CAGCCGGCCTGTGACCACCTGAACTTAACATCCTTTAAGTTTCTGGGGAAAAATGAAGAT
GGCAAAGGAAGATGTCCCTTTGACCCAGCACACAGCTACACATCCGTCATGGTTGATGGA

-continued

GAACTTTATTCGGGGACGTCGTATAATTTTTTGGGAAGTGAACCCATCATCTCCCGAAAT
TCTTCCCACAGTCCTCTGAGGACAGAATATGCAATCCCTTGGCTGAACGAGCCTAGTTTC
GTGTTTGCTGACGTGATCCGAAAAAGCCCAGACAGCCCCGACGGCGAGGATGACAGGGTC
TACTTCTTCTTCACGGAGGTGTCTGTGGAGTATGAGTTTGTGTTCAGGGTGCTGATCCCA
CGGATAGCAAGAGTGTGCAAGGGGGACCAGGGCGGCCTGAGGACCTTGCAGAAGAAATGG
ACCTCCTTCCTGAAAGCCCGACTCATCTGCTCCCGGCCAGACAGCGGCTTGGTCTTCAAT
GTGCTGCGGGATGTCTTCGTGCTCAGGTCCCCGGGCCTGAAGGTGCCTGTGTTCTATGCA
CTCTTCACCCCACAGCTGAACAACGTGGGGCTGTCGGCAGTGTGCGCCTACAACCTGTCC
ACAGCCGAGGAGGTCTTCTCCCACGGGAAGTACATGCAGAGCACCACAGTGGAGCAGTCC
CACACCAAGTGGGTGCGCTATAATGGCCCGGTACCCAAGCCGCGGCCTGGAGCGTGCATC
GACAGCGAGGCACGGGCCGCCAACTACACCAGCTCCTTGAATTTGCCAGACAAGACGCTG
CAGTTCGTTAAAGACCACCCTTTGATGGATGACTCGGTAACCCCAATAGACAACAGGCCC
AGGTTAATCAAGAAAGATGTGAACTACACCCAGATCGTGGTGGACCGGACCCAGGCCCTG
GATGGGACTGTCTATGATGTCATGTTTGTCAGCACAGACCGGGGAGCTCTGCACAAAGCC
ATCAGCCTCGAGCACGCTGTTCACATCATCGAGGAGACCCAGCTCTTCCAGGACTTTGAG
CCAGTCCAGACCCTGCTGCTGTCTTCAAAGAAGGGCAACAGGTTTGTCTATGCTGGCTCT
AACTCGGGCGTGGTCCAGGCCCCGCTGGCCTTCTGTGGGAAGCACGGCACCTGCGAGGAC
TGTGTGCTGGCGCGGGACCCCTACTGCGCCTGGAGCCCGCCCACAGCGACCTGCGTGGCT
CTGCACCAGACCGAGAGCCCCAGCAGGGGTTTGATTCAGGAGATGAGCGGCGATGCTTCT
GTGTGCCCGGATAAAAGTAAAGGAAGTTACCGGCAGCATTTTTTCAAGCACGGTGGCACA
GCGGAACTGAAATGCTCCCAAAAATCCAACCTGGCCCGGGTCTTTTGGAAGTTCCAGAAT
GGCGTGTTGAAGGCCGAGAGCCCCAAGTACGGTCTTATGGGCAGAAAAAACTTGCTCATC
TTCAACTTGTCAGAAGGAGACAGTGGGGTGTACCAGTGCCTGTCAGAGGAGAGGGTTAAG
AACAAAACGGTCTTCCAAGTGGTCGCCAAGCACGTCCTGGAAGTGAAGGTGGTTCCAAAG
CCCGTAGTGGCCCCCACCTTGTCAGTTGTTCAGACAGAAGGTAGTAGGATTGCCACCAAA
GTGTTGGTGGCATCCACCCAAGGGTCTTCTCCCCCAACCCCAGCCGTGCAGGCCACCTCC
TCCGGGGCCATCACCCTTCCTCCCAAGCCTGCGCCCACCGGCACATCCTGCGAACCAAAG
ATCGTCATCAACACGGTCCCCCAGCTCCACTCGGAGAAAACCATGTATCTTAAGTCCAGC
GACAACCGCCTCCTCATGTCCCTCTTCCTCTTCTTCTTTGTTCTCTTCCTCTGCCTCTTT
TTCTACAACTGCTATAAGGGATACCTGCCCAGACAGTGCTTGAAATTCCGCTCGGCCCTA
CTAATTGGGAAGAAGAAGCCCAAGTCAGATTTCTGTGACCGTGAGCAGAGCCTGAAGGAG
ACGTTAGTAGAGCCAGGGAGCTTCTCCCAGCAGAATGGGGAGCACCCCAAGCCAGCCCTG
GACACCGGCTATGAGACCGAGCAAGACACCATCACCAGCAAAGTCCCCACGGATAGGGAG
GACTCACAGAGGATCGACGACCTTTCTGCCAGGGACAAGCCCTTTGACGTCAAGTGTGAG
CTGAAGTTCGCTGACTCAGACGCAGATGGAGACTGAGGCCGGCTGTGCATCCCCGCTGGT
GCCTCGGCTGCGACGTGTCCAGGCGTGGAGAGTTTTGTGTTTCTCCTGTTCAGTATCCGA
GTCTCGTGCAGTGCTGCGTAGGTTAGCCCGCATCGTGCAGACAACCTCAGTCCTCTTGTC
TATTTTCTCTTGGGTTGAGCCTGTGACTTGGTTTCTCTTTGTCCTTTTGGAAAAATGACA
AGCATTGCATCCCAGTCTTGTGTTCCGAAGTCAGTCGGAGTACTTGAAGAAGGCCCACGG
GCGGCACGGAGTTCCTGAGCCCTTTCTGTAGTGGGGGAAAGGTGGCTGGACCTCTGTTGG
CTGAGAAGAGCATCCCTTCAGCTTCCCCTCCCCGTAGCAGCCACTAAAAGATTATTTAAT
TCCAGATTGGAAATGACATTTTAGTTTATCAGATTGGTAACTTATCGCCTGTTGTCCAGA
TTGGCACGAACCTTTTCTTCCACTTAATTATTTTTTTAGGATTTTGCTTTGATTGTGTTT
ATGTCATGGGTCATTTTTTTTTAGTTACAGAAGCAGTTGTGTTAATATTTAGAAGAAGAT
GTATATCTTCCAGATTTTGTTATATATTTGGCATAAAATACGGCTTACGTTGCTTAAGAT
TCTCAGGGATAAACTTCCTTTTGCTAAATGCATTCTTTCTGCTTTTAGAAATGTAGACAT
AAACACTCCCCGGAGCCCACTCACCTTTTTTCTTTTTCTTTTTTTTTTTTTAACTTTATT
CCTTGAGGGAAGCATTGTTTTTGGAGAGATTTTCTTTCTGTACTTCGTTTTACTTTTCTT
TTTTTTTAACTTTTACTCTCTCGAAGAAGAGGACCTTCCCACATCCACGAGGTGGGTTTT
GAGCAAGGGAAGGTAGCCTGGATGAGCTGAGTGGAGCCAGGCTGGCCCAGAGCTGAGATG
GGAGTGCGGTACAATCTGGAGCCCACAGCTGTCGGTCAGAACCTCCTGTGAGACAGATGG
AACCTTCACAAGGGCGCCTTTGGTTCTCTGAACATCTCCTTTCTCTTCTTGCTTCAATTG
CTTACCCACTGCCTGCCCAGACTTTCTATCCAGCCTCACTGAGCTGCCCACTACTGGAAG
GGAACTGGGCCTCGGTGGCCGGGGCCGCGAGCTGTGACCACAGCACCCTCAAGCATACGG
CGCTGTTCCTGCCACTGTCCTGAAGATGTGAATGGGTGGTACGATTTCAACACTGGTTAA
TTTCACACTCCATCTCCCCGCTTTGTAAATACCCATCGGGAAGAGACTTTTTTTCCATGG
TGAAGAGCAATAAACTCTGGATGTTTGTGCGCGTGTGTGGACAGTCTTATCTTCCAGCAT
GATAGGATTTGACCATTTTGGTGTAAACATTTGTGTTTTATAAGATTTACCTTGTTTTTA
TTTTTCTACTTTGAATTGTATACATTTGGAAAGTACCCAAATAAATGAGAAGCTTCTATC
CTTAAAAAAAAAAAAAA

>AA993639
CCCNTCCCCAGAGGCAGGAAAANCAGTNTGCCGAAAGGATAGACTGNGGTGCNGTCTTTC
CCCAAGTTNTGAACTAGTTTTAAGGTAGCTTAGGATGAAAAATGGAGAATGATTGGGGGT
TCCAAACCACTTTCTTCTCCCTTGGCTTATATCTCTTCACCATTTGGTGGTCAACTGTGG
GCCTACCCTGGACCTCATCTACTCAGCGAGAATTGGACATGAAGCTAGAGGCAGCTGCCT
TGGAAGGGAAGTCAGGCTCACTTGGACAGCCCAGGCCATGGCAGGAAGAATCCCTTCCTC
TTGGGGTCCTTGATGGGCATGTGTGATGGGGAAGGAGCAGTCTCCCAGCCCTGGGTCTGC
TCCCCACATCTCTCCTAATTCCACTTCACCTTTTGCCACCCCCTCCCCACCAGAGGCCTA
GCCCTTTTGTCACCGAAGGCCCCCAGAGTGTTTCTGTGTGAAACCCTCTCATTTACACTG
TGGCATCAAAATCCACAAAAGATGGATTAATTGCACTCTGGTTAATAGCAGCAGCACAAT
GATTAAAATCTATATTCCTATCTTCTCTAGCACCCTGGTGTGGGGATGGGGCGGAAGGGT
GTCTTGAGGGGCAGGGAGGACCCCATAAAACAATCCCTCCTGCATTCTCAGGCTAAATAG
GGCCCCCAGTGACTACCTGTTCTTGGCTGTCCCCTCTGAAGAGCTCTGCCTTCTCACAGC
CACCACCAGTTGCCCCACTCCCAGGAAAACAGCACATGTTCTTCTTCTCCTGCCTTGAGA
CTGCGTGTTAGTCTTCCATTCATAACTCATCAGCAGCTCAGTCCTTCTTATGTCTAGTCT
CAGTTCATTCAGCCAAAGCTCATTTTTGTCCTATCCAAAGTAGAAAGGGTTCTTTTAGAA
AACTTGAAGAATGTGCCTCCTCTTAGCATCTGTTTCTGACTCCCAGTTATTTTTAAAATA
AATGATGAATAAAATGCCTGCCCTGAAGGGTTCTGGAGGAGTCAGGTATCAAAAAAAAAA
AAA

-continued

>BE552004
TTTTTAAGATGATCTTGCTCCGTCACCCAGGCTGGAGTGCAGTGGCGTAATCATGGCTTC
CTGCAGCCTCAAACTCCTGGGCTCAATGAGTTCCTTGAGATCTTCCATCCTCAGCTTCCC
AAGTAGCTAGTAGTAGTAGTGGCTTGCACCAACGCTCCTGCCCTAATTTTCAATATTTTT
TTTGTAGAGATAGGATCTCACTGTGTTACCCAAGCTAGACTTGAACTCCTGGCCTCAAGC
GATCCTTCCGCCTTGGCCTCCCAAAGTGTTGGGATTACAGGCATTAGCTACCACACCTGG
CCAAGGCCCAGGTTTCGACAGAAAGGGAGAGAAAACCTGCCAGAGATGCCATTTCGGAGC
CACTCTGCTTGGCAGGGACCTGTGTTCCCCTCATGCAGGTTCATCCTTAGAGGGCTGCGG
TCTTATCTGGTTGTGCAAAAGTCCCACAACCTTTCTGGATTGATAGTTTGTGGTGAAATA
AACAATTTTAGTTTGTTTGGAGAATCTTTTGTATACAAAATACAAATAAAACCTAAATCA
AAGAAACAGA

>BC010437
GAGGGGCCGGAGGCGTCCCCGCTCCCGCTCGCTACTAGCCCGCGGGCCAGCGCCGCGTCC
CGAGCCCCGGCGGGAGCCATGGCTCTAAAAGGACAAGAAGATTATATTTATCTTTTCAAG
GATTCAACACATCCAGTGGATTTTCTGGATGCATTCAGAACATTTTACTTGpATGGATTA
TTTACTGATATTACTCTTCAGTGTCCTTCAGGCATAATTTTCCATTGTCACCGAGCCGTT
TTAGCTGCTTGCAGCAATTATTTTAAGGCAATGTTCACAGCTGACATGAAAGAAAAATTT
AAAAATAAAATAAAACTCTCTGGCATCCACCATGATATTCTGGAAGGCCTTGTAAATTAT
GCATACACTTCCCAAATTGAAATAACTAAAAGAAATGTTCAAAGCCTGCTTGAGGCAGCG
GATCTGCTACAGTTCCTTTCAGTAAAGAAGGCTTGTGAGCGGTTTTTGGTAAGGCACTTG
GATATTGATAATTGTATTGGAATGCACTCCTTTGCAGAATTTCATGTGTGTCCAGAACTA
GAGAAGGAATCTCGAAGAATTCTATGTTCAAAGTTTAAGGAAGTGTGGCAACAAGAAGAA
TTTCTGGAAATCAGCCTTGAAAAGTTTCTCTTTATCTTGTCCAGAAAGAATCTCAGTGTT
TGGAAAGAAGAAGCTATCATAGAGCCAGTTATTAAGTGGACTGCTCATGATGTAGAAAAT
CGAATTGAATGCCTCTATAATCTACTGAGCTATATCAACATTGATATAGATCCAGTGTAC
TTAAAAACAGCCTTAGGCCTTCAAAGAAGCTGCCTGCTCACCGAAAATAAGATCCGCTCC
CTAATATACAATGCCTTGAATCCCATGCATAAAGAGATTTCCCAGAGGTCCACAGCCACA
ATGTATATAATTGGAGGCTATTACTGGCATCCTTTATCAGAGGTTCACATATGGGATCCT
TTGACAAATGTTTGGATTCAGGGAGCAGAAATACCAGATTATACCAGGGAGAGCTATGGT
GTTACATGTTTAGGACCCAACATTTATGTAACTGGGGGCTACAGGACGGATAACATAGAA
GCTCTTGACACAGTGTGGATCTATAACAGTGAAAGTGATGAATGGACAGAAGGTTTGCCA
ATGCTCAATGCCAGGTATTACCACTGTGCAGTCACCTTGGGTGGCTGTGTCTATGCTTTA
GGTGGTTACAGAAAAGGGGCTCCAGCAGAAGAGGCTGAGTTCTATGATCCTTTAAAAGAG
AAATGGATTCCTATTGCAAACATGATTAAAGGTGTGGGAAATGCTACTGCCTGTGTCTTA
CATGATGTTATCTACGTCATTGGTGGCCACTGTGGCTACAGAGGAAGCTGCACCTATGAC
AAAGTTCAGAGCTACAATTCCGATATCAACGAATGGAGCCTCATCACCTCCAGTCCACAT
CCAGAATATGGATTGTGCTCAGTTCCGTTTGAAAATAAGCTCTATCTAGTCGGTGGACAA
ACTACAATCACAGAATGCTATGACCCTGAACAAAATGAATGGAGAGAGATAGCTCCCATG
ATGGAAAGGAGGATGGAGTGCGGTGCCGTCATCATGAATGGATGTATTTATGTCACTGGA
GGATACTCCTACTCAAAGGGAACGTATCTTCAGGGCATTGAGAAATATGATCCAGATCTT
AATAAGTGGGAAATAGTGGGTAATCTTCCCAGTGCCATGCGGTCTCATGGGTGTGTTTGT
GTGTATAATGTCTAATTGAATCTGCAGAAATGACCAAGCAATCACTTTTTTGGAGTATAG
TTTTATAAAAAAAGAATGCAGGGTTTGAAGTTCCTTACCTGATAATTGTGTCTGGCACAT
GATAGGGGATCAGTAAATTGTAATTCCTAACCCTACTGTACTCCCAAACATGGTGATTCA
TGGTCAAGAAAAATCTTATATATATATATACACACACATATATATGTGTTCATATATATG
TATACATATATGTGTATATATACGCATGTATGTATACATATATGTGTATATATACGCATG
TATGTATGCATATGTGTGTATATATACGTATGTATGTATACATATGTGTATATATACGTA
TGTATGTATACATATATGTGTATATATGCGTATGTATGTATACATATATGTGTATATATA
CGTATGTATGTATACATATATGTGTATATATACGTATGTATGTATACATATATGTGTATA
TATACGTATGTATGTATACATATATGTGTGTATATACGTGTGTATGTATACATATATGTG
TATATATACGTGTGTATGTATACATATATGTGTATATATGCGTGTGTATGTATACATATA
TGTGTATATATACGTGTGTATGTATACATATATGTGTATATATACGTGTGTATGTATACA
TATATGTGTATATATGCGTGTGTATATATATACACATATATACGTATATATGTATATATA
TATACACAGTTGAATCAGTGGGATTAATACCTATAATCTCTGGTTTTCAAAGGTAATATG
GAATATTTGACACTTGGTAAAAGGTGAACTACCTTTGTAGTGAATCTTTTCCTCTTGGTA
GCATCAACACTGGGGATAAATCAGAACCATTCTGTGGAATGAAATGTTTCTCAAGAGCCT
ATAATATAGTAGATAGTGCATATTAAGATGTCTGGCTGGGCATGGTGGCTCATGCCTGTA
ATCCCAGCACTTTGGGAGGCTGAGGCGGGAGGATCACTTGAGCCTAGAAGTTGGAGACTA
ACCTGGCGAGACCCTGTCTCAAAAAAAAAAAAAAAAAA

>R15881
ACCCTTTTGTGACCAGCTGCATACCCCAAAACCTTTTGGAATCTGGGCTAACTGGCTGTG
CCTACATCAACAGCACCCGTGAACCCCCGTGTGCTATGCtCTGTGCAACAAAACATTCAG
AACCCACTTTCAAGATGCTGCTGCTGTGCCAGTGTGACAAAAAAAAGAGGCGCAAGCAGC
AGTACCAGCAGAGACAGTCGGTCATTTTTCACAAGCGCGCACCCGAGCAGGCCTTGTAGA
ATGAGGTTGTATCAATAGCAGTGACAAAACGCACACATCAACCCACAGACCTTAGGAGGA
GGAAGGCGAGGGCGGGGTGACTTCTGGTGATGATAAAAATGGTTTTATCACCCAGATGTG
AAAGAAGCTGCCTGTTTACTGATCCATTGAATAAACCCATTTTAATAGAAAAAGTCAATA
CCAATTCAGCAAAAAAAAA

>AF191770
TATCTATGTAACAAATCGCAGCACAGGAGTCCCCTGGGCTCCCTCAGGCTCTGGTATGAC
ATATTTGAGCCATATAAATTCAGCTTCTCCTCTGGCATCTGTTAGCCGACTCACTTGCAA
CTCCACCTCAGCAGTGGTCTCTCAGTCCTCTCAAAGCAAGGAAAGAGTACTGTGTGCTGA
GAGACCATGGCAAAGAATCCTCCAGAGAATTGTGAAGACTGTCACATTCTAAATGCAGAA
GCTTTTAAATCCAAGAAAATATGTAAATCACTTAAGATTTGTGGACTGGTGTTTGGTATC
CTGACCCTAACTCTAATTGTCCTGTTTTGGGGGAGCAAGCACTTCTGGCCGGAGGTACCC
AAAAAAGCCTATGACATGGAGCACACTTTCTACAGCAGTGGAGAGAAGAAGAAGATTTAC
ATGGAAATTGATCCTGTGACCAGAACTGAAATATTCAGAAGCGGAAATGGCACTGATGAA
ACATTGGAAGTACACGACTTTAAAAACGGATACACTGGCATCTACTTCGTGGGTCTTCAA

-continued

AAATGTTTTATCAAAACTCAGATTAAAGTGATTCCTGAATTTTCTGAACCAGAAGAGGAA
ATAGATGAGAATGAAGAAATTACCACAACTTTCTTTGAACAGTCAGTGATTTGGGTCCCA
GCAGAAAAAGCCTATTGAAAACCGAGATTTTCTTAAAAATTCCAAAATTCTGGAGATTTGT
GATAACGTGACCATGTATTGGATCAATCCCACTCTAATATCAGTTTCTGAGTTACAAGAC
TTTGAGGAGGAGGGAGAAGATCTTCACTTTCCTGCCAACGAAAAAAAAGGGATTGAACAA
AATGAACAGTGGGTGGTCCCTCAAGTGAAAGTAGAGAAGACCCGTCACGCCAGACAAGCA
AGTGAGGAAGAACTTCCAATAAATGACTATACTGAAAATGGAATAGAATTTGATCCCATG
CTGGATGAGAGAGGTTATTGTTGTATTTACTGCCGTCGAGGCAACCGCTATTGCCGCCGC
GTCTGTGAACCTTTACTAGGCTACTACCCATATCCATACTGCTACCAAGGAGGACGAGTC
ATCTGTCGTGTCATCATGCCTTGTAACTGGTGGGTGGCCCGCATGCTGGGGAGGGTCTAA
TAGGAGGTTTGAGCTCAAATGCTTAAACTGCTGGCAACATATAATAAATGCATGCTATTC
AATGAATTTCTGCCTATGAGGCATCTGGCCCCTGGTAGCCAGCTCTCCAGAATTACTTGT
AGGTAATTCCTCTCTTCATGTTCTAATAAACTTCTACATTATCAAAAAA

>BC005364
GCGGATCGCTGCTCCCTCTCGCCATGGCGCAGGTGCTGATCGTGGGCGCCGGGATGACAG
GAAGCTTGTGCGCTGCGCTGCTGAGGAGGCAGACGTCCGGTCCCTTGTACCTTGCTGTGT
GGGACAAGGCTGACGACTCAGGGGGAAGAATGACTACAGCCTGCAGTCCTCATAATCCTC
AGTGCACAGCTGACTTGGGTGCTCAGTACATCACCTGCACTCCTCATTATGCCAAAAAAC
ACCAACGTTTTTATGATGAACTGTTAGCCTATGGCGTTTTGAGGCCTCTAAGCTCGCCTA
TTGAAGGAATGGTGATGAAAGAAGGAGACTGTAACTTTGTGGCACCTCAAGGAATTTCTT
CAATTATTAAGCATTACTTGAAAGAATCAGGTGCAGAAGTCTACTTCAGACATCGTGTGA
CACAGATCAACCTAAGAGATGACAAATGGGAAGTATCCAAACAAACAGGCTCCCCTGAGC
AGTTTGATCTTATTGTTCTCACAATGCCAGTTCCTGAGATTCTGCAGCTTCAAGGTGACA
TCACCACCTTAATTAGTGAATGCCAAAGGCAGCAACTGGAGGCTGTGAGCTACTCCTCTC
GATATGCTCTGGGCCTCTTTTATGAAGCTGGTACGAAGATTGATGTCCCTTGGGCTGGGC
AGTACATCACCAGTAATCCCTGCATACGCTTCGTCTCCATTGATAATAAGAAGCGCAATA
TAGAGTCATCAGAAATTGGGCCTTCCCTCGTGATTCACACCACTGTCCCATTTGGAGTTA
CATACTTGGAACACAGCATTGAGGATGTGCAAGAGTTAGTCTTCCAGCAGCTGGAAAACA
TTTTGCCGGGTTTGCCTCAGCCAATTGCTACCAAATGCCAAAAATGGAGACATTCACAGG
TTACAAATGCTGCTGCCAACTGTCCTGGCCAAATGACTCTGCATCACAAACCTTTCCTTG
CATGTGGAGGGGATGGATTTACTCAGTCCAACTTTGATGGCTGCATCACTTCTGCCCTAT
GTGTTCTGGAAGCTTTAAAGAATTATATTTAGTGCCTATATCCTTATTCTCTATATGTGT
ATTGGGTTTTTATTTTCACAATTTTCTGTTATTGATTATTTTGTTTTCTATTTTGCTAAG
AAAAATTACTGGAAAATTGTTCTTCACTTATTATCATTTTTCATGTGGAGTATAAAATCA
ATTTTGTAATTTTGATAGTTACAACCCATGCTAGAATGGAAATTCCTCACACCTTGCACC
TTCCCTACTTTTCTGAATTGCTATGACTACTCCTTGTTGGAGGAAAAGTGGTACTTAAAA
AATAACAAACGACTCTCTCAAAAAAATTACATTAAATCACAATAACAGTTGTATGCCAA
AAACTTGATTATCCTTATGAAAATTTCAATTCTGAATAAAGAATAATCACATTATCAAAG
CCCCATC

>NM_001337
ACTCGTCTCTGGTAAAGTCTGAGCAGGACAGGGTGGCTGACTGGCAGATCCAGAGGTTCC
CTTGGCAGTCCACGCCAGGCCTTCACCATGGATCAGTTCCCTGAATCAGTGACAGAAAAC
TTTGAGTACGATGATTTGGCTGAGGCCTGTTATATTGGGGACATCGTGGTCTTTGGGACT
GTGTTCCTGTCCATATTCTACTCCGTCATCTTTGCCATTGGCCTGGTGGGAAATTTGTTG
GTAGTGTTTGCCCTCACCAACAGCAAGAAGCCCAAGAGTGTCACCGACATTTACCTCCTG
AACCTGGCCTTGTCTGATCTGCTGTTTGTAGCCACTTTGCCCTTCTGGACTCACTATTTG
ATAAATGAAAAGGGCCTCCACAATGCCATGTGCAAATTCACTACCGCCTTCTTCTTCATC
GGCTTTTTTGGAAGCATATTCTTCATCACCGTCATCAGCATTGATAGGTACCTGGCCATC
GTCCTGGCCGCCAACTCCATGAACAACCGGACCGTGCAGCATGGCGTCACCATCAGCCTA
GGCGTCTGGGCAGCAGCCATTTTGGTGGCAGCACCCCAGTTCATGTTCACAAAGCAGAAA
GAAAATGAATGCCTTGGTGACTACCCCGAGGTCCTCCAGGAAATCTGGCCCGTGCTCCGC
AATGTGGAAACAAATTTTCTTGGCTTCCTACTCCCCCTGCTCATTATGAGTTATTGCTAC
TTCAGAATCATCCAGACGCTGTTTTCCTGCAAGAACCACAAGAAAGCCAAAGCCATTAAA
CTGATCCTTCTGGTGGTCATCGTGTTTTTCCTCTTCTGGACACCCTACAACGTTATGATT
TTCCTGGAGACGCTTAAGCTCTATGACTTCTTTCCCAGTTGTGACATGAGGAAGGATCTG
AGGCTGGCCCTCAGTGTGACTGAGACGGTTGCATTTAGCCATTGTTGCCTGAATCCTCTC
ATCTATGCATTTGCTGGGGAGAAGTTCAGAAGATACCTTTACCACCTGTATGGGAAATGC
CTGGCTGTCCTGTGTGGGCGCTCAGTCCACGTTGATTTCTCCTCATCTGAATCACAAAGG
AGCAGGCATGGAAGTGTTCTGAGCAGCAATTTTACTTACCACACGAGTGATGGAGATGCA
TTGCTCCTTCTCTGAAGGGAATCCCAAAGCCTTGTGTCTACAGAGAACCTGGAGTTCCTG
AACCTGATGCTGACTAGTGAGGAAAGATTTTTGTTGTTATTTCTTACAGGCACAAAATGA
TGGACCCAATGCACACAAAACAACCCTAGAGTGTTGTTGAGAATTGTGCTCAAAATTTGA
AGAATGAACAAATTGAACTCTTTGAATGACAAAGAGTAGACATTTCTCTTACTGCAAATG
TCATCAGAACTTTTTGGTTTGCAGATGACAAAAATTCAACTCAGACTAGTTTAGTTAAAT
GAGGGTGGTGAATATTGTTCATATTGTGGCACAAGCAAAAGGGTGTCTGAGCCCTCAAAG
TGAGGGGAAACCAGGGCCTGAGCCAAGCTAGAATTCCCTCTCTCTGACTCTCAAATCTTT
TAGTCATTATAGATCCCCCAGACTTTACATGACACAGCTTTATCACCAGAGAGGGACTGA
CACCCATGTTTCTCTGGCCCCAAGGGAAAATTCCCAGGGAAGTGCTCTGATAGGCCAAGT
TTGTATCAGGTGCCCATCCCTGGAAGGTGCTGTTATCCATGGGGAAGGGATATATAAGAT
GGAAGCTTCCAGTCCAATCTCATGGAGAAGCAGAAATACATATTTCCAAGAAGTTGGATG
GGTGGGTACTATTCTGATTACACAAAACAAATGCCACACATCACCCTTACCATGTGCCTG
ATCCAGCCTCTCCCCTGATTACACCAGCCTCGTCTTCATTAAGCCCTCTTCCATCATGTC
CCCAAACCTGCAAGGGCTCCCCACTGCCTACTGCATCGAGTCAAAACTCAAATGCTTGGC
TTCTCATACGTCCACCATGGGGTCCTACCAATAGATTCCCCATTGCCTCCTCCTTCCCAA
AGGACTCCACCCATCCTATCAGCCTGTCTCTTCCATATGACCTCATGCATCTCCACCTGC
TCCCAGGCCAGTAAGGGAAATAGAAAAACCCTGCCCCCAAATAAGAAGGGATGGATTCCA
ACCCCAACTCCAGTAGCTTGGGACAAATCAAGCTTCAGTTTCCTGGTCTGTAGAAGAGGG
ATAAGGTACCTTTCACATAGAGATCATCCTTTCCAGCATGAGGAACTAGCCACCAACTCT
TGCAGGTCTCAACCCTTTTGTCTGCCTCTTAGACTTCTGCTTTCCACACCTGCACTGCTG

-continued

TGCTGTGCCCAAGTTGTGGTGCTGACAAAGCTTGGAAGAGCCTGCAGGTGCCTTGGCCGC
GTGCATAGCCCAGACACAGAAGAGGCTGGTTCTTACGATGGCACCCAGTGAGCACTCCCA
AGTCTACAGAGTGATAGCCTTCCGTAACCCAACTCTCCTGGACTGCCTTGAATATCCCCT
CCCAGTCACCTTGTGCAAGCCCCTGCCCATCTGGGAAAATACCCCATCATTCATGCTACT
GCCAACCTGGGGAGCCAGGGCTATGGGAGCAGCTTTTTTTCCCCCCTAGAAACGTTTGG
AACAATGTAAAACTTTAAAGCTCGAAAACAATTGTAATAATGCTAAAGAAAAAGTCATCC
AATCTAACCACATCAATATTGTCATTCCTGTATTCACCCGTCCAGACCTTGTTCACACTC
TCACATGTTTAGAGTTGCAATCGTAATGTACAGATGGTTTTATAATCTGATTTGTTTTCC
TCTTAACGTTAGACCACAAATAGTGCTCGCTTTCTATGTAGTTTGGTAATTATCATTTTA
GAAGACTCTACCAGACTGTGTATTCATTGAAGTCAGATGTGGTAACTGTTAAATTGCTGT
GTATCTGATAGCTCTTTGGCAGTCTATATGTTTGTATAATGAATGAGAGAATAAGTCATG
TTCCTTCAAGATCATGTACCCCAATTTACTTGCCATTACTCAATTGATAAACATTTAACT
TGTTTCCAATGTTTAGCAAATACATATTTTATAGAACTTC

>AI041545
TGAACATATTCAGGCTGATTGGGGACGTGTCCCACCTGGCGGCCATCGTCATCTTGATGG
TAGAGATCTGGAAGACGCGCTCCTGCGCCGGTATTTCTGGGAAAAGCCAGCTTCTGTCTG
CACTGGTCTTCACAACTCGTGACCTGGATCTTTTCACTTCATTTATTTCAGTGTATCACA
CATCTATCAAGGTTATCTACGTTGCCTGCTCGTATGCCACAGTGTACCTGATCTACCTTA
AATTTAAGGCAACATCGGATGGAAATCATGATACCTTCCGAGTGGAGTTTCTGGTGGTCC
CTGTGGGAGGCCTCCTCATTTTTAGTTAATCACGATTTCTCTCCTCTTGAGTACTCAAGG
GAAAGAAGCTCAGTTTGCCAGCATAAGTGCCAAAGACCATCGCCAGCATCTGTCCTTCAG
GGTGTTCGGACAGAATTCTTACCACAGCAAAGGCATAAGATGCTTGATACGGAAAATCAA
GAACTTAACTTTTTTGTTGCAGATAGTCATCAGTGGTTCTGTAAAAACGCAGAGGAAAAG
AGCCAGAAGGTTTCTGTTTAATGCATCTTGCCTTATCTTTTTTTATTACTGTGCACAAAG
ATTTTTTTACACAAACATCCTTAATGCTGTTTTAATAAATTCAGTGTGTAGCTTCAAAAA
AA

>NM_024423
GGCAGGTCTCGCTCTCGGCACCCTCCCGGCGCCCGCGTTCTCCTGGCCCTGCCCGGCATC
CCGATGGCCGCCGCTGGGCCCCGGCGCTCCGTGCGCGGAGCCGTCTGCCTGCATCTGCTG
CTGACCCTCGTGATCTTCAGTCGTGATGGTGAAGCCTGCAAAAAGGTGATACTTAATGTA
CCTTCTAAACTAGAGGCAGACAAAATAATTGGCAGAGTTAATTTGGAAGAGTGCTTCAGG
TCTGCAGACCTCATCCGGTCAAGTGATCCTGATTTCAGAGTTCTAAATGATGGGTCAGTG
TACACAGCCAGGGCTGTTGCGCTGTCTGATAAGAAAAGATCATTTACCATATGGCTTTCT
GACAAAAGGAAACAGACACAGAAAGAGGTTACTGTGCTGCTAGAACATCAGAAGAAGGTA
TCGAAGACAAGACACACTAGAGAAACTGTTCTCAGGCGTGCCAAGAGGAGATGGGCACCT
ATTCCTTGCTCTATGCAAGAGAATTCCTTGGGCCCTTTCCCATTGTTTCTTCAACAAGTT
GAATCTGATGCAGCACAGAACTATACTGTCTTCTACTCAATAAGTGGACGTGGAGTTGAT
AAAGAACCTTTAAATTTGTTTTATATAGAAAGAGACACTGGAAATCTATTTTGCACTCGG
CCTGTGGATCGTGAAGAATATGATGTTTTTGATTTGATTGCTTATGCGTCAACTGCAGAT
GGATATTCAGCAGATCTGCCCCTCCCACTACCCATCAGGGTAGAGGATGAAAATGACAAC
CACCCTGTTTTCACAGAAGCAATTTATAATTTTGAAGTTTTGGAAAGTAGTAGACCTGGT
ACTACAGTGGGGGTGGTTTGTGCCACAGACACAGATGAACCGGACACAATGCATACGCGC
CTGAAATACAGCATTTTGCAGCAGACACCAAGGTCACCTGGGCTCTTTTCTGTGCATCCC
AGCACAGGCGTAATCACCACAGTCTCTCATTATTTGGACAGAGAGGTTGTAGACAAGTAC
TCATTGATAATGAAAGTACAAGACATGGATGGCCAGTTTTTTGGATTGATAGGCACATCA
ACTTGTATCATAACAGTAACAGATTCAAATGATAATGCACCCACTTTCAGACAAAATGCT
TATGAAGCATTTGTAGAGGAAAATGCATTCAATGTGGAAATCTTACGAATACCTATAGAA
GATAAGGATTTAATTAACACTGCCAATTGGAGAGTCAATTTTACCATTTTAAAGGGAAAT
GAAAATGGACATTTCAAAATCAGCACAGACAAAGAAACTAATGAAGGTGTTCTTTCTGTT
GTAAAGCCACTGAATTATGAAGAAAACCGTCAAGTGAACCTGGAAATTGGAGTAAACAAT
GAAGCGCCATTTGCTAGAGATATTCCCAGAGTGACAGCCTTGAACAGAGCCTTGGTTACA
GTTCATGTGAGGGATCTGGATGAGGGGCCTGAATGCACTCCTGCAGCCCAATATGTGCGG
ATTAAAGAAAACTTAGCAGTGGGGTCAAAGATCAACGGCTATAAGGCATATGACCCCGAA
AATAGAAATGGCAATGGTTTAAGGTACAAAAAATTGCATGATCCTAAAGGTTGGATCACC
ATTGATGAAATTTCAGGGTCAATCATAACTTCCAAAATCCTGGATAGGGAGGTTGAAACT
CCCAAAAATGAGTTGTATAATATTACAGTCCTGGCAATAGACAAAGATGATAGATCATGT
ACTGGAACACTTGCTGTGAACATTGAAGATGTAAATGATAATCCACCAGAAATACTTCAA
GAATATGTAGTCATTTGCAAACCAAAAATGGGGTATACCGACATTTTAGCTGTTGATCCT
GATGAACCTGTCCATGGAGCTCCATTTTATTTCAGTTTGCCCAATACTTCTCCAGAAATC
AGTAGACTGTGGAGCCTCACCAAAGTTAATGATACAGCTGCCCGTCTTTCATATCAGAAA
AATGCTGGATTTCAAGAATATACCATTCCTATTACTGTAAAAGACAGGGCCGGCCAAGCT
GCAACAAAATTATTGAGAGTTAATCTGTGTGAATGTACTCATCCAACTCAGTGTCGTGCG
ACTTCAAGGAGTACAGGAGTAATACTTGGAAAATGGGCAATCCTTGCAATATTACTGGGT
ATAGCACTGCTCTTTTCTGTATTGCTAACTTTAGTATGTGGAGTTTTTGGTGCAACTAAA
GGGAAACGTTTTCCTGAAGATTTAGCACAGCAAAACTTAATTATATCAAACACAGAAGCA
CCTGGAGACGATAGAGTGTGCTCTGCCAATGGATTTATGACCCAAACTACCAACAACTCT
AGCCAAGGTTTTTGTGGTACTATGGGATCAGGAATGAAAAATGGAGGGCAGGAAACCATT
GAAATGATGAAAGGAGGAAACCAGACCTTGGAATCCTGCCGGGGGGCTGGGCATCATCAT
ACCCTGGACTCCTGCAGGGGAGGACACACGGAGGTGGACAACTGCAGATACACTTACTCG
GAGTGGCACAGTTTTACTCAACCCCGTCTCGGTGAAGAATCCATTAGAGGACACACTGGT
TAAAAATTAAACATAAAAGAAATTGCATCGATGTAATCAGAATGAAGACCGCATGCCATC
CCAAGATTATGTCCTCACTTATAACTATGAGGGAAGAGGATCTCCAGCTGGTTCTGTGGG
CTGCTGCAGTGAAAAGCAGGAAGAAGATGGCCTTGACTTTTTAAATAATTTGGAACCCAA
ATTTATTACATTAGCAGAAGCATGCACAAAGAGATAATGTCACAGTGCTACAATTAGGTC
TTTGTCAGACATTCTGGAGGTTTCCAAAAATAATATTGTAAAGTTCAATTTCAACATGTA
TGTATATGATGATTTTTTTCTCAATTTTGAATTATGCTACTCACCAATTTATATTTTTAA
AGCCAGTTGTTGCTTATCTTTTCCAAAAAGTGAAAAATGTTAAAACAGACAACTGGTAAA
TCTCAAACTCCAGCACTGGAATTAAGGTCTCTAAAGCATCTGCTCTTTTTTTTTTTTACG
GATATTTTAGTAATAAATATGCTGGATAAATATTAGTCCAACAATAGCTAAGTTATGCTA

-continued

ATATCACATTATTATGTATTCACTTTAAGTGATAGTTTAAAAAATAAACAAGAAATATTG
AGTATCACTATGTGAAGAAAGTTTTGGAAAAGAAACAATGAAGACTGAATTAAATTAAAA
ATGTTGCAGCTCATAAAGAATTGGGACTCACCCCTACTGCACTACCAAATTCATTTGACT
TTGGAGGCAAAATGTGTTGAAGTGCCCTATGAAGTAGCAATTTTCTATAGGAATATAGTT
GGAAATAAATGTGTGTGTGTATATTATTATTAATCAATGCAATATTTAAAATGAAATGAG
AACAAAGAGGAAAATGGTAAAAACTTGAAATGAGGCTGGGGTATAGTTTGTCCTACAATA
GAAAAAAGAGAGAGCTTCCTAGGCCTGGGCTCTTAAATGCTGCATTATAACTGAGTCTAT
GAGGAAATAGTTCCTGTCCAATTTGTGTAATTTGTTTAAAATTGTAAATAAATTAAACTT
TTCTGGTTTCTGTGGGAAGGAAATAGGGAATCCAATGGAACAGTAGCTTTGCTTTGCAGT
CTGTTTCAAGATTTCTGCATCCACAAGTTAGTAGCAAACTGGGGAATACTCGCTGCAGCT
GGGGTTCCCTGCTTTTTGGTAGCAAGGGTCCAGAGATGAGGTGTTTTTTTCGGGGAGCTA
ATAACAAAAACATTTTAAAACTTACCTTTACTGAAGTTAAATCCTCTATTGCTGTTTCTA
TTCTCTCTTATAGTGACCAACATCTTTTTAATTTAGATCCAAATAACCATGTCCTCCTAG
AGTTTAGAGGCTAGAGGGAGCTGAGGGGAGGATCTTACTGAAAGCACCCTGGGGAGATTG
ATTGTCCTTAAACCTAAGCCCCACAAACTTGACACCTGATCAGGTCTGGGAGCTACAAAA
TTTCATTTTTCTCCTCACTGCCCTTCTTCTGAGTGGCATTGGCCTGAATCAAGGAAAGCC
AGGCCTTGTGGGCCCCCTTCTTTCGGCTTTCTGCTAAAGCAACACCTCCAGCAGAGATTC
CCTTAAGTGACTCCAGGTTTTCCACCATCCTTCAGCGTGAATTAATTTTTAATCAGTTTG
CTTTCTCCAGAGAAATTTTAAAATAATAGAAGAAATAGAAATTTTGAATGTATAAAAGAA
AAAGATCAAGTTGTCATTTTAGAACAGAGGGAACTTTGGGAGAAAGCAGCCCAAGTAGGT
TATTTGTACAGTCAGAGGGCAACAGGAAGATGCAGGCCTTCAAGGGCAAGGAGAGGCCAC
AAGGAATATGGGTGGGAGTAAAAGCAACATCGTCTGCTTCATACTTTTTCCTAGGCTTGG
CACTGCCTTTTCCTTTCTCAGGCCAATGGCAACTGCCATTTGAGTCCGGTGAGGGATCAG
CCAACCTCTTCTCTATGGCTCACCTTATTTGGAGTGAGAAATCAAGGAGACAGAGCTGAC
TGCATGATGAGTCTGAAGGCATTTGCAGGATGAGCCTGAACTGGTTGTGCAGAACAAACA
AGGCATTCATGGGAATTGTTGTATTCCTTCTGCAGCCCTCCTTCTGGGCACTAAGAAGGT
CTATGAATTAAATGCCTATCTAAAATTCTGATTTATTCCTACATTTTCTGTTTTCTAATT
TGACCCTAAAATCTATGTGTTTTAGACTTAGACTTTTTATTGCCCCCCCCCCCTTTTTTT
TTGAGACGGAGTCTCGCTCTGACGCACAGGCTGGAGTGCAGTGGCTCCGATCTCTGCTCA
CTGAAAGCTCCGCCTCCCGGGTTCATGCCATTCTCCTGCCTCAGCCTCCTGAGTAGCTGG
GACTACAGGCGCCCACCACCACGCCCGGCTAATTTTTTGTATTTTTAATAGAGACGGGGT
TTCACTGTGTTAGCCAGGATGGTCTCGATCTCCTGACCTCGTGATCCGCCTGCCTCGGCC
TCCCAAAGTGCTGGGATTACAGGCATGACCCACCGCTCCCGGCCTTGTTTTCCGTTTAAA
GTCGTCTTCTTTTAATGTAATCATTTTGAACATGTGTGAAAGTTGATCATACGAATTGGA
TCAATCTTGAAATACTCAACCAAAAGACAGTCGAGAAGCCAGGGGGAGAAAGAACTCAGG
GCACAAAATATTGGTCTGAGAATGGAATTCTCTGTAAGCCTAGTTGCTGAAATTTCCTGC
TGTAACCAGAAGCCAGTTTTATCTAACGGCTACTGAAACACCCACTGTGTTTTGCTCACT
CCCACTCACCGATCAAAACCTGCTACCTCCCCAAGACTTTACTAGTGCCGATAAACTTTC
TCAAAGAGCAACCAGTATCACTTCCCTGTTTATAAAACCTCTAACCATCTCTTTGTTCTT
TGAACATGCTGAAAACCACCTGGTCTGCATGTATGCCCGAATTTGTAATTCTTTTCTCTC
AAATGAAAATTTAATTTTAGGGATTCATTTCTATATTTTCACATATGTAGTATTATTATT
TCCTTATATGTGTAAGGTGAAATTTATGGTATTTGAGTGTGCAAGAAAATATATTTTTAA
AGCTTTCATTTTTCCCCCAGTGAATGATTTAGAATTTTTTATGTAAATATACAGAATGTT
TTTTCTTACTTTTATAAGGAAGCAGCTGTCTAAAATGCAGTGGGGTTTGTTTTGCAATGT
TTTAAACAGAGTTTTAGTATTGCTATTAAAAGAAGTTACTTTGCTTTTAAAGAAACTTGG
CTGCTTAAAATAAGCAAAAATTGGATGCATAAAGTAATATTTACAGATGTGGGGAGATGT
AATAAAACAATATTAACTTGGAAAAAAA

>AA745593
GACTCAGNCTTCAGCCGCTCTCCTCCCCCTGGGCAAACAGGACTCATCTGATGATGTGAG
AAGAGTTCAGAGGAGGGAGAAAAATCGTATTGCCGCCCAGAAGAGCCGACAGAGGCAGAC
ACAGAAGGCCGACACCCTGCACCTGGAGAGCGAAGACCTGGAGAAACAGAACGCGGCTCT
ACGCAAGGAGATCAAGCAGCTCACAGAGGAACTGAAGTACTTCACGTCGGTGCTGAACAG
CCACGAGCCCCTGTGCTCGGTGCTGGCCGCCAGCACGCCCTCGCCCCCCGAGGTGGTGTA
CAGCGCCCACGCATTCCACCAACCTCATGTCAGCTCCCCGCGCTTCCAGCCCTGAGCTTC
CGATGCGGGGAGAGCAGAGCCTCGGGAGGGGCACACAGACTGTGGCAGAGCTGCGCCCAT
CCCGCAGAGGCCCCTGTCCACCTGGAGACCCGGAGACAGAGGCCTGGACAAGGAGTGAAC
ACGGGAACTGTCACGACTGGAAGGGCGTGAGGCCTCCCAGCAGTGCCGCAGCGTTTCGAG
GGGCGTGTGCTGGACCCCACCACTGTGGGTTGCAGGCCCAATGCAGAAGAGTATTAAGAA
AGATGCTCAAGTCCCATGGCACAGAGCAAGGCGGGCAGGGAACGGTTATTTTTCTAAATA
AATGCTTTAAAAGAAAAAAAAAAAAAAAAAAAAAA

>AI985118
ATGCAAGGNNTAGGCAAAGATTGTTGACCCNGGAGATAGAGGTNNCAATGAGCCAGATCA
TTCCATTGCATTCCAGCTTGGGCGACAGAATGAGACTCTGTCTCAAAATTAAAAANCAAA
AAACCAAAANCAAATAGATGAAAAAGTAGACTGGAGACAAATAAAAGTGAGTTTCTAAAG
GAAATTCACAGTAATGCTGCATTAAACACTAAGCTCACTTAGGTCACTTTCTAGTGAGCT
AACCGTAACAGAGAGCCTACAGGATACACGTGAGATAATGTCACGTGTAGAAGATCGTTG
TGAATTAAAGTTCAAAATTAAGACTTCTTAGATTATGATGTAGATTTTAGAGCTCCTTAA
AACATAAAGCGAATCTTATAAATGTTCAATTCTAAAGTTATTCCACTTGGAAAAATTAGC
TTTTGGGACAATTTTTAAGAACTTTTGTGTAAAATGCAGCTCCATGTTTAGCATAATCTA
AAAATAATTTCAAGCAATCCAGAATCTTCCAAGAATGTTATTAAAGCTTTAAAACAAAGC
AAAACAAAAAGACCCTTTTGTGCCTTATATGGGAAGACTAAAAAAA

>AB038160
ACCGGGCACCGGACGGCTCGGGTACTTTCGTTCTTAATTAGGTCATGCCCGTGTGAGCCA
GGAAAGGGCTGTGTTTATGGGAAGCCAGTAACACTGTGGCCTACTATCTCTTCCGTGGTG
CCATCTACATTTTTGGGACTCGGGAATTATGAGGTAGAGGTGGAGGCGGAGCCGGATGTC
AGAGGTCCTGAAATAGTCACCATGGGGGAAAATGATCCGCCTGCTGTTGAAGCCCCCTTC
TCATTCCGATCGCTTTTTGGCCTTGATGATTTGAAAATAAGTCCTGTTGCACCAGATGCA
GATGCTGTTGCTGCACAGATCCTGTCACTGCTGCCATTGAAGTTTTTTCCAATCATCGTC

-continued

ATTGGGATCATTGCATTGATATTAGCACTGGCCATTGGTCTGGGCATCCACTTCGACTGC
TCAGGGAAGTACAGATGTCGCTCATCCTTTAAGTGTATCGAGCTGATAGCTCGATGTGAC
GGAGTCTCGGATTGCAAAGACGGGGAGGACGAGTACCGCTGTGTCCGGGTGGGTGGTCAG
AATGCCGTGCTCCAGGTGTTCACAGCTGCTTCGTGGAAGACCATGTGCTCCGATGACTGG
AAGGGTCACTACGCAAATGTTGCCTGTGCCCAACTGGGTTTCCCAAGCTATGTGAGTTCA
GATAACCTCAGAGTGAGCTCGCTGGAGGGGCAGTTCCGGGAGGAGTTTGTGTCCATCGAT
CACCTCTTGCCAGATGACAAGGTGACTGCATTACACCACTCAGTATATGTGAGGGAGGGA
TGTGCCTCTGGCCACGTGGTTACCTTGCAGTGCACAGCCTGTGGTCATAGAAGGGGCTAC
AGCTCACGCATCGTGGGTGGAAACATGTCCTTGCTCTCGCAGTGGCCCTGGCAGGCCAGC
CTTCAGTTCCAGGGCTACCACCTGTGCGGGGCTCTGTCATCACGCCCCTGTGGATCATC
ACTGCTGCACACTGTGTTTATGACTTGTACCTCCCCAAGTCATGGACCATCCAGGTGGGT
CTAGTTTCCCTGTTGGACAATCCAGCCCCATCCCACTTGGTGGAGAAGATTGTCTACCAC
AGCAAGTACAAGCCAAAGAGGCTGGGCAATGACATCGCCCTTATGAAGCTGGCCGGGCCA
CTCACGTTCAATGGTACATCTGGGTCTCTATGTGGTTCTGCAGCTCTTCCTTTGTTTCAA
GAGGATTTGCAATTGCTCATTGAAGCATTCTTATGATGGCTGCTTTATAATCCTTGTCAG
ATATTAATAATTCCAACTCCTGATTCATGTTGGTGTTGGCATCAGTTGATTATCTTTTCT
CATTAAAATTGTGATGCTCCTAA

>X69699
TTCAGAAGGAGGAGAGACACCGGGCCCAGGGCACCCTCGCGGGCGGGCGGACCCAAGCAG
TGAGGGCCTGCAGCCGGCCGGCCAGGGCAGCGGCAGGCGCGGCCCGGACCTACGGGAGGA
AGCCCCGAGCCCTCGGCGGGCTGCGAGCGACTCCCCGGCGATGCCTCACAACTCCATCAG
ATCTGGCCATGGAGGGCTGAACCAGCTGGGAGGGGCCTTTGTGAATGGCAGACCTCTGCC
GGAAGTGGTCCGCCAGCGCATCGTAGACCTGGCCCACCAGGGTGTAAGGCCCTGCGACAT
CTCTCGCCAGCTCCGCGTCAGCCATGGCTGCGTCAGCAAGATCCTTGGCAGGTACTACGA
GACTGGCAGCATCCGGCCTGGAGTGATAGGGGGCTCCAAGCCCAAGGTGGCCACCCCCAA
GGTGGTGGAGAAGATTGGGGACTACAAACGCCAGAACCCTACCATGTTTGCCTGGGAGAT
CCGAGACCGGCTCCTGGCTGAGGGCGTCTGTGACAATGACACTGTGCCCAGTGTCAGCTC
CATTAATAGAATCATCCGGACCAAAGTGCAGCAACCATTCAACCTCCCTATGGACAGCTG
CGTGGCCACCAAGTCCCTGAGTCCCGGACACACGCTGATCCCCAGCTCAGCTGTAACTCC
CCCGGAGTCACCCCAGTCGGATTCCCTGGGCTCCACCTACTCCATCAATGGGCTCCTGGG
CATCGCTCAGCCTGGCAGCGACAAGAGGAAAATGGATGACAGTGATCAGGATAGCTGCCG
ACTAAGCATTGACTCACAGAGCAGCAGCAGCGGACCCCGAAAGCACCTTCGCACGGATGC
CTTCAGCCAGCACCACCTCGAGCCGCTCGAGTGCCCATTTGAGCGGCAGCACTACCCAGA
GGCCTATGCCTCCCCCAGCCACACCAAAGGCGAGCAGGGCCTCTACCCGCTGCCCTTGCT
CAACAGCACCCTGGACGACGGGAAGGCCACCCTGACCCCTTCCAACACGCCACTGGGGCG
CAACCTCTCGACTCACCAGACCTACCCCGTGGTGGCAGATCCTCACTCACCCTTGGCCAT
AAAGCAGGAAACCCCCGAGGTGTCCAGTTCTAGCTCCACCCCTTGCTCTTTATCTAGCTC
CGCCCTTTTGGATCTGCAGCAAGTCGGCTCCGGGGTCCCGCCCTTCAATGCCTTTCCCCA
TGCTGCCTCCGTGTACGGGCAGTTCACGGGCCAGGCCCTCCTCTCAGGGCGAGAGATGGT
GGGGCCCACGCTGCCCGGATACCCACCCCACATCCCCACCAGCGGACAGGGCAGCTATGC
CTCCTCTGCCATCGCAGGCATGGTGGCAGGAAGTGAATACTCTGGCAATGCCTATGGCCA
CACCCCCTACTCCTCCTACAGCGAGGCCTGGGGCTTCCCCAACTCCAGCTTGCTGAGTTC
CCCATATTATTACAGTTCCACATCAAGGCCGAGTGCACCGCCCACCACTGCCACGGCCTT
TGACCATCTGTAGTTGCCATGGGGACAGTGGGAGCGACTGAGCAACAGGAGGACTCAGCC
TGGGACAGGCCCCAGAGAGTCACACAAAGGAATCTTTATTATTACATGAAAAATAACCAC
AAGTCCAGCATTGCGGCACACTCCCTGTGTGGTTAATTTAATGAACCATGAAAGACAGGA
TGACCTTGGACAAGGCCAAACTGTCCTCCAAGACTCCTTAATGAGGGGCAGGAGTCCCAG
GGAAAGAGAACCATGCCATGCTGAAAAAGACAAAATTGAAGAAGAAATGTAGCCCCAGCC
GGTACCCTCCAAAGGAGAGAAGAAGCAATAGCCGAGGAACTTGGGGGGATGGCGAATGGT
TCCTGCCCGGGCCCAAGGGTGCACAGGGCACCTCCATGGCTCCATTATTAACACAACTCT
AGCAATTATGGACCATAAGCACTTCCCTCCAGCCCACAAGTCACAGCCTGGTGCCGAGGC
TCTGCTCACCAGCCACCCAGGGAGTCACCTCCCTCAGCCTCCCGCCTGCCCCACACGGAG
GCTCTGGCTGTCCTCTTTCCTCCACTCCATTTGCTTGGCTCTTTCTACACCTCCCTCTTG
GATGGGCTGAGGGCTGGAGCGAGTCCCTCAGAAATTCCACCAGGCTGTCAGCTGACCTCT
TTTTCCTGCTGCTGTGAAGGTATAGCACCACCCAGGTCCTCCTGCAGTGCGGCATCCCCT
TGGCAGCTGCCGTCAGCCAGGCCAGCCCCAGGGAGCTTAAAACAGACATTCCACAGGGCC
TGGGCCCCTGGGAGGTGAGGTGTGGTGTGCGGCTTCACCCAGGGCAGAACAAGGCAGAAT
CGCAGGAAACCCGCTTCCCCTTCCTGACAGCTCCTGCCAAGCCAAATGTGCTTCCTGCAG
CTCACGCCCACCAGCTACTGAAGGGACCCAAGGCACCCCCTGAAGCCAGCGATAGAGGGT
CCCTCTCTGCTCCCCAGCAGCTCCTGCCCCCAAGGCCTGACTGTATATACTGTAAATGAA
ACTTTGTTTGGGTCAAGCTTCCTTCTTTCTAACCCCCAGACTTTGGCCTCTGAGTGAAAT
GTCTCTCTTTGCCCTGTGGGGCTTCTCTCCTTGATGCTTCTTTCTTTTTTTAAAGACAAC
CTGCCATTACCACATGACTCAATAAACCATTGCTCTTCAAAAAAAAAAAAAAAAAAAAAA
AAAAAAAAAAA

>AK025615
TGCTTCATAAAATTTACCTAAGCAAGTGGTCTTGCTTGCCTCAAATCCAAGCAGTCTTGA
ACACTTGGAGGCAATTAATGAGTATATCTTAGTCAAAAGAATTGTTGGAGCTTTTTATTA
AAGCTGCAGTTTCAGTTCTGCTTTTGGGGAATTGTGCTATGAAAGCAGCTGCCAAAATAA
GCTCATTTATTTTCTTCAATCCCACTCAGTGCTCAGTCACTATATTCTGTTTCCTTTTTT
TTTTTCAAGTTGCATATTTGGTTTCCCCTTATGATTGGGAAAGATGAATTTTCAGCAGAA
AACAGTGTTTGTTCACTTTCAAAGAGTGATAGTTTCTAAAACATTTAGAGCAATAAATAT
TCATCAGAGGTACCAAGTAAGCCAGCAGAAGAGTTAAGGGTTAGAGAAATCCCTTATTTC
ATGTCTTGACTCTAAAATGATCAAAGTACTTTTCCTTGTAATGTGGATTTCTTCTTATGC
GGATATGCAAAAACTTCAGTTATACGTAGTAATGCTAGCAGGTAATTTTAGTGGACATTT
TATAACAACTGTCACTTTGTTTTGCCACATGTAGAGTTTGTTCAGCTATTTTCCAGATAT
CTCCCCACAAAAGGAGGCAAAGGGTACCAGCTTTTCAATGAGCATTACCTATTACTTGGC
AAAGATGATGAAGACTCTATTAATAGTTCATTTGATAAATGTTGACATAACCAACAATAG
AGATTAGGAAGTTAGTTTTAAGAAATCAATAGCATATAGACATTACCCTCATGGAGTTTG
TATTCTACTACTTGAACTGATTGTAGCTATAAAAGCATAGTTAGATAGCTGAATAGTTAG

-continued

ATCATAAGCAAAGAAGGCCAGAACACATCTCTTATCAAGAAATCAATGAATAGTTTATCT
CATTTTTAAAGCAACTTTATCCTTCTTTAATTCCTTCCTTTCTTCTAGTGCAAAACTACT
TAATAAGGTTGGTGTTTAGGTTAGTGTTCACACCATTCCTCATCTGGTGTGAATTACCTT
CTCTTTCTTTACTATTTACTACCAACCTAGTACATGTGTTGACTGAATTCTTTTCAAACA
ATGTTGAGTTATCATGGTGCACCTAATAAATTAACACCACAGATTACAGCATCCTTGCTG
ATTTTCTCAGCAAAGCCAGATTAGATGGAAATAAACAAAGAAAATGATCCTAGAGTGAAT
TTTTCTAGAAAATATCTATTATGAACCATGCTGTTTAAAGTATTAGCTTGAAGGTGATGG
ATCCAGCTATTCAGAAAATAACTTTCATATAACCATGATTTTGCACAGTATGAGGTCTTA
AATGTGTGGAAAGAGATAAATTTTTTATCATTACCACAAACCCCTTTTAAAGATTCAAAG
GTGGAAGAAAGTGATTTATTTTTTCTCTTCAGCATACATATATAAAAGACTTGTCAGATG
TTTAATTTGGGGAGGTTGATAATGAAACATATCAACAGAGTATAGTAGTTATAGTAGTGT
TTGTGGGTAAATAATTTCCTGGGGTCAGACATATATAAACATATTTGCTTCAAAATGATA
AAGGCATGAAATCAGTCTTAAAAATTGAAATGGGGGTGATGGGGGAGAAAAAGAAGAACA
AATTTGAAGTGCCCTTTCAAATCTGCTGGATACAAGTATTGAAGTTTTAAGTCATCTTAT
TCTGTCTGAAAGTGTATTTTTCATTCTACAATAGACCCAATCAACAAGACGTATAACTTG
AGTTGCATGATGTTCAGTTTATGTAATCTACTGTTGGGATGGTAAGAATTGATGTAGGCT
GTGGTGTAAGAATGAATTAAAATATAGTTTCACTGGCTTTTCTCTACATATCCACTATCA
CAATGGCTAGGTTTCCTGTTGCTCACTGTTGGATTCTGGAGAAAAATTTAATGAAAGATG
ATATCAGAGGAAGAATAAGTGGAGGTAGAGAAGAAAGGAGTGATAGAGGAGGGGAAAAAA
ACAAAACATATTTTTGTGTTATCCAAAGGAGCTTTTTCCTTATTCTGTCAAGCATTGAGA
TCTTCTTCAGCTTTCAATGTAGTTGCTAAATACAAATAATGCTACTAGGTAGTGACTAAA
TATAGCAAACACTTCATCAGATATTAGAATTAGGTCACACTATTGAGGTTATAATCTGAA
GGTTGTGTTACATAGAAACCACTTTAGATTATTATCAACTTGGGCTAGGCTTTATTTTAT
AATAGCATAGTAAGTAATATCTATTGTGTCATTTCTTCAACCATTTTATTCTAAGATCCA
TGAAGCTTCTTGAGGCCAAATAAAATAATAAGTTTAGACAAGAAGTAGATTGTGACTTTT
TTTCCCTTAGAGATACTATTTACTATCTCCTATCCTGATAGGTGGAAGGTTTACTGAATT
GGAAATTGGTTGACTATTAGTTTTTAACTAAAATGTGCAATAACACATTGCAGTTTCCTC
AAACTAGTTTCCTATGATCATTAAACTCATTCTCAGGGTTAAGAAAGGAATGTAAATTTC
TGCCTCAATTTGTACTTCATCAATAAGTTTTTGAAGAGTGCAGATTTTTAGTCAGGTCTT
AAAAATAAACTCACAAATCTGGATGCATTTCTAAATTCTGCAAATGTTTCCTGGGGTGAC
TTAACAAGGAATAATCCCACAATATACCTAGCTACCTAATACATGGAGCTGGGGCTCAAC
CCACTGTTTTTAAGGATTTGCGCTTACTTGTGGCTGAGGAAAAATAAGTAGTTCGAGGAA
GTAGTTTTTAAATGTGAGCTTATAGATAGAAACAGAATATCAACTTAATTATGAAATTGT
TAGAACCTGTTCTCTTGTATCTGAATCTGATTGCAATTACTATTGTACTGATAGACTCCA
GCCATTGCAAGTCTCAGATATCTTAGCTGTGTAGTGATTCTTGAAATTCTTTTTAAGAAA
AATTGAGTAGAAAGAAATAAACCCTTTGTAAATGAGGCTTGGCTTTTGTGAAAGATCATC
CGCAGGCTATGTTAAAAGGATTTTAGCTCACTAAAAGTGTAATAATGGAAATGTGGAAAA
TATCGTAGGTAAAGGAAACTACCTCATGCTCTGAAGGTTTTGTAGAAGCACAATTAAACA
TCTAAAATGGCTTTGTTACACCAGAGCCATCTGGTGTGAAGAACTCTATATTTGTATGTT
GAGAGGGCATGGAATAATTGTATTTTGCTGGCAATAGACACATTCTTTATTATTTGCAGA
TTCCTCATCAAATCTGTAATTATGCACAGTTTCTGTTATCAATAAAACAAAAGAATCCTG
TTAAAAAAAAAAAAAAAAAAAA

>AW118445
TGGCTCTCTCCTTCAAAAGGNCCAGGCCCTGTCCCCCTTTCTCCCCGANTCCAACCCCAG
CTCCCCTGTGAAGAAAAAAGTTAAAAAATTTGTTATTTATTTGCTTTTTGCGTTGGGATG
GGTTCGTGTCCAGTCCCGGGGGTCTGATATGGCCATCACAGGCTGGGTGTTCCCAGCAGC
CCTGGCTTGGGGGCTTGACGCCCTTCCCCTTGCCCCAGGCCATCATCTCCCCACCTCTCC
TCCCCTCTCCTCAGTTTTGCCGACTGCTTTTCATCTGAGTCACCATTTACTCCAAGCATG
TATTCCAGACTTGTCACTGACTTTCCTTCTGGAGCAGGTGGCTAGAAAAAGAGGCTGTGG
GCAGGAAAGAAAGGCTCCTGTTTCTCATTTGTGAGGCCAGCCTCTGGCTTTTCTGCCGTG
GATTCTCCCCCTGTCTTCTCCCCTCAGCAATTCCTGCAAAGGGTTAAAAATTTAACTGGT
TTTTACTACTGATGACTTGATTTAAAAAAAATACAAAGATGCTGGATGCTAACTTGATAC
TAACCATCAGATTGTACAGTTTGGTTGTTGCTGTAAATATGGTAGCGTTTTGTTGTTGTT
GTTTTTTCATGCCCCATACTACTGAATAAACTAGTTCTGTGCGGGTAAAAAAAAAAAAAA
AAAAAAAAAAA

>AL137761
CACAAAGAAAAAAGAAATACCTGTAGAAGCGCATCGAAAGCTCCTGGAACAGAGTTGTGT
CTCATATTTGCAAAGATGCAGAAAAAATAAACCCGGGACATCCAGCTTTCTTTTCCTTTC
TTCTTTGACTATTCTGAGAAGCTATGCGACTAGGAGCACATTTTAGGTAAACACGTGGCT
TGAGTAGCCATAAGGCCACTCTTCCCTGTCGTGTGACCCGCGCCTGGGCCTTTAAGAGAT
ATTGGTGTTTGAAAAGGGAGGAATCTGTTTGCCCTCAGATATTTAGTTCAACTGCCTGCA
TTGCTTCCTATTTTGTTGTCCAACTCTGTAGTAGTTAGCACTGGCCTTACCAACATGTAA
AGAAATTTTCTTTACTGCCCCATGAGTAGTTGGAGGCAAAGAGAAATTTTTAAAGCGCAG
AAAAAGGCCTGCAGGGAGATGGAATTTGTTCTGCCAGAGAAACGAGATGATAGCTGTATT
TAATAAAGTTACTGACCTCTTGTCAAAATTTAAAACGCAAAAGAAGATGTTTCAAAATGC
AGAGAATGTCAGAAAACAAAAACTACAGGGACCAGACCAGTATAATGTTTAGTTTTCATT
ATACTAACTTTTGTCTAGACTGGAGTTGATTCACTATTTTTTCTTTAACTCCTCAGGAAG
CAAACCTTCCCGATGATGAAGACTTCTTGAAGGATTTCATGGGTGATTTGGGATCCCAGG
ACCATTTGGCTAGTGTGCCTAGGTGACCACATGATTGCTGTTTTACCAGGAATGCAGCAT
CCCATTGACAAAACAAGTGCTCTGAGAAGGTTTAAAATACTACAGAGAATATGGGAACAC
AGACCTTGAAATTTAGCTGAGTTGTAACAGCTGAAACTCCAAGAGGTGTCTTCCTTGTTT
GAGGTGAAACTAGTGTTGCTTCCAGAGGGCAGCTGGAAACCGTAAAGCTGTTTGGAAATC
TTTTTGACTGACTTGCTGACAAAGAGGTACTGTGATGCATTTTAACAATATCTAAGTTGA
TTTTTTTTTAAATCAAGGAAAATAAAAACCAAGCATGAATGCTATGGTATGTGCCCCTTT
TGACCATCCTGGGCTGATTAACATCATTTAAATCAAAGTAATCATAAAAAGGCATATTCT
ACTTCAATTATGTGGTCAAATAAGAGTAAACACACACACTCACACATGCTGACCCCAATT
GCCAGAGCATTACTGCACTATAAATTACGGTTAATTCCCAAATTATACTACTGTTTATCT
TATTTAACAAGTCAGAAAGCACTTTTAAAATAACTTGAGGGCTACAAGGTCATTCTATTA
ATGTCATTCTCCATTCGGGTTGTAGGCATGTGGAAGTACCCATTAAAAGATAAGTTAGAG

-continued

TTTAAATACTGATAAACAAAACCTTTTATTGCAACTGGACAGTTTCTGGAGAGTTAGCGG
AAGAATCTTGGAGTTTCCTTTGGTCAGATGAATACAACATTTCACTTTTGCAGCACTATT
TAGAATGTACTCCATGGTTCTCTTGTTCCCAACTTCCAAAAAGAACAGAAAACTTTGGTT
TACACAGAACACGGGCATCTGAGGCAGGACCTCTTCCCTGCCCTTTGATCTGACTCACAC
CTCCACATATGACGTAATCAACCCAAATTTGACACCAATTCACTCTTTTCTGCAAAGGGC
ATATTTTGAAACAAGGGACAGCCTGAGGGCGGCTATAATGAGAATGTTCATGGGGGTTAC
TGGGTCCCTAATTCTGAACTTGCTTATGACACCCAGAGTGAATAGATTCAGATTCAGAAC
CTTCTGAGAAATAACCCAAAGAAAATTTGTTACCCAGCCAATTCTTCGAAAGCTTAATAT
CAAAATATATCTTTTCAAGAAGAAAATCGTTAGAGAGAAGAATGTGGAGGGGAGAGAAAT
GGGTTTCTCATTGATATGATATTTTGTTAACCATTTCATTTTGAATTATTCAAGTTTTGG
TTAATATTGTATTCTTTTTTCGTAACTATTTTACCGTGAGAGTAGGTCATTGGGTTACTT
AGATATTTATTTTTACACAGTTATTAGTCTTCAGATAGTTTTATTTTACTTCATATGATT
TTAGTTTTTGTCAGTATAATTTTAAATCATGTTTTTCTTGGTCATCTCTTTGTGTATATT
GTGTAATTGGATTTTCATTGACTGCAAGTGGAGTGTTTGCCACTCAATTCAGTACTCAGT
ACTATGGTGACTTGTTTTCAAATAAGTCTCAGATACACATTTAGGGAGCCTTTGCTGGCC
GAATATAGACTCTGTCAGGACAGCAGGTCCCCTGATCTAAGAATTTTCCCCAATGGTTGC
TCTAAAAATGCTGCTATTTTGCTGTTCACTGTATTGCACTTAGTTAAAAAGAAGATAATG
TGAAAGATGAGAGCAGTTTTTTAAAGGATCTTTTCATATACCCAATTCCCTTATTTTCAG
ATGTCCCATCAATTTTAGATATGAAAGCTTTAAGTAAAAGTGTGTATGCCTTTCTACTGT
CAGAACAGGATGGATGCAGCCTGGGTCAGATTTATTTAAGATAAAAATCATGCAGACTCA
TCATTCATATCATAGGTGAAAAATGTAAAAACCAAATGGTTTCCACTAAAGCCACCAAGA
TCTTTTAGAAATGTTTGCACCTTTGGTGGTGGCACAGGAAAAGAGAAGAATTCAGCTGGA
GTGAATTCTAGAAGTAGATATCAGAAACGGGGCATGAAGAACAGGGGAACTGGGTGGCAT
CAGACTCCTAAAGAAGTGAGTTAATTTTCCTTCCCTTCCATTCAGATTCATGCCACAGCT
CCATATCTTGAGTATGTGTAAGAGGTGAGTTCCTTCTTCAGCCAGGGGCGGTGGCTCATG
CCTTTAATCCCAATGCTTTGGGAGGCCAAGGTGGGAGGATCACTTGTGCCTTGGGGTTCA
AGGTTGCAGTGAACCATGATTGCACCACTGCACTCCAGCCTGAGTGACAGAGCAAGACCC
TGTCTCTAAAAATATATATAAAAAGTAAAACTAAAGAACTTCTTGCCTAAACCTGAATTA
CCGCAATTTGCTGAGTGACTTTGAGAAAAATCAGACTGTTTAGTTCAGTCGGGATGAAAA
GCTTGCGATTGCTTCCCACAAGAATGGGCAATAGTGACGGCTGCAAGGTACTTTTATTTG
TTCATGAAAGAACGACAATTTTTCAAAATGTAATTAAACATAATAGAATGTTTTAAACTA
CTGGGCACTGAAACTGGAAGAAAAAGGAGGCTTTATTGAACATTCCCCTTTTTCAGTTGG
TTCAAAGTTCAGCACTGTGGTTATCATTGGTGATGCCAGAAAACATTAGTAGACTTAGAC
AATTGCTATGGCAGTTTCTAAACAGAGCTTTTTCTATACACTATTTGCAACTGGAGTGCA
ATATTGTATATTCTGTGTTAAAGAAATAAAGTATTTTTATCATTTATTAAAAAAAAAAAA
AAAAA

>AF038191
CCATCCAGAACGATGAGGCCGTGGCCCCGCTCATGAAGTACCTGGATGAGAAGCTGGCCC
TGCTGAACGCCTCGCTGGTGAAGGGGAACCTGAGCAGGGTGCTGGAGGCCCTGTGGGAGC
TACTCCTCCAGGCCATTCTGCAGGCGCTGGGTGCAAACCGTGACGTCTCTGCTGATTTCT
ACAGCCGCTTCCATTTCACGCTGGAGGCCCTGGTCAGTTTTTTCCACGCAGAGGGTCAGG
GTTTGCCCCTGGAGAGCCTGAGGGATGGAAGCTACAAGAGGCTGAAGGAGGAGCTGCGGC
TGCACAAATGTTCCACCCGCGAGTGCATCGAGCAGTTCTACCTGGACAAGCTCAAACAGA
GGACCCTGGAGCAGAACCGGTTTGGACGCCTGAGCGTCCGTTGCCATTACGAGGCGGCTG
AGCAGCGGCTGGCCGTGGAGGTGCTGCACGCCGCGGACCTGCTCCCCCTGGATGCCAACG
GCTTAAGTGACCCCTTTGTGATTGTGGAGCTGGGCCCACCGCATCTCTTTCCACTGGTCC
GCAGCCAGAGGACCCAGGTGAAGACCCGGACGCTGCACCCTGTATACGACGAACTCTTCT
ACTTTTCCGTGCCTGCCGAGGCGTGCCGCCGCGCGGCCTGTGTGTTGTTCACCGTCA
TGGACCACGACTGGCTGTCCACCAACGACTTCGCTGGGGAGGCGGCCCTCGGCCTAGGTG
GCGTCACTGGTGTCGCCCGGCCCCAGGTGGGCGGGGGTGCAAGGGCTGGGCAGCCTGTCA
CCCTGCACCTGTGCCGGCCCAGAGCCCAGGTGAGATCTGCGCTGAGGAGGCTGGAAGGCC
GCACCAGCAAGGAGGCGCAGGAGTTCGTGAAGAAACTCAAGGAGCTGGAGAAGTGCATGG
AGGCGGACCCCTGAGTCCATCAGCTGCCAGCCCCGGCCCTGGCCCCCACCCCAAGTTCCC
TGAAGCATCCTCCAGCTCACTGTGGCCAGCTTTGTGCAACCAGGGCCCACGGCGCCCCTC
CTGTGCTGTGACGTGTGTGTCGTGGCTGGCCCCGCGGCGCCTACCGCCCTGGCCGTGTCT
GTCTGGTGTGTGCTGTGAACCCCTGCACCCAACCCCACATCTGGGTGGCCAACTTGGCAG
GACTTGGCCAGCAGCTGCCCAGGACACAGTGCAGGCCAGAGCGGGCTTGACCACCTGGTG
GGCCTCCCTGCCCGCTTCCTTGGGCTCCCCGGCCCTGGGTGGGCGGTGCGCAGCTGGTCT
CCAGGGACTCAGTGAGTGGCTGTGCTCTCTGCACAACGGGCAATGTGCAGACGCATTTTT
GGTAATCACAGCTGGGGAGTGAAAAGGGTGCCACTGGCACCACTGGGTGGATGGTCCAGA
GCCTCCACCCACAGAGGGGATGCAAAGGGCAGGTGAGTCAAGAACCGCATAGGTCTCCAG
TCCCCACGGGGCTCCCAGGCCGGGGAAAGGTTCCCCTGAGGTCACTCTGAGGCCAGGGAC
GTCACCCAAGGCTGGTGGTCAGTGTGAAGGGCTCCGTGCCAACTGGTCAGCTGTCCTTCA
CGCACATATCCGTGGCCACCTGAGACCTGCTCCACGACCCTTCCAGGCAGAGCCGAGAGT
TCGCCCCAACCCTTCCCCAGGCCCAGTGTGAAAAACAGACTCACAAGGGGCTTCTTGGCC
TGCAGCTTCATTTGCGAGAGCGCCGAGGCAGGACACAGAGCACAGCTGTGCTGGAAGTGT
GGGGAGAACCCGGACAGCTCAGTCCTGCCAGCAGCCGCAAAGAGCCGAGGCTGCCAGGCC
CATTTATGTCCCTCATGTCTCTAGATTTTCTCGTCACCCAGCCTCAAAAATATATGTGTC
TGCAACCCTC

>BC016340
GGGGGGGCTCCGTGACAGCCAACGCAGTGACCCTCGCCCCTTCCTTGGCAGCACATCATG
CTTGTGCAGCGGCAGATGTCTGTGATGGAAGAGGACCTGGAAGAATTCCAGCTCGCTCTG
AAACACTACGTGGAGAGTGCTTCCTCCCAAAGTGGATGCTTGCGTATTTCTATACAGAAG
CTTTCAAATGAATCTCGCTACATGATCTATGAGTTCTGGGAGAATAGTAGTGTATGGAAT
AGCCACCTTCAGACAAATTATAGCAAGACATTCCAAAGAAGTAATGTGGATTTCTTGGAA
ACTCCAGAACTCACATCTACAATGCTAGTTCCTGCTTCGTGGTGGATCCTGAACAACTAG
ATGTTCCTAGACATTTTCTTTATGGTTCCAAGTGCAAAACAGGTGTTCTTATCTAAAACG
TCAATTAGAAAATTATCTGCGGTTGTTAATCTACTGTATATTTTTGTTTGGTATATTTAC
TAAGTGCACTCTTTCAAAACTTATTCTATAACTTTATCAATTCATGTGAATTTTAGCTCA

-continued

ATTTTCAAAGTTCACTAATATTCTCAATATTTAATGCTAAATGCTTTGCTACATTGTAAC
TCACCTAAAACCTTTTAGTGACAAAATCCTAATATGTGGAAAAAAGCATATGCATAAAGG
AATAATATTGTGAAAATGAATCTGTTATGATAAAGAAAAAATAAAGTGGAAACTTTTAGA
GTATTACTTCATAGGGCAGATTTTGTAAACTGTCGTATACTGTAAAGGGTTAAATCAGCG
TTTTGTGATTTTTAAGTAACTGTGAGTGAAGTTTATTCTTCAACAATGTCTACTCCATCC
CCAACCCAACTCACAGCCCTATGACTACTATCTTTGCATTAGTTAAAAAGTTAGTATATA
GGCATCAAACAACCTTGGCTGTAACCTATAGAATCTCTATCCATGTATCAGGTTATAGAC
TGGTTTTTCAAAAGTGAACAATCCTGTGATAAGTTGGAGTACCATTTAGTAATACAGCAA
CATTGTGTCATTTATTAGCATCATAATTCTTTGTTATGTAAGTTAAATATATCAAGAAAG
AAGAGACTGTTTGGAAAAATGTGGTTCAAGTTTTATGCTATATAGTTTTGGTATGCGATA
CAGACAGCTAACTTTTCTTATGAAAAATACATATTTGCATGTAAACAATGATTTCAAAAT
ACTTGAAAAATAAAATTTTAACCCAAATGAATAACTAAGAAATATAAAACAAGCACAAAA
TCTTAGGGAAGTCATAAAATAGTAGTGAAAGTATTAGACAGAAGACATCTGTTTTCGAAT
TTCAACACTAGAATGACTAAAACTATCTACCTATAGAACTATCTGTAGATAGTATACTAT
CTACACTCTGCTCAACAAGCTCAGAAATTAAATATTTTTAGTAATAAAAATCTGTTCTGG
TTATAAACCTTGCTAATGAAAATACAATACATATAAAAATGTATAGCCATGTTATTTTCT
AGTATAAATTCCTTTGAAACTATAAGTCTTTGAGGAAAATTATAAGGTAAAATTTTCCTG
TTTTTCCCCCTTTGAAAAACTCAGGAAAAAAGGAAGATTGAACTAATAAAATTTTATTTC
TTAAATATAAATTTGACCTAAAATATTTTCTCAAACTAATTCATGAAACAGCAACTTTTA
CCAATACCTTTGTATACTCTCAGTTCTCATTCLGTATAAATAAAATTTTAAAATCCTTTC
ATAGTTCTATTAGAAATAAGTAGTAAATTTTGATATATTGTACATACACACGTGTGTGTG
TGTGTGTGTGTGTGTGTGTATTTGTGTGCCTCTGGTCAACTCTAAGGATGACAGACACTG
TGTAACAACACCTGGGTCAACTCTTTTAATTTATATACAAAGCAAAGAACAACATTAATG
GAGATGCACAATGATTATTCAAACAAGCTATATATATGTACAAAGGCAAACAGACACATA
ACAGTCTCTGCAGACTGATTGTATATAGTAAGAAAAGATCAAAAGACTTTAAAACCTAAA
TGACTTTTGACATACAAACTCTTCTTGAGAATGTTTGTTGTAAATGGTTTCAAAAATACA
AATTATAGCCAATCAAAACATTGCTTTGGTTGGTGCATTTAAGTATCCAACTCAAAAAGC
ATATCAAATATTTTGGGTACTAGGCAGTTTCCAAAGTAGCATGGTAGTATTACTTGTTAA
AAGGGTTCTGTTTTCATTAACAGTACTAAGTGGAAGGGATCTGCAGATTCCAAATTGGAA
TAAGCTCTATCATATTCTGAAACAAGAATTAGAATGACTTGAGAACGGGCAAATAACAAA
GCAAACCAATATAATTATATGGTCATTCTGACCCCAGCTCTTATACAAATTATACATGTA
TTTTTGTGTATGTTTGTGAGAGTTGTATGTATGTGAATGTGTGTGAGTGTGTATTCACAT
ACACATATATACTGGAACCTATAGTAGAAAAGGAAACTAGTAGGGCCAAAAAAAAAAAGA
AAAAGAAAAAGAAAAAAGAAAAAAAAAGAAAAAACTGGGACCTAAGTATAAATATCTCAT
CCTAAAGTAAACAATAAGTTTATAGTTAACGAAGATTTTTTTCTATTTAAAACCCCATTT
TCCTAAAGAACAAAAAAAA

>BC013282

GGCACGAGGGCAGGGGGAAGGGAAGTGCGGCTCGGTCGGCGCGGGTGGAGGGGGCGTGAG
GCCGCCCTACGGTGGCCGTCGAGGGACGGCGCTACGGCTCCCACGCTAGGCCAAACGCCT
CCGGCGGCCGCGCCCGAGAGCCCCTTCACCTGCAGGGCGACCCCAGCCGGCGACGCGTGA
ACCACGCCCTCAGCCGCCTTGCCAGCGCCCCCAGCCGCGCGCCCCAGCACCATGCGGCCG
CCCTGCGCACGGAGCCCCGAGGGACAGGGGCACCCGCAGGCCCGGCCCCTAGCACCGCCG
GCCGGCCCCGAGGTCCGGGACGCCGGCGCCGCCGCGGAGAGGGCACCGGGCCGACGCCTC
CCCCCAGGGTCAGCTGCGGGCTCCCAGGCCTAGGCGCCCATGACCCCTACGCCAACCGCC
GCCTGGACACCGCCGCCGCCACTGCGACCTAGCGCCGCCGCCGCCGGGGCCCAATGCCGG
TCATGCCCATTCCGCGGCGGGTGCGCTCCTTCCACGGCCCGCACACCACCTGCCTGCATG
CGGCCTGCGGGCCCGTGCGCGCCTCCCACCTGGCCCGCACCAAGTACAACAACTTCGACG
TGTACATCAAGACGCGCTGGCTGTACGGCTTCATCCGCTTCCTACTCTACTTTAGCTGCA
GCCTGTTCACTGCGGCGCTCTGGGGTGCGCTGGCCGCCCTCTTCTGCCTACAGTACCTGG
GCGTTCGCGTCCTGCTGCGCTTCCAGCGCAAGCTGTCGGTGCTGCTGCTGCTGCTGGGCC
GCCGGCGCGTGGACTTCCGCCTGGTGAACGAGCTGCTCGTCTATGGCATCCACGTCACCA
TGCTGCTGGTCGGGGGCCTGGGCTGGTGCTTCATGGTCTTCGTGGACATGTGAGGGCCGT
GGGTGCGAGCTTGATGTATCGTCCCGGCCTGTGGCTGTGTTCTCTCCATGGGTGGGGTCG
GCCAGCGCCTTCCCTTCGCCCATCCCCCAGGCAGTCGCTGCTGCCCGGCGCCCACGGAGA
GAAAAGAAAGGGCTGAGACTTCTGTGATGGGGGCGCGGACACCACCCCTAGGCTGGCTTC
CTGGACCCACCCTCCCCGTATGCACTCTCAGGGGCAGCGCCCACCTGCCGGTGGCTCCTG
CTCACATGTCTTCGGGTCGTACTGCGGGGTGGGCCCTCCGTTCCGCCTCTCTGTGGGCCT
CTCTCCAGGACCACAGCTGCCAGGGACTTTAGACATCACCCTGGGAGGCCCCTGGACACA
GAGGGCTGTGTGCCCAGGAGCAATTCCGGAGGGGGGCCCTCCTGGCTGCACAGCCCCTTC
TGCGTGCCCTGGCCCCAGCCCCAGCCAACGGGACACGGAAGGCTCCCCTCGCTGACACAC
CACACTGCCACAAAGCTGCTTACTCTGCCCTGGGCCGCCTGAGGCCTGGCACTGCCCGCG
GACCACCCTGTGTGTGTCATCCTGAGGGGCTGTGTGGGTCCTGAGTCCCCAGCCAGCCTT
CAGGGTCCCCTTGGATTGTGTAGATGCAGTCTAGCGGGGGGCCGGAGAAGGGCTCAGGTG
GGAGGGGCCTCAGCAGGCTCCCAGCTCAGGGGCTGGCCTGGGGGGAACCCTGGGAGCCAG
GGGCTGACTCCAGCAACACTGGCCTGTCTGCCTGTTCTGGGAGGGCTGTGAGGATGTCTT
GCAGATGCTCTGGATTTCTGCGGAGGCACCTCCATTCCTTTCTGGCTTTTTTTGCGGGGG
AGGGCTTTGGGCCTCTTTCTTTGAGGGAACACCGTCAAAGAAAGCCTGGGAGATCGAGGC
TTCAGTGAGCCAGGATGGAAACGCGTGTCCCAAGTGTCCGGAGCAGGCGGCAGAGGCCTC
AGTGCGGCAAACACAGCCCCAGAGCCTGTGTGGCACCAGCAGCATCTTAGAGCCCCAGGT
ATATGCTGAGATCTTATCTCACGCTGTCCTCCAGTGTCTGGGGGGCCCAAATGATGGCAC
AGGGTCAGGTGGGCTGGAGGGGCGCAGATGCCTGTGTTCAGGGAGGGTGGCCACCATGGG
CCGAGGTCTCACCCAGGACCCCTTGCTCTGCTCCTCAGCCTTGCAGTCACGGCAGCACTA
TGGTGGACTGCCCATGGCCGTGTGACTTTGGGGGCAAGTGGGAGGGCGCCCTGAATAATG
ATTGCAAGGACAACAGGCAGAGGCTACCCTAGAGCAGGACACAGGGTGTGGTACTGACAA
CCCTAGTGTCACCTCAAATCCATGTCCCCACACTCTGGGCATGGGTGGGACTTGTGACCC
TACCCTGTCAGGCGGACCAGTGGCCCAGGAGCCATGAGGACAGTTGTGTGCCACTGGAAG
AGAAACTTTTTGAAAAACCCTAAATCAGGTAGAGAAAGCAAAAAATCTCTGGCCGTAAAC
CGTGCTCTCTAATTTATCGGCAGCTTCTGTGGATGACCTCTGATGAGCCCGGGCTGCGTC
CACGCCCTGGGCAGGTAGGCGGGAGCTTCCCTCCGTGGGCCTCATTTCTTGCTGCAGAGA
ATCTTTTGCACTAAGTCATGCTGTTTCCTCAAAGAAGCTTTGTTTTTTGTTAACGTATTA

-continued

CTCAGAGTCACCCAAGCCTCTTGGCTGAGGGTGAAGGTGGGACGGGAGGCGGGAGGGGGC
TGGTGGTGCCGCTCGTGCGGTGTCAACGCTGCAGGGAGTTGTGGCACCTTGGTGCCCTCT
GAGCACCTGGCCGCCTGCTGTCCCCGGTGCCTGTGAAATTCGTCATGCCATGACCCACCT
GCATTACCTATTTTTTTAATGTGTTAAAA

>H09748
GNGGAAACACGGGCCAAACCCGTGANTTTGGTGCCCCTTGTAAACTCANCCCCTGCAAAN
CCAAAGACCCCAATGGATTTAAAGTTGNTTGGCATTTGTACTGGCAAGGCAAAANATTTT
TAANTACCTTTTCCTAATACTTATTGTATGAGCTTTTGNTGTTTACTTGGAGGTTTTGTC
TTTTACTACAAGTTTGGAACTATTTANTATTGCCTTGGTATTTGTGCTCTGTTTAAGAAA
CAGGCACTTTTTTTTATTATGGATAAAATGTTGAGATGACAGGAGGTCATTTCAATATGG
CTTAGTAAAATATTTATTGTTCCTTTATTCTCTGTACAAGATTTTGGGCCTCTTTTTTTC
CTTAATGTCACAATGTTGAGTTCAGCATGTGTCTGTCCATTTCATTTGTACGCTTGTTCA
AAACCAAGTTTGTTCTGGTTTCAAGTTATAAAAATAAATTGGACATTTAACTTGATCTCC
AAAAAAAAAAAAAAAA

>BC001665
GGCACGAGGCAATCTGAGGAGCAGGAGGACCGGGGCGCCGGTGTCCTGCCGCCTCCTTCT
CCTTGCTCTCACCTGCGCCTATTAGTCCACGCGCCTTCAAGGCCAGGGGCTACAGCCCAG
ACAGAGAGGGGACAGCAGAGGGAGAGAGAGCACCTGAGGATACAGAGCTGGCACTGGACT
GCCTTTTCACCCCCCAGGTGATGAGTGAGGTTCGAAGAACGGAAGATTTAAAAAGCAGCC
GGGGCCTCCGTATTGAATGAAAGACCCAGTGCAAAGACATCACCATGAACACTAGCATTC
CTTATCAGCAGAATCCTTACAATCCACGGGGCAGCTCCAATGTCATCCAGTGCTACCGCT
GTGGAGACACCTGCAAAGGGGAAGTGGTCCGCGTGCACAACAACCACTTCCACATCAGAT
GCTTCACCTGTCAAGTATGTGGCTGTGGCCTGGCCCAGTCAGGCTTCTTCTTCAAGAACC
AGGAGTACATCTGCACCCAGGACTACCAGCAACTCTATGGCACCCGCTGTGACAGCTGCC
GGGACTTCATCACAGGCGAAGTCATCTCGGCCCTGGGCCGCACTTACCACCCCAAGTGCT
TCGTGTGCAGCTTGTGCAGGAAGCCTTTCCCCATTGGAGACAAGGTGACCTTCAGCGGTA
AAGAATGTGTGTGCCAAACGTGCTCCCAGTCCATGGCCAGCAGTAAGCCCATCAAGATTC
GTGGACCAAGCCACTGTGCCGGGTGCAAGGAGGAGATCAAGCACGGCCAGTCACTCCTGG
CTCTGGACAAGCAGTGGCACGTCAGCTGCTTCAAGTGCCAGACCTGCAGCGTCATCCTCA
CCGGGGAGTATATCAGCAAGGATGGTGTTCCATACTGTGAGTCCGACTACCATGCCCAGT
TTGGCATTAAATGTGAGACTTGTGACCGATACATCAGTGGCAGAGTCTTGGAGGCAGGAG
GGAAGCACTACCACCCAACCTGTGCCAGGTGTGTACGCTGCCACCAGATGTTCACCGAAG
GAGAGGAAATGTACCTCACAGGTTCCGAGGTTTGGCACCCCATCTGCAAACAGGCAGCCC
GGGCAGAGAAGAAGTTAAAGCATAGACGGACATCTGAAACCTCCATCTCACCCCCTGGAT
CCAGCATTGGGTCACCCAACCGAGTCATCTGCGACATCTACGAGAACCTGGACCTCCGGC
AGAGACGGGCCTCCAGCCCGGGGTACATAGACTCCCCCACCTACAGCCGGCAGGGCATGT
CCCCCACCTTCTCCCGCTCACCTCACCACTACTACCGCTCTGGTGATTTGTCTACAGCAA
CCAAGAGCAAAACAAGTGAAGACATCAGCCAGACCTCCAAGTACAGTCCCATCTACTCGC
CAGACCCCTACTATGCTTCGGAGTCTGAGTACTGGACCTACCATGGGTCCCCCAAAGTGC
CCCGAGCCAGAAGGTTCTCGTCTGGAGGAGAGGAGGATGATTTTGACCGCAGCATGCACA
AGCTCCAAAGTGGAATTGGCCGGCTGATTCTGAAGGAAGAAATGAAGGCCCGGTCGAGCT
CCTATGCAGATCCCTGGACCCCTCCCCGGAGCTCCACCAGCAGCCGGGAAGCCCTGCACA
CAGCTGGCTATGAGATGTCCCTCAATGGCTCCCCTCGGTCGCACTACCTGGCTGACAGTG
ATCCTCTCATCTCCAAATCTGCCTCCCTGCCTGCCTACCGAAGAAATGGGCTGCACAGGA
CACCCAGCGCAGACCTCTTCCACTACGACAGCATGAACGCAGTCAACTGGGGCATGCGAG
AGTACAAGATCTACCCTTATGAACTGCTGCTGGTGACTACAAGAGGAAGAAACCGACTGC
CCAAGGATGTAGACAGGACCCGTTTAGAGGGAAACTTTTGGAAGAGTGGCTGCTTATGAG
ATTCCAAAATGAAGTGTTGGCCAACACCGCTCATGGCCATCCTGGATTTTCCCAGTGGCT
TCCCTTCCTGCTCGCCTCCCTGAACAGGGGAGAAAGCTTAACCTCTCTTCTCCTCTCCAA
ACCTTTCACCTTGAATGGGTAATGTTTGGTGGGGGCTGTTCCTTCTTGGAGAAGCCTTGA
GTCGGACCATTTTGAGATCATGGAGGAAGGATGAAGAAGTGAAAATGACAATAATGACTC
TCAAGAGGCTGGCGATGTGACATGGCAAATGTAGAACTGACTTAAATTGAACAAACCCTC
ACTGAGCACCTCTGATGTTGAGCACCTGCTGAATACTGAGCACTGAATGGGGGAGGGGGA
GGGGAGCACGGGGTGAGTCAACCTGGGACTCGGTCTCAGGGATATGCCTACCAATAGCGG
GTATCGTAAGGCATGTACCCAAACATAACGGATGTAAGGCAGAAAGTGATCGGAGAAGGA
ATGAGAAAGTGTGCGTGATGTTAATGAAAAGTCATATGCAGCTAGAGCAGACCCAGGAAA
GCTTTCTGGAAGAGATTGCATCTGAGGAAATTCAGGAAGGATCTTTGTAGATTGGGGGGA
GATTCTAAATTGAAGGGGTGATGGGGTGAGGGGCCAGAGGGAAGTCTGCTGTGTTCTCAT
GTAGGATGTCAGCCCTCCCTGCAACTTCTCTTTTTGGCCAATGTCTTTTCACTTTCCTGA
CCCTTTAGAATCATCCCCAGCCAGACGCAATCATGGAAGTTGCCTTATTGTCACTGGTTA
AGAACTTGGCGAGATTGAAGGGCTTTTGTTATTGTTGTTGGATATTTTTGTTTCCCATAA
AAGCACATCATTTCACCCTA

>BC016451
GAAGAATTAGATACTTTTGAGTGGGCTTTGAAGAGCTGGTCTCAGTGTTCCAAACCCTGT
GGTGGAGGTTTCCAGTACACTAAATATGGATGCCGTAGGAAAAGTGATAATAAAATGGTC
CATCGCAGCTTCTGTGAGGCCAACAAAAAGCCGAAACCTATTAGACGAATGTGCAATATT
CAAGAGTGTACACATCCACTCTGGGTAGCAGAAGAATGGGAACACTGCACCAAAACCTGT
GGAAGTTCTGGCTATCAGCTTCGCACTGTACGCTGCCTTCAGCCACTCCTTGATGGCACC
AACCGCTCTGTGCACAGCAAATACTGCATGGGTGACCGTCCCGAGAGCCGCCGGCCCTGT
AACAGAGTGCCCTGCCCTGCACAGTGGAAAACAGGACCCTGGAGTGAGTGTTCAGTGACC
TGCGGTGAAGGAACGGAGGTGAGGCAGGTCCTCTGCAGGGCTGGGGACCACTGTGATGGT
GAAAAGCCTGAGTCGGTCAGAGCCTGTCAACTGCCTCCTTGTAATGATGAACCATGTTTG
GGAGACAAGTCCATATTCTGTCAAATGGAAGTGTTGGCACGATACTGCTCCATACCAGGT
TATAACAAGTTATGTTGTGAGTCCTGCAGCAAGCGCAGTAGCACCCTGCCACCACCATAC
CTTCTAGAAGCTGCTGAAACTCATGATGATGTCATCTCTAACCCTAGTGACCTCCCTAGA
TCTCTAGTGATGCCTACATCTTTGGTTCCTTATCATTCAGAGACCCCTGCAAAGAAGATG
TCTTTGAGTAGCATCTCTTCAGTGGGAGGTCCAAATGCATATGCTGCTTTCAGGCCAAAC
AGTAAACCTGATGGTGCTAATTTACGCCAGAGGAGTGCTCAGCAAGCAGGAAGTAAGACT

-continued

GTGAGACTGGTCACCGTACCATCCTCCCCACCCACCAAGAGGGTCCACCTCAGTTCAGCT
TCACAAATGGCTGCTGCTTCCTTCTTTGCAGCCAGTGATTCAATAGGTGCTTCTTCTCAG
GCAAGAACCTCAAAGAAAGATGGAAAGATCATTGACAACAGACGTCCGACAAGATCATCC
ACCTTAGAAAGATGAGAAAGTGAACCAAAAAGGCTAGAAACCAGAGGAAAACCTGGACAA
CCTCTCTCTTCCCATGGTGCATATGCTTGTTTAAAGTGGAAATCTCTATAGATCGTCAGC
TCATTTTATCTGTAATTGGAAGAACAGAAAGTGCTGGCTCACTTTCTAGTTGCTTTCATC
CTCCTTTTGTTCTGCATTGACTCATTTACCAGAATTCATTGGAAGAAATCACCAAAGATT
ATTACAAAAGAAAAATATGTTGCTAAGATTGTGTTGGTCGCTCTCTGAAGCAGAAAAGGG
ACTGGAACCAATTGTGCATATCAGCTGACTTTTTGTTTGTTTTAGAAAAGTTACAGTAAA
AATTAAAAAGAGATACCAATGGTTTACACTTTAACAAGAAATTTTGGATATGGAACAAAG
AATTCTTAGACTTGTATTCCTATTTATCTATATTAGAAATATTGTATGAGCAAATTTGCA
GCTGTTGTGTAAATACTGTATATTGCAAAAATCAGTATTATTTTAAGAGATGTGTTCTCA
AATGATTGTTTACTATATTACATTTCTGGATGTTCTAGGTGCCTGTCGTTGAGTATTGCC
TTGTTTGACATTCTATAGGTTAATTTTCAAAGCAGAGTATTACAAAAGAGAAGTTAGAAT
TACAGCTACTGACAATATAAAGGGTTTTGTTGAATCAACAATGTGATACGTAAATTATAG
AAAAAGAAAAGAAACACAAAAGCTATAGATATACAGATATCAGCTTACCTATTGCCTTCT
ATACTTATAATTTAAAGGATTGGTGTCTTAGTACACTTGTGGTCACAGGGATCAACGAAT
AGTAAATAATGAACTCGTGCAAGACAAAACTGAAACCCTCTTTCCAGGACCTCAGTAGGC
ACCGTTGAGGTGTCCTTTGTTTTTGTGTGTGTGTGTTCTTTTTTAATTTTCGCATTGTTG
ACAGATACAAACAGTTATACTCAATGTACTGTAATAATCGCAAAGGAAAAAGTTTTGGGA
TAACTTATTTGTATGTTGGTAGCTGAGAAAAATATCATCAGTCTAGAATTGATATTTGAG
TATAGTAGAGCTTTGGGGCTTTGAAGGCAGGTTCAAGAAAGCATATGTCGATGGTTGAGA
TATTTATTTTCCATATGGTTCATGTTCAAATGTTCACAACCACAATGCATCTGACTGCAA
TAATGTGCTAATAATTTATGTCAGTAGTCACCTTGCTCACAGCAAAGCCAGAAATGCTCT
CTCCAGGGAGTAGATGTAAAGTACTTGTACATAGAATTCAGAACTGAAGATATTTATTAA
AAGTTGATTTTTTTTTCTTGATAGTATTTTTATGTACTAAATATTTACACTAATATCAAT
TACATATTTTGGTAAACTAGAGAGACATAATTAGAGATGCATGCTTTGTTCTGTGCATAG
AGACCTTTAAGCAAACTACTACAGCCAACTCAAAAGCTAAAACTGAACAAATTTGATGTT
ATGCAAACATCTTGCATTTTTAGTAGTTGATATTAAGTTGATGACTTGTTTCCCTTCAAG
GAAACATTAAATTGTATGGACTCAGCTAGCTGTTCAATGAAATTGTGAATTAGAAACATT
TTTAAAAGTTTTTGAAAGAGATAAGTGCATCATGAATTACATGTACATGAGAGGAGATAG
TGATATCAGCATAATGATTTTGAGGTCAGTACCTGAGCTGTCTAAAAATATATTATACAA
ACTAAAATGTAGATGAATTAACCTCTCAAAGCACAGAATGTGCAAGAACTTTTGCATTTT
AATCGTTGTAAACTAACAGCTTAAACTATTGACTCTATACCTCTAAAGAATTGCTGCTAC
TTTGTGCAAGAACTTTGAAGGTCAAATTAGGCAAATTCCAGATAGTAAAACAATCCCTAA
GCCTTAAGTCTTTTTTTTTTTCCTAAAAATTCCCATAGAATAAAATTCTCTCTAGTTTAC
TTGTGTGTGCATACATCTCATCCACAGGGGAAGATAAAGATGGTCACACAAACAGTTTCC
ATAAAGATGTACATATTCATTATACTTCTGACCTTTGGGCTTTCTTTTCTACTAAGCTAA
AAATTCCTTTTATCAAAGTGTACACTACTGATGCTGTTTGTTGTACTGAGAGCACGTAC
CAATAAAAAATGTTAACAAAATATAAAAAAAAAAAAAA

>BF510316
TCCTGTGTTCTAGACCTCTGGAGGCTGCTGTGGGGACCACACTGATCCTGGAGAAAAGGG
ATGGAGCTGAAAAAGATGGAATGCTTGCAGAGCATGACCTGAGGAGGGAGGAACGTGGTC
AACTCACACCTGCCTCTTCCTGCAGCCTCACCTCTACCTGCCCCCATCATAAGGGCACTG
AGCCCTTCCCAGGCTGGATACTAAGCACAAAGCCCATAGCACTGGGCTCTGATGGCTGCT
CCACTGGGTTACAGAATCACAGCCCTCATGATCATTCTCAGTGAGGGCTCTGGATTGAGA
GGGAGGCCCTGGGAGGAGAGAAGGGGGCAGAGTCTTCCCTACCAGGTTTCTACACCCCCG
CCAGGCTGCCCATCAGGGCCCAGGGAGCCCCCAGAGGACTTTATTCGGACCAAGCAGAGC
TCACAGCTGGACAGGTGTTGTATATAGAGTGGAATCTCTTGGATGCAGCTTCAAGAATAA
ATTTTTCTTCTCTTTTCAAAAATGTATAAAAATCATTATACATAGCATTAAAGAAACATT
TTTGAGAAGTACAAAACAAAAAAAAAA

>AF301598
CGGGCGCCGCAGGAGCGAGTGAGCTGGGAGCGAGGGGCGAAGGCGCGGAGAAGCCCGGCC
GCCCGGTGGGCGGCAGAAGGCTCAGCCGAGGCGGCGGCGCCGACTCCGTTCCACTCTCGG
CCCGGATCCAGGCCTCCGGGTTCCCAGGCGCTCACCTCCCTCTGACGCACTTTAAAGAGT
CTCCCCCCTTCCACCTCAGGGCGAGTAATAGCGACCAATCATCAAGCCATTTACCAGGCT
TCGGAGGAAGCTGTTTATGTGATCCCCGCACTAATTAGGCTCATGAACTAACAAATCGTT
TGCACAACTTGTGAAGAAGCGAACACTTCCATGGATTGTCCTTGGACTTAGGGCGCCCTG
CCCGCCTTTTGCAGAGGAGAAAAAACTTTTTTTTTTTTTTGCCTCCCCCGAGAACTTTCC
CCCCTTCTCCTCCCTGCCTCTAACTCCGATCCCCCCACGCCATCTCGCCAAAAAAAAAAA
AAAAAAAAAAAAAGAAAAAAAAAGAAAAAAAAAGAAAAAAAAATTACCCCAATCCACGCCT
GCAAATTCTTCTGGAAGGATTTTCCCCCCTCTCTTCAGGTTGGGCGCGTTTGGTGCAAGA
TTCTCGGGATCCTCGGCTTTGCCTCTCCCTCTCCCTCCCCCCTCCTTTCCTTTTTCCTTT
CCTTTCCTTTCTTTCTTCCTTTCCTTCCCCCCACCCCCACCCCCACCCCAAACAAACGAG
TCCCCAATTCTCGTCCGTCCTCGCCGCGGGCAGCGGGCGGCGGAGGCAGCGTGCGGCGGT
CGCCAGGAGCTGGGAGCCCAGGGCGCCCGCTCCTCGGCGCAGCATGTTCCAGCCGGCGCC
CAAGCGCTGCTTCACCATCGAGTCGCTGGTGGCCAAGGACAGTCCCCTGCCCGCCTCGCG
CTCCGAGGACCCCATCCGTCCCGCGGCACTCAGCTACGCTAACTCCAGCCCCATAAATCC
GTTCCTCAACGGCTTCCACTCGGCCGCCGCCGCCGCCGCCGGTAGGGGCGTCTACTCCAA
CCCGGACTTGGTGTTCGCCGAGGCGGTCTCGCACCCGCCCAACCCCGCCGTGCCAGTGCA
CCCGGTGCCGCCGCCGCACGCCCTGGCCGCCCACCCCCTACCCTCCTCGCACTCGCCACA
CCCCCTATTCGCCTCGCAGCAGCGGGATCCGTCCACCTTCTACCCCTGGCTCATCCACCG
CTACCGATATCTGGGTCATCGCTTCCAAGGGAACGACACTAGCCCCGAGAGTTTCCTTTT
GCACAACGCGCTGGCCCGAAAGCCCAAGCGGATCCGAACCGCCTTCTCCCCGTCCCAGCT
TCTAAGGCTGGAACACGCCTTTGAGAAGAATCACTACGTGGTGGGCGCCGAAAGGAAGCA
GCTGGCACACAGCCTCAGCCTCACGGAAACTCAGGTAAAAGTATGGTTTCAGAACCGAAG
AACAAAGTTCAAAAGGCAGAAGCTGGAGGAAGAAGGCTCAGATTCGCAACAAAAGAAAAA
AGGGACGCACCATATTAACCGGTGGAGAATCGCCACCAAGCAGGCGAGTCCGGAGGAAAT
AGACGTGACCTCAGATGATTAAAAACATAAACCTAACCCCACAGAAACGGACAACATGGA

-continued

GCAAAAGAGACAGGGAGAGGTGGAGAAGGAAAAAACCCTACAAAACAAAAACAAACCGCA
TACACGTTCACCGAGAAAGGGAGAGGGAATCGGAGGGAGCAGCGGAATGCGGCGAAGACT
CTGGACAGCGAGGGCACAGGGTCCCAAACCGAGGCCGCGCCAAGATGGCAGAGGATGGAG
GCTCCTTCATCAACAAGCGACCCTCGTCTAAAGAGGCAGCTGAGTGAGAGACACAGAGAG
AAGGAGAAAGAGGGAGGGAGAGAGAGAAAGAGAGAGAAAGAGAGAGAGAGAGAGAGAG
AGAAAGCTGAACGTGCACTCTGACAAGGGGAGCTGTCAATCAAACACCAAACCGGGGAGA
CAAGATGATTGGCAGGTATTCCGTTTATCACAGTCCACTTAAAAAATGATGATGATGATA
AAAACCACGACCCAACCAGGCACAGGACTTTTTTGTTTTTTGCACTTCGCTGTGTTTCCC
CCCCATCTTTAAAAATAATTAGTAATAAAAAACAAAAATTCCATATCTAGCCCCATCCCA
CACCTGTTTCAAATCCTTGAAATGCATGTAGCAGTTGTTGGGCGAATGGTGTTTAAAGAC
CGAAAATGAATTGTAATTTTCTTTTCCTTTTAAAGACAGGTTCTGTGTGCTTTTTATTTT
GATTTTTTTTCCCAAGAAATGTGCAGTCTGTAAACACTTTTTGATACCTTCTGATGTCAA
AGTGATTGTGCAAGCTAAATGAAGTAGGCTCAGCGATAGTGGTCCTCTTACAGAGAAACG
GGGAGCAGGACGACGGGGGGGCTGGGGGTGGCGGGGGAGGGTGCCCACAAAAAGAATCAG
GACTTGTACTGGGAAAAAAACCCCTAAATTAATTATATTTCTTGGACATTCCCTTTCCTA
ACATCCTGAGGCTTAAAACCCTGATGCAAACTTCTCCTTTCAGTGGTTGGAGAAATTGGC
CGAGTTCAACCATTCACTGCAATGCCTATTCCAAACTTTAAATCTATCTATTGCAAAACC
TGAAGGACTGTAGTTAGCGGGGATGATGTTAAGTGTGGCCAAGCGCACGGCGGCAAGTTT
TCAAGCACTGAGTTTCTATTCCAAGATCATAGACTTACTAAAGAGAGTGACAAATGCTTC
CTTAATGTCTTCTATACCAGAATGTAAATATTTTTGTGTTTTGTGTTAATTTGTTAGAAT
TCTAACACACTATATACTTCCAAGAAGTATGTCAATGTCAATATTTTGTCAATAAAGATT
TATCAATATGCCAAAAAAAAAAAAAAA

>Hs.77031_mRNA_1 gi|16741772|gb|BC016680.1|BC016680 *Homo sapiens* clone
MGC:21349 IMAGE:4338754 polyA 3
GTGGCGGCGGAGGCGGCGGAGGCCAGGGAGGAAGATGTCGTAATGAGCGATCCACAGACC
AGCATGGCTGCCACTGCTGCTGTGAGTCCCAGTGACTACCTGCAGCCTGCCGCCTCCACC
ACCCAGGACTCCCAGCCATCTCCCTTAGCCCTGCTTGCTGCAACATGTAGCAAAATTGGC
CCTCCAGCAGTTGAAGCTGCTGTGACACCTCCTGCTCCCCCACAGCCCACACCGCGGAAA
CTTGTCCCTATCAAACCTGCCCCTCTCCCTCTCAGCCCCGGCAAGAATAGCTTTGGAATC
TTGTCCTCCAAAGGAAATATACTTCAGATTCAGGGGTCACAACTGAGCGCCTCCTATCCT
GGAGGGCAGCTGGTGTTCGCTATCCAGAATCCCACCATGATCAACAAAGGGACCCGATCA
AATGCCAATATCCAGTACCAGGCGGTCCCTCAGATTCAGGCAAGCAATTCCCAAACCATC
CAAGTACAGCCCAATCTCACCAACCAGATCCAGATCATCCCTGGCACCAACCAAGCCATC
ATCACCCCCTCACCGTCCAGTCACAAGCCTGTCCCCATCAAGCCAGCCCCCATCCAGAAG
TCGAGTACGACCACCACCCCCGTGCAGAGCGOGGCCAATGTGGTGAAGTTGACAGGTGGG
GGCGGCAATGTGACGCTCACTCTGCCCGTCAACAACCTCGTGAACGCCAGTGACACCGGG
GCCCCTACTCAGCTCCTCACTGAAAGCCCCCCAACCCCGCTGTCTAAGACTAACAAGAAA
GCAAGGAAGAAGAGCCTTCCTGCCTCCCAGCCCCCTGTGGCTGTGGCTGAGCAGGTGGAG
ACGGTGCTGATCGAGACCACCGCGGACAACATCATCCAGGCAGGAAATAACCTGCTCATT
GTTCAGAGCCCTGGTGGGGGCCAGCCAGCTGTGGTCCAGCAGGTCCAGGTGGTGCCCCCC
AAGGCCGAGCAGCAGCAGGTGGTACAGATCCCCCAGCAGGCTCTGCGGGTGGTGCAGGCG
GCATCTGCCACCCTCCCCACTGTACCCCAGAAGCCCTCCCAGAACTTTCAGATCCAGGCA
GCTGAGCCGACACCTACTCAGGTCTACATCCGCACGCCTTCCGGTGAGGTGCAGACAGTC
CTTGTCCAGGACAGCCCCCCAGCAACAGCTGCAGCCACCTCTAACACCACCTGTAGCAGC
CCTGCATCCCGTGCTCCCCATCTGAGTGGGACCAGCAAAAAGCACTCAGCTGCAATTCTC
CGAAAAGAGCGTCCCCTGCCAAAGATTGCCCCAGCCGGGAGCATCATCAGCCTGAATGCA
GCCCAGTTGGCGGCAGCTGCCCAGGCAATGCAGACCATCAACATCAATGGTGTCCAGGTC
CAGGGCGTGCCTGTCACCATCACCAACACAGGCGGGCAGCAGCAGCTGACAGTGCAGAAT
GTTTCTGGGAACAACCTGACCATCAGTGGGCTGAGCCCCACCCAGATCCAGCTGCAAATG
GAACAAGCCCTGGCCGGAGAGACCCAGCCCGGGGAGAAGCGGCGCCGCATGGCCTGCACG
TGTCCCAACTGCAAGGATGGGGAGAAGAGGTCTGGAGAGCAGGGCAAGAAGAAGCACGTG
TGCCACATCCCCGACTGTGGCAAGACGTTCCGTAAGACGTCCTTGCTGCGTGCCCATGTG
CGCCTGCACACTGGCGAGCGGCCCTTTGTCTGCAACTGGTTCTTCTGTGGGAAGAGGTTC
ACACGGAGTGACGAGCTCCAACGGCATGCTCGCACCCACACAGGGGACAAACGCTTCGAG
TGCGCCCAGTGTCAGAAGCGCTTCATGAGGAGTGACCACCTCACCAAGCATTACAAGACC
CACCTGGTCACGAAGAACTTGTAAGGCCAACTGCGGCGGGAGGCCCTGAAGATGCAGTCC
CCCACCTGTGTCCTCCCTGGGCCCCTGGTGGAAAGGAGCCCTGTGGCTGCCTTGGGCCTG
CCCTCAGCCCCACTCCTGTTCTGCAACTGTCCCCACAGGAAGGGGCTCTGTTCCCTGTAT
TGTCCTCCTTCTGAAGCCCCTTGGCTCTGCCTTGGCCCTTCCCCTCACCACGAGCTCCCG
GCCTGCCCAGACTGTGGACACTGGCCGTGCCCAATGAGACGTTCTAAACCAGGACGCGTG
GGAACCCTTATTTCCAAAGGAAAAACATGCATTTCACTCCGTCGAGGAGCAAAGTGAGCC
CCTACCCCCCACCCCGATCCCCGCTCCCAACACTGCCGGAGTCGCGTCATGCCATGCCCC
CTCTCCTGCACCTCCCTGGCCCTGCCGGCCACTGTGGACGCCCTGGGGCTTGGCACCCAC
CTCTGGAGAAACTCGGGGCCACCTCCACTCCATGTGCCCAGCCCCGCCACAACCTCTCCT
CCAGCACATTCCAGCTCTATTTAAAAAGTAAAGACACCCACCGACTCCTGATCCCCCTCT
TTTTCTATGGAGAACGTTGCCTTATACTCTCTACTTCAGATGATGAACACTGTGTACTGT
GTGTGCTTTAAAGAAGTTTTATTTAATTGCTCCCTTCTTCCTTTCCTTGTTATTCACCTC
CCTGATGCCTGCTTTCAGTTGAGGGTTGGGGGCAATGATGAGCATATGAATTTTTTCTCA
CTCTAGCAATTCCCTTTTCTAAATGACACAGCATTTAAACTCAAATCTGGATTCAGATAA
CAGCACCTGCACATCCTGCACCTCCTCCCTCTCCCTTCACCTCACCCCTGCCCGGCCCAA
GCTCTACTTGTGTACAGTGTATATTGTATAATAGACAATTGTGTCTACTACATGTTTAAA
AACACATTGCTTGTTATTTTTGAGGCTTTTAAATTAAACAAAAATCCAACTTTAAAAAAA
AAAAAAAA >Hs.77541_mRNA_1 gi|12804364|gb|BC003043.1|BC003043 *Homo sapiens* clone
MGC:4370 IMAGE:2822973 polyA = 3
CCCGCGTCGGTGCCCGCGCCCCTCCCCGGGCCCCGCCATGGGCCTCACCGTGTCCGCGCT
CTTTTCGCGGATCTTCGGGAAGAAGCAGATGCGGATTCTCATGGTTGGCTTGGATGCGGC
TGGCAAGACCACAATCCTGTACAAACTGAAGTTGGGGGAGATTGTCACCACCATCCCAAC
CATAGGCTTCAATGTAGAAACAGTGGAATATAAGAACATCTGTTTCACAGTCTGGGACGT -continued GGGAGGCCAGGACAAGATTCGGCCTCTGTGGCGGCACTACTTCCAGAACACTCAGGGCCT
CATCTTTGTGGTGGACAGTAATGACCGGGAGCGGGTCCAAGAATCTGCTGATGAACTCCA
GAAGATGCTGCAGGAGGACGAGCTGCGGGATGCAGTGCTGCTGGTATTTGCCAACAAGCA
GGACATGCCCAACGCCATGCCCGTGAGCGAGCTGACTGACAAGCTGGGGCTACAGCACTT
ACGCAGCCGCACGTGGTATGTCCAGGCCACCTGTGCCACCCAAGGCACAGGTCTGTACGA
TGGTCTGGACTGGCTGTCCCACGAGCTGTCAAAGCGCTAACCAGCCAGGGGCAGGCCCCT
GATGCCCGGAAGCTCCTGCGTGCATCCCCGGATGACCATACTCCCGGACTCCTCAGGCAG
TGCCCTTTCCTCCCACTTTTCCTCCCCCATAGCCACAGGCCTCTGCTCCTGCTCCTGCCT
GCATGTTCTCTCTGTTGTTGGAGCCTGGAGCCTTGCTCTCTGGGCACAGAGGGGTCCACT
CTCCTGCCTGCTGGGACCTATGGAAGGGGCTTCCTGGCCAAGGCCCCCTCTTCCAGAGGA
GGAGCAGGGATCTGGGTTTCCTTTTTTTTTTCTGTTTTGGGTGTACTCTAGGGGCCAGGT
TGGGAGGGGGAAGGTGAGGGCTTCGGGTGGTGCTATAATGTGGCACTGGATCTTGAGTAA
TAAATTTGCTGTGGTTTGAAAA >Hs.7001_mRNA_1 gi|6808256|emb|AL137727.1|HSM802274 *Homo sapiens* mRNA; cDNA DKFZp434M0519 (from clone DKFZp434M0519); partial cds polyA = 3

GTGGCGGTGGCTGCGGCGACGGCAGAGGCGAAGGGAGCCGGATCGCCGACCTGAGCGGGA
GGCGGCGGTGGCGGCCATGGCGGCAGATGGAGAGCGTTCCCCGCTGCTGTCTGAGCCCAT
CGACGGTGGCGCGGGCGGCAACGGTTTAGTGGGGCCCGGCGGGAGTGGGGCTGGGCCCGG
GGGAGGCCTGACCCCCTCCGCACCACCGTACGGAGCCGGTAAACATGCCCCGCCCCAGGG
TAAGCCGGGGCGGGTCCGAGGTGCTCCCCGGGGTACTCTGAAAGCCGGGGAGGGGGCGGG
ACCGAGGGCGGAGGCGGGTCCCAGTCGCCAGGTGCGGGACTGCTGCACCTGTGACTGGGC
GAGGCTTCCTTCCCTCCGTAATCGCGACCACAGCCTAGGGACGGAAGGGGGTTCTGAGCA
ACCTGATAGAAGTGCCAATTATGAGAAGCCCTCCGAGCTTGGTCAGAGGGTTGAAGATCA
GAAGGACTTCCCTACCACCGTGGAGCATCAGTGGGGGTGTAAGTGATCCCAGCCCTTCTA
TTTGCTTCCTCTCCAGCATTTCCCCCGTTTCCCGAGGGGCATCCAGCCGTGTTGCCTGGG
GAGGACCCACCCCCCTATTCACCCTTAACTAGCCCGGACAGTGGGAGTGCCCCTATGATC
ACCTGCCGAGTCTGCCAATCTCTCATCAACGTGGAAGGCAAGATGCATCAGCATGTAGTC
AAATGTGGTGTCTGCAATGAAGCCACCGTGAGTTACACATATCTATGAAATGGGCCCTGT
TTCCTGGATCCTCTTTCTGATGTCTTGGTTCTAGACCCTGACCTTCCGGCTATTAGCCAA
GTGCTTTTGATGATACCCAGGTTTCAGTTCCAGGTGTCTCACACAGCCATTTCCCCAGAA
GCCACTCACCAAAGCTAATGTTCACTTTCTCTCACTTTTACACCTAGCCTAGTTCCTATT
TGCAAATCTCATGATATAGTCTTTCTTTTATTTCTCCTTCCTGGTTAGCACCTTATTTTT
CTGATCTCATAAAGTGTTTTTGGAGGGAAGTGGAGGGGATTGGGATTAGAGGTTTGCTTG
CTGATGACCCTATTATTCTCTAGCCAATCAAGAATGCACCCCCAGGGAAAAAATATGTTC
GATGCCCCTGTAACTGTCTCCTTATCTGCAAAGTGACATCCCAACGGATTGCATGCCCTC
GTCCCTACTGGTAAGAGGCATAAGGTGGGGAAGGGCCTAAGTGGGGAACTGGAAAGTCAA
AAAAGGATGAGCGTATACAGAGAATGTAAAGGTGAGAGAGCCTAGTGTTTATTTAGGAGA
AAAGGCTTTGAAGCATGTGCCTCAGGAATGTTATAGCTGTCTTTCTCGTTTCTCAATAAA
AATATTGAGATGAAATGATGTCGTTTCGGAGAATAGAGAGCCTTGGGGACTGGGTGTGTT
ATCCTGAGGTCGGAGGGGAATTGGGGACCTGAAGTTTAAACAGTGCTCTTTCTTTCTCAA
GGATTCTTGAGGGTATACAGTTGGGGGACAGAGTATCTTAAGTACAGAGAAGTCGAGTGA
CTTAATAGACAGGGAGTGGGGGATGTGGAACAGGGACTGTGAAGATTTTTAGGATTAAAA
ATTTTTCAAACACAAGTTTGAAAATACAAGTCTTTTTCTTTTGTATAGCAAAAGAATCAT
CAACCTGGGGCCTGTGCATCCCGGACCTCTGAGTCCAGAACCCCAACCCATGGGTGTCAG
GGTTATCTGTGGACATTGCAAGAATACTTTTCTGGTGAGGAAGGGGTATTGGGAAGGGGA
GGGGAAAGGAGACTAAGAGTCATTTCGAGTATATTTCTTAGAGTAATGGTAATGACCCCT
GAAAGGTCTGTCCTATGGGAACATGTTCTGCATCCCCACCCCAAGGTTCTCATTGAGGGA
GACCCTGCTTGTGCTATTATTTTTGTTTTCTTTCTCCATAGTGGACAGAGTTCACAGACC
GCACTTTGGCACGTTGTCCTCACTGCAGGAAAGTGTCATCTATTGGGCGCAGATACCCAC
GTAAGAGATGTATCTGCTGCTTCTTGCTTGGCTTGCTTTTGGCAGTCACTGCCACTGGCC
TTGCCGTGAGTACCCTTGCCCCAACCTCTTTCATTCTGCAGCCTCATCTCCATAGGCTAA
GATTTGGGAAACTGCTACCCTAAAAAAAAGTGGAAGAAACTTAGGGGACTAGTTTGTTTT
GTTTTAAGATATGGATGAGCTAAAGTGCAAAGTGGCTGATCAAACAGACTTTATTACTAC
TACAAGAGTGAAAAACAGCCTTCCTTTCTCTGTAGGATGAGGATAGGACAGTGAAATTCT
TAATTTAAGAGTTGCTATTTTTCAAACCTGGCTCAGTTGTCAGATATTAAGAAAAACTGA
GATACAGTGTGGGATGGGATGAGTATGTTACGCCTAAGGGAAGGAAGCTGATCAGCTCTG
CCTTTAAGAAGGTCCCTGAGGGTGGCTACATGTGGATAAGGAACAAGGACTGAAGCGTGA
GTTATTACTGTTCTTAGAACTAATAGGAGGTAGTGGAGACCAACATTAACCCCATCTTTC
TTTTCTTCTCCCTCCTTATCTTCATCAGTTTGGCACATGGAAGCATGCACGGCGATATGG
AGGCATCTATGCAGCCTGGGCATTTGTCATCCTGTTGGCTGTGCTGTGTTTGGGCCGGGC
TCTTTATTGGGCCTGTATGAAGGTCAGCCACCCTGTCCAGAACTTCTCCTGAGCCTGATG
ACCCACAGACTGTGCCTGGCCCCTCCCTGGTGGGGACAGTGACACTACGAAGGGAGCTGG
GGTAGTTAAAGGCTCCCGGGGCTTCTAGAAGGAAGCCAAGCAGCTGCCTTCCTTTTCCCT
GGGGAGAGGTAGGAAGGAACCAGGCCCTCACTTAGGTTTGGAGGGGCAGATAAGAGCACT
GCTGACCATCTGCTTTCCTCCAAGGGTTGCTGTGTCTAGGGTGAAGTAGGCAAAACGTTG
CCCTTAAAACTGGGCCCTGAAGACGGTTCCAGCCTTGTCCTTCCTGTGTGCTCCCTGAGA
GCCATTCCTGTCCCTTACACATTCCAGGGCAGGGTGGGGGTGGGTAGCCCTGGGGGTTCC
CCTCCCTCTTGTGCACCATTAGGACTTTGCTGCTGCTATTGCACTTCACCAGAGGTTGGC
TCTGGCCTCAGTACCCTCAGTCTCCTCTCCCCACATTGTGTCCTGTGGGGGTGGGGTCAG
CCGCTGCTCTGTACAGAACCACAGGAACTGATGTGTATATAACTATTTAATGTGGGATAT
GTTCCCCTATTCCTGTATTTCCCTTAATTCCTCCTCCCGACCTTTTTTACCCCCCCAGTT
GCAGTATTTAACTGGGCTGGGTAGGGTTGCTCAGTCTTTGGGGGAGGTTAGGGACTTATC
CTGTGCTTGTAAATAAATAAGGTCATGACTCT
AAAAAAA

>Hs.302144 mRNA_1 gi|11493400|g|AF130047.1|AF130047 *Homo sapiens* clone FLB3020 poLyA = 0

CTGTCAGCACGGGGCCTGGCATGTAATTGGTCTGCACCCACTGGTGCACTGAACTGCCAT
AACCTCAGGTTTTCTTTCTTGCTGATACCCCTGGGTCATGTTCTTTGGCAAATAACATGA
TTCATTATGAAGTAGAGTTCAGCAAAGGACAAGGATGAAAGTTGTCATTTAGAGAACTGC

-continued

CATTCAGACTTTCTTGTCTAGGTAAAGAGCAAGGTCTTCTCTCTTTTCAACTCATTTTCT
AAATTTAAACTGACGATGAGAATATGGATGATGTGTAGCTTCCTTCTCCCCCACTGATTT
TTGGTTCAGGCTCTGGGTTTTTGGCAAGAACTTACAGATCTCACTTATTATTGGCCACCC
TTCTGCTTTAAGACCTGTCAGGGCTTGTCTGAAATAAAACTGGAAGCACTTCTGATTCCA
TCCTCACTGCTTTCCTCCTTCACCGTCAGACAGCATTACTGTATAGCACTGAGTGAGGGG
CCCTGACACTGGAAGGTGGCAGGTGGGGCCTGGCCGCCAGTGAGGTATCATCATTTGTGT
GTGCTCATGTGTGCGTTGGGCTTGTTGTATCTGAGGCATGAACATTCCATATACACGGCT
TAAAGAGTTTTCTTCCCATACCGAAAGCATATATTCGGAGAGGACCCAACTTATTCAGCA
TAGCCTTGTTCCCATAGTAGCCATCCTATTCCCCCACAGCCTCTACTTTAGGAAAGCTCC
CCGTCCCCATATGAAATCCAAACCAAAAAAGATATATCACTTTCAGCTCAATTATTCCAT
AATTACAAGATATTAGGCTAGTGGGCTCTTTATTGGTTGGGTCTTATATTAATGTTATAT
GCTAGCCTTGTAATTTTGAGCTCCTCTATGGATGTTAATTTTAGTGAAACTCTATATTGA
AGAAAAGATGGGACTAAGGGGGAGACAGGAGGAGGAAAGAAAGCAGAGACAGGCAAAGAA
TCATAGCCTGAAATTCAACAGCAAGCATGGCTTATGAAGATCAAGTTATATTTTTGCTTC
ATGAATCATTGTCAGACAAATTAAGAACATATTGTTTCTTATTTATCTATTGTCAAGGAT
TCACTATCAGACACTAAGAATGAATCTTGATTTTCATAAGCTCTGTTGACACCATGGAGC
CACAGAGCATAAAACTTGCATCTAATAAAGAAAGTGCAACATGGAACAGCAGGGAGTGGA
ATACCAGCACAACTCACAGCTGCTTCCTGTTCCTCGTCCCTGTTTTCAGGAATGTTTCTT
AGCAGGAAGTTTTTTAATAGACCGAGAATTTGTTATATGTATTCTAAGAAAAGTTGTAGT
TGTAGATGCATTACTCTCCCAAATCTTAGAGATCAGGGATGATTATGTTCCATTTTTGTT
TGGTGAGTTCCCATCTTTGTATGTACCTCCTTGCTCCCGGCTGTCCTCCTCTCCTCTTCC
CTAGTGAGTGGTTAATGAGTGTTAATGCCTAAACCATACTTGTTTTATGGACACTTCTAT
AATGGATTCGTTGCATAATTTTCATGCAGTGTATAGTGTTACTAGTTGGAAATTCTTGGA
GGACTCTTAGCTGTCTGATGAAATTCCTAGTAGAAATTTTTGTTTTGAATTCCTAAAGTT
GAAATATGAAAATTATATTTTAATTTGATTC

>Hs.26510_mRNA_2 gi|11345385|gb|AF308803.1|AF308803 *Homo sapiens* chromosome 15 map 15q26 polyA = 3

AGTTTTTCTGGTAGAAGGCGGGGTTCTCCTCGTACGCTGCGGAGTCTCTGCGGGGTGTAG
ACCGGAATCCTGCTGACGGGCAGAGTGGATCAGGGAGGGAGGGTCGAGACACGGTGGCTG
CAGGTCTGAGACAAGGCTGCTCCGAGGTAGTAGCTCTCTTGCCTGGAGGTGGCCATTCAT
TCCTGGAGTGCTGCTGAGGAGCGAGGGCCCATCTGGGGTCTCTGGAAGTCGGTGCCCAGG
CCTGAAGGATAGCCCCCCTTGCGCTTCCCTGGGCTGCGGCCGGCCTTCTCAGAACGAAGG
GCGTCCTTCCACCCCGCGGCGCAGGTGACCGCTGCCATGGCTTTTCCCCATCGGCCGGAC
GCCCCTGAGCTGCCTGACTTCTCCATGCTGAAGAGGCTGGCTCGAGACCAGCTCATCTAT
CTGCTGGAGCAGCTTCCTGGAAAAAAGGATTTATTCATTGAGGCAGATCTCATGAGCCCT
TTGGATCGAATTGCCAATGTCTCCATCCTGAAGCAACACGAAGTAGACAAGCTATACAAG
GTGGAGAACAAGCCAGCCCTCAGCTCCAATGAACAATTGTGCTTCTTGGTCAGACCCCGC
ATCAAGAATATGCGATACATTGCCAGTCTTGTCAATGCTGACAAATTGGCTGGCCGAACT
CGCAAATACAAAGTGATCTTCAGCCCTCAAAAGTTCTATGCGTGTGAGATGGTGCTTGAG
GAAGAGGGAATCTATGGAGATGTGAGCTGTGATGAATGGGCCTTCTCTTTGCTGCCTCTT
GATGTGGATCTGCTGAGCATGGAACTACCAGAATTTTTCAGGGATTACTTTCTGGAAGGA
GATCAGCGTTGGATCAACACTGTAGCTCAGGCCTTACACCTTCTCAGCACTCTCTATGGA
CCCTTTCCAAACTGCTATGGAATTGGCAGGTGCGCCAAGATGGCATATGAATTGTGGAGG
AACCTGGAGGAGGAGGAGGATGGCGAAACCAAGGGCCGAAGGCCAGAGATTGGACATATC
TTTCTCTTGGACAGAGATGTGGACTTTGTGACAGCACTTTGCTCCCAAGTGGTTTATGAG
GGCCTAGTAGATGACACCTTCCGCATCAAGTGTGGGAGTGTCGACTTTGGCCCAGAAGTC
ACATCCTCTGACAAGAGCCTGAAGGTGCTACTCAATGCCGAGGACAAGGTGTTTAATGAG
ATTCGGAACGAGCACTTCTCCAATGTCTTTGGCTTCTTGAGCCAGAAGGCCCGGAACTTG
CAGGCCCAGTATGATCGCCGGAGAGGCATGGACATTAAGCAGATGAAGAATTTCGTGTCC
CAGGAGCTCAAGGGCCTGAAACAGGAGCACCGCCTGCTGAGTCTCCATATTGGGGCCTGT
GAATCCATCATGAAGAAGAAAACCAAGCAGGATTTCCAGGAGCTAATCAAGACTGAGCAT
GCACTGCTAGAGGGGTTCAACATCCGGGAGAGCACCAGCTACATTGAGGAACACATAGAC
CGGCAGGTGTCGCCTATAGAAAGCCTGCGCCTCATGTGCCTTTTGTCCATCACTGAGAAT
GGTTTGATCCCCAAGGATTACCGATCTCTGAAAACACAGTATCTGCAGAGCTATGGCCCT
GAGCACCTGCTAACCTTCTCCAATCTGCGAAGACCTGGGCTCCTAACGGAGCAGGCCCCC
GGGGACACCCTCACAGCCGTGGAGAGTAAAGTGAGCAAGCTGGTGACCGACAAGGCTGCA
GGAAAGATTACTGATGCCTTCAGTTCTCTGGCCAAGAGGAGCAATTTTCGTGCCATCAGC
AAAAAGCTGAATTTGATCCCACGTGTGGACGGCGAGTATGATCTGAAAGTGCCCCGAGAC
ATGGCTTACGTCTTCAGTGGTGCTTATGTGCCCCTGAGCTGCCGAATCATTGAGCAGGTG
CTAGAGCGGCGAAGCTGGCAGGGCCTTGATGAGGTGGTACGGCTGCTCAACTGCAGTGAC
TTTGCATTCACAGATATGACTAAGGAAGACAAGGCTTCCAGTGAGTCCCTGCGCCTCATC
TTGGTGGTGTTCTTGGGTGGTTGTACATTCTCTGAGATCTCAGCCCTCCGGTTCCTGGGC
AGAGAGAAAGGCTACAGGTTCATTTTCCTGACGACAGCAGTCACAAACAGCGCTCGCCTT
ATGGAGGCCATGAGTGAGGTGAAAGCCTGATGTTTTTCCCGGCCAGTGTTGACATCTTCC
CTGAACACATTCCTCAGTGAGATGCAGGCATCTGGCACCCAGCTGCTATAACCAAGTGTC
CACCAACTACCTGCTAAGAGCCGGGAGCATGGAACGTGTTGGGATTTAGAGAACATTATC
TGAGAAAAGAGTTCACTTCCTGCTCCCAGGATATTTCTCTTTTCTGTTTATGAAGTACAA
CCCATGCTGCTAAGATGCGAGCAGGAAGAGGCATCCTTTGCTAAATCCTGTTTGAATGTC
ATTGTAAATAAAGCCTCTGCTCTCAGATGTAAAAAAAA

>Hs.324709_mRNA_2 gi|12655026|gb|BC001361.1|BC00136| *Homo sapiens* clone MGC:2474 IMAGE:3050694 polyA = 2

GGCACGAGGGGTCGCGCTGCCGCCGTTTTATTTGAAGACATCGTCCAGTTCTGACCATGG
ACTCGCAGCCATCGGCCCTTAGTTTCCATCCCCTCTAGTGGGCCTTCGGGGGCTCTACTG
ACGTCCCTCCTTCCCTTGGTACCGGGCCGGGGAAGTGTTCTCGGGCGCGGGAGGTTCCGC
ATGCCCAGGCCTGGCCAGGGGAGATGACCGATCCGTCGCTGGGGCTGACAGTCCCCATGG
CGCCGCCTCTGGCCCCGCTCCCTCCCCGGGACCCAAACGGGGCGGGATCCGAGTGGAGAA
AGCCCGGGGCCGTGAGCTTCGCCGACGTGGCCGTGTACTTCTCCCGGGAGGAGTGGGGCT
GCCTGCGGCCCGCGCAGAGGGCCCTGTACCGGGACGTGATGCGGGAGACCTACGGCCACC
TGGGCGCGCTCGGTGAGAGCCCCACCTGCTTGCCTGGGCCCTGCGCCTCCACAGGCCCTG

-continued

CCGCGCCTCTGGGAGCTGCGTGTGGAGTTGGGGGCCCCGGGGCCGGGCAGGCGGCCTCCT
CGCAGCGTGGGGTTTGCGTTCTTCTCCCCCAGGAGTCGGAGGCAGCAAGCCGGCGCTCAT
CTCCTGGGTGGAGGAGAAGGCCGAACTGTGGGATCCGGCTGCCCAGGATCCGGAGGTGGC
GAAGTGTCCGACAGAAGCGGACCCAGCAGATTCCAGAAACAAGGAAGAGGAAAGACAAAG
GGAAGGGACGGGAGCCCTGGAGAAGCCCGACCCTGTGGCCGCCGGGTCTCCTGGGCTGAA
GGCTCCCCAAGCCCCCTTTGCCGGGTTGGAGCAGCTGTCCAAGGCCCGGCGCCGGAGTCG
CCCCCGCTTTTTTGCCCACCCCCCTGTCCCCCGAGCTGACCAGCGTCACGGCTGCTACGT
GTGCGGGAAGAGCTTCGCCTGGCGCTCCACACTGGTGGAGCACATTTACAGCCACAGGGG
CGAGAAGCCCTTCCACTGCGCAGACTGCGGCAAGGGCTTCGGCCACGCTTCCTCCCTGAG
CAAACACCGGGCCATCCATCGTGGGGAGCGGCCCCACCGCTGTCCCGAGTGTGGTCGGGC
CTTCATGCGCCGCACGGCGCTGACTTCTCACCTGCGCGTTCACACTGGCGAGAAGCCCTA
CCGCTGCCCGCAGTGTGGCCGCTGCTTCGGCCTGAAGACCGGCATGGCCAAGCACCAATG
GGTCCATCGGCCCGGGGGCGAGGGGCGTAGGGGCCGGCGCCCTGGGGGGCTGTCTGTGAC
CCTGACTCCTGTCCGCGGGGACCTGGACCCGCCTGTGGGCTTCCAGCTGTATCCAGAGAT
ATTCCAGGAATGTGGGTGACGGCCTAAAAAGTGACCATCTAGACATTGTGGGCGGCCCGA
GATGGGCTCAGGGGCCCGAACCTCTGCAGCGGCCTGCAGGGAGGTCCCAGAATCCACCGC
AAGAGCTGGCCTGGGGTGCGGACAGTCTGATCTTGGGCTCTCAGCAGCCTCTTCTGCCAG
CACCTTGCTCCCCGCTGCCCTGGGCTCTCCAAGGCCCCCTTTGCTGAGGCAGGGCTGAGG
TGAGAACCCCCCAGACCTCCATACAGGGAAGCAAAAGCTGTTTCTCCTCCCAGAGATGCT
AAGAGGATTGAGGTAGAGAAGAACCTTGTTTTCTCTGTTGTCTTTTTCTTTTTACTTTTT
TAATTTTTTGAGACGGAGTTTTGCTCTTGTTGCCCAGGCTGGAGTGCAATGGTGCGATCT
CGACTCACTGCAACTTCCACCTCCTGGAGTCAAGCGATTCTCCTGCCTCAGCCACCCAAG
TAGCTGGAATTACAGGCACCTGCCACTATGCCCGGCTAACTTTTTGTATTTTTAGTAGAG
ATGGGGTTTCACCATGTTGGCTAGGCTGGTCTCGAACTCCTGCCCTCAGGTGATCCACCC
ACCTCTGCCTCCCAAAGTGCTGGGATTACAGGCGTGAGCCACCTCACCTGGCCTTTTCTT
TTTTATTCTTTGACCTTCCCACAAGACAATACCCATTGTCTGTTTTTTTTGTTTATTTAT
TTACTTATTAAGACAGCATCTTGCTCCTCACCCAGGCTGGAATGCAGTGGTGTGAACTGG
GCTCACTGCAGCCTAGACCTGCTGGGCTCAAGGAATCCTCCTGCCCCAGCCTCTCAGATG
GCTGTGACTACAGGTGGGCAACACTATGCCTGGTTAATTTTTAAATTTTTTTGCAGAGAT
GGGGTTCCCACTATGTTGATCAGGCTGGTCTCAAACTCCTCGGTTCAAGCAATTCGCCCA
CCTTGGCCTCCCAAAGTGCTGGGATTACAGGGGAGCCACTGCACTGGCCTTCATTGTCTT
TTTGCTGCACAACCTAAAAAACCAGTGACCCTGTATTGGAAAAAAAAAAAAAAAAAAAAA
A

>Hs.65756_mRNA_3 gi|3641494|gb|AF035154.1|AF035154 *Homo sapiens* chromosome
16 map 16p13.3 polyA = 3
GCCATGGCCGCCGGCCCCGCGCCGCCCCCCGGCCGCCCCCGGGCGCAGATGCCGCATCTG
AGGAAGGTGCGAGGCGGATGGAGCGGGTGGTCGTGAGCATGCAGGACCCCGACCAGGGCG
TGAAGATGCGGAGCCAGCGCCTGCTGGTCACCGTCATTCCCCACGCGGTGACAGGCAGCG
ACGTCGTGCAGTGGTTGGCCCAGAAGTTCTGCGTCTCGGAGGAGGAGGCCCTGCACCTGG
GCGCCGTCCTGGTGCAGCATGGCTACATCTACCCGCTGCGCGACCCCCGTAGCCTCATGC
TCCGGCCAGACGAGACGCCCTACAGGTTCCAGACCCCGTACTTCTGGACAAGTACCCTGA
GGCCGGCTGCAGAGCTGGACTATGCCATCTACCTGGCCAAGAAGAACATCCGAAAACGGG
GGACCCTGGTGGATTATGAGAAGGACTGCTATGACCGGCTACACAAGAAGATCAACCACG
CATGGGACCTGGTGCTGATGCAGGCGAGGGAGCAGCTGAGGGCAGCCAAGCAGCGCAGCA
AGGGGGACAGGCTGGTCATTGCGTGCCAGGAGCAGACCTACTGGCTGGTGAACAGGCCCC
CGCCCGGGGCCCCCGATGTGCTGGAGCAGGGTCCAGGGCGGGGATCCTGCGCTGCCAGCC
GTGTGCTCATGACCAAGAGTGCAGATTTCCATAAGCGGGAGATCGAGTACTTCAGGAAAG
CGCTGGGCAGGACCCGAGTGAAGTCCTCCGTCTGCCTTGAGGCGTACCTGAGTTTCTGCG
GCCAGCGTGGACCCCACGATCCCCTCGTGTCGGGGTGCCTGCCCAGCAATCCCTGGATCT
CAGACAATGACGCCTACTGGGTCATGAATGCCCCCACGGTGGCTGCCCCCACGAAGCTCC
GTGTGGAGAGATGGGGCTTCAGCTTCCGGGAGCTCCTGGAGGACCCCGTGGGGCGGGCCC
ACTTCATGGACTTTCTGGGAAAGGAGTTCAGTGGAGAAAACCTCAGCTTCTGGGAGGCAT
GTGAGGAGCTTCGATATGGAGCGCAGGCCCAGGTCCCCACCCTGGTGGATGCCGTGTACG
AGCAGTTCCTGGCCCCCGGAGCTGCCCACTGGGTCAACATCGACAGCCGGACCATGGAGC
AGACCCTGGAGGGGCTGCGCCAGCCCCACCGCTATGTCCTGGATGACGCCCAGCTGCACA
TATACATGCTCATGAAGAAGGACTCCTACCCAAGGTTCCTGAAGTCTGACATGTACAAGG
CCCTCCTGGCAGAGGCTGGGATCCCGCTGGAGATGAAGAGACGCGTGTTCCCCGTTTACGT
GGAGGCCACGGCACTCGAGCCCCAGCCCTGCACTCCTTCCCACCCCTGTGGAGCCCACAG
CGGCTTGTGGCCCTGGGGGTGGAGATGGGGTGGCCTAGTGGACCTGGCCCATCTGCCACT
CTAGTCCCTGCAGCTCAACGTCCTGCGTGAATGCAGCAGCCACCCCCGTCTTGGCCCAGG
TCCTGGGGGCTGCTGAACCCAGCACCAGTGTCCCCTTGTGCCCAGGGGGCCCAGTCTTCT
GTGGGGTGCACAGCCTCCCTCCCTCCAGCAAGCCCTCCCTGCCCAGAAGGAATGGGTCCA
GGTGTGGATTCCCAGGGAGGGGGTTCATTGGCTCAGCTTGGGTCAGGGCAGAGCCTGTTA
CCTGAAGAGAGGTGAGACCAAGGCCACAGGGAGCTCCACCTTCTCTGGTCTTCAGTCCAG
CACTGGGTGCCCATCCCCATCTCTAAAACCAGTAAATCAGCCAGCGAATACCCGGAAGCA
AGATGCACAGGCGGGCGGCTTCCCACACACCCGTCACAAGACGCGGACATGCAGGTCTCG
GCGCGAGCTCTGCCCCGTCCAAGAGCCTCTCCGCTGTCGCCCAGTGTGAGCCTGGAAGAG
GACCCAAGAGAGTGCCGTGCTGAGGCTGCCTCGAGGTCACTGCCTTCCGGAGCTGCGCCT
ATTCCTCCCTCGCCAAACGCGTTCCAGAATTTGTCCACAGGTGCGCCGGCACCTGCTTTC
CCACCTCGAGGCCGCGGCCTCCCCCCCGATTTATAGACAACTCTGACATTGTCACCCCAC
TGACGAGGCCCGATTCCATAGGGTGGATCCTTGCCAGGCGTCCCTGATCCTCCCTGCCCA
AGTCTTCCTTCGTGAGCTGGCCTTGCTCCCCATCCCCCAAGTGCCTCACCAGTCCCCCAG
ACTGGGTGAAGGTACAGCTGGCTCCTTTCGGGGGTGCAGCTTCAACTCTCTCGGCGGTAG
GGCGGTGCCATCCCCACCCATAGGGCTGGCTCACATCCAGTCACTCCCAACAGCGTCCAG
CACACAAATAAAAGACCCTTGGGCCCTGGCTCTGAGAAAAAAAA >Hs.165743_mRNA_2 gi|13543889|gb|BC006091.1|BC006091 *Homo sapiens* clone
MGC:12673 IMAGE:3677524 polyA = 3
AGACTGCCGAGCAGCCTTGAGCCGTTGAGCAGCTGAACAGAGGCCATGCCGGGGCACTCC
GAGGCCTGAGACGACCACGCCTGTGCCGCTGAGGACCTTCATCAGGGCTCCGTCCACTTG -continued

```
GCCCGCTTGGCTGTCCAATCACACTCCAGTGTCAACCACTGGCACCCAGCAGCCAAGAGA
GGTGTGGCGTGGCCCTGGGGACGCATGGCTGAGGCAGGAACAGGTGAGCCGTCCCCCAGC
GTGGAGGGCGAACACGGGACGGAGTATGACACGCTGCCTTCCGACACAGTCTCCCTCAGT
GACTCGGACTCTGACCTCAGCTTGCCCGGTGGTGCTGAAGTGGAAGCACTGTCCCCGATG
GGGCTGCCTGGGGAGGAGGATTCAGGTCCTGATGAGCCGCCCTCACCCCCGTCAGGCCTC
CTCCCAGCCACGGTGCAGCCATTCCATCTGAGAGGCATGAGCTCCACCTTCTCCCAGCGC
AGCCGTGACATCTTTGACTGCCTGGAGGGGGCGGCCAGACGGGCTCCATCCTCTGTGGCC
CACACCAGCATGAGTGACAACGGAGGCTTCAAGCGGCCCCTAGCGCCCTCAGGCCGGTCT
CCAGTGGAAGGCCTGGGCAGGGCCCATCGGAGCCCTGCCTCACCAAGGGTGCCTCCGGTC
CCCGACTACGTGGCACACCCCGAGCGCTGGACCAAGTACAGCCTGGAAGATGTGACCGAG
GTCAGCGAGCAGAGCAATCAGGCCACCGCCCTGGCCTTCCTGGGCTCCCAGAGCCTGGCT
GCCCCCACTGACTGCGTGTCCTCCTTCAACCAGGATCCCTCCAGCTGTGGGGAGGGGAGG
GTCATCTTCACCAAACCAGTCCGAGGGGTCGAAGCCAGACACGAGAGGAAGAGGGTCCTG
GGGAAGGTGGGAGAGCCAGGCAGGGGCGGCCTTGGGAATCCTGCCACAGACAGGGGCGAG
GGCCCTGTGGAGCTGGCCCATCTGGCCGGGCCCGGGAGCCCAGAGGCTGAGGAGTGGGGC
AGCCCCCATGGAGGCCTGCAGGAGGTGGAGGCACTGTCAGGGTCTGTCCACAGTGGGTCT
GTGCCAGGTCTCCCGCCGGTGGAAACTGTTGGCTTCCATGGCAGCAGGAAGCGGAGTCGA
GACCACTTCCGGAACAAGAGCAGCAGCCCCGAGGACCCAGGTGCTGAGGTCTGAGAGGGA
GATGGCCCAGCCTGACCCCACTGGCCACTGCCATCCTGCTGCCTTCCCAGTGGGGCTGGT
CAGGGGGCAGCCTGGCCACTGCCTAGCTGGAATGGGAGGAAGCCTGCAGGTGGCACCGGT
GGCCCTGGCTGCAGTTCTGGGCAGCATCCTCCCAAGCAGAGACCTTGCTGAAGCTCCTGG
GGTGTGGGGTGTGGGCTGGAAGCACTGGCTCCCTGGTAGOGACAATAAAGGTTTTGGGTC
TTTCAAAAAAAAAAAAAAAAAAAAAAAAAAAAAAAAAAAAAAAAAAAAAAAAAAAAAC
```

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of classifying a tumor cell-containing sample obtained from a human subject based on a tumor type or origin, wherein the tumor type or origin is selected from a plurality of known tumor types or origins, the method comprising:

amplifying five to 49 transcribed sequences, wherein each transcribed sequence is a unique portion of one of SEQ ID NOS: 1-74 or a complement thereof; wherein the unique portion is unique relative to other sequences expressed in the tumor cell-containing sample;

determining the expression levels of the transcribed sequences and normalizing the expression levels to one or more reference genes;

comparing the normalized expression levels of the transcribed sequences from the tumor cell-containing sample to normalized expression levels of the same transcribed sequences from at least ten known tumor types or origins of a plurality of known tumor types or origins, wherein the plurality of known tumor types or origins comprises adrenal gland, brain, breast, carcinoid-intestine, cervix-adenocarcinoma, cervix-squamous, endometrium, gall bladder, germ cell-ovary, GIST, kidney, leiomyosarcoma, liver, lung-adenocarcinoma-large cell, lung-small cell, lung-squamous, lymphoma-B cell, lymphoma-Hodgkin's, lymphoma-T cell, meningioma, mesothelioma, osteosarcoma, ovary-clear cell, ovary-serous, pancreas, prostate, skin-basal cell, skin-melanoma, skin-squamous, small and large bowel, soft tissue-liposarcoma, soft tissue-MFH, soft tissue-sarcoma-synovial, stomach-adenocarcinoma, testis-non-seminoma, testis-seminoma, thyroid-follicular-papillary, thyroid-medullary, and urinary bladder, determining five nearest neighbors by determining five of the at least ten known tumor types or origins that have the most similar expression levels compared to the expression levels of the tumor cell-containing sample; and a) if at least four of the five nearest neighbors share a tumor type or origin, classifying the tumor cell-containing sample as containing tumor cells of the tumor type or origin shared by at the least four of the five nearest neighbors; and b) if fewer than four of the five nearest neighbors share a tumor type or origin, classifying the tumor cell-containing sample as containing a non-squamous cell tumor.

2. The method of claim 1, wherein the expression levels are determined by use of a microarray and the method further comprises hybridizing the amplified transcribed sequences to the microarray.

3. The method of claim 1, wherein the amplification comprises reverse transcription PCR, quantitative PCR, or real time PCR.

4. The method of claim 1, wherein the amplification comprises linear RNA amplification or quantitative PCR.

5. The method of claim 3, wherein the amplification is of sequences present within 600 nucleotides of the polyadenylation sites of the transcribed sequences.

6. The method of claim 3, wherein the amplification is quantitative PCR amplification of at least 50 nucleotides of the transcribed sequences.

7. The method of claim 1, wherein the tumor cell-containing sample is a formalin fixed, paraffin embedded sample.

8. The method of claim 1, further comprising, before the determining of the expression levels of the transcribed sequences, diagnosing the human subject as in need of the determining; or obtaining the tumor cell-containing sample from the human subject; or receiving the tumor cell-containing sample; or sectioning the tumor cell-containing sample; or isolating cells from the tumor cell-containing sample; or obtaining RNA from cells of the tumor cell-containing sample.

* * * * *

SEQUENCE LISTING

<160> NUMBER OF SEQ ID NOS: 268

<210> SEQ ID NO 1
<211> LENGTH: 2930
<212> TYPE: DNA
<213> ORGANISM: Homo sapiens

<400> SEQUENCE: 1

```
ggccactctg cagacagctc cagacaatca ggcactcgtc acacagagtc ttcctctcgt      60

ggacaggctg cgtcatccca tgaacaggca agatcaagtg caggagaaag acatggatcc     120

caccaccagc agtcagcaga cagctccaga cacgcaggca ttgggcacgg acaagcttca     180

tctgcagtca gagacagtgg acaccgaggg tacagaggta gtcaggccac tgacagtgag     240

ggacattcag aagactcaga cacacagtca gtgtcagcac agggacaagc tgggccccat     300

cagcagagcc accaagagtc cgcacgtggc cagtcagggg aaagctctgg acgttcaggg     360

tctttcctct accaggtgag cactcatgaa cagtctgagt ccacccatgg acagtctgtg     420

cccagcactg gaggaagaca aggatcccac catgatcagg cacaagacag ctccaggcac     480

tcagcatccc aagagggtca ggacaccatt cgtggacacc cggggccaag cagaggagga     540

agacaggggt cccaccacga gcaatcggta gataggtctg gacactcagg gtcccatcac     600

agccacacca catcccaggg aaggtctgat gcctcccgtg ggcagtcagg atccagaagt     660

gcaagcagac aaacacatga ccaggaacaa tcaggagacg gctctaggca ctcagggtcg     720

cgtcatcagg aagcttcctc ttgggccgac agctctagac actcacaggc agtccaggga     780

caatcagagg ggtccaggac aagcaggcgc cagggatcca gtgttagcca ggacagtgac     840

agtcagggac actcagaaga ctctgagagg cggtctgggt ctgcttccag aaaccatcgt     900
```

-continued ggatctgctc aggagcagtc aagagatggc tccagacacc ccaggtccca tcacgaagac 960
agagccggtc acggggactc tgcagagagc tccagacaat caggcactca tcatgcagag 1020
aattcctctg gtggacaggc tgcatcatcc catgaacagg caagatcaag tgcaggagag 1080
agacatggat cccactacca gcagtcagca gacagctcca gacactcagg cattgggcac 1140
ggacaagctt catctgcagt cagagacagt ggacaccgag ggtccagtgg tagtcaggcc 1200
agtgacaatg agggacattc agaagactca gacacacagt cagtgtcagc ccaccgacag 1260
gctgggcgcc atcacgagag ccaccaagag tccacacgtg gccggtcacg aggaaggtct 1320
ggacgttcag ggtctttcct ctaccaggtg agcactcatg aacagtctga gtctgcccat 1380
ggacgggctg ggcccagtac tggaggaaga caaggatccc gccacgagca ggcacgagac 1440
agctccaggc actcagcgtc ccaagagggt caggacacca ttcgtggaca cccggggtca 1500
aggagaggag gaagacaggg atcctaccac gagcaatcgg tagataggtc tggacactca 1560
gggtcccatc acagccacac cacatcccag ggaaggtctg atgcctccca tgggcagtca 1620
ggatccagaa gtgcaagcag agaaacacgt aatgaggaac agtcaggaga cggctccagg 1680
cactcagggt cgcgtcacca tgaagcttcc actcaggctg acagctctag acactcacag 1740
tccggccagg gtgaatcagc ggggtccagg agaagcaggc gccagggatc cagtgttagc 1800
caggacagtg acagtgaggc atacccagag gactctgaga ggcgatctga gtctgcttcc 1860
agaaaccatc atggatcttc tcgggagcag tcaagagatg gctccagaca ccccggatcc 1920
tctcaccgcg atacagccag tcatgtacag tcttcacctg tacagtcaga ctctagtacc 1980
gctaaggaac atggtcactt tagtagtctt tcacaagatt ctgcgtatca ctcaggaata 2040
cagtcacgtg gcagtcctca cagttctagt tcttatcatt atcaatctga gggcactgaa 2100
aggcaaaaag gtcaatcagg tttagtttgg agacatggca gctatggtag tgcagattat 2160
gattatggtg aatccgggtt tagacactct cagcacggaa gtgttagtta caattccaat 2220
cctgttcttt tcaaggaaag atctgatatc tgtaaagcaa gtgcgtttgg taaagatcat 2280
ccaaggtatt atgcaacgta tattaataag gacccaggtt tatgtggcca ttctagtgat 2340
atatcgaaac aactgggatt tagtcagtca cagagatact attactatga gtaagaaatt 2400
aatggcaaag gaattaatcc aagaatagaa gaatgaagca agttcacttt caatcaagaa 2460
acttcataat actttcaggg aagttatctt ttcctgtcaa tctgtttaaa atatgctata 2520
gtatttcatt agtttggtgg taacttattt ttattgtgta atgatcttta aacgctatat 2580
ttcagaaata ttaaatggaa gaaatcaata tcatggagag ctaactttag aaaactagct 2640
ggagtatttt aggagattct gggtcaagta atgttttatg tttttgaaag tttaagtttt 2700
agacactccc caaatttcta aattaatctt tttcagaaat atcgaaggag ccaaaaatat 2760
aaaacagttc tgatatccaa agtggctata tcaacatcag ggctagcaca tctttctcta 2820
ttatccttct attggaattc tagtattctg tattcaaaaa atcatcttgg acataattaa 2880
tattttagta agctgcatct aaattaaaaa taaactattc atcatataat 2930

<210> SEQ ID NO 2
<211> LENGTH: 1591
<212> TYPE: DNA
<213> ORGANISM: Homo sapiens

<400> SEQUENCE: 2
tagaatcggg ggtttcagct cactgctcct tttctttttt ttctttctct cccccgccca 60

-continued

```
ccccccccaaa aataattgat ttgctttaca atcatccaca ctgtgttttg tggatcttta    120
attatatata acaatagtag tcattttaaa tatatattct gaaatctttg caaattttaa    180
cagaagagtc gaagctctgc gagacccaat atttgccaat aagaatggtt atgataatta    240
gcaccatgga gcctcaggtg tcaaatggtc cgacatccaa tacaagcaat ggaccctcca    300
gcaacaacag aaactgtcct tctcccatgc aaacaggggc aaccacagat gacagcaaaa    360
ccaacctcat cgtcaactat ttaccccaga atatgaccca agaagaattc aggagtctct    420
tcgggagcat tggtgaaata gaatcctgca aacttgtgag agacaaaatt acaggacaga    480
gtttagggta tggatttgtt aactatattg atccaaagga tgcagagaaa gccatcaaca    540
ctttaaatgg actcagactc cagaccaaaa ccataaaggt ctcatatgcc cgtccgagct    600
ctgcctcaat cagggatgct aacctctatg ttagcggcct tcccaaaacc atgacccaga    660
aggaactgga gcaacttttc tcgcaatacg gccgtatcat cacctcacga atcctggttg    720
atcaagtcac aggagtgtcc agaggggtgg gattcatccg ctttgataag aggattgagg    780
cagaagaagc catcaaaggg ctgaatggcc agaagcccag cggtgctacg gaaccgatta    840
ctgtgaagtt tgccaacaac cccagccaga agtccagcca ggccctgctc tcccagctct    900
accagtcccc taaccggcgc tacccaggtc cacttcacca ccaggctcag aggttcaggc    960
tggacaattt gcttaatatg gcctatggcg taaagagact gatgtctgga ccagtccccc   1020
cttctgcttg ttcccccagg ttctccccaa ttaccattga tggaatgaca agccttgtgg   1080
gaatgaacat ccctggtcac acaggaactg ggtggtgcat ctttgtctac aacctgtccc   1140
ccgattccga tgagagtgtc ctctggcagc tctttggccc ctttggagca gtgaacaacg   1200
taaaggtgat tcgtgacttc aacaccaaca agtgcaaggg attcggcttt gtcaccatga   1260
ccaactatga tgaggcggcc atggccatcg ccagcctcaa cgggtaccgc ctgggagaca   1320
gagtgttgca agtttccttt aaaaccaaca aagcccacaa gtcctgaatt tcccattctt   1380
acttactaaa atatatatag aaatatatac gaacaaaaca cacgcgcgca cacacacaca   1440
tacacgaaag agagagaaac aaacttttca aggcttatat tcaaccatgg actttataag   1500
ccagtgttgc ctaagtatta aaacattgga ttatcctgag gtgtaccagg aaaggatttt   1560
ataatgctta gaaaaaaaaa aaaaaaaaaa a                                  1591
```

<210> SEQ ID NO 3
<211> LENGTH: 2872
<212> TYPE: DNA
<213> ORGANISM: Homo sapiens

<400> SEQUENCE: 3

```
tccaggaatc gatagtgcat tcgtgcgcgc ggccgcccgt cgcttcgcac agggctggat     60
ggttgtattg ggcagggtgg ctccaggatg ttaggaactg tgaagatgga agggcatgaa    120
accagcgact ggaacagcta ctacgcagac acgcaggagg cctactcctc ggtcccggtc    180
agcaacatga actcaggcct gggctccatg aactccatga acacctacat gaccatgaac    240
accatgacta cgagcggcaa catgaccccg gcgtccttca acatgtccta tgccaacccg    300
gccttagggg ccggcctgag tcccggcgca gtagccggca tgccgggggg ctcggcgggc    360
gccatgaaca gcatgactgc ggccggcgtg acggccatgg gtacggcgct gagcccgagc    420
ggcatgggcg ccatgggtgc gcagcaggcg gcctccatga tgaatggcct gggcccctac    480
gcggccgcca tgaacccgtg catgagcccc atggcgtacg cgccgtccaa cctgggccgc    540
agccgcgcgg gcggcggcgg cgacgccaag acgttcaagc gcagttaccc gcacgccaag    600
```

-continued

```
ccgccctact cgtacatctc gctcatcacc atggccatcc agcgggcgcc cagcaagatg    660
ctcacgctga gcgagatcta ccagtggatc atggacctct tcccctatta ccggcagaac    720
cagcagcgct ggcagaactc catccgccac tcgctgtcct tcaatgactg cttcgtcaag    780
gtggcacgct ccccggacaa gccgggcaag ggctcctact ggacgctgca cccggactcc    840
ggcaacatgt tcgagaacgg ctgctacttg cgccgccaga agcgcttcaa gtgcgagaag    900
cagccggggg ccggcggcgg gggcgggagc ggaagcgggg gcagcggcgc caagggcggc    960
cctgagagcc gcaaggaccc ctctggcgcc tctaacccca gcgccgactc gcccctccat   1020
cggggtgtgc acgggaagac cggccagcta gagggcgcgc cggcccccgg cccggccgcc   1080
agcccccaga ctctggacca cagtggggcg acggcgacag gggcgcctc ggagttgaag    1140
actccagcct cctcaactgc gccccccata agctccgggc ccggggcgct ggcctctgtg   1200
cccgcctctc acccggcaca cggcttggca ccccacgagt cccagctgca cctgaaaggg   1260
gacccccact actccttcaa ccacccgttc tccatcaaca acctcatgtc ctcctcggag   1320
cagcagcata agctggactt caaggcatac gaacaggcac tgcaatactc gccttacggc   1380
tctacgttgc ccgccagcct gcctctaggc agcgcctcgg tgaccaccag gagccccatc   1440
gagccctcag ccctggagcc ggcgtactac caaggtgtgt attccagacc cgtcctaaac   1500
acttcctagc tcccgggact ggggggtttg tctggcatag ccatgctggt agcaagagag   1560
aaaaaatcaa cagcaaacaa aaccacacaa accaaaccgt caacagcata ataaaatcca   1620
acaactattt ttatttcatt tttcatgcac aaccttgccc ccagtgcaaa agactgttac   1680
tttattattg tattcaaaat tcattgtgta tattactaca aagacggccc caaaccaatt   1740
tttttcctgc gaagtttaat gatccacaag tgtatatatg aaattctcct ccttccttgc   1800
cccctctct ttcttccctc ttggccctcc agacattcta gtttgtggag ggttatttaa    1860
aaaacaaaaa ggaagatggt caagtttgta aaatatttgt ttgtgctttt ccccccctcct  1920
tacctgaccc cctacgagtt tacaggcttg tggcaatact cttaaccata agaattgaaa   1980
tggtgaagaa acaagtatac actagaggct cttaaaagta ttgaaaagac aatactgctg   2040
ttatatagca agacataaac agattataaa catcagagcc atttgcttct cagtttacat   2100
ttctgataca tgcagatagc agatgtcttt aaatgaaata catgtatatt gtgtatggac   2160
ttaattatgc acatgctcag atgtgtagac atcctccgta tatttacata acatatagag   2220
gtaatagata ggtgatatac gtgatacgtt ctcaagagtt gcttgaccga aagttacaag   2280
gaccccaacc cctttgctct ctacccacag atggccctgg gaacaatcct caggaattgc   2340
cctcaagaac tcgcttcttt gctttgagag tgccatggtc atgtcattct gaggtacata   2400
acacataaat tagtttctat gagtgtatac catttaaaga ttttttcagt aaagggaata   2460
ttacatgttg ggaggaggag ataagttata gggagctgga tttcaaacgg tggtccaaga   2520
ttcaaaaatc ctattgatag tggccatttt aatcattgcc atcgtgtgct tgtttcatcc   2580
agtgttatgc actttccaca gttggtgtta gtatagccag agggtttcat tattatttct   2640
ctttgctttc tcaatgttaa tttattgcat ggtttattct ttttctttac agctgaaatt   2700
gctttaaatg atggttaaaa ttacaaatta aattgggaat ttttatcaat gtgattgtaa   2760
ttaaaaatat tttgatttaa ataacaaaaa taataccaga ttttaagccg cggaaaatgt   2820
tcttgatcat ttgcagttaa ggactttaaa taaatcaaat gttaacaaaa aa           2872
```

<210> SEQ ID NO 4

<211> LENGTH: 540
<212> TYPE: DNA
<213> ORGANISM: Homo sapiens

<400> SEQUENCE: 4
tgtttttcta gttcattttg tgtttccaac ttttcatgta aaattttaat tatttttgaa 60
tgtgtggatg tgagactgag gtgccttttg gtactgaaat tctttttcca tgtacctgaa 120
gtgttacttt tgtgatatag gaaatccttg tatatatact ttattggtcc ctaggcttcc 180
tattttgtta ccttgctttc tctatggcat ccaccatttt gattgttcta cttttatgat 240
atgttttcat aagtggttaa gcaagtattc tcgttacttt tgctcttaaa tccctattca 300
ttacagcaat gttggtggtc aaagaaaatg ataaacaact tgaatgttca atggtcctga 360
aatacataac aacattttag tacattgtaa agtagaatcc tctgttcata atgaacaaga 420
tgaaccaatg tggattagaa agaagtccga gatattaatt ccaaaatatc cagacattgt 480
taaagggaaa aaattgcaat aaaatatttg taacataaaa aaaaaaaaaa aaaaaaaaaa 540

<210> SEQ ID NO 5
<211> LENGTH: 2508
<212> TYPE: DNA
<213> ORGANISM: Homo sapiens

<400> SEQUENCE: 5
agctctcccc accaataaaa ggaccaggga ggatcagaga gagcagaagg atcctgagcc 60
tcgcactctg ccgcccgcac caccttccgc tgcctctcag actctgctca gcctcacacg 120
atgtcgtgcc gctcctacag gatcagctca ggatgcgggg tcaccaggaa cttcagctcc 180
tgctcagctg tggcccccaa aactggcaac cgctgctgca tcagcgccgc cccctaccga 240
ggggtgtcct gctaccgagg gctgacgggc ttcggcagcc gcagcctctg caacctgggc 300
tcctgcgggc cccggatagc tgtaggtggc ttccgagccg gctcctgcgg acgcagcttc 360
ggctaccgct ccgggggcgt gtgcggaccc agcccccccat gcatcactac cgtgtcggtc 420
aacgagagcc tcctcacgcc cctcaacctg gagatcgacc ccaacgcaca gtgcgtgaag 480
caggaggaga aggagcagat caagtccctc aacagcaggt tcgcggcctt catcgacaag 540
gtgcgcttcc tggagcagca gaacaagctg ctggagacca agtggcagtt ctaccagaac 600
cagcgctgct gcgagagcaa cctggagcca ctgttcagtg gctacatcga gactctgcgg 660
cgggaggccg agtgcgtgga ggccgacagc gggaggctgg cctcagagct caaccatgtg 720
caggaggtgc tggagggcta caagaagaag tatgaagagg aggtggccct gagagccaca 780
gcagagaatg agtttgtcgt tctaaagaag gacgtggact gtgcctacct gcggaaatca 840
gacctggagg ccaatgtgga ggccctggtg gaggagtcta gcttcctgag gcgcctctat 900
gaagaggaga tccgcgttct ccaagcccac atctcagaca cctcggtcat agtcaagatg 960
gacaacagcc gagacctgaa catggactgc atcatcgctg agatcaaggc tcagtatgac 1020
gatgttgcca gccgcagccg ggccgaggct gagtcctggt accgtagcaa gtgtgaggag 1080
atgaaggcca cggtgatcag gcatggggag accctgcgcc gcaccaagga ggagatcaac 1140
gagctgaacc gcatgatcca gaggctgacg gccgagattg agaatgccaa gtgccagcgt 1200
gccaagctgg aggctgctgt ggctgaggca gagcagcagg gtgaggcggc cctcagcgat 1260
gcccgctgca agctggctga gctggagggc gccctgcaga aggccaagca ggacatggcc 1320
tgcctgctca aggagtacca ggaggtgatg aactccaagc tgggcctgga catcgagatc 1380
gccacctaca ggcgcctgct ggagggcgag gaacacaggc tgtgtgaagg tgtgggctct 1440

```
gtgaatgtct gtgtcagcag ctcccgtggt ggagtctcct gtgggggcct ctcctacagc   1500

accaccccag ggcgccagat cacttctggc ccctcagcca taggcggcag catcacggtg   1560

gtggcccctg actcctgtgc cccctgccag cctcgttcct ccagcttcag ctgcgggagt   1620

agccggtcgg tccgctttgc ctagtagagt catggagcca gggcttcctg ccaagcacct   1680

gcctgcctgc atcactgcac tgaatggcat gtgaatggaa aatgtgtgct tgcttccaga   1740

atcttctgga tgttcctaca gagggaaaga cctacagagg gaaagaccct cgggccgctc   1800

ccctgcgcct tttcatgcta gggagatgca tcctagttgt cctcctggca gctgttttca   1860

gaggcattcc cagcccttca cttaactcct acttagctcc aaaatacctg tatccaattt   1920

gtattattcc cccagctctc agggacaaga ccagtccccc agcgtggtgg tcagcacgga   1980

agctccacct tctgggtgga ggcgccatcc taaccatcca gccaggccac ccacaacccg   2040

agaatcaggg agaaagtccc tccccagcag ccccctcctc ctggctggga agaatggtcc   2100

cccagcaagc acttgcctgt tcattcccgt tcatgttttg cttctctctc agactgcctt   2160

cctgcttctg ggctaacctg ttccagccag gctcctcatg tgacctcgca gttgagaagc   2220

ccattatcgt ggggcatcct tttgcctaca gcccctggtt agggcacttt ggacaggtct   2280

tgctattcag tgaacctttg tacatttcaa agaagactcc atggctgctc cagatgcccc   2340

cttgctgggt gcaggtgggg actgtccaat gcagagctgg cgggacagag agttaagcca   2400

cttcctgggt ctccttctta tgactgtcta tgggtgcatt gccttctggg ttgtctcgat   2460

ctgtgtttca ataaatgccg ctgcaatgca aaaaaaaaaa aaaaaaaa               2508
```

<210> SEQ ID NO 6
<211> LENGTH: 1354
<212> TYPE: DNA
<213> ORGANISM: Homo sapiens
<220> FEATURE:
<221> NAME/KEY: misc_feature
<222> LOCATION: (57)..(57)
<223> OTHER INFORMATION: a or g or c or t/u

<400> SEQUENCE: 6

```
caatcagtga aaattctata ttcctttggc atttttgtga catattcaat tcagttntat     60

gttccagcag agatcattat ccctgggatc acatccaaat ttcatactaa atggaagcaa    120

atctgtgaat ttgggataag atccttcttg gttagtatta cttgcgccgg agcaatgtct    180

tattcctcgt ttagacattg tgatttcctt cgttggagct gtgagcagca gcacattggc    240

cctaatcctg ccacctttgg ttgaaattct tacattttcg aaggaacatt ataatatatg    300

gatggtcctg aaaaatattt ctatagcatt cactggagtt gttggcttct tattaggtac    360

atatataact gttgaagaaa ttatttatcc tactcccaaa gttgtagctg gcactccaca    420

gagtcctttt ctaaatttga attcaacatg cttaacatct ggtttgaaat agtaaaagca    480

gaatcatgag tcttctattt ttgtcccatt tctgaaaatt atcaagataa ctagtaaaat    540

acattgctat atacataaaa atggtaacaa actctgtttt ctttggcacg atattaatat    600

tttggaagta atcataactc tttaccagta gtggtaaacc tatgaaaaat ccttgctttt    660

aagtgttagc aatagttcaa aaaattaagt tctgaaaatt gaaaaaatta aaatgtaaaa    720

aaattaaaga ataaaaatac ttctattatt cttttatctc agtaagaaat accttaacca    780

agatatctct cttttatgct actcttttgc cactcacttg agaacagaat aggatttcaa    840

caataagaga ataaaataag aacatgtata acaaaaagct ctctccagat catccctgtg    900
```

-continued

```
aatgccaaag taaactttat gtacagtgta aaaaaaaaaa aatctcagtt atgtttttat    960

tagccaaatt ctaatgattg gctcctggaa gtatagaaaa ctcccattaa cataatataa   1020

gcatcagaaa attgcaaaca ctagaattaa ttttacactc taatggtagt tgatcttcat   1080

agtcaagagg cactgttcaa gatcatgact tagtgtttca atgaaatttg aaaagggact   1140

ttaaaactta tccagtgcaa ctcccttgtt tttcgtcaga ggaaaaggag gcctagaaag   1200

gttaagtaac ttggtcgaga ccactcagcc ttgagatcaa gaaaacctaa tcttctgact   1260

cccaggccag gatgttttat ttctcacatc atgtccaaga aaaagaataa attatgttca   1320

gcttaaaaaa aaaaaaaaaa aaaaaaaaaa aaaa                               1354


<210> SEQ ID NO 7
<211> LENGTH: 2460
<212> TYPE: DNA
<213> ORGANISM: Homo sapiens

<400> SEQUENCE: 7

cggaggcggc gccgacgggg actgctgagg cgcgcagagg gtcggcggcg cccgggagcc     60

tgtcgctggc gcggtccggg cgggaggctc ggcggcgggc ggcagcatgt cggtggcggg    120

gctgaagaag cagttctaca aggcgagcca gctggtcagt gagaaggtcg gaggggccga    180

ggggaccaag ctggatgatg acttcaaaga gatggagaag aaggtggatg tcaccagcaa    240

ggcggtgaca gaagtgctgg ccaggaccat cgagtacctg cagcccaacc cagcctcgcg    300

ggctaagctg accatgctca acacggtgtc caagatccgg ggccaggtga agaaccccgg    360

ctacccgcag tcggaggggc ttctgggcga gtgcatgatc cgccacggga aggagctggg    420

cggcgagtcc aactttggtg acgcattgct ggatgccggc gagtccatga agcgcctggc    480

agaggtgaag gactccctgg acatcgaggt caagcagaac ttcattgacc ccctccagaa    540

cctgtgcgag aaagacctga aggagatcca gcaccacctg aagaaactgg agggccgccg    600

cctggacttt gactacaaga agaagcggca gggcaagatc cccgatgagg agctacgcca    660

ggcgctggag aagttcgagg agtccaagga ggtggcagaa accagcatgc acaacctcct    720

ggagactgac atcgagcagg tgagtcagct ctcggccctg gtggatgcac agctggacta    780

ccaccggcag gccgtgcaga tcctggacga gctggcggag aagctcaagc gcaggatgcg    840

ggaagcttcc tcacgcccta agcgggagta taagccgaag ccccgggagc cctttgacct    900

tggagagcct gagcagtcca acgggggctt cccctgcacc acagccccca agatcgcagc    960

ttcatcgtct ttccgatctt ccgacaagcc catccggacc cctagccgga gcatgccgcc   1020

cctggaccag ccgagctgca aggcgctgta cgacttcgag cccgagaacg acggggagct   1080

gggcttccat gagggcgacg tcatcacgct gaccaaccag atcgatgaga actggtacga   1140

gggcatgctg gacggccagt cgggcttctt cccgctcagc tacgtggagg tgcttgtgcc   1200

cctgccgcag tgactcaccc gtgtccccgc cccgcccctc cgtccacact ggccggcacc   1260

ccctgctggg tctcctgcat tccacggagc ccctgctgcc agggcggtgt ctgagcctgc   1320

cggcgccacc tgggccccgg cccttgaggt actccctgag caggacccca cacttgggtg   1380

ggggggctta tctgggtggg tggggatgcc tgtttacact agcgctgact cccaacggtg   1440

acggctccct tccccactcc atggcgccag cctcctcccc cgctccccaa cttctcgccc   1500

agctggccga ggcggggcaa cactaaggtg ctcttagaaa cactaatgtt cctctggggc   1560

agcccccacc tccgtcctga cccgacgggg gcccggccca ctgcctaccc tcgagtcccg   1620

cagccttaac aggatgggat cgagggtccc catggggtgg ctcagagata ggaccctggt   1680
```

```
tttaaatccc tcccagcctg gtgctggtga tgggccctgg ccctactcca gggccaatgc   1740

acccccgcct cacacacgca ctccttctcc tcaaggccag ggcagagggc ctcaccgcct   1800

cccgggcctg ctgtcagctt gcagcccggg gacagaggcc agctgggatc tgcctgagga   1860

cagagaacat ggtctcctgc agggccctgc ctcccaagcc ccgccctcag aaagccaagt   1920

accttttcag ctttttaact gcccccatcc caacccaggg aggcctgtgt cactctggca   1980

caagctgcca ccaccagcca cccacaccca ccccagcaca cctcacacgg gaccacagcc   2040

gcgctgccga gggccaagca caaaggttcc agtgagcgca tgtcccagcc cctggtggcc   2100

aggctcccct tgctgagccg ctgccacttc accctgtggg aagtggcccc agccatctcc   2160

tctagaccaa ggcaggcagc cccgacatct gcttcctcta tcgcccaatg caaaatcgat   2220

gaaatgggga gttctctggg ccaggccaca ttcacattcc cctccccctg tggtccagtg   2280

aagcctccgg accccaggct ctgctctgcc ctgccctgca cccccctcgt cagaagtaca   2340

tgaggggcgc agagatgagc acacagcttt gggcacggtc cagggcaaac tgaaatgtac   2400

gcctgaattt tgtaaacaga agtattaaat gtctctttct acaaaaaaaa aaaaaaaaaa   2460
```

<210> SEQ ID NO 8
<211> LENGTH: 1112
<212> TYPE: DNA
<213> ORGANISM: Homo sapiens

<400> SEQUENCE: 8

```
ggcacgaggg aggtgcagag ctgagaatga ggcgatttcg gaggatggag aaatagcccc     60

gagtcccgtg gaaaatgagg ccggcggact tgctgcagct ggtgctgctg ctcgacctgc    120

ccagggacct gggcggaatg ggtgttcgt ctccaccctg cgagtgccat caggaggagg     180

acttcagagt cacctgcaag gatattcaac gcatccccag cttaccgccc agtacgcaga    240

ctctgaagct tattgagact cacctgagaa ctattccaag tcatgcattt tctaatctgc    300

ccaatatttc cagaatctac gtatctatag atgtgactct gcagcagctg gaatcacact    360

ccttctacaa tttgagtaaa gtgactcaca tagaaattcg gaataccagg aacttaactt    420

acatagaccc tgatgccctc aaagagctcc ccctcctaaa gttccttggc attttcaaca    480

ctggacttaa aatgttccct gacctgacca aagtttattc cactgatata ttctttatac    540

ttgaaattac agacaaccct tacatgacgt caatccctgt gaatgctttt cagggactat    600

gcaatgaaac cttgacactg aagctgtaca acaatggctt tacttcagtc caaggatatg    660

ctttcaatgg gacaaagctg gatgctgttt acctaaacaa gaataaatac ctgacagtta    720

ttgacaaaga tgcatttgga ggagtataca gtggaccaag cttgctgctg cctcttggaa    780

gaaagtcctt gtcctttgag actcagaagg ccccaagctc cagtatgcca tcatgatgcc    840

tgctaaggca gccaccttgg tgtacatgct cacagaggct ctgttcatgg agcagctgct    900

gtttgaaaaa ttttgaaatg caagatccac aactagatgg aaggcactct agtctttgca    960

gaaaaaaatg tacctgaatg tacattgcac aatgcctggc acaaagaagg aagaatataa   1020

atgatagttc gactcgtctg tggaagaact tacaatcatg ggaaagatg gaataaaaac    1080

attttttaaa cagcaaaaaa aaaaaaaaaa aa                                1112
```

<210> SEQ ID NO 9
<211> LENGTH: 478
<212> TYPE: DNA
<213> ORGANISM: Homo sapiens

<400> SEQUENCE: 9
ccccagcccc actcacccac cctccttccc accagcctgc tctccgcagg cccactgtct 60
ttgggtttaa tgacgtctct tctctgtgga acttcacgat tccttcccac ggtcaactcg 120
ggacctccca gcgaccactg cagcctgcgg acgaggccgg gacttggccg agcggatcct 180
aataagggga aaatggtaaa tgcaaacgtc ccgttacaat tttaccgcca gtgtgctgtc 240
gttccccctc cccctctccg agtcctcgtg ggacacggc ggggtctgta ggaagttggg 300
ccgggttggg ggttgctaga aggcgctggt gttttgctct gagttttaag agatcccttc 360
cttcctcttc ggtgaatgca ggttatttaa actttgggaa atgtactttt agtctgtcat 420
atcaaggcat gagtcactgt cttttttgt gtgaataaat ggtttctagt acaatgga 478

<210> SEQ ID NO 10
<211> LENGTH: 845
<212> TYPE: DNA
<213> ORGANISM: Homo sapiens

<400> SEQUENCE: 10
gcggccgccc gcacgtccgc gggtcccggc cgcgccgccg ccgcgcgccc ctgcccgaga 60
gagctctggc cccgctagcg gggccaggag ccgggcctcc caccgcagcg tcccccgccg 120
cgccagtccc cgctagtggt agtatctcgt aatagcttct gtgtgtgagc taccgtggat 180
ctccttccct tctcttgggg gccgggggga aagaaaagga tttaagcaaa ggctccctcg 240
ccctgtgagg gcgagcggca aaggcccggc tgagcccccc atgcccctcc cctccccgtg 300
taaaaagcct ccttgtgcaa ttgtcttttt tttcctttga acgtgcttct ttgtaatgac 360
caaggtaccg atttctgcta agttctccca acaacatgaa actgcctatt cacgccgtaa 420
ttctttctgt ctcccttctc tctctctctc tcgctcgctc gctctcgctc tcgctctctc 480
tcgctgcgtc ctcatttccc ctcccaatcc tctctcccct ctgcaacccc ccagctcgct 540
ggctttctct ctggcttctc tcttttcctc ctccacccac cccctttggt ttgacaattt 600
tgtcttaagt gtttctcaaa agaggttact ttagttagca tgcgcgctgt gggcaattgt 660
tacaagtgtt cttaggttta ctgtgaagag aatgtattct gtatccgtga attgctttat 720
gggggggagg gagggctaat tatatatttt gttgttcctc tatactttgt tctgttgtct 780
gcgcctgaaa agggcggaag agttacaata aagtttacaa gcgagaaccc gaaaaaaaaa 840
aaaaa 845

<210> SEQ ID NO 11
<211> LENGTH: 1721
<212> TYPE: DNA
<213> ORGANISM: Homo sapiens

<400> SEQUENCE: 11
caccagcaca gcaaacccgc cgggatcaaa gtgtaccagt cggcagcatg gctacgaaat 60
gtgggaattg tggacccggc tactccaccc ctctggaggc catgaaagga cccagggaag 120
agatcgtcta cctgccctgc atttaccgaa acacaggcac tgaggcccca gattatctgg 180
ccactgtgga tgttgacccc aagtctcccc agtattgcca ggtcatccac cggctgccca 240
tgcccaacct gaaggacgag ctgcatcact caggatggaa cacctgcagc agctgcttcg 300
gtgatagcac caagtcgcgc accaagctgg tgctgcccag tctcatctcc tctcgcatct 360
atgtggtgga cgtgggctct gagccccggg ccccaaagct gcacaaggtc attgagccca 420
aggacatcca tgccaagtgc gaactggcct ttctccacac cagccactgc ctggccagcg 480

```
gggaagtgat gatcagctcc ctgggagacg tcaagggcaa tggcaaaggg ggttttgtgc    540
tgctggatgg ggagacgttc gaggtgaagg ggacatggga gagacctggg ggtgctgcac    600
cgttgggcta tgacttctgg taccagcctc gacacaatgt catgatcagc actgagtggg    660
cagctcccaa tgtcttacga gatggcttca accccgctga tgtggaggct ggactgtacg    720
ggagccactt atatgtatgg gactggcagc gccatgagat tgtgcagacc ctgtctctaa    780
aagatgggct tattcccttg gagatccgct tcctgcacaa cccagacgct gcccaaggct    840
ttgtgggctg cgcactcagc tccaccatcc agcgcttcta caagaacgag ggaggtacat    900
ggtcagtgga gaaggtgatc caggtgcccc ccaagaaagt gaagggctgg ctgctgcccg    960
aaatgccagg cctgatcacc gacatcctgc tctccctgga cgaccgcttc ctctacttca   1020
gcaactggct gcatggggac ctgaggcagt atgacatctc tgacccacag agaccccgcc   1080
tcacaggaca gctcttcctc ggaggcagca ttgttaaggg aggccctgtg caagtgctgg   1140
aggacgagga actaaagtcc cagccagagc cctagtggt caagggaaaa cgggtggctg   1200
gaggccctca gatgatccag ctcagcctgg atgggaagcg cctctacatc accacgtcgc   1260
tgtacagtgc ctgggacaag cagttttacc ctgatctcat cagggaaggc tctgtgatgc   1320
tgcaggttga tgtagacaca gtaaaaggag ggctgaagtt gaaccccaac ttcctggtgg   1380
acttcgggaa ggagcccctt ggcccagccc ttgcccatga gctccgctac cctgggggcg   1440
attgtagctc tgacatctgg atttgaactc caccctcatc acccacactc cctattttgg   1500
gccctcactt ccttggggac ctggcttcat tctgctctct cttggcaccc gacccttggc   1560
agcatgtacc acacagccaa gctgagactg tggcaatgtg ttgagtcata tacatttact   1620
gaccactgtt gcttgttgct cactgtgctg cttttccatg agctcttgga ggcaccaaga   1680
aataaactcg taaccctgtc cttcaaaaaa aaaaaaaaaa a                       1721
```

<210> SEQ ID NO 12
<211> LENGTH: 1061
<212> TYPE: DNA
<213> ORGANISM: Homo sapiens

<400> SEQUENCE: 12

```
ccggagataa cttgagggct atagaggacc ggctaatact ggtcctgaat ttggcttcag     60
gcctcaccaa ccaagtggcc gtggccttgc cgtcttgccc gtcggccccc ggtgaggcct    120
ggacccctgg ggtcccggca ccaggccccg gcttccgacc ctggcagaag cccaagatct    180
ggtccctcgc ggagactgcc acaagccccg gacacccgcg ccggctcgcc tcccggcgcg    240
ggggggtctc caccgggggg caacggtcgc gcctttccgc cctgcagctc tctccgggcc    300
gccgccgccg ccgccgctca cagactggtc tcagcgccgc tgggcaagtt cccggcttgg    360
accaaccggc cgtttccagg cccaccgccc ggcccccgcc cgcacccgct ctccctgctg    420
ggctctgccc ctccgcacct gctgggactt cccggagccg cgggccaccc ggctgccgcc    480
gccgccttcg ctcggccagc ggagcccgaa ggcggaacag atcgctgtag tgccttggaa    540
gtggagaaaa agttactcaa gacagctttc catcccgtgc ccaggcggcc ccagaaccat    600
ctggacgccg ccctggtctt atcggctctc tcctcatcct agttctttaa aaaaaaacaa    660
aaaaacaaaa aaaacttttt ttaatcgttg taataattgt ataaaaaaaa tcgctctgta    720
tagttacaac ttgtaagcat gtccgtgtat aaatacctaa aagcaaaact aaacaaagaa    780
agtaagaaaa agaaataaaa ccagtcctcc tcagccctcc ccaagtcgct tctgtggcac    840
```

cccgcattcg ctgtgaggtt tgtttgtccg gttgattttg gggggtggag tttcagtgag 900
aataaacgtg tctgcctttg tgtgtgtgta tatatacaga gaaatgtaca tatgtgtgaa 960
ccaaattgta cgagaaagta tctatttttg gctaaataaa tgagctgctg ccactttgac 1020
tataaaaaaa aaaaaaaaaa aaaaaaaaaa aaaaaaaaaa a 1061

<210> SEQ ID NO 13
<211> LENGTH: 577
<212> TYPE: DNA
<213> ORGANISM: Homo sapiens

<400> SEQUENCE: 13
tatgagcacc ttcacatgga tccacttgag gaaagaaggt ggaccgaatt tgtaaacggt 60
gtgcagcaat atatatcaat tcgttctgag ataatcgcca cttacgctct ctgtggtttt 120
gccaatatcg ggtccctagg aatcgtgatc ggcggactca catccatggc tccttccaga 180
aagcgtgata tcgcctcggg ggcagtgaga gctctgattg cggggaccgt ggcctgcttc 240
atgacagcct gcatcgcagg catactctcc agcactcctg tggacatcaa ctgccatcac 300
gttttagaga atgccttcaa ctccactttc cctggaaccc caaccaaggg tgatagcttg 360
ttgccaaagt ctgttgagca gccctgttgc ccagggtcct ggtgaagtca tcccaggagg 420
aaaccccagt ctgtattctt tgaagggctg ctgcacattg ttgaatccat cgacctttag 480
ctgcaatggg atctctaata cattttgagg tcagccactt ctccagtgga actctgaagt 540
acagatgctg aattttctgc tttggaaaga aaaaaaa 577

<210> SEQ ID NO 14
<211> LENGTH: 456
<212> TYPE: DNA
<213> ORGANISM: Homo sapiens

<400> SEQUENCE: 14
actcggcatg tgatgaacac ccatagttaa gaaaccatgg agcaagaaag cttgtggaaa 60
gtctctctcc ttcctcataa gacatgcaca ctaatacaca tacacaccaa aaaattacac 120
attttaaaac tgctaagctt ggatttaact gaatcatata tcttttatca tgttatccta 180
aaagtgagaa gacataacca agacatggaa ataaatgtga aagctggagc cgaagagtca 240
aagagctaaa aaattaagtc tagaacattc tatgaggata gtataaataa aaagaaatac 300
agtctagaca tgctgcaagg aaagaagatt ctaaagtccg tttatggagg caattccata 360
tcctttcttg aacgcacatt cagcttaccc cagagagcaa gtgaggcaat ctggcaaaag 420
attaataaag atgtaaaccc ctggaaaaaa aaaaaa 456

<210> SEQ ID NO 15
<211> LENGTH: 3628
<212> TYPE: DNA
<213> ORGANISM: Homo sapiens

<400> SEQUENCE: 15
gaattcggca cgagatagtt ttcaggttaa gaaagccaga atctttgttc agccacactg 60
actgaacaga cttttagtgg ggttacctgg ctaacagcag cagcggcaac ggcagcagca 120
gcagcagcag cagcagcagc agcagcaggg ctcctgggat aactcaggca tagttcaaca 180
ctatgggtcc tcctctgaag ctcttcaaaa accagaaata ccaggaactg aagcaggaat 240
gcatcaaaga cagcagactt ttctgtgatc caacatttct gcctgagaat gattctcttt 300
tctacttccg actgcttcct ggaaaggtgg tgtggaaacg tccccaggac atctgtgatg 360

```
acccccatct gattgtgggc aacattagca accaccagct gacccaaggg agactggggc    420
acaagccaat ggtttctgca ttttcctgtt tggctgttca ggagtctcat tggacaaaga    480
caattcccaa ccataaggaa caggaatggg accctcaaaa aacagaaaaa tacgctggga    540
tatttcactt tcgtttctgg cattttggag aatggactga agtggtgatt gatgacttgt    600
tgcccaccat taacggagat ctggtcttct ctttctccac ttccatgaat gagttttgga    660
atgctctgct ggaaaaagct tatgcaaagc tgctaggctg ttatgaggcc ctggatggtt    720
tgaccatcac tgatattatt gtggacttca cgggcacatt ggctgaaact gttgacatgc    780
agaaaggaag atacactgag cttgttgagg agaagtacaa gctattcgga gaactgtaca    840
aaacatttac caaaggtggt ctgatctgct gttccattga gtctcccaat caggaggagc    900
aagaagttga aactgattgg ggtctgctga agggccatac ctataccatg actgatattc    960
gcaaaattcg tcttggagag agacttgtgg aagtcttcag tgctgagaag gtgtatatgg   1020
ttcgcctgag aaaccccttg ggaagacagg aatggagtgg cccctggagt gaaatttctg   1080
aagagtggca gcaactgact gcatcagatc gcaagaacct ggggcttgtt atgtctgatg   1140
atggagagtt ttggatgagc ttggaggact tttgccgcaa ctttcacaaa ctgaatgtct   1200
gccgcaatgt gaacaaccct atttttggcc gaaaggagct ggaatcggtg ttgggatgct   1260
ggactgtgga tgatgatccc ctgatgaacc gctcaggagg ctgctataac aaccgtgata   1320
ccttcctgca gaatccccag tacatcttca ctgtgcctga ggatgggcac aaggtcatta   1380
tgtcactgca gcagaaggac ctgcgcactt accgccgaat gggaagacct gacaattaca   1440
tcattggctt tgagctcttc aaggtggaga tgaaccgcaa attccgcctc caccacctct   1500
acatccagga gcgtgctggg acttccacct atattgacac ccgcacagtg tttctgagca   1560
agtacctgaa gaagggcaac tatgtgcttg tcccaaccat gttccagcat ggtcgcacca   1620
gcgagtttct cctgagaatc ttctctgaag tgcctgtcca gctcagggaa ctgactctgg   1680
acatgcccaa aatgtcctgc tggaacctgg ctcgtggcta cccgaaagta gttactcaga   1740
tcactgttca cagtgctgag gacctggaga agaagtatgc caatgaaact gtaaacccat   1800
atttggtcat caaatgtgga aaggaggaag tccgttctcc tgtccagaag aatacagttc   1860
atgccatttt tgacacccag gccattttct acagaaggac cactgacatt cctattatag   1920
tacaggtctg gaacagccga aaattctgtg atcagttctt ggggcaggtt actctggatg   1980
ctgaccccag cgactgccgt gatctgaagt ctctgtacct gcgtaagaag ggtggtccaa   2040
ctgccaaagt caagcaaggc cacatcagct tcaaggttat ttccagcgat gatctcactg   2100
agctctaaat ctgcaatccc agagaatcct gacaaagcgt gccacccttt tattttccgt   2160
caggtgccag gtcttagtta agattcacaa tctttagaaa gaatgagatt cacaataatt   2220
aactcttcct ctcttctgat aaattcccca tacctcccaa tccaagtagc atctgtagct   2280
acataaccta tatacctcca gcagctggac atggggagcg acagtcctat ctagacatca   2340
tacacatttg ccaagaaagg atctctgggg cttccggggg tgagattcaa gcaggacaat   2400
aacaagaggc tggacaccct acagatgtct ttgatgtttt cagttgtttg atatatctcc   2460
cctgtagggc atgttgagga aggaggaggg ctgatcaagg ccaagctggt ctagcctgac   2520
atcctagctc ctgactgaac actatagact tcccagcagc attttcaccc agcagccaga   2580
gccggcttta agtccccaac ccttacagac accactgcca ccaccaccaa ccacgaccac   2640
caccaccacc accactcacc accatcatca cctccggaaa gtgtagtcct gccctaaccc   2700
```

-continued

```
taaccccaag tcacccccca cagtaaattt taccttcatg ttgagaaagc ttcctggtgc   2760
ttaatcaaga gctggagttc aatgagtcct agacagtgag aggggcctga gcttcagctc   2820
aatggaagcc tgctgtgtgc tcacaagacg gaaaagtgga agaagctgca gtgggagaca   2880
aagcctcggt cccccaccca tccacacaca cctacactca cacacgcgca catgggcgcg   2940
caacggaact accatttcag gcagtcagtg ggcaagagga aagataagta agtaccatac   3000
acaccttaaa agatgaggag aattcatcca gacatattac agccagtttg gggcccctga   3060
cttgcaatgt gaaacctctt cgcttgctgc taggtttaca aacaagccca ttgttcctgt   3120
gcctcctaat attcatttgt tactgaagga ccccatctgg ggacttgaga ctttggtccc   3180
agcccagacg cctcagactg gtctcaaagt caagcaaggc ttcacatcag ctgcaagtgt   3240
tagtttgcca gcgcatgatc tcactgagct tctacagaat ctgcaatccc agagtcaatc   3300
atgacgaaat gtacgtccca ccatcttaac ctatcaactt tctgcccctc cttcaaggcc   3360
cagtataaat gccacctcct ccatgaagcc ttccctaatt ccaccccaaa cccccacctt   3420
caacaatatt tcaacgcttc tgcaatgatg aaaaagaaac atagttgtag tacttagcct   3480
acctagacca gcaagcattc atttttagct cgctcatttt ttaccatgtt ttccagtctg   3540
tttaacttct gcagtgcctt cactacactg ccttacataa accaaatcac aataaagttc   3600
atattcagta caattaaaaa aaaaaaaa                                      3628
```

<210> SEQ ID NO 16
<211> LENGTH: 1580
<212> TYPE: DNA
<213> ORGANISM: Homo sapiens

<400> SEQUENCE: 16

```
tatgcaagtg tttaacagat gcttcactat taaaatattt tccccccaag tctcaaatat     60
tgaagaatct ctaaccaggg acaccagtcc ctacgaagac cttgggcgat tttgaagtgc    120
gggcacctcg attccccgaa tctgtagtgt ggctggtatc ggtgttcccc tggtttaact    180
agcctgtttg aaggcacaga tcattcatgg ggaagtataa ccgaatccag tcctctccac    240
cgcctgggga tcttcacttt cgcagtctac gactgcctgt gactccagaa agacaaactg    300
cagattggcc aagatgggga aattgaggca gagaagccaa gacatgtgct aaaggtcatg    360
caggctatga atggagctgg aatgtgaacg caggccatat gaccccagag cccatgttct    420
tgaaccctta gaaagacagc agcaacacac ctggtgcagc agctgcttag ttggagtggc    480
tgacaaggag agaatgattt ccaggaagag cggaacacat atggaaggcc ttagcttatc    540
tttagcgcct catacacccg ttctggactt cagaaaggcc agtgagtggg attaggcctc    600
agagatagga tgtcagtccc agtgagggat ggcctagagc attctttaat tctttccttt    660
gggtcacaca taagaaacaa ttttccagca ctgatgagtg ttattaacaa tgagatggga    720
tagaatttag ttttccctat ggctgtgctt caaaaataga aaagctgtct tttctctgga    780
atgattgaat gaagctctgg ggaggaaaag gtggattggc agatctctta aaggaagctt    840
ctccttctag gcactattct aaggcttaat attttaactc cctatattaa cctagttcaa    900
ctaaacagtg atctgagtaa ttttattttt attaaagctc agatcaaaat gccattaaca    960
ttgattgaga aaatcaaagg aatctttgat gtgagtggtt aaattgctga attatttcag   1020
tcccataccc tcacagcatg agtacctgat ctgatagact tctttggaat tcctttttttg   1080
tttgagacag agtcttgctc tgtcgcccag gctggagtgc agcggtgtga tctcaaccat   1140
tgcaacctcc acctcccagg ttcaggtgat tctcatgcct cagcctcctg agtagctggg   1200
```

-continued

```
attacagatg tgcaccacca tgcccggcta attattttgt atctttagta gagatgaagt   1260

tttgccatgt gggccaggct gttctcaaac tactggcctc aagtgatctg cccgcctcgg   1320

cctcccagac tgctgggatt acaggcgtga ggcaccgtgc ctggctggga ttccataata   1380

aatccctctg tgtctatttc ttttttcaaa tataattttc ttcatttcca aacatcatct   1440

ttaagactcc aaggattttt ccaggcacag tggctcatac ctgtaatccc attgcttgga   1500

gaggccaagg tggaagttca tttgaggcca ggagttcgag accaggtggg caacatagtg   1560

aaaccttgtc tctacaacat                                               1580
```

```
<210> SEQ ID NO 17
<211> LENGTH: 809
<212> TYPE: DNA
<213> ORGANISM: Homo sapiens

<400> SEQUENCE: 17

tgtttatata actgtgttcg tttttgttgt tccgtcccgt cgtccttgta gactctcatc     60

ctcgtgtgtt ttggaccctc caggggtgac atcgggtctt gtgttcagct ctcctggact    120

gttattcctt gtccgcgtgt tcgtgttaga cattgtccac gatctgtatc atgcctatgt    180

ctcactttgg tctcttattt cagcgtgaac actatagttc caagtttgtt cggataattc    240

tgattcttgt caccagcgtg agatttcaac agaacttgtt tggaacaaat actcacttaa    300

aacttcagca gaagaaaaat tacttagtcc ttaggccaac caatttaact gcagtgtcat    360

gtttcacagg ccttcctaca tttagaaatc gtcacacagc tgtgataaga gtagattatt    420

ttactatgaa ataattctga atagatgaaa gcataaaatg tgagaaactg aatgtattat    480

tcaggaagaa tactgagtgc cttcatttaa ctaaagttga atgtaaaagt caatttgcac    540

ttctttataa tcctctggtt tagaattata aattgttaaa accttgataa ttgtcattta    600

attatatttc aggtgtcctg aacaggtcac tagactctac attgggcagc ctttaaatat    660

gattctttgt aatgctaaat agcctttttt tctcttttta ctgcaactta atatttctat    720

ttagaacaca gaaaatgaaa atatttagaa taagttgtac atttgatgac aaataaatca    780

ctattaaaat aaaaaaaaaa aaaaaaaaa                                      809
```

```
<210> SEQ ID NO 18
<211> LENGTH: 488
<212> TYPE: DNA
<213> ORGANISM: Homo sapiens
<220> FEATURE:
<221> NAME/KEY: misc_feature
<222> LOCATION: (95)..(95)
<223> OTHER INFORMATION: a or g or c or t/u

<400> SEQUENCE: 18

aggaacccct gtgggaaagg tttaaaccta aaacagtgcc ccctttggct cctcctccct     60

tggcggaatg ggttcctgga ccatgtgcat ttcantgggc catgggattt acatttcctt    120

gcatccccag gtggtttgat ccctgccagg gccccttcct tcctgctcat ggttttcagg    180

gggcctgatc atggaaagta agggggttgg gccttccctt ttgggggtga accctgactc    240

catcccccta ttgcccccct aaccaatcat gcaaactttt ccccccctgg ggtaattcac    300

cagttaaaaa aagctttttt taaatgtttt gttttggggg gggggcaggg ccccctttttt   360

gtttttttaa ggagttggtt ttggtttttg gctgatgttt tgttttttaa catgccccca    420

gtttgtaagg ccaaaggtaa aaaaaaaaaa aaaaaaaaaa aaaaaaaaaa aaaaaaaaaa    480
```

aaaaaaaa 488

<210> SEQ ID NO 19
<211> LENGTH: 463
<212> TYPE: DNA
<213> ORGANISM: Homo sapiens

<400> SEQUENCE: 19
taagctttaa aggctctgtg ttagggcata gtctagaaac atggggccca agggcaccgg 60
gaaaacttac aaagggaaga gatggaactg ggagggttca agctaccagt tccatctctc 120
catgttttag agaattgggg cactaagtca gccaggtaag gtcaggtcag aggagggccc 180
ggatgaagca tgagatgcag agggacagtg cgtgaatgga gaccttgggt agcaccaacg 240
tgtagcggca gaggtggggt ggatgtggct gatgtcaggg agagaatggg gagcatgcac 300
agggctcagt cttatacata cattgaaaat cctttagcct ttcaaagatt attaacccaa 360
atcacctttc ttgcttactc cagatgcctc agcctctgat ataattgcta agtatctgcc 420
gtgttaaaaa taaacatttg agaatcaaaa aaaaaaaaaa aaa 463

<210> SEQ ID NO 20
<211> LENGTH: 2148
<212> TYPE: DNA
<213> ORGANISM: Homo sapiens

<400> SEQUENCE: 20
gcttcagggt acagctcccc cgcagccaga agccgggcct gcagcgcctc agcaccgctc 60
cgggacaccc cacccgcttc ccaggcgtga cctgtcaaca gcaacttcgc ggtgtggtga 120
actctctgag gaaaaaccat tttgattatt actctcagac gtgcgtggca acaagtgact 180
gagacctaga aatccaagcg ttggaggtcc tgaggccagc ctaagtcgct tcaaaatgga 240
acgaaggcgt ttgtggggtt ccattcagag ccgatacatc agcatgagtg tgtggacaag 300
cccacggaga cttgtggagc tggcagggca gagcctgctg aaggatgagg ccctggccat 360
tgccgccctg gagttgctgc ccagggagct cttcccgcca ctcttcatgg cagcctttga 420
cgggagacac agccagaccc tgaaggcaat ggtgcaggcc tggcccttca cctgcctccc 480
tctgggagtg ctgatgaagg gacaacatct tcacctggag accttcaaag ctgtgcttga 540
tggacttgat gtgctccttg cccaggaggt tcgccccagg aggtggaaac ttcaagtgct 600
ggatttacgg aagaactctc atcaggactt ctggactgta tggtctggaa acagggccag 660
tctgtactca tttccagagc cagaagcagc tcagcccatg acaaagaagc gaaaagtaga 720
tggtttgagc acagaggcag agcagccctt cattccagta gaggtgctcg tagacctgtt 780
cctcaaggaa ggtgcctgtg atgaattgtt ctcctacctc attgagaaag tgaagcgaaa 840
gaaaaatgta ctacgcctgt gctgtaagaa gctgaagatt tttgcaatgc ccatgcagga 900
tatcaagatg atcctgaaaa tggtgcagct ggactctatt gaagatttgg aagtgacttg 960
tacctggaag ctacccacct tggcgaaatt ttctccttac ctgggccaga tgattaatct 1020
gcgtagactc ctcctctccc acatccatgc atcttcctac atttccccgg agaaggaaga 1080
gcagtatatc gcccagttca cctctcagtt cctcagtctg cagtgcctgc aggctctcta 1140
tgtggactct ttatttttcc ttagaggccg cctggatcag ttgctcaggc acgtgatgaa 1200
ccccttggaa accctctcaa taactaactg ccggctttcg gaaggggatg tgatgcatct 1260
gtcccagagt cccagcgtca gtcagctaag tgtcctgagt ctaagtgggg tcatgctgac 1320
cgatgtaagt cccgagcccc tccaagctct gctggagaga gcctctgcca ccctccagga 1380
cctggtcttt gatgagtgtg ggatcacgga tgatcagctc cttgccctcc tgccttccct 1440
gagccactgc tcccagctta caaccttaag cttctacggg aattccatct ccatatctgc 1500
cttgcagagt ctcctgcagc acctcatcgg gctgagcaat ctgacccacg tgctgtatcc 1560 tgtcccccctg gagagttatg aggacatcca tggtaccctc cacctggaga ggcttgccta 1620
tctgcatgcc aggctcaggg agttgctgtg tgagttgggg cggcccagca tggtctggct 1680
tagtgccaac ccctgtcctc actgtgggga cagaaccttc tatgacccgg agcccatcct 1740
gtgcccctgt ttcatgccta actagctggg tgcacatatc aaatgcttca ttctgcatac 1800
ttggacacta aagccaggat gtgcatgcat cttgaagcaa caaagcagcc acagtttcag 1860
acaaatgttc agtgtgagtg aggaaaacat gttcagtgag gaaaaaacat tcagacaaat 1920
gttcagtgag gaaaaaaagg ggaagttggg gataggcaga tgttgacttg aggagttaat 1980
gtgatctttg gggagataca tcttatagag ttagaaatag aatctgaatt tctaaaggga 2040
gattctggct tgggaagtac atgtaggagt taatccctgt gtagactgtt gtaaagaaac 2100
tgttgaaaat aaagagaagc aatgtgaagc aaaaaaaaaa aaaaaaaa 2148

<210> SEQ ID NO 21
<211> LENGTH: 707
<212> TYPE: DNA
<213> ORGANISM: Homo sapiens
<220> FEATURE:
<221> NAME/KEY: misc_feature
<222> LOCATION: (17)..(17)
<223> OTHER INFORMATION: a or g or c or t/u
<220> FEATURE:
<221> NAME/KEY: misc_feature
<222> LOCATION: (83)..(83)
<223> OTHER INFORMATION: a or g or c or t/u

<400> SEQUENCE: 21
aacacagccc taccaancaa tgatgaccag tggaaaacaa tgaagtcacc aaaccctgga 60
cagggctcat gctccaggac aanttgctgt ggcgtaaatg gtccatcaga ctggcaaaaa 120
tacacatctg ccttccggac tgagaataat gatgctgact atccctggcc tcgtcaatgc 180
tgtgttatga acaatcttaa agaacctctc aacctggagg cttgtaaact aggcgtgcct 240
ggtttttatc acaatcaggg ctgctatgaa ctgatctctg gtccaatgaa ccgacacgcc 300
tggggggttg cctggtttgg atttgccatt ctctgctgga ctttttgggt tctcctgggt 360
accatgttct actggagcag aattgaatat taagcataaa gtgttgccac catacctcct 420
tccccgagtg actctggatt tggtgctgga accagctctc tcctaatatt ccacgtttgt 480
gccccacact aacgtgtgtg tcttacattg ccaagtcaga tggtacggac ttcctttagg 540
atctcaggct tctgcagttc tcatgactcc tacttttcat cctagtctag cattctgcaa 600
catttatata gactgttgaa aggagaattt gaaaaatgca taataactac ttccatccct 660
gcttattttt aatttgggaa aataaataca ttcgaaggaa aaaaaaa 707

<210> SEQ ID NO 22
<211> LENGTH: 2832
<212> TYPE: DNA
<213> ORGANISM: Homo sapiens

<400> SEQUENCE: 22
ggcacgaggg cgaaattgag gtttcttggt attgcgcgtt tctcttcctt gctgactctc 60
cgaatggcca tggactcgtc gcttcaggcc cgcctgtttc ccggtctcgc tatcaagatc 120

-continued

```
caacgcagta atggtttaat tcacagtgcc aatgtaagga ctgtgaactt ggagaaatcc    180
tgtgtttcag tggaatgggc agaaggaggt gccacaaagg gcaaagagat tgattttgat    240
gatgtggctg caataaaccc agaactctta cagcttcttc ccttacatcc gaaggacaat    300
ctgcccttgc aggaaaatgt aacaatccag aaacaaaaac ggagatccgt caactccaaa    360
attcctgctc caaaagaaag tcttcgaagc cgctccactc gcatgtccac tgtctcagag    420
cttcgcatca cggctcagga gaatgacatg gaggtggagc tgcctgcagc tgcaaactcc    480
cgcaagcagt tttcagttcc tcctgccccc actaggcctt cctgccctgc agtggctgaa    540
ataccattga ggatggtcag cgaggagatg gaagagcaag tccattccat ccgaggcagc    600
tcttctgcaa accctgtgaa ctcagttcgg aggaaatcat gtcttgtgaa ggaagtggaa    660
aaaatgaaga acaagcgaga agagaagaag gcccagaact ctgaaatgag aatgaagaga    720
gctcaggagt atgacagtag ttttccaaac tgggaatttg cccgaatgat taaagaattt    780
cgggctactt tggaatgtca tccacttact atgactgatc ctatcgaaga gcacagaata    840
tgtgtctgtg ttaggaaacg cccactgaat aagcaagaat tggccaagaa agaaattgat    900
gtgatttcca ttcctagcaa gtgtctcctc ttggtacatg aacccaagtt gaaagtggac    960
ttaacaaagt atctggagaa ccaagcattc tgctttgact ttgcatttga tgaaacagct   1020
tcgaatgaag ttgtctacag gttcacagca aggccactgg tacagacaat ctttgaaggt   1080
ggaaaagcaa cttgttttgc atatggccag acaggaagtg gcaagacaca tactatgggc   1140
ggagacctct ctgggaaagc ccagaatgca tccaaaggga tctatgccat ggcctcccgg   1200
gacgtcttcc tcctgaagaa tcaaccctgc taccggaagt tgggcctgga agtctatgtg   1260
acattcttcg agatctacaa tgggaagctg tttgacctgc tcaacaagaa ggccaagctg   1320
cgcgtgctgg aggacggcaa gcaacaggtg caagtggtgg ggctgcagga gcatctggtt   1380
aactctgctg atgatgtcat caagatgatc gacatgggca gcgcctgcag aacctctggg   1440
cagacatttg ccaactccaa ttcctcccgc tcccacgcgt gcttccaaat tattcttcga   1500
gctaaaggga gaatgcatgg caagttctct ttggtagatc tggcagggaa tgagcgaggc   1560
gcggacactt ccagtgctga ccggcagacc cgcatggagg gcgcagaaat caacaagagt   1620
ctcttagccc tgaaggagtg catcagggcc ctgggacaga acaaggctca caccccgttc   1680
cgtgagagca agctgacaca ggtgctgagg gactccttca ttggggagaa ctctaggact   1740
tgcatgattg ccacgatctc accaggcata agctcctgtg aatatacttt aaacaccctg   1800
agatatgcag acagggtcaa ggagctgagc ccccacagtg ggcccagtgg agagcagttg   1860
attcaaatgg aaacagaaga gatggaagcc tgctctaacg gggcgctgat tccaggcaat   1920
ttatccaagg aagaggagga actgtcttcc cagatgtcca gctttaacga agccatgact   1980
cagatcaggg agctggagga gaaggctatg gaagagctca aggagatcat acagcaagga   2040
ccagactggc ttgagctctc tgagatgacc gagcagccag actatgacct ggagaccttt   2100
gtgaacaaag cggaatctgc tctggcccag caagccaagc atttctcagc cctgccagat   2160
gtcatcaagg ccttgcgcct ggccatgcag ctggaagagc aggctagcag acaaataagc   2220
agcaagaaac ggccccagtg acgactgcaa ataaaaatct gtttggtttg acacccagcc   2280
tcttccctgg ccctccccag agaactttgg gtacctggtg ggtctaggca gggtctgagc   2340
tgggacaggt tctggtaaat gccaagtatg gggcatctg ggcccagggc agctggggag   2400
ggggtcagag tgacatggga cactcctttt ctgttcctca gttgtcgccc tcacgagagg   2460
aaggagctct tagttaccct tttgtgttgc ccttctttcc atcaagggga atgttctcag   2520
```

catagagctt tctccgcagc atcctgcctg cgtggactgg ctgctaatgg agagctccct 2580
ggggttgtcc tggctctggg gagagagacg gagcctttag tacagctatc tgctggctct 2640
aaaccttcta cgcctttggg ccgagcactg aatgtcttgt actttaaaaa aatgtttctg 2700
agacctcttt ctactttact gtctccctag agatcctaga ggatccctac tgttttctgt 2760
tttatgtgtt tatacattgt atgtaacaat aaagagaaaa aataaaaaaa aaaaaaaaaa 2820
aaaaaaaaaa aa 2832

<210> SEQ ID NO 23
<211> LENGTH: 670
<212> TYPE: DNA
<213> ORGANISM: Homo sapiens
<220> FEATURE:
<221> NAME/KEY: misc_feature
<222> LOCATION: (14)..(14)
<223> OTHER INFORMATION: a or g or c or t/u
<220> FEATURE:
<221> NAME/KEY: misc_feature
<222> LOCATION: (19)..(19)
<223> OTHER INFORMATION: a or g or c or t/u
<220> FEATURE:
<221> NAME/KEY: misc_feature
<222> LOCATION: (37)..(37)
<223> OTHER INFORMATION: a or g or c or t/u
<220> FEATURE:
<221> NAME/KEY: misc_feature
<222> LOCATION: (113)..(113)
<223> OTHER INFORMATION: a or g or c or t/u

<400> SEQUENCE: 23
atcggacttc ggtnaactnt ggcaaggatt ggacagncta ggtaggctaa atgtgtgctc 60
tgtccctgtt tgcttcaaca gaggagcaag cctcagctga gaaggagggc acntggaaca 120
cctagctcct cccgtgattc cccaaaccca taacattctt ccatagggct ggaaccagtg 180
ccccgtcctg acagggatga aaagtgaacc cctcaggtca ggagaggcca gagttgaggt 240
tctgccactt cctgtccctg gggagccact caagttacca gggctaccgg ctgaaataaa 300
tcttttccgg gtagggtcaa gggcagtgtg ttccaaggca actgatgtag gccagttgcg 360
tgactccagg tttgtcctgg tactcagtgg gtccaatcac ctggcattga tcacctggca 420
ttgatcagca cccaccccac ccctgaggct tgcccagccc ccaggccctc agatccctgc 480
tcttcctgcc tttcctgccc atgtgtcacc cagcacccaa ggttcagtga cacagggtgg 540
tttggagctg gtcactgtca tagcagctgt gatttcacaa ggaagggtgc tgcaggggga 600
cctggttgat ggggagtggg aaggggaagg aataaagaga tcttcctcag gtaaaaaaaa 660
aaaaaaaaaa 670

<210> SEQ ID NO 24
<211> LENGTH: 964
<212> TYPE: DNA
<213> ORGANISM: Homo sapiens

<400> SEQUENCE: 24
acctcgtttg ctcccagtta cttcttatct ggagcagtaa tgtagtccac ttcactcatg 60
cctaccccgc gtgtctcgtc tcctgacatg tctcacagac gctcctgaag ttaggtcatt 120
acctaaccca tagttattta ccttgaaaga tgggtctccg cacttggaaa ggtttcaaga 180
cttgatactg caataaatta tggctcttca cctgggcgcc aactgctgat caacgaaatg 240
cttgttgaat caggggcaaa cggagtacag acgtctcaag actgaaacgg ccccattgcc 300

```
tggtctagta gcggatctca ctcagccgca gacaagtaat cactaacccg ttttattcta    360

ttcctatctg tggatgtgta aatggctggg gggccagccc tggataggtt tttatgggaa    420

ttctttacaa taaacatagc ttgtaacttg agatctacaa atccattcat cctgattggg    480

catgaaatcc atggtcaaga ggacaagtgg aaagtgagag ggaaggtttg ctagacacct    540

tcgcttgtta tcttgtcaag atagaaaaga tagtatcatt tcacccttgc cagtaaaaac    600

ctttccatcc acccattctc agcagactcc agtattggca cagtcactca ctgccattct    660

cacactataa caagaaaaga aatgaagtgc ataagtctcc tgggaaaaga accttaaccc    720

cttctcgtgc catgactggt gatttcatga ctcataagcc cctccgtagg catcattcaa    780

gatcaatggc ccatgcatgc tgtttgcagc agtcaattga gttgaattag aattccaacc    840

atacatttta aaggtatttg tgctgtgtgt atattttgat aaaatgttgt gacttcatgg    900

caaacaggtg gatgtgtaaa aatggaataa aaaaaaaaaa agagtcaaaa aaaaaaaaaa    960

aatt                                                                 964
```

<210> SEQ ID NO 25
<211> LENGTH: 1568
<212> TYPE: DNA
<213> ORGANISM: Homo sapiens

<400> SEQUENCE: 25

```
ggcgcccaag ccgccgccgc cagatcggtg ccgattcctg ccctgccccg accgccagcg     60

cgaccatgtc ccatcactgg gggtacggca aacacaacgg acctgagcac tggcataagg    120

acttccccat tgccaaggga gagcgccagt cccctgttga catcgacact catacagcca    180

agtatgaccc ttccctgaag cccctgtctg tttcctatga tcaagcaact tccctgagga    240

tcctcaacaa tggtcatgct ttcaacgtgg agtttgatga ctctcaggac aaagcagtgc    300

tcaagggagg acccctggat ggcacttaca gattgattca gtttcacttt cactggggtt    360

cacttgatgg acaaggttca gagcatactg tggataaaaa gaaatatgct gcagaacttc    420

acttggttca ctggaacacc aaatatgggg attttgggaa agctgtgcag caacctgatg    480

gactggccgt tctaggtatt tttttgaagg ttggcagcgc taaaccgggc cttcagaaag    540

ttgttgatgt gctggattcc attaaaacaa agggcaagag tgctgacttc acaaactttg    600

cagctcgtgg cctccttcct gaatccctgg attactggac ctacccaggc tcactgacca    660

cccctcctct tctggaatgt gtgacctgga ttgtgctcaa ggaacccatc agcgtcagca    720

gcgagcaggt gttgaaattc cgtaaactta acttcaatgg ggagggtgaa cccgaagaac    780

tgatggtgga caactggcgc ccagctcagc cactgaagaa caggcaaatc aaagcttcct    840

tcaaataaga tggtcccata gtctgtatcc aaataatgaa tcttcgggtg tttccctta     900

gctaagcaca gatctacctt ggtgatttgg accctggttg ctttgtgtct agttttctag    960

acccttcatc tcttacttga tagacttact aataaaatgt gaagactaga ccaattgtca   1020

tgcttgacac aactgctgtg gctggttggt gctttgttta tggtagtagt ttttctgtaa   1080

cacagaatat aggataagaa ataagaataa agtaccttga ctttgttcac agcatgtagg   1140

gtgatgagca ctcacaattg ttgactaaaa tgctgccttt aaaacatagg aaagtagaat   1200

ggttgagtgc aaatccatag cacaagataa attgagctag ttaaggcaaa tcaggtaaaa   1260

tagtcatgat tctatgtaat gtaaaccaga aaaaataaat gttcatgatt tcaagatgtt   1320

atattaaaga aaaactttaa aaattattat atatttatag caaagttatc ttaaatatga   1380

attctgttgt aatttaatga cttttgaatt acagagatat aaatgaagta ttatctgtaa   1440
```

aaattgttat aattagagtt gtgatacaga gtatatttcc attcagacaa tatatcataa 1500
cttaataaat attgtatttt agatatattc tctaataaaa ttcagaattc taaaaaaaaa 1560
aaaaaaaa 1568

<210> SEQ ID NO 26
<211> LENGTH: 1964
<212> TYPE: DNA
<213> ORGANISM: Homo sapiens

<400> SEQUENCE: 26
ggcacgaggc atggaggcgc tgctgctggg cgcggggttg ctgctgggcg cttacgtgct 60
tgtctactac aacctggtga aggccccgcc gtgcggcggc atgggcaacc tgcggggccg 120
cacggccgtg gtcacgggtg agtgcggagg cgggtgagtg cgagctggcg gggcgcgcgg 180
agaggaggcc gggccggcgg tagcagcggc ccgccgggct cagctcagct cggctcccgc 240
ccgcggtccg caggcgccaa cagcggcatc ggaaagatga cggcgctgga gctggcgcgc 300
cggggagcgc gcgtggtgct ggcctgccgc agccaggagc gcggggaggc ggctgccttc 360
gacctccgcc aggagagtgg gaacaatgag gtcatcttca tggccttgga cttggccagt 420
ctggcctcgg tgcgggcctt tgccactgcc tttctgagct ctgagccacg gttggacatc 480
ctcatccaca atgccggtat cagttcctgt ggccggaccc gtgaggcgtt taacctgctg 540
cttcgggtga accatatcgg tccctttctg ctgacacatc tgctgctgcc ttgcctgaag 600
gcatgtgccc ctagccgcgt ggtggtggta gcctcagctg cccactgtcg gggacgtctt 660
gacttcaaac gcctggaccg cccagtggtg ggctggcggc aggagctgcg ggcatatgct 720
gacactaagc tggctaatgt actgtttgcc cgggagctcg ccaaccagct tgaggccact 780
ggcgtcacct gctatgcagc ccacccaggg cctgtgaact cggagctgtt cctgcgccat 840
gttcctggat ggctgcgccc acttttgcgc ccattggctt ggctggtgct ccgggcacca 900
agagggggtg cccagacacc cctgtattgt gctctacaag agggcatcga gcccctcagt 960
gggagatatt ttgccaactg ccatgtggaa gaggtgcctc cagctgcccg agacgaccgg 1020
gcagcccatc ggctatggga ggccagcaag aggctggcag ggcttgggcc tggggaggat 1080
gctgaacccg atgaagaccc ccagtctgag gactcagagg ccccatcttc tctaagcacc 1140
ccccaccctg aggagcccac agtttctcaa ccttacccca gccctcagag ctcaccagat 1200
ttgtctaaga tgacgcaccg aattcaggct aaagttgagc ctgagatcca gctctcctaa 1260
ccctcaggcc aggatgcttg ccatggcact tcatggtcct tgaaaacctc ggatgtgtgc 1320
gaggccatgc cctggacact gacgggtttg tgatcttgac ctccgtggtt actttctggg 1380
gccccaagct gtgccctgga catctctttt cctggttgaa ggaataatgg gtgattattt 1440
cttcctgaga gtgacagtaa ccccagatgg agagataggg gtatgctaga cactgtgctt 1500
ctcggaaatt tggatgtagt attttcaggc cccaccctta ttgattctga tcagctctgg 1560
agcagaggca gggagtttgc aatgtgatgc actgccaaca ttgagaatta gtgaactgat 1620
ccctttgcaa ccgtctagct aggtagttaa attacccccca tgttaatgaa gcggaattag 1680
gctcccgagc taagggactc gcctagggtc tcacagtgag taggaggagg gcctgggatc 1740
tgaacccaag ggtctgaggc cagggccgac tgccgtaaga tgggtgctga gaagtgagtc 1800
agggcagggc agctggtatc gaggtgcccc atgggagtaa ggggacgcct tccgggcgga 1860
tgcagggctg gggtcatctg tatctgaagc ccctcggaat aaagcgcgtt gaccgccaaa 1920

-continued aaaaaaaaaa aaaaaaaaaa aaaaaaaaaa aaaaaaaaaa aaaa 1964

<210> SEQ ID NO 27
<211> LENGTH: 953
<212> TYPE: DNA
<213> ORGANISM: Homo sapiens

<400> SEQUENCE: 27
agcggtggag aaaaggcaga accagagtag agattgacag tgagctgagc caatcaggct 60
gtgaatctgc agcagtgatc ccaggtcctc caattaatac taagagagtg gaccagggcc 120
cctgaggaag acagatggca gggacagcgc gccatgaccg agagatggcg atccaggcca 180
agaaaaagct caccacggcc accaacccca ttgaaagact ccgactgcag tgcctggcca 240
ggggctctgc tgggatcaaa ggacttggca gagtgtttag aattatggat gacgataata 300
atcgaaccct tgattttaaa gaatttatga aagggttaaa tgattatgct gtggtcatgg 360
aaaaagaaga ggtggaagaa cttttccgga ggtttgataa agatggaaat ggaacaatag 420
acttcaatga atttcttctc acattaagac ctccaatgtc cagagccaga aaagaggtaa 480
tcatgcaagc ttttagaaag ttagacaaga ctggagatgg tgttataaca atcgaagacc 540
ttcgtgaagt atataatgca aaacaccacc caaagtacca gaatggggaa tggagtgagg 600
aacaagtatt taggaaattt ctggataact tgattcacc ctatgacaaa gatggattgg 660
tgacccctga ggagttcatg aactactatg caggtgtgag cgcatccatt gacactgatg 720
tgtacttcat catcatgatg agaaccgcct ggaagcttta agcacatgac ctggggacca 780
ggccctggga cagccatgtg gctccaaatg actaaatgtc agctcaaaaa ccagaatcgt 840
atttgatttc acactcatcc taatgttttt ttctgtgtca aaatattgca ttttctgggg 900
ccaaaaaaca ggcagaaata aaagacattg agtagtcaaa aaaaaaaaaa aaa 953

<210> SEQ ID NO 28
<211> LENGTH: 850
<212> TYPE: DNA
<213> ORGANISM: Homo sapiens

<400> SEQUENCE: 28
tagagcatta aaataactat caggcagaag aatctttctt ctcgcctagg atttcagcca 60
tgcgcgcgct ctctctcttt ctctctcttt tcctctctct ccctctttct agcctggggc 120
ttgaatttgc atgtctaatt catttactca ccatatttga attggcctga acagatgtaa 180
atcgggaagg atgggaaaaa ctgcagtcat caacaatgat taatcagctg ttgcaggcag 240
tgtcttaagg agactggtag gaggaggcat ggaaaccaaa aggccgtgtg tttagaagcc 300
taattgtcac atcaagcatc attgtcccca tgcaacaacc accaccttat acatcacttc 360
ctgttttaag cagctctaaa acatagactg aagatttatt tttaatatgt tgactttatt 420
tctgagcaaa gcatcggtca tgtgtgtatt ttttcatagt cccaccttgg agcatttatg 480
tagacattgt aaataaattt tgtgcaaaaa ggactggaaa aatgaactgt attattgcaa 540
tttttttttg taaaagtagc agtttggtat gagttggcat gcatacaaga tttactaagt 600
gggataagct aattatactt tttgttgtgg ataaacaaat gcttgttgat agccttttc 660 tatcaagaaa ccaaggagct aattattaat aacaatcatt gcacactgag tcttagcgtt 720
tctgatggaa acagtttgga ttgtataata acgccaagcc cagttgtagt cgtttgagtg 780
cagtaatgaa atctgaatct aaaataaaaa caagattatt tttgtcaaaa aaaaaaaaaa 840
aaaaaaaaaa 850

<210> SEQ ID NO 29
<211> LENGTH: 4670
<212> TYPE: DNA
<213> ORGANISM: Homo sapiens

<400> SEQUENCE: 29
gcggcgcgca cactgctcgc tgggccgcgg ctcccgggtg tcccaggccc ggccggtgcg 60
cagagcatgg cgggtgcggg cccgaagcgg cgcgcgctag cggcgccggc ggccgaggag 120
aaggaagagg cgcgggagaa gatgctggcc gccaagagcg cggacggctc ggcgccggca 180
ggcgagggcg agggcgtgac cctgcagcgg aacatcacgc tgctcaacgg cgtggccatc 240
atcgtgggga ccattatcgg ctcgggcatc ttcgtgacgc ccacgggcgt gctcaaggag 300
gcaggctcgc cggggctggc gctggtggtg tgggccgcgt gcggcgtctt ctccatcgtg 360
ggcgcgctct gctacgcgga gctcggcacc accatctcca aatcgggcgg cgactacgcc 420
tacatgctgg aggtctacgg ctcgctgccc gccttcctca agctctggat cgagctgctc 480
atcatccggc cttcatcgca gtacatcgtg gccctggtct tcgccaccta cctgctcaag 540
ccgctcttcc ccacctgccc ggtgcccgag gaggcagcca agctcgtggc ctgcctctgc 600
gtgctgctgc tcacggccgt gaactgctac agcgtgaagg ccgccacccg ggtccaggat 660
gcctttgccg ccgccaagct cctggccctg gccctgatca tcctgctggg cttcgtccag 720
atcgggaagg gtgatgtgtc caatctagat cccaacttct catttgaagg caccaaactg 780
gatgtgggga acattgtgct ggcattatac agcggcctct ttgcctatgg aggatggaat 840
tacttgaatt tcgtcacaga ggaaatgatc aacccctaca gaaacctgcc cctggccatc 900
atcatctccc tgcccatcgt gacgctggtg tacgtgctga ccaacctggc ctacttcacc 960
accctgtcca ccgagcagat gctgtcgtcc gaggccgtgg ccgtggactt cgggaactat 1020
cacctgggcg tcatgtcctg gatcatcccc gtcttcgtgg gcctgtcctg cttcggctcc 1080
gtcaatgggt ccctgttcac atcctccagg ctcttcttcg tggggtcccg ggaaggccac 1140
ctgccctcca tcctctccat gatccaccca cagctcctca cccccgtgcc gtccctcgtg 1200
ttcacgtgtg tgatgacgct gctctacgcc ttctccaagg acatcttctc cgtcatcaac 1260
ttcttcagct tcttcaactg gctctgcgtg gccctggcca tcatcggcat gatctggctg 1320
cgccacagaa agcctgagct tgagcggccc atcaaggtga acctggccct gcctgtgttc 1380
ttcatcctgg cctgcctctt cctgatcgcc gtctccttct ggaagacacc cgtggagtgt 1440
ggcatcggct tcaccatcat cctcagcggg ctgcccgtct acttcttcgg ggtctggtgg 1500
aaaaacaagc ccaagtggct cctccagggc atcttctcca cgaccgtcct gtgtcagaag 1560
ctcatgcagg tggtccccca ggagacatag ccaggaggcc gagtggctgc cggaggagca 1620
tgcgcagagg ccagttaaag tagatcacct cctcgaaccc actccggttc cccgcaaccc 1680
acagctcagc tgcccatccc agtccctcgc cgtccctccc aggtcgggca gtggaggctg 1740
ctgtgaaaac tctggtacga atctcatccc tcaactgagg gccagggacc caggtgtgcc 1800
tgtgctcctg cccaggagca gcttttggtc tccttgggcc ctttttccct tccctccttt 1860
gtttacttat atatatattt tttttaaact taaattttgg gtcaacttga caccactaag 1920
atgatttttt aaggagctgg gggaaggcag gagccttcct ttctcctgcc ccaagggccc 1980
agaccctggg caaacagagc tactgagact tggaacctca ttgctacgac agacttgcac 2040
tgaagccgga cagctgccca gacacatggg cttgtgacat tcgtgaaaac caaccctgtg 2100

-continued

```
ggcttatgtc tctgccttag ggtttgcaga gtggaaactc agccgtaggg tggcactggg   2160
aggggtggg ggatctgggc aaggtgggtg attcctctca ggaggtgctt gaggccccga   2220
tggactcctg accataatcc tagccctgag acaccatcct gagccaggga acagccccag   2280
ggttgggggg tgccggcatc tcccctagct caccaggcct ggcctctggg cagtgtggcc   2340
tcttggctat ttctgtgtcc agttttggag gctgagttct ggttcatgca gacaaagccc   2400
tgtccttcag tcttctagaa acagagacaa gaaaggcaga cacaccgcgg ccaggcaccc   2460
atgtgggcgc ccaccctggg ctccacacag cagtgtcccc tgccccagag gtcgcagcta   2520
ccctcagcct ccaatgcatt ggcctctgta ccgcccggca gccccttctg gccggtgctg   2580
ggttcccact cccggcctag gcacctcccc gctctccctg tcacgctcat gtcctgtcct   2640
ggtcctgatg cccgttgtct aggagacaga gccaagcact gctcacgtct ctgccgcctg   2700
cgtttggagg cccctgggct ctcacccagt ccccacccgc ctgcagagag ggaactaggg   2760
cacccettgt ttctgttgtt cccgtgaatt tttttcgcta tgggaggcag ccgaggcctg   2820
gccaatgcgg cccactttcc tgagctgtcg ctgcctccat ggcagcagcc aaggaccccc   2880
agaacaagaa gacccccccg caggatccct cctgagctcg gggggctctg ccttctcagg   2940
ccccgggctt cccttctccc cagccagagg tggagccaag tggtccagcg tcactccagt   3000
gctcagctgt ggctggagga gctggcctgt ggcacagccc tgagtgtccc aagccgggag   3060
ccaacgaagc cggacacggc ttcactgacc agcggctgct caagccgcaa gctctcagca   3120
agtgcccagc ggagcctgcc gcccccacct gggcaccggg accccctcac catccagtgg   3180
gcccggagaa acctgatgaa cagtttgggg actcaggacc agatgtccgt ctctcttgct   3240
tgaggaatga agacctttat tcacccctgc cccgttgctt cccgctgcac atggacagac   3300
ttcacagcgt ctgctcatag gacctgcatc cttcctgggg acgaattcca ctcgtccaag   3360
ggacagccca cggtctggag gccgaggacc accagcaggc aggtggactg actgtgttgg   3420
gcaagacctc ttccctctgg gcctgttctc ttggctgcaa ataaggacag cagctggtgc   3480
cccacctgcc tggtgcattg ctgtgtgaat ccaggaggca gtggacatcg taggcagcca   3540
cggccccggg tccaggagaa gtgctccctg gaggcacgca ccactgcttc ccactggggc   3600
cggcggggcc cacgcacgac gtcagcctct taccttcccg cctcggctag ggtcctcgg    3660
gatgccgttc tgttccaacc tcctgctctg ggacgtggac atgcctcaag gatacaggga   3720
gccggcggcc tctcgacggc acgcacttgc ctgttggctg ctgcggctgt gggcgagcat   3780
gggggctgcc agcgtctgtt gtggaaagta gctgctagtg aaatggctgg ggccgctggg   3840
gtccgtcttc acactgcgca ggtctcttct gggcgtctga gctggggtgg gagctcctcc   3900
gcagaaggtt ggtgggggt ccagtctgtg atccttggtg ctgtgtgccc cactccagcc    3960
tggggacccc acttcagaag gtaggggccg tgtcccgcgg tgctgactga ggcctgcttc   4020
cccctccccc tcctgctgtg ctggaattcc acagggacca gggccaccgc aggggactgt   4080
ctcagaagac ttgatttttc cgtccctttt tctccacact ccactgacaa acgtccccag   4140
cggtttccac ttgtgggctt caggtgtttt caagcacaac ccaccacaac aagcaagtgc   4200
attttcagtc gttgtgcttt tttgttttgt gctaacgtct tactaattta aagatgctgt   4260
cggcaccatg tttatttatt tccagtggtc atgctcagcc ttgctgctct gcgtggcgca   4320
ggtgccatgc ctgctccctg tctgtgtccc agccacgcag ggccatccac tgtgacgtcg   4380
gccgaccagg ctggacaccc tctgccgagt aatgacgtgt gtggctggga ccttctttat   4440
tctgtgttaa tggctaacct gttacactgg gctgggttgg gtagggtgtt ctggcttttt   4500
```

```
tgtggggttt ttatttttaa agaaacactc aatcatccta aaaaaaaaaa aaaaaaaaaa   4560

aaaaaaaaaa aaaaaaaaaa aaaaaaaaaa aaaaaaaaaa aaaaaaaaaa aaaaaaaaaa   4620

aaaaaaaaaa aaaaaaaaaa aaaaaaaaaa aaaaaaaaaa aaaaaaaaaa              4670


<210> SEQ ID NO 30
<211> LENGTH: 176
<212> TYPE: DNA
<213> ORGANISM: Homo sapiens

<400> SEQUENCE: 30

gggacttgga aaggggaact gggatttggg gaggggctgg aggacttccg cacgcttcca     60

cctccttcga cctccactgc gccccacctc cctgcctgtg tgtgttattt caaaggaaaa    120

gaacaaaagg aataaatttt ctaagctctt taaaaaaaaa aaaaaaaaaa aaaaaa        176


<210> SEQ ID NO 31
<211> LENGTH: 2255
<212> TYPE: DNA
<213> ORGANISM: Homo sapiens

<400> SEQUENCE: 31

gcaggctctg cctgtggcca ctagcagaga agctgctgtc cttccaccac cagcaccgga     60

ccacctgctc caagaccagc ctcctggggg gaccaggcac ccggccttca ctggcaccca    120

gggagccgtc ctcagcagcg tcaacatgtc aaggcccagc agcagagcca tttacttgca    180

ccggaaggag tactcccaga acctcacctc agagcccacc ctcctgcagc acagggtgga    240

gcacttgatg acatgcaagc aggggagtca gagagtccag gggcccgagg atgccttgca    300

gaagctgttc gagatggatg cacagggccg ggtgtggagc caagacttga tcctgcaggt    360

cagggacggc tggctgcagc tgctggacat tgagaccaag gaggagctgg actcttaccg    420

cctagacagc atccaggcca tgaatgtggc gctcaacaca tgttcctaca actccatcct    480

gtccatcacc gtgcaggagc cgggcctgcc aggcactagc actctgctct tccagtgcca    540

ggaagtgggg gcagagcgac tgaagaccag cctgcagaag gctctggagg aagagctgga    600

gcaaagcaga cctcgacttg gaggccttca gccaggccag gacagatgga gggggcctgc    660

tatggaaagg ccgctcccta tggagcaggc acgctatctg gagccgggga tccctccaga    720

acagccccac cagaggaccc tagagcacag cctcccacca tccccaaggc ccctgccacg    780

ccacaccagt gcccgagaac caagtgcctt tactctgcct cctccaaggc ggtcctcttc    840

ccccgaggac ccagagaggg acgaggaagt gctgaaccat gtcctaaggg acattgagct    900

gttcatggga aagctggaga aggcccaggc aaagaccagc aggaagaaga aatttgggaa    960

aaaaaacaag gaccagggag gtctcaccca ggcacagtac attgactgct tccagaagat   1020

caagtacagc ttcaacctcc tgggaaggct ggccacctgg ctgaaggaga caagtgcccc   1080

tgagctcgta cacatcctct tcaagtccct gaacttcatc ctggccaggt gccctgaggc   1140

tggcctagca gcccaagtga tctcacccct cctcacccct aaagctatca acctgctaca   1200

gtcctgtcta agcccacctg agagtaacct ttggatgggg ttgggcccag cctggaccac   1260

tagccgggcc gactggacag gcgatgagcc cctgccctac caacccacat tctcggatga   1320

ctggcaactt ccagagccct ccagccaagc acccttagga taccaggacc ctgtttccct   1380

tcggcgggga agtcataggt tagggagcac ctcacacttt cctcaggaga agacacacaa   1440

ccatgaccct cagcctgggg accccaactc caggccctcc agccccaaac ctgcccagcc   1500
```

-continued agccctgaaa atgcaagtct tgtacgagtt tgaagctagg aacccacggg aactgactgt 1560
ggtccaggga gagaagctgg aggttctgga ccacagcaag cggtggtggc tggtgaagaa 1620
tgaggcggga cggagcggct acattccaag caacatcctg gagcccctac agccggggac 1680
ccctgggacc cagggccagt caccctctcg ggttccaatg cttcgactta gctcgaggcc 1740
tgaagaggtc acagactggc tgcaggcaga gaacttctcc actgccacgg tgaggacact 1800
tgggtccctg acggggagcc agctacttcg cataagacct ggggagctac agatgctatg 1860
tccacaggag gccccacgaa tcctgtcccg gctggaggct gtcagaagga tgctggggat 1920
aagcccttag gcaccagctt agacacctcc aagaaccagg ccccgctgat gcaagatggc 1980
agatctgata cccattagag ccccgagaat tcctcttctg gatcccagtt tgcagcaaac 2040
cccacacccc agctcacaca gcaaaaacaa tggacaggcc cagagggtga agcaaacagt 2100
gtcccttctg gctgtgttgg agcctcccca gtaaccacct atttatttta cctctttccc 2160
aaacctggag catttatgcc taggcttgtc aagaatctgt tcagtccctc tccttctcaa 2220
taaaagcatc ttcaagcttg aaaaaaaaaa aaaaa 2255

<210> SEQ ID NO 32
<211> LENGTH: 945
<212> TYPE: DNA
<213> ORGANISM: Homo sapiens
<220> FEATURE:
<221> NAME/KEY: misc_feature
<222> LOCATION: (36)..(36)
<223> OTHER INFORMATION: a or g or c or t/u

<400> SEQUENCE: 32
ccttccattg aattccacca gacacattca ggttancttc gtaatgtctt catatgagta 60
tcaatcaaca ccttccccaa ctcaattgta ctaggttgta gagcacaagg atggtctcgt 120
gctgctctgt ggcacctgtg cctacactgc tctgagcttt gaggaggctg ctctctttgc 180
tgaccccatg atcttttctg cccttctgtt aagggcattg gccacagcaa cggggcaaat 240
gccccaagct ggctgtaagt gacccatccc tttggctccc atgattagac caaggagagg 300
catggggtcc agctgagcca ttcagaacca ttccttagca ttttccactc aaaggttaga 360
gatgagattt tctcttccca aggctacctc tggccatggt tccagcttca tgggggcaat 420
gggattagga aaatgaggtc aacctgcaaa ggaaagcaga tgcaagagat ggagacagaa 480
tgggggtgtc ctggggatct tggagcctga attcattggc acaaaaggca gcagcatcct 540
cactgtatct gcagtccatt tggactcaat aaaaactttg aaagtcacat gtgttatgga 600
attccttctc agtgacacat tcatctgtgc tcagttgtcc cagcaagggt cagcccctca 660 taccccctgca gcatccgctg ctatgaagca gagctgtaaa cgccctccct gtgtatagga 720
aaagctacat ggagcaaatc ctcctgcctg aagaagtgca tctcagcatc acttcagctg 780
tcggggcatt tgtggggaga accagaccac ctctgcggaa ggcagcagac cctcttccag 840
ccatggatgg agttgaattc tctataaacg gttcaccagc aaaccaccaa tacattccat 900
tgtttgccta gagagaaatt taaaaataaa taaatgttca cttat 945

<210> SEQ ID NO 33
<211> LENGTH: 736
<212> TYPE: DNA
<213> ORGANISM: Homo sapiens

<400> SEQUENCE: 33
tgcggccgcg gcatgaaagg cggcgaggag aggcagcact gctgctcttg acttctgagc 60
agggcttaga gagcctgccc cggcttaagc cgagctgctg gtgctgaccc tgagcgccga 120
gtccgcgagc tctgagtccg gagcctccca gccgtggagc cgtgggatga ggggggcgtt 180
gggggacagg gcaaagtcga tcttggttgt acagccgccc gatcctagcg cggagctgcg 240
agcctgaccg gccgcgtctg gcatggtcag agaaagaatt ttcttttccc aactccggct 300
tttggttttg tgtgtccacc ttgcgcaact ccggagccag ccgaccccac atggattctc 360
aacaggtggc cggcacatct tctgagcctc gctctctcat ctgaaagtgg agtgtaagtc 420
caagaagatt catttagaca aagaaggtgg aaaaaaagga ctttctgggc cagcaagtcg 480
gatgaccacc ctccaagggg cagaggaggg cccattttgt gaagaagaaa tcaactaccc 540
ggaaaacgcc acaggaggac atgtttctgc agatgtagtt gccctagaaa cagaagagta 600
tgggggtgtg aatgtcttct cttttggggg caaacactat gtccttttct ttttctagat 660
acagttaatt cctggaaatt ttagcgagtt tgttcttgtg gatattttga acaataaaga 720
gtgaaaatca aaaaaa 736

<210> SEQ ID NO 34
<211> LENGTH: 2104
<212> TYPE: DNA
<213> ORGANISM: Homo sapiens

<400> SEQUENCE: 34
cccaatcact cctggaatac acagagagag gcagcagctt gctcagcgga caaggatgct 60
gggcgtgagg gaccaaggcc tgccctgcac tcgggcctcc tccagccagt gctgaccagg 120
gacttctgac ctgctggcca gccaggacct gtgtggggag gccctcctgc tgccttgggg 180
tgacaatctc agctccaggc tacagggaga ccgggaggat cacagagcca gcatgttaca 240
ggatcctgac agtgatcaac ctctgaacag cctcgatgtc aaacccctgc gcaaaccccg 300
tatccccatg gagaccttca gaaaggtggg gatccccatc atcatagcac tactgagcct 360
ggcgagtatc atcattgtgg ttgtcctcat caaggtgatt ctggataaat actacttcct 420
ctgcgggcag cctctccact tcatcccgag gaagcagctg tgtgacggag agctggactg 480
tcccttgggg gaggacgagg agcactgtgt caagagcttc cccgaagggc ctgcagtggc 540
agtccgcctc tccaaggacc gatccacact gcaggtgctg gactcggcca cagggaactg 600
gttctctgcc tgtttcgaca acttcacaga agctctcgct gagacagcct gtaggcagat 660
gggctacagc agcaaaccca ctttcagagc tgtggagatt ggcccagacc aggatctgga 720
tgttgttgaa atcacagaaa acagccagga gcttcgcatg cggaactcaa gtgggccctg 780
tctctcaggc tccctggtct ccctgcactg tcttgcctgt gggaagagcc tgaagacccc 840
ccgtgtggtg ggtggggagg aggcctctgt ggattcttgg ccttggcagg tcagcatcca 900
gtacgacaaa cagcacgtct gtggagggag catcctggac ccccactggg tcctcacggc 960
agcccactgc ttcaggaaac ataccgatgt gttcaactgg aaggtgcggg caggctcaga 1020
caaactgggc agcttcccat ccctggctgt ggccaagatc atcatcattg aattcaaccc 1080
catgtacccc aaagacaatg acatcgccct catgaagctg cagttcccac tcactttctc 1140
aggcacagtc aggcccatct gtctgccctt ctttgatgag gagctcactc cagccacccc 1200
actctggatc attggatggg gctttacgaa gcagaatgga gggaagatgt ctgacatact 1260
gctgcaggcg tcagtccagg tcattgacag cacacggtgc aatgcagacg atgcgtacca 1320
gggggaagtc accgagaaga tgatgtgtgc aggcatcccg gaagggggtg tggacacctg 1380

```
ccagggtgac agtggtgggc ccctgatgta ccaatctgac cagtggcatg tggtgggcat   1440

cgttagctgg ggctatggct gcgggggccc gagcacccca ggagtataca ccaaggtctc   1500

agcctatctc aactggatct acaatgtctg gaaggctgag ctgtaatgct gctgcccctt   1560

tgcagtgctg ggagccgctt ccttcctgcc ctgcccacct ggggatcccc caaagtcaga   1620

cacagagcaa gagtcccctt gggtacaccc ctctgcccac agcctcagca tttcttggag   1680

cagcaaaggg cctcaattcc tgtaagagac cctcgcagcc cagaggcgcc cagaggaagt   1740

cagcagccct agctcggcca cacttggtgc tcccagcatc ccagggagag acacagccca   1800

ctgaacaagg tctcaggggt attgctaagc caagaaggaa ctttcccaca ctactgaatg   1860

gaagcaggct gtcttgtaaa agcccagatc actgtgggct ggagaggaga aggaaagggt   1920

ctgcgccagc cctgtccgtc ttcacccatc cccaagccta ctagagcaag aaaccagttg   1980

taatataaaa tgcactgccc tactgttggt atgactaccg ttacctactg ttgtcattgt   2040

tattacagct atggccacta ttattaaaga gctgtgtaac atcaaaaaaa aaaaaaaaaa   2100

aaaa                                                                2104
```

<210> SEQ ID NO 35
<211> LENGTH: 3865
<212> TYPE: DNA
<213> ORGANISM: Homo sapiens

<400> SEQUENCE: 35

```
tttttcaatt ttgaacattt tgcaaaacga ggggttcgag gcaggtgaga gcatcctgca     60

cgtcgccggg gagcccgcgg gcacttggcg cgctctcctg ggaccgtctg cactggaaac    120

ccgaaagttt ttttttaata tatattttta tgcagatgta tttataaaga tataagtaat    180

tttttcttc cctttctcc accgccttga gagcgagtac ttttggcaaa ggacggagga     240

aaagctcagc aacattttag gggcggttg tttctttctt tcttatttct tttttaaggg     300

gaaaaaattt gagtgcatcg cgatggagaa aatgtcccga ccgctccccc tgaatcccac    360

ctttatcccg cctccctacg gcgtgctcag gtccctgctg gagaacccgc tgaagctccc    420

ccttcaccac gaagacgcat ttagtaaaga taaagacaaa gaaaagaagc tggatgatga    480

gagtaacagc ccgacggtcc cccagtcggc attcctgggg cctaccttat gggacaaaac    540

ccttccctat gacggagata ctttccagtt ggaatacatg gacctggagg agtttttgtc    600

agaaaatggc attcccccca gcccatctca gcatgaccac agccctcacc ctcctgggct    660

gcagccagct tcctcggctg ccccctcggt catggacctc agcagccggg cctctgcacc    720

ccttcaccct ggcatcccat ctccgaactg tatgcagagc cccatcagac caggtcagct    780

gttgccagca aaccgcaata caccaagtcc cattgatcct gacaccatcc aggtcccagt    840

gggttatgag ccagacccag cagatcttgc cctttccagc atccctggcc aggaaatgtt    900

tgaccctcgc aaacgcaagt tctctgagga agaactgaag ccacagccca tgatcaagaa    960

agctcgcaaa gtcttcatcc ctgatgacct gaaggatgac aagtactggg caaggcgcag   1020

aaagaacaac atggcagcca agcgctcccg cgacgcccgg aggctgaaag agaaccagat   1080

cgccatccgg gcctcgttcc tggagaagga gaactcggcc ctccgccagg aggtggctga   1140

cttgaggaag gagctgggca aatgcaagaa catacttgcc aagtatgagg ccaggcacgg   1200

gcccctgtag gatggcattt ttgcaggctg gctttggaat agatggacag tttgtttcct   1260

gtctgatagc accacacgca aaccaacctt tctgacatca gcactttacc agaggcataa   1320

acacaactga ctcccatttt ggtgtgcatc tgtgtgtgtg tgcgtgtata tgtgcttgtg   1380
```

```
ctcatgtgtg tggtcagcgg tatgtgcgtg tgcgtgttcc tttgctcttg ccattttaag   1440
gtagccctct catcgtcttt tagttccaac aaagaaaggt gccatgtctt tactagactg   1500
aggagccctc tcgcgggtct cccatcccct ccctccttca ctcctgcctc ctcagctttg   1560
cttcatgttc gagcttacct actcttccag gactctctgc ttggattcac taaaaagggc   1620
cctggtaaaa tagtggatct cagtttttaa gagtacaagc tcttgtttct gtttagtccg   1680
taagttacca tgctaatgag gtgcacacaa taacttagca ctactccgca gctctagtcc   1740
tttataagtt gctttcctct tactttcagt tttggtgata atcgtcttca aattaaagtg   1800
ctgtttagat ttattagatc ccatatttac ttactgctat ctactaagtt tccttttaat   1860
tctaccaacc ccagataagt aagagtacta ttaatagaac acagagtgtg tttttgcact   1920
gtctgtacct aaagcaataa tcctattgta cgctagagca tgctgcctga gtattactag   1980
tggacgtagg atattttccc tacctaagaa tttcactgtc ttttaaaaaa caaaaagtaa   2040
agtaatgcat ttgagcatgg ccagactatt ccctaggaca aggaagcaga gggaaatggg   2100
aggtctaagg atgaggggtt aatttatcag tacatgagcc aaaaactgcg tcttggatta   2160
gcctttgaca ttgatgtgtt cggttttgtt gttccccttc cctcacaccc tgcctcgccc   2220
ccacttttct agttaacttt ttccatatcc ctcttgacat tcaaaacagt tacttaagat   2280
tcagttttcc cactttttgg taatatatat atttttgtga attatacttt gttgttttta   2340
aaaagaaaat cagttgatta agttaataag ttgatgtttt ctaaggccct ttttcctagt   2400
ggtgtcattt ttgaatgcct cataaattaa tgattctgaa gcttatgttt cttattctct   2460
gtttgctttt gaacgtatgt gctcttataa agtggacttc tgaaaaatga atgtaaaaga   2520
cactggtgta tctcagaagg ggatggtgtt gtcacaaact gtggttaatc caatcaattt   2580
aaatgtttac tatagaccaa aaggagagat tattaaatcg tttaatgttt atacagagta   2640
attataggaa gttctttttt gtacagtatt tttcagatat aaatactgac aatgtatttt   2700
ggaagacata tattatatat agaaaagagg agaggaaaac tattccatgt tttaaaatta   2760
tatagcaaag atatatattc accaatgttg tacagagaag aagtgcttgg gggtttttga   2820
agtctttaat attttaagcc ctatcactga cacatcagca tgttttctgc tttaaattaa   2880
aattttatga cagtatcgag gcttgtgatg acgaatcctg ctctaaaata cacaaggagc   2940
tttcttgttt cttattaggc ctcagaaaga agtcagttaa cgtcacccaa aagcacaaaa   3000
tggattttag tcaaatattt attggatgat acagtgtttt ttaggaaaag catctgccac   3060
aaaaatgttc acttcgaaat tctgagttcc tggaatggca cgttgctgcc agtgccccag   3120
acagttcttt tctaccctgc gggcccgcac gttttatgag gttgatatcg gtgctatgtg   3180
tttggtttat aatttgatag atgtttgact ttaaagatga ttgttctttt gtttcattaa   3240
gttgtaaaat gtcaagaaat tctgctgtta cgacaaagaa acattttacg ctagattaaa   3300
atatcctttc atcaatggga ttttctagtt tcctgccttc agagtatcta atcctttaat   3360
gatctggtgg tctcctcgtc aatccatcag caatgcttct ctcatagtgt catagacttg   3420
ggaaacccaa ccagtaggat atttctacaa ggtgttcatt ttgtcacaag ctgtagataa   3480
cagcaagaga tgggggtgta ttggaattgc aatacattgt tcaggtgaat aataaaatca   3540
aaaacttttg caatcttaag cagagataaa taaaagatag caatatgaga cacaggtgga   3600
cgtagagttg gcctttttac aggcaaagag gcgaattgta gaattgttag atggcaatag   3660
tcattaaaaa catagaaaaa tgatgtcttt aagtggagaa ttgtggaagg attgtaacat   3720
```

ggaccatcca aatttatggc cgtatcaaat ggtagctgaa aaaactatat ttgagcactg 3780
gtctctcttg gaattagatg tttatatcaa atgagcatct caaatgtttt ctgcagaaaa 3840
aaataaaaag attctaataa aaaaa 3865

<210> SEQ ID NO 36
<211> LENGTH: 359
<212> TYPE: DNA
<213> ORGANISM: Homo sapiens
<220> FEATURE:
<221> NAME/KEY: misc_feature
<222> LOCATION: (17)..(17)
<223> OTHER INFORMATION: a or g or c or t/u

<400> SEQUENCE: 36
ttccttccct ccctccnttc ctcaggagcc gccagtcccc aagttggctg tggttgggca 60
cctggtttgg gtcctgcaga gctgggctca ggccctgggc tctgaacctg tgaacccttg 120
ctgtgttacg aaactttcct tcctctgagg gccttgaacc ctctcctttt cttcttttgg 180
gggtgggggt taactttatt ttctcttccc tgtatctgcc tctcccttcc ctcaatttcc 240
tgttttaaaa ctgaatggca cgaaattgtt ttcctcaact cggagattcc tgtatggaga 300
gaatcaattt ctatatttgc aataaatttc ttatttaaag ctaaaaaaaa aaaaaaaaa 359

<210> SEQ ID NO 37
<211> LENGTH: 1848
<212> TYPE: DNA
<213> ORGANISM: Homo sapiens

<400> SEQUENCE: 37
ggcacgaggg ccatctgtgg gggctttggg ccaggggtct ccggacagca tgagcgtggg 60
cttcatcggc gctggccagc tggcttttgc cctggccaag ggcttcacag cagcaggcgt 120
cttggctgcc cacaagataa tggctagctc cccagacatg gacctggcca cagtttctgc 180
tctcaggaag atgggggtga agttgacacc ccacaacaag gagacggtgc agcacagtga 240
tgtgctcttc ctggctgtga agccacacat catccccttc atcctggatg aaataggcgc 300
cgacattgag gacagacaca ttgtggtgtc ctgcgcggcc ggcgtcacca tcagctccat 360
tgagaagaag ctgtcagcgt ttcggccagc ccccagggtc atccgctgca tgaccaacac 420
tccagtcgtg gtgcgggagg gggccaccgt gtatgccaca ggcacgcacg cccaggtgga 480
ggacgggagg ctcatggagc agctgctgag cagcgtgggc ttctgcacgg aggtggaaga 540
ggacctgatt gatgccgtca cggggctcag tggcagcggc cccgcctacg cattcacagc 600
cctggatgcc ctggctgatg gggcgtgaa gatgggactt ccaaggcgcc tggcagtccg 660
cctcggggcc caggccctcc tgggggctgc caagatgctg ctgcactcag aacagcaccc 720
aggccagctc aaggacaacg tcagctctcc tggtggggcc accatccatg ccttgcatgt 780
gctggagagt gggggcttcc gctccctgct catcaacgct gtggaggcct cctgcatccg 840
cacacgggag ctgcagtcca tggctgacca ggagcaggtg tcaccagccg ccatcaagaa 900
gaccatcctg gacaaggtga agctggactc ccctgcaggg accgctctgt cgccttctgg 960
ccacaccaag ctgctccccc gcagcctggc cccagcgggc aaggattgac acgtcctgcc 1020
tgaccaccat cctgccacca ccttctcttc tcttgtcact agggggacta gggggtcccc 1080
aaagtggccc actttctgtg gctctgatca gcgcaggggc cagccaggga catagccagg 1140
gaggggccac atcacttccc actggaaatc tctgtggtct gcaagtgctt cccagcccag 1200
aacaggggtg gattccccaa cctcaacctc ctttcttctc tgctcccaaa ccatgtcagg 1260

```
accaccttcc tctagagctc gggagcccgg agggtcttca cccactccta ctccagtatc   1320
agctggcacg ggctccttcc tgagagcaaa ggtcaaggac cccctctgtg aaggctcagc   1380
agaggtggga tcccacgccc cctcccggcc cctccctgcc ctccattcag ggagaaacct   1440
ctccttcccg tgtgagaagg gccagagggt ccaggcatcc caagtccagc gtgaagggcc   1500
acagcccctc ttggctgcca agcacgcaga tcccatggac atttggggaa agggctcctt   1560
gggctgctgg tgaacttctg tggccaccac ctcctgctcc tgacctccct gggagggtgc   1620
tatcagttct gtcctggccc tttcagtttt ataagttggt ttccagcccc cagtgtcctg   1680
acttctgtct gccacatgag gagggaggcc ctgcctgtgt gggagggtgg ttactgtggg   1740
tggaatagtg gaggccttca actgattaga caaggcccgc ccacatcttg gagggcatct   1800
gccttactga ttaaaatgtc aatgtaatct aaaaaaaaaa aaaaaaaa               1848
```

<210> SEQ ID NO 38
<211> LENGTH: 3003
<212> TYPE: DNA
<213> ORGANISM: Homo sapiens

<400> SEQUENCE: 38

```
gataaatgcg gagggacggt ccagctttag ctctctgctc gccgccgccg ctgtcgccgc     60
cacctcctct gatctacgaa agtcatgtta cccaacaccg ggaggctggc aggatgtaca    120
gtttttatca caggtgcaag ccgtggcatt ggcaaagcta ttgcattgaa agcagcaaag    180
gatggagcaa atattgttat tgctgcaaag accgcccagc cacatccaaa acttctaggc    240
acaatctata ctgctgctga agaaattgaa gcagttggag gaaaggcctt gccatgtatt    300
gttgatgtga gagatgaaca gcagatcagt gctgcagtgg agaaagccat caagaaattt    360
ggagcttata ccattgctaa gtatggtatg tctatgtatg tgcttggaat ggcagaagaa    420
tttaaaggtg aaattgcagt caatgcatta tggcctaaaa cagccataca cactgctgct    480
atggatatgc tgggaggacc tggtatcgaa agccagtgta gaaaagttga tatcattgca    540
gatgcagcat attccatttt ccaaaagcca aaaagtttta ctggcaactt tgtcattgat    600
gaaaatatct taaaagaaga aggaatagaa aattttgacg tttatgcaat taaaccaggt    660
catcctttgc aaccagattt cttcttagat gaatacccag aagcagttag caagaaagtg    720
gaatcaactg gtgctgttcc agaattcaaa gaagagaaac tgcagctgca accaaaacca    780
cgttctggag ctgtggaaga aacatttaga attgttaagg actctctcag tgatgatgtt    840
gttaaagcca ctcaagcaat ctatctgttt gaactctccg gtgaagatgg tggcacgtgg    900
tttcttgatc tgaaaagcaa gggtgggaat gtcggatatg gagagccttc tgatcaggca    960
gatgtggtga tgagtatgac tactgatgac tttgtaaaaa tgttttcagg gaaactaaaa   1020
ccaacaatgg cattcatgtc agggaaattg aagattaaag gtaacatggc cctagcaatc   1080
aaattggaga agctaatgaa tcagatgaat gccagactgt gaaggaaaat ataaaaaaaa   1140
agtcgactgc tatgctcaaa aagtaaaaaa agctcaacag ttaaaatcta atgtttgttt   1200
tctttcctgt tatattataa ggatatgcac gtttgttctg gaaaagatag aatttgtctc   1260
taaaagactt gaaattgtaa ttaaaatggc aagctaatca aacataagct tcattaagtg   1320
ggattctaag acagtctgtg tttttatatt tcaagggttt aaccctttga gccttacatc   1380
tcattcactg tctttctcca agaaaagtat tttgggcgga cagtcagatc aagcagtaaa   1440
attagctctt tcaaatcttc ttgtcatgta aaatgaagct agtctgtttt aaaattttta   1500
```

```
gttttggatt gtatactaat gaaaatctta atgatgtttt tgatttttat atacttattt   1560
taaagaaaat cttatatagt acattttaca aaaattataa aaaatgaatt agtactggcg   1620
aggactaaat gaaacaataa tttttcattt tgataactag ctttccaggt ggacttagcc   1680
ataggaaaat attactaatg taatttaaca aattgctgca tgtattccat ttaaaaatat   1740
gtttaaattg tcctaaaaca aaataatttt ctccctagga gtatgcattt ggctacagtg   1800
ttttgaaaca gaaaccttag aataggtcat tggtatgggc tgaactgtgt atcccccaat   1860
tcatttgttg aggtcctaac tcccatttct tttgaatgtg actgttcgga gatgaggcct   1920
ttaaagaggt gacttaagtt caaaggaggc tgttagtcta atccaacatg gtgtcctttg   1980
gacataagag ataccagcaa tgtgtgcaca gaacaaagac caggagagga cacagtgaga   2040
aggcagttat ctgcaagcaa agagagaggc ttcagaagaa acaaaatcac cagcaccttg   2100
atctttgact tctaatctcc agaatagtga gaaataaatt tctgttgtta agccgtccac   2160
tgtgggaggc cgacgcagga ggattgcttg aggccaggag ttcaaggcca gcctggacaa   2220
catagtaaga ccctatctct acccccctaa taaattaatt taaaaagccc cccaatctgt   2280
ggtattttat tatggcagcc ctagcaagct aatacagtgg tttgagaggc tgggagggtt   2340
gaggggaaga taaactttta aaaagctctt atctttcatt tcaatcagtt aaaaatactt   2400
gctcagtgta acaattttgc ttctcagctt ccactctaat attgttgtgc cattaagcaa   2460
tttagctaat cctgacattt cttagattca taatgttagg agcatttaat ctgtatttta   2520
caagttagga agcagaggat cagagatggg aaaggactag cccaaggcca acattaacaa   2580
gccctctaac aaaaacttta caatacattt atgttgaatg gaactccaag atctcacctc   2640
tccatccagg aatggagtcc atgtaatcaa agtgaactta aaaataggac agtttcaaca   2700
agtcaggaga ttcacagcaa ctgatcaaag ggagtccagt caacgtgagc aagcgtgatt   2760
atgatgagga agcccccctct gctttaatcc acacaaggaa cgtaacctga agtaacctga   2820
tgttaaccaa tctgctgtgt ctactatgct gtttccttgt tcctgctagt gctgctttac   2880
aaatgcagac cattctatca tacctggcag ggcttctgtt ttattttgta ggctggatgc   2940
tacccagttc atgaatcgct aataaaagcc aattagatct ttaaaaaaaa aaaaaaaaaa   3000
aaa                                                                 3003
```

<210> SEQ ID NO 39
<211> LENGTH: 1824
<212> TYPE: DNA
<213> ORGANISM: Homo sapiens

<400> SEQUENCE: 39

```
tattaaaagt accccatgga tggacctcca aatgagttta gggtaattgc gcttaaaata     60
ttaggaccaa agtacattta ttttatagat ggaggagggg aggagacgag tggggaccag    120
cttgacatcc agtcttcacc tggacatatg gaaagaacaa atgtgcgatc tgctcgttcc    180
ctctgaaggt ctctgttacg tatttcctcc tctcctccag agcataataa ccaatgactg    240
ctctcagaaa ggtactgtga ccaccacttg cttggctctc caacttcctc ccccatttcc    300
ctcttgactc ctgtttgcca taacaccttc tgtcccctag ccttgcctca ggtccccgac    360
gaatcctgcc cttaatctgt gggggtggta ggtggcactg gtttgaagag cttactggat    420
ctccctcagt gagtcagcct ggagttgtgt ttgaaaacca caggccctga ctgtggctgt    480
aagacctccc agacaccacc tgctgctgcc tatcatcatc ttcaggtgct gggctcccct    540
gtgggcctcg tctgcccgcc ctctgctgca gctgtcccat gggcgcccgc cctctctgac    600
```

-continued

```
accacaagag agcccatcta gattccagga aaaaactcat ctttatttgc cttcttccca     660
ctgaaggtaa aagcaacatt aataaccaca acaaatactt agtgagtgct tactattatt     720
catttaattg taggcccttc catccctggc catgatgaga gacatgccat agcttactcc     780
taaagagacc tgaggacaca cgtgcacaaa catattgggc atatcatcaa tggcatcaaa     840
actgattttc cctgtctacc cagaacaggc ctgagggaga gggaaaagcg gatacccacc     900
tgtgtcgctg tttgcgtgcc aagtccagga acagtccata cagccctgct gcatcccacg     960
acgctgtcac aaagcaggag ttcatccgag gccaaggtat ggagaaactg aggcccagaa    1020
attgatgtcc agaatgcttt gctcttagcc actgtactat tatggcatat tttatcttta    1080
tgtattgcat catttcatgg attcaagttt atcaatgtcc tttgacaagt ttaaaaatct    1140
gtctgctaaa atctatcaaa tacattaagg aaaagtccca cttggcacat ctcccacacc    1200
agatgttaat tattcatact gcatgactga ggattttgga ggcagagaga gattcatctg    1260
caatatttgg aacaccaatg gaggtctatg tcaacacaga atttatacag cagctggtgc    1320
tagtcagagc taatgacaga atttcagttt aataaaaaga cccccaactg agcacaccat    1380
cttgaaaaaa gtatacttat caaacagctt tcaatcagtt caagagagac accttaattg    1440
gggagaggaa gaattgcaga gtagtttgta atcatgccaa ttccagatca ataactgcat    1500
gtctgttctt tggtagaaat agcttttgct ttatattaag taatcacata tatattctct    1560
ctatttggat aaggaaacct tcgctttatt tgacaatgta taatgatata ctcttctaat    1620
tcacctctgt gtcttcacaa taaacatgag taaaatttag acaagtgatg gtaaaggtca    1680
atataattat ttatttttaa aataaatttt gtatctaaca ggaaagcagt tcttatgaaa    1740
tttttatatt ttcaaaaatt gttttgttca aataaaattt tatgagtaaa gttaaaaaaa    1800
aaaaaaaaaa aaaaaaaaaa aaaa                                           1824
```

<210> SEQ ID NO 40
<211> LENGTH: 630
<212> TYPE: DNA
<213> ORGANISM: Homo sapiens

<400> SEQUENCE: 40

```
gggtacctgg tggggccaat caccgagcca tgaacatcag taacgtactc taaagaccaa      60
ggctacgatg gctatgatgg tcagaattac taccaccacc agtgaagctc cagcctggga     120
tgaattcatc cattctggct ttgcatccgg ctaccatttt cgaagttcaa ctcaggaagg     180
tgcaatataa caaatgtgca tattataatg aggaatggta ctaccgttcc agattttctg     240
taattgcttc tgcaaagtaa taggcttctt gtcccttttt tttctggcat gttatggaat     300
gatcattgta aatcaggacc atttatcaag cagtacacca actcataaga tcaaatttca     360
ttgaatggtt tgaggttgta gctctataaa tagtagtttt taacatgcct gtagtattgc     420
taactgcaaa aacatactct ttgtacaaga agtgcttcta agaatttcat tgacattaat     480
gacactgtat acaataaatg tgtagtttct taatcgcact acctatgcaa cactgtgtat     540
taggtttatc atcctcatgt atttttatgt gacctgtatg tatattctaa tctacgagtt     600
ttatcacaaa taaaaatgca atccttcaaa                                     630
```

<210> SEQ ID NO 41
<211> LENGTH: 970
<212> TYPE: DNA
<213> ORGANISM: Homo sapiens

<400> SEQUENCE: 41
aaggtgggct ttcattgtga tttttgttct gttgcagtaa tataggagca cattttggcc 60
attgtaatta cagggaacaa agggattgcg gacacatatc tggacttctt ttcctccctt 120
attgttgtgg aagagacact agaaatgctc aaacacctgc aatatacaga atatacacaa 180
ttttattcca gtatttccct aacatatggt ttaaaattat tccaggtata cagtgtatgc 240
aattctgcat tatcacagag gaacaacttc ttttttaaaa aataaatagg tcagccattt 300
ttattaacgt gcaaaaactt tatcactcta acatgctcta ggtagttgag gaaaagaggt 360
ctgatcactg tttgtatttt attttctttg tgggaacatt tcacctgctg agtgtacatg 420
aatttgcttt ctataaaagg cttttatgag tttacagtag aatcagtgga aggaagagtt 480
aataagggct gtttttaaaa aaacaaacaa acaaacaaaa caaataatta aaaaaaaatt 540
ttacattcct tcctattctc taactacact tgggaagtgc acttcagata agtttgcagt 600
gtgactgaga gatgaaggaa atccatagaa aaggtcctct tagtgaacaa aatttagtta 660
ttaactttat agctatgaaa tttccccggg catttgtttt tgttcaaaca gactttaacc 720
tctgcatcat acttaaccct gcgacatgcg tacagtatgc atattttgtt ttgaaaaaaa 780
atgtttcgtt ccagtctgtt aagaatattc aaaaataata aaggtattgc ttaataaaat 840
tgctagaatt gtttagcagt acatgcacaa tattttacta gattctttgt tttaatagtg 900
ttttgttgag actgaaaatc ttaaaatggt ctgcgcaaat acaaaaaaaa agaaaacacc 960
aaaaaaaaaa 970

<210> SEQ ID NO 42
<211> LENGTH: 1743
<212> TYPE: DNA
<213> ORGANISM: Homo sapiens

<400> SEQUENCE: 42
ggtgttgttc cggacacata gaaagataac gacgggaaga gcggggcccg ctttggggtc 60
caggcaggtt ttggggcctc ctgtctggtg ggaggaggcc gcagcgcagc accctgctcg 120
tcacttggga tggagaccgg ctttcccgca atcatgtacc ctggatcttt tattgggggc 180
tggggagaag agtatctcag ctgggaagga ccggggctcc cagatttcgt cttccagcag 240
cagcccgtgg agtctgaagc aatgcactgc agcaacccca agagtggagt tgtgctggct 300
acagtggccc gaggtcccga tgcttgtcag atactcacca gagccccgct gggccaggat 360
cccccgcaga ggacagtgct agggctgcta actgcaaatg ggcagtacag gaggacctgt 420
ggccagggga tcacaagaat caggtgttat tctggatcag aaaatgcctt ccctccagct 480
ggaaagaaag cactccctga ctgtggggtc caagagcccc ccaagcaagg gtttgacatc 540
tacatggatg aactagagca gggggacaga gacagctgct cggtcagaga ggggatggca 600
tttgaggatg tgtatgaagt agacaccggc acactcaagt cagacctgca cttcctgctg 660
gatttcaaca cagtttcccc tatgctggta gattcatctc tcctctccca gtctgaagat 720
atatccagtc ttggcacaga tgtgataaat gtgactgaat atgctgaaga aatttatcag 780
taccttaggg aagctgaaat aaggcacaga cccaaagcac actacatgaa gaagcagcca 840
gacatcacgg aaggcatgcg cacgattctg gtggactggc tggtggaggt tggggaagaa 900
tataaacttc gagcagagac cctgtatctg gctgtcaact tcctggacag gttcctttca 960
tgtatgtctg ttctgagagg gaaactgcag ctcgtaggaa cagcagctat gcttttggct 1020
tcgaaatatg aagagatata tcctcctgaa gtagacgagt ttgtctatat caccgatgat 1080

```
acatacacaa aacgacaact gttaaaaatg gaacacttgc ttctgaaagt tctagctttt   1140

gatctgacag taccaaccac caaccagttt ctccttcagt acttgaggcg acaaggagtg   1200

tgcgtcagga ctgagaacct ggctaagtac gtagcagagc tgagtctact tgaagcagat   1260

ccattcttga aatatcttcc ttcactgata gctgcagcag ctttttgcct ggcaaactat   1320

actgtgaaca agcacttttg gccagaaacc cttgctgcat ttacagggta ttcattaagt   1380

gaaattgtgc cttgcctgag tgagcttcat aaagcgtacc ttgatatacc ccatcgacct   1440

cagcaagcaa ttagggagaa gtacaaggct tcaaagtacc tgtgtgtgtc cctcatggag   1500

ccacctgcag ttcttcttct acaataagtt tctgaatgga agcacttcca gaacttcacc   1560

tccatatcag aagtgccaat aatcgtcata ggcttctgca cgttggatca actaatgttg   1620

tttacaatat agatgacatt ttaaaaatgt aaatgaattt agtttccctt agactttagt   1680

agtttgtaat atagtccaac atttttttaaa caataaactg cttgtcttat gacaaaaaaa   1740

aaa                                                                  1743
```

<210> SEQ ID NO 43
<211> LENGTH: 697
<212> TYPE: DNA
<213> ORGANISM: Homo sapiens

<400> SEQUENCE: 43

```
tccaagccat taaggactgt ggaacttgct atgatcatgg acgtgctgta tggtggcgtt     60

tgttatgcag gaattgatac agatcctgag ctaaaatacc caaaaggtgc tgggcgagtt    120

gctttctcca atcagcagag ctatattgct gccattagtg ctcggtttgt tcagcttcag    180

catggtgata ttgataaacg tgtggaggta aagccatatg tgctagatga ccagatgtgt    240

gatgaatgcc agggcgcacg ctgtggtgga aaatttgctc cctttttttg tgccaatgtc    300

acttgcctgc agtattactg tgagttttgt tgggcaaata tccactctcg tgctggacgt    360

gagttccata agccattggt aaaggaaggt gctgatcgcc cacgtcagat ccacttccgc    420

tggaactaag aatagcaaac tggcctctgt ttaacaagga aagaaagggt gcatgtggct    480

tactgtgtct gaagatactg acatgcagaa gaaataagtg cattcttctg cttttcaccc    540

cagctatcaa tacatgcatc tttatcagca gccaaaacac tacaagcctc ttgtttttca    600

ccaaaaccct acatctcagg cttactaatt tttgtgatat tttcatgttc aaataaaatg    660

ttttttgta ttttcaaaaa aaaaaaaaaa aaaaaaa                              697
```

<210> SEQ ID NO 44
<211> LENGTH: 2227
<212> TYPE: DNA
<213> ORGANISM: Homo sapiens

<400> SEQUENCE: 44

```
ctcgatgtag aggggttggt agcagacagg tggttacatt agaatagtca cacaaactgt     60

tcagtgttgc aggaaccttt tcttgggggt gggggagttt cccttttcta aaaatgcaat    120

gcactaaaac tattttaaga atgtagttaa ttctgcttat tcataaagtg ggcatcttct    180

gtgttttagg tgtaatatcg aagtcctggc ttttctcgtt ttctcacttg ctctcttgtt    240

ctctgttttt ttaaaccaat tttactttat gaatatattc atgacatttg taataaatgt    300

cttgagaaag aatttgtttc atggcttcat ggtcatcact caagctcccg taaggatatt    360

accgtctcag gaaaggatca ggactccatg tcacagtcct gccatcttac tttcctcttg    420
```

-continued

```
tcgagttctg agtggaaata actgcattat ggctgcttta acctcagtca tcaaaagaaa    480

cttgctgttt tttaggcttg atctttttcc tttgtggtta attttcctgt atattgtgaa    540

aatgggggat tttccctctg ctcccaccca cctaaacaca gcagccattt gtacctgttt    600

gcttcccatc ccacttggca cccactctga cctcttgtca gtttcctgtt cctggttcca    660

tctttttgaa aaaggccctc ctttgagcta caaacatctg gtaagacaag tacatccact    720

catgaatgca gacacagcag ctggtggttt tgtgtatacc tgtaaagaca agctgagagg    780

cttacttttt ggggaagtaa aagaagatgg aaatggatgt ttcatttgta tgagtttgga    840

gcagtgctga aggccaaagc cgcctactgg tttgtagtta acctagagaa ggttgaaaaa    900

ttaatcctac ctttaaaggg atttgaggta ggctggattc catcgccaca ggactttagt    960

tagaattaaa ttcctgcttg taatttatat ccatgtttag gcttttcata agatgaaaca   1020

tgccacagtg aacacactcg tgtacatatc aagagaagaa ggaaaggcac aggtggagaa   1080

cagtaaaagg tgggcagatg tctttgaaga aatgctcaat gtctgatgct aagtgggaga   1140

aggcagagaa caaaggatgt ggcataatgg tcttaacatt atccaaagac ttgaagctcc   1200

atgtctgtaa gtcaaatgtt acacaaaaaa aaatgcaaat ggtgtttcat tggaattacc   1260

aagtgcttag aacttgctgg ctttcccata ggtggtaaag gggtctgagc tcacaccgag   1320

ttgtgcttgg cttgcttgtg cagctccagg cacccggtgg gcactctggt ggtgtttgtg   1380

gtgaactgaa ttgaatccat tgttgggctt aagttactga aattggaaca ccctttgtcc   1440

ttctcggcgg gggcttcctg gtctgtgctt tacttggctt ttttccttcc cgtcttagcc   1500

tcacccccctt gtcaaccaga ttgagttgct atagcttgat gcagggaccc agtgaagttt   1560

ctccgttaaa gattgggagt cgtcgaaatg tttagattct tttaggaaag gaattatttt   1620

cccccctttt acagggtagt aacttctcca cagaagtgcc aatatggcaa aattacacaa   1680

gaaaacagta ttgcaatgac accattacat aaggaacatt gaactgttag aggagtgctc   1740

ttccaaacaa aacaaaaatg tctctaggtt tagtcagagc tttcacaagt aataaccttt   1800

ctgtattaaa atcagagtaa ccctttctgt attgagtgca gtgtttttta ctcttttctc   1860

atgcacatgt tacgttggag aaaatgttta caaaaaatggt tttgttacac taatgcgcac   1920

cacatattta tggtatattt taagtgactt tttatgggtt atttaggttt tcgtcttagt   1980

tgtagcacac ttaccctaat tttgccaatt attaatttgc taaatagtaa tacaaatgac   2040

aactgcatta aatttactaa ttataaaagc tgcaagcaga ctggtggcaa gtacacagcc   2100

cttttttttg cagtgctaac ttgtctactg tgtattatga aaattactgt tgtcccccca   2160

cccttttttc cttaaataaa gtaaaaatga caccctaaaa aaaaaaaaaa aaaaaaaaaa   2220

aaaaaaa                                                             2227
```

<210> SEQ ID NO 45
<211> LENGTH: 267
<212> TYPE: DNA
<213> ORGANISM: Homo sapiens

<400> SEQUENCE: 45

```
tatacggctg ctagaagacg acagaaggtg gcttgggggt ggatatcttt gggttgctgg     60

aaaaggtgtg ggaaggttca ggatggtggg agggactgag gtccctgagg tgaagaggcc    120

cttggtcctg acgggtttga cccgtgcctg gacccttgga gcagtgttgt gtgaacttgc    180

ctagaactct gccttctccg ttgtcaataa agcctccccc tcatgaccta aaaaaaaaaa    240

aaaaaaaaaa aaaaaaagtc gtatcga                                        267
```

<210> SEQ ID NO 46
<211> LENGTH: 4415
<212> TYPE: DNA
<213> ORGANISM: Homo sapiens

<400> SEQUENCE: 46
gagcaggaaa atatataccc taaacagaaa ctcttacttg ttttatgagc aagtctgagt 60
gagtcctaaa atggctggcg aagagctacc aatactgact gacaggtcac cttaaagcct 120
ctaggtgtgc caagtttgat ttatcttagg gactagaacc tagtcttcta aatgtgattt 180
tgccttgctg tttcgtcctg atgtgaaggt aaccacacag agagattggg ctgcatcagt 240
aatgatatgc atacctttcg tgcatcagtg agcttcttcc ctgttaactg tatgaccaca 300
aaatttagct ggagtaaata aatatgcgac agaaatcctg gaacaagatg gtgaaattgc 360
ttaagaatcg agacttcagg gctcaatgac ctctgagcat gtttcccaaa gtgtgaccca 420
catgaccatc tgtctctcag tctcctggtc cctccgtaga gcttctgaaa ctgaatcttt 480
gtggggtggg ggtagcgttc aagaatcaaa agttgaacca agctctttgg gtgatactta 540
tgtatactga ggttcaggaa ctgctggaga gatgactggg caccaagagg atgacagtga 600
ctcagctggc atcccttagc tggttcatgg cagagctgag tgggcactcc tgtctctgac 660
cccagcttca gtgctcttta tctcctccat gcctcctcag tcgtgctgct ctaagactgc 720
ttactggctt tccttcatgt cctgggcaca gagcagttct tttggtagca gatttgagtc 780
cacttccccc gtgcacagat cactgctcag gacccagaga ggagcagctc tgctccagca 840
gggttttcca ttgcatcaca cacccaaacg gtaggatcca acagtcacac ttgaaagcaa 900
ccataattgt gaggtttctg atgctgtaga cttccttaca tttctcacaa cctagttaga 960
gagtcacatg ggggtgaagt gtggctcgcg acctgcccca acaagtgcgt gcagaagcca 1020
ggaaacaaag gagtaaattc acttcaaatg ggatgcacat ggtgtccgtg atgaagagac 1080
acattcagaa ttgcccaagg acaggaaaat gaccagagag agccagagct gagctggtaa 1140
taaagagact ccgagactga gtggagttaa tgagggaagc atgcaacgag tggggcaatt 1200
tcagttggtt tctctcattg ctttaagcga aatgaactat acggacagga gaacagcctg 1260
cttgccccag tctctccttg gccgccctct gttgtccctg tcaactcagg tgcccacggt 1320
gctcagagga ggtgctggca aagcccctgg agccttatgt aggccatggg ggctcctaaa 1380
aggaacctga atgaatcatt tacagcaggt ctctcttgta aagcccagcc acagtaactc 1440
gtacactgac tgtttcaaaa gacagccttt cttaatcatt taattgtttc atattcaaat 1500
atatctccta attgttttta ttttttcctg atctagaaga tatgacaaca gggtagaact 1560
tgggaagagg gaataggaag ctcgcccttc ctccttccct cctcccctct ctactttcct 1620
tccttccttg gtcatcaggt accttctttg tgcctgctgt tgtaggctac accctatgtt 1680
tggtggaagg caaaaagaaa aatcagtagg atacaactca gtagggaaga cagagatatt 1740
caagcccctt gtcctcccag tgtgataagt gtggtggttg aggtgtgaac aaggggctct 1800
gtgaacagag aggacgaaag aggagctcct cctgaggctg ttgggaaaag catcactgaa 1860
gagtgacttt cagaagaaga gaagaaaaag aggagaacat gcgtgatttt ataatgaaat 1920
agattagata aggggaaaaa aggcatttaa acaaggcaaa aagaacagga gaatagagaa 1980
gagatgtgga ggagaaggag cactgtagta aacacgcaga aggacaggaa cacttagaca 2040
tgcaacccac tcccaccctc cgtcttgggg gaggaaagca cactactgtc ccaaagaact 2100

-continued

```
aatactgaac cagtgctgcc ttgtggagag aggcatggcc aaggcgttca gagacctggg   2160
cctggtccca ccgctgccca cagcactcag cctctgagca cagcctgggg tcatctgtgt   2220
gccctctggc caaggctgat ggtagttctc tgagtaattg agagtcattg cctgtctgtg   2280
cagtattgtg aaaacaagtc accttttaac tttaaaacta ctttaaaaaa ctttaaagtt   2340
ttaaaaaaac ttctttaaaa actactcatg agatgacagt ttctctgacc ctcagaggaa   2400
ggctgggctg cgcatacgtg aggaattttt acatgaacat cccaggactt gctgttcgca   2460
ggtgataaac tgcacctccc caggactccc gctgcactca catgcagctc cctggacttc   2520
tggtatctga cccggcccat ttctgtgttt caggggagaa tttggcttgc gggagtactc   2580
agaagttaag acggtgacag taaagatccc ccagaagaac tcctaagaag gccaagaagg   2640
aggatgaagc ccagcctgca cgtctgtccc tctctgcttt ctctgtaggg cccagctctc   2700
aggaatacaa agttgagcca cggtccttac ttaaagattg aaaagataac atgtaggcca   2760
ggcaggtcac tgcacaacta aagcaaacca gctgggtaca gtttcttggc actctgtaag   2820
gggccacctt aatcatacca aatattgggg aaagtgggat aaagggagga ggaggagcta   2880
gcagacacat ccagtatctc cttctggagc acaggatgaa ataagggagc tgtattattt   2940
catgtctttg tcacaaagaa ctttcctctc aaggaaaggt gacctttctc ctgtcttcat   3000
tttcctcctt ccaggccctc ctcgctcacc cacccctccc tctcttccaa ggagatgtca   3060
gctgagctca ttctggggca gatgtttggg ccgggaacaa tttttcaagg ttgtaaagcc   3120
aaattatcat ttcatgttat ccatttcttc aaagcaaaac atgaaatggt tttagctaga   3180
gtcagaccag aatgaaaatg ccaggagctg gtacactaca gatgtagtaa gaacctggga   3240
tattcctgac ccaatctggt tttcttttac ccataaataa catgaatgaa aaaagattgg   3300
gacaatagag actggaagtc atcatgtgca gttcaccgct tctgagcttg ctgcagtttt   3360
ggggtgtgtg tgtattagat tccttctcag ttattctgga ataaggcaag gagtgggttg   3420
tttttcatag ctagataaga tcttttccaa agtttttctt agaaccaacc aaaaaacaat   3480
ccgagtaggc ccgagaattt gataatgctg gatgccttgc agacatcatt cagtttctaa   3540
tattgggcaa caattattat taaatgaatt atttctgtag ttggaatctg taccttctga   3600
acctctacac caataactgc tgcaggtgtg attttggtct gtcacactgt acatctatca   3660
taatgtgccc tgtatctatt ggcagtgacc ttggaaaatc tggccaagcc taggggtttc   3720
cttttccatt tgccaagttc cattgtgcca ggactgccgt gctccactga gctcctctgt   3780
cacaccccat tcttgcccct cactgggcag gccatggcct acagcttgca gggagtaaag   3840
caggcccgcc tccctttctt cccatccaca tactcctctt ctgctttcca gtgactccac   3900
cagtttgatg tgggaagtgt tagcttcctt tccttcttcc atcccttctt ccatctttcc   3960
agctgtcaaa tccaatccag tctctaacct aaatgcagat catttattta aaagtaccaa   4020
acataaccca gagtatgtgg aatatgggca acatatatat agccttctgt atttaacgat   4080
cttctgcttc ttaaccgtac cagttttcta tttataactc ttatctatcc atgatgtttt   4140
aaagtctcca cttgctgtta tttacaaacg acagtgcatt cagcagccca gtgccgtgag   4200
ccctgacaga tgccgtattt ctgagtgctt ccatgtgaat gctgccctcc tgtagcatgt   4260
gtccaagtgg acatagccac taaccaacta gttacctttg gactgcaaca aaaaatgtga   4320
aaatgaagat ttatttcttt taatttactt aaaaagaaac ctctgtgcta gcaataaagc   4380
atttatattg tgcaaaaaaa aaaaaaaaaa aaaac                              4415
```

<210> SEQ ID NO 47
<211> LENGTH: 453
<212> TYPE: DNA
<213> ORGANISM: Homo sapiens

<400> SEQUENCE: 47
tgaaaattta tataactgtt gttgataagg aacattatcc aggaattgat acgtttatta 60
ggaaaagata tttttatagg cttggatgtt tttagttctg actttgaatt tatataaagt 120
atttttataa tgactggtct tccttacctg gaaaaacatg cgatgttagt tttagaatta 180
caccacaagt atctaaattt ggaacttaca aagggtctat cttgtaaata ttgttttgca 240
ttgtctgttg gcaaatttgt gaactgtcat gatacgctta aggtggaaag tgttcattgc 300
acaatatatt tttactgctt tctgaatgta gacggaacag tgtggaagca gaaggctttt 360
ttaactcatc cgtttgccaa tcattgcaaa caactgaaat gtggatgtga ttgcctcaat 420
aaagctcgtc cccattgctt aagccttcaa aaa 453

<210> SEQ ID NO 48
<211> LENGTH: 1587
<212> TYPE: DNA
<213> ORGANISM: Homo sapiens

<400> SEQUENCE: 48
cttttagctg ccagccctgg cccatcatgt agctgcagca cagccttccc taacgttgca 60
actgggggaa aaatcacttt ccagtctgtt ttgcaaggtg tgcatttcca tcttgattcc 120
ctgaaagtcc atctgctgca tcggtcaaga gaaactccac ttgcatgaag attgcacgcc 180
tgcagcttgc atctttgttg caaaactagc tacagaagag aagcaaggca aagtcttttg 240
tgctcccctc ccccatcaaa ggaaagggga aaatgtctca gtcgaaaggc aagaagcgaa 300
accctggcct taaaattcca aaagaagcat ttgaacaacc tcagaccagt tccacaccac 360
ctagagattt agactccaag gcttgcattt ctattggaaa tcagaacttt gaggtgaagg 420
cagatgacct ggagcctata atggaactgg gacgaggtgc gtacggggtg gtggagaaga 480
tgcggcacgt gcccagcggg cagatcatgg cagtgaagcg gatccgagcc acagtaaata 540
gccaggaaca gaaacggcta ctgatggatt tggatatttc catgaggacg gtggactgtc 600
cattcactgt caccttttat ggcgcactgt ttcgggaggg tgatgtgtgg atctgcatgg 660
agctcatgga tacatcacta gataaattct acaaacaagt tattgataaa ggccagacaa 720
ttccagagga catcttaggg aaaatagcag tttctattgt aaaagcatta gaacatttac 780
atagtaagct gtctgtcatt cacagagacg tcaagccttc taatgtactc atcaatgctc 840
tcggtcaagt gaagatgtgc gattttggaa tcagtggcta cttggtggac tctgttgcta 900
aaacaattga tgcaggttgc aaaccataca tggcccctga aagaataaac ccagagctca 960
accagaaggg atacagtgtg aagtctgaca tttggagtct gggcatcacg atgattgagt 1020
tggccatcct tcgatttccc tatgattcat ggggaactcc atttcagcag ctcaaacagg 1080
tggtagagga gccatcgcca caactcccag cagacaagtt ctctgcagag tttgttgact 1140
ttacctcaca gtgcttaaag aagaattcca aagaacggcc tacataccca gagctaatgc 1200
aacatccatt tttcacccta catgaatcca aaggaacaga tgtggcatct tttgtaaaac 1260
tgattcttgg agactaaaaa gcagtggact taatcggttg accctactgt ggattggtgg 1320
gtttcggggt gaagcaagtt cactacagca tcaatagaaa gtcatctttg agataattta 1380
accctgcctc tcagagggtt ttctctccca attttctttt tactccccct cttaaggggg 1440
ccttggaatc tatagtatag aatgaactgt ctagatggat gaattatgat aaaggcttag 1500
gacttcaaaa ggtgattaaa tatttaatga tgtgtcatat gaaaaaaaaa aaaaaaaaaa 1560
aaaaaaaaaa aaaaaaaaaa aaaaaaa 1587

<210> SEQ ID NO 49
<211> LENGTH: 558
<212> TYPE: DNA
<213> ORGANISM: Homo sapiens

<400> SEQUENCE: 49
cagtcccacc atgtattttg ctttgtttct aaaaagcttt ttaaaaactg ttatttaata 60
ccaaagggag gaatcgtatg ggttcttctg cccaccgttg tgactaagaa tgcacaggga 120
cttggttctc gttgcacctt tttttagtaa catgtttcat ggggacccac tgtacagccc 180
ttcattctgc tgtgtcagtt tggcctggcc tgacactggc tgccccagcg gggaccacgg 240
aagcagagtg agagccttcg ctgagtcaat gctaccttca gccccagacg catcccattt 300
ccatgtcttc catgctcact gctcatgcac tttttacacg gtttcttcca aacagcccgg 360
tcttgatgca ggagagtctg gaaaaggaag aaaatggttt cagtttcaaa attcaaagga 420
aaaagttgag gacttatttt gtcctgtcaa gattgcaaga acatgtaaaa tgtacggagc 480
ttcataatac gttatattgt tccgaagcag ctcgttgaga aacatttgtt ttcaataaca 540
ttttagctta aaaaaaaa 558

<210> SEQ ID NO 50
<211> LENGTH: 841
<212> TYPE: DNA
<213> ORGANISM: Homo sapiens
<220> FEATURE:
<221> NAME/KEY: misc_feature
<222> LOCATION: (54)..(54)
<223> OTHER INFORMATION: a or g or c or t/u

<400> SEQUENCE: 50
tcacctcgtg gcgtagggga gaggtaacac cgagaagagg cagcggcggt ggcncagaga 60
cgattggtgc caaacagggc agaacgcaac tcagctctgg gtttgtgaat agcacaatgg 120
aagaagctgg actttgtggg ttaagagaga aagcagatat gttgtgtaac tctgaatcac 180
atgatattct tcaacatcaa gactcaaatt gcagtgccac aagtaataaa catttattgg 240
aagatgaaga aggccgtgac tttataacaa agaacaggag ttgggtgagc ccagtgcact 300
gcacacaaga gtcaagaagg gagcttcctg agcaagaagt agcccctccg tctggtcagc 360
aagctttaca attgcaacag gaacaaagaa aaagtcttag gaaaagaagt tttattattg 420
atgcaagccc taaacactct ttccgactcc agaggagaag ctggcagctc tctgtaagaa 480
atatgctgat cttggaaatt cacctcttct atagaagagt ttgttttgaa ctatacgatt 540
tgaaacaaaa ttcttttttt ggagactatg gaaacattct caacagggaa accctactag 600
actttgtaaa gcaaataatg gaaaagatac agaacttttt gaagaatcat gggaaatttt 660
tataattaaa taaatgctaa aattctgttt tgtgaaacat ttatgggaat tatcactgac 720
agtttttgta cactttcaaa tagtgttaaa gcagcaactc catgttgtaa atgcacaaaa 780
caaatattta gttaataatc aactccaaga ataaagctgt aacaataata gttaaaaaaa 840
a 841

<210> SEQ ID NO 51
<211> LENGTH: 2384

<212> TYPE: DNA
<213> ORGANISM: Homo sapiens

<400> SEQUENCE: 51
ggcacgaggg tcagcagccg ccagacttcc tgccgaagtc cgagcccccct cccggggctg 60 gaggggggca agcgggttcc gaggtgcaaa gcctggtgcc ccgagccctg cggagctcgg 120
ggccagcatg gcccccacgc tgcaacaggc gtaccggagg cgctggtgga tggcctgcac 180
ggctgtgctg gagaacctct tcttctctgc tgtactcctg ggctggggct ccctgttgat 240
cattctgaag aacgagggct tctattccag cacgtgccca gctgagagca gcaccaacac 300
cacccaggat gagcagcgca ggtggccagg ctgtgaccag caggacgaga tgctcaacct 360
gggcttcacc attggttcct tcgtgctcag cgccaccacc ctgccactgg ggatcctcat 420
ggaccgcttt ggcccccgac ccgtgcggct ggttggcagt gcctgcttca ctgcgtcctg 480
caccctcatg gccctggcct cccgggacgt ggaagctctg tctccgttga tattcctggc 540
gctgtccctg aatggctttg gtggcatctg cctaacgttc acttcactca cgctgcccaa 600
catgtttggg aacctgcgct ccacgttaat ggccctcatg attggctctt acgcctcttc 660
tgccattacg ttcccaggaa tcaagctgat ctacgatgcc ggtgtggcct tcgtggtcat 720
catgttcacc tggtctggcc tggcctgcct tatctttctg aactgcaccc tcaactggcc 780
catcgaagcc tttcctgccc ctgaggaagt caattacacg aagaagatca agctgagtgg 840
gctggccctg gaccacaagg tgacaggtga cctcttctac acccatgtga ccaccatggg 900
ccagaggctc agccagaagg cccccagcct ggaggacggt tcggatgcct tcatgtcacc 960
ccaggatgtt cggggcacct cagaaaacct tcctgagagg tctgtcccct tacgcaagag 1020
cctctgctcc cccactttcc tgtggagcct cctcaccatg ggcatgaccc agctgcggat 1080
catcttctac atggctgctg tgaacaagat gctggagtac cttgtgactg gtggccagga 1140
gcatgagaca aatgaacagc aacaaaaggt ggcagagaca gttgggttct actcctccgt 1200
cttcggggcc atgcagctgt tgtgccttct cacctgcccc ctcattggct acatcatgga 1260
ctggcggatc aaggactgcg tggacgcccc aactcagggc actgtcctcg gagatgccag 1320
ggacggggtt gctaccaaat ccatcagacc acgctactgc aagatccaaa agctcaccaa 1380
tgccatcagt gccttcaccc tgaccaacct gctgcttgtg ggttttggca tcacctgtct 1440
catcaacaac ttacacctcc agtttgtgac ctttgtcctg cacaccattg ttcgaggttt 1500
cttccactca gcctgtggga gtctctatgc tgcagtgttc ccatccaacc actttgggac 1560
gctgacaggc ctgcagtccc tcatcagtgc tgtgttcgcc ttgcttcagc agccactttt 1620
catggcgatg gtgggacccc tgaaaggaga gcccttctgg gtgaatctgg gcctcctgct 1680
attctcactc ctgggattcc tgttgccttc ctacctcttc tattaccgtg cccggctcca 1740
gcaggagtac gccgccaatg ggatgggccc actgaaggtg cttagcggct ctgaggtgac 1800
cgcatagact tctcagacca agggacctgg atgacaggca atcaaggcct gagcaaccaa 1860
aaggagtgcc ccatatggct tttctacctg taacatgcac atagagccat ggccgtagat 1920
ttataaatac caagagaagt tctatttttg taaagactgc aaaaaggagg aaaaaaaacc 1980
ttcaaaaacg ccccctaagt caacgctcca ttgactgaag acagtcccta tcctagaggg 2040
gttgagcttt cttcctcctt gggttggagg agaccagggt gcctcttatc tccttctagc 2100
ggtctgcctc ctggtacctc ttggggggat cggcaaacag gctacccctg aggtcccatg 2160
tgccatgagt gtgcacacat gcatgtgtct gtgtatgtgt gaatgtgaga gagacacagc 2220

-continued cctcctttca gaaggaaagg ggcctgaggt gccagctgtg tcctgggtta ggggttgggg 2280
gtcggcccct tccagggcca ggagggcagg ttccctctct ggtgctgctg cttgcaagtc 2340
ttagaggaaa taaaaaggga agtgagaaaa aaaaaaaaaa aaaa 2384

<210> SEQ ID NO 52
<211> LENGTH: 1923
<212> TYPE: DNA
<213> ORGANISM: Homo sapiens

<400> SEQUENCE: 52
ggcacgaggg aggcggcggc tccagccggc gcggcgcgag gctcggcggt gggatccggc 60
gggcggtgct agctccgcgc tccctgcctc gctcgctgcc gggggcggtc ggaaggcgcg 120
gcgcgaagcc cgggtggccc gagggcgcga tggctgctcc tgtcccgtgg gcctgctgtg 180
ctgtgcttgc cgccgccgcc gcagttgtct acgcccagag acacagtcca caggaggcac 240
cccatgtgca gtacgagcgc ctgggctctg acgtgacact gccatgtggg acagcaaact 300
gggatgctgc ggtgacgtgg cgggtaaatg ggacagacct ggcccctgac ctgctcaacg 360
gctctcagct ggtgctccat ggcctggaac tgggccacag tggcctctac gcctgcttcc 420
accgtgactc ctggcacctg cgccaccaag tcctgctgca tgtgggcttg ccgccgcggg 480
agcctgtgct cagctgccgc tccaacactt accccaaggg cttctactgc agctggcatc 540
tgcccacccc cacctacatt cccaacacct tcaatgtgac tgtgctgcat ggctccaaaa 600
ttatggtctg tgagaaggac ccagccctca agaaccgctg ccacattcgc tacatgcacc 660
tgttctccac catcaagtac aaggtctcca taagtgtcag caatgccctg ggccacaatg 720
ccacagctat cacctttgac gagttcacca ttgtgaagcc tgatcctcca gaaaatgtgg 780
tagcccggcc agtgcccagc aaccctcgcc ggctggaggt gacgtggcag acccccctcga 840 cctggcctga ccctgagtct tttcctctca agttctttct gcgctaccga cccctcatcc 900
tggaccagtg gcagcatgtg gagctgtccg acggcacagc acacaccatc acagatgcct 960
acgccgggaa ggagtacatt atccaggtgg cagccaagga caatgagatt gggacatgga 1020
gtgactggag cgtagccgcc cacgctacgc cctggactga ggaaccgcga cacctcacca 1080
cggaggccca ggctgcggag accacgacca gcaccaccag ctccctggca cccccaccta 1140
ccacgaagat ctgtgaccct ggggagctgg gcagcggcgg gggaccctcg gcacccttct 1200
tggtcagcgt ccccatcact ctggccctgg ctgccgctgc cgccactgcc agcagtctct 1260
tgatctgagc ccggcacccc atgaggacat gcagagcacc tgcagaggag caggaggccg 1320
gagctgagcc tgcagacccc ggtttctatt ttgcacacgg gcaggaggac cttttgcatt 1380
ctcttcagac acaatttgtg gagaccccgg cgggcccggg cctgccgccc cccagccctg 1440
ccgcaccaag ctggccctcc ttcctccctc aggggaggtg ggccatgcag ctaacccacc 1500
caccaaagac cccctcaccc tggccccttg ggctggaccc tccaatgcca gcgactccca 1560
ggagcccttg ggggacgtga ggggagcctc tcacatccga tttctcctcc tgccccagcc 1620
tcctgtctat cccagggtct ctgttgccac catcagatta taagctcctg atgctggggg 1680
ggcccagcca tccccctccc cccagcaccc acaattttca gtcccctccc ctctgccctg 1740
ttttgtatac ccctcccctg accctgctcc tatcccacag tatttaatgc cctgtcagtc 1800
ccttctagtc tgactcaatg gtaacttgct gtatttgaat tttttataga tgtatataca 1860
gggtgggggg agtgggcggt tctcattaaa cgtcaccatt tcatgaaaaa aaaaaaaaaa 1920
aaa 1923

<210> SEQ ID NO 53
<211> LENGTH: 2065
<212> TYPE: DNA
<213> ORGANISM: Homo sapiens

<400> SEQUENCE: 53
ggcacgagga gtttcataat ttccgtgggt cgggccgggc gggccaggcg ctgggcacgg 60
tgatggccac cactggggcc ctgggcaact actacgtgga ctcgttcctg ctgggcgccg 120
acgccgcgga tgagctgagc gttggccgct atgcgccggg gaccctgggc cagcctcccc 180
ggcaggcggc gacgctggcc gagcaccccg acttcagccc gtgcagcttc cagtccaagg 240
cgacggtgtt tggcgcctcg tggaacccag tgcacgcggc gggcgccaac gctgtacccg 300
ctgcggtgta ccaccaccat caccaccacc cctacgtgca cccccaggcg cccgtggcgg 360
cggcggcgcc ggacggcagg tacatgcgct cctggctgga gcccacgccc ggtgcgctct 420
ccttcgcggg cttgccctcc agccggcctt atggcattaa acctgaaccg ctgtcggcca 480
gaaggggtga ctgtcccacg cttgacactc acactttgtc cctgactgac tatgcttgtg 540
gttctcctcc agttgataga gaaaaacaac ccagcgaagg cgccttctct gaaaacaatg 600
ctgagaatga gagcggcgga gacaagcccc ccatcgatcc caataaccca gcagccaact 660
ggcttcatgc gcgctccact cggaaaaagc ggtgccccta tacaaaacac cagaccctgg 720
aactggagaa agagtttctg ttcaacatgt acctcaccag ggaccgcagg tacgaggtgg 780
ctcgactgct caacctcacc gagaggcagg tcaagatctg gttccagaac cgcaggatga 840
aaatgaagaa aatcaacaaa gaccgagcaa aagacgagtg atgccatttg ggcttattta 900
gaaaaaaggg taagctagag agaaaaagaa agaactgtcc gtcccccttc cgccttctcc 960
cttttctcac ccccacccta gcctccacca tccccgcaca aagcggctct aaacctcagg 1020
ccacatcttt tccaaggcaa accctgttca ggctggctcg taggcctgcc gctttgatgg 1080
aggaggtatt gtaagctttc cattttctat aagaaaaagg aaaagttgag gggggggcat 1140
tagtgctgat agctgtgtgt gttagcttgt atatatattt ttaaaaatct acctgttcct 1200
gacttaaaac aaaaggaaag aaactacctt tttataatgc acaactgttg atggtaggct 1260
gtatagtttt tagtctgtgt agttaattta atttgcagtt tgtgcggcag attgctctgc 1320
caagatactt gaacactgtg ttttattgtg gtaattatgt tttgtgattc aaacttctgt 1380
gtactgggtg atgcacccat tgtgattgtg gaagatagaa ttcaatttga actcaggttg 1440
tttatgaggg gaaaaaaaca gttgcataga gtatagctct gtagtggaat atgtcttctg 1500
tataactagg ctgttaacct atgattgtaa agtagctgta agaatttccc agtgaaataa 1560
aaaaaaattt taagtgttct cggggatgca tagattcatc attttctcca ccttaaaaat 1620
gcgggcattt aagtctgtcc attatctata tagtcctgtc ttgtctattg tatatataat 1680
ctatatgatt aaagaaaata tgcataatca gacaagcttg aatattgttt ttgcaccaga 1740
cgaacagtga ggaaattcgg agctatacat atgtgcagaa ggttactacc tagggtttat 1800
gcttaatttt aatcggagga aatgaatgct gattgtaacg gagttaattt tattgataat 1860
aaattataca ctatgaaacc gccattgggc tactgtagat ttgtatcctt gatgaatctg 1920
gggtttccat cagactgaac ttacactgta tattttgcaa tagttacctc aaggcctact 1980
gaccaaattg ttgtgttgag atgatattta actttttgcc aaataaaata tattgattct 2040
tttctaaaaa aaaaaaaaaa aaaaa 2065

<210> SEQ ID NO 54
<211> LENGTH: 1045
<212> TYPE: DNA
<213> ORGANISM: Homo sapiens

<400> SEQUENCE: 54

```
aaaccagtgt atccagtcat ggaaaagaag gaggaagatg gcaccctgga gcgggggcac     60
tggaacaaca agatggagtt tgtgctgtca gtggctgggg agatcattgg cttaggcaac    120
gtctggaggt ttccctatct ctgctacaaa aatgggggag gtgagatgag agcccttgtg    180
ccaccccacc cactcctgga aggaggatac ttccatctcc tgcacttacg gcccctctgg    240
ggagtcccat agatgtatag aattctggag gtaggaggac gcttggaggt cattaaggac    300
actctgtaag agactaagac ctagaaaggt tacgtgacta tcccagggct ctttctatta    360
taacgtggca tcgtagaaat atgagcacaa gctggaacca ggtggatgag agtttggatt    420
ctggctctgc tacttaacac tctgtgtgat cttggacaag ttacttaagc tctcagagca    480
tcaattgccg ctcctgcaaa ttgagataat aatgcctgcc tttcaaggtc attgtaagga    540
ttagagacaa tgtgtgtaaa gcacttaata aatagtagct ctgctgatga tgacgttgat    600
aaccaaactg ttctgtggtc ttaagtaata aatagtagct ctgctgatga tgacgttgat    660
aaccaaactg ttctgtggtc ttaagtaata agtagtagct ctgttgatga tgacgttgat    720
aaccaaactg ttctgtggtc ttaagtaata agtagtagct ctgctgatga tgacgttgat    780
aaccaaactg ttctgtggtc ttaagtaata aatagtagct ctgctgatga tgatgttgat    840
aaccaaactg ttctgtggtc ttaagtaata aatagtagct ctgctgatga tgacgttgat    900
aaccaaactg ttctgtggtc ttaagtaata aatagtagct ctgctgatga tgacgttgat    960
aaccaaactg ttctgtggtc ttaagtaata aatagtagct ctgctgatga tgacgttgat   1020
aaaaaaaaaa aaaaaaaaaa aaaaa                                         1045
```

<210> SEQ ID NO 55
<211> LENGTH: 2024
<212> TYPE: DNA
<213> ORGANISM: Homo sapiens

<400> SEQUENCE: 55

```
ggaagacatc aggatgtacc atctgccctt ctgtcggacc ccagggtacg tcccatgagc     60
gcggccgagc tgcgtcgagg gcagcagagc gtgctgcact gctcagggac ccggactctg    120
cagtttctcc tgcactgttt tcacctttgg ccagacgggc tctgggaaga cctacaccct    180
gactggaccc cctccccagg gggagggggt gcctgtaccc cccagcctgg ctggcatcat    240
gcagaggacc ttcgcctggc tgttggaccg cgtgcagcac ctgggtgccc ctgtcaccct    300
tcgcgcctct tatctggaga tctacaatga gcaggttcgg gacttgctga gcctggggtc    360
tccccggccc ctccctgttc gctggaacaa gactcggggc ttctatgtgg agcagctgcg    420
ggtggtggaa tttgggagtc tggaggccct gatggaactt ttgcaaacgg gtctcagccg    480
tcgaaggaac tcagcccaca ccctgaacca ggcctccagc cgaagccatg ccctgctcac    540
cctttacatc agccgtcaaa ctgcccagca gatgccttct gtggaccctg gggagccccc    600
tgttggtggg aagctgtgct ttgtggacct ggcaggcagt gagaaggtag cagccacggg    660
atcccgtggg gagctgatgc ttgaggctaa cagcatcaac cgaagcctgc tggccctggg    720
tcactgcatc tccctgctgc tggacccaca gcggaagcag agccacatcc ctttccggga    780
cagcaagctc accaagttgc tggcagactc actgggaggg cgcggggtca ccctcatggt    840
```

```
ggcctgcgtg tccccctcag cccagtgcct tcctgagact ctcagcaccc tgcgatatgc    900

aagccgagct cagcgggtca ccacccgacc acaggccccc aagtctcctg tggcaaagca    960

gccccagcgt ttggagacag agatgctgca gctccaggag gagaaccgtc gcctgcagtt   1020

ccagctggac caaatggact gcaaggcctc agggctcagt ggagcccggg tggcctgggc   1080

ccagcggaac ctgtacggga tgctacagga gttcatgcta gagaatgaga ggctcaggaa   1140

agaaaagagc cagctgcaga atagccgaga cctggcccag aatgagcagc gcatcctggc   1200

ccagcaggtc catgcactag agaggcgtct cctctctgcc tgctaccatc accagcaggg   1260

tcctggcctg accccaccgt gtccctgctt gatggcccca gctccccctt gccatgcact   1320

gccacccctc tactcctgcc cctgctgcca catctgccca ctgtgtcgag tgcccctggc   1380

ccactgggcc tgcctgccag gggagcacca cctgccccag gtgttggacc ctgaggcctc   1440

aggtggcagg cccccatctg cccggccccc accctgggca cccccatgca gccctggctc   1500

tgccaagtgc ccaagagaga ggagtcacag tgactggact cagacccgag tcctggcaga   1560

gatgttgacg gaggaggagg tggtaccttc tgcacctccc ctgcctgtga ggcccccgaa   1620

gacatcacca gggctcagag gtggggccgg ggttccaaac ctggcccaga gactggaggc   1680

cctcagagac cagattggca gctccctgcg acgtggccgc agccagccac cctgcagtga   1740

gggcgcacgg agcccaggcc aagtcctccc tccccattga aggccaagtg ggaacccagg   1800

agactgctgt gtgacctcag actgggctcc acactcttgg gcttcagtct gcccatctgc   1860

tgaatggaga cagcagctgc tactccacct gcagctgggc taggggcggg gactgggggt   1920

gctatttagg ggaacaaggg gattcaggag aaaccaggca gcaggggatg aaatacatga   1980

ataaagagag gcatcagctc caaaaaaaaa aaaaaaaaaa aaaa                    2024
```

<210> SEQ ID NO 56
<211> LENGTH: 3334
<212> TYPE: DNA
<213> ORGANISM: Homo sapiens

<400> SEQUENCE: 56

```
ctccccctga gagaggctgg gcagcacccc ccttctgcca ggagtgccag ccaaggtgcc     60

agacccctgt ccagtggcaa gctggaaggc tttcagagca tcgatgaagc tatagcctgg    120

ctcaggaagg aactgacgga gatgcggctg caggaccagc aactggccag acagctcatg    180

cgcctgcgtg gcgacatcaa caagctgaaa atcgaacaca cctgccgcct ccacaggagg    240

atgctcaacg atgccaccta cgagctggag gagcgggatg agctggccga cctcttctgt    300

gactcccctc ttgcctcctc cttcagcctc tccacaccac tcaagcttat tggcgtgacc    360

aagatgaaca tcaactctcg gaggttctct ctctgctgag gagccctcag actgggcgga    420

ggggctggag cggagggctt gggctggagg ggtgtcagag gaagctgagg ccaagttact    480

ccagtgggtc tcccggaggc aggggtccct gggactggcg actcaagggc cccaggacct    540

attcagtggt gctctcccac ccaggggccc tgggtgtgga tgccagtgtc tctgtgactg    600

gctcttgctt actacccaaa gagctctgca gaagggccgc tccaaccaag atgttaaagg    660

agacctgggt tcccaccata atccatccct ccacggtcac gttcctgttt cctggaatca    720

ctggtgctat gaactgggat tcccaaaggg aggcccccca acaaagctgt catttttgca    780

gaaggctgtc ccgcaagggc cttgggggaa attaggcatg tcagatgtgc ctgtctcacg    840

tgctgttgct gtcctctaag tattgtctca aattcaccct aagtacatga ctcagcaaca    900
```

-continued

```
ttgacaggga gctactagga agggaaaatc gaaaggcatg acaaatgggc acttggggac    960
gcagccccag tggctggcag ccagtgtctc tggtgagcct gacactacaa ggctgtgtaa   1020
attgtaaatt ctggcgtgtg ctgggacatg tgatgggggc actagcgtag cttgggtgca   1080
acaagcacag atgtccccat tgtctcccct ggccacatgc atctccaaag agcctcttca   1140
ctgccaccca caccccaggg tgacagcctg ggagaccact ggtgactgaa ccaggcaggt   1200
cctgaaagca ttttccataa ctgaattctc ctgcaggggc gtgaccgggg cctcctggtg   1260
gattctggtg gtgtcacctt actgccctct ctggaaagac aatctaggga gcccagaggc   1320
ccatcctgag cctcctctga gattttgtgc ctgacctaaa caactagttt taataagact   1380
gttactgatg tgttgttcac ttgttagtaa ctgatttttg tccaaatgcg gaagccactt   1440
gtgtaggtca actacagtgc gtaggatttg attttaagag tttctccctc ccaacaggct   1500
tgaggatcag caagttaaga ccccagcagg ttagggaggt cagtctgggg tcatacggca   1560
tggcaggggt ccctcggcca gacccgtaga atcctgagat aaggagtgtt tctgaccttt   1620
ggtgtcatct agtcgagtcc tctcattagt aaaggagcaa agtgaaacct gggggaggag   1680
aaggacttcc ctcaggttgc acagctgttt aggctataga atattgatgt gtgaaaccat   1740
tattgataat gcctagtaga tcacatgtca atgaacttga accccaaaga tggtcgtgat   1800
gctttgccaa acccgcacac tgccaacccc tctactctcc acctcagccc ccacccacat   1860
ctcccagagt attgcaattc agaacatttg ggtcaaggtg gagcaaggca ctgacagtgg   1920
ccccacaggg catgtgtcac taatcactgt cccatggtct acgcacggca tctggctgct   1980
ctgtctactg tgacttcttc ctgtgtaatc tcagtggggc ccgtgtccac ccacacatcg   2040
tgacccacat aggggagagg ttgcttttct tttgtgggct gagagtagga caatgcaaat   2100
gaatgatctc tagtagacag aaaagaactt ggtctctttt ttaaaatttc aaagagccag   2160
aagttctatg cctccttcaa agtaggcaga acaacgcagc caagatctac tgtctgccat   2220
gctctgtgca atgaagtctg caggcctgag gaccatgtac tgctgtcctt cctcagagct   2280
ctgcacaaac actgccaagt cctgaagacg cattcctttc ctgccaacct ctttccagat   2340
aagcccttga ggtctcgggc tgacctacac acacacacac acacacacac acacacacac   2400
acacccccac acacacacac acacgacaga gaacatgcca taaacatcct tgaacccatg   2460
caggaaagcc catcccatat tctgaaaaaa tgccaaatta ggtttttctt tctttttgga   2520
aatcagtcat tacagtaacc gaaaccattg ggttcagcga aaatggaaag atttagctga   2580
atgtagtcag tccaattaag ttggatgcaa ctgagtgatt tagttgcttg ggtaacccag   2640
tgcttgcttg ctttcttcat tctctgggtg gaaactaaga tcaagacaca tgtttgggga   2700
taagttaaat gtctgagcta ttttgctcgg tttatcctaa gagaacttta ttatgggatg   2760
aggaggtgac ccaagatgag aagtggaggg ggacagcgat gttttctaaa catcgtccag   2820
tgttgactgg cttccttact ttgcacagtg aacacaacta accacattaa ttcagctttg   2880
tgaagtccct gctctctgtg ggttctatga gtcagcagca acattggcct aacctccgtc   2940
ccagcctcct ggctcaccac atgtgtacag tgctgtttgc agttgtactc attatccatc   3000
catctctctg ccatccccaa gcatcgctgg gtgtaaaacg caaactctcc accgacactg   3060
ccatgcgtgg tcatgtcttg atgccttcag gggctcagta gctatcaaag aggcctggag   3120
ggcctgggca ggcttgacga tgcctgaccg agttcaagac ccacaccctg tagcaatacc   3180
aagtgctatt acataatcaa tggacgattt atacttttat tttttatgat tatttgtttc   3240
tatattgctg ttagaaaaag tgaaataaaa atacttcaaa agaaaaaaaa aaaaaaaaaa   3300
```

aaaaaaaaaa aaaagaaaaa aaaaaaaaaa aaaa 3334

<210> SEQ ID NO 57
<211> LENGTH: 573
<212> TYPE: DNA
<213> ORGANISM: Homo sapiens
<220> FEATURE:
<221> NAME/KEY: misc_feature
<222> LOCATION: (567)..(569)
<223> OTHER INFORMATION: a or g or c or t/u

<400> SEQUENCE: 57
tgaaggaccg cgatcctaaa gagattgaat gggacgacct ggcccagctg cccttcctga 60
ccatgtgcgt gaaggagagc ctgaggttac atcccccagc tcccttcatc tcccgatgct 120
gcacccagga cattgttctc ccagatggcc gagtcatccc caagggcatt acctgcctca 180
tcgatattat aggggtccat cacaacccaa ctgtgtggcc ggatcctgag tctacgaccc 240
cttccgcttt gacccagaga acagcaaggg gaggtcacct ctggctttta attcccttct 300
ccgcagggcc caggaactgc atcgggccag cgtttcccat ggcggagatg aaagtggttc 360
ctggcgttga tgctgctgca cttccggttc ctgccagacc acactgagcc ccgcaggaag 420
ctggaactga tcattgcggc cgagggcggg ctttggctgc gggtggagcc cctgaatgta 480
ggcttgcagt gactttctga cccatccacc tgtttttttg cagattgtca tgaataaaac 540
ggtgctgtca cctcaaaaaa aaaaaannna aaa 573

<210> SEQ ID NO 58
<211> LENGTH: 2534
<212> TYPE: DNA
<213> ORGANISM: Homo sapiens

<400> SEQUENCE: 58
gagtcctctc gttggtcccg gaggtggggt tgcgctcaca aggggcgacc gtcgccacgg 60
tggcggccac tgcatcgcgt cccacctccg cggccctggg cgccgtggtg tcgacgggcc 120
ccgagcctat gacgggccag ggccagtcgg cgtccgggtc gtcggcgtgg agcacggtat 180
tccgccacgt ccggtatgag aacctgatag cgggcgtgag cggcggcgtc ttatccaacc 240
ttgcgctgca tccgctcgac ctcgtgaaga tccgcttcgc cgtgagtgat ggattggaac 300
tgagaccgaa atataatgga attttacatt gcttgactac catttggaaa cttgatggac 360
tacggggact ttatcaagga gtaaccccaa atatatgggg tgcaggttta tcctggggac 420
tctacttttt cttttacaat gccatcaagt catataaaac agaaggaaga gctgaacatt 480
tagaggcaac agaatacctt gtctcagctg ctgaagctgg agccatgacc ctctgcatta 540
caaacccatt atgggtaaca aaaactcgcc ttatgttaca gtatgatgct gttgttaact 600
ccccacaccg acaatataaa ggaatgtttg atacacttgt gaaaatatat aagtatgaag 660
gtgtgcgtgg attatataag ggatttgttc ctgggctgtt tggaacatcg catggtgccc 720
ttcagtttat ggcatatgaa ttgctgaagt tgaagtacaa ccagcatatc aatagattac 780
cagaagccca gttgagcaca gtagaatata tatctgttgc agcactatcc aaaatatttg 840
ctgtcgcagc aacataccca tatcaagtcg taagagctcg tcttcaggat caacacatgt 900
tttacagtgg tgtaatagat gtaatcacaa agacatggag gaaagaaggc gtcggtggat 960
tttacaaggg aattgctcct aatttgatta gagtgactcc agcctgctgt attacctttg 1020
tggtatatga aaacgtctca cattttttac ttgaccttag agaaaagaga aagtaagctc 1080

-continued

```
aaagaggaca attccagtat atctgcccaa ggcagcaaca agctcttttg tgtttaaggc   1140

ataaaagaag aattctgcat agaaacatgg ctcatattcg aaattgctct atagtcatta   1200

gaagccagag aactgctaag tctcctgcaa tgtttttctt gctttttgcc ttccccatat   1260

atatggaact tggctacctc tgcctgaaat ggctgccatc aacacaatgt taaaactgac   1320

acgaaggata gagtttcaca gatttctacg ttttattggt ggaagctgat ttgcaacatt   1380

tgctaaatgg attagatgaa tgtacttctt tttgtgagct tacttgcctg gattgcttta   1440

aaattaacct ttgtgcaata ccaagaaaat agctctttaa aagaatgtct ttgtatgtct   1500

caaggtaaat taaggattta ctgaataagg tgttgaccaa atccagacca ttttatttta   1560

tttttttatt tatttatttt ttgagatgga gtcttgcttt gtcgcccagg ctggagtgca   1620

gtggcgtgat ctcagctcac tgcaacctcc acctcccggg ttcacgccat tctcctgcct   1680

cagcctcctg agtagctggg actacaggca cctgccacca cgcctggcta acttttttt    1740

atattttgag tagaaatggg gtttcaccat gttagccagg atggtctcaa tctcctgacc   1800

ttgtgatccg cctgccttgg cctcccaaag tgctgggatt acaggcgtga gccactgcgc   1860

ctggccagac cattttagaa ttgggaaatt ttagtgagaa aaaatgcact gtaaatatgc   1920

tttagtttta attcagttgg gatgcactac ctagcgaaaa ttgagaaact atatacttct   1980

cagagaaata tctgacatct attgtcattc cattgctatt ttttttcccc agagacttcc   2040

ataatttaaa ataaaatcct agatccagtt cttgtttttt ggcataaata cttaatctat   2100

tttaaattta taaaatctga gcttctagga tccagctgtg tcaaccttta tttagcatat   2160

ataactataa atcacttatt acagatgcta aatagatcac cttttacaga tgctgaaatg   2220

tttgggatat gtttgttgac aaggtaaatg gaaatgagaa actttatact tcagttttca   2280

gatatatgga tctagatccc aaataaatga ttaatcttca ttggtttctc aaattcaggt   2340

tgaaatacaa attaatagcc tttattgatt ttacttttat gagtcattgt agacatctat   2400

aaatataaaa gggcctgtac ccaaaggatg ccagaatact agtattttta tttatcgtaa   2460

acatccacga gtgctgttgc actaccatct atttgttgta aataaaagtg ttgttttcaa   2520

aaaaaaaaaa aaaa                                                     2534
```

<210> SEQ ID NO 59
<211> LENGTH: 1232
<212> TYPE: DNA
<213> ORGANISM: Homo sapiens

<400> SEQUENCE: 59

```
ctagaggggc ggaaagtaac aaggaggtgg gggtacaaat cctcagctcc tgcttccgca     60

agcactaacc tgctctgaag tgagccaggc agctctggcc atcttttccc agccacagaa    120

tcaggtgatg gtccagaatt aagagctgtc acctgtgtca ttcactcaca atggaagaaa    180

tgaagaagac tgccatccgg ctgcccaaag gcaaacagaa gcctataaag acggaatgga    240

attcccggtg tgtccttttc acctacttcc aaggggacat cagcagcgta gtggatgaac    300

acttctccag agctctgagc aatatcaaga gcccccagga attgaccccc tcgagtcaga    360

gtgaaggtgt gatgctgaaa aacgatgata gcatgtctcc aaatcagtgg cgttactcgt    420

ctccatggac aaagccacaa ccagaagtac ctgtcacaaa ccgtgccgcc aactgcaact    480

tgcatgtgcc tggtcccatg gctgtgaatc agttctcacc gtccctggct aggagggcct    540

ctgttcggcc tggggagctg tggcatttct cctccctggc gggcaccagc tccttagagc    600

ctggctactc tcatcccttc cccgctcggc acctggttcc agagccccag cctgatggga    660
```

```
aacgtgagcc tctcctaagt ctcctccagc aagacagatg cctagcccgt cctcaggaat    720

ctgccgccag ggagaatggc aaccctggcc agatagctgg aagcacaggg ttgctcttca    780

acctgcctcc cggctcagtt cactataaga aactatatgt atctcgtgga tctgccagta    840

ccagccttcc aaatgaaact ctttcagagt tagagacacc tgggaaatac tcacttacac    900

caccaaacca ctggggccac ccacatcgat acctgcagca tctttagtca agttggagga    960

gaaagacaac acttggtcta agacacggca gcaagacatc cctgcatatt gttccagata   1020

aaaatgaaag ctgctcacac ccacttgcct ccccaatctg ttaaacagct tcgtgtctag   1080

tatgagctca gtacttgccc tgtgaaaatc ccagaagccc ccgctgtcaa tgttccccat   1140

ccacaccctg cttgctcctg tgtaacagct cagatgatga ataataataa aactgtactt   1200

ttttggatgg tgaaaaaaaa aaaaaaaaaa aa                                 1232
```

<210> SEQ ID NO 60
<211> LENGTH: 3551
<212> TYPE: DNA
<213> ORGANISM: Homo sapiens

<400> SEQUENCE: 60

```
ttgccttgtg ttagctagca ataagaaaag aagctttgtt tggattaaca tatataccct     60

cttcattctg catacctatt ttttccccaa taatttgcag cttaggtccg aggacaccac    120

aaactctgct taaagggcct ggaggctctc aaggcatggc cagacgctct gtcttgtact    180

tcatcctgct gaatgctctg atcaacaagg gccaagcctg cttctgtgat cactatgcat    240

ggactcagtg gaccagctgc tcaaaaactt gcaattctgg aacccagagc agacacagac    300

aaatagtagt agataagtac taccaggaaa acttttgtga acagatttgc agcaagcagg    360

agactagaga atgtaactgg caaagatgcc ccatcaactg cctcctggga gattttggac    420

catggtcaga ctgtgaccct tgtattgaaa aacagtctaa agttagatct gtcttgcgtc    480

ccagtcagtt tgggggacag ccatgcactg agcctctggt agcctttcaa ccatgcattc    540

catctaagct ctgcaaaatt gaagaggctg actgcaagaa taaatttcgc tgtgacagtg    600

gccgctgcat tgccagaaag ttagaatgca atggagaaaa tgactgtgga gacaattcag    660

atgaaaggga ctgtgggagg acaaaggcag tatgcacacg gaagtataat cccatcccta    720

gtgtacagtt gatgggcaat gggtttcatt ttctggcagg agagcccaga ggagaagtcc    780

ttgataactc tttcactgga ggaatatgta aaactgtcaa aagcagtagg acaagtaatc    840

cataccgtgt tccggccaat ctggaaaatg tcggctttga ggtacaaact gcagaagatg    900

acttgaaaac agatttctac aaggatttaa cttctcttgg acacaatgaa aatcaacaag    960

gctcattctc aagtcagggg gggagctctt tcagtgtacc aatttttttat tcctcaaaga   1020

gaagtgaaaa tatcaaccat aattctgcct tcaaacaagc cattcaagcc tctcacaaaa   1080

aggattctag ttttattagg atccataaag tgatgaaagt cttaaacttc acaacgaaag   1140

ctaaagatct gcacctttct gatgtctttt tgaaagcact taaccatctg cctctagaat   1200

acaactctgc tttgtacagc cgaatattcg atgactttgg gactcattac ttcacctctg   1260

gctccctggg aggcgtgtat gaccttctct atcagtttag cagtgaggaa ctaaagaact   1320

caggtttaac cgaggaagaa gccaaacact gtgtcaggat tgaaacaaag aaacgcgttt   1380

tatttgctaa gaaaacaaaa gtggaacata ggtgcaccac caacaagctg tcagagaaac   1440

atgaaggttc atttatacag ggagcagaga aatccatatc cctgattcga ggtggaagga   1500
```

gtgaatatgg agcagctttg gcatgggaga aagggagctc tggtctggag gagaagacat 1560
tttctgagtg gttagaatca gtgaaggaaa atcctgctgt gattgacttt gagcttgccc 1620
ccatcgtgga cttggtaaga aacatcccct gtgcagtgac aaaacggaac aacctcagga 1680
aagctttgca agagtatgca gccaagttcg atccttgcca gtgtgctcca tgccctaata 1740
atggccgacc caccctctca gggactgaat gtctgtgtgt gtgtcagagt ggcacctatg 1800
gtgagaactg tgagaaacag tctccagatt ataaatccaa tgcagtagac ggacagtggg 1860
gttgttggtc ttcctggagt acctgtgatg ctacttataa gagatcgaga acccgagaat 1920
gcaataatcc tgccccccaa cgaggaggga aacgctgtga gggggagaag cgacaagagg 1980
aagactgcac attttcaatc atggaaaaca atggacaacc atgtatcaat gatgatgaag 2040
aaatgaaaga ggtcgatctt cctgagatag aagcagattc cgggtgtcct cagccagttc 2100
ctccagaaaa tggatttatc cggaatgaaa agcaactata cttggttgga gaagatgttg 2160
aaatttcatg ccttactggc tttgaaactg ttggatacca gtacttcaga tgcttaccag 2220
acgggacctg gagacaaggg gatgtggaat gccaacggac ggagtgcatc aagccagttg 2280
tgcaggaagt cctgacaatt acaccatttc agagattgta tagaattggt gaatccattg 2340
agctaacttg ccccaaaggc tttgttgttg ctgggccatc aaggtacaca tgccagggga 2400
attcctggac accacccatt tcaaactctc tcacctgtga aaaagatact ctaacaaaat 2460
taaaaggcca ttgtcagctg ggacagaaac aatcaggatc tgaatgcatt tgtatgtctc 2520
cagaagaaga ctgtagccat cattcagaag atctctgtgt gtttgacaca gactccaacg 2580
attactttac ttcacccgct tgtaagtttt tggctgagaa atgtttaaat aatcagcaac 2640
tccattttct acatattggt tcctgccaag acggccgcca gttagaatgg ggtcttgaaa 2700
ggacaagact ttcatccaac agcacaaaga aagaatcctg tggctatgac acctgctatg 2760
actgggaaaa atgttcagcc tccacttcca aatgtgtctg cctattgccc ccacagtgct 2820
tcaagggtgg aaaccaactc tactgtgtca aaatgggatc atcaacaagt gagaaaacat 2880
tgaacatctg tgaagtggga actataagat gtgcaaacag gaagatggaa atactgcatc 2940
ctggaaagtg tttggcctag cacaattact gctaggccca gcacaatgaa cagatttacc 3000
atcccgaaga accaactcct acaaatgaga attcttgcac aaacagcaga ctggcatgct 3060
caaagttact gacaaaaatt attttctgtt agtttgagat cattattctc ccctgactct 3120
cctgtttggg catgtcttat tcagttccag ctcatgacgc cctgtagcat acccctaggt 3180
accaacttcc acagcagtct cgtaaattct cctgttcaca ttgtacaaaa ataatgtgac 3240
ttctgaggcc cttatgtagc ctgtgacatt aagcattctc acaattagaa ataagaataa 3300
aacccataat tttcttcaat gagttaataa acagaaatct ccagaacctc tgaaacacat 3360
tcttgaagcc cagctttcat atcttcattc aacaaataat ttctgagtgt gtatacagga 3420
tgtcaagtac tgaccaaagt cctgagaact cggcagataa taaaacagac aaaagccttt 3480
gccttcatga agcatacatt cattcagggg tagacacaca aaaaatgaaa taaacaggta 3540
aaatatgtag c 3551

<210> SEQ ID NO 61
<211> LENGTH: 1673
<212> TYPE: DNA
<213> ORGANISM: Homo sapiens

<400> SEQUENCE: 61
ctctcctcgc ccgctgggtg ctgaagttgg gcggatggca gcaaaccggc tccgctagag 60

```
gaccgagccg cccagccccg ctcccccgga cccatcggcg cgctgcccac acctccaggc    120
gaccggccaa ctgggtcctg aagtagctga aatgcgaaaa aggcagcagt cccaaaatga    180
aggaacacct gccgtgtctc aagctcctgg aaaccagagg cccaacaaca cctgttgctt    240
ttgttggtgc tgttgttgca gctgctcctg cctcactgtg aggaatgaag aaagagggga    300
aaatgcggga agacccacac acactacaaa aatggagagt atccaggtcc tagaggaatg    360
ccaaaacccc actgcagagg aagtcttgtc ctggtctcaa aattttgaca agatgatgaa    420
ggccccagca ggaagaaacc ttttcagaga gttcctccga acagaataca gtgaagagaa    480
cctacttttc tggcttgctt gtgaagactt aaagaaggag cagaacaaaa aagtaattga    540
agaaaaggct aggatgatat atgaagatta catttctata ctatcaccaa aagaggtcag    600
tcttgattct cgagttagag aggtgatcaa tagaaatctg ttggatccca atcctcacat    660
gtatgaagat gcccaacttc agatatatac tttaatgcac agagattctt ttccaaggtt    720
tttgaactct caaatttata agtcatttgt tgaaagtact gctggctctt cttctgaatc    780
ttaatgttca tttaaaaaca atcattttgg agggctgaga tgggaaataa aagtagttaa    840
ataacatcag aaactgagtt cctggagaac tacagtttag cattcctcag gctactgtga    900
aaacacaacc gttatggtct ttgtctccat ttttatcaag gttttccatg gttaagtttg    960
gagaaaatac cacacaaaac aatgaattgc caaattgttt gttttattca agactcattc   1020
tacttgcaag caaagtgtat ttgtagtcct atgaacagtc tcctcgtgta tctccagaga   1080
ctgcatgtgc aaagtaaaat gcttcatttg ccacatagtt gttgtaatat ttaatccagt   1140
agcataactt atatctgtat ttaaggactt ttgtgcaata tggtcttaag aaataattgc   1200
caaaaaaatc ggccatggtt ctgcattttt aacataatct aagacagaaa aaaagcaatt   1260
tttactatgt aacaatggta ttcaacattc tatatactgt gtttagtaca ctaattttga   1320
agccaatatt tctgtacatg aaaaagagct atttatctct gtttgttgga aaatcctaat   1380
ggggattcct ctggttgttc actgccaaaa ctgtggcatt ttcattacag gagagtttac   1440
tatgctaaaa gcaaaaaaca aaaaaaaaaa aaaagggaag aaggaaaaaa gcaaaaaaca   1500
atttgaagat atcctatctc aatgacaaat caaaagagtg atattgcttt taactgtaat   1560
agaagaaaat gaatttatgt atatatcaga tgtccaatac tgtaattaat ttattaaaga   1620
ctggctctcc agttttaaaa aaaaaaaaaa aaaaaaaaaa aaaaaaaaaa aaa          1673
```

<210> SEQ ID NO 62
<211> LENGTH: 1867
<212> TYPE: DNA
<213> ORGANISM: Homo sapiens

<400> SEQUENCE: 62

```
aaaagaacca ggattgcatt tgaagttaag ctgcaaaaaa ccagtcgatc aacagatttt     60
cgagtcccac agtcaatatg caccatgttt aatgttatgg ttgatgccaa agctcaatca    120
acaaaacttt gcagcatgga aatgggccaa gagtttgcta aaatgtggca tcaataccat    180
tcaaaaatag acgaactaat tgaagaaact gttaaagaaa tgataacact cttggttgca    240
aagttcgtta ctatcttgga aggagtgctg gcaaaattat ccagatatga cgaagggact    300
ttgttttctt cttttctgtc atttaccgtg aaggcagctt ccaaatatgt ggatgtacct    360
aaacccggga tggacgtggc cgacgcctac gtgactttcg tccgccattc tcaggatgtc    420
ctgcgtgata aggtcaatga ggagatgtac atagaaaggt tatttgatca atggtacaac    480
```

-continued

```
agctccatga acgtgatctg cacctggttg acggaccgga tggacttaca gcttcatatt    540

tatcagttga aaacactaat taggatggta aagaaaacct acagagattt ccgattgcaa    600

ggggtcctgg actccacctt aaacagcaag acctatgaaa cgatccggaa ccgtctcact    660

gtggaggaag ccacagcatc agtgagtgaa ggtgggggac tgcagggcat cagcatgaag    720

gacagcgatg aggaagacga agaagacgat tagaccattt ggtcctagag tctgctggga    780

cagagtcctg taatcagtgc atgtccttag tctgttagtt aaacccatta ggaattttct    840

gtcaactacc atgcccatga gatgtttatc aatacaactg ccattttagc tatgtggtac    900

caagattagc aaatgacctt catatccact gatttcctga tgtccatgtc tatatgttta    960

caagcaatat ggagcaccat tctttaaata ctgttcatgg agaatacata gtctaaccac   1020

taggcgtgtc cctgttatca gcaaagatca atgatgcttc attcatgtac tatgtatgca   1080

ttggtggtaa atggatgtga gggcaagtac atcaagtaca ttcactctgt ttcacgtatg   1140

tggatgccag ttaattaaat gagtacgtaa ataaattaat taaaacacat agatctgctt   1200

tgtgttttta tttttatttt ttgaaaaaca aaaggcaagt ctccaacaat taacttttga   1260

tgctttctgt tcccctaaaa ccaaaaaatg aaccccttgt gtcgttgtta acccatcctt   1320

tcatttactc atataattag ccaaaaaaaa aaggatggct acataccaat ggattgattc   1380

tcttaattgc cacggcaagg gggcgatcct atcatgactt aacatcaagc gcgcagttca   1440

aaactactgt cttctgtcaa agttttctcc tcttaaatgt tattttgctt ttacgtctca   1500

actgtgtatg taaaaaaaac gaatatttaa attacaaccc tagactaaaa atgtgtttat   1560

aataagatgt ggatatttcc ttcagtagat tgtaaccata atttaaatta ttttgttcca   1620

cactgttttt tatatctgtc atgtacattg catttttgatc tgtaactgca caaccctggg   1680

gtttgctgca gagctatttc tttccatgta aagtagtgga tccatcttgc ttttgcctta   1740

tataaagcct acagttatgg aagtgtggaa aactgtggct tctcaataaa tattcagatg   1800

tcctaagaaa aaaaaaaaaa aaaaaaaaaa aaaaaaaaaa aaaaaaaaaa aaaaaaaaaa   1860

aaaaaaa                                                             1867
```

<210> SEQ ID NO 63
<211> LENGTH: 601
<212> TYPE: DNA
<213> ORGANISM: Homo sapiens

<400> SEQUENCE: 63

```
acctgaactg tctaagatat tctaagcaaa gttgacaaag acaattctcc acttgagccc     60

ttaaaaatgt aaccactata aaggtttcac gcggtggttc ttattgattc gctgtgtcat    120

cacatcagct ccactgttgc caaactttgt cgcatgcata atgtatgatg gaggcttgga    180

tgggaatatg ctgattttgt tctgcactta aaggcttctc ctcctggagg gctgcctagg    240

gccacttgct tgatttatca tgagagaaga ggagagagag agagactgag cgctaggagt    300

gtgtgtatgt gtgtgtgtgt gtgtgtgtgt gtgtgtgtat gtgtgtagcg ggagatgtgg    360

gcggagcgag agcaaaagga ctgcggcctg atgcatgctg gaaaaagaca cgcttttcat    420

ttctgatcag ttgtacttca tcctatatca gcacagctgc catacttcga cttatcagga    480

ttctggctgg tggcctgcgc gagggtgcag tcttacttaa aagactttca gttaattctc    540

actggtatca tcgcagtgaa cttaaagcaa agacctctta gtaaaaaata aaaaaaataa    600

a                                                                    601
```

<210> SEQ ID NO 64
<211> LENGTH: 367
<212> TYPE: DNA
<213> ORGANISM: Homo sapiens

<400> SEQUENCE: 64
gcttctcttt aaaattgacc caaggcatga gccactgcgc ctggccagca aatgcttttt 60
gtgcagaata cacttctttc aggcattgtc aggtgctgtt ttgtttaagc tctaactcac 120
ccctggaata caggggaatg atgacaacca gcccagccag gcctgactca tcatggtcac 180
atccagcccc cacccccggc caactaacca ctgcaggctc ctcttccaga ctcaccaggg 240
ggcctcgagg ccccggcatc tcccttggcc ctgggtgtgg gttttacaag actgtgtctt 300
tcatgacatc atagcccaac catgtgagaa gaaggagaag gcccccccttt cttcattaat 360 ctgaaaa 367

<210> SEQ ID NO 65
<211> LENGTH: 2484
<212> TYPE: DNA
<213> ORGANISM: Homo sapiens

<400> SEQUENCE: 65
ggcacgagga agggcctgtg ggtttattat aaggcggagc tcggcgggag aggtgcgggc 60
cgaatccgag ccgagcggag aggaatccgg cagtagagag cggactccag ccggcggacc 120
ctgcagccct cgcctgggac agcggcgcgc tgggcaggcg cccaagagag catcgagcag 180
cggaacccgc gaagccggcc cgcagccgcg acccgcgcag cctgccgctc tcccgccgcc 240
ggtccgggca gcatgaggcg cgcggcgctc tggctctggc tgtgcgcgct ggcgctgagc 300
ctgcagccgg ccctgccgca aattgtggct actaatttgc cccctgaaga tcaagatggc 360
tctggggatg actctgacaa cttctccggc tcaggtgcag gtgctttgca agatatcacc 420
ttgtcacagc agaccccctc cacttggaag gacacgcagc tcctgacggc tattcccacg 480
tctccagaac ccaccggcct ggaggctaca gctgcctcca cctccaccct gccggctgga 540
gaggggccca aggagggaga ggctgtagtc ctgccagaag tggagcctgg cctcaccgcc 600
cgggagcagg aggccacccc ccgacccagg gagaccacac agctcccgac cactcatcag 660
gcctcaacga ccacagccac cacggcccag gagcccgcca cctcccaccc ccacagggac 720
atgcagcctg gccaccatga gacctcaacc cctgcaggac ccagccaagc tgaccttcac 780
actccccaca cagaggatgg aggtccttct gccaccgaga gggctgctga ggatggagcc 840
tccagtcagc tcccagcagc agagggctct ggggagcagg acttcacctt tgaaacctcg 900
ggggagaata cggctgtagt ggccgtggag cctgaccgcc ggaaccagtc cccagtggat 960
cagggggcca cgggggcctc acagggcctc ctggacagga aagaggtgct gggaggggtc 1020
attgccgtag gcctcgtggg gctcatcttt gctgtgtgcc tggtgggttt catgctgtac 1080
cgcatgaaga agaaggacga aggcagctac tccttggagg agccgaaaca agccaacggc 1140
ggggcctacc agaagcccac caaacaggag gaattctatg cctgacgcgg gagccatgcg 1200
ccccctccgc cctgccactc actaggcccc cacttgcctc ttccttgaag aactgcaggc 1260
cctggcctcc cctgccacca ggccacctcc ccagcattcc agcccctctg gtcgctcctg 1320
cccacggagt cgtggggtgt gctgggagct ccactctgct tctctgactt ctgcctggag 1380
acttagggca ccaggggttt ctcgcatagg acctttccac cacagccagc acctggcatc 1440
gcaccattct gactcggttt ctccaaactg aagcagcctc tccccaggtc cagctctgga 1500

```
ggggaggggg atccgactgc tttggaccta aatggcctca tgtggctgga agatcctgcg   1560
ggtggggctt ggggctcaca cacctgtagc acttactggt aggaccaagc atcttggggg   1620
ggtggccgct gagtggcagg ggacaggagt ccactttgtt tcgtggggag gtctaatcta   1680
gatatcgact tgtttttgca catgtttcct ctagttcttt gttcatagcc cagtagacct   1740
tgttacttct gaggtaagtt aagtaagttg attcggtatc cccccatctt gcttccctaa   1800
tctatggtcg ggagacagca tcagggttaa gaagactttt tttttttttt tttttaaact   1860
aggagaacca aatctggaag ccaaaatgta ggcttagttt gtgtgttgtc tcttgagttt   1920
gtcgctcatg tgtgcaacag ggtatggact atctgtctgg tggccccgtt tctggtggtc   1980
tgttggcagg ctggccagtc caggctgccg tggggccgcc gcctctttca agcagtcgtg   2040
cctgtgtcca tgcgctcagg gccatgctga ggcctgggcc gctgccacgt tggagaagcc   2100
cgtgtgagaa gtgaatgctg ggactcagcc ttcagacaga gaggactgta gggagggcgg   2160
caggggcctg gagatcctcc tgcagaccac gcccgtcctg cctgtggcgc cgtctccagg   2220
ggctgcttcc tcctggaaat tgacgagggg tgtcttgggc agagctggct ctgagcgcct   2280
ccatccaagg ccaggttctc cgttagctcc tgtggcccca ccctgggccc tgggctggaa   2340
tcaggaatat tttccaaaga gtgatagtct tttgcttttg gcaaaactct acttaatcca   2400
atgggttttt ccctgtacag tagattttcc aaatgtaata aactttaata taaagtaaaa   2460
aaaaaaaaaa aaaaaaaaaa aaaa                                          2484
```

<210> SEQ ID NO 66
<211> LENGTH: 1989
<212> TYPE: DNA
<213> ORGANISM: Homo sapiens

<400> SEQUENCE: 66

```
cggatgggga aaaaaaaaga tgtcagctcc tccgctgtag tattgctcct taaaaacccc     60
tctctctgaa aatgacatgc cctcgcaatg taactccgaa ctcgtacgcg gagcccttgg    120
ctgcgcccgg cggaggagag cgctatagcc ggagcgcagg catgtatatg cagtctggga    180
gtgacttcaa ttgcggggtg atgaggggct gcgggctcgc gccctcgctc tccaagaggg    240
acgagggcag cagccccagc ctcgccctca acacctatcc gtcctacctc tcgcagctgg    300
actcctgggg cgaccccaaa gccgcctatc gcctggaaca acctgttggc aggccgctgt    360
cctcctgctc ctacccacct agtgtcaagg aggagaatgt ctgctgcatg tacagcgcag    420
agaagcgggc gaaaagtggc cccgaggcag ctctctactc ccaccccttg ccggagtcct    480
gccttgggga gcacgaggta cccgtgccca gctactaccg cgccagcccg agctactccg    540
cgctggacaa gacgccccac tgttctgggg ccaacgactt cgaagcccct ttcgagcagc    600
gggccagtct caacccgcgc gccgaacatc tggaatcgcc tcagctgggg ggcaaagtga    660
gtttccctga gacccccaag tccgacagcc agacccccag ccccaatgaa atcaagacgg    720
agcagagcct ggcgggccct aaagggagcc cctcggagag cgaaaaggag agggccaaag    780
ctgccgactc cagcccagac acctcggata acgaagcgaa agaggagata aaggcagaaa    840
acaccacagg aaattggctg acagcaaaga gcggaaggaa gaagaggtgc ccctatacta    900
aacaccagac gctggaattg gagaaagaat ttctgttcaa tatgtatttg acgcgagagc    960
gccgcctgga gattagcaag accattaacc ttacagacag acaagtcaaa atctggtttc   1020
aaaatcgcag aatgaaactc aagaaaatga accgagagaa tcggatccgg gaactgacct   1080
ccaattttaa tttcacctga gagcgcggcc tctcctcctc ccttcccgct ccttcctctc   1140
```

```
cccgcccctc ctccctttgt gcctggtgat atattttttt ttcctccctg agtataaatg   1200
caatgcgact gcaaaaaagg caaagacctc agactctcct tccaagggac ctgtggttcg   1260
tgctgcgaag atgcttccac ttaaagcatg agaaatgggg tgccgggatg tggggtgtgg   1320
tgtgtgccct catagatggg ggtgggagtg tggctggtgt gtgtgtcaaa ccctcactca   1380
cccacgcact cacacacagc attctgttct ccatgcaaag ttaagatcga atccatccgc   1440
ttgtagggga aaaaaaggaa aaaaattaac cagagagggt ctgtaatctc gcagagcaca   1500
ggcagaatcg ttccttcctt gctgcatttc ctccttagac taatagacgt tttggaaagt   1560
tcggctagtg ttcgtgtgtt tgtcgtagca cccagagcct ccaccaaacc ctctccatgt   1620
ctttacctcc cagtcgctct aagaatctgc ttgaagtctc gtatttgtac tgctttctgc   1680
ttttctccca cccctcctag cacccccaca tcccccatct agtaacatct cagaaatttc   1740
atccagagga acaaaaaaat taaaaataga acatagcaaa gcaaagacag aatgcccccc   1800
cccaaatatt gtcctgtccc tgtctgggag ttgtgttatt taaagatatt ctgtatgttg   1860
tatcttttgc atgtagcttc cttaatggag aaaaaaaaat cctaataaat ttccagaatc   1920
ataatcctca aaaaaaaaaa aaaaaaaaaa aaaaaaaaaa aaaaaaaaaa aaaaaaaaaa   1980
aaaaaaaaa                                                           1989
```

<210> SEQ ID NO 67
<211> LENGTH: 2125
<212> TYPE: DNA
<213> ORGANISM: Homo sapiens

<400> SEQUENCE: 67

```
gcagtggcca cgagaggcag gctggctggg acatgaggtt ggcagagggc aggcaagctg     60
gcccttggtg ggcctcgtcc tgagcactcg gaggcactcc tatgcttgga aagctcgcta    120
tgctgctgtg ggtccagcag gcgctgctcg ccttgctcct ccccacactc ctggcacagg    180
gagaagccag gaggagccga aacaccacca ggcccgctct gctgaggctg tcggattacc    240
ttttgaccaa ctacaggaag ggtgtgcgcc ccgtgaggga ctggaggaag ccaaccaccg    300
tatccattga cgtcattgtc tatgccatcc tcaacgtgga tgagaagaat caggtgctga    360
ccacctacat ctggtaccgg cagtactgga ctgatgagtt tctccagtgg aaccctgagg    420
actttgacaa catcaccaag ttgtccatcc ccacggacag catctgggtc ccggacattc    480
tcatcaatga gttcgtggat gtggggaagt ctccaaatat cccgtacgtg tatattcggc    540
atcaaggcga agttcagaac tacaagcccc ttcaggtggt gactgcctgt agcctcgaca    600
tctacaactt ccccttcgat gtccagaact gctcgctgac cttcaccagt tggctgcaca    660
ccatccagga catcaacatc tctttgtggc gcttgccaga aaaggtgaaa tccgacagga    720
gtgtcttcat gaaccaggga gagtgggagt tgctgggggt gctgccctac tttcgggagt    780
tcagcatgga aagcagtaac tactatgcag aaatgaagtt ctatgtggtc atccgccggc    840
ggcccctctt ctatgtggtc agcctgctac tgcccagcat cttcctcatg gtcatggaca    900
tcgtgggctt ctacctgccc cccaacagtg gcgagagggt ctctttcaag attacactcc    960
tcctgggcta ctcggtcttc ctgatcatcg tttctgacac gctgccggcc actgccatcg   1020
gcactcctct cattggtgtc tactttgtgg tgtgcatggc tctgctggtg ataagtttgg   1080
ccgagaccat cttcattgtg cggctggtgc acaagcaaga cctgcagcag cccgtgcctg   1140
cttggctgcg tcacctggtt ctggagagaa tcgcctggct actttgcctg agggagcagt   1200
```

caacttccca gaggccccca gccacctccc aagccaccaa gactgatgac tgctcagcca 1260
tgggaaacca ctgcagccac atgggaggac cccaggactt cgagaagagc ccgagggaca 1320
gatgtagccc tcccccacca cctcgggagg cctcgctggc ggtgtgtggg ctgctgcagg 1380
agctgtcctc catccggcaa ttcctggaaa agcgggatga gatccgagag gtggcccgag 1440
actggctgcg cgtgggctcc gtgctggaca agctgctatt ccacatttac ctgctggcgg 1500
tgctggccta cagcatcacc ctggttatgc tctggtccat ctggcagtac gcttgagtgg 1560
gtacagccca gtggaggagg gggtacagtc ctggttaggt ggggacagag gatttctgct 1620
taggcccctc aggacccagg gaatgccagg gacattttca agacacagac aaagtcccgt 1680
gccctgtttc caatgccaat tcatctcagc aatcacaagc caaggtctga acccttccac 1740
caaaaactgg gtgttcaagg cccttacacc cttgtcccac ccccagcagc tcaccatggc 1800
tttaaaacat gctctcttag atcaggagaa actcgggcac tccctaagtc cactctagtt 1860
gtggactttt ccccattgac cctcacctga ataagggact ttggaattct gcttctcttt 1920
cacaactttg cttttaggtt gaaggcaaaa ccaactctct actacacagg cctgataact 1980
ctgtacgagg cttctctaac ccctagtgtc ttttttttct tcacctcact tgtggcagct 2040
tccctgaaca ctcatccccc atcagatgat gggagtggga agaataaaat gcagtgaaac 2100
cctaaaaaaa aaaaaaaaaa aaaaa 2125

<210> SEQ ID NO 68
<211> LENGTH: 574
<212> TYPE: DNA
<213> ORGANISM: Homo sapiens

<400> SEQUENCE: 68
tcttcgctcc tctaccccat aaaattccct acaaatgcaa aaattcgaga tagaagaagc 60
cgtccctgaa attgctgtct aacattcacc ggaaacctct ccataaacaa ggagaaacga 120
atgcacacgc atttttgcta agaagcccgg gattaagatt taaggataca agctgaaaga 180
aaaaatgaaa aatgcttctc cgcgcgtcaa tcgaggggtg gatgcgccac gcagctgagc 240
ccagctcaca gccacgcgta agaccaaaag ctgccatggg ttctgcgcgc ggagacctca 300
gagccgaaga gagaagtccc cgcgtcagaa acgctgcgga tgccaggtct tgaaaatgct 360
gacttctgag gctaagaatt atttcaaaga caaaaagaaa agactggtga ggaggccttc 420
cggtgcaagg gcgcctatcc gctaattttg gatggggaag tagggattat tcgtttaaat 480
tcaatcgcga gcaccaagtc ggactggccg gggatggaga agggcaaccc ccacctttag 540
aaaaataaaa gatctcgaag gccaaaaaaa aaaa 574

<210> SEQ ID NO 69
<211> LENGTH: 3697
<212> TYPE: DNA
<213> ORGANISM: Homo sapiens

<400> SEQUENCE: 69
agggagtgtt cccgggggag atactccagt cgtagcaaga gtctcgacca ctgaatggaa 60
gaaaaggact tttaaccacc attttgtgac ttacagaaag gaatttgaat aaagaaaact 120
atgatacttc aggcccatct tcactccctg tgtcttctta tgctttattt ggcaactgga 180
tatggccaag aggggaagtt tagtggaccc ctgaaaccca tgacattttc tatttatgaa 240
ggccaagaac cgagtcaaat tatattccag tttaaggcca atcctcctgc tgtgactttt 300
gaactaactg ggagacagac caacatattt gtgatagaac gggagggact tctgtattac 360

```
aacagagcct tggacaggga aacaagatct actcacaatc tccaggttgc agccctggac    420
gctaatggaa ttatagtgga gggtccagtc cctatcacca tagaagtgaa ggacatcaac    480
gacaatcgac ccacgtttct ccagtcaaag tacgaaggct cagtaaggca gaactctcgc    540
ccaggaaagc ccttcttgta tgtcaatgcc acagacctgg atgatccggc cactcccaat    600
ggccagcttt attaccagat tgtcatccag cttcccatga tcaacaatgt catgtacttt    660
cagatcaaca acaaaacggg agccatctct cttacccgag agggatctca ggaattgaat    720
cctgctaaga atccttccta taatctggtg atctcagtga aggacatggg aggccagagt    780
gagaattcct tcagtgatac cacatctgtg gatatcatag tgacagagaa tatttggaaa    840
gcaccaaaac ctgtggagat ggtggaaaac tcaactgatc ctcaccccat caaaatcact    900
caggtgcggt ggaatgatcc cggtgcacaa tattccttag ttgacaaaga gaagctgcca    960
agattcccat tttcaattga ccaggaagga gatatttacg tgactcagcc cttggaccga   1020
gaagaaaagg atgcatatgt tttttatgca gttgcaaagg atgagtacgg aaaaccactt   1080
tcatatccgc tggaaattca tgtaaaagtt aaagatatta atgataatcc acctacatgt   1140
ccgtcaccag taaccgtatt tgaggtccag gagaatgaac gactgggtaa cagtatcggg   1200
acccttactg cacatgacag ggatgaagaa aatactgcca acagttttct aaactacagg   1260
attgtggagc aaactcccaa acttcccatg gatggactct tcctaatcca aacctatgct   1320
ggaatgttac agttagctaa acagtccttg aagaagcaag atactcctca gtacaactta   1380
acgatagagg tgtctgacaa agatttcaag accctttgtt ttgtgcaaat caacgttatt   1440
gatatcaatg atcagatccc catctttgaa aaatcagatt atggaaacct gactcttgct   1500
gaagacacaa acattgggtc caccatctta accatccagg ccactgatgc tgatgagcca   1560
tttactggga gttctaaaat tctgtatcat atcataaagg gagacagtga gggacgcctg   1620
ggggttgaca cagatcccca taccaacacc ggatatgtca taattaaaaa gcctcttgat   1680
tttgaaacag cagctgtttc caacattgtg ttcaaagcag aaaatcctga gcctctagtg   1740
tttggtgtga agtacaatgc aagttctttt gccaagttca cgcttattgt gacagatgtg   1800
aatgaagcac ctcaattttc ccaacacgta ttccaagcga aagtcagtga ggatgtagct   1860
ataggcacta aagtgggcaa tgtgactgcc aaggatccag aaggtctgga cataagctat   1920
tcactgaggg gagacacaag aggttggctt aaaattgacc acgtgactgg tgagatcttt   1980
agtgtggctc cattggacag agaagccgga agtccatatc gggtacaagt ggtggccaca   2040
gaagtagggg ggtcttcctt gagctctgtg tcagagttcc acctgatcct tatggatgtg   2100
aatgacaacc ctcccaggct agccaaggac tacacgggct tgttcttctg ccatcccctc   2160
agtgcacctg gaagtctcat tttcgaggct actgatgatg atcagcactt atttcggggt   2220
ccccatttta cattttccct cggcagtgga agcttacaaa acgactggga agtttccaaa   2280
atcaatggta ctcatgcccg actgtctacc aggcacacag agtttgagga gagggagtat   2340
gtcgtcttga tccgcatcaa tgatgggggt cggccaccct tggaaggcat tgtttcttta   2400
ccagttacat tctgcagttg tgtggaagga agttgtttcc ggccagcagg tcaccagact   2460
gggataccca ctgtgggcat ggcagttggt atactgctga ccacccttct ggtgattggt   2520
ataattttag cagttgtgtt tatccgcata aagaaggata aaggcaaaga taatgttgaa   2580
agtgctcaag catctgaagt caaacctctg agaagctgaa tttgaaaagg aatgtttgaa   2640
tttatatagc aagtgctatt tcagcaacaa ccatctcatc ctattacttt tcatctaacg   2700
```

-continued

```
tgcattataa ttttttaaac agatattccc tcttgtcctt taatatttgc taaatatttc   2760

ttttttgagg tggagtcttg ctctgtcgcc caggctggag tacagtggtg tgatcccagc   2820

tcactgcaac ctccgcctcc tgggttcaca tgattctcct gcctcagctt cctaagtagc   2880

tgggtttaca ggcacccacc accatgccca gctaattttt gtatttttaa tagagacggg   2940

gtttcgccat ttggccaggc tggtcttgaa ctcctgacgt caagtgatct gcctgccttg   3000

gtctcccaat acaggcatga accactgcac ccacctactt agatatttca tgtgctatag   3060

acattagaga gatttttcat ttttccatga catttttcct ctctgcaaat ggcttagcta   3120

cttgtgtttt tcccttttgg ggcaagacag actcattaaa tattctgtac atttttttctt   3180

tatcaaggag atatatcagt gttgtctcat agaactgcct ggattccatt tatgtttttt   3240

ctgattccat cctgtgtccc cttcatcctt gactcctttg gtatttcact gaatttcaaa   3300

catttgtcag agaagaaaaa cgtgaggact caggaaaaat aaataaataa aagaacagcc   3360

ttttccctta gtattaacag aaatgtttct gtgtcattaa ccatctttaa tcaatgtgac   3420

atgttgctct ttggctgaaa ttcttcaact tggaaatgac acagacccac agaaggtgtt   3480

caaacacaac ctactctgca aaccttggta aaggaaccag tcagctggcc agatttcctc   3540

actacctgcc atgcatacat gctgcgcatg ttttcttcat tcgtatgtta gtaaagtttt   3600

ggttattata tatttaacat gtggaagaaa acaagacatg aaaagagtgg tgacaaatca   3660

agaataaaca ctggttgtag tcagttttgt ttgttaa                            3697
```

<210> SEQ ID NO 70
<211> LENGTH: 2530
<212> TYPE: DNA
<213> ORGANISM: Homo sapiens

<400> SEQUENCE: 70

```
aaatccttct tccaatgttc ctccccctctc tgtatgaacc ctgtgttggg gggcagaaga     60

tggaagccct tggcaagctc gatcgaacca agctactaaa ttgctgagct cgttttaact    120

gaagtgtgag aaggaggttt aaggcaagta gacaacatcc tgttgttggg gtgcttctct    180

ctttttgca catctggctg aactgggagt caggtggttg acttgtgcct ggctgcagta    240

gcagcggcat ctcccttgca cagttctcct cctcggcctg cccaagagtc caccaggcca    300

tggacgcagt ggctgtgtat catggcaaaa tcagcaggga aaccggcgag aagctcctgc    360

ttgccactgg gctggatggc agctatttgc tgagggacag cgagagcgtg ccaggcgtgt    420

actgcctatg tgtgctgtat cacggttaca tttatacata ccgagtgtcc cagacagaaa    480

caggttcttg gagtgctgag acagcacctg ggtacataa aagatatttc cggaaaataa    540

aaaatctcat ttcagcattt cagaagccag atcaaggcat tgtaatacct ctgcagtatc    600

cagttgagaa gaagtcctca gctagaagta cacaaggtac tacagggata agagaagatc    660

ctgatgtctg cctgaaagcc ccatgaagaa aaataaaaca ccttgtactt tattttctat    720

aatttaaata tatgctaagt cttatatatt gtagataata cagttcggtg agctacaaat    780

gcatttctaa agccattgta gtcctgtaat ggaagcatct agcatgtcgt caaagctgaa    840

atggactttt gtacatagtg aggagctttg aaacgaggat tgggaaaaag taattccgta    900

ggttattttc agttattata tttacaaatg ggaaacaaaa ggataatgaa tactttataa    960

aggattaatg tcaattcttg ccaaatataa ataaaaataa tcctcagttt ttgtgaaaag   1020

ctccattttt agtgaaatat tattttatag ctactaattt taaaatgtct tgcttgattg   1080

tatggtggga agttggctgg tgtcccttgt ctttgccaag ttctccacta gctatggtgt   1140
```

-continued

```
catagggctct tttgggattt ttgaagctgt atactgtgtg ctaaaacaag cactaaacaa   1200
agagtgaagg atttatgttt aattctgaaa gcaaccttct tgcctagtgt tctgatattg   1260
gacagtaaaa tccacagacc aacctggagt tgaaaatctt ataatttaaa atatgctcta   1320
aacatgttta tcgtatttga tgctacagga tttgaaattg tattacaaat ccaatgaaat   1380
gagtttttct tttcatttac ctctgcccca gttgtttcta ctacatggaa gacctcattt   1440
tgaagggaaa tttcagcagc tgcagctcat gagtaactga tttgtaacaa gcctcctttt   1500
aaagtaaccc tacaaaacca ctggaaagtt tatggttgta ttattttta aaaaaattcc     1560
aagtgattga aacctacacg agatacagaa ttttatgcgg cattttcttc tcacatttat   1620
atttttgtga ttttgtgatt gattatatgt cactttgcta cagggctcac agaattcatt   1680
cactcaacaa acataatagg gcgctgaggg catagaagta aaaacacctg gtccctgctc   1740
tcagttcact gtcttgttgg acgagaaaag aaacaataac gataaaagac agtgaaagaa   1800
aataacgata aaagacagtg aaagaaaata acaataaaag acaaggaaaa aataacaatg   1860
aaagttgata agtacatgat aagcgaggtt ccccgtgtgt aggtagatct ggtctttaga   1920
ggcagataga taggtcagtg caaatactct ggtccatggg ccatatgaaa aggctaagct   1980
tcactgtaaa ataataactg ggaattctgg attgtgtatg ggtgttggtg aacttggttt   2040
taattagtga actgctgaga gacagagcta ttctccatgt actggcaaga cctgatttct   2100
gagcatttaa tatggatgcc gtgggagtac aaaagtggag tgtggcctga gtaatgcatt   2160
atgggtggtt taccatttct tgaggtaaaa gcatcacatg aacttgtaaa ggaatttaaa   2220
aatcctactt tcataataag ttgcataggt ttaataattt ttaattatat ggcttgagtt   2280
taaattgtaa taggcgtaac taattttaac tctataatgt gttcattctg gaataatcct   2340
aaacatatga attatgtttg catgttcact tccaagagcc tttttttgaa aaaaagcttt   2400
ttttgaatca tcaagtcttt cacatttaaa taaagtgttt gaaagcttta tttaaaaaaa   2460
aaaaaaaaaa aaaaaaaaaa aaaaaaaaaa aaaaaaaaaa aaaaaaaaaa aaaaaaaaaa   2520
aagaaaaaaa                                                          2530
```

<210> SEQ ID NO 71
<211> LENGTH: 601
<212> TYPE: DNA
<213> ORGANISM: Homo sapiens

<400> SEQUENCE: 71

```
aattgttttc taagtaattg ctgcctctat tatggcactt catttttgca ctgtcttttg     60
agattcaaga aaaatttcta ttcttttttt tgcatccaat tgtgcctgaa cttttaaaat    120
atgtaaatgc tgccatgttc caaacccatc gtcagtgtgt gtgtttagag ctgtgcaccc    180
tagaaacaac atattgtccc atgagcaggt gcctgagaca cagacccctt tgcattcaca    240
gagaggtcat tggttataga gacttgaatt aataagtgac attatgccag tttctgttct    300
ctcacaggtg ataaacaatg ctttttgtgc actacatact cttcagtgta gagctcttgt    360
tttatgggaa aaggctcaaa tgccaaattg tgtttgatgg attaatatgc ccttttgccg    420
atgcatacta ttactgatgt gactcggttt tgtcgcagct ttgctttgtt taatgaaaca    480
cacttgtaaa cctcttttgc actttgaaaa agaatccagc gggatgctcg agcacctgta    540
aacaattttc tcaacctatt tgatgttcaa ataaagaatt aaactaaaaa aaaaaaaaaa    600
a                                                                    601
```

<210> SEQ ID NO 72
<211> LENGTH: 1286
<212> TYPE: DNA
<213> ORGANISM: Homo sapiens

<400> SEQUENCE: 72
ggcgccgcgg acgctgctgg agtcgcctgg caacgatgtc gcctggcaac tgaataggtt 60
ggccagtggc gcgggctact ggaagcagaa agggctgcgg aggcagtgag tggtttctgc 120
agagcttcat ttggaaaggc ctctgtagtt ggggaaagat ggcccattcc cagaactcct 180
tggagcttcc cattaacatc aatgccaccc agattaccac tgcctatggc catcgggccc 240
tgcccaagct gaaggaggag ctgcagtcag aggacctcca gacgaggcag aaagccctca 300
tggccctgtg tgacctcatg catgaccccg agtgtatcta caaggccatg aacataggct 360
gtatggagaa cctgaaagct ttgctgaagg atagcaacag tatggtgcgc ataaagacca 420
ccgaggtgct ccacatcacg gcaagccata gcgtgggcag atacgccttt ctagagcacg 480
acatcgtcct tgccctgtcc ttcctgctga atgaccccag cccagtctgc cgggggaacc 540
tgtacaaggc atacatgcag ctggtccagg tgcctagagg ggcccaagag atcatcagca 600
aaggtctgat ttcctcactg gtatggaagc tgcaggtgga ggtggaggag gaggagttcc 660
aggagttcat cctggacaca ctggtcctct gcctgcagga ggatgccacc gaggccctgg 720
gcagcaatgt ggtgcttgtc ctgaagcaga agctcctcag cgccaaccag aacatccgca 780
gcaaggccgc ccgtgcgctc cttaatgtca gcatatctcg agagggcaag aaacaggtgt 840
gtcattttga cgtcatcccc atcctggtcc atctgctgaa agacccagtg gagcatgtga 900
agtctaacgc tgccggtgcc ctgatgttcg ccacagtgat cactgaaggg aagtatgcgg 960
ccctggaggc acaagccatc ggcctgctcc tggagctgct gcactccccc atgaccatag 1020
cgcgcctgaa tgccaccaag gcccttacca tgctggcaga ggcccccgag ggccgcaagg 1080
ccctgcagac gcacgtgccc actttccgtg ccatggaggt ggagacttac gaaaagcctc 1140
aagtggccga agccttacag cgggcagccc ggatcgccat cagtgtcatc gagttcaaac 1200
cctgagccct tcattcacct ctgtgagtga ataaatgtgc taagtctctt taaaaaaaaa 1260
aaaaaaaaaa aaaaaaaaaa aaaaaa 1286

<210> SEQ ID NO 73
<211> LENGTH: 2651
<212> TYPE: DNA
<213> ORGANISM: Homo sapiens

<400> SEQUENCE: 73
agagcagtaa gcttgtgata aaggccaatt ccaggtagct cttgaaggtg atagccatct 60
actttccagt ggctgccaac cacagggagt gccagttaac actggaagga ttaaggcaag 120
gtcccttctc ttgagactcc cctctgagat ctgaaaaatg aagtggctta ggaacatcag 180
cagtgaagaa ctgccaagag ttggtgaagg ttgtctcttc cgagggcctt ctgaagacag 240
ggctcttgaa cagacaagtg gaagggctgt accagggata aaggaaagaa gtgcctgtcc 300
agcagggagc ttgaatttaa gttccatgta tgaagtcatt ggctctatct gcatttttct 360
gtcattctct tcatttgttt taaggtggaa aatttcttta cagttgatgc aaagtatcaa 420
ctactttacc ctaccttctc cccttttaga tgggttcttc ctgagttttg gagtcttgta 480
tgattatcag tattcccctg tcaaaatcaa atctattcag gtttcttcac tgttgagaac 540
acctaaatgt ttttattttt gagaagtggg gacagagtct cactatgtca cccaggctgg 600

```
agtgcaatgg catgatctca gctcactgca accttcgcct cctgggttca agcgattctc    660
ctgcctccgc ctcctgagta gctgggatta taggcacgca ccaccacgcc cagctaattt    720
tttgtatttt tagtagagac agagtttcac catgttggcc aggctggtct tgaactcctg    780
accttgtgat ccacccacct cggcctccca gagtgctggg attacaggca tgagccacca    840
cgcttggcta agaacaccta aatttttatg tttcttggct caaaaaccag ttccatttct    900
aatgttgtcc tcacaagaag gctaattggt ggtgagacag caggggagga ggaagagctg    960
tggtttgtaa cttgttcaac tcaggcaata agcgatttta gctttattta aagtcttctg   1020
tccagcttta agcactttgt aagacatggc tgaaagtagc ttttctatca gaattgcaga   1080
tagtcatgtt gggctaacag tcaattggat atattccttt acctcacatg accccagcaa   1140
ctgtggtggt atctagaggt gaaacaggca agtgaaatgg acacctctgc tgtgaatgtt   1200
ttagagaagg aaattcaaaa aatgttgtaa ctgaaagcac tgttgaatat gggtatcggc   1260
tttctttttc actttgactc ttaacattat cagtcaactt ccacattaat gaaagttgac   1320
catagttatt tccaaataaa aagaaaccaa ctcttaccag gtcttggact gtgatgtcat   1380
attattcagt tttatgcttg ttcctgagca gaactcataa gagtgacata gtcagctgct   1440
gacggcacct cagccacgcc actcttactc agttcagtgg gtgtgcttgc gtggtaggat   1500
gtggtgcagc cctctctacg ctcttctatt tttggtatat ttcctatcta accttcaaat   1560
agcttccaat tcttttttc ttggactggc ttcattctga atttgtgcta aaataatctt   1620
tcataaagag acctcagttt atagcgtaac agactacaca atgcactgat gttttcataa   1680
tgtttaaggg acccactgca agaagcttgc tgcctccttt taattgtatt catttagatt   1740
ttgattttcc atgttaagaa ggtgaggtcc atgttggtgc ccttcagagt agagaaccat   1800
gtaaacatta ggaatgaaca gaggccttag gaatgaatag agagtttgcc ttatacaatt   1860
tcctgttaca aagctctccc tctcatgcaa agtagggaac accttttgag catctttgaa   1920
tttgacaaat ggtgctgttg caaacacttt tttttgaga tgaagtctcg cggttgtcac   1980
ccgggctgga gtgcagtggc gtgatctcgg ctcactgcaa cttccacctc ctgggttcca   2040
gcagttctcc tgcctcagcc tcccaagtag ctgagattac aggcgcctgc caccccacct   2100
ggctgatttt tgtaatttta gtagagacgg ggtttcacca tgttggccag gctgattaac   2160
tcctgacctc aggtgatcca cctttctcgg cctcccaaag tgctgggatt acgggtgtga   2220
gccaccgtgc ccggcctgca aacacatttt aattgacaac actagggctg ttgtacaaaa   2280
tagtaatgat agccatggaa gttttacctt attctgtgag aagtgttctt aaacttatta   2340
agtgtctaaa ctaaggttta gtgctttttt aaaggaaagt tgtcccagga ttcatcctaa   2400
agaaagcaaa agttaattca actgatccac caatggaatt agatgggtag agttgggttc   2460
ttgagtttta ccaccactta gttcccactg aattttgtaa cttcctgtgt ttgcatcctc   2520
tgttcctatt ctgcccttgc tctgtgtcat ctcagtcatt tgacttagaa agtgcccttc   2580
aaaaggaccc tgttcactgc tgcacttttc aatgaattaa aatttatttc tgttctaaaa   2640
aaaaaaaaaa a                                                        2651
```

<210> SEQ ID NO 74
<211> LENGTH: 3403
<212> TYPE: DNA
<213> ORGANISM: Homo sapiens

<400> SEQUENCE: 74

-continued

```
tgatcaacaa ctgtcagctc ccagtcagag agaaagggcc tcttcagtct gtctcaggag     60
actgggagaa acagcataaa ggaccccaca aggaagggag aggtaccctg ggtcaggcgc    120
ttgtggagag agggcttcgc atgtaaagtg acgtcaggga aaatagaaca gaaaaaaagc    180
cagggccagc ccagaggcac ctgagaagaa tcagacccac agctcagccc agccctggca    240
cagagaagag acaggcctgg cagcacccag ggaccccctt tcctcagcct ccacctgcag    300
gacagcagga gcactgatgc gctgaaggta cgttctggag tctggaagca gcagaactga    360
aggaagtaaa cacgggtgtc tgggaagacc cctcaagctg cagtaaagcc caggactgaa    420
ttggccacct gaggccaagg gtggcactcc aacctcctcc taaaggctgg ctagagccac    480
aggaaagggc cagaagccag agaaagggca aaggtggacc cctgcctcca aacctcctct    540
ggagactgac ctcctctttc ctgtgcctta ttgtttctcc ctcttctctt tgttcgccac    600
tgggcggtga cctcagggat cctggcctaa cctggtgatt gtgcaggcaa ctgtgtccga    660
gaagaccctt ctctggaaga ttgaacccca attcagccat ggtgactcct ttgatgtcaa    720
actggtaagg gctgagccgt gggcacagga taccactcct tccagctctt ctgctgtgac    780
ctgcccatgg aagtccctgt ggacacgaaa tcctgtttgg atcatctaac tggaggctct    840
ctgttcttca cctccacgcg ccctcttgac cccaggaggt tcaggggagg aagtacgcca    900
ctctccactg gcaccctcct tggcctacac agagtcaccc ctgagcccct caatgtgtgc    960
tgaggtgggc cctgctctct gcaggggtat ggagagaaat agcttggggt gctgtgaggc   1020
cccgaagaag ctgggcctgt ccttctccat cgaggcgatc ctaaagaggc ctgccaggag   1080
gagtgatatg gacagaccag aagggccagg tgaagagggc cccggagaag ctgcggcctc   1140
aggctctggg ctagaaaagc ctccaaagga ccagccccag gaaggaagga agagcaagcg   1200
gagggttcgt accaccttca ccactgagca gctgcatgag ctggagaaga tcttccactt   1260
tacccactac ccagacgttc acatccgcag ccagctggca gccaggatca acctcccaga   1320
agctcgggtg cagatctggt tccagaatca gcgagccaag tggcggaagc aggagaagat   1380
tggcaacctg gggctccac agcagctgag tgaagccagt gtggtcctgc ccacaaatct   1440
ggatgtggct gggcccacgt ggacatccac tgctctgcgc aggctggctc ctcccacgag   1500
ctgttgtcca tcggctcaag atcagctggc ctctgcctgg ttccctgcct ggatcaccct   1560
cctcccagcg cacccatggg aaacacagcc tgtcccaggt cttcccatcc atcaaacttg   1620
catccctgtg ctatgcatcc ttccacctcc acaccccaaa tggggcagca tctgtgctac   1680
ttcaacatag agattggaca tgctctcccc aaatgagcca ctttcctctc caggtgaagg   1740
caggtagcag atgtgccctg ggcctctggg gaaatcgatc tcacaatcca aaaatggccc   1800
acagcccagg aagctaccct gaacatgcca gttggaaggc tgcaccagac tcaaaagcaa   1860
actaaacaat aaaggacagc tctcttctct cctggctaaa gctgctctcc tggttcagaa   1920
gacaggctgg atgagatctc aggccgagct ctgaaatagg gaggtaatcc tccagcacct   1980
gtgtttcctc taacttgctg tgtgacctcc agccggtcac tcaccctctc tggacctcat   2040
ctgtaagagg agccagctgg ataagatgat ttctgaagac gcttccatgg tgggcactga   2100
ggcacagagg aggccaagga gaggttgttt gttcatgcat gcattcatcc gtgacacatg   2160
agtacctact gaggactcca taaacagaac gggatacaga gataaacaat ttgggttctg   2220
tccacgtttg tcaaaaggtg gtgctggccc acctctgaaa gcagaacact tgctcaacaa   2280
ccttgctgtt ggcccaagtc taacacattc tttatgactg tgagcatctc agagtgagag   2340
aaaaatgtag aaagtttttt aaattctaaa caggatttag tgtctttagt tatcttgctg   2400
```

-continued gatgggaaag ggatgttgtc atttctggca caaatgaaaa gtaggacgga aagctccttt 2460
cattcagttt atctttccag gatatatgaa aagggaccag ctggaagact agcctcactc 2520
tgtcctcgaa agcctgagct ttcattcaac tccctatttc catgcaaaga cgctgggcaa 2580
accacatgtt ctgtctgagc ctcagttttc ctatccataa aatgaaggta gccaggcctg 2640
cctcaaagag cattcaggag gctctgagag gacatgagag tattttgcaa agtgagggca 2700
aggcccagtg tggagtgata ttgttattcc aagattccac tgcaaaagtg gctgctttgg 2760
atgccagccc aggatgagta gttcctgttc tcagggaggt catccgctga gcatcccttc 2820
tgcacagatg tctctgattc ttgtccttgc aggtggagga cagggcctgc tcccctaagc 2880
tgggaagcct ggaatgacct cttgcacaag cctaaattcc aggaatcttc cccaaatccc 2940
agatcctctg caatctacct gcacccctga cccacccagg agttggaccg ggagttggga 3000
agcctaggtc ttagtcctac actccttcta atttgctgtg taaccttacc attaatctct 3060
ctgggtctca gttttctcat ctgtattgga ggtagcagtg ctagctctgc cttcaggcat 3120
gcaatatgcc agaactacag acaacagccc acaggatgca aaagtgcttt gccatcttaa 3180
aaatgccaga tcactcagag cctatgaatg tggatatcaa caccaggtct ctagcaccgc 3240
tggatgaaag gagaaggcta gaggctgagg gaggaaagag cagttaacaa acaaaggcag 3300
tagctcatca cttgggtagc aggtacccat tttaggaccc tacactcaaa tgtgcaaaat 3360
aaaatttcta tcattttgct ataaaaaaaa aaaaaaaaaa aaa 3403

<210> SEQ ID NO 75
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 75
cccggatcgc catcagtgtc atcgagttca aaccctgagc ccttcattca cctctgtgag 60

<210> SEQ ID NO 76
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 76
tgcccttgct ctgtgtcatc tcagtcattt gacttagaaa gtgcccttca aaaggaccct 60

<210> SEQ ID NO 77
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 77
ggagggaggg ctaattatat attttgttgt tcctctatac tttgttctgt tgtctgcgcc 60

<210> SEQ ID NO 78
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 78
cagtttggat tgtataataa cgccaagccc agttgtagtc gtttgagtgc agtaatgaaa 60

<210> SEQ ID NO 79
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 79
aaatcagagt aaccctttct gtattgagtg cagtgttttt tactcttttc tcatgcacat 60

<210> SEQ ID NO 80
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 80
tgcctggcac aaagaaggaa gaatataaat gatagttcga ctcgtctgtg gaagaactta 60

<210> SEQ ID NO 81
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 81
agtcttttgc ttttggcaaa actctactta atccaatggg tttttccctg tacagtagat 60

<210> SEQ ID NO 82
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 82
ggttactgtg ggtggaatag tggaggcctt caactgatta gacaaggccc gcccacatct 60

<210> SEQ ID NO 83
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 83
taaaatgcac tgccctactg ttggtatgac taccgttacc tactgttgtc attgttatta 60

<210> SEQ ID NO 84
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 84
ttctcttttg ggggcaaaca ctatgtcctt ttctttttct agatacagtt aattcctgga 60

<210> SEQ ID NO 85
<211> LENGTH: 60

<212> TYPE: DNA
<213> ORGANISM: Artificial Sequence
<220> FEATURE:
<223> OTHER INFORMATION: Synthetic construct - oligonucleotide

<400> SEQUENCE: 85
aagacccaca ccctgtagca ataccaagtg ctattacata atcaatggac gatttatact 60

<210> SEQ ID NO 86
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 86
agtgttgcaa gtttccttta aaaccaacaa agcccacaag tcctgaattt cccattctta 60

<210> SEQ ID NO 87
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 87
gtcactgtca tagcagctgt gatttcacaa ggaagggtgc tgcaggggga cctggttgat 60

<210> SEQ ID NO 88
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 88
tttcatccag tgttatgcac tttccacagt tggtgttagt atagccagag ggtttcatta 60

<210> SEQ ID NO 89
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 89
gggaagtagg gattattcgt ttaaattcaa tcgcgagcac caagtcggac tggccgggga 60

<210> SEQ ID NO 90
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 90
gggaccaggc cctgggacag ccatgtggct ccaaatgact aaatgtcagc tcaaaaacca 60

<210> SEQ ID NO 91
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 91
tccgtttatg gaggcaattc catatccttt cttgaacgca cattcagctt accccagaga 60

<210> SEQ ID NO 92
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 92
agagttaagc cacttcctgg gtctccttct tatgactgtc tatgggtgca ttgccttctg 60

<210> SEQ ID NO 93
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 93
gtggcctgag taatgcatta tgggtggttt accatttctt gaggtaaaag catcacatga 60

<210> SEQ ID NO 94
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 94
acacatgcat gtgtctgtgt atgtgtgaat gtgagagaga cacagccctc ctttcagaag 60

<210> SEQ ID NO 95
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 95
tctgtaactg cacaaccctg gggtttgctg cagagctatt tctttccatg taaagtagtg 60

<210> SEQ ID NO 96
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 96
aaacactctt tccgactcca gaggagaagc tggcagctct ctgtaagaaa tatgctgatc 60

<210> SEQ ID NO 97
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 97
gcttcctcta tcgcccaatg caaaatcgat gaaatgggga gttctctggg ccaggccaca 60

<210> SEQ ID NO 98
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 98
gtagaatcct ctgttcataa tgaacaagat gaaccaatgt ggattagaaa gaagtccgag 60

<210> SEQ ID NO 99
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 99
ctgttttaaa actgaatggc acgaaattgt tttcctcaac tcggagattc ctgtatggag 60

<210> SEQ ID NO 100
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 100
aataaatagt agctctgctg atgatgacgt tgataaccaa actgttctgt ggtcttaagt 60

<210> SEQ ID NO 101
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 101
caaacagccc ggtcttgatg caggagagtc tggaaaagga agaaaatggt ttcagtttca 60

<210> SEQ ID NO 102
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 102
aacatggacc atccaaattt atggccgtat caaatggtag ctgaaaaaac tatatttgag 60

<210> SEQ ID NO 103
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 103
ttgtaatcat gccaattcca gatcaataac tgcatgtctg ttctttggta gaaatagctt 60

<210> SEQ ID NO 104
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 104
aaagattatt aacccaaatc acctttcttg cttactccag atgcctcagc ctctgatata 60

<210> SEQ ID NO 105
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 105
gacttccttt aggatctcag gcttctgcag ttctcatgac tcctactttt catcctagtc 60

<210> SEQ ID NO 106
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 106
ctgtatattt tgcaatagtt acctcaaggc ctactgacca aattgttgtg ttgagatgat 60

<210> SEQ ID NO 107
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 107
tgttcaaaca gactttaacc tctgcatcat acttaaccct gcgacatgcg tacagtatgc 60

<210> SEQ ID NO 108
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 108
tgagtcatat acatttactg accactgttg cttgttgctc actgtgctgc ttttccatga 60

<210> SEQ ID NO 109
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 109
ctgaaatgtg gatgtgattg cctcaataaa gctcgtcccc attgcttaag ccttcaaaaa 60

<210> SEQ ID NO 110
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 110
atcaagaaaa cctaatcttc tgactcccag gccaggatgt tttatttctc acatcatgtc 60

<210> SEQ ID NO 111
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 111
ttcatttcca aacatcatct ttaagactcc aaggattttt ccaggcacag tggctcatac 60

<210> SEQ ID NO 112
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 112
agttagaaat agaatctgaa tttctaaagg gagattctgg cttgggaagt acatgtagga 60

<210> SEQ ID NO 113
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 113
caattttctt tttactcccc ctcttaaggg ggccttggaa tctatagtat agaatgaact 60

<210> SEQ ID NO 114
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 114
gggtggagtt tcagtgagaa taaacgtgtc tgcctttgtg tgtgtgtata tatacagaga 60

<210> SEQ ID NO 115
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 115
ctcgctcatt ttttaccatg ttttccagtc tgtttaactt ctgcagtgcc ttcactacac 60

<210> SEQ ID NO 116
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 116
ctttgggccg agcactgaat gtcttgtact ttaaaaaaat gtttctgaga cctctttcta 60

<210> SEQ ID NO 117
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 117
ctggaccctt ggagcagtgt tgtgtgaact tgcctagaac tctgccttct ccgttgtcaa 60

<210> SEQ ID NO 118

<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 118
ccacctcctt cgacctccac tgcgccccac ctccctgcct gtgtgtgtta tttcaaagga 60

<210> SEQ ID NO 119
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 119
tctggctggt ggcctgcgcg agggtgcagt cttacttaaa agactttcag ttaattctca 60

<210> SEQ ID NO 120
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 120
agatgctgtc ggcaccatgt ttatttattt ccagtggtca tgctcagcct tgctgctctg 60

<210> SEQ ID NO 121
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 121
tccttcctct tcggtgaatg caggttattt aaactttggg aaatgtactt ttagtctgtc 60

<210> SEQ ID NO 122
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 122
gtcctgtccc tgtctgggag ttgtgttatt taaagatatt ctgtatgttg tatcttttgc 60

<210> SEQ ID NO 123
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 123
attatatttc aggtgtcctg aacaggtcac tagactctac attgggcagc ctttaaatat 60

<210> SEQ ID NO 124
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 124

-continued aggaatggta ctaccgttcc agattttctg taattgcttc tgcaaagtaa taggcttctt 60

<210> SEQ ID NO 125
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 125
ctgtacccaa aggatgccag aatactagta tttttattta tcgtaaacat ccacgagtgc 60

<210> SEQ ID NO 126
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 126
attgcccccc taaccaatca tgcaaacttt tcccccctg gggtaattca ccagttaaaa 60

<210> SEQ ID NO 127
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 127
cccacagtat ttaatgccct gtcagtccct tctagtctga ctcaatggta acttgctgta 60

<210> SEQ ID NO 128
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 128
aaaaccaact ctctactaca caggcctgat aactctgtac gaggcttctc taacccctag 60

<210> SEQ ID NO 129
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 129
ctcagactgg gctccacact cttgggcttc agtctgccca tctgctgaat ggagacagca 60

<210> SEQ ID NO 130
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 130
cctaatgggg attcctctgg ttgttcactg ccaaaactgt ggcattttca ttacaggaga 60

<210> SEQ ID NO 131
<211> LENGTH: 60
<212> TYPE: DNA

<213> ORGANISM: Artificial Sequence
<220> FEATURE:
<223> OTHER INFORMATION: Synthetic construct - oligonucleotide

<400> SEQUENCE: 131
cactcacaat tgttgactaa aatgctgcct ttaaaacata ggaaagtaga atggttgagt 60

<210> SEQ ID NO 132
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 132
ctttgaaggg ctgctgcaca ttgttgaatc catcgacctt tagctgcaat gggatctcta 60

<210> SEQ ID NO 133
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 133
tgcctcatcg atattatagg ggtccatcac aacccaactg tgtggccgga tcctgagtct 60

<210> SEQ ID NO 134
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 134
aaaacagaca aaagcctttg ccttcatgaa gcatacattc attcaggggt agacacacaa 60

<210> SEQ ID NO 135
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 135
taacaaacaa aggcagtagc tcatcacttg ggtagcaggt acccatttta ggaccctaca 60

<210> SEQ ID NO 136
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 136
atatcagaag tgccaataat cgtcataggc ttctgcacgt tggatcaact aatgttgttt 60

<210> SEQ ID NO 137
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 137
atcatagccc aaccatgtga gaagaaggag aaggcccccc tttcttcatt aatctgaaaa 60

<210> SEQ ID NO 138
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 138
gcagaccatt ctatcatacc tggcagggct tctgttttat tttgtaggct ggatgctacc 60

<210> SEQ ID NO 139
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 139
actacaagcc tcttgttttt caccaaaacc ctacatctca ggcttactaa tttttgtgat 60

<210> SEQ ID NO 140
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 140
gccatgcata catgctgcgc atgttttctt cattcgtatg ttagtaaagt tttggttatt 60

<210> SEQ ID NO 141
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 141
cacctattta ttttacctct ttcccaaacc tggagcattt atgcctaggc ttgtcaagaa 60

<210> SEQ ID NO 142
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 142
gtggacatag ccactaacca actagttacc tttggactgc aacaaaaaat gtgaaaatga 60

<210> SEQ ID NO 143
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 143
acttgtaaac ctcttttgca ctttgaaaaa gaatccagcg ggatgctcga gcacctgtaa 60

<210> SEQ ID NO 144
<211> LENGTH: 60
<212> TYPE: DNA
<213> ORGANISM: Artificial Sequence
<220> FEATURE:

<223> OTHER INFORMATION: Synthetic construct - oligonucleotide

<400> SEQUENCE: 144
aattctctat aaacggttca ccagcaaacc accaatacat tccattgttt gcctagagag 60

<210> SEQ ID NO 145
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 145
aatggcccat gcatgctgtt tgcagcagtc aattgagttg aattagaatt ccaaccatac 60

<210> SEQ ID NO 146
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 146
gagctcagta cttgccctgt gaaaatccca gaagcccccg ctgtcaatgt tccccatcca 60

<210> SEQ ID NO 147
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 147
atgaagcgga attaggctcc cgagctaagg gactcgccta gggtctcaca gtgagtagga 60

<210> SEQ ID NO 148
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 148
agtggctata tcaacatcag ggctagcaca tctttctcta ttatccttct attggaattc 60

<210> SEQ ID NO 149
<211> LENGTH: 1108
<212> TYPE: DNA
<213> ORGANISM: Homo sapiens

<400> SEQUENCE: 149
gagtgagtga gagggcagag gaaatactca atctgtgcca ctcactgcct tgagcctgct 60
tcctcactcc aggactgcca gaggctcact cccttgagcc tgcttcctca ctccaggact 120
gccagaggaa gcaatcacca aaatgaagac tgctttaatt ttgctcagca ttttgggaat 180
ggcctgtgct ttctcaatga aaaatttgca tcgaagagtc aaaatagagg attctgaaga 240
aaatggggtc tttaagtaca ggccacgata ttatctttac aagcatgcct acttttatcc 300
tcatttaaaa cgatttccag ttcagggcag tagtgactca tccgaagaaa atggagatga 360
cagttcagaa gaggaggagg aagaagagga gacttcaaat gaaggagaaa acaatgaaga 420
atcgaatgaa gatgaagact ctgaggctga gaataccaca ctttctgcta caacactggg 480
ctatggagag gacgccacgc ctggcacagg gtatacaggg ttagctgcaa tccagcttcc 540
caagaaggct ggggatataa caaacaaagc tacaaaagag aaggaaagtg atgaagaaga 600
agaggaggaa gaggaaggaa atgaaaacga agaaagcgaa gcagaagtgg atgaaaacga 660
acaaggcata aacggcacca gtaccaacag cacagaggca gaaaacggca acggcagcag 720
cggaggagac aatggagaag aaggggaaga agaaagtgtc actggagcca atgcagaagg 780
caccacagag accggagggc agggcaaggg cacctcgaag acaacaacct ctccaaatgg 840
tgggtttgaa cctacaaccc caccacaagt ctatagaacc acttccccac cttttgggaa 900
aaccaccacc gttgaatacg agggggagta cgaatacacg ggcgtcaatg aatacgacaa 960
tggatatgaa atctatgaaa gtgagaacgg ggaacctcgt ggggacaatt accgagccta 1020
tgaagatgag tacagctact ttaaaggaca aggctacgat ggctatgatg gtcagaatta 1080
ctaccaccac cagtgaagct ccagcctg 1108

<210> SEQ ID NO 150
<211> LENGTH: 4767
<212> TYPE: DNA
<213> ORGANISM: Homo sapiens

<400> SEQUENCE: 150
gcctcccgcc gcctcccgcg cggccatgga ctgagcgccg ccggccaggc cgcggggatg 60
gggccgccgc tcccgctgct gctgctgcta ctgctgctgc tgccgccacg cgtcctgcct 120
gccgcccctt cgtccgtccc ccgcggccgg cagctcccgg ggcgtctggg ctgcctgctc 180
gaggagggcc tctgcggagc gtccgaggcc tgtgtgaacg atggagtgtt tggaaggtgc 240
cagaaggttc cggcaatgga cttttaccgc tacgaggtgt cgcccgtggc cctgcagcgc 300
ctgcgcgtgg cgttgcagaa gctttccggc acaggtttca cgtggcagga tgactatact 360
cagtatgtga tggaccagga acttgcagac ctcccgaaaa cctacctgag gcgtcctgaa 420
gcatccagcc cagccaggcc ctcaaaacac agcgttggca gcgagaggag gtacagtcgg 480
gagggcggtg ctgccctggc caacgccctc cgacgccacc tgcccttcct ggaggccctg 540
tcccaggccc cagcctcaga cgtgctcgcc aggacccata cggcgcagga cagaccccc 600 gctgagggtg atgaccgctt ctccgagagc atcctgacct atgtggccca cacgtctgcg 660
ctgacctacc ctcccgggcc ccggacccag ctccgcgagg acctcctgcc gcggaccctc 720
ggccagctcc agccagatga gctcagccct aaggtggaca gtggtgtgga cagacaccat 780
ctgatggcgg ccctcagtgc ctatgctgcc cagaggcccc cagctccccc cggggagggc 840
agcctggagc cacagtacct tctgcgtgca ccctcaagaa tgcccaggcc tttgctggca 900
ccagccgccc cccagaagtg gccttcacct ctgggagatt ccgaagaccc ctccagcaca 960
ggcgatggag cacggattca taccctcctg aaggacctgc agaggcagcc ggctgaggtg 1020
aggggcctga gtggcctgga gctggacggc atggctgagc tgatggctgg cctgatgcaa 1080
ggcgtggacc atggagtagc tcgaggcagc cctgggagag cggccctggg agagtctgga 1140
gaacaggcgg atggccccaa ggccaccctc cgtggagaca gctttccaga tgacggagtg 1200
caggacgacg atgatagact ttaccaagag gtccatcgtc tgagtgccac actcgggggc 1260
ctcctgcagg accacgggtc tcgactctta cctggagccc tcccctttgc aaggcccctc 1320
gacatggaga ggaagaagtc cgagcaccct gagtcttccc tgtcttcaga agaggagact 1380
gccggagtgg agaacgtcaa gagccagacg tattccaaag atctgctggg gcagcagccg 1440
cattcggagc ccggggccgc tgcgtttggg gagctccaaa accagatgcc tgggccctcg 1500

-continued

```
aaggaggagc agagccttcc agcgggtgct caggaggccc tcagcgacgg cctgcaattg   1560
gaggtccagc cttccgagga agaggcgcgg ggctacatcg tgacagacag agaccccctg   1620
cgccccgagg aaggaaggcg gctggtggag gacgtcgccc gcctcctgca ggtgcccagc   1680
agtgcgttcg ctgacgtgga ggttctcgga ccagcagtga ccttcaaagt gagcgccaat   1740
gtccaaaacg tgaccactga ggatgtggag aaggccacag ttgacaacaa agacaaactg   1800
gaggaaacct ctggactgaa aattcttcaa accggagtcg ggtcgaaaag caaactcaag   1860
ttcctgcctc ctcaggcgga gcaagaagac tccaccaagt tcatcgcgct caccctggtc   1920
tccctcgcct gcatcctggg cgtcctcctg gcctctggcc tcatctactg cctccgccat   1980
agctctcagc acaggctgaa ggagaagctc tcgggactag ggggcgaccc aggtgcagat   2040
gccactgccg cctaccagga gctgtgccgc cagcgtatgg ccacgcggcc accagaccga   2100
cctgagggcc cgcacacgtc acgcatcagc agcgtctcat cccagttcag cgacgggccg   2160
atccccagcc cctccgcacg cagcagcgcc tcatcctggt ccgaggagcc tgtgcagtcc   2220
aacatggaca tctccaccgg ccacatgatc ctgtcctaca tggaggacca cctgaagaac   2280
aagaaccggc tggagaagga gtgggaagcg ctgtgcgcct accaggcgga gcccaacagc   2340
tcgttcgtgg cccagaggga ggagaacgtg cccaagaacc gctccctggc tgtgctgacc   2400
tatgaccact cccgggtcct gctgaaggcg gagaacagcc acagccactc agactacatc   2460
aacgctagcc ccatcatgga tcacgacccg aggaaccccg cgtacatcgc cacccaggga   2520
ccgctgcccg ccaccgtggc tgacttttgg cagatggtgt gggagagcgg ctgcgtggtg   2580
atcgtcatgc tgacacccct cgcggagaac ggcgtccggc agtgctacca ctactggccg   2640
gatgaaggct ccaatctcta ccacatctat gaggtgaacc tggtctccga gcacatctgg   2700
tgtgaggact tcctggtgag gagcttctat ctgaagaacc tgcagaccaa cgagacgcgc   2760
accgtgacgc agttccactt cctgagttgg tatgaccgag gagtcccttc ctcctcaagg   2820
tccctcctgg acttccgcag aaaagtaaac aagtgctaca ggggccgttc ttgtccaata   2880
attgttcatt gcagtgacgg tgcaggccgg agcggcacct acgtcctgat cgacatggtt   2940
ctcaacaaga tggccaaagg tgctaaagag attgatatcg cagcgaccct ggagcacttg   3000
agggaccaga gacccggcat ggtccagacg aaggagcagt ttgagttcgc gctgacagcc   3060
gtggctgagg aggtgaacgc catcctcaag gcccttcccc agtgagcggc agcctcaggg   3120
gcctcagggg agcccccacc ccacggatgt tgtcaggaat catgatctga ctttaattgt   3180
gtgtcttcta ttataactgc atagtaatag ggcccttagc tctcccgtag tcagcgcagt   3240
ttagcagtta aaagtgtatt tttgtttaat caaacaataa taaagagaga tttgtggaaa   3300
aatccagtta cgggtggagg ggaatcggtt catcaatttt cacttgctta aaaaaaatac   3360
tttttcttaa agcacccgtt caccttcttg gttgaagttg tgttaacaat gcagtagcca   3420
gcacgttcga ggcggtttcc aggaagagtg tgcttgtcat ctgccacttt cgggagggtg   3480
gatccactgt gcaggagtgg ccggggaagc tggcagcact cagtgaggcc gcccggcaca   3540
caaggcacgt ttggcatttc tctttgagag agtttatcat tgggagaagc cgcggggaca   3600
gaactgaacg tcctgcagct tcggggcaag tgagacaatc acagctcctc gctgcgtctc   3660
catcaacact gcgccgggta ccatggacgg ccccgtcagc cacacctgtc agcccaagca   3720
gagtgattca ggggctcccc gggggcagac acctgtgcac cccatgagta gtgcccactt   3780
gaggctggca ctcccctgac ctcacctttg caaagttaca gatgcacccc aacattgaga   3840
tgtgttttta atgttaaaat attgatttct acgttatgaa aacagatgcc cccgtgaatg   3900
```

cttacctgtg agataaccac aaccaggaag aacaaatctg ggcattgagc aagctatgag 3960
ggtccccggg agcacacgaa ccctgccagg cccccgctgg ctcctccagg cacgtcccgg 4020
acctgtgggg ccccagagag gggacatttc cctcctggga gagaaggaga tcagggcaac 4080
tcggagaggg ctgcgagcat ttccctcccg ggagaggaga tcagggcgac ctgcacgcac 4140
tgcgtagagc ctggaaggga agtgagaaac cagccgaccg gccctgcccc tcttcccggg 4200
atcacttaat gaaccacgtg ttttgacatc atgtaaacct aagcacgtag agatgattcg 4260
gatttgacaa aataacattt gagtatccga ttcgccatca cccccctaccc cagaaatagg 4320 acaattcact tcattgacca ggatgatcac atggaaggcg gcgcagaggc agctgtgtgg 4380
gctgcagatt tcctgtgtgg ggttcagcgt agaaaacgca cctccatccc gcccttccca 4440
cagcattcct ccatcttaga tagatggtac tctccaaagg ccctaccaga gggaacacgg 4500
cctactgagc ggacagaatg atgccaaaat attgcttatg tctctacatg gtattgtaat 4560
gaatatctgc tttaatatag ctatcatttc ttttccaaaa ttacttctct ctatctggaa 4620
tttaattaat cgaaatgaat ttatctgaat ataggaagca tatgcctact tgtaatttct 4680
aactccttat gtttgaagag aaacctccgg tgtgagatat acaaatatat ttaattgtgt 4740
catattaaac ttctgattca aaaaaaa 4767

<210> SEQ ID NO 151
<211> LENGTH: 1148
<212> TYPE: DNA
<213> ORGANISM: Homo sapiens

<400> SEQUENCE: 151
ggcacgaggc cacgagctgt tgtgcatcca gaggtggaat tggggcccgg cattccctcc 60
tcgtcccggg ctggcccttg cccccaccct gcaactcctg gttgagatgg gctcagccaa 120
gagcgtccca gtcacaccag cgcggcctcc gccgcacaac aagcatctgg ctcgagtggc 180
ggacccccgt tcacctagtg ctggcatcct gcgcactccc atccaggtgg agagctctcc 240
acagccaggc ctaccagcag gggagcaact ggagggtctt aaacatgccc aggactcaga 300
tccccgctct cctactcttg gtattgcacg gacacctatg aagaccagca gtggagaccc 360
cccaagccca ctggtgaaac agctgagtga agtatttgaa actgaagact ctaaatcaaa 420
tcttccccca gagcctgttc tgcccccaga ggcaccttta tcttctgaat tggacttgcc 480
tctgggtacc cagttatctg ttgaggaaca gatgccacct tggaaccaga ctgagttccc 540
ctccaaacag gtgttttcca aggaggaagc aagacagccc acagaaaccc ctgtggccag 600
ccagagctcc gacaagccct caagggaccc tgagactccc agatcttcag gttctatgcg 660
caatagatgg aaaccaaaca gcagcaaggt actagggaga tccccccctca ccatcctgca 720 ggatgacaac tcccctggca ccctgacact acgacagggt aagcggcctt cacccctaag 780
tgaaaatgtt agtgaactaa aggaaggagc cattcttgga actggacgac ttctgaaaac 840
tggaggacga gcatgggagc aaggccagga ccatgacaag gaaaatcagc actttccctt 900
ggtggagagc taggccctgc atggccccag caatgcagtc acccagggcc tggtgatatc 960
tgtgtcctct cacccccttct ttcccaggga tactgaggaa tggcttgttt tcttagactc 1020
ctcctcagct accaaactgg gactcacagc tttattgggc tttctttgtg tcttgtgtgt 1080
ttcttttata ttaaaggaag taattttaaa tgttacttta aaaaggtaaa aaaaaaaaaa 1140
aaaaaaaa 1148

<210> SEQ ID NO 152
<211> LENGTH: 539
<212> TYPE: DNA
<213> ORGANISM: Homo sapiens

<400> SEQUENCE: 152
gcattcgtag taaaggtgcc caagaaatta ttttggccat ttattgtttt gtccttttct 60
ttaaagaact gttttttttt cttttgttta cttttagacc aaagattggg ttctagaaaa 120
tgcacttggt atactaagta ttaaaacaaa caaaaaggaa agttgtttca gttggcaaca 180
ctgcccattc aattgaatca gaaggggaca aaattaacga ttgccttcag tttgtgttgt 240
gtatattttg atgtatgtgg tcactaacag gtcactttta ttttttctaa atgtagtgaa 300
atgttaatac ctattgtact tataggtaaa ccttgcaaat atgtaacctg tgttgcgcaa 360
atgccgcata aatttgagtg attgttaatg ttgtcttaaa atttcttgat tgtgatactg 420
tggtcatatg cccgtgtttg tcacttacaa aaatgtttac tatgaacaca cagaaataaa 480
aaataggcta aattcatata aaaaaaaaaa aaaaaaaaaa aaaaaaaaaa aaaaaaaaa 539

<210> SEQ ID NO 153
<211> LENGTH: 1673
<212> TYPE: DNA
<213> ORGANISM: Homo sapiens

<400> SEQUENCE: 153
gaggcagtaa ggacttggac tcctctgtcc agcttttaac aatctaagtt acggttaccc 60
tcttctgggt cacgctagaa tcagatctgc tctccagcat cttctgtttc ctggcaagtg 120
tttcctgcta ctttggattg gccacgatgg gctggagctg ccttgtgaca ggagcaggag 180
ggcttctggg tcagaggatc gtccgcctgt tggtggaaga gaaggaactg aaggagatca 240
gggccttgga caaggccttc agaccagaat tgagagagga attttctaag ctccagaaca 300
ggaccaagct gactgtactt gaaggagaca ttctggatga gccattcctg aaaagagcct 360
gccaggacgt ctcggtcgtc atccacaccg cctgtatcat tgatgtcttt ggtgtcactc 420
acagagagtc catcatgaat gtcaatgtga aaggtaccca gctactgttg gaggcctgtg 480
tccaagccag tgtgccagtc ttcatctaca ccagtagcat agaggtagcc gggcccaact 540
cctacaagga aatcatccag aacggccacg aagaagagcc tctggaaaac acatggccca 600
ctccataccc gtacagcaaa aagcttgctg agaaggctgt gctggcggct aatgggtgga 660
atctaaaaaa tggtgatacc ttgtacactt gtgcgttaag acccacatat atctatgggg 720
aaggaggccc attcctttct gccagtataa atgaggccct gaacaacaat gggatcctgt 780
caagtgttgg aaagttctct acagtcaacc cagtctatgt tggcaacgtg gcctgggccc 840
acattctggc cttgagggct ctgcgggacc ccaagaaggc cccaagtgtc cgaggtcaat 900
tctattacat ctcagatgac acgcctcacc aaagctatga taaccttaat tacatcctga 960
gcaaagagtt tggcctccgc cttgattcca gatggagcct tcctttaacc ctgatgtact 1020
ggattggctt cctgctggaa gtagtgagct tcctactcag cccaatttac tcctatcaac 1080 ccccccttcaa ccgccacaca gtcacattat caaatagtgt gttcaccttc tcttacaaga 1140
aggctcagcg agatctggcg tataagccac tctacagctg ggaggaagcc aagcagaaaa 1200
ccgtggagtg ggttggttcc cttgtggacc ggcacaagga gaccctgaag tccaagactc 1260
agtgatttaa ggatgacaga gatgtgcatg tgggtattgt taggaaatgt catcaaactc 1320
cacccacctg gcttcataca gaaggcaaca ggggcacaag cccaggtcct gctgcctctc 1380
tttcacacaa tgcccaactt actgtcttct tcatgtcatc aaaatctgca cagtcactgg 1440
cccaaccaga actttctgtc ctaatcatac accagaagac aaacaatatg atttgctgtt 1500
accaaatctc agtggctgat tctgaacaat tgtggtctct cttaacttga ggttctcttt 1560
tgactaatag agctccattt cccctcttaa atgagaaagc atttcttttc tctttaatct 1620
cctattcctt cacacagttc aacataaaga gcaataaatg ttttaatgct taa 1673

<210> SEQ ID NO 154
<211> LENGTH: 518
<212> TYPE: DNA
<213> ORGANISM: Homo sapiens

<400> SEQUENCE: 154
aaattttgac cccatataaa gaaatgtgtt atgtatgttg tgcctcctta gagacataaa 60
tttagtgtca aaacatggga gatggcttac tcagaagcat actccactta acataccatg 120
gcctgagcta agtaccatgt cctgtttgtg tcttattttt aaatattttc tttgtccaca 180
tgggccgttg accttagagt taaggcggtt gctttttttga agaaatcacc aaagtttctg 240
ggaaactatg ttcaaggttg aaatggagag tagatttaat tttatttgtc ttgtagggaa 300
gaaatcttcc tttgaaccgc ttttcttgct ttttcccttt ttcccaaact aggttacagg 360
ttcttatctg caaggttcaa gttgcttaga cattgttttc cagtattctg cagggccagt 420
cagttgtaca gaagttggaa tattctgttc cagaattaaa gaagttttta gattatgaaa 480
tattatgata ataaagctat atttctgaaa aaaaaaaa 518

<210> SEQ ID NO 155
<211> LENGTH: 2833
<212> TYPE: DNA
<213> ORGANISM: Homo sapiens

<400> SEQUENCE: 155
gaaggagctc tcttcttgct tggcagctgg accaagggag ccagtcttgg gcgctggagg 60
gcctgtcctg accatggtcc ctgcctggct gtggctgctt tgtgtctccg tcccccaggc 120
tctccccaag gcccagcctg cagagctgtc tgtggaagtt ccagaaaact atggtggaaa 180
tttcccttta tacctgacca agttgccgct gccccgtgag gggggctgaag gccagatcgt 240 gctgtcaggg gactcaggca aggcaactga gggcccattt gctatggatc cagattctgg 300
cttcctgctg gtgaccaggg ccctggaccg agaggagcag gcagagtacc agctacaggt 360
caccctggag atgcaggatg gacatgtctt gtggggtcca cagcctgtgc ttgtgcacgt 420
gaaggatgag aatgaccagg tgccccattt ctctcaagcc atctacagag ctcggctgag 480
ccggggtacc aggcctggca tccccttcct cttccttgag gcttcagacc gggatgagcc 540
aggcacagcc aactcggatc ttcgattcca catcctgagc caggctccag cccagccttc 600
cccagacatg ttccagctgg agcctcggct gggggctctg gccctcagcc ccaaggggag 660
caccagcctt gaccacgccc tggagaggac ctaccagctg ttggtacagg tcaaggacat 720
gggtgaccag gcctcaggcc accaggccac tgccaccgtg gaagtctcca tcatagagag 780
cacctgggtg tccctagagc ctatccacct ggcagagaat ctcaaagtcc tatacccgca 840
ccacatggcc caggtacact ggagtggggg tgatgtgcac tatcacctgg agagccatcc 900
cccgggaccc tttgaagtga atgcagaggg aaacctctac gtgaccagag agctggacag 960
agaagcccag gctgagtacc tgctccaggt gcgggctcag aattcccatg gcgaggacta 1020

```
tgcggcccct ctggagctgc acgtgctggt gatggatgag aatgacaacg tgcctatctg   1080
ccctccccgt gaccccacag tcagcatccc tgagctcagt ccaccaggta ctgaagtgac   1140
tagactgtca gcagaggatg cagatgcccc cggctccccc aattcccacg ttgtgtatca   1200
gctcctgagc cctgagcctg aggatggggt agaggggaga gccttccagg tggaccccac   1260
ttcaggcagt gtgacgctgg gggtgctccc actccgagca ggccagaaca tcctgcttct   1320
ggtgctggcc atggacctgg caggcgcaga gggtggcttc agcagcacgt gtgaagtcga   1380
agtcgcagtc acagatatca atgatcacgc ccctgagttc atcacttccc agattgggcc   1440
tataagcctc cctgaggatg tggagcccgg gactctggtg gccatgctaa cagccattga   1500
tgctgacctc gagcccgcct tccgcctcat ggattttgcc attgagaggg gagacacaga   1560
agggactttt ggcctggatt gggagccaga ctctgggcat gttagactca gactctgcaa   1620
gaacctcagt tatgaggcag ctccaagtca tgaggtggtg gtggtggtgc agagtgtggc   1680
gaagctggtg gggccaggcc caggccctgg agccaccgcc acggtgactg tgctagtgga   1740
gagagtgatg ccaccccccca agttggacca ggagagctac gaggccagtg tccccatcag   1800
tgccccagcc ggctctttcc tgctgaccat ccagccctcc gaccccatca gccgaaccct   1860
caggttctcc ctagtcaatg actcagaggg ctggctctgc attgagaaat tctccgggga   1920
ggtgcacacc gcccagtccc tgcagggcgc ccagcctggg gacacctaca cggtgcttgt   1980
ggaggcccag gatacagatg agccgagact gagcgcttct gcacccctgg tgatccactt   2040
cctaaaggcc cctcctgccc cagccctgac tcttgcccct gtgccctccc aatacctctg   2100
cacaccccgc caagaccatg gcttgatcgt gagtggaccc agcaaggacc ccgatctggc   2160
cagtgggcac ggtccctaca gcttcaccct tggtcccaac cccacggtgc aacgggattg   2220
gcgcctccag actctcaatg gttcccatgc ctacctcacc ttggccctgc attgggtgga   2280
gccacgtgaa cacataatcc ccgtggtggt cagccacaat gcccagatgt ggcagctcct   2340
ggttcgagtg atcgtgtgtc gctgcaacgt ggaggggcag tgcatgcgca aggtgggccg   2400
catgaagggc atgcccacga agctgtcggc agtgggcatc cttgtaggca ccctggtagc   2460
aataggaatc ttcctcatcc tcattttcac ccactggacc atgtcaagga agaaggaccc   2520
ggatcaacca gcagacagcg tgcccctgaa ggcgactgtc tgaatggccc aggcagctct   2580
agctgggagc ttggcctctg gctccatctg agtcccctgg gagagagccc agcacccaag   2640
atccagcagg ggacaggaca gagtagaagc ccctccatct gccctggggt ggaggcacca   2700
tcaccatcac caggcatgtc tgcagagcct ggacaccaac tttatggact gcccatggga   2760
gtgctccaaa tgtcagggtg tttgcccaat aataaagccc cagagaactg ggctgggccc   2820
tatgggattg gta                                                      2833
```

<210> SEQ ID NO 156
<211> LENGTH: 592
<212> TYPE: DNA
<213> ORGANISM: Homo sapiens

<400> SEQUENCE: 156

```
tctttaccta tgtgaagcga ggtgacgtga tacgtcactg gcgccgtctt ataatttaga     60
tgtaaaaatc tttagaaaca aataaaactc tctatatatg tgtatgtctg tgtacaaaaa    120
aatgacagag ctgatggcca gtgtatacag agcgtggccc gcggtgtaca atacccatat    180
aaggtacatt gtgcaggagg ggaattgctg gctgctttta cttcctgacc aagactgaaa    240
aattatttac tgaaatctgt aaaccttttt atgaaacttt taagcaccag gctgtttact    300
```

tacacaattt aggtctgcca gaaaattcta tctgtgatag atctgtaaag agggtcaggg 360
gttagagttt actatttttg aagtttacat tgttacatat gaaatggaaa cattattttg 420
aaacgttgtc ataacccaat ggtgcattct gtaaccatgg agtcttctgt ttcctggggg 480
aaaggggcat tcatgacctg aactttttag caaattatta ttctcagttt ccattacctg 540
tttggccaaa cagattaata aaatatttga aaaagaagca ataaaaaaaa aa 592

<210> SEQ ID NO 157
<211> LENGTH: 818
<212> TYPE: DNA
<213> ORGANISM: Homo sapiens
<220> FEATURE:
<221> NAME/KEY: misc_feature
<222> LOCATION: (60)..(60)
<223> OTHER INFORMATION: a or g or c or t/u
<220> FEATURE:
<221> NAME/KEY: misc_feature
<222> LOCATION: (80)..(80)
<223> OTHER INFORMATION: a or g or c or t/u
<220> FEATURE:
<221> NAME/KEY: misc_feature
<222> LOCATION: (114)..(114)
<223> OTHER INFORMATION: a or g or c or t/u
<220> FEATURE:
<221> NAME/KEY: misc_feature
<222> LOCATION: (121)..(121)
<223> OTHER INFORMATION: a or g or c or t/u

<400> SEQUENCE: 157
ctgagaaagt ccggtcccta taaggggaca tcagtgcgag acctgctccg tgctgtgagn 60
acaagaggca ccatacaagn aagctcccag ttgaggtgcg acaggcactc gccnaagtcc 120
ntgatggctt cgtccagtac tcacaaaacg gctccccccg gctggtcctt cacacgcacc 180
gagccatgag gagctggcgc ctctgagagc ctcttcctgc cctactaccc gccagactca 240
gaggccagga ggccatgccc tggggccaca gggaggtgag gtgggctgga tgccacacag 300
atggtctccg tgctggctca ctgaagagct gagcctgtgg ctggcctcag aatcaggctg 360
ggtgcagtgg ctcacacctg taatcccagc attttgggag gctgagtgag aggatcactt 420
gagctcagga gttcgagacc agcctggcca acatggcaac accccatttc tacaaaaaat 480
ttgtaaaatt agccaggcat ggtggcgcac gcctgtagtc ccagctgctt gggaggctga 540
ggtgggagaa tcacttgagc ccaggagttc gaggctgcag tgagccagga tcatgccact 600
gcactccagc ctggtccaca gagagacact gtcacccccct ttcccccaca agactggcag 660
aggctgggca gcctggggct gatgaagcag agatgttcgc tggatcccag gccctggcac 720
ccctcaggaa atacaagaaa aagaatattc acatctgttt aatgtgcata aagccaagga 780
aaggacagtt ccgaattcaa aaaaaaaaaa aaaaaaaa 818

<210> SEQ ID NO 158
<211> LENGTH: 753
<212> TYPE: DNA
<213> ORGANISM: Homo sapiens

<400> SEQUENCE: 158
tttttttttt ttttttaaa tatttaactt atttatttaa caaagtagaa gggaatccat 60
tgctagcttt tctgtgttgg tgtctaatat ttgggtaggg tgggggatcc ccaacaatca 120
ggtcccctga gatagctggt cattgggctg atcattgcca gaatcttctt ctcctggggt 180
ctggcccccc aaaatgccta acccaggacc ttgggaattc tactcatccc aaatgataat 240
tccaaatgct gttacccaag gttagggtgt tgaaggaagg tagagggtgg ggcttcaggt 300
ctcaacggct tccctaacca cccctcttct cttggcccag cctggttccc cccacttcca 360
ctcccctcta ctctctctag gactgggctg atgaaggcac tgcccaaaat ttcccctacc 420
cccaactttc ccctaccccc aactttcccc accagctcca caaccctgtt tggagctact 480
gcaggaccag aagcacaaag tgcggtttcc caagcctttg tccatctcag cccccagagt 540
atatctgtgc ttggggaatc tcacacagaa actcaggagc accccctgcc tgagctaagg 600
gaggtcttat ctctcagggg gggtttaagt gccgtttgca ataatgtcgt cttatttatt 660
tagcggggtg aatattttat actgtaagtg agcaatcaga gtataatgtt tatggtgaca 720
aaattaaagg ctttcttata tgtttaaaaa aaa 753

<210> SEQ ID NO 159
<211> LENGTH: 516
<212> TYPE: DNA
<213> ORGANISM: Homo sapiens

<400> SEQUENCE: 159
gccttataaa gcaccaagag gctgccagtg ggacattttc tcggccctgc cagcccccag 60
gaggaaggtg ggtctgaatc tagcaccatg acggaactag agacagccat gggcatgatc 120
atagacgtct tttcccgata ttcgggcagc gagggcagca cgcagaccct gaccaagggg 180
gagctcaagg tgctgatgga gaaggagcta ccaggcttcc tgcagagtgg aaaagacaag 240
gatgccgtgg ataaattgct caaggacctg gacgccaatg gagatgccca ggtggacttc 300
agtgagttca tcgtgttcgt ggctgcaatc acgtctgcct gtcacaagta ctttgagaag 360
gcaggactca aatgatgccc tggagatgtc acagattcct ggcagagcca tggtcccagg 420
cttcccaaaa gtgtttgtgg caattattcc cctaggctga gcctgctcat gtacctctga 480
ttaataaatg cttatgaaat gaaaaaaaaa aaaaaa 516

<210> SEQ ID NO 160
<211> LENGTH: 354
<212> TYPE: DNA
<213> ORGANISM: Homo sapiens

<400> SEQUENCE: 160
ccagcaaagt ctcttttgac cacacgcttt atccgagatg cttagaagta tatttggctg 60
ttttatttgc atctttgatt aagatgtcta tcattgtaaa aaggtattca aaacaaaagt 120
gtactctttt attattatga atcacattgt actgagctgt gaagtcagtg ttttaaaaat 180
gtagagttta ttcatggagc atgccattga ggtttggatg gtggcaggta aaacagaaag 240
gcaagatgtc atctgacatt aggctactta taaataaatg tttatctagc ttttatttca 300
tgccctaatg aataaaacat gcttcgaaaa agaaagtaaa aaaaaaaaac aaaa 354

<210> SEQ ID NO 161
<211> LENGTH: 2904
<212> TYPE: DNA
<213> ORGANISM: Homo sapiens

<400> SEQUENCE: 161
ggcgagagag acgctcccgc tcgccgccag ctctgattgg cccagcggta ggaaaggtta 60
aaccaaaaat ttttttacag ccctagtgtg cgcctgtagc tcggaaaatt aattgtggct 120
atagccgcct cgatcgctgt ctccccagcc tcgccgcgga cgctccggga cgcgcccgcc 180
cgccgcccgg ttctcccccc ctttgggctg gtgctgctgc tgctgtgact gctgctgcga 240

```
aaggaggagg aggaggagga agcagcgggg gggggagcgg tgggtgtggg ggaaaccaag    300
agtacagtgg acgaggactc accccggcgt ggtgttcttt tttcttcttc tttttctttc    360
ctttttttt ttttttcta attcctgagg ggtggttgct gcttttgcta catgacttgc    420
cagcgcccga gcctgcggtc caactgcgct gctgccggag cgctcagtgc cgccgctgcc    480
gcccgtgccc cccgcgcccc gttcggcacc caccggtcgc cgccccgccc gcgcgccgct    540
gtcccgctcc cgcgccgccg ccgccgtttc cccccgacga ctgggtgatg ctggacatgg    600
gagataggaa agaggtgaaa atgatcccca agtcctcgtt cagcatcaac agcctggtgc    660
ccgagggcct ccagaacgac aaccaccacg cgagccacgg ccaccacaac agccaccacc    720
cccagcacca ccaccaccac caccaccatc accaccaccc gccgccgccc gccccgcaac    780
cgccgccgcc gccgcagcag cagcagccgc cgccgccgcc gagacgcggg gcccggcgcc    840
gacgacgacg aggccccagc agttgttgtt ccgccgcgca cgcacacggc gcgcctgagg    900
gccaacggca gctggcgcaa ggcgaccggc gcggccgggg gatctgcccc gtcgggccgg    960
acgagaagga gaaggcccgc gccggggggg aggagaagaa gggggcgggc gagggcggca   1020
aggacgggga ggggggcaag gagggcgaga agaagaacgg caagtacgag aagccgccgt   1080
tcagctacaa cgcgctcatc atgatggcca tgcggcagag ccccgagaag cggctcacgc   1140
tcaacggcat ctacgagttc atcatgaaga acttccctta ctaccgcgag aacaagcagg   1200
gctggcagaa ctccatccgc cacaatctgt ccctcaacaa gtgcttcgtg aaggtgccgc   1260
gccactacga cgacccgggc aagggcaact actggatgct ggacccgtcg agcgacgacg   1320
tgttcatcgg cggcaccacg ggcaagctgc ggcgctccac cacctcgccg gccaagccgg   1380
ccttcaagcg cggtgccgcg ctcacctcca ccggcctcac cttcatggac gcgccggctc   1440
cctctactgg cccatgtcgc ccttcctgtc cctgcaccac ccccgccagc agcactttga   1500
gttacaacgg gaccacgtcg gcctacccca gccaccccat gccctacagc tccgtgttga   1560
ctcaaaactc gctgggcaac aaccactcct cctccaccgc caacgggctg agcgtggacc   1620
ggctggtcaa cggggggaatc ccgtacgcca cgcaccacct cacggccgcc gcgctaaccg   1680
cctcggtgcc ctgcggcctg ctggtgccct gctctgggac ctactccctc aacccctgct   1740
ccgtcaacct gctcgcgggc cagaccagtt actttttccc ccacgtcccg cacccgtcaa   1800
tgacttcgca gagcagcacg tccatgagcg ccagggccgc gtcctcctcc acgtcgccgg   1860
caggcccccc tcgacccctg ccctgtgagt ctttaagacc ctctttgcca agttttacga   1920
cgggactgtc tgggggactg tctgattatt tcacacatca aaatcagggg tcttcttcca   1980
accctttaat acattaacat ccctgggacc agactgtaag tgaacgtttt acacacattt   2040
gcattgtaaa tgataattaa aaaaataagt ccaggtattt tttattaagc cccccccctcc   2100
catttctgta cgtttgttca gtctctaggg ttgtttatta ttctaacaag gtgtggagtg   2160
tcagcgaggt gcaatgtggg gagaatacat tgtagaatat aaggtttgga agtcaaatta   2220
tagtagaatg tgtatctaaa tagtgactgc tttgccattt cattcaaacc tgacaagtct   2280
atctctaaga gccgccagat ttccatgtgt gcagtattat aagttatcat ggaactatat   2340
ggtggacgca gaccttgaga acaacctaaa ttatggggag aattttaaaa tgttaaactg   2400
taatttgtat ttaaaaagca ttcgtagtaa aggtgcccaa gaaattattt tggccattta   2460
ttgttttctc cttttcttta aagaactgtt ttttttcttt ttgtttactt ttagaccaaa   2520
gattgggcgg ttctagaaaa tgcgccttgg tatactaagt attaaaacaa acaaaaagga   2580
```

-continued

```
aagttgtttc agttaacgct gcccattcaa ttgaatcaga aggggacaaa attaacgatt   2640

gccttcagtt tgtgttgtgt atattttgat gtatgtggtc actaacaggt cacttttatt   2700

ttttctaaat gtagtgaaat gttaatacct attgtactta taggtaaacc ttgcaaatat   2760

gtaacctgtg ttgcgcaaat gccgcataaa tttgagtgat tgttaatgtt gtcttaaaat   2820

ttcttgattg tgactatgtg gtcatatgcc cgtgtttgtc acttacaaaa atgtttacta   2880

tgaacacaca taaataaaaa atag                                          2904
```

<210> SEQ ID NO 162
<211> LENGTH: 2327
<212> TYPE: DNA
<213> ORGANISM: Homo sapiens

<400> SEQUENCE: 162

```
aaaatgctta ctcttgtggg ctacttgttg tgtggaaaaa ggaaaacgga ttcattttcc     60

catcggcgac tttatgacga cagaaatgaa ccagttctgc gattagacaa tgcaccggaa    120

ccttatgatg tgagttttgg gaattctagc tactacaatc caactttgaa tgattcagcc    180

atgccagaaa gtgaagaaaa tgcacgtgat ggcattccta tggatgacat acctccactt    240

cgtacttctg tatagaacta acagcaaaaa ggcgttaaac agcaagtgtc atctacatcc    300

tagccttttg acaaattcat ctttcaaaag gttacacaaa attactgtca cgttggattt    360

tgtcaaggag aatcataaaa gcaggagacc agtagcagaa atgtagacag gatgtatcat    420

ccaaaggttt tctttcttac aatttttggc catcctgagg catttactaa gtagccttaa    480

tttgtatttt agtagtattt tcttagtaga aaatatttgt ggaatcagat aaaactaaaa    540

gatttcacca ttacagccct gcctcataac taaataataa aaattattcc accaaaaaat    600

tctaaaacaa tgaagatgac tctttactgc tctgcctgaa gccctagtac cataattcaa    660

gattgcattt tcttaaatga aaattgaaag ggtgcttttt aaagaaaatt tgacttaaag    720

ctaaaaagag gacatagccc agagtttctg ttattgggaa attgaggcaa tagaaatgac    780

agacctgtat tctagtacgt tataattttc tagatcagca cacacatgat cagcccactg    840

agttatgaag ctgacaatga ctgcattcaa cggggccatg gcaggaaagc tgaccctacc    900

caggaaagta atagcttctt taaaagtctt caaaggtttt gggaatttta acttgtctta    960

atatatctta ggcttcaatt atttgggtgc cttaaaaact caatgagaat catggtaaaa   1020

aaaaaaagtt aaccaaagaa tatacctgta cataatttgt acagttttaa gttgttagat   1080

aggaactgga tttcttatgt attagacatt attgctcaat cataatggaa tagattctgc   1140

atccctaaat gtatgaacca taaggttaaa aaagatgaat ggaaatatca aacaactttt   1200

cactgagcat cagtttcata atcaataata taagaagatt aatttggatt ctagtatgtt   1260

tcagtttgtt tttaattacc accttccttt ggtagaaaaa atatgttcct tgatgtagga   1320

aagtctaggt tttagagatt agaggatgag atcaagagtt aaattcctaa agaagcactg   1380

aatatatgaa gagagcaaac aaatcaagta ccaacctaga ggctttattt ttgaattgat   1440

tcatggtgtg tgtgtgtgtg tgtgtgtgtg tgtgtgtgtg tgtgtaacac agaaacagct   1500

ttcagaaaat aagggataga aagtaatgaa gaaagtactt accccatatt gccataaaaa   1560

tagcaaagaa gactgtccct ccattatcga acaaatatgt cacctgagta gaaaacaaac   1620

agaaatatta gtcatgcaaa ttgattataa taagccagtg aatactgttt gcactcaggt   1680

actatgattt tttctcaaat agaatcatat tattttatag tacagaaata ttatatatga   1740

attcctttca tgggtcttgc aacaatttca catgattttt ctcatgggga gaggtgaaga   1800
```

aacaacatta gccctcttct ctcctctctt gattcccttt ataccccacc atcatttctg 1860
attataaata attctaccat tctatggaag tatttgtggg tcacagattg tcaaactact 1920
taatgaaagt tgtatgaaat tagtttttca ggtgaggcat tcctagttgc aattcctgtt 1980
agcaaaactt ctaggagtgg ggaagttgga aaatgcagga ttcttccagt gagccagcat 2040
ttcccatagc taaccctatt ctcttagtct ttcaaaatgt agaatgggtc caataatggc 2100
tataagatgt aataaatccc atcttaattt gttttaaaag tttcataaat cactgaacac 2160
ttatgaaaca aagtgttttt taatcagata tcaactgaaa cttcataaag gatgcatagt 2220
tttataatgt tattgaatca aattttaagg cttgtattgt ttgattttaa taaagtataa 2280
tctccttttt aaaaaaaaaa aaaaaaaaaa aaaaaaaaaa aaaaaaa 2327

<210> SEQ ID NO 163
<211> LENGTH: 1841
<212> TYPE: DNA
<213> ORGANISM: Homo sapiens

<400> SEQUENCE: 163
ggcacgaggc tgcctgcccc ccgggtgggg ctgcggctct ggcctcccag gcccatcctc 60
aacagctacc ccagccaaca ccaaggccac aaggggaccc cggcctagga ggcaggaagc 120
caaggtacag agagcagcct ggccctcacc agtgcgcaag ctggggcagc aaggctgaca 180
gttgctgcat gcccagggca gggtgtggta ctggcaccca agttcagcat ggcagagctg 240
gccaacagct tgtccccgat ctgcctccag ccccaagatg cctacagccc ccaggcccct 300
tcggcagcac tgcctctgcc cacctgcctt taagagactc cagggctgct cctgtcatgc 360
agcgaaggtt ttgtctgttt caaagttcga gactcaactt gagggactgt ttttgacaat 420
ccccgctgac ctccgctcct cgtggcgccc tggccctaca cccagcctgg cccagggccg 480
gctttgcctg gtgaggctgg agggagcacc aggacctgct gtctgctgtc agcccctcct 540
ggtgctggtg ccctgatgct gtgccttgtc acccattgag ctgcaagagg gaccaagagg 600
gggccacgca gccagccaga tgcctggccc tgtgctgggg cagacaacgc tgcagagccc 660
agggagcctg gcgctaggac gtgcgtcctt gtgacactgg cctgtctgaa ctcacctggc 720
ctgggaagca ccgtctgccc gggcccaagc cctgcccctc cagagtccag agccaggaag 780
gggctgctga gggcgagcat cctgctgggc tctctgcccg gcccacccct ccaaggggct 840
ggcctgtgag ccttgactgg gattcatgat gtggaggccc ccaacttcca gaagcagctg 900
gtactctgct cacacaagcg actgggccgg ccggccctgg accccctagac cccgagccgc 960 ctgccgactg cctgcacagg gagagcagtt gaggcccggg cagggccccc acaccagacc 1020
ccaacatagc ttccccaccc aggcaccccc tcccggggca gcaggcgtgg gagtcagggc 1080
tgcatgctcc tcccctccca cctcacaggc ggccttaggc aagtcatttt ctgtcatcac 1140
aaggtcgcct ctgcctagtc aggtcctggc gtccagagta aggatgtgcg gcccccaggc 1200
ccccgcacac ctccctcagc accaagaccg ggaccccccc acccacgtgt ctcattgtgg 1260
ctgcctatgg actcccgggc cttgtgtgca ggccaggccc ttccactgat tttttaaagt 1320
gaaccattgc tggatctcag attctgtggc atctaaggcc tagcaggggt gggcacacgg 1380
gtcacccgag gcccatacca agactctgtt cctgccctag gcccagtctc aaaggaagcc 1440
acaaggcgcg ggggccactg aggaaggaaa tgttcatttt catttgtcca aaaccacctt 1500
aagttttaag tatattaatc ttgatgcttt ttaactattg ctttttaact tgctgagatt 1560
tagaaatact gttataaaaa cttttttaat ttctgtattt tttttctgta ttgtatcttc 1620
atgggacatt aggggttttc tatggtaagc acacctatgg ttttggtaaa aacattatca 1680
aatatatatc cagacggttc ttccctagaa gaaaaacaag tctttacacc tgataaaata 1740
ttttgcgaag agaggtgttc tttttcctta ctggtgctga aaggaaggat ggataacgag 1800
gagaaaataa aactgtgagg ctcaaaaaaa aaaaaaaaaa a 1841

<210> SEQ ID NO 164
<211> LENGTH: 848
<212> TYPE: DNA
<213> ORGANISM: Homo sapiens

<400> SEQUENCE: 164
cctgcccttc tctatatgta ccatctccaa aaaccatgta catctccaaa aactggagta 60
gaaagttaga ttgctcaact acaactcctc tagaactcta tagctctgac atacagattc 120
acactctcct ctatttgcta agtatgtaaa gaatgttttc ttttaaaatg ttctcttttg 180
agaacaactg cttatttgtt ataaaagcat ttggttaaaa tgatgtcatc ataaagaaca 240
gtggctttgt ttcaatacat atttttgaga tgattatcta gaagccagat taataaaatc 300
agcttgtgac cttgctaagc atataaactg gaaattcaga tacattcaaa attatgggtt 360
catttaaaag tgttctacct tttgggtatg agactaatat cactaattcc tcaatagtta 420
tcatggctct atcttaatta attagaaaat atgtgtgttt aattctttga gaattaaaat 480
agagaatatt aacagagggt taaaaactgc ttcaactcca ataagataaa ggaagctcaa 540
aatctatgag ctgagtgttc aattagcttt gcctactgag ttcaatttta tgtcaataca 600
acagtggatc agacagtacg actttgaact ggtgaatgta aacaattgtt tttcacctaa 660
gctgctttgg aagaactgat gcttgctgct aactaaagtt ttggatgtat cgatttagag 720
aaccaattaa tacctgcaaa ataaagcata ctgtggtact tctgtttgat ctagtatgtg 780
tgattttaga ttgatggatt aaaaattaat aaagatcata cattccatac caaaaaaaaa 840
aaaaaaaa 848

<210> SEQ ID NO 165
<211> LENGTH: 1767
<212> TYPE: DNA
<213> ORGANISM: Homo sapiens

<400> SEQUENCE: 165
ccagaagcct gcatttctgc attctgctta attccctttc cttagatttg aaagaagcca 60
acactaaacc acaaatatac aacaaggcca ttttctcaaa cgagagtcag cctttaacga 120
aatgaccatg gttgacacag agatgccatt ctggcccacc aactttggga tcagctccgt 180
ggatctctcc gtaatggaag accactccca ctcctttgat atcaagccct tcactactgt 240
tgacttctcc agcatttcta ctccacatta cgaagacatt ccattcacaa gaacagatcc 300
agtggttgca gattacaagt atgacctgaa acttcaagag taccaaagtg caatcaaagt 360
ggagcctgca tctccacctt attattctga gaagactcag ctctacaata agcctcatga 420
agagccttcc aactccctca tggcaattga atgtcgtgtc tgtggagata aagcttctgg 480
atttcactat ggagttcatg cttgtgaagg atgcaagggt ttcttccgga gaacaatcag 540
attgaagctt atctatgaca gatgtgatct taactgtcgg atccacaaaa aaagtagaaa 600
taaatgtcag tactgtcggt ttcagaaatg ccttgcagtg gggatgtctc ataatgccat 660
caggtttggg cggatgccac aggccgagaa ggagaagctg ttggcggaga tctccagtga 720
tatcgaccag ctgaatccag agtccgctga cctccgggcc ctggcaaaac atttgtatga 780
ctcatacata aagtccttcc cgctgaccaa agcaaaggcg agggcgatct tgacaggaaa 840
gacaacagac aaatcaccat tcgttatcta tgacatgaat tccttaatga tgggagaaga 900
taaaatcaag ttcaaacaca tcaccccccct gcaggagcag agcaaagagg tggccatccg 960
catctttcag ggctgccagt ttcgctccgt ggaggctgtg caggagatca cagagtatgc 1020
caaaagcatt cctggttttg taaatcttga cttgaacgac caagtaactc tcctcaaata 1080
tggagtccac gagatcattt acacaatgct ggcctccttg atgaataaag atggggttct 1140
catatccgag ggccaaggct tcatgacaag ggagtttcta aagagcctgc gaaagccttt 1200
tggtgacttt atggagccca agtttgagtt tgctgtgaag ttcaatgcac tggaattaga 1260
tgacagcgac ttggcaatat ttattgctgt cattattctc agtggagacc gcccaggttt 1320
gctgaatgtg aagcccattg aagacattca agacaacctg ctacaagccc tggagctcca 1380
gctgaagctg aaccaccctg agtcctcaca gctgtttgcc aagctgctcc agaaaatgac 1440
agacctcaga cagattgtca cggaacacgt gcagctactg caggtgatca agaagacgga 1500
gacagacatg agtcttcacc cgctcctgca ggagatctac aaggacttgt actagcagag 1560
agtcctgagc cactgccaac atttcccttc ttccagttgc actattctga gggaaaatct 1620
gacacctaag aaatttactg tgaaaaagca ttttaaaaag aaaaggtttt agaatatgat 1680
ctattttatg catattgttt ataaagacac atttacaatt tacttttaat attaaaaatt 1740
accatattat gaaaaaaaaa aaaaaaa 1767

<210> SEQ ID NO 166
<211> LENGTH: 8448
<212> TYPE: DNA
<213> ORGANISM: Homo sapiens

<400> SEQUENCE: 166
gcagtggttt ctcctccttc ctcccaggaa gggccaggaa aatggccctg gtcctggaga 60
tcttcaccct gctggcctcc atctgctggg tgtcggccaa tatcttcgag taccaggttg 120
atgcccagcc ccttcgtccc tgtgagctgc agagggaaac ggcctttctg aagcaagcag 180
actacgtgcc ccagtgtgca gaggatggca gcttccagac tgtccagtgc cagaacgacg 240
gccgctcctg ctggtgtgtg ggtgccaacg gcagtgaagt gctgggcagc aggcagccag 300
gacggcctgt ggcttgtctg tcattttgtc agctacagaa acagcagatc ttactgagtg 360
gctacattaa cagcacagac acctcctacc tccctcagtg tcaggattca ggggactacg 420
cgcctgttca gtgtgatgtg cagcatgtcc agtgctggtg tgtggacgca gaggggatgg 480
aggtgtatgg gacccgccag ctggggaggc caaagcgatg tccaaggagc tgtgaaataa 540
gaaatcgtcg tcttctccac ggggtgggag ataagtcacc accccagtgt tctgcggagg 600
gagagtttat gcctgtccag tgcaaatttg tcaacaccac agacatgatg atttttgatc 660
tggtccacag ctacaacagg tttccagatg catttgtgac cttcagttcc ttccagagga 720
ggttccctga ggtatctggg tattgccact gtgctgacag ccaagggcgg gaactggctg 780
agacaggttt ggagttgtta ctggatgaaa tttatgacac catttttgct ggcctggacc 840
ttccttccac cttcactgaa accaccctgt accggatact gcagagacgg ttcctcgcag 900
ttcaatcagt catctctggc agattccgat gccccacaaa atgtgaagtg gagcggttta 960
cagcaaccag ctttggtcac ccctatgttc caagctgccg ccgaaatggc gactatcagg 1020

-continued

```
cggtgcagtg ccagacggaa gggccctgct ggtgtgtgga cgcccagggg aaggaaatgc   1080
atggaacccg gcagcaaggg gagccgccat cttgtgctga aggccaatct tgtgcctccg   1140
aaaggcagca ggccttgtcc agactctact ttgggacctc aggctacttc agccagcacg   1200
acctgttctc ttccccagag aaaagatggg cctctccaag agtagccaga tttgccacat   1260
cctgcccacc cacgatcaag gagctctttg tggactctgg gcttctccgc ccaatggtgg   1320
agggacagag ccaacagttt tctgtctcag aaaatcttct caaagaagcc atccgagcaa   1380
tttttccctc ccgagggctg gctcgtcttg cccttcagtt taccaccaac ccaaagagac   1440
tccagcaaaa cctttttgga gggaaatttt tggtgaatgt tggccagttt aacttgtctg   1500
gagcccttgg cacaagaggc acatttaact tcagtcaatt tttccagcaa cttggtcttg   1560
caagcttctt gaatggaggg agacaagaag atttggccaa gccactctct gtgggattag   1620
attcaaattc ttccacagga acccctgaag ctgctaagaa ggatggtact atgaataagc   1680
caactgtggg cagctttggc tttgaaatta acctacaaga gaaccaaaat gccctcaaat   1740
tccttgcttc tctcctggag cttccagaat tccttctctt cttgcaacat gctatctctg   1800
tgccagaaga tgtggcaaga gatttaggtg atgtgatgga aacggtactc gactcccaga   1860
cctgtgagca gacacctgaa aggctatttg tcccatcatg cacgacagaa ggaagctatg   1920
aggatgtcca atgcttttcc ggagagtgct ggtgtgtgaa ttcctggggc aaagagcttc   1980
caggctcaag agtcagagat ggacagccaa ggtgccccac agactgtgaa aagcaaaggg   2040
ctcgcatgca aagcctcatg ggcagccagc ctgctggctc caccttgttt gtccctgctt   2100
gtactagtga gggacatttc ctgcctgtcc agtgcttcaa ctcagagtgc tactgtgttg   2160
atgctgaggg tcaggccatt cctggaactc gaagtgcaat agggaagccc aagaaatgcc   2220
ccacgccctg tcaattacag tctgagcaag ctttcctcag gacggtgcag gccctgctct   2280
ctaactccag catgctaccc acccttttccg acacctacat cccacagtgc agcaccgatg   2340
ggcagtggag acaagtgcaa tgcaatgggc ctcctgagca ggtcttcgag ttgtaccaac   2400
gatgggaggc tcagaacaag ggccaggatc tgacgcctgc caagctgcta gtgaagatca   2460
tgagctacag agaagcagct tccggaaact tcagtctctt tattcaaagt ctgtatgagg   2520
ctggccagca agatgtcttc ccggtgctgt cacaataccc ttctctgcaa gatgtcccac   2580
tagcagcact ggaagggaaa cggccccagc ccagggagaa tatcctcctg gagccctacc   2640
tcttctggca gatcttaaat ggccaactca gccaataccc ggggtcctac tcagacttca   2700
gcactccttt ggcacatttt gatcttcgga actgctggtg tgtggatgag gctggccaag   2760
aactggaagg aatgcggtct gagccaagca agctcccaac gtgtcctggc tcctgtgagg   2820
aagcaaagct ccgtgtactg cagttcatta gggaaacgga agagattgtt tcagcttcca   2880
acagttctcg gttccctctg gggagagttt tcctggtggc caagggaatc cggctgagga   2940
atgaggacct cggccttcct ccgctcttcc cgccccggga ggctttcgcg gagtttctgc   3000
gtgggagtga ttacgccatt cgcctggcgg ctcagtctac cttaagcttc tatcagagac   3060
gccgcttttc cccggacgac tcggctggag catccgccct tctgcggtcg ggcccctaca   3120
tgccacagtg tgatgcgttt ggaagttggg agcctgtgca gtgccacgct gggactgggc   3180
actgctggtg tgtagatgag aaaggagggt tcatccctgg ctcactgact gcccgctctc   3240
tgcagattcc acagtgcccg acaacctgcg agaaatctcg aaccagtggg ctgctttcca   3300
gttggaaaca ggctagatcc caagaaaacc catctccaaa agacctgttc gtcccagcct   3360
gcctagaaac aggagaatat gccaggctgc aggcatcggg ggctggcacc tggtgtgtgg   3420
```

-continued accctgcatc aggagaagag ttgcggcctg gctcgagcag cagtgcccag tgcccaagcc 3480
tctgcaatgt gctcaagagt ggagtcctct ctaggagagt cagcccaggc tatgtcccag 3540
cctgcagggc agaggatggg ggcttttccc cagtgcaatg tgaccaggcc cagggcagct 3600
gctggtgtgt catggacagc ggagaagagg tgcctgggac gcgcgtgacc gggggccagc 3660
ccgcctgtga gagcccgcgg tgtccgctgc cattcaacgc gtcggaggtg gttggtggaa 3720
caatcctgtg tgagacaatc tcgggcccca caggctctgc catgcagcag tgccaattgc 3780
tgtgccgcca aggctcctgg agcgtgtttc caccagggcc attgatatgt agcctggaga 3840
gcggacgctg ggagtcacag ctgcctcagc cccgggcctg ccaacggccc cagctgtggc 3900
agaccatcca gacccaaggg cactttcagc tccagctccc gccgggcaag atgtgcagtg 3960
ctgactacgc gggtttgctg cagactttcc aggttttcat attggatgag ctgacagccc 4020
gcggcttctg ccagatccag gtgaagactt ttggcaccct ggtttccatt cctgtctgca 4080
acaactcctc tgtgcaggtg ggttgtctga ccagggagcg tttaggagtg aatgttacat 4140
ggaaatcacg gcttgaggac atcccagtgg cttctcttcc tgacttacat gacattgaga 4200
gagccttggt gggcaaggat ctccttgggc gcttcacaga tctgatccag agtggctcat 4260
tccagcttca tctggactcc aagacgttcc cagcggaaac catccgcttc ctccaagggg 4320
accactttgg cacctctcct aggacacggt ttgggtgctc ggaaggattc taccaagtct 4380
tgacaagtga ggccagtcag gacggactgg gatgcgttaa gtgccatgaa ggaagctatt 4440
cccaagatga ggaatgcatt ccttgtcctg ttggattcta ccaagaacag gcagggagct 4500
tggcctgtgt cccatgtcct gtgggcagaa cgaccatttc tgccggagct ttcagccaga 4560
ctcactgtgt cactgactgt cagaggaacg aagcaggcct gcaatgtgac cagaatggcc 4620
agtatcgagc cagccagaag gacaggggca gtgggaaggc cttctgtgtg gacggcgagg 4680
ggcggaggct gccatggtgg gaaacagagg cccctcttga ggactcacag tgtttgatga 4740
tgcagaagtt tgagaaggtt ccagaatcaa aggtgatctt cgacgccaat gctcctgtgg 4800
ctgtcagatc caaagttcct gattctgagt tccccgtgat gcagtgcttg acagattgca 4860
cagaggacga ggcctgcagc ttcttcaccg tgtccacgac ggagccagag atttcctgtg 4920
atttctatgc ttggacaagt gacaatgttg cctgcatgac ttctgaccag aaacgagatg 4980
cactggggaa ctcaaaggcc accagctttg gaagtcttcg ctgccaggtg aaagtgagga 5040
gccatggtca agattctcca gctgtgtatt tgaaaaaggg ccaaggatcc accacaacac 5100
ttcagaaacg ctttgaaccc actggtttcc aaaacatgct ttctggattg tacaacccca 5160
ttgtgttctc agcctcagga gccaatctaa ccgatgctca cctcttctgt cttcttgcat 5220
gcgaccgtga tctgtgttgc gatggcttcg tcctcacaca ggttcaagga ggtgccatca 5280
tctgtgggtt gctgagctca cccagtgtcc tgctttgtaa tgtcaaagac tggatggatc 5340
cctctgaagc ctgggctaat gctacatgtc ctggtgtgac atatgaccag gagagccacc 5400
aggtgatatt gcgtcttgga gaccaggagt tcatcaagag tctgacaccc ttagaaggaa 5460
ctcaagacac ctttaccaat tttcagcagg tttatctctg gaaagattct gacatggggt 5520
ctcggcctga gtctatggga tgtagaaaaa acacagtgcc aaggccagca tctccaacag 5580
aagcaggttt gacaacagaa cttttctccc ctgtggacct caaccaggtc attgtcaatg 5640
gaaatcaatc actatccagc cagaagcact ggcttttcaa gcacctgttt tcagcccagc 5700
aggcaaacct atggtgcctt tctcgttgtg tgcaggagca ctctttctgt cagctcgcag 5760

-continued

```
agataacaga gagtgcatcc ttgtacttca cctgcaccct ctacccagag gcacaggtgt   5820
gtgatgacat catggagtcc aatacccagg gctgcagact gatcctgcct cagatgccaa   5880
aggccctgtt ccggaagaaa gttatactgg aagataaagt gaagaacttt tacactcgcc   5940
tgccgttcca aaaactgatg gggatatcca ttagaaataa agtgcccatg tctgaaaaat   6000
ctatttctaa tgggttcttt gaatgtgaac gacggtgcga tgcggaccca tgctgcactg   6060
gctttggatt tctaaatgtt tcccagttaa aaggaggaga ggtgacatgt ctcactctga   6120
acagcttggg aattcagatg tgcagtgagg agaatggagg agcctggcgc attttggact   6180
gtggctctcc tgacattgaa gtccacacct atcccttcgg atggtaccag aagcccattg   6240
ctcaaaataa tgctcccagt tttgcccttt tggttgttct gccttccctc acagagaaag   6300
tgtctctgga atcgtggcag tccctggccc tctcttcagt ggttgttgat ccatccatta   6360
ggcactttga tgttgcccat gtcagcactg ctgccaccag caatttctct gctgtccgag   6420
acctctgttt gtcggaatgt tcccaacatg aggcctgtct catcaccact ctgcaaaccc   6480
aactcggggc tgtgagatgt atgttctatg ctgatactca aagctgcaca catagtctgc   6540
agggtcggaa ctgccgactt ctgcttcgtg aagaggccac ccacatctac cggaagccag   6600
gaatctctct gctcagctat gaggcatctg taccttctgt gcccatttcc acccatggcc   6660
ggctgctggg caggtcccag gccatccagg tgggtacctc atggaagcaa gtggaccagt   6720
tccttggagt tccatatgct gccccgcccc tggcagagag gcacttccag gcaccagagc   6780
ccttgaactg gacaggctcc tgggatgcca gcaagccaag gccagctgc tggcagccag    6840
gcaccagaac atccacgtct cctggagtca gtgaagattg tttgtatctc aatgtgttca   6900
tccctcagaa tgtggcccct aacgcgtctg tgctggtgtt cttccacaac accatggaca   6960
gggaggagag tgaaggatgg ccggctatcg acggctcctt cttggctgct gttggcaacc   7020
tcatcgtggt cactgccagc taccgagtgg gtgtcttcgg cttcctgagt tctggatccg   7080
gagaggtgag tggcaactgg gggctgctgg accaggtggc ggctctgacc tgggtgcaga   7140
cccacatccg aggatttggc ggggaccctc ggcgcgtgtc cctggcagca gaccgtggcg   7200
gggctgatgt ggccagcatc caccttctca cggccagggc caccaactcc caacttttcc   7260
ggagagctgt gctgatggga ggctccgcac tctccccggc cgccgtcatc agccatgaga   7320
gggctcagca gcaggcaatt gctttggcaa aggaggtcag ttgccccatg tcatccagcc   7380
aagaagtggt gtcctgcctc cgccagaagc ctgccaatgt cctcaatgat gcccagacca   7440
agctcctggc cgtgagtggc cctttccact actggggtcc tgtgatcgat ggccacttcc   7500
tccgtgagcc tccagccaga gcactgaaga ggtctttatg ggtagaggtc gatctgctca   7560
ttgggagttc tcaggacgac gggctcatca acagagcaaa ggctgtgaag caatttgagg   7620
aaagtcgagg ccggaccagt agcaaaacag cctttacca ggcactgcag aattctctgg    7680
gtggcgagga ctcagatgcc cgcgtcgagg ctgctgctac atggtattac tctctggagc   7740
actccacgga tgactatgcc tccttctccc gggctctgga gaatgccacc cgggactact   7800
ttatcatctg ccctataatc gacatggcca gtgcctgggc aaagagggcc cgaggaaacg   7860
tcttcatgta ccatgctcct gaaaactacg gccatggcag cctggagctg ctggcggatg   7920
ttcagtttgc cttggggctt cccttctacc cagcctacga ggggcagttt tctctggagg   7980
agaagagcct gtcgctgaaa atcatgcagt acttttccca cttcatcaga tcaggaaatc   8040
ccaactaccc ttatgagttc tcacggaaag tacccacatt tgcaaccccc tggcctgact   8100
ttgtaccccg tgctggtgga gagaactaca aggagttcag tgagctgctc cccaatcgac   8160
```

agggcctgaa gaaagccgac tgctccttct ggtccaagta catctcgtct ctgaagacat 8220
ctgcagatgg agccaagggc gggcagtcag cagagagtga agaggaggag ttgacggctg 8280
gatctgggct aagagaagat ctcctaagcc tccaggaacc aggctctaag acctacagca 8340
agtgaccagc ccttgagctc cccaaaaacc tcacccgagg ctgcccacta tggtcatctt 8400
tttctctaaa atagttactt accttcaata aagtatctac atgcggtg 8448

<210> SEQ ID NO 167
<211> LENGTH: 4424
<212> TYPE: DNA
<213> ORGANISM: Homo sapiens

<400> SEQUENCE: 167
agatctctcc agatcacact gtcacgtgta cctagcacat ctcgagaact cctttgggcc 60
gtctggggcc cgggaaggaa gcctgagttc tcaagattcc aggactgaga gtgccagctt 120
gtctcaaagc caggtcaatg gtttctttgc cagccattta ggtgaccaaa cctggcagga 180
atcacagcat ggcagccctt ccccatctgt aatatccaaa gccaccgaga aagagacttt 240
cactgatagt aaccaaagca aaactaaaaa gccaggcatt tctgatgtaa ctgattactc 300
agaccgtgga gattcagaca tggatgaagc cacttactcc agcagtcagg atcatcaaac 360
accaaaacag gaatcttcct cttcagtgaa tacatccaac aagatgaatt ttaaaacttt 420
tccttcatca cctcctaggt ctggagatat ctttgaggtt gaactggcta aaaatgataa 480
cagcttgggg ataagtgtca cgggaggtgt gaatacgagt gtcagacatg gtggcattta 540
tgtgaaagct gttattcccc agggagcagc agagtctgat ggtagaattc acaaaggtga 600
tcgcgtccta gctgtcaatg gagttagtct agaaggagcc acccataagc aagctgtgga 660
aacactgaga aatacaggac aggtggttca tctgttatta gaaaagggac aatctccaac 720
atctaaagaa catgtcccgg taaccccaca gtgtaccctt tcagatcaga atgcccaagg 780
tcaaggccca gaaaaagtga agaaaacaac tcaggtcaaa gactacagct ttgtcactga 840
agaaaataca tttgaggtaa aattatttaa aaatagctca ggtctaggat tcagtttttc 900
tcgagaagat aatcttatac cggagcaaat taatgccagc atagtaaggg ttaaaaagct 960
ctttcctgga cagccagcag cagaaagtgg aaaaattgat gtaggagatg ttatcttgaa 1020
agtgaatgga gcctctttga aaggactatc tcagcaggaa gtcatatctg ctctcagggg 1080
aactgctcca gaagtattct tgcttctctg cagacctcca cctggtgtgc taccggaaat 1140
tgatactgcg cttttgaccc cacttcagtc tccagcacaa gtacttccaa acagcagtaa 1200
agactcttct cagccatcat gtgtggagca aagcaccagc tcagatgaaa atgaaatgtc 1260
agacaaaagc aaaaaacagt gcaagtcccc atccagaaaa gacagttaca gtgacagcag 1320
tgggagtgga gaagatgact tagtgacagc tccagcaaac atatcaaatt cgacctggag 1380
ttcagctttg catcagactc taagcaacat ggtatcacag gcacagagtc atcatgaagc 1440
accaagagtc aagaagatac catttgtacc atgttttact atcctcagga aaaggcccaa 1500
taaaccagag tttgaggaca gtaatccttc ccctctacca ccggatatgg ctcctgggca 1560
gagttatcaa ccccaatcag aatctgcttc ctctagttcg atggataagt atcatataca 1620
tcacatttct gaaccaacta gacaagaaaa ctggacacct ttgaaaaatg acttggaaaa 1680
tcaccttgaa gactttgaac tggaagtaga actcctcatt accctaatta aatcagaaaa 1740
aggaagcctg ggttttacag taaccaaagg caatcagaga attggttgtt atgttcatga 1800

-continued

```
tgtcatacag gatccagcca aaagtgatgg aaggctaaaa cctggggacc ggctcataaa   1860
ggttaatgat acagatgtta ctaatatgac tcatacagat gcagttaatc tgctccgggg   1920
atccaaaaca gtcagattag ttattggacg agttctagaa ttacccagaa taccaatgtt   1980
gcctcatttg ctaccggaca taacactaac gtgcaacaaa gaggagttgg gtttttcctt   2040
atgtggaggt catgacagcc tttatcaagt ggtatatatt agtgatatta atccaaggtc   2100
cgtcgcagcc attgagggta atctccagct attagatgtc atccattatg tgaacggagt   2160
cagcacacaa ggaatgacct tggaggaagt taacagagca ttagacatgt cacttccttc   2220
attggtattg aaagcaacaa gaaatgatct tccagtggtc cccagctcaa agaggtctgc   2280
tgtttcagct ccaaagtcaa ccaaaggcaa tggttcctac agtgtggggt cttgcagcca   2340
gcctgccctc actcctaatg attcattctc cacggttgct ggggaagaaa taaatgaaat   2400
atcgtacccc aaaggaaaat gttctactta tcagataaag ggatcaccaa acttgactct   2460
gcccaaagaa tcttatatac aagaagatga catttatgat gattcccaag aagctgaagt   2520
tatccagtct ctgctggatg ttgtggatga ggagtcccag aatcttttaa acgaaaataa   2580
tgcagcagga tactcctgtg gtccaggtac attaaagatg aatgggaagt tatcagaaga   2640
gagaacagaa gatacagact gcgatggttc acctttacct gagtatttta ctgaggccac   2700
caaaatgaat ggctgtgaag aatattgtga agaaaaagta aaaagtgaaa gcttaattca   2760
gaagccacaa gaaaagaaga ctgatgatga tgaaataaca tggggaaatg atgagttgcc   2820
aatagagaga acaaaccatg aagattctga taaagatcat tcctttctga caaacgatga   2880
gctcgctgta ctccctgtcg tcaaagtgct tccctctggt aaatacacgg gcgccaactt   2940
aaaatcagtc attcgagtcc tgcgggttgc tagatcagga attccttcta aggagctgga   3000
gaatcttcaa gaattaaaac ctttggatca gtgtctaatt gggcaaacta aggaaaacag   3060
aaggaagaac agatataaaa atatacttcc ctatgatgct acaagagtgc ctcttggaga   3120
tgaaggtggc tatatcaatg ccagcttcat taagatacca gttgggaaag aagagttcgt   3180
ttacattgcc tgccaaggac cactgcctac aactgttgga gacttctggc agatgatttg   3240
ggagcaaaaa tccacagtga tagccatgat gactcaagaa gtagaaggag aaaaaatcaa   3300
atgccagcgc tattggccca acatcctagg caaaacaaca atggtcagca acagacttcg   3360
actggctctt gtgagaatgc agcagctgaa gggctttgtg gtgagggcaa tgacccttga   3420
agatattcag accagagagg tgcgccatat ttctcatctg aatttcactg cctggccaga   3480
ccatgataca ccttctcaac cagatgatct gcttactttt atctcctaca tgagacacat   3540
ccacagatca ggcccaatca ttacgcactg cagtgctggc attggacgtt cagggaccct   3600
gatttgcata gatgtggttc tgggattaat cagtcaggat cttgattttg acatctctga   3660
tttggtgcgc tgcatgagac tacaaagaca cggaatggtt cagacagagg atcaatatat   3720
tttctgctat caagtcatcc tttatgtcct gacacgtctt caagcagaag aagagcaaaa   3780
acagcagcct cagcttctga agtgacatga aaagagcctc tggatgcatt tccatttctc   3840
tccttaacct ccagcagact cctgctctct atccaaaata aagatcacag agcagcaagt   3900
tcatacaaca tgcatgttct cctctatctt agaggggtat tcttcttgaa aataaaaaat   3960
attgaaatgc tgtattttta cagctacttt aacctatgat aattatttac aaaattttaa   4020
cactaaccaa acaatgcaga tcttagggat gattaaaggc agcatttgat gatagcagac   4080
attgttacaa ggacatggtg agtctatttt taatgcacca atcttgttta tagcaaaaat   4140
gttttccaat attttaataa agtagttatt tataggcata cttgaaacca gtatttaagc   4200
```

tttaaatgac agtaatattg gcatagaaaa aagtagcaaa tgtttactgt atcaatttct 4260
aatgtttact atatagaatt tcctgtaata tatttatata ctttttcatg aaaatggagt 4320
tatcagttat ctgtttgtta ctgcatcatc tgtttgtaat cattatctca ctttgtaaat 4380
aaaaacacac cttaaaacat gaacaagcca aaaaaaaaaa aaaa 4424

<210> SEQ ID NO 168
<211> LENGTH: 1450
<212> TYPE: DNA
<213> ORGANISM: Homo sapiens

<400> SEQUENCE: 168
ccaggcagca gttagcccgc cgcccgcctg tgtgtcccca gagccatgga gagagccagt 60
ctgatccaga aggccaagct ggcagagcag gccgaacgct atgaggacat ggcagccttc 120
ccaggcagca gttagcccgc cgcccgcctg tgtgtcccca gagccatgga gagagccagt 180
ctgatccaga aggccaagct ggcagagcag gccgaacgct atgaggacat ggcagccttc 240
atgaaaggcg ccgtggagaa gggcgaggag ctctcctgcg aagagcgaaa cctgctctca 300
gtagcctata agaacgtggt gggcggccag agggctgcct ggagggtgct gtccagtatt 360
gagcagaaaa gcaacgagga gggctcggag gagaaggggc ccgaggtgcg tgagtaccgg 420
gagaaggtgg agactgagct ccagggcgtg tgcgacaccg tgctgggcct gctggacagc 480
cacctcatca aggaggccgg ggacgccgag agccgggtct tctacctgaa gatgaagggt 540
gactactacc gctacctggc cgaggtggcc accggtgacg acaagaagcg catcattgac 600
tcagcccggt cagcctacca ggaggccatg gacatcagca agaaggagat gccgcccacc 660
aaccccatcc gcctgggcct ggccctgaac ttttccgtct tccactacga gatcgccaac 720
agccccgagg aggccatctc tctggccaag accactttcg acgaggccat ggctgatctg 780
cacaccctca gcgaggactc ctacaaagac agcaccctca tcatgcagct gctgcgagac 840
aacctgacac tgtggacggc cgacaacgcc ggggaagagg ggggcgaggc tccccaggag 900
ccccagagct gagtgttgcc cgccaccgcc ccgccctgcc ccctccagtc cccgccctgc 960
cgagaggact agtatggggt gggaggcccc acccttctcc cctaggcgct gttcttgctc 1020
caaagggctc cgtggagagg gactggcaga gctgaggcca cctggggctg ggatcccac 1080 tcttcttgca gctgttgagc gcacctaacc actggtcatg cccccacccc tgctctccgc 1140
acccgcttcc tcccgacccc aggaccaggc tacttctccc ctcctcttgc ctccctcctg 1200
cccctgctgc ctcttgattc gtaggaattg aggagtgtct ccgccttgtg gctgagaact 1260
ggacagtggc aggggctgga gatgggtgtg tgtgtgtgtg tgtgtgtgtg tgtgtgcgcg 1320
cgcgccagtg caagaccgag actgagggaa agcatgtctg ctgggtgtga ccatgtttcc 1380
tctcaataaa gttcccctgt gacactcaaa aaaaaaaaaa aaaaaaaaaa aaaaaaaaaa 1440
aaaaaaaaaa 1450

<210> SEQ ID NO 169
<211> LENGTH: 798
<212> TYPE: DNA
<213> ORGANISM: Homo sapiens

<400> SEQUENCE: 169
cggccgcgag gccctgagat gaggctccaa agaccccgac aggccccggc gggtgggagg 60
cgcgcgcccc ggggcgggcg gggctccccc taccggccag acccggggag aggcgcgcgg 120
aggctgcgaa ggttccagaa gggcggggag ggggcgccgc gcgctgaccc tccctgggca 180
ccgctgggga cgatggcgct gctcgccttg ctgctggtcg tggccctacc gcgggtgtgg 240
acagacgcca acctgactgc gagacaacga gatccagagg actcccagcg aacggacgag 300
ggtgacaata gagtgtggtg tcatgtttgt gagagagaaa acactttcga gtgccagaac 360
ccaaggaggt gcaaatggac agagccatac tgcgttatag cggccgtgaa aatatttcca 420 cgtttttca tggttgcgaa gcagtgctcc gctggttgtg cagcgatgga gagacccaag 480
ccagaggaga agcggtttct cctggaagag cccatgccct tcttttacct caagtgttgt 540
aaaattcgct actgcaattt agaggggcca cctatcaact catcagtgtt caaagaatat 600
gctgggagca tgggtgagag ctgtggtggg ctgtggctgg ccatcctcct gctgctggcc 660
tccattgcag ccggcctcag cctgtcttga gccacgggac tgccacagac tgagccttcc 720
ggagcatgga ctcgctccag accgttgtca cctgttgcat taaacttgtt ttctgttgat 780
taaaaaaaaa aaaaaaaa 798

<210> SEQ ID NO 170
<211> LENGTH: 3726
<212> TYPE: DNA
<213> ORGANISM: Homo sapiens

<400> SEQUENCE: 170
ttcagccgga acgttactcc gtgtccaccc ggatcgtgtg tgtgatcgag gctgcggaga 60
cgcctttcac ggggggtgtc gaggtggacg tcttcgggaa actgggccgt tcgcctccca 120
atgtccagtt caccttccaa cagcccaagc ctctcagtgt ggagccgcag cagggaccgc 180
aggcgggcgg caccacactg accatccacg gcacccacct ggacacgggc tcccaggagg 240
acgtgcgggt gaccctcaac ggcgtcccgt gtaaagtgac gaagtttggg gcgcagctcc 300
agtgtgtcac tggcccccag gcgacacggg gccagatgct tctggaggtc tcctacgggg 360
ggtcccccgt gcccaacccc ggcatcttct tcacctaccg cgaaaacccc gtactgcgag 420
ccttcgagcc gctacgaagc tttgccagtg gtggccgcag catcaacgtc acgggtcagg 480
gcttcagcct gatccagagg tttgccatgg tggtcatcgc ggagcccctg cagtcctggc 540
agccgccgcg ggaggctgaa tccctgcagc ccatgacggt ggtgggtaca gactacgtgt 600
tccacaatga caccaaggtc gtcttcctgt ccccggctgt gcctgaggag ccagaggtct 660
acaacctcac ggtgctgatc gagatggacg ggcaccgtgc cctgctcaga acagaggccg 720
gggccttcga gtacgtgcct gaccccaccc ttgagaactt cacaggtggc gtcaagaagc 780
aggtcaacaa gctcatccac gcccggggca ccaatctgaa caaggcgatg acgctgcagg 840
aggccgaggc cttcgtgggt gccgagcgct gcaccatgaa gacgctgacg gagaccgacc 900
tgtactgtga gccccccggag gtgcagcccc cgcccaagcg gcggcagaaa cgagacacca 960
cacacaacct gcccgagttc attgtgaagt tcggctctcg cgagtgggtg ctgggccgcg 1020
tggagtacga cacacgggtg agcgacgtgc cgctcagcct catcttgccg ctggtcatcg 1080
tgcccatggt ggtcgtcatc gcggtgtctg tctactgcta ctggaggaag agccagcagg 1140
ccgaacgaga gtatgagaag atcaagtccc agctggaggg cctggaggag agcgtgcggg 1200
accgctgcaa gaaggaattc acagacctga tgatcgagat ggaggaccag accaacgacg 1260
tgcacgaggc cggcatcccc gtgctggact acaagaccta caccgaccgc gtcttcttcc 1320
tgccctccaa ggacggcgac aaggacgtga tgatcaccgg caagctggac atccccgagc 1380
cgcggcggcc ggtggtggag caggccctct accagttctc caacctgctg aacagcaagt 1440

```
ctttcctcat caatttcatc cacaccctgg agaaccagcg ggagttctcg gcccgcgcca   1500
aggtctactt cgcgtccctg ctgacggtgg cgctgcacgg gaaactggag tactacacgg   1560
acatcatgca cacgctcttc ctggagctcc tggagcagta cgtggtggcc aagaacccca   1620
agctgatgct gcgcaggtct gagactgtgg tggagaggat gctgtccaac tggatgtcca   1680
tctgcctgta ccagtacctc aaggacagtg ccggggagcc cctgtacaag ctcttcaagg   1740
ccatcaaaca tcaggtggaa aagggcccgg tggatgcggt acagaagaag gccaagtaca   1800
ctctcaacga cacggggctg ctgggggatg atgtggagta cgcacccctg acggtgagcg   1860
tgatcgtgca ggacgaggga gtggacgcca tcccggtgaa ggtcctcaac tgtgacacca   1920
tctcccaggt caaggagaag atcattgacc aggtgtaccg tgggcagccc tgctcctgct   1980
ggcccaggcc agacagcgtg gtcctggagt ggcgtccggg ctccacagcg cagatcctgt   2040
cggacctgga cctgacgtca cagcgggagg gccggtggaa gcgcgtcaac acccttatgc   2100
actacaatgt ccgggatgga gccaccctca tcctgtccaa ggtgggggtc tcccagcagc   2160
cggaggacag ccagcaggac ctgcctgggg agcgccatgc cctcctggag gaggagaacc   2220
gggtgtggca cctggtgcgg ccgaccgacg aggtggacga gggcaagtcc aagagaggca   2280
gcgtgaaaga gaaggagcgg acgaaggcca tcaccgagat ctacctgacg cggctgctct   2340
cagtcaaggg cacactgcag cagtttgtgg acaacttctt ccagagcgtg ctggcgcctg   2400
ggcacgcggt gccacctgca gtcaagtact tcttcgactt cctggacgag caggcagaga   2460
agcacaacat ccaggatgaa gacaccatcc acatctggaa gacgaacagt ttaccgctcc   2520
ggttctgggt gaacatcctc aagaaccccc acttcatctt tgacgtgcat gtccacgagg   2580
tggtggacgc ctcgctgtca gtcatcgcgc agaccttcat ggatgcctgc acgcgcacgg   2640
agcataagct gagccgcgat tctcccagca acaagctgct gtacgccaag gagatctcca   2700
cctacaagaa gatggtggag gattactaca aggggatccg gcagatggtg caggtcagcg   2760
accaggacat gaacacacac ctggcagaga tttcccgggc gcacacggac tccttgaaca   2820
ccctcgtggc actccaccag ctctaccaat acacgcagaa gtactatgac gagatcatca   2880
atgccttgga ggaggatcct gccgcccaga agacgcagct ggccttccgc ctgcagcaga   2940
ttgccgctgc actggagaac aaggtcactg acctctgacc tacaatctcc agtgctgcct   3000
tgggacatag gtacctgagg tacctgagag cccctcaggg gaggaggccg agtggctgtg   3060
gctgaggccc ccaccctccc ctggaacgcg ccccaagccg gagtgggtgc agccggaacc   3120
cgcccagcgt ctagactgta gcatcttcct ctgagcaata ccgccgggca ccgcaccagc   3180
accagcccca gccccagctc cctccggccg cagaaccagc atcgggtgtt cactgtcgag   3240
tctcgagtga tttgaaaatg tgccttacgc tgccacgctg ggggcagctg gcctccgcct   3300
ccgcccacgc accagcagcc gcctccatgc cctaggttgg gcccctgggg gatctgaggg   3360
cctgtggccc ccagggcaag ttcccagatc ctatgtctgt ctgtccacca cgagatggga   3420
ggaggagaaa aagcggtacg atgccttcct gacctcaccg gcctccccaa gggtgccggc   3480
actctgggtg gactcacggc tgctgggccc cacgtcaaag gtcaagtgag acgtaggtca   3540
agtcctacgt cggggcccag acatcctggg gtcctggtct gtcagacagg ctgccctaga   3600
gccccaccca gtccgggggg actgggagca gttccaagac caccccaccc ctttttgtaa   3660
atcttgttca ttgtaaatca aatacagcgt ctttttcact ccgaaaaaaa aaaaaaaaaa   3720
aaaaaa                                                              3726
```

<210> SEQ ID NO 171
<211> LENGTH: 2255
<212> TYPE: DNA
<213> ORGANISM: Homo sapiens

<400> SEQUENCE: 171
gatgtgggca cgcctcagag ccagaagttt atggctccca cctgctcaat ctgacaggaa 60
gcttctgctc cccagttctc cccagccact gtggtctaca gattccagga aacccatccc 120
cctgtgacct cagggtgtgc tctgttctcc accctaggga ccagaaggag ccaggagtaa 180
agaactggct tacttggccg ccactgggaa attctgggta attcgagacg ccctggaatt 240
tggacccact ccgctgatag gtggtgggca gggttctagg gaacacaaga ggcggagcca 300
ggtggcttcc ctgtgctggc attcttggct ctctctctct ctctttctct ctctctgtct 360
ctctctctct ctctgtctct cagccttgaa gccgtttccc tctgcgattc atgtaagtgt 420
gactcgattt cagggaaagg gaactcgcgt gggctgagga gaccggagtg gacgggctgg 480
ggaaggcacc gtgatgcccg caaccccgtc cctgaaggtg gtccatgagc tgcctgcctg 540
taccctctgt gcggggccgc tggaggatgc ggtgaccgtt ccctgtggac acaccttctg 600
ccggctctgc ctccccgcgc tctcccagat gggggcccaa tcctcgggca agatcctgct 660
ctgcccgctc tgccaagagg aggagcaggc agagactccc atggcccctg tgcccctggg 720
cccgctggga gaaacttact gcgaggagca cggcgagaag atctacttct tctgcgagaa 780
cgatgccgag ttcctctgtg tgttctgcag ggagggtccc acgcaccagg cgcacaccgt 840
ggggttcctg gacgaggcca ttcagcccta ccgggatcgt ctcaggagtc gactggaagc 900
tctgagcacg gagagagatg agattgagga tgtaaagtgt caagaagacc agaagcttca 960
agtgctgctg actcagatcg aaagcaagaa gcatcaggtg gaaacagctt ttgagaggct 1020
gcagcaggag ctggagcagc agcgatgtct cctgctggcc aggctgaggg agctggagca 1080
gcagatttgg aaggagaggg atgaatatat cacaaaggtc tctgaggaag tcacccggct 1140
tggagcccag gtcaaggagc tggaggagaa gtgtcagcag ccagcaagtg agcttctaca 1200
agatgtcaga gtcaaccaga gcaggtgtga gatgaagact tttgtgagtc ctgaggccat 1260
ttctcctgac cttgtcaaga agatccgtga tttccacagg aaaatactca ccctcccaga 1320
gatgatgagg atgttctcag aaaacttggc gcatcatctg gaaatagatt caggggtcat 1380
cactctggac cctcagaccg ccagccggag cctggttctc tcggaagaca ggaagtcagt 1440
gaggtacacc cggcagaaga agagcctgcc agacagcccc ctgcgcttcg acggcctccc 1500
ggcggttctg ggcttcccgg gcttctcctc cgggcgccac cgctggcagg ttgacctgca 1560
gctgggcgac ggcggcggct gcacggtggg ggtggccggg gagggggtga ggaggaaggg 1620
agagatggga ctcagcgccg aggacggcgt ctgggccgtg atcatctcgc accagcagtg 1680
ctgggccagc acctccccgg gcaccgacct gccgctgagc gagatcccgc gcggcgtgag 1740
agtcgccctg gactacgagg cggggcaggt gaccctccac aacgcccaga cccaggagcc 1800
catcttcacc ttcactgcct ctttctccgg caaagtcttc cctttctttg ccgtctggaa 1860
aaaaggttcc tgccttacgc tgaaaggctg aagtggggcg cgcgaagggc ggcgaagcgg 1920
agacggcggc tctccgggat ccagctccgc ccctggccag tgtgcggccc gggggctccc 1980
tgtgcccgcg tgaggcgaga gaacagggga cttgagtctc gaacagcggt tgtttttact 2040
ttatttatct taggccctca gctccctgac gtcctgagcc tccctgtgac gctctggcct 2100
tctctgcacc tcagagtgca gaaccacaga cggcttcggc tgtgcctagg gcaacagcca 2160
acctaggagc cagcgggctt tcggggaaaa aaaagaaaaa gacatctaaa ataaaatgtt 2220
taaactgttt caaaataaaa aaaaaaaaaa aaaaa 2255

<210> SEQ ID NO 172
<211> LENGTH: 942
<212> TYPE: DNA
<213> ORGANISM: Homo sapiens

<400> SEQUENCE: 172
tttatacatt ctaaatctcc ccagtttctt tggggctgga agatgcaact tccatttaat 60
agaaactttg aaatcttggg gtaagggagc agtgggggga ctagggagaa ggataagaaa 120
tagaattatt gaaaagcccc caccagggac cttcctggcc agaatatgca gagtaattcc 180
tgctggcttc acctttgaaa gtccctcgaa actatgcaga tgaaactgag tctgtttttg 240
atattgtcag atgtattcta ccttggaagt cccaacacct aaactggaat tcttgtattt 300
acatctcctc cactgtcccc cacaccaccc ctcaattcct gctgcccctg ctaatgttaa 360
gcatttttct cttgttatca tcaggttcac attaaaaaca gatacttaca aactgacttg 420
aagcacagat acttttacga atgtgataaa atattttctt aagaaaagga aagaggatgt 480
gggtcaaata aaacaccgca tggatgttga ttggtgaata ctggtgtaag aaaagggagc 540
tcaggaattt ttattactgt atttgtaaat gagtttgaag gaatttgtaa atgccactgg 600
tacattttta aggtgacaca tttgctcctt ataaagttat taaaaattac agggtaagct 660
taaatgacgt ttgccagtag ttttacttta tataatcaat attgatattg ttgctgaact 720
atgtaacttt atgatgcatt tttcagtccc ttttcagagc aaatgctttt gcaatggtag 780
taatgtttag tttaaattga cttaataaat tattacctga gcaaaaaaaa aaaaaaaaaa 840
aaaaaaaaaa taaaaaaaaa aaaaaaaaaa aaaaaaaaaa taataaaaaa aaaaaaaaca 900
aacaaatcaa taaaacttaa acaaaaaaaa aataaaaaaa aa 942

<210> SEQ ID NO 173
<211> LENGTH: 1070
<212> TYPE: DNA
<213> ORGANISM: Homo sapiens

<400> SEQUENCE: 173
gcagagatcg ccacatcgtc ggacaaggtc aaggacgggg gcggcgggaa cgagggctct 60
ccatgcccac cgtgtcccgg gcccatagcc gggcaagccc taggaggcag ccgggcgtcg 120
ccggccccgg cgccgtcacg ctcgccctcg gcgcagtgtc cttttccagg cgggacggtg 180
ctgtcccggc ctctctacta caccgcgccc ttctatcccg gctacacgaa ctatggctcc 240
ttcggacacc ttcatggcca cccggggccg gggccgggcc ccacacccgg tccggggtct 300
catttcaatg gattaaacca gaccgtgttg aaccgagcgg acgctttggc taaagacccg 360
aaaatgttgc ggagccagtc tcagctagac ctgtgcaaag actctcccta tgaattgaag 420
aaaggtatgt ccgacattta acgcgggctg cgtcggtccc ggacttttct aatttattaa 480
aaacatggcc ttggcagtta tttttccatc accgagagag agagacagag agagaaaata 540
aactacccct cctattcaga agtttatagt ttatggagat ggatgacata aaaatgtaaa 600
catctccaca cacacaaaaa aatgtcttaa ccaaccgaaa agaaaaatta aaaaaggatt 660
tgtattaaat cttattctgt atatttaatg tagcattttt gtatttaaat tgataattca 720
atatctttga agtaaattat gaaatcaaga cacctgtaca ggcatttaat gttttttgt 780

-continued aatataaata tatacatttg tgtttccccc aaaactgttt catagttaaa aaatacaagt 840
ttaatttaat tttttacacc tattgattct gctgggtatg agctaaagta ttacggaaag 900
gaaacaggtt atactcttag atttaaaaag tgaaagaaac tgcaggcgcc tttgtaaaat 960
gcaaaatatt taattaaaag agattttaac ataatgagag ccactcatta ctttttagaa 1020
gcctcaataa actgtccatt gccttggtca aaaaaaaaaa aaaaaaaaaa 1070

<210> SEQ ID NO 174
<211> LENGTH: 668
<212> TYPE: DNA
<213> ORGANISM: Homo sapiens
<220> FEATURE:
<221> NAME/KEY: misc_feature
<222> LOCATION: (60)..(60)
<223> OTHER INFORMATION: a or g or c or t/u

<400> SEQUENCE: 174
atatccaaga aatttggaca cctataccta cagaataatg aaatagaaaa gatgaatctn 60
acagtgatgt gtccttctat tgacccacta cattaccacc atttaacata cattcgtgtg 120
gaccaaaata aactaaaaga accaataagc tcatacatct tcttctgctt ccctcatata 180
cacactattt attatggtga acaacgaagc actaatggtc aaacaataca actaaagacc 240
caagttttca ggagatttcc agatgatgat gatgaaagtg aagatcacga tgatcctgac 300
aatgctcatg agagcccaga acaagaagga gcagaagggc actttgacct tcattattat 360
gaaaatcaag aatagcaaga aactatatag gtatacactt acgacttcac aaaacctata 420
cttaatatag taaatctaag taaacatgta ttactcaaag taatatattt agaattatgt 480
attagtataa gatcagaatt gaatttaagt tgttggtgac atctgcatca tttcatagga 540
ttagaactta ctcaaaataa tgtaaatctt taaaaatata aattagaatg acaagtggga 600
atcataaatt aaacgttaat ggtttcttat gctcttttta aatatagaaa tatcatgtta 660
aaaaaaaa 668

<210> SEQ ID NO 175
<211> LENGTH: 2953
<212> TYPE: DNA
<213> ORGANISM: Homo sapiens

<400> SEQUENCE: 175
atgattgcaa cagtggattt aaaagtcaat gaatatgaga aaaaccaaaa atggcttgag 60
atcctaaata agattgaaaa caaaacatac acgaagctca aaaatggaca tgtgtttagg 120
aagcaggcac tgatgagtga agaaaggact ctgttatatg atggccttgt ttactggaaa 180
actgctacag gtcgtttcaa agatatccta gctctacttc taactgatgt gctgctcttt 240
ttacaagaaa aagaccagaa atacatcttt gcagccgttg atcagaagcc atcagttatt 300
tcccttcaaa agcttattgc tagagaagtt gctaatgagg agagaggaat gtttctgatc 360
agtgcttcat ctgctggtcc tgagatgtat gaaattcaca ccaattccaa ggaggaacgc 420
aataactgga tgagacggat ccagcaggct gtagaaagtt gtcctgaaga aaaagggggga 480 aggacaagtg aatctgatga agacaagagg aaagctgaag ccagagtggc caaaattcag 540
caatgtcaag aaatactcac taaccaagac caacaaattt gtgcgtattt ggaggagaag 600
ctgcatatct atgctgaact tggagaactg agcggatttg aggacgtcca tctagagccc 660
cacctcctta ttaaacctga cccaggcgag cctccccagg cagcctcatt actggcagca 720
gcactgaaag aagcattagt cacaggaggg agagaaggaa gaggctgttc ggatgtggat 780

```
cccgggatcc agggtgtggt aaccgacttg gccgtctctg atgcagggga gaaggtggaa    840
tgtagaaatt ttccaggttc ttcacaatca gagattatac aagccataca gaatttaacc    900
cgtctcttat acagccttca ggccgccttg accattcagg acagccacat tgagatccac    960
aggctggttc tccagcagca ggagggcctg tctctcggcc actctatcct ccgaggcggc   1020
cccttgcagg accagaagtc tcgcgacgcg gacaggcagc atgaggagct ggccaatgtg   1080
caccagcttc agcaccagct ccagcagggg cagcggcgct ggctgcgcag gtgtgagcag   1140
cagcagcggg cgcaggcgac cagggagagc tggctgcagg agcgggagcg gagtgccag    1200
tcgcaggagg agctgctgct gcggagccgg ggcgagctgg acctccagct ccaggagtac   1260
cagcacagcc tggagcggct gagggagggc cagcgcctgg tggagaggga gcaggcgagg   1320
atgcgggccc agcagagcct gctgggccac tggaagcacg gccggcagag gagcctgtcc   1380
gcggtgctcc ttccgggtgg ccccgaggta atggaactta atcgatctga gagtttatgt   1440
catgaaaact cattcttcat caatgaagct ttagtacaaa tgtcatttaa cactttcaac   1500
aaactgaatc catcagttat ccatcaggat gccacttacc ctacaactca atctcattct   1560
gacttggtga ggactagtga acatcaagta gacctcaagg tggacccttc tcagccttcg   1620
aatgtcagtc acaaactgtg gacagccgct ggttccggcc atcagatact tcctttccat   1680
gaaagcagca aggattcttg taaaaatggc tccagtatga caaagtgcag ttgtacgttg   1740
acatctcccc cgggactgtg gactggaacc acatctactt tgaaggattt ggacacctcc   1800
cacactgagt ccccaacccc ccatgactca aattcacacc gccctcaact gcaggcgttt   1860
ataacagaag caaagctaaa tctaccgaca aggacaatga ccagacaaga tggggaaact   1920
ggagatggag ccaaagaaaa tattgtttac ctctaattgt gttgtcattt ttccaaacaa   1980
aacaaaacac tggcactttt gggagaaact ttttgtctcc attccttatg tatgtgtgat   2040
tgtctgtgtc caaattgctt taagaataat atttaatatt tcctggaagc tcattttttt   2100
ggcatgagtc taattaaatt attgaaagcc accctgtttg tataatcttt aacttatcaa   2160
atctaatttc agatttctgg aggagaaact aacttgaata agcaggacta ttttaaaagt   2220
tgttttgacg ctagagtaaa attccatgtc acattttcta cccaatcatc tggatttcaa   2280
gattcctttt aagatctcaa tgaagcaatt tggatttaaa gagtggtatt cacaaggggt   2340
gaactttcac agtcagggca gttgcctcag tgcccacata ggcagaggag gatgtgggaa   2400
agggcttttc tcagctagtt tttgtgtgct catttcttct gggagcatta aaagtggtga   2460
tctgttacag tcactattca actgggcacg tgttgtgatt ggtcagtcac tgagccaggg   2520
atacagtccg gacttgctta gtacctaagc ctaatgctgg tggggtttca agacatggtt   2580
cagcatcatc ttttaacaag gcccagaggc ccagagcccg catcaagtca ttttgatgta   2640
aatagtgaac tttgttagag ccctcacttc tatcaatcag ctgtcctgtc cctgccagca   2700
cctggagcac caactaccac tccctggaaa gaacccttcc ctgcagtttt ttaaggacaa   2760
aactgcccac tcctcattaa gtttgctgcc tggatacact tttccacaaa ggaaaactgg   2820
catatcctgc cttccgagta gtatgggtct ctgtgtgaga aaccaggaga tattttcatc   2880
ttgttcggaa atacttgtat gtattttggt gtcaataaat atcttgtacc tcattaaaaa   2940
aaaaaaaaaa aaa                                                      2953
```

<210> SEQ ID NO 176
<211> LENGTH: 4157
<212> TYPE: DNA

<213> ORGANISM: Homo sapiens

<400> SEQUENCE: 176
ctgagccgca tctgcaatag cacacttgcc cggccacctg ctgccgtgag cctttgctgc 60
tgaagcccct ggggtcgcct ctacctgatg aggatgtgca cccccattag gggctgctc 120
atggcccttg cagtgatgtt tgggacagcg atggcatttg cacccatacc ccggatcacc 180
tgggagcaca gagaggtgca cctggtgcag tttcatgagc cagacatcta caactactca 240
gccttgctgc tgagcgagga caaggacacc ttgtacatag gtgcccggga ggcggtcttc 300
gctgtgaacg cactcaacat ctccgagaag cagcatgagg tgtattggaa ggtctcagaa 360
gacaaaaaag caaaatgtgc agaaaagggg aaatcaaaac agacagagtg cctcaactac 420
atccgggtgc tgcagccact cagcgccact tccctttacg tgtgtgggac caacgcattc 480
cagccggcct gtgaccacct gaacttaaca tcctttaagt ttctggggaa aaatgaagat 540
ggcaaaggaa gatgtccctt tgacccagca cacagctaca catccgtcat ggttgatgga 600
gaactttatt cggggacgtc gtataatttt ttgggaagtg aacccatcat ctcccgaaat 660
tcttcccaca gtcctctgag gacagaatat gcaatccctt ggctgaacga gcctagtttc 720
gtgtttgctg acgtgatccg aaaaagccca gacagccccg acggcgagga tgacagggtc 780
tacttcttct tcacggaggt gtctgtggag tatgagtttg tgttcagggt gctgatccca 840
cggatagcaa gagtgtgcaa gggggaccag ggcggcctga ggaccttgca gaagaaatgg 900
acctccttcc tgaaagcccg actcatctgc tcccggccag acagcggctt ggtcttcaat 960
gtgctgcggg atgtcttcgt gctcaggtcc ccgggcctga aggtgcctgt gttctatgca 1020
ctcttcaccc cacagctgaa caacgtgggg ctgtcggcag tgtgcgccta caacctgtcc 1080
acagccgagg aggtcttctc ccacgggaag tacatgcaga gcaccacagt ggagcagtcc 1140
cacaccaagt gggtgcgcta taatggcccg gtacccaagc cgcggcctgg agcgtgcatc 1200
gacagcgagg cacgggccgc caactacacc agctccttga atttgccaga caagacgctg 1260
cagttcgtta aagaccaccc tttgatggat gactcggtaa ccccaataga caacaggccc 1320
aggttaatca agaaagatgt gaactacacc cagatcgtgg tggaccggac ccaggccctg 1380
gatgggactg tctatgatgt catgtttgtc agcacagacc ggggagctct gcacaaagcc 1440
atcagcctcg agcacgctgt tcacatcatc gaggagaccc agctcttcca ggactttgag 1500
ccagtccaga ccctgctgct gtcttcaaag aagggcaaca ggtttgtcta tgctggctct 1560
aactcgggcg tggtccaggc ccgctggcc ttctgtggga agcacggcac ctgcgaggac 1620
tgtgtgctgg cgcgggaccc ctactgcgcc tggagcccgc ccacagcgac ctgcgtggct 1680
ctgcaccaga ccgagagccc cagcaggggt ttgattcagg agatgagcgg cgatgcttct 1740
gtgtgcccgg ataaaagtaa aggaagttac cggcagcatt ttttcaagca cggtggcaca 1800
gcggaactga aatgctccca aaaatccaac ctggcccggg tcttttggaa gttccagaat 1860
ggcgtgttga aggccgagag ccccaagtac ggtcttatgg gcagaaaaaa cttgctcatc 1920
ttcaacttgt cagaaggaga cagtggggtg taccagtgcc tgtcagagga gagggttaag 1980
aacaaaacgg tcttccaagt ggtcgccaag cacgtcctgg aagtgaaggt ggttccaaag 2040
cccgtagtgg cccccacctt gtcagttgtt cagacagaag gtagtaggat tgccaccaaa 2100
gtgttggtgg catccaccca agggtcttct cccccaaccc cagccgtgca ggccacctcc 2160
tccggggcca tcacccttcc tcccaagcct gcgcccaccg gcacatcctg cgaaccaaag 2220
atcgtcatca acacggtccc ccagctccac tcggagaaaa ccatgtatct taagtccagc 2280

```
gacaaccgcc tcctcatgtc cctcttcctc ttcttctttg ttctcttcct ctgcctcttt   2340
ttctacaact gctataaggg atacctgccc agacagtgct tgaaattccg ctcggcccta   2400
ctaattggga agaagaagcc caagtcagat ttctgtgacc gtgagcagag cctgaaggag   2460
acgttagtag agccagggag cttctcccag cagaatgggg agcaccccaa gccagccctg   2520
gacaccggct atgagaccga gcaagacacc atcaccagca aagtccccac ggatagggag   2580
gactcacaga ggatcgacga cctttctgcc agggacaagc cctttgacgt caagtgtgag   2640
ctgaagttcg ctgactcaga cgcagatgga gactgaggcc ggctgtgcat ccccgctggt   2700
gcctcggctg cgacgtgtcc aggcgtggag agttttgtgt ttctcctgtt cagtatccga   2760
gtctcgtgca gtgctgcgta ggttagcccg catcgtgcag acaacctcag tcctcttgtc   2820
tattttctct tgggttgagc ctgtgacttg gtttctcttt gtccttttgg aaaaatgaca   2880
agcattgcat cccagtcttg tgttccgaag tcagtcggag tacttgaaga aggcccacgg   2940
gcggcacgga gttcctgagc cctttctgta gtgggggaaa ggtggctgga cctctgttgg   3000
ctgagaagag catcccttca gcttcccctc cccgtagcag ccactaaaag attatttaat   3060
tccagattgg aaatgacatt ttagtttatc agattggtaa cttatcgcct gttgtccaga   3120
ttggcacgaa ccttttcttc cacttaatta tttttttagg attttgcttt gattgtgttt   3180
atgtcatggg tcattttttt ttagttacag aagcagttgt gttaatattt agaagaagat   3240
gtatatcttc cagattttgt tatatatttg gcataaaata cggcttacgt tgcttaagat   3300
tctcagggat aaacttcctt ttgctaaatg cattctttct gcttttagaa atgtagacat   3360
aaacactccc cggagcccac tcaccttttt tctttttctt tttttttttt taactttatt   3420
ccttgaggga agcattgttt ttggagagat tttctttctg tacttcgttt tacttttctt   3480
ttttttaac ttttactctc tcgaagaaga ggaccttccc acatccacga ggtgggtttt   3540
gagcaaggga aggtagcctg gatgagctga gtggagccag gctggcccag agctgagatg   3600
ggagtgcggt acaatctgga gcccacagct gtcggtcaga acctcctgtg agacagatgg   3660
aaccttcaca agggcgcctt tggttctctg aacatctcct ttctcttctt gcttcaattg   3720
cttacccact gcctgcccag actttctatc cagcctcact gagctgccca ctactggaag   3780
ggaactgggc ctcggtggcc ggggccgcga gctgtgacca cagcaccctc aagcatacgg   3840
cgctgttcct gccactgtcc tgaagatgtg aatgggtggt acgatttcaa cactggttaa   3900
tttcacactc catctccccg ctttgtaaat acccatcggg aagagacttt ttttccatgg   3960
tgaagagcaa taaactctgg atgtttgtgc gcgtgtgtgg acagtcttat cttccagcat   4020
gataggattt gaccattttg gtgtaaacat ttgtgtttta taagatttac cttgttttta   4080
tttttctact ttgaattgta tacatttgga aagtacccaa ataaatgaga agcttctatc   4140
cttaaaaaaa aaaaaaa                                                  4157
```

<210> SEQ ID NO 177
<211> LENGTH: 1023
<212> TYPE: DNA
<213> ORGANISM: Homo sapiens
<220> FEATURE:
<221> NAME/KEY: misc_feature
<222> LOCATION: (4)..(4)
<223> OTHER INFORMATION: a or g or c or t/u
<220> FEATURE:
<221> NAME/KEY: misc_feature
<222> LOCATION: (23)..(23)
<223> OTHER INFORMATION: a or g or c or t/u
<220> FEATURE:

<221> NAME/KEY: misc_feature
<222> LOCATION: (28)..(28)
<223> OTHER INFORMATION: a or g or c or t/u
<220> FEATURE:
<221> NAME/KEY: misc_feature
<222> LOCATION: (47)..(47)
<223> OTHER INFORMATION: a or g or c or t/u
<220> FEATURE:
<221> NAME/KEY: misc_feature
<222> LOCATION: (53)..(53)
<223> OTHER INFORMATION: a or g or c or t/u
<220> FEATURE:
<221> NAME/KEY: misc_feature
<222> LOCATION: (69)..(69)
<223> OTHER INFORMATION: a or g or c or t/u

<400> SEQUENCE: 177
cccntcccca gaggcaggaa aancagtntg ccgaaaggat agactgnggt gcngtctttc 60
cccaagttnt gaactagttt taaggtagct taggatgaaa aatggagaat gattgggggt 120
tccaaaccac tttcttctcc cttggcttat atctcttcac catttggtgg tcaactgtgg 180
gcctaccctg gacctcatct actcagcgag aattggacat gaagctagag gcagctgcct 240
tggaagggaa gtcaggctca cttggacagc ccaggccatg gcaggaagaa tcccttcctc 300
ttggggtcct tgatgggcat gtgtgatggg gaaggagcag tctcccagcc ctgggtctgc 360
tccccacatc tctcctaatt ccacttcacc ttttgccacc ccctccccac cagaggccta 420
gcccttttgt caccgaaggc ccccagagtg tttctgtgtg aaaccctctc atttacactg 480
tggcatcaaa atccacaaaa gatggattaa ttgcactctg gttaatagca gcagcacaat 540
gattaaaatc tatattccta tcttctctag caccctggtg tggggatggg gcggaagggt 600
gtcttgaggg gcagggagga ccccataaaa caatccctcc tgcattctca ggctaaatag 660
ggcccccagt gactacctgt tcttggctgt cccctctgaa gagctctgcc ttctcacagc 720
caccaccagt tgccccactc ccaggaaaac agcacatgtt cttcttctcc tgccttgaga 780
ctgcgtgtta gtcttccatt cataactcat cagcagctca gtccttctta tgtctagtct 840
cagttcattc agccaaagct catttttgtc ctatccaaag tagaaagggt tcttttagaa 900
aacttgaaga atgtgcctcc tcttagcatc tgtttctgac tcccagttat ttttaaaata 960
aatgatgaat aaaatgcctg ccctgaaggg ttctggagga gtcaggtatc aaaaaaaaaa 1020
aaa 1023

<210> SEQ ID NO 178
<211> LENGTH: 550
<212> TYPE: DNA
<213> ORGANISM: Homo sapiens

<400> SEQUENCE: 178
tttttaagat gatcttgctc cgtcacccag gctggagtgc agtggcgtaa tcatggcttc 60
ctgcagcctc aaactcctgg gctcaatgag ttccttgaga tcttccatcc tcagcttccc 120
aagtagctag tagtagtagt ggcttgcacc aacgctcctg ccctaatttt caatattttt 180
tttgtagaga taggatctca ctgtgttacc caagctagac ttgaactcct ggcctcaagc 240
gatccttccg ccttggcctc ccaaagtgtt gggattacag gcattagcta ccacacctgg 300
ccaaggccca ggtttcgaca gaaagggaga gaaaacctgc cagagatgcc atttcggagc 360
cactctgctt ggcagggacc tgtgttcccc tcatgcaggt tcatccttag agggctgcgg 420
tcttatctgg ttgtgcaaaa gtcccacaac ctttctggat tgatagtttg tggtgaaata 480
aacaatttta gtttgtttgg agaatctttt gtatacaaaa tacaaataaa acctaaatca 540

-continued aagaaacaga 550

<210> SEQ ID NO 179
<211> LENGTH: 2798
<212> TYPE: DNA
<213> ORGANISM: Homo sapiens

<400> SEQUENCE: 179
gaggggccgg aggcgtcccc gctcccgctc gctactagcc cgcgggccag cgccgcgtcc 60
cgagccccgg cgggagccat ggctctaaaa ggacaagaag attatattta tcttttcaag 120
gattcaacac atccagtgga ttttctggat gcattcagaa cattttactt ggatggatta 180
tttactgata ttactcttca gtgtccttca ggcataattt tccattgtca ccgagccgtt 240
ttagctgctt gcagcaatta ttttaaggca atgttcacag ctgacatgaa agaaaaattt 300
aaaaataaaa taaaactctc tggcatccac catgatattc tggaaggcct tgtaaattat 360
gcatacactt cccaaattga aataactaaa agaaatgttc aaagcctgct tgaggcagcg 420
gatctgctac agttcctttc agtaaagaag gcttgtgagc ggtttttggt aaggcacttg 480
gatattgata attgtattgg aatgcactcc tttgcagaat ttcatgtgtg tccagaacta 540
gagaaggaat ctcgaagaat tctatgttca aagtttaagg aagtgtggca acaagaagaa 600
tttctggaaa tcagccttga aaagtttctc tttatcttgt ccagaaagaa tctcagtgtt 660
tggaaagaag aagctatcat agagccagtt attaagtgga ctgctcatga tgtagaaaat 720
cgaattgaat gcctctataa tctactgagc tatatcaaca ttgatataga tccagtgtac 780
ttaaaaacag ccttaggcct tcaaagaagc tgcctgctca ccgaaaataa gatccgctcc 840
ctaatataca atgccttgaa tcccatgcat aaagagattt cccagaggtc cacagccaca 900
atgtatataa ttggaggcta ttactggcat cctttatcag aggttcacat atgggatcct 960
ttgacaaatg tttggattca gggagcagaa ataccagatt ataccaggga gagctatggt 1020
gttacatgtt taggacccaa catttatgta actgggggct acaggacgga taacatagaa 1080
gctcttgaca cagtgtggat ctataacagt gaaagtgatg aatggacaga aggtttgcca 1140
atgctcaatg ccaggtatta ccactgtgca gtcaccttgg gtggctgtgt ctatgcttta 1200
ggtggttaca gaaaaggggc tccagcagaa gaggctgagt tctatgatcc tttaaaagag 1260
aaatggattc ctattgcaaa catgattaaa ggtgtgggaa atgctactgc ctgtgtctta 1320
catgatgtta tctacgtcat tggtggccac tgtggctaca gaggaagctg cacctatgac 1380
aaagttcaga gctacaattc cgatatcaac gaatggagcc tcatcacctc cagtccacat 1440
ccagaatatg gattgtgctc agttccgttt gaaaataagc tctatctagt cggtggacaa 1500
actacaatca cagaatgcta tgaccctgaa caaaatgaat ggagagagat agctcccatg 1560
atggaaagga ggatggagtg cggtgccgtc atcatgaatg gatgtattta tgtcactgga 1620
ggatactcct actcaaaggg aacgtatctt cagagcattg agaaatatga tccagatctt 1680
aataagtggg aaatagtggg taatcttccc agtgccatgc ggtctcatgg gtgtgtttgt 1740
gtgtataatg tctaattgaa tctgcagaaa tgaccaagca atcacttttt tggagtatag 1800
ttttataaaa aaagaatgca gggtttgaag ttccttacct gataattgtg tctggcacat 1860
gataggggat cagtaaattg taattcctaa ccctactgta ctcccaaaca tggtgattca 1920
tggtcaagaa aaatcttata tatatatata cacacacata tatatgtgtt catatatatg 1980
tatacatata tgtgtatata tacgcatgta tgtatacata tatgtgtata tatacgcatg 2040

-continued

```
tatgtatgca tatgtgtgta tatatacgta tgtatgtata catatgtgta tatatacgta   2100

tgtatgtata catatatgtg tatatatgcg tatgtatgta tacatatatg tgtatatata   2160

cgtatgtatg tatacatata tgtgtatata tacgtatgta tgtatacata tatgtgtata   2220

tatacgtatg tatgtataca tatatgtgtg tatatacgtg tgtatgtata catatatgtg   2280

tatatatacg tgtgtatgta tacatatatg tgtatatatg cgtgtgtatg tatacatata   2340

tgtgtatata tacgtgtgta tgtatacata tatgtgtata tatacgtgtg tatgtataca   2400

tatatgtgta tatatgcgtg tgtatatata tacacatata tacgtatata tgtatatata   2460

tatacacagt tgaatcagtg ggattaatac ctataatctc tggttttcaa aggtaatatg   2520

gaatatttga cacttggtaa aaggtgaact acctttgtag tgaatctttt cctcttggta   2580

gcatcaacac tggggataaa tcagaaccat tctgtggaat gaaatgtttc tcaagagcct   2640

ataatatagt agatagtgca tattaagatg tctggctggg catggtggct catgcctgta   2700

atcccagcac tttgggaggc tgaggcggga ggatcacttg agcctagaag ttggagacta   2760

acctggcgag accctgtctc aaaaaaaaaa aaaaaaaa                           2798
```

<210> SEQ ID NO 180
<211> LENGTH: 439
<212> TYPE: DNA
<213> ORGANISM: Homo sapiens

<400> SEQUENCE: 180

```
accctttgt gaccagctgc ataccccaaa accttttgga atctgggcta actggctgtg     60

cctacatcaa cagcacccgt gaaccccgt gtgctatgct ctgtgcaaca aaacattcag    120

aacccacttt caagatgctg ctgctgtgcc agtgtgacaa aaaaaagagg cgcaagcagc    180

agtaccagca gagacagtcg gtcatttttc acaagcgcgc acccgagcag gccttgtaga    240

atgaggttgt atcaatagca gtgacaaaac gcacacatca acccacagac cttaggagga    300

ggaaggcgag ggcggggtga cttctggtga tgataaaaat ggttttatca cccagatgtg    360

aaagaagctg cctgtttact gatccattga ataaacccat tttaatagaa aaagtcaata    420

ccaattcagc aaaaaaaaa                                                 439
```

<210> SEQ ID NO 181
<211> LENGTH: 1309
<212> TYPE: DNA
<213> ORGANISM: Homo sapiens

<400> SEQUENCE: 181

```
tatctatgta acaaatcgca gcacaggagt cccctgggct ccctcaggct ctggtatgac     60

atatttgagc catataaatt cagcttctcc tctggcatct gttagccgac tcacttgcaa    120

ctccacctca gcagtggtct ctcagtcctc tcaaagcaag gaaagagtac tgtgtgctga    180

gagaccatgg caaagaatcc tccagagaat tgtgaagact gtcacattct aaatgcagaa    240

gcttttaaat ccaagaaaat atgtaaatca cttaagattt gtggactggt gtttggtatc    300

ctgaccctaa ctctaattgt cctgttttgg gggagcaagc acttctggcc ggaggtaccc    360

aaaaaagcct atgacatgga gcacactttc tacagcagtg gagagaagaa gaagatttac    420

atggaaattg atcctgtgac cagaactgaa atattcagaa gcggaaatgg cactgatgaa    480

acattggaag tacacgactt taaaaacgga tacactggca tctacttcgt gggtcttcaa    540

aaatgtttta tcaaaactca gattaaagtg attcctgaat tttctgaacc agaagaggaa    600

atagatgaga atgaagaaat taccacaact ttctttgaac agtcagtgat ttgggtccca    660
```

gcagaaaagc ctattgaaaa ccgagatttt cttaaaaatt ccaaaattct ggagatttgt 720
gataacgtga ccatgtattg gatcaatccc actctaatat cagtttctga gttacaagac 780
tttgaggagg agggagaaga tcttcacttt cctgccaacg aaaaaaaagg gattgaacaa 840
aatgaacagt gggtggtccc tcaagtgaaa gtagagaaga cccgtcacgc cagacaagca 900
agtgaggaag aacttccaat aaatgactat actgaaaatg gaatagaatt tgatcccatg 960
ctggatgaga gaggttattg ttgtatttac tgccgtcgag gcaaccgcta ttgccgccgc 1020
gtctgtgaac ctttactagg ctactaccca tatccatact gctaccaagg aggacgagtc 1080
atctgtcgtg tcatcatgcc ttgtaactgg tgggtggccc gcatgctggg gagggtctaa 1140
taggaggttt gagctcaaat gcttaaactg ctggcaacat ataataaatg catgctattc 1200
aatgaatttc tgcctatgag gcatctggcc cctggtagcc agctctccag aattacttgt 1260
aggtaattcc tctcttcatg ttctaataaa cttctacatt atcaaaaaa 1309

<210> SEQ ID NO 182
<211> LENGTH: 1477
<212> TYPE: DNA
<213> ORGANISM: Homo sapiens

<400> SEQUENCE: 182
gcggatcgct gctccctctc gccatggcgc aggtgctgat cgtgggcgcc gggatgacag 60
gaagcttgtg cgctgcgctg ctgaggaggc agacgtccgg tcccttgtac cttgctgtgt 120
gggacaaggc tgacgactca gggggaagaa tgactacagc ctgcagtcct cataatcctc 180
agtgcacagc tgacttgggt gctcagtaca tcacctgcac tcctcattat gccaaaaaac 240
accaacgttt ttatgatgaa ctgttagcct atggcgtttt gaggcctcta agctcgccta 300
ttgaaggaat ggtgatgaaa gaaggagact gtaactttgt ggcacctcaa ggaatttctt 360
caattattaa gcattacttg aaagaatcag gtgcagaagt ctacttcaga catcgtgtga 420
cacagatcaa cctaagagat gacaaatggg aagtatccaa acaaacaggc tcccctgagc 480
agtttgatct tattgttctc acaatgccag ttcctgagat tctgcagctt caaggtgaca 540
tcaccacctt aattagtgaa tgccaaaggc agcaactgga ggctgtgagc tactcctctc 600
gatatgctct gggcctcttt tatgaagctg gtacgaagat tgatgtccct tgggctgggc 660
agtacatcac cagtaatccc tgcatacgct tcgtctccat tgataataag aagcgcaata 720
tagagtcatc agaaattggg ccttccctcg tgattcacac cactgtccca tttggagtta 780
catacttgga acacagcatt gaggatgtgc aagagttagt cttccagcag ctggaaaaca 840
ttttgccggg tttgcctcag ccaattgcta ccaaatgcca aaaatggaga cattcacagg 900
ttacaaatgc tgctgccaac tgtcctggcc aaatgactct gcatcacaaa cctttccttg 960
catgtggagg ggatggattt actcagtcca actttgatgg ctgcatcact tctgccctat 1020
gtgttctgga agctttaaag aattatattt agtgcctata tccttattct ctatatgtgt 1080
attgggtttt tattttcaca attttctgtt attgattatt ttgttttcta ttttgctaag 1140
aaaaattact ggaaaattgt tcttcactta ttatcatttt tcatgtggag tataaaatca 1200
attttgtaat tttgatagtt acaacccatg ctagaatgga aattcctcac accttgcacc 1260
ttccctactt ttctgaattg ctatgactac tccttgttgg aggaaaagtg gtacttaaaa 1320
aataacaaac gactctctca aaaaaattac attaaatcac aataacagtt tgtatgccaa 1380
aaacttgatt atccttatga aaatttcaat tctgaataaa gaataatcac attatcaaag 1440

-continued

```
ccccatcaaa aaaaaaaaaa aaaaaaaaaa aaaaaaa                          1477


<210> SEQ ID NO 183
<211> LENGTH: 3100
<212> TYPE: DNA
<213> ORGANISM: Homo sapiens

<400> SEQUENCE: 183

actcgtctct ggtaaagtct gagcaggaca gggtggctga ctggcagatc cagaggttcc     60

cttggcagtc cacgccaggc cttcaccatg gatcagttcc ctgaatcagt gacagaaaac    120

tttgagtacg atgatttggc tgaggcctgt tatattgggg acatcgtggt ctttgggact    180

gtgttcctgt ccatattcta ctccgtcatc tttgccattg gcctggtggg aaatttgttg    240

gtagtgtttg ccctcaccaa cagcaagaag cccaagagtg tcaccgacat ttacctcctg    300

aacctggcct tgtctgatct gctgtttgta gccactttgc ccttctggac tcactatttg    360

ataaatgaaa agggcctcca caatgccatg tgcaaattca ctaccgcctt cttcttcatc    420

ggctttttg gaagcatatt cttcatcacc gtcatcagca ttgataggta cctggccatc    480

gtcctggccg ccaactccat gaacaaccgg accgtgcagc atggcgtcac catcagccta    540

ggcgtctggg cagcagccat tttggtggca gcaccccagt tcatgttcac aaagcagaaa    600

gaaaatgaat gccttggtga ctaccccgag gtcctccagg aaatctggcc cgtgctccgc    660

aatgtggaaa caaattttct tggcttccta ctcccccctgc tcattatgag ttattgctac    720

ttcagaatca tccagacgct gttttcctgc aagaaccaca agaaagccaa agccattaaa    780

ctgatccttc tggtggtcat cgtgtttttc ctcttctgga caccctacaa cgttatgatt    840

ttcctggaga cgcttaagct ctatgacttc tttcccagtt gtgacatgag gaaggatctg    900

aggctggccc tcagtgtgac tgagacggtt gcatttagcc attgttgcct gaatcctctc    960

atctatgcat ttgctgggga gaagttcaga agatacctttt accacctgta tgggaaatgc   1020

ctggctgtcc tgtgtgggcg ctcagtccac gttgatttct cctcatctga atcacaaagg   1080

agcaggcatg gaagtgttct gagcagcaat tttacttacc acacgagtga tggagatgca   1140

ttgctccttc tctgaaggga atcccaaagc cttgtgtcta cagagaacct ggagttcctg   1200

aacctgatgc tgactagtga ggaaagattt ttgttgttat ttcttacagg cacaaaatga   1260

tggacccaat gcacacaaaa caaccctaga gtgttgttga gaattgtgct caaaatttga   1320

agaatgaaca aattgaactc tttgaatgac aaagagtaga catttctctt actgcaaatg   1380

tcatcagaac tttttggttt gcagatgaca aaaattcaac tcagactagt ttagttaaat   1440

gagggtggtg aatattgttc atattgtggc acaagcaaaa gggtgtctga gccctcaaag   1500

tgaggggaaa ccagggcctg agccaagcta gaattccctc tctctgactc tcaaatcttt   1560

tagtcattat agatccccca gactttacat gacacagctt tatcaccaga gagggactga   1620

cacccatgtt tctctggccc caagggaaaa ttcccaggga agtgctctga taggccaagt   1680

ttgtatcagg tgcccatccc tggaaggtgc tgttatccat ggggaaggga tatataagat   1740

ggaagcttcc agtccaatct catggagaag cagaaataca tatttccaag aagttggatg   1800

ggtgggtact attctgatta cacaaaacaa atgccacaca tcacccttac catgtgcctg   1860

atccagcctc tcccctgatt acaccagcct cgtcttcatt aagccctctt ccatcatgtc   1920

cccaaacctg caagggctcc ccactgccta ctgcatcgag tcaaaactca aatgcttggc   1980

ttctcatacg tccaccatgg ggtcctacca atagattccc cattgcctcc tccttcccaa   2040

aggactccac ccatcctatc agcctgtctc ttccatatga cctcatgcat ctccacctgc   2100
```

tcccaggcca gtaagggaaa tagaaaaacc ctgcccccaa ataagaaggg atggattcca 2160
accccaactc cagtagcttg ggacaaatca agcttcagtt tcctggtctg tagaagaggg 2220
ataaggtacc tttcacatag agatcatcct ttccagcatg aggaactagc caccaactct 2280
tgcaggtctc aacccttttg tctgcctctt agacttctgc tttccacacc tgcactgctg 2340
tgctgtgccc aagttgtggt gctgacaaag cttggaagag cctgcaggtg ccttggccgc 2400
gtgcatagcc cagacacaga agaggctggt tcttacgatg gcacccagtg agcactccca 2460
agtctacaga gtgatagcct tccgtaaccc aactctcctg gactgccttg aatatcccct 2520
cccagtcacc ttgtgcaagc ccctgcccat ctgggaaaat accccatcat tcatgctact 2580
gccaacctgg ggagccaggg ctatgggagc agcttttttt tccccccctag aaacgtttgg 2640 aacaatgtaa aactttaaag ctcgaaaaca attgtaataa tgctaaagaa aaagtcatcc 2700
aatctaacca catcaatatt gtcattcctg tattcacccg tccagacctt gttcacactc 2760
tcacatgttt agagttgcaa tcgtaatgta cagatggttt tataatctga tttgttttcc 2820
tcttaacgtt agaccacaaa tagtgctcgc tttctatgta gtttggtaat tatcatttta 2880
gaagactcta ccagactgtg tattcattga agtcagatgt ggtaactgtt aaattgctgt 2940
gtatctgata gctctttggc agtctatatg tttgtataat gaatgagaga ataagtcatg 3000
ttccttcaag atcatgtacc ccaatttact tgccattact caattgataa acatttaact 3060
tgtttccaat gtttagcaaa tacatatttt atagaacttc 3100

<210> SEQ ID NO 184
<211> LENGTH: 662
<212> TYPE: DNA
<213> ORGANISM: Homo sapiens

<400> SEQUENCE: 184
tgaacatatt caggctgatt ggggacgtgt cccacctggc ggccatcgtc atcttgatgg 60
tagagatctg gaagacgcgc tcctgcgccg gtatttctgg gaaaagccag cttctgtctg 120
cactggtctt cacaactcgt gacctggatc ttttcacttc atttatttca gtgtatcaca 180
catctatcaa ggttatctac gttgcctgct cgtatgccac agtgtacctg atctacctta 240
aatttaaggc aacatcggat ggaaatcatg ataccttccg agtggagttt ctggtggtcc 300
ctgtgggagg cctcctcatt tttagttaat cacgatttct ctcctcttga gtactcaagg 360
gaaagaagct cagtttgcca gcataagtgc caaagaccat cgccagcatc tgtccttcag 420
ggtgttcgga cagaattctt accacagcaa aggcataaga tgcttgatac ggaaaatcaa 480
gaacttaact tttttgttgc agatagtcat cagtggttct gtaaaaacgc agaggaaaag 540
agccagaagg tttctgttta atgcatcttg ccttatcttt ttttattact gtgcacaaag 600 attttttttac acaaacatcc ttaatgctgt tttaataaat tcagtgtgta gcttcaaaaa 660
aa 662

<210> SEQ ID NO 185
<211> LENGTH: 5920
<212> TYPE: DNA
<213> ORGANISM: Homo sapiens

<400> SEQUENCE: 185
ggcaggtctc gctctcggca ccctcccggc gcccgcgttc tcctggccct gcccggcatc 60
ccgatggccg ccgctgggcc ccggcgctcc gtgcgcggag ccgtctgcct gcatctgctg 120

-continued

```
ctgaccctcg tgatcttcag tcgtgatggt gaagcctgca aaaaggtgat acttaatgta    180
ccttctaaac tagaggcaga caaaataatt ggcagagtta atttggaaga gtgcttcagg    240
tctgcagacc tcatccggtc aagtgatcct gatttcagag ttctaaatga tgggtcagtg    300
tacacagcca gggctgttgc gctgtctgat aagaaaagat catttaccat atggctttct    360
gacaaaagga aacagacaca gaaagaggtt actgtgctgc tagaacatca gaagaaggta    420
tcgaagacaa gacacactag agaaactgtt ctcaggcgtg ccaagaggag atgggcacct    480
attccttgct ctatgcaaga gaattccttg ggccctttcc cattgtttct tcaacaagtt    540
gaatctgatg cagcacagaa ctatactgtc ttctactcaa taagtggacg tggagttgat    600
aaagaacctt taaatttgtt ttatatagaa agagacactg gaaatctatt ttgcactcgg    660
cctgtggatc gtgaagaata tgatgttttt gatttgattg cttatgcgtc aactgcagat    720
ggatattcag cagatctgcc cctcccacta cccatcaggg tagaggatga aaatgacaac    780
caccctgttt tcacagaagc aatttataat tttgaagttt tggaaagtag tagacctggt    840
actacagtgg gggtggtttg tgccacagac agagatgaac cggacacaat gcatacgcgc    900
ctgaaataca gcattttgca gcagacacca aggtcacctg ggctcttttc tgtgcatccc    960
agcacaggcg taatcaccac agtctctcat tatttggaca gagaggttgt agacaagtac   1020
tcattgataa tgaaagtaca agacatggat ggccagtttt ttggattgat aggcacatca   1080
acttgtatca taacagtaac agattcaaat gataatgcac ccactttcag acaaaatgct   1140
tatgaagcat ttgtagagga aaatgcattc aatgtggaaa tcttacgaat acctatagaa   1200
gataaggatt taattaacac tgccaattgg agagtcaatt ttaccatttt aaagggaaat   1260
gaaaatggac atttcaaaat cagcacagac aaagaaacta atgaaggtgt tctttctgtt   1320
gtaaagccac tgaattatga agaaaaccgt caagtgaacc tggaaattgg agtaaacaat   1380
gaagcgccat ttgctagaga tattcccaga gtgacagcct tgaacagagc cttggttaca   1440
gttcatgtga gggatctgga tgaggggcct gaatgcactc ctgcagccca atatgtgcgg   1500
attaaagaaa acttagcagt ggggtcaaag atcaacggct ataaggcata tgaccccgaa   1560
aatagaaatg gcaatggttt aaggtacaaa aaattgcatg atcctaaagg ttggatcacc   1620
attgatgaaa tttcagggtc aatcataact tccaaaatcc tggataggga ggttgaaact   1680
cccaaaaatg agttgtataa tattacagtc ctggcaatag acaaagatga tagatcatgt   1740
actggaacac ttgctgtgaa cattgaagat gtaaatgata atccaccaga aatacttcaa   1800
gaatatgtag tcatttgcaa accaaaaatg gggtataccg acattttagc tgttgatcct   1860
gatgaacctg tccatggagc tccattttat ttcagtttgc ccaatacttc tccagaaatc   1920
agtagactgt ggagcctcac caaagttaat gatacagctg cccgtctttc atatcagaaa   1980
aatgctggat ttcaagaata taccattcct attactgtaa aagacagggc cggccaagct   2040
gcaacaaaat tattgagagt taatctgtgt gaatgtactc atccaactca gtgtcgtgcg   2100
acttcaagga gtacaggagt aatacttgga aaatgggcaa tccttgcaat attactgggt   2160
atagcactgc tcttttctgt attgctaact ttagtatgtg gagtttttgg tgcaactaaa   2220
gggaaacgtt ttcctgaaga tttagcacag caaaacttaa ttatatcaaa cacagaagca   2280
cctggagacg atagagtgtg ctctgccaat ggatttatga cccaaactac caacaactct   2340
agccaaggtt tttgtggtac tatgggatca ggaatgaaaa atggagggca ggaaaccatt   2400
gaaatgatga aaggaggaaa ccagaccttg gaatcctgcc ggggggctgg gcatcatcat   2460
accctggact cctgcagggg aggacacacg gaggtggaca actgcagata cacttactcg   2520
```

```
gagtggcaca gttttactca accccgtctc ggtgaagaat ccattagagg acacactggt   2580
taaaaattaa acataaaaga aattgcatcg atgtaatcag aatgaagacc gcatgccatc   2640
ccaagattat gtcctcactt ataactatga gggaagagga tctccagctg gttctgtggg   2700
ctgctgcagt gaaaagcagg aagaagatgg ccttgacttt ttaaataatt tggaacccaa   2760
atttattaca ttagcagaag catgcacaaa gagataatgt cacagtgcta caattaggtc   2820
tttgtcagac attctggagg tttccaaaaa taatattgta aagttcaatt tcaacatgta   2880
tgtatatgat gatttttttc tcaattttga attatgctac tcaccaattt atatttttaa   2940
agccagttgt tgcttatctt ttccaaaaag tgaaaaatgt taaaacagac aactggtaaa   3000
tctcaaactc cagcactgga attaaggtct ctaaagcatc tgctcttttt tttttttacg   3060
gatattttag taataaatat gctggataaa tattagtcca acaatagcta agttatgcta   3120
atatcacatt attatgtatt cactttaagt gatagtttaa aaaataaaca agaaatattg   3180
agtatcacta tgtgaagaaa gttttggaaa agaaacaatg aagactgaat taaattaaaa   3240
atgttgcagc tcataaagaa ttgggactca cccctactgc actaccaaat tcatttgact   3300
ttggaggcaa aatgtgttga agtgccctat gaagtagcaa ttttctatag gaatatagtt   3360
ggaaataaat gtgtgtgtgt atattattat taatcaatgc aatatttaaa atgaaatgag   3420
aacaaagagg aaaatggtaa aaacttgaaa tgaggctggg gtatagtttg tcctacaata   3480
gaaaaaagag agagcttcct aggcctgggc tcttaaatgc tgcattataa ctgagtctat   3540
gaggaaatag ttcctgtcca atttgtgtaa tttgtttaaa attgtaaata aattaaactt   3600
ttctggtttc tgtgggaagg aaatagggaa tccaatggaa cagtagcttt gctttgcagt   3660
ctgtttcaag atttctgcat ccacaagtta gtagcaaact ggggaatact cgctgcagct   3720
ggggttccct gctttttggt agcaagggtc cagagatgag gtgttttttt cggggagcta   3780
ataacaaaaa cattttaaaa cttaccttta ctgaagttaa atcctctatt gctgtttcta   3840
ttctctctta tagtgaccaa catcttttta atttagatcc aaataaccat gtcctcctag   3900
agtttagagg ctagagggag ctgaggggag gatcttactg aaagcaccct ggggagattg   3960
attgtcctta aacctaagcc ccacaaactt gacacctgat caggtctggg agctacaaaa   4020
tttcattttt ctcctcactg cccttcttct gagtggcatt ggcctgaatc aaggaaagcc   4080
aggccttgtg ggccccccttc tttcggcttt ctgctaaagc aacacctcca gcagagattc   4140
ccttaagtga ctccaggttt tccaccatcc ttcagcgtga attaattttt aatcagtttg   4200
ctttctccag agaaatttta aaataataga agaaatagaa attttgaatg tataaaagaa   4260
aaagatcaag ttgtcatttt agaacagagg gaactttggg agaaagcagc ccaagtaggt   4320
tatttgtaca gtcagagggc aacaggaaga tgcaggcctt caagggcaag gagaggccac   4380
aaggaatatg ggtgggagta aaagcaacat cgtctgcttc atactttttc ctaggcttgg   4440
cactgccttt tcctttctca ggccaatggc aactgccatt tgagtccggt gagggatcag   4500
ccaacctctt ctctatggct caccttattt ggagtgagaa atcaaggaga cagagctgac   4560
tgcatgatga gtctgaaggc atttgcagga tgagcctgaa ctggttgtgc agaacaaaca   4620
aggcattcat gggaattgtt gtattccttc tgcagccctc cttctgggca ctaagaaggt   4680
ctatgaatta aatgcctatc taaaattctg atttattcct acattttctg ttttctaatt   4740
tgaccctaaa atctatgtgt tttagactta gactttttat tgcccccccc cccttttttt   4800
ttgagacgga gtctcgctct gacgcacagg ctggagtgca gtggctccga tctctgctca   4860
```

-continued

```
ctgaaagctc cgcctcccgg gttcatgcca ttctcctgcc tcagcctcct gagtagctgg   4920

gactacaggc gcccaccacc acgcccggct aattttttgt atttttaata gagacggggt   4980

ttcactgtgt tagccaggat ggtctcgatc tcctgacctc gtgatccgcc tgcctcggcc   5040

tcccaaagtg ctgggattac aggcatgacc caccgctccc ggccttgttt tccgtttaaa   5100

gtcgtcttct tttaatgtaa tcattttgaa catgtgtgaa agttgatcat acgaattgga   5160

tcaatcttga aatactcaac caaaagacag tcgagaagcc agggggagaa agaactcagg   5220

gcacaaaata ttggtctgag aatggaattc tctgtaagcc tagttgctga aatttcctgc   5280

tgtaaccaga agccagtttt atctaacggc tactgaaaca cccactgtgt tttgctcact   5340

cccactcacc gatcaaaacc tgctacctcc ccaagacttt actagtgccg ataaactttc   5400

tcaaagagca accagtatca cttccctgtt tataaaacct ctaaccatct ctttgttctt   5460

tgaacatgct gaaaaccacc tggtctgcat gtatgcccga atttgtaatt cttttctctc   5520

aaatgaaaat ttaattttag ggattcattt ctatattttc acatatgtag tattattatt   5580

tccttatatg tgtaaggtga aatttatggt atttgagtgt gcaagaaaat atatttttaa   5640

agctttcatt tttcccccag tgaatgattt agaatttttt atgtaaatat acagaatgtt   5700

ttttcttact tttataagga agcagctgtc taaaatgcag tggggtttgt tttgcaatgt   5760

tttaaacaga gttttagtat tgctattaaa agaagttact ttgcttttaa agaaacttgg   5820

ctgcttaaaa taagcaaaaa ttggatgcat aaagtaatat ttacagatgt ggggagatgt   5880

aataaaacaa tattaacttg gaaaaaaaaa aaaaaaaaaa                         5920
```

<210> SEQ ID NO 186
<211> LENGTH: 696
<212> TYPE: DNA
<213> ORGANISM: Homo sapiens
<220> FEATURE:
<221> NAME/KEY: misc_feature
<222> LOCATION: (8)..(8)
<223> OTHER INFORMATION: a or g or c or t/u

<400> SEQUENCE: 186

```
gactcagnct tcagccgctc tcctccccct gggcaaacag gactcatctg atgatgtgag     60

aagagttcag aggagggaga aaaatcgtat tgccgcccag aagagccgac agaggcagac    120

acagaaggcc gacaccctgc acctggagag cgaagacctg gagaaacaga acgcggctct    180

acgcaaggag atcaagcagc tcacagagga actgaagtac ttcacgtcgg tgctgaacag    240

ccacgagccc ctgtgctcgg tgctggccgc cagcacgccc tcgccccccg aggtggtgta    300

cagcgcccac gcattccacc aacctcatgt cagctccccg cgcttccagc cctgagcttc    360

cgatgcgggg agagcagagc ctcgggaggg gcacacagac tgtggcagag ctgcgcccat    420

cccgcagagg cccctgtcca cctggagacc cggagacaga ggcctggaca aggagtgaac    480

acgggaactg tcacgactgg aagggcgtga ggcctcccag cagtgccgca gcgtttcgag    540

gggcgtgtgc tggaccccac cactgtgggt tgcaggccca atgcagaaga gtattaagaa    600

agatgctcaa gtcccatggc acagagcaag gcgggcaggg aacggttatt tttctaaata    660

aatgctttaa aagaaaaaaa aaaaaaaaaa aaaaaa                              696
```

<210> SEQ ID NO 187
<211> LENGTH: 586
<212> TYPE: DNA
<213> ORGANISM: Homo sapiens
<220> FEATURE:
<221> NAME/KEY: misc_feature
<222> LOCATION: (9)..(10)
<223> OTHER INFORMATION: a or g or c or t/u
<220> FEATURE:
<221> NAME/KEY: misc_feature
<222> LOCATION: (31)..(31)
<223> OTHER INFORMATION: a or g or c or t/u
<220> FEATURE:
<221> NAME/KEY: misc_feature
<222> LOCATION: (44)..(45)
<223> OTHER INFORMATION: a or g or c or t/u
<220> FEATURE:
<221> NAME/KEY: misc_feature
<222> LOCATION: (116)..(116)
<223> OTHER INFORMATION: a or g or c or t/u
<220> FEATURE:
<221> NAME/KEY: misc_feature
<222> LOCATION: (130)..(130)
<223> OTHER INFORMATION: a or g or c or t/u

<400> SEQUENCE: 187
atgcaaggnn taggcaaaga ttgttgaccc nggagataga ggtnncaatg agccagatca 60
ttccattgca ttccagcttg ggcgacagaa tgagactctg tctcaaaatt aaaaancaaa 120
aaaccaaaan caaatagatg aaaaagtaga ctggagacaa ataaaagtga gtttctaaag 180
gaaattcaca gtaatgctgc attaaacact aagctcactt aggtcacttt ctagtgagct 240
aaccgtaaca gagagcctac aggatacacg tgagataatg tcacgtgtag aagatcgttg 300
tgaattaaag ttcaaaatta agacttctta gattatgatg tagattttag agctccttaa 360
aacataaagc gaatcttata aatgttcaat tctaaagtta ttccacttgg aaaaattagc 420
ttttgggaca atttttaaga acttttgtgt aaaatgcagc tccatgttta gcataatcta 480
aaaataattt caagcaatcc agaatcttcc aagaatgtta ttaaagcttt aaaacaaagc 540
aaaacaaaaa gacccttttg tgccttatat gggaagacta aaaaaa 586

<210> SEQ ID NO 188
<211> LENGTH: 1359
<212> TYPE: DNA
<213> ORGANISM: Homo sapiens

<400> SEQUENCE: 188
accgggcacc ggacggctcg ggtactttcg ttcttaatta ggtcatgccc gtgtgagcca 60
ggaaagggct gtgtttatgg gaagccagta acactgtggc ctactatctc ttccgtggtg 120
ccatctacat ttttgggact cgggaattat gaggtagagg tggaggcgga gccggatgtc 180
agaggtcctg aaatagtcac catgggggaa aatgatccgc ctgctgttga agccccccttc 240 tcattccgat cgctttttgg ccttgatgat ttgaaaataa gtcctgttgc accagatgca 300
gatgctgttg ctgcacagat cctgtcactg ctgccattga agtttttttcc aatcatcgtc 360 attgggatca ttgcattgat attagcactg gccattggtc tgggcatcca cttcgactgc 420
tcagggaagt acagatgtcg ctcatccttt aagtgtatcg agctgatagc tcgatgtgac 480
ggagtctcgg attgcaaaga cggggaggac gagtaccgct gtgtccgggt gggtggtcag 540
aatgccgtgc tccaggtgtt cacagctgct tcgtggaaga ccatgtgctc cgatgactgg 600
aagggtcact acgcaaatgt tgcctgtgcc caactgggtt tcccaagcta tgtgagttca 660
gataacctca gagtgagctc gctggagggg cagttccggg aggagtttgt gtccatcgat 720
cacctcttgc cagatgacaa ggtgactgca ttacaccact cagtatatgt gagggaggga 780
tgtgcctctg gccacgtggt taccttgcag tgcacagcct gtggtcatag aaggggctac 840
agctcacgca tcgtgggtgg aaacatgtcc ttgctctcgc agtggccctg gcaggccagc 900
cttcagttcc agggctacca cctgtgcggg ggctctgtca tcacgcccct gtggatcatc 960
actgctgcac actgtgttta tgacttgtac ctccccaagt catggaccat ccaggtgggt 1020
ctagtttccc tgttggacaa tccagcccca tcccacttgg tggagaagat tgtctaccac 1080
agcaagtaca agccaaagag gctgggcaat gacatcgccc ttatgaagct ggccgggcca 1140
ctcacgttca atggtacatc tgggtctcta tgtggttctg cagctcttcc tttgtttcaa 1200
gaggatttgc aattgctcat tgaagcattc ttatgatggc tgctttataa tccttgtcag 1260
atattaataa ttccaactcc tgattcatgt tggtgttggc atcagttgat tatcttttct 1320
cattaaaatt gtgatgctcc taaaaaaaaa aaaaaaaaa 1359

<210> SEQ ID NO 189
<211> LENGTH: 2711
<212> TYPE: DNA
<213> ORGANISM: Homo sapiens

<400> SEQUENCE: 189
ttcagaagga ggagagacac cgggcccagg gcaccctcgc gggcgggcgg acccaagcag 60
tgagggcctg cagccggccg gccagggcag cggcaggcgc ggcccggacc tacgggagga 120
agccccgagc cctcggcggg ctgcgagcga ctccccggcg atgcctcaca actccatcag 180
atctggccat ggagggctga accagctggg aggggccttt gtgaatggca gacctctgcc 240
ggaagtggtc cgccagcgca tcgtagacct ggcccaccag ggtgtaaggc cctgcgacat 300
ctctcgccag ctccgcgtca gccatggctg cgtcagcaag atccttggca ggtactacga 360
gactggcagc atccggcctg gagtgatagg gggctccaag cccaaggtgg ccaccccccaa 420 ggtggtggag aagattgggg actacaaacg ccagaaccct accatgtttg cctgggagat 480
ccgagaccgg ctcctggctg agggcgtctg tgacaatgac actgtgccca gtgtcagctc 540
cattaataga atcatccgga ccaaagtgca gcaaccattc aacctcccta tggacagctg 600
cgtggccacc aagtccctga gtcccggaca cacgctgatc cccagctcag ctgtaactcc 660
cccggagtca ccccagtcgg attccctggg ctccacctac tccatcaatg ggctcctggg 720
catcgctcag cctggcagcg acaagaggaa aatggatgac agtgatcagg atagctgccg 780
actaagcatt gactcacaga gcagcagcag cggaccccga aagcaccttc gcacggatgc 840
cttcagccag caccacctcg agccgctcga gtgcccattt gagcggcagc actacccaga 900
ggcctatgcc tcccccagcc acaccaaagg cgagcagggc ctctacccgc tgcccttgct 960
caacagcacc ctggacgacg ggaaggccac cctgacccct tccaacacgc cactggggcg 1020
caacctctcg actcaccaga cctaccccgt ggtggcagat cctcactcac ccttggccat 1080
aaagcaggaa acccccgagg tgtccagttc tagctccacc ccttgctctt tatctagctc 1140
cgcccttttg gatctgcagc aagtcggctc cggggtcccg cccttcaatg cctttcccca 1200
tgctgcctcc gtgtacgggc agttcacggg ccaggccctc ctctcagggc gagagatggt 1260
ggggcccacg ctgcccggat acccacccca catccccacc agcggacagg gcagctatgc 1320
ctcctctgcc atcgcaggca tggtggcagg aagtgaatac tctggcaatg cctatggcca 1380
caccccctac tcctcctaca gcgaggcctg ggcttcccc aactccagct tgctgagttc 1440
cccatattat tacagttcca catcaaggcc gagtgcaccg cccaccactg ccacggcctt 1500
tgaccatctg tagttgccat ggggacagtg ggagcgactg agcaacagga ggactcagcc 1560
tgggacaggc cccagagagt cacacaaagg aatctttatt attacatgaa aaataaccac 1620
aagtccagca ttgcggcaca ctccctgtgt ggttaattta atgaaccatg aaagacagga 1680

```
tgaccttgga caaggccaaa ctgtcctcca agactcctta atgaggggca ggagtcccag   1740

ggaaagagaa ccatgccatg ctgaaaaaga caaaattgaa gaagaaatgt agccccagcc   1800

ggtaccctcc aaaggagaga agaagcaata gccgaggaac ttggggggat ggcgaatggt   1860

tcctgcccgg gcccaagggt gcacagggca cctccatggc tccattatta acacaactct   1920

agcaattatg gaccataagc acttccctcc agcccacaag tcacagcctg gtgccgaggc   1980

tctgctcacc agccacccag ggagtcacct ccctcagcct cccgcctgcc ccacacggag   2040

gctctggctg tcctctttcc tccactccat ttgcttggct ctttctacac ctccctcttg   2100

gatgggctga gggctggagc gagtccctca gaaattccac caggctgtca gctgacctct   2160

ttttcctgct gctgtgaagg tatagcacca cccaggtcct cctgcagtgc ggcatcccct   2220

tggcagctgc cgtcagccag gccagcccca gggagcttaa aacagacatt ccacagggcc   2280

tgggcccctg ggaggtgagg tgtggtgtgc ggcttcaccc agggcagaac aaggcagaat   2340

cgcaggaaac ccgcttcccc ttcctgacag ctcctgccaa gccaaatgtg cttcctgcag   2400

ctcacgccca ccagctactg aagggaccca aggcaccccc tgaagccagc gatagagggt   2460

ccctctctgc tccccagcag ctcctgcccc caaggcctga ctgtatatac tgtaaatgaa   2520

actttgtttg ggtcaagctt ccttctttct aacccccaga ctttggcctc tgagtgaaat   2580

gtctctcttt gccctgtggg gcttctctcc ttgatgcttc tttctttttt taaagacaac   2640

ctgccattac cacatgactc aataaaccat tgctcttcaa aaaaaaaaaa aaaaaaaaaa   2700

aaaaaaaaaa a                                                        2711
```

<210> SEQ ID NO 190
<211> LENGTH: 3323
<212> TYPE: DNA
<213> ORGANISM: Homo sapiens

<400> SEQUENCE: 190

```
tgcttcataa aatttaccta agcaagtggt cttgcttgcc tcaaatccaa gcagtcttga     60

acacttggag gcaattaatg agtatatctt agtcaaaaga attgttggag ctttttatta    120

aagctgcagt ttcagttctg cttttgggga attgtgctat gaaagcagct gccaaaataa    180

gctcatttat tttcttcaat cccactcagt gctcagtcac tatattctgt ttcctttttt    240

tttttcaagt tgcatatttg gtttcccctt atgattggga aagatgaatt ttcagcagaa    300

aacagtgttt gttcactttc aaagagtgat agtttctaaa acatttagag caataaatat    360

tcatcagagg taccaagtaa gccagcagaa gagttaaggg ttagagaaat cccttatttc    420

atgtcttgac tctaaaatga tcaaagtact tttccttgta atgtggattt cttcttatgc    480

ggatatgcaa aaacttcagt tatacgtagt aatgctagca ggtaatttta gtggacattt    540

tataacaact gtcactttgt tttgccacat gtagagtttg ttcagctatt ttccagatat    600

ctccccacaa aaggaggcaa agggtaccag cttttcaatg agcattacct attacttggc    660

aaagatgatg aagactctat taatagttca tttgataaat gttgacataa ccaacaatag    720

agattaggaa gttagtttta agaaatcaat agcatataga cattaccctc atggagtttg    780

tattctacta cttgaactga ttgtagctat aaaagcatag ttagatagct gaatagttag    840

atcataagca aagaaggcca gaacacatct cttatcaaga aatcaatgaa tagtttatct    900

catttttaaa gcaactttat ccttctttaa ttccttcctt tcttctagtg caaaactact    960

taataaggtt ggtgtttagg ttagtgttca caccattcct catctggtgt gaattacctt   1020
```

-continued

```
ctctttcttt actatttact accaacctag tacatgtgtt gactgaattc ttttcaaaca   1080
atgttgagtt atcatggtgc acctaataaa ttaacaccac agattacagc atccttgctg   1140
attttctcag caaagccaga ttagatggaa ataaacaaag aaaatgatcc tagagtgaat   1200
ttttctagaa aatatctatt atgaaccatg ctgtttaaag tattagcttg aaggtgatgg   1260
atccagctat tcagaaaata actttcatat aaccatgatt ttgcacagta tgaggtctta   1320
aatgtgtgga aagagataaa ttttttatca ttaccacaaa ccccttttaa agattcaaag   1380
gtggaagaaa gtgatttatt ttttctcttc agcatacata tataaaagac ttgtcagatg   1440
tttaatttgg ggaggttgat aatgaaacat atcaacagag tatagtagtt atagtagtgt   1500
ttgtgggtaa ataatttcct ggggtcagac atatataaac atatttgctt caaaatgata   1560
aaggcatgaa atcagtctta aaaattgaaa tgggggtgat gggggagaaa aagaagaaca   1620
aatttgaagt gccctttcaa atctgctgga tacaagtatt gaagttttaa gtcatcttat   1680
tctgtctgaa agtgtatttt tcattctaca atagacccaa tcaacaagac gtataacttg   1740
agttgcatga tgttcagttt atgtaatcta ctgttgggat ggtaagaatt gatgtaggct   1800
gtggtgtaag aatgaattaa aatatagttt cactggcttt tctctacata tccactatca   1860
caatggctag gtttcctgtt gctcactgtt ggattctgga gaaaaattta atgaaagatg   1920
atatcagagg aagaataagt ggaggtagag aagaaaggag tgatagagga ggggaaaaaa   1980
acaaaacata tttttgtgtt atccaaagga gctttttcct tattctgtca agcattgaga   2040
tcttcttcag ctttcaatgt agttgctaaa tacaaataat gctactaggt agtgactaaa   2100
tatagcaaac acttcatcag atattagaat taggtcacac tattgaggtt ataatctgaa   2160
ggttgtgtta catagaaacc actttagatt attatcaact tgggctaggc tttattttat   2220
aatagcatag taagtaatat ctattgtgtc atttcttcaa ccattttatt ctaagatcca   2280
tgaagcttct tgaggccaaa taaaataata agtttagaca agaagtagat tgtgactttt   2340
tttcccttag agatactatt tactatctcc tatcctgata ggtggaaggt ttactgaatt   2400
ggaaattggt tgactattag tttttaacta aaatgtgcaa taacacattg cagtttcctc   2460
aaactagttt cctatgatca ttaaactcat tctcagggtt aagaaaggaa tgtaaatttc   2520
tgcctcaatt tgtacttcat caataagttt ttgaagagtg cagattttta gtcaggtctt   2580
aaaaataaac tcacaaatct ggatgcattt ctaaattctg caaatgtttc ctggggtgac   2640
ttaacaagga ataatcccac aatataccta gctacctaat acatggagct ggggctcaac   2700
ccactgtttt taaggatttg cgcttacttg tggctgagga aaaataagta gttcgaggaa   2760
gtagttttta aatgtgagct tatagataga aacagaatat caacttaatt atgaaattgt   2820
tagaacctgt tctcttgtat ctgaatctga ttgcaattac tattgtactg atagactcca   2880
gccattgcaa gtctcagata tcttagctgt gtagtgattc ttgaaattct ttttaagaaa   2940
aattgagtag aaagaaataa accctttgta aatgaggctt ggcttttgtg aaagatcatc   3000
cgcaggctat gttaaaagga ttttagctca ctaaaagtgt aataatggaa atgtggaaaa   3060
tatcgtaggt aaaggaaact acctcatgct ctgaaggttt tgtagaagca caattaaaca   3120
tctaaaatgg ctttgttaca ccagagccat ctggtgtgaa gaactctata tttgtatgtt   3180
gagagggcat ggaataattg tattttgctg gcaatagaca cattctttat tatttgcaga   3240
ttcctcatca aatctgtaat tatgcacagt ttctgttatc aataaaacaa aagaatcctg   3300
ttaaaaaaaa aaaaaaaaaa aaa                                            3323
```

<210> SEQ ID NO 191
<211> LENGTH: 671
<212> TYPE: DNA
<213> ORGANISM: Homo sapiens
<220> FEATURE:
<221> NAME/KEY: misc_feature
<222> LOCATION: (21)..(21)
<223> OTHER INFORMATION: a or g or c or t/u
<220> FEATURE:
<221> NAME/KEY: misc_feature
<222> LOCATION: (49)..(49)
<223> OTHER INFORMATION: a or g or c or t/u

<400> SEQUENCE: 191
tggctctctc cttcaaaagg nccaggccct gtccccccttt ctccccgant ccaaccccag 60
ctcccctgtg aagaaaaaag ttaaaaaatt tgttatttat ttgctttttg cgttgggatg 120
ggttcgtgtc cagtcccggg ggtctgatat ggccatcaca ggctgggtgt tcccagcagc 180
cctggcttgg gggcttgacg cccttcccct tgccccaggc catcatctcc ccacctctcc 240
tcccctctcc tcagttttgc cgactgcttt tcatctgagt caccatttac tccaagcatg 300
tattccagac ttgtcactga ctttccttct ggagcaggtg gctagaaaaa gaggctgtgg 360
gcaggaaaga aaggctcctg tttctcattt gtgaggccag cctctggctt ttctgccgtg 420
gattctcccc ctgtcttctc ccctcagcaa ttcctgcaaa gggttaaaaa tttaactggt 480
ttttactact gatgacttga tttaaaaaaa atacaaagat gctggatgct aacttgatac 540
taaccatcag attgtacagt ttggttgttg ctgtaaatat ggtagcgttt tgttgttgtt 600
gttttttcat gccccatact actgaataaa ctagttctgt gcgggtaaaa aaaaaaaaaa 660
aaaaaaaaaa a 671

<210> SEQ ID NO 192
<211> LENGTH: 3485
<212> TYPE: DNA
<213> ORGANISM: Homo sapiens

<400> SEQUENCE: 192
cacaaagaaa aaagaaatac ctgtagaagc gcatcgaaag ctcctggaac agagttgtgt 60
ctcatatttg caaagatgca gaaaaaataa acccgggaca tccagctttc ttttcctttc 120
ttctttgact attctgagaa gctatgcgac taggagcaca ttttaggtaa acacgtggct 180
tgagtagcca taaggccact cttccctgtc gtgtgacccg cgcctgggcc tttaagagat 240
attggtgttt gaaaagggag gaatctgttt gccctcagat atttagttca actgcctgca 300
ttgcttccta ttttgttgtc caactctgta gtagttagca ctggccttac caacatgtaa 360
agaaattttc tttactgccc catgagtagt tggaggcaaa gagaaatttt taaagcgcag 420
aaaaaggcct gcagggagat ggaatttgtt ctgccagaga aacgagatga tagctgtatt 480
taataaagtt actgacctct tgtcaaaatt taaaacgcaa aagaagatgt ttcaaaatgc 540
agagaatgtc agaaaacaaa aactacaggg accagaccag tataatgttt agttttcatt 600
atactaactt ttgtctagac tggagttgat tcactatttt ttctttaact cctcaggaag 660
caaaccttcc cgatgatgaa gacttcttga aggatttcat gggtgatttg ggatcccagg 720
accatttggc tagtgtgcct aggtgaccac atgattgctg ttttaccagg aatgcagcat 780
cccattgaca aaacaagtgc tctgagaagg tttaaaatac tacagagaat atgggaacac 840
agaccttgaa atttagctga gttgtaacag ctgaaactcc aagaggtgtc ttccttgttt 900
gaggtgaaac tagtgttgct tccagagggc agctggaaac cgtaaagctg tttggaaatc 960

-continued

```
tttttgactg acttgctgac aaagaggtac tgtgatgcat tttaacaata tctaagttga   1020
ttttttttta aatcaaggaa aataaaaacc aagcatgaat gctatggtat gtgccccttt   1080
tgaccatcct gggctgatta acatcattta aatcaaagta atcataaaaa ggcatattct   1140
acttcaatta tgtggtcaaa taagagtaaa cacacacact cacacatgct gaccccaatt   1200
gccagagcat tactgcacta taaattacgg ttaattccca aattatacta ctgtttatct   1260
tatttaacaa gtcagaaagc acttttaaaa taacttgagg gctacaaggt cattctatta   1320
atgtcattct ccattcgggt tgtaggcatg tggaagtacc cattaaaaga taagttagag   1380
tttaaatact gataaacaaa acctttttatt gcaactggac agtttctgga gagttagcgg   1440
aagaatcttg gagtttcctt tggtcagatg aatacaacat ttcacttttg cagcactatt   1500
tagaatgtac tccatggttc tcttgttccc aacttccaaa aagaacagaa aactttggtt   1560
tacacagaac acgggcatct gaggcaggac ctcttccctg ccctttgatc tgactcacac   1620
ctccacatat gacgtaatca acccaaattt gacaccaatt cactcttttc tgcaaagggc   1680
atattttgaa acaagggaca gcctgagggc ggctataatg agaatgttca tgggggttac   1740
tgggtcccta attctgaact tgcttatgac acccagagtg aatagattca gattcagaac   1800
cttctgagaa ataacccaaa gaaaatttgt tacccagcca attcttcgaa agcttaatat   1860
caaaatatat cttttcaaga agaaaatcgt tagagagaag aatgtggagg ggagagaaat   1920
gggtttctca ttgatatgat attttgttaa ccatttcatt ttgaattatt caagttttgg   1980
ttaatattgt attctttttt cgtaactatt ttaccgtgag agtaggtcat tgggttactt   2040
agatatttat ttttacacag ttattagtct tcagatagtt ttattttact tcatatgatt   2100
ttagtttttg tcagtataat tttaaatcat gtttttcttg gtcatctctt tgtgtatatt   2160
gtgtaattgg attttcattg actgcaagtg gagtgtttgc cactcaattc agtactcagt   2220
actatggtga cttgttttca aataagtctc agatacacat ttagggagcc tttgctggcc   2280
gaatatagac tctgtcagga cagcaggtcc cctgatctaa gaattttccc caatggttgc   2340
tctaaaaatg ctgctatttt gctgttcact gtattgcact tagttaaaaa gaagataatg   2400
tgaaagatga gagcagtttt ttaaaggatc ttttcatata cccaattccc ttattttcag   2460
atgtcccatc aattttagat atgaaagctt taagtaaaag tgtgtatgcc tttctactgt   2520
cagaacagga tggatgcagc ctgggtcaga tttatttaag ataaaaatca tgcagactca   2580
tcattcatat cataggtgaa aaatgtaaaa accaaatggt ttccactaaa gccaccaaga   2640
tcttttagaa atgtttgcac ctttggtggt ggcacaggaa aagagaagaa ttcagctgga   2700
gtgaattcta gaagtagata tcagaaacgg ggcatgaaga acaggggaac tgggtggcat   2760
cagactccta aagaagtgag ttaattttcc ttcccttcca ttcagattca tgccacagct   2820
ccatatcttg agtatgtgta agaggtgagt tccttcttca gccaggggcg gtggctcatg   2880
cctttaatcc caatgctttg ggaggccaag gtgggaggat cacttgtgcc ttggggttca   2940
aggttgcagt gaaccatgat tgcaccactg cactccagcc tgagtgacag agcaagaccc   3000
tgtctctaaa aatatatata aaaagtaaaa ctaaagaact tcttgcctaa acctgaatta   3060
ccgcaatttg ctgagtgact ttgagaaaaa tcagactgtt tagttcagtc gggatgaaaa   3120
gcttgcgatt gcttcccaca agaatgggca atagtgacgg ctgcaaggta cttttatttg   3180
ttcatgaaag aacgacaatt tttcaaaatg taattaaaca taatagaatg ttttaaacta   3240
ctgggcactg aaactggaag aaaaaggagg ctttattgaa cattcccctt tttcagttgg   3300
ttcaaagttc agcactgtgg ttatcattgg tgatgccaga aaacattagt agacttagac   3360
```

```
aattgctatg gcagtttcta aacagagctt tttctataca ctatttgcaa ctggagtgca   3420

atattgtata ttctgtgtta aagaaataaa gtatttttat catttattaa aaaaaaaaaa   3480

aaaaa                                                               3485
```

<210> SEQ ID NO 193
<211> LENGTH: 1915
<212> TYPE: DNA
<213> ORGANISM: Homo sapiens

<400> SEQUENCE: 193

```
ccatccagaa cgatgaggcc gtggccccgc tcatgaagta cctggatgag aagctggccc     60

tgctgaacgc ctcgctggtg aaggggaacc tgagcagggt gctggaggcc ctgtgggagc    120

tactcctcca ggccattctg caggcgctgg gtgcaaaccg tgacgtctct gctgatttct    180

acagccgctt ccatttcacg ctggaggccc tggtcagttt tttccacgca gagggtcagg    240

gtttgcccct ggagagcctg agggatggaa gctacaagag gctgaaggag gagctgcggc    300

tgcacaaatg ttccacccgc gagtgcatcg agcagttcta cctggacaag ctcaaacaga    360

ggaccctgga gcagaaccgg tttggacgcc tgagcgtccg ttgccattac gaggcggctg    420

agcagcggct ggccgtggag gtgctgcacg ccgcggacct gctcccccctg gatgccaacg    480

gcttaagtga ccccctttgtg attgtggagc tgggcccacc gcatctcttt ccactggtcc    540

gcagccagag gacccaggtg aagacccgga cgctgcaccc tgtatacgac gaactcttct    600

acttttccgt gcctgccgag gcgtgccgcc gccgcgcggc ctgtgtgttg ttcaccgtca    660

tggaccacga ctggctgtcc accaacgact tcgctgggga ggcggccctc ggcctaggtg    720

gcgtcactgg tgtcgcccgg ccccaggtgg gcgggggtgc aagggctggg cagcctgtca    780

ccctgcacct gtgccggccc agagcccagg tgagatctgc gctgaggagg ctggaaggcc    840

gcaccagcaa ggaggcgcag gagttcgtga agaaactcaa ggagctggag aagtgcatgg    900

aggcggaccc ctgagtccat cagctgccag ccccggccct ggccccccacc ccaagttccc    960

tgaagcatcc tccagctcac tgtggccagc tttgtgcaac cagggcccac ggcgcccctc   1020

ctgtgctgtg acgtgtgtgt cgtggctggc ccccgcggcgc ctaccgccct ggccgtgtct   1080

gtctggtgtg tgctgtgaac ccctgcaccc aaccccacat ctgggtggcc aacttggcag   1140

gacttggcca gcagctgccc aggacacagt gcaggccaga gcgggcttga ccacctggtg   1200

ggcctccctg cccgcttcct tgggctcccc ggccctgggt gggcggtgcg cagctggtct   1260

ccagggactc agtgagtggc tgtgctctct gcacaacggg caatgtgcag acgcattttt   1320

ggtaatcaca gctggggagt gaaaagggtg ccactggcac cactgggtgg atggtccaga   1380

gcctccaccc acagagggga tgcaaagggc aggtgagtca agaaccgcat aggtctccag   1440

tccccacggg gctcccaggc cggggaaagg ttcccctgag gtcactctga ggccagggac   1500

gtcacccaag gctggtggtc agtgtgaagg gctccgtgcc aactggtcag ctgtccttca   1560

cgcacatatc cgtggccacc tgagacctgc tccacgaccc ttccaggcag agccgagagt   1620

tcgccccaac ccttccccag gcccagtgtg aaaaacagac tcacaagggg cttcttggcc   1680

tgcagcttca tttgcgagag cgccgaggca ggacacagag cacagctgtg ctggaagtgt   1740

ggggagaacc cggacagctc agtcctgcca gcagccgcaa agagccgagg ctgccaggcc   1800

catttatgtc cctcatgtct ctagattttc tcgtcaccca gcctcaaaaa tatatgtgtc   1860

tgcaaccctc aaaaaaaaaa aaaaaaaaaa aaaaaaaaaa aaaaaaaaaa aaaaa         1915
```

<210> SEQ ID NO 194
<211> LENGTH: 2681
<212> TYPE: DNA
<213> ORGANISM: Homo sapiens

<400> SEQUENCE: 194

```
ggggggctc cgtgacagcc aacgcagtga ccctcgcccc ttccttggca gcacatcatg     60
cttgtgcagc ggcagatgtc tgtgatggaa gaggacctgg aagaattcca gctcgctctg    120
aaacactacg tggagagtgc ttcctcccaa agtggatgct tgcgtatttc tatacagaag    180
ctttcaaatg aatctcgcta catgatctat gagttctggg agaatagtag tgtatggaat    240
agccaccttc agacaaatta tagcaagaca ttccaaagaa gtaatgtgga tttcttggaa    300
actccagaac tcacatctac aatgctagtt cctgcttcgt ggtggatcct gaacaactag    360
atgttcctag acattttctt tatggttcca agtgcaaaac aggtgttctt atctaaaacg    420
tcaattagaa aattatctgc ggttgttaat ctactgtata tttttgtttg gtatatttac    480
taagtgcact ctttcaaaac ttattctata actttatcaa ttcatgtgaa ttttagctca    540
attttcaaag ttcactaata ttctcaatat ttaatgctaa atgctttgct acattgtaac    600
tcacctaaaa ccttttagtg acaaaatcct aatatgtgga aaaaagcata tgcataaagg    660
aataatattg tgaaaatgaa tctgttatga taaagaaaaa ataaagtgga aacttttaga    720
gtattacttc atagggcaga ttttgtaaac tgtcgtatac tgtaaagggt taaatcagcg    780
ttttgtgatt tttaagtaac tgtgagtgaa gtttattctt caacaatgtc tactccatcc    840
ccaacccaac tcacagccct atgactacta tctttgcatt agttaaaaag ttagtatata    900
ggcatcaaac aaccttggct gtaacctata gaatctctat ccatgtatca ggttatagac    960
tggtttttca aaagtgaaca atcctgtgat aagttggagt accatttagt aatacagcaa   1020
cattgtgtca tttattagca tcataattct ttgttatgta agttaaatat atcaagaaag   1080
aagagactgt ttggaaaaat gtggttcaag ttttatgcta tatagttttg gtatgcgata   1140
cagacagcta acttttctta tgaaaaatac atatttgcat gtaaacaatg atttcaaaat   1200
acttgaaaaa taaaatttta acccaaatga ataactaaga aatataaaac aagcacaaaa   1260
tcttagggaa gtcataaaat agtagtgaaa gtattagaca gaagacatct gttttcgaat   1320
ttcaacacta gaatgactaa aactatctac ctatagaact atctgtagat agtatactat   1380
ctacactctg ctcaacaagc tcagaaatta aatattttta gtaataaaaa tctgttctgg   1440
ttataaacct tgctaatgaa aatacaatac atataaaaat gtatagccat gttattttct   1500
agtataaatt cctttgaaac tataagtctt tgaggaaaat tataaggtaa aattttcctg   1560
tttttccccc tttgaaaaac tcaggaaaaa aggaagattg aactaataaa attttatttc   1620
ttaaatataa atttgaccta aaatattttc tcaaactaat tcatgaaaca gcaactttta   1680
ccaatacctt tgtatactct cagttctcat tcagtataaa taaaatttta aaatcctttc   1740
atagttctat tagaaataag tagtaaattt tgatatattg tacatacaca cgtgtgtgtg   1800
tgtgtgtgtg tgtgtgtgta tttgtgtgcc tctggtcaac tctaaggatg acagacactg   1860
tgtaacaaca cctgggtcaa ctcttttaat ttatatacaa agcaaagaac aacattaatg   1920
gagatgcaca atgattattc aaacaagcta tatatatgta caaaggcaaa cagacacata   1980
acagtctctg cagactgatt gtatatagta agaaaagatc aaaagacttt aaaacctaaa   2040
tgacttttga catacaaact cttcttgaga atgtttgttg taaatggttt caaaaataca   2100
aattatagcc aatcaaaaca ttgctttggt tggtgcattt aagtatccaa ctcaaaaagc   2160
```

atatcaaata ttttgggtac taggcagttt ccaaagtagc atggtagtat tacttgttaa 2220
aagggttctg ttttcattaa cagtactaag tggaagggat ctgcagattc caaattggaa 2280
taagctctat catattctga aacaagaatt agaatgactt gagaacgggc aaataacaaa 2340
gcaaaccaat ataattatat ggtcattctg accccagctc ttatacaaat tatacatgta 2400
tttttgtgta tgtttgtgag agttgtatgt atgtgaatgt gtgtgagtgt gtattcacat 2460
acacatatat actggaacct atagtagaaa aggaaactag tagggccaaa aaaaaaaaga 2520
aaaagaaaaa gaaaaaagaa aaaaaaagaa aaaactggga cctaagtata aatatctcat 2580
cctaaagtaa acaataagtt tatagttaac gaagattttt ttctatttaa aaccccattt 2640
tcctaaagaa caaaaaaaaa aaaaaaaaaa aaaaaaaaaa a 2681

<210> SEQ ID NO 195
<211> LENGTH: 2805
<212> TYPE: DNA
<213> ORGANISM: Homo sapiens

<400> SEQUENCE: 195
ggcacgaggg caggggggaag ggaagtgcgg ctcggtcggc gcgggtggag ggggcgtgag 60
gccgccctac ggtggccgtc gagggacggc gctacggctc ccacgctagg ccaaacgcct 120
ccggcggccg cgcccgagag ccccttcacc tgcagggcga ccccagccgg cgacgcgtga 180
accacgccct cagccgcctt gccagcgccc ccagccgcgc gccccagcac catgcggccg 240
ccctgcgcac ggagccccga gggacagggg cacccgcagg cccggcccct agcaccgccg 300
gccggccccg aggtccggga cgccggcgcc gccgcggaga gggcaccggg ccgacgcctc 360
cccccagggt cagctgcggg ctcccaggcc taggcgccca tgacccctac gccaaccgcc 420
gcctggacac cgccgccgcc actgcgacct agcgccgccg ccgccggggc ccaatgccgg 480
tcatgcccat tccgcggcgg gtgcgctcct tccacggccc gcacaccacc tgcctgcatg 540
cggcctgcgg gcccgtgcgc gcctcccacc tggcccgcac caagtacaac aacttcgacg 600
tgtacatcaa gacgcgctgg ctgtacggct tcatccgctt cctactctac tttagctgca 660
gcctgttcac tgcggcgctc tggggtgcgc tggccgccct cttctgccta cagtacctgg 720
gcgttcgcgt cctgctgcgc ttccagcgca agctgtcggt gctgctgctg ctgctgggcc 780
gccggcgcgt ggacttccgc ctggtgaacg agctgctcgt ctatggcatc cacgtcacca 840
tgctgctggt cgggggcctg ggctggtgct tcatggtctt cgtggacatg tgagggccgt 900
gggtgcgagc ttgatgtatc gtcccggcct gtggctgtgt tctctccatg ggtggggtcg 960
gccagcgcct tcccttcgcc catcccccag gcagtcgctg ctgcccggcg cccacggaga 1020
gaaaagaaag ggctgagact tctgtgatgg gggcgcggac accaccccta ggctggcttc 1080
ctggacccac cctccccgta tgcactctca ggggcagcgc ccacctgccg gtggctcctg 1140
ctcacatgtc ttcgggtcgt actgcggggt gggccctccg ttccgcctct ctgtgggcct 1200
ctctccagga ccacagctgc cagggacttt agacatcacc ctgggaggcc cctggacaca 1260
gagggctgtg tgcccaggag caattccgga ggggggccct cctggctgca cagccccttc 1320
tgcgtgccct ggccccagcc ccagccaacg ggacacggaa ggctcccctc gctgacacac 1380
cacactgcca caaagctgct tactctgccc tgggccgcct gaggcctggc actgcccgcg 1440
gaccaccctg tgtgtgtcat cctgaggggc tgtgtgggtc ctgagtcccc agccagcctt 1500
cagggtcccc ttggattgtg tagatgcagt ctagcggggg gccggagaag ggctcaggtg 1560

```
ggaggggcct cagcaggctc ccagctcagg ggctggcctg gggggaaccc tgggagccag   1620

gggctgactc cagcaacact ggcctgtctg cctgttctgg gagggctgtg aggatgtctt   1680

gcagatgctc tggatttctg cggaggcacc tccattcctt tctggctttt tttgcggggg   1740

agggctttgg gcctctttct ttgagggaac accgtcaaag aaagcctggg agatcgaggc   1800

ttcagtgagc caggatggaa acgcgtgtcc caagtgtccg gagcaggcgg cagaggcctc   1860

agtgcggcaa acacagcccc agagcctgtg tggcaccagc agcatcttag agccccaggt   1920

atatgctgag atcttatctc acgctgtcct ccagtgtctg gggggcccaa atgatggcac   1980

agggtcaggt gggctggagg ggcgcagatg cctgtgttca gggagggtgg ccaccatggg   2040

ccgaggtctc acccaggacc ccttgctctg ctcctcagcc ttgcagtcac ggcagcacta   2100

tggtggactg cccatggccg tgtgactttg ggggcaagtg ggagggcgcc ctgaataatg   2160

attgcaagga caacaggcag aggctaccct agagcaggac acagggtgtg gtactgacaa   2220

ccctagtgtc acctcaaatc catgtcccca cactctgggc atgggtggga cttgtgaccc   2280

taccctgtca ggcggaccag tggcccagga gccatgagga cagttgtgtg ccactggaag   2340

agaaactttt tgaaaaaccc taaatcaggt agagaaagca aaaaatctct ggccgtaaac   2400

cgtgctctct aatttatcgg cagcttctgt ggatgacctc tgatgagccc gggctgcgtc   2460

cacgccctgg gcaggtaggc gggagcttcc ctgcgtgggc ctcatttctt gctgcagaga   2520

atcttttgca ctaagtcatg ctgtttcctc aaagaagctt tgttttttgt taacgtatta   2580

ctcagagtca cccaagcctc ttggctgagg gtgaaggtgg gacgggaggc gggagggggc   2640

tggtggtgcc gctcgtgcgg tgtcaacgct gcagggagtt gtggcacctt ggtgccctct   2700

gagcacctgg ccgcctgctg tccccggtgc ctgtgaaatt cgtcatgcca tgacccacct   2760

gcattaaacc tattttttta atgtgttaaa aaaaaaaaaa aaaaa                   2805
```

<210> SEQ ID NO 196
<211> LENGTH: 496
<212> TYPE: DNA
<213> ORGANISM: Homo sapiens
<220> FEATURE:
<221> NAME/KEY: misc_feature
<222> LOCATION: (2)..(2)
<223> OTHER INFORMATION: a or g or c or t/u
<220> FEATURE:
<221> NAME/KEY: misc_feature
<222> LOCATION: (26)..(26)
<223> OTHER INFORMATION: a or g or c or t/u
<220> FEATURE:
<221> NAME/KEY: misc_feature
<222> LOCATION: (49)..(49)
<223> OTHER INFORMATION: a or g or c or t/u
<220> FEATURE:
<221> NAME/KEY: misc_feature
<222> LOCATION: (60)..(60)
<223> OTHER INFORMATION: a or g or c or t/u
<220> FEATURE:
<221> NAME/KEY: misc_feature
<222> LOCATION: (88)..(88)
<223> OTHER INFORMATION: a or g or c or t/u
<220> FEATURE:
<221> NAME/KEY: misc_feature
<222> LOCATION: (115)..(115)
<223> OTHER INFORMATION: a or g or c or t/u
<220> FEATURE:
<221> NAME/KEY: misc_feature
<222> LOCATION: (124)..(124)
<223> OTHER INFORMATION: a or g or c or t/u
<220> FEATURE:
<221> NAME/KEY: misc_feature
<222> LOCATION: (159)..(159)
<223> OTHER INFORMATION: a or g or c or t/u
<220> FEATURE:
<221> NAME/KEY: misc_feature
<222> LOCATION: (207)..(207)
<223> OTHER INFORMATION: a or g or c or t/u

<400> SEQUENCE: 196
gnggaaacac gggccaaacc cgtgantttg gtgccccttg taaactcanc ccctgcaaan 60
ccaaagaccc caatggattt aaagttgntt ggcatttgta ctggcaaggc aaaanatttt 120
taantacctt ttcctaatac ttattgtatg agcttttgnt gtttacttgg aggttttgtc 180
ttttactaca agtttggaac tatttantat tgccttggta tttgtgctct gtttaagaaa 240
caggcacttt tttttattat ggataaaatg ttgagatgac aggaggtcat ttcaatatgg 300
cttagtaaaa tatttattgt tcctttattc tctgtacaag attttgggcc tctttttttc 360
cttaatgtca caatgttgag ttcagcatgt gtctgtccat ttcatttgta cgcttgttca 420
aaaccaagtt tgttctggtt tcaagttata aaaataaatt ggacatttaa cttgatctcc 480
aaaaaaaaaa aaaaaa 496

<210> SEQ ID NO 197
<211> LENGTH: 2802
<212> TYPE: DNA
<213> ORGANISM: Homo sapiens

<400> SEQUENCE: 197
ggcacgaggc aatctgagga gcaggaggac cggggcgccg gtgtcctgcc gcctccttct 60
ccttgctctc acctgcgcct attagtccac gcgccttcaa ggccaggggc tacagcccag 120
acagagaggg gacagcagag ggagagagag cacctgagga tacagagctg gcactggact 180
gccttttcac cccccaggtg atgagtgagg ttcgaagaac ggaagattta aaaagcagcc 240
ggggcctccg tattgaatga aagacccagt gcaaagacat caccatgaac actagcattc 300
cttatcagca gaatccttac aatccacggg gcagctccaa tgtcatccag tgctaccgct 360
gtggagacac ctgcaaaggg gaagtggtcc gcgtgcacaa caaccacttc cacatcagat 420
gcttcacctg tcaagtatgt ggctgtggcc tggcccagtc aggcttcttc ttcaagaacc 480
aggagtacat ctgcacccag gactaccagc aactctatgg cacccgctgt gacagctgcc 540
gggacttcat cacaggcgaa gtcatctcgg ccctgggccg cacttaccac cccaagtgct 600
tcgtgtgcag cttgtgcagg aagcctttcc ccattggaga caaggtgacc ttcagcggta 660
aagaatgtgt gtgccaaacg tgctcccagt ccatggccag cagtaagccc atcaagattc 720
gtggaccaag ccactgtgcc gggtgcaagg aggagatcaa gcacggccag tcactcctgg 780
ctctggacaa gcagtggcac gtcagctgct tcaagtgcca gacctgcagc gtcatcctca 840
ccggggagta tatcagcaag gatggtgttc catactgtga gtccgactac catgcccagt 900
ttggcattaa atgtgagact tgtgaccgat acatcagtgg cagagtcttg gaggcaggag 960
ggaagcacta ccacccaacc tgtgccaggt gtgtacgctg ccaccagatg ttcaccgaag 1020
gagaggaaat gtacctcaca ggttccgagg tttggcaccc catctgcaaa caggcagccc 1080
gggcagagaa gaagttaaag catagacgga catctgaaac ctccatctca ccccctggat 1140
ccagcattgg gtcacccaac cgagtcatct gcgacatcta cgagaacctg gacctccggc 1200
agagacgggc ctccagcccg gggtacatag actcccccac ctacagccgg cagggcatgt 1260
cccccacctt ctcccgctca cctcaccact actaccgctc tggtgatttg tctacagcaa 1320
ccaagagcaa aacaagtgaa gacatcagcc agacctccaa gtacagtccc atctactcgc 1380

```
cagaccccta ctatgcttcg gagtctgagt actggaccta ccatgggtcc cccaaagtgc   1440

cccgagccag aaggttctcg tctggaggag aggaggatga ttttgaccgc agcatgcaca   1500

agctccaaag tggaattggc cggctgattc tgaaggaaga aatgaaggcc cggtcgagct   1560

cctatgcaga tccctggacc cctccccgga gctccaccag cagccgggaa gccctgcaca   1620

cagctggcta tgagatgtcc ctcaatggct cccctcggtc gcactacctg gctgacagtg   1680

atcctctcat ctccaaatct gcctccctgc ctgcctaccg aagaaatggg ctgcacagga   1740

cacccagcgc agacctcttc cactacgaca gcatgaacgc agtcaactgg ggcatgcgag   1800

agtacaagat ctacccttat gaactgctgc tggtgactac aagaggaaga aaccgactgc   1860

ccaaggatgt agacaggacc cgtttagagg gaaacttttg gaagagtggc tgcttatgag   1920

attccaaaat gaagtgttgg ccaacaccgc tcatggccat cctggatttt cccagtggct   1980

tcccttcctg ctcgcctccc tgaacagggg agaaagctta acctctcttc tcctctccaa   2040

acctttcacc ttgaatgggt aatgtttggt gggggctgtt ccttcttgga gaagccttga   2100

gtcggaccat tttgagatca tggaggaagg atgaagaagt gaaaatgaca ataatgactc   2160

tcaagaggct ggcgatgtga catggcaaat gtagaactga cttaaattga acaaaccctc   2220

actgagcacc tctgatgttg agcacctgct gaatactgag cactgaatgg gggaggggga   2280

ggggagcacg gggtgagtca acctgggact cggtctcagg gatatgccta ccaatagcgg   2340

gtatcgtaag gcatgtaccc aaacataacg gatgtaaggc agaaagtgat cggagaagga   2400

atgagaaagt gtgcgtgatg ttaatgaaaa gtcatatgca gctagagcag acccaggaaa   2460

gctttctgga agagattgca tctgaggaaa ttcaggaagg atctttgtag attgggggga   2520

gattctaaat tgaaggggtg atggggtgag gggccagagg gaagtctgct gtgttctcat   2580

gtaggatgtc agccctccct gcaacttctc tttttggcca atgtcttttc actttcctga   2640

ccctttagaa tcatccccag ccagacgcaa tcatggaagt tgccttattg tcactggtta   2700

agaacttggc gagattgaag ggcttttgtt attgttgttg gatatttttg tttcccataa   2760

aagcacatca tttcaaccct aaaaaaaaaa aaaaaaaaaa aa                      2802
```

<210> SEQ ID NO 198
<211> LENGTH: 3278
<212> TYPE: DNA
<213> ORGANISM: Homo sapiens

<400> SEQUENCE: 198

```
gaagaattag atacttttga gtgggctttg aagagctggt ctcagtgttc caaaccctgt     60

ggtggaggtt tccagtacac taaatatgga tgccgtagga aaagtgataa taaaatggtc    120

catcgcagct tctgtgaggc caacaaaaag ccgaaaccta ttagacgaat gtgcaatatt    180

caagagtgta cacatccact ctgggtagca gaagaatggg aacactgcac caaaacctgt    240

ggaagttctg gctatcagct tcgcactgta cgctgccttc agccactcct tgatggcacc    300

aaccgctctg tgcacagcaa atactgcatg ggtgaccgtc ccgagagccg ccggccctgt    360

aacagagtgc cctgccctgc acagtggaaa acaggaccct ggagtgagtg ttcagtgacc    420

tgcggtgaag gaacggaggt gaggcaggtc ctctgcaggg ctggggacca ctgtgatggt    480

gaaaagcctg agtcggtcag agcctgtcaa ctgcctcctt gtaatgatga accatgtttg    540

ggagacaagt ccatattctg tcaaatggaa gtgttggcac gatactgctc cataccaggt    600

tataacaagt tatgttgtga gtcctgcagc aagcgcagta gcaccctgcc accaccatac    660

cttctagaag ctgctgaaac tcatgatgat gtcatctcta accctagtga cctccctaga    720
```

```
tctctagtga tgcctacatc tttggttcct tatcattcag agacccctgc aaagaagatg    780
tctttgagta gcatctcttc agtgggaggt ccaaatgcat atgctgcttt caggccaaac    840
agtaaacctg atggtgctaa tttacgccag aggagtgctc agcaagcagg aagtaagact    900
gtgagactgg tcaccgtacc atcctcccca cccaccaaga gggtccacct cagttcagct    960
tcacaaatgg ctgctgcttc cttctttgca gccagtgatt caataggtgc ttcttctcag   1020
gcaagaacct caaagaaaga tggaaagatc attgacaaca gacgtccgac aagatcatcc   1080
accttagaaa gatgagaaag tgaaccaaaa aggctagaaa ccagaggaaa acctggacaa   1140
cctctctctt cccatggtgc atatgcttgt ttaaagtgga aatctctata gatcgtcagc   1200
tcattttatc tgtaattgga agaacagaaa gtgctggctc actttctagt tgctttcatc   1260
ctccttttgt tctgcattga ctcatttacc agaattcatt ggaagaaatc accaaagatt   1320
attacaaaag aaaaatatgt tgctaagatt gtgttggtcg ctctctgaag cagaaaaggg   1380
actggaacca attgtgcata tcagctgact ttttgtttgt tttagaaaag ttacagtaaa   1440
aattaaaaag agataccaat ggtttacact ttaacaagaa attttggata tggaacaaag   1500
aattcttaga cttgtattcc tatttatcta tattagaaat attgtatgag caaatttgca   1560
gctgttgtgt aaatactgta tattgcaaaa atcagtatta ttttaagaga tgtgttctca   1620
aatgattgtt tactatatta catttctgga tgttctaggt gcctgtcgtt gagtattgcc   1680
ttgtttgaca ttctataggt taattttcaa agcagagtat tacaaaagag aagttagaat   1740
tacagctact gacaatataa agggttttgt tgaatcaaca atgtgatacg taaattatag   1800
aaaaagaaaa gaaacacaaa agctatagat atacagatat cagcttacct attgccttct   1860
atacttataa tttaaaggat tggtgtctta gtacacttgt ggtcacaggg atcaacgaat   1920
agtaaataat gaactcgtgc aagacaaaac tgaaaccctc tttccaggac ctcagtaggc   1980
accgttgagg tgtcctttgt ttttgtgtgt gtgtgttctt ttttaatttt cgcattgttg   2040
acagatacaa acagttatac tcaatgtact gtaataatcg caaaggaaaa agttttggga   2100
taacttattt gtatgttggt agctgagaaa aatatcatca gtctagaatt gatatttgag   2160
tatagtagag ctttggggct ttgaaggcag gttcaagaaa gcatatgtcg atggttgaga   2220
tatttatttt ccatatggtt catgttcaaa tgttcacaac cacaatgcat ctgactgcaa   2280
taatgtgcta ataatttatg tcagtagtca ccttgctcac agcaaagcca gaaatgctct   2340
ctccagggag tagatgtaaa gtacttgtac atagaattca gaactgaaga tatttattaa   2400
aagttgattt tttttcttg atagtatttt tatgtactaa atatttacac taatatcaat   2460
tacatatttt ggtaaactag agagacataa ttagagatgc atgctttgtt ctgtgcatag   2520
agacctttaa gcaaactact acagccaact caaaagctaa aactgaacaa atttgatgtt   2580
atgcaaacat cttgcatttt tagtagttga tattaagttg atgacttgtt tcccttcaag   2640
gaaacattaa attgtatgga ctcagctagc tgttcaatga aattgtgaat tagaaacatt   2700
tttaaaagtt tttgaaagag ataagtgcat catgaattac atgtacatga gaggagatag   2760
tgatatcagc ataatgattt tgaggtcagt acctgagctg tctaaaaata tattatacaa   2820
actaaaatgt agatgaatta acctctcaaa gcacagaatg tgcaagaact tttgcatttt   2880
aatcgttgta aactaacagc ttaaactatt gactctatac ctctaaagaa ttgctgctac   2940
tttgtgcaag aactttgaag gtcaaattag gcaaattcca gatagtaaaa caatccctaa   3000
gccttaagtc tttttttttt tcctaaaaat tcccatagaa taaaattctc tctagtttac   3060
```

ttgtgtgtgc atacatctca tccacagggg aagataaaga tggtcacaca aacagtttcc 3120
ataaagatgt acatattcat tatacttctg acctttgggc tttcttttct actaagctaa 3180
aaattccttt ttatcaaagt gtacactact gatgctgttt gttgtactga gagcacgtac 3240
caataaaaat gttaacaaaa tataaaaaaa aaaaaaaa 3278

<210> SEQ ID NO 199
<211> LENGTH: 567
<212> TYPE: DNA
<213> ORGANISM: Homo sapiens

<400> SEQUENCE: 199
tcctgtgttc tagacctctg gaggctgctg tggggaccac actgatcctg gagaaaaggg 60
atggagctga aaaagatgga atgcttgcag agcatgacct gaggagggag gaacgtggtc 120
aactcacacc tgcctcttcc tgcagcctca cctctacctg cccccatcat aagggcactg 180
agcccttccc aggctggata ctaagcacaa agcccatagc actgggctct gatggctgct 240
ccactgggtt acagaatcac agccctcatg atcattctca gtgagggctc tggattgaga 300
gggaggccct gggaggagag aagggggcag agtcttccct accaggtttc tacacccccg 360
ccaggctgcc catcagggcc cagggagccc ccagaggact ttattcggac caagcagagc 420
tcacagctgg acaggtgttg tatatagagt ggaatctctt ggatgcagct tcaagaataa 480
atttttcttc tcttttcaaa aatgtataaa aatcattata catagcatta aagaaacatt 540
tttgagaagt acaaaacaaa aaaaaaa 567

<210> SEQ ID NO 200
<211> LENGTH: 2907
<212> TYPE: DNA
<213> ORGANISM: Homo sapiens

<400> SEQUENCE: 200
cgggcgccgc aggagcgagt gagctgggag cgaggggcga aggcgcggag aagcccggcc 60
gcccggtggg cggcagaagg ctcagccgag gcggcggcgc cgactccgtt ccactctcgg 120
cccggatcca ggcctccggg ttcccaggcg ctcacctccc tctgacgcac tttaaagagt 180 ctccccccctt ccacctcagg gcgagtaata gcgaccaatc atcaagccat ttaccaggct 240
tcggaggaag ctgtttatgt gatccccgca ctaattaggc tcatgaacta acaaatcgtt 300
tgcacaactt gtgaagaagc gaacacttcc atggattgtc cttggactta gggcgccctg 360
cccgcctttt gcagaggaga aaaaactttt tttttttttt gcctcccccg agaactttcc 420
ccccttctcc tccctgcctc taactccgat ccccccacgc catctcgcca aaaaaaaaaa 480
aaaaaaaaaa aaagaaaaaa aaagaaaaaa aaagaaaaaa aattacccca atccacgcct 540
gcaaattctt ctggaaggat tttcccccct ctcttcaggt tgggcgcgtt tggtgcaaga 600
ttctcgggat cctcggcttt gcctctccct ctccctcccc cctcctttcc tttttccttt 660
cctttccttt ctttcttcct ttccttcccc ccaccccccac ccccacccca aacaaacgag 720
tccccaattc tcgtccgtcc tcgccgcggg cagcgggcgg cggaggcagc gtgcggcggt 780
cgccaggagc tgggagccca gggcgcccgc tcctcggcgc agcatgttcc agccggcgcc 840
caagcgctgc ttcaccatcg agtcgctggt ggccaaggac agtcccctgc ccgcctcgcg 900
ctccgaggac ccccatccgtc ccgcggcact cagctacgct aactccagcc ccataaatcc 960
gttcctcaac ggcttccact cggccgccgc cgccgccgcc ggtaggggcg tctactccaa 1020
cccggacttg gtgttcgccg aggcggtctc gcacccgccc aaccccgccg tgccagtgca 1080
cccggtgccg ccgccgcacg ccctggccgc ccacccccta ccctcctcgc actcgccaca 1140
ccccctattc gcctcgcagc agcgggatcc gtccaccttc tacccctggc tcatccaccg 1200
ctaccgatat ctgggtcatc gcttccaagg gaacgacact agccccgaga gtttcctttt 1260
gcacaacgcg ctggcccgaa agcccaagcg gatccgaacc gccttctccc cgtcccagct 1320
tctaaggctg gaacacgcct ttgagaagaa tcactacgtg gtgggcgccg aaaggaagca 1380
gctggcacac agcctcagcc tcacggaaac tcaggtaaaa gtatggtttc agaaccgaag 1440
aacaaagttc aaaaggcaga agctggagga agaaggctca gattcgcaac aaaagaaaaa 1500
agggacgcac catattaacc ggtggagaat cgccaccaag caggcgagtc cggaggaaat 1560
agacgtgacc tcagatgatt aaaaacataa acctaacccc acagaaacgg acaacatgga 1620
gcaaaagaga cagggagagg tggagaagga aaaaacccta caaaacaaaa acaaaccgca 1680
tacacgttca ccgagaaagg gagagggaat cggagggagc agcggaatgc ggcgaagact 1740
ctggacagcg agggcacagg gtcccaaacc gaggccgcgc caagatggca gaggatggag 1800
gctccttcat caacaagcga ccctcgtcta aagaggcagc tgagtgagag acacagagag 1860
aaggagaaag agggagggag agagagaaag agagagaaag agagagagag agagagagag 1920
agaaagctga acgtgcactc tgacaagggg agctgtcaat caaacaccaa accggggaga 1980
caagatgatt ggcaggtatt ccgtttatca cagtccactt aaaaaatgat gatgatgata 2040
aaaaccacga cccaaccagg cacaggactt ttttgttttt tgcacttcgc tgtgtttccc 2100
ccccatcttt aaaaataatt agtaataaaa aacaaaaatt ccatatctag ccccatccca 2160
cacctgtttc aaatccttga aatgcatgta gcagttgttg ggcgaatggt gtttaaagac 2220
cgaaaatgaa ttgtaatttt cttttccttt taaagacagg ttctgtgtgc tttttatttt 2280
gatttttttt cccaagaaat gtgcagtctg taaacacttt ttgatacctt ctgatgtcaa 2340
agtgattgtg caagctaaat gaagtaggct cagcgatagt ggtcctctta cagagaaacg 2400
gggagcagga cgacgggggg gctgggggtg gcgggggagg gtgcccacaa aaagaatcag 2460
gacttgtact gggaaaaaaa cccctaaatt aattatattt cttggacatt ccctttccta 2520
acatcctgag gcttaaaacc ctgatgcaaa cttctccttt cagtggttgg agaaattggc 2580
cgagttcaac cattcactgc aatgcctatt ccaaacttta aatctatcta ttgcaaaacc 2640
tgaaggactg tagttagcgg ggatgatgtt aagtgtggcc aagcgcacgg cggcaagttt 2700
tcaagcactg agtttctatt ccaagatcat agacttacta aagagagtga caaatgcttc 2760
cttaatgtct tctataccag aatgtaaata tttttgtgtt ttgtgttaat ttgttagaat 2820
tctaacacac tatatacttc caagaagtat gtcaatgtca atattttgtc aataaagatt 2880
tatcaatatg ccaaaaaaaa aaaaaaa 2907

<210> SEQ ID NO 201
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 201
acttctggtg atgataaaaa tggttttatc acccagatgt gaaagaagct gcctgtttac 60

<210> SEQ ID NO 202
<211> LENGTH: 60
<212> TYPE: DNA

<213> ORGANISM: Artificial Sequence
<220> FEATURE:
<223> OTHER INFORMATION: Synthetic construct - oligonucleotide

<400> SEQUENCE: 202
gtggttctgt aaaaacgcag aggaaaagag ccagaaggtt tctgtttaat gcatcttgcc 60

<210> SEQ ID NO 203
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 203
tttataagga agcagctgtc taaaatgcag tggggtttgt tttgcaatgt tttaaacaga 60

<210> SEQ ID NO 204
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 204
cttatgaagc tggccgggcc actcacgttc aatggtacat ctgggtctct atgtggttct 60

<210> SEQ ID NO 205
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 205
gtgagccagc atttcccata gctaacccta ttctcttagt ctttcaaaat gtagaatggg 60

<210> SEQ ID NO 206
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 206
ctttacacct gataaaatat tttgcgaaga gaggtgttct ttttccttac tggtgctgaa 60

<210> SEQ ID NO 207
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 207
gcatacatct catccacagg ggaagataaa gatggtcaca caaacagttt ccataaagat 60

<210> SEQ ID NO 208
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 208
tgagttcagc atgtgtctgt ccatttcatt tgtacgcttg ttcaaaacca agtttgttct 60

<210> SEQ ID NO 209
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 209
aagaccgaga ctgagggaaa gcatgtctgc tgggtgtgac catgtttcct ctcaataaag 60

<210> SEQ ID NO 210
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 210
ggcatctggc ccctggtagc cagctctcca gaattacttg taggtaattc ctctcttcat 60

<210> SEQ ID NO 211
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 211
tggatgtttg tgcgcgtgtg tggacagtct tatcttccag catgatagga tttgaccatt 60

<210> SEQ ID NO 212
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 212
tcctggcaga gccatggtcc caggcttccc aaaagtgttt gtggcaatta ttcccctagg 60

<210> SEQ ID NO 213
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 213
tttgatgata gcagacattg ttacaaggac atggtgagtc tatttttaat gcaccaatct 60

<210> SEQ ID NO 214
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 214
ttcttccagt tgcactattc tgagggaaaa tctgacacct aagaaattta ctgtgaaaaa 60

<210> SEQ ID NO 215
<211> LENGTH: 60
<212> TYPE: DNA
<213> ORGANISM: Artificial Sequence
<220> FEATURE:

<223> OTHER INFORMATION: Synthetic construct - oligonucleotide

<400> SEQUENCE: 215
gaacaattgt ggtctctctt aacttgaggt tctcttttga ctaatagagc tccatttccc 60

<210> SEQ ID NO 216
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 216
gttaagtgtg gccaagcgca cggcggcaag ttttcaagca ctgagtttct attccaagat 60

<210> SEQ ID NO 217
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 217
cggcctactg agcggacaga atgatgccaa aatattgctt atgtctctac atggtattgt 60

<210> SEQ ID NO 218
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 218
cagggtgttt gcccaataat aaagccccag agaactgggc tgggccctat gggattggta 60

<210> SEQ ID NO 219
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 219
tgtacagttt ggttgttgct gtaaatatgg tagcgttttg ttgttgttgt tttttcatgc 60

<210> SEQ ID NO 220
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 220
taccaaactg ggactcacag ctttattggg ctttctttgt gtcttgtgtg tttcttttat 60

<210> SEQ ID NO 221
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 221
cattgaggtt tggatggtgg caggtaaaac agaaaggcaa gatgtcatct gacattaggc 60

<210> SEQ ID NO 222
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 222
agttcagcac tgtggttatc attggtgatg ccagaaaaca ttagtagact tagacaattg 60

<210> SEQ ID NO 223
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 223
taaaatttct tgattgtgac tatgtggtca tatgcccgtg tttgtcactt acaaaaatgt 60

<210> SEQ ID NO 224
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 224
agccatctgg tgtgaagaac tctatatttg tatgttgaga gggcatggaa taattgtatt 60

<210> SEQ ID NO 225
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 225
cttattgtca ctggttaaga acttggcgag attgaagggc ttttgttatt gttgttggat 60

<210> SEQ ID NO 226
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 226
ctttctagtg agctaaccgt aacagagagc ctacaggata cacgtgagat aatgtcacgt 60

<210> SEQ ID NO 227
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 227
ttgtcttaaa atttcttgat tgtgatactg tggtcatatg cccgtgtttg tcacttacaa 60

<210> SEQ ID NO 228
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 228
cctgggggaa aggggcattc atgacctgaa ctttttagca aattattatt ctcagtttcc 60

<210> SEQ ID NO 229
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 229
ttcattaaca gtactaagtg gaagggatct gcagattcca aattggaata agctctatca 60

<210> SEQ ID NO 230
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 230
ccaatgcaga agagtattaa gaaagatgct caagtcccat ggcacagagc aaggcgggca 60

<210> SEQ ID NO 231
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 231
caaggctacg atggctatga tggtcagaat tactaccacc accagtgaag ctccagcctg 60

<210> SEQ ID NO 232
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 232
agctcacagc tggacaggtg ttgtatatag agtggaatct cttggatgca gcttcaagaa 60

<210> SEQ ID NO 233
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 233
tccaaagtag aaagggttct tttagaaaac ttgaagaatg tgcctcctct tagcatctgt 60

<210> SEQ ID NO 234
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 234
gatgcatttt tcagtccctt ttcagagcaa atgcttttgc aatggtagta atgtttagtt 60

<210> SEQ ID NO 235
<211> LENGTH: 60

<212> TYPE: DNA
<213> ORGANISM: Artificial Sequence
<220> FEATURE:
<223> OTHER INFORMATION: Synthetic construct - oligonucleotide

<400> SEQUENCE: 235
cctgtggggc ttctctcctt gatgcttctt tcttttttta aagacaacct gccattacca 60

<210> SEQ ID NO 236
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 236
ttgcactaag tcatgctgtt tcctcaaaga agctttgttt tttgttaacg tattactcag 60

<210> SEQ ID NO 237
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 237
ctggatccca ggccctggca cccctcagga aatacaagaa aaagaatatt cacatctgtt 60

<210> SEQ ID NO 238
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 238
ttagaggggc cacctatcaa ctcatcagtg ttcaaagaat atgctgggag catgggtgag 60

<210> SEQ ID NO 239
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 239
ggcccattta tgtccctcat gtctctagat tttctcgtca cccagcctca aaaatatatg 60

<210> SEQ ID NO 240
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 240
tccccaaaaa cctcacccga ggctgcccac tatggtcatc tttttctcta aaatagttac 60

<210> SEQ ID NO 241
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 241
gaaattcctc acaccttgca ccttccctac ttttctgaat tgctatgact actccttgtt 60

<210> SEQ ID NO 242
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 242
tgtctgtcca ccacgagatg ggaggaggag aaaaagcggt acgatgcctt cctgacctca 60

<210> SEQ ID NO 243
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 243
gtcttatctc tcaggggggg tttaagtgcc gtttgcaata atgtcgtctt atttatttag 60

<210> SEQ ID NO 244
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 244
ccgagtagta tgggtctctg tgtgagaaac caggagatat tttcatcttg ttcggaaata 60

<210> SEQ ID NO 245
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 245
ttgtgcaaaa gtcccacaac ctttctggat tgatagtttg tggtgaaata aacaatttta 60

<210> SEQ ID NO 246
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 246
tccagtattc tgcagggcca gtcagttgta cagaagttgg aatattctgt tccagaatta 60

<210> SEQ ID NO 247
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 247
gtctcgaaca gcggttgttt ttactttatt tatcttaggc cctcagctcc ctgacgtcct 60

<210> SEQ ID NO 248
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 248
agtgaatctt ttcctcttgg tagcatcaac actggggata aatcagaacc attctgtgga 60

<210> SEQ ID NO 249
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 249
tgagagccca gaacaagaag gagcagaagg gcactttgac cttcattatt atgaaaatca 60

<210> SEQ ID NO 250
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 250
ggaagaactg atgcttgctg ctaactaaag ttttggatgt atcgatttag agaaccaatt 60

<210> SEQ ID NO 251
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 251
gaatgagaga ataagtcatg ttccttcaag atcatgtacc ccaatttact tgccattact 60

<210> SEQ ID NO 252
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 252
tacggaaagg aaacaggtta tactcttaga tttaaaaagt gaaagaaact gcaggcgcct 60

<210> SEQ ID NO 253
<211> LENGTH: 2888
<212> TYPE: DNA
<213> ORGANISM: Homo sapiens

<400> SEQUENCE: 253
gtggcggcgg aggcggcgga ggccagggag gaagatgtcg taatgagcga tccacagacc 60
agcatggctg ccactgctgc tgtgagtccc agtgactacc tgcagcctgc cgcctccacc 120
acccaggact cccagccatc tcccttagcc ctgcttgctg caacatgtag caaaattggc 180
cctccagcag ttgaagctgc tgtgacacct cctgctcccc cacagcccac accgcggaaa 240
cttgtcccta tcaaacctgc ccctctccct ctcagccccg gcaagaatag ctttggaatc 300
ttgtcctcca aaggaaatat acttcagatt caggggtcac aactgagcgc ctcctatcct 360
ggagggcagc tggtgttcgc tatccagaat cccaccatga tcaacaaagg gacccgatca 420
aatgccaata tccagtacca ggcggtccct cagattcagg caagcaattc ccaaaccatc 480
caagtacagc ccaatctcac caaccagatc cagatcatcc ctggcaccaa ccaagccatc 540
atcacccccct caccgtccag tcacaagcct gtccccatca agccagcccc catccagaag 600
tcgagtacga ccaccacccc cgtgcagagc ggggccaatg tggtgaagtt gacaggtggg 660
ggcggcaatg tgacgctcac tctgcccgtc aacaacctcg tgaacgccag tgacaccggg 720
gcccctactc agctcctcac tgaaagcccc ccaaccccgc tgtctaagac taacaagaaa 780
gcaaggaaga agagccttcc tgcctcccag ccccctgtgg ctgtggctga gcaggtggag 840
acggtgctga tcgagaccac cgcggacaac atcatccagg caggaaataa cctgctcatt 900
gttcagagcc ctggtggggg ccagccagct gtggtccagc aggtccaggt ggtgcccccc 960
aaggccgagc agcagcaggt ggtacagatc ccccagcagg ctctgcgggt ggtgcaggcg 1020
gcatctgcca ccctccccac tgtaccccag aagccctccc agaactttca gatccaggca 1080
gctgagccga cacctactca ggtctacatc cgcacgcctt ccggtgaggt gcagacagtc 1140
cttgtccagg acagcccccc agcaacagct gcagccacct ctaacaccac ctgtagcagc 1200
cctgcatccc gtgctcccca tctgagtggg accagcaaaa agcactcagc tgcaattctc 1260
cgaaaagagc gtcccctgcc aaagattgcc ccagccggga gcatcatcag cctgaatgca 1320
gcccagttgg cggcagctgc ccaggcaatg cagaccatca acatcaatgg tgtccaggtc 1380
cagggcgtgc ctgtcaccat caccaacaca ggcgggcagc agcagctgac agtgcagaat 1440
gtttctggga acaacctgac catcagtggg ctgagcccca cccagatcca gctgcaaatg 1500
gaacaagccc tggccggaga gacccagccc ggggagaagc ggcgccgcat ggcctgcacg 1560
tgtcccaact gcaaggatgg ggagaagagg tctggagagc agggcaagaa gaagcacgtg 1620
tgccacatcc ccgactgtgg caagacgttc cgtaagacgt ccttgctgcg tgcccatgtg 1680
cgcctgcaca ctggcgagcg gccctttgtc tgcaactggt tcttctgtgg gaagaggttc 1740
acacggagtg acgagctcca acggcatgct cgcacccaca caggggacaa acgcttcgag 1800
tgcgcccagt gtcagaagcg cttcatgagg agtgaccacc tcaccaagca ttacaagacc 1860
cacctggtca cgaagaactt gtaaggccaa ctgcggcggg aggccctgaa gatgcagtcc 1920
cccacctgtg tcctccctgg gcccctggtg gaaaggagcc ctgtggctgc cttgggcctg 1980
ccctcagccc cactcctgtt ctgcaactgt ccccacagga aggggctctg ttccctgtat 2040
tgtcctcctt ctgaagcccc ttggctctgc cttggccctt cccctcacca cgagctcccg 2100
gcctgcccag actgtggaca ctggccgtgc ccaatgagac gttctaaacc aggacgcgtg 2160
ggaaccctta tttccaaagg aaaaacatgc atttcactcc gtcgaggagc aaagtgagcc 2220
cctacccccc accccgatcc ccgctcccaa cactgccgga gtcgcgtcat gccatgcccc 2280
ctctcctgca cctccctggc cctgccggcc actgtggacg ccctggggct tggcacccac 2340
ctctggagaa actcggggcc acctccactc catgtgccca gccccgccac aacctctcct 2400
ccagcacatt ccagctctat ttaaaaagta aagacaccca ccgactcctg atccccctct 2460
ttttctatgg agaacgttgc cttatactct ctacttcaga tgatgaacac tgtgtactgt 2520
gtgtgcttta aagaagtttt atttaattgc tcccttcttc ctttccttgt tattcacctc 2580
cctgatgcct gctttcagtt gagggttggg ggcaatgatg agcatatgaa ttttttctca 2640
ctctagcaat tccctttttct aaatgacaca gcatttaaac tcaaatctgg attcagataa 2700
cagcacctgc acatcctgca cctcctccct ctcccttcac ctcacccctg cccggcccaa 2760
gctctacttg tgtacagtgt atattgtata atagacaatt gtgtctacta catgtttaaa 2820
aacacattgc ttgttatttt tgaggctttt aaattaaaca aaaatccaac tttaaaaaaa 2880
aaaaaaaa 2888

<210> SEQ ID NO 254
<211> LENGTH: 999
<212> TYPE: DNA
<213> ORGANISM: Homo sapiens

<400> SEQUENCE: 254
cccgcgtcgg tgcccgcgcc cctccccggg ccccgccatg ggcctcaccg tgtccgcgct 60
cttttcgcgg atcttcggga agaagcagat gcggattctc atggttggct tggatgcggc 120
tggcaagacc acaatcctgt acaaactgaa gttgggggag attgtcacca ccatcccaac 180
cataggcttc aatgtagaaa cagtggaata taagaacatc tgtttcacag tctgggacgt 240
gggaggccag gacaagattc ggcctctgtg gcggcactac ttccagaaca ctcagggcct 300
catctttgtg gtggacagta atgaccggga gcgggtccaa gaatctgctg atgaactcca 360
gaagatgctg caggaggacg agctgcggga tgcagtgctg ctggtatttg ccaacaagca 420
ggacatgccc aacgccatgc ccgtgagcga gctgactgac aagctggggc tacagcactt 480
acgcagccgc acgtggtatg tccaggccac ctgtgccacc caaggcacag gtctgtacga 540
tggtctggac tggctgtccc acgagctgtc aaagcgctaa ccagccaggg gcaggcccct 600
gatgcccgga agctcctgcg tgcatccccg gatgaccata ctcccggact cctcaggcag 660
tgccctttcc tcccactttt cctcccccat agccacaggc ctctgctcct gctcctgcct 720
gcatgttctc tctgttgttg gagcctggag ccttgctctc tgggcacaga ggggtccact 780
ctcctgcctg ctgggaccta tggaaggggc ttcctggcca aggccccctc ttccagagga 840
ggagcaggga tctgggtttc cttttttttt tctgttttgg gtgtactcta ggggccaggt 900
tgggaggggg aaggtgaggg cttcgggtgg tgctataatg tggcactgga tcttgagtaa 960
taaatttgct gtggtttgaa aaaaaaaaaa aaaaaaaaa 999

<210> SEQ ID NO 255
<211> LENGTH: 3487
<212> TYPE: DNA
<213> ORGANISM: Homo sapiens

<400> SEQUENCE: 255
gtggcggtgg ctgcggcgac ggcagaggcg aagggagccg gatcgccgac ctgagcggga 60
ggcggcggtg gcggccatgg cggcagatgg agagcgttcc ccgctgctgt ctgagcccat 120
cgacggtggc gcgggcggca acggtttagt ggggcccggc gggagtgggg ctgggcccgg 180
gggaggcctg accccctccg caccaccgta cggagccggt aaacatgccc cgccccaggg 240
taagccgggg cgggtccgag gtgctccccg gggtactctg aaagccgggg agggggcggg 300
accgagggcg gaggcgggtc ccagtcgcca ggtgcgggac tgctgcacct gtgactgggc 360
gaggcttcct tccctccgta atcgcgacca cagcctaggg acggaagggg gttctgagca 420
acctgataga agtgccaatt atgagaagcc ctccgagctt ggtcagaggg ttgaagatca 480
gaaggacttc cctaccaccg tggagcatca gtgggggtgt aagtgatccc agcccttcta 540
tttgcttcct ctccagcatt tccccgttt cccgaggggc atccagccgt gttgcctggg 600
gaggacccac cccccctattc acccttaact agcccggaca gtgggagtgc ccctatgatc 660
acctgccgag tctgccaatc tctcatcaac gtggaaggca agatgcatca gcatgtagtc 720
aaatgtggtg tctgcaatga agccaccgtg agttacacat atctatgaaa tgggccctgt 780

-continued

```
ttcctggatc ctctttctga tgtcttggtt ctagaccctg accttccggc tattagccaa    840
gtgcttttga tgatacccag gtttcagttc caggtgtctc acacagccat ttccccagaa    900
gccactcacc aaagctaatg ttcactttct ctcactttta cacctagcct agttcctatt    960
tgcaaatctc atgatatagt ctttctttta tttctccttc ctggttagca ccttattttt   1020
ctgatctcat aaagtgtttt tggagggaag tggaggggat tgggattaga ggtttgcttg   1080
ctgatgaccc tattattctc tagccaatca agaatgcacc cccagggaaa aaatatgttc   1140
gatgcccctg taactgtctc cttatctgca aagtgacatc ccaacggatt gcatgccctc   1200
gtccctactg gtaagaggca taaggtgggg aagggcctaa gtggggaact ggaaagtcaa   1260
aaaaggatga gcgtatacag agaatgtaaa ggtgagagag cctagtgttt atttaggaga   1320
aaaggctttg aagcatgtgc ctcaggaatg ttatagctgt ctttctcgtt tctcaataaa   1380
aatattgaga tgaaatgatg tcgtttcgga gaatagagag ccttggggac tgggtgtgtt   1440
atcctgaggt cggaggggaa ttggggacct gaagtttaaa cagtgctctt tctttctcaa   1500
ggattcttga gggtatacag ttgggggaca gagtatctta agtacagaga agtcgagtga   1560
cttaatagac agggagtggg ggatgtggaa cagggactgt gaagattttt aggattaaaa   1620
atttttcaaa cacaagtttg aaaatacaag tctttttctt ttgtatagca aaagaatcat   1680
caacctgggg cctgtgcatc ccggacctct gagtccagaa ccccaaccca tgggtgtcag   1740
ggttatctgt ggacattgca agaatacttt tctggtgagg aaggggtatt gggaagggga   1800
ggggaaagga gactaagagt catttcgagt atatttctta gagtaatggt aatgacccct   1860
gaaaggtctg tcctatggga acatgttctg catccccacc ccaaggttct cattgaggga   1920
gaccctgctt gtgctattat ttttgttttc tttctccata gtggacagag ttcacagacc   1980
gcactttggc acgttgtcct cactgcagga aagtgtcatc tattgggcgc agatacccac   2040
gtaagagatg tatctgctgc ttcttgcttg gcttgctttt ggcagtcact gccactggcc   2100
ttgccgtgag taccccttgcc ccaacctcttt tcattctgca gcctcatctc cataggctaa   2160
gatttgggaa actgctaccc taaaaaaaag tggaagaaac ttaggggact agtttgtttt   2220
gttttaagat atggatgagc taaagtgcaa agtggctgat caaacagact ttattactac   2280
tacaagagtg aaaaacagcc ttcctttctc tgtaggatga ggataggaca gtgaaattct   2340
taatttaaga gttgctattt ttcaaacctg gctcagttgt cagatattaa gaaaaactga   2400
gatacagtgt gggatgggat gagtatgtta cgcctaaggg aaggaagctg atcagctctg   2460
cctttaagaa ggtccctgag ggtggctaca tgtggataag gaacaaggac tgaagcgtga   2520
gttattactg ttcttagaac taataggagg tagtggagac caacattaac cccatctttc   2580
ttttcttctc cctccttatc ttcatcagtt tggcacatgg aagcatgcac ggcgatatgg   2640
aggcatctat gcagcctggg catttgtcat cctgttggct gtgctgtgtt tgggccgggc   2700
tctttattgg gcctgtatga aggtcagcca ccctgtccag aacttctcct gagcctgatg   2760
acccacagac tgtgcctggc ccctccctgg tggggacagt gacactacga agggagctgg   2820
ggtagttaaa ggctcccggg gcttctagaa ggaagccaag cagctgcctt ccttttccct   2880
ggggagaggt aggaaggaac caggccctca cttaggtttg gaggggcaga taagagcact   2940
gctgaccatc tgctttcctc caagggttgc tgtgtctagg gtgaagtagg caaaacgttg   3000
cccttaaaac tgggccctga agacggttcc agccttgtcc ttcctgtgtg ctccctgaga   3060
gccattcctg tcccttacac attccagggc agggtggggg tgggtagccc tgggggttcc   3120
cctccctctt gtgcaccatt aggactttgc tgctgctatt gcacttcacc agaggttggc   3180
```

tctggcctca gtaccctcag tctcctctcc ccacattgtg tcctgtgggg gtggggtcag 3240
ccgctgctct gtacagaacc acaggaactg atgtgtatat aactatttaa tgtgggatat 3300
gttcccctat tcctgtattt cccttaattc ctcctcccga cctttttac cccccagtt 3360 gcagtattta actgggctgg gtagggttgc tcagtctttg ggggaggtta gggacttatc 3420
ctgtgcttgt aaataaataa ggtcatgact ctaaaaaaaa aaaaaaaaaa aaaaaaaaaa 3480
aaaaaaa 3487

<210> SEQ ID NO 256
<211> LENGTH: 1651
<212> TYPE: DNA
<213> ORGANISM: Homo sapiens

<400> SEQUENCE: 256
ctgtcagcac ggggcctggc atgtaattgg tctgcaccca ctggtgcact gaactgccat 60
aacctcaggt tttctttctt gctgataccc ctgggtcatg ttctttggca aataacatga 120
ttcattatga agtagagttc agcaaaggac aaggatgaaa gttgtcattt agagaactgc 180
cattcagact ttcttgtcta ggtaaagagc aaggtcttct ctcttttcaa ctcattttct 240
aaatttaaac tgacgatgag aatatggatg atgtgtagct tccttctccc ccactgattt 300
ttggttcagg ctctgggttt ttggcaagaa cttacagatc tcacttatta ttggccaccc 360
ttctgcttta agacctgtca gggcttgtct gaaataaaac tggaagcact tctgattcca 420
tcctcactgc tttcctcctt caccgtcaga cagcattact gtatagcact gagtgagggg 480
ccctgacact ggaaggtggc aggtggggcc tggccgccag tgaggtatca tcatttgtgt 540
gtgctcatgt gtgcgttggg cttgttgtat ctgaggcatg aacattccat atacacggct 600
taaagagttt tcttcccata ccgaaagcat atattcggag aggacccaac ttattcagca 660
tagccttgtt cccatagtag ccatcctatt cccccacagc ctctacttta ggaaagctcc 720
ccgtccccat atgaaatcca aaccaaaaaa gatatatcac tttcagctca attattccat 780
aattacaaga tattaggcta gtgggctctt tattggttgg gtcttatatt aatgttatat 840
gctagccttg taattttgag ctcctctatg gatgttaatt ttagtgaaac tctatattga 900
agaaaagatg ggactaaggg ggagacagga ggaggaaaga aagcagagac aggcaaagaa 960
tcatagcctg aaattcaaca gcaagcatgg cttatgaaga tcaagttata tttttgcttc 1020
atgaatcatt gtcagacaaa ttaagaacat attgtttctt atttatctat tgtcaaggat 1080
tcactatcag acactaagaa tgaatcttga ttttcataag ctctgttgac accatggagc 1140
cacagagcat aaaacttgca tctaataaag aaagtgcaac atggaacagc agggagtgga 1200
ataccagcac aactcacagc tgcttcctgt tcctcgtccc tgttttcagg aatgtttctt 1260
agcaggaagt tttttaatag accgagaatt tgttatatgt attctaagaa aagttgtagt 1320
tgtagatgca ttactctccc aaatcttaga gatcagggat gattatgttc catttttgtt 1380
tggtgagttc ccatctttgt atgtacctcc ttgctcccgg ctgtcctcct ctcctcttcc 1440
ctagtgagtg gttaatgagt gttaatgcct aaaccatact tgttttatgg acacttctat 1500
aatggattcg ttgcataatt ttcatgcagt gtatagtgtt actagttgga aattcttgga 1560
ggactcttag ctgtctgatg aaattcctag tagaaatttt tgttttgaat tcctaaagtt 1620
gaaatatgaa aattatattt taatttgatt c 1651

<210> SEQ ID NO 257

<211> LENGTH: 2511
<212> TYPE: DNA
<213> ORGANISM: Homo sapiens

<400> SEQUENCE: 257

```
agtttttctg gtagaaggcg gggttctcct cgtacgctgc ggagtctctg cggggtgtag     60
accggaatcc tgctgacggg cagagtggat cagggaggga gggtcgagac acggtggctg    120
caggtctgag acaaggctgc tccgaggtag tagctctctt gcctggaggt ggccattcat    180
tcctggagtg ctgctgagga gcgagggccc atctggggtc tctggaagtc ggtgcccagg    240
cctgaaggat agcccccctt gcgcttccct gggctgcggc cggccttctc agaacgaagg    300
gcgtccttcc accccgcggc gcaggtgacc gctgccatgg cttttcccca tcggccggac    360
gcccctgagc tgcctgactt ctccatgctg aagaggctgg ctcgagacca gctcatctat    420
ctgctggagc agcttcctgg aaaaaaggat ttattcattg aggcagatct catgagccct    480
ttggatcgaa ttgccaatgt ctccatcctg aagcaacacg aagtagacaa gctatacaag    540
gtggagaaca agccagccct cagctccaat gaacaattgt gcttcttggt cagaccccgc    600
atcaagaata tgcgatacat tgccagtctt gtcaatgctg acaaattggc tggccgaact    660
cgcaaataca aagtgatctt cagccctcaa aagttctatg cgtgtgagat ggtgcttgag    720
gaagagggaa tctatggaga tgtgagctgt gatgaatggg ccttctcttt gctgcctctt    780
gatgtggatc tgctgagcat ggaactacca gaatttttca gggattactt tctggaagga    840
gatcagcgtt ggatcaacac tgtagctcag gccttacacc ttctcagcac tctctatgga    900
ccctttccaa actgctatgg aattggcagg tgcgccaaga tggcatatga attgtggagg    960
aacctggagg aggaggagga tggcgaaacc aagggccgaa ggccagagat tggacatatc   1020
tttctcttgg acagagatgt ggactttgtg acagcacttt gctcccaagt ggtttatgag   1080
ggcctagtag atgacacctt ccgcatcaag tgtgggagtg tcgactttgg cccagaagtc   1140
acatcctctg acaagagcct gaaggtgcta ctcaatgccg aggacaaggt gtttaatgag   1200
attcggaacg agcacttctc caatgtcttt ggcttcttga gccagaaggc ccggaacttg   1260
caggcccagt atgatcgccg gagaggcatg gacattaagc agatgaagaa tttcgtgtcc   1320
caggagctca agggcctgaa acaggagcac cgcctgctga gtctccatat tggggcctgt   1380
gaatccatca tgaagaagaa aaccaagcag gatttccagg agctaatcaa gactgagcat   1440
gcactgctag aggggttcaa catccgggag agcaccagct acattgagga acacatagac   1500
cggcaggtgt cgcctataga aagcctgcgc ctcatgtgcc ttttgtccat cactgagaat   1560
ggtttgatcc ccaaggatta ccgatctctg aaaacacagt atctgcagag ctatggccct   1620
gagcacctgc taaccttctc caatctgcga agagctgggc tcctaacgga gcaggccccc   1680
ggggacaccc tcacagccgt ggagagtaaa gtgagcaagc tggtgaccga caaggctgca   1740
ggaaagatta ctgatgcctt cagttctctg gccaagagga gcaattttcg tgccatcagc   1800
aaaaagctga atttgatccc acgtgtggac ggcgagtatg atctgaaagt gccccgagac   1860
atggcttacg tcttcagtgg tgcttatgtg cccctgagct gccgaatcat tgagcaggtg   1920
ctagagcggc gaagctggca gggccttgat gaggtggtac ggctgctcaa ctgcagtgac   1980
tttgcattca cagatatgac taaggaagac aaggcttcca gtgagtccct gcgcctcatc   2040
ttggtggtgt tcttgggtgg ttgtacattc tctgagatct cagccctccg gttcctgggc   2100
agagagaaag gctacaggtt cattttcctg acgacagcag tcacaaacag cgctcgcctt   2160
atggaggcca tgagtgaggt gaaagcctga tgtttttccc ggccagtgtt gacatcttcc   2220
```

ctgaacacat tcctcagtga gatgcaggca tctggcaccc agctgctata accaagtgtc 2280
caccaactac ctgctaagag ccgggagcat ggaacgtgtt gggatttaga gaacattatc 2340
tgagaaaaga gttcacttcc tgctcccagg atatttctct tttctgttta tgaagtacaa 2400
cccatgctgc taagatgcga gcaggaagag gcatcctttg ctaaatcctg tttgaatgtc 2460
attgtaaata aagcctctgc tctcagatgt aaaaaaaaaa aaaaaaaaaa a 2511

<210> SEQ ID NO 258
<211> LENGTH: 2401
<212> TYPE: DNA
<213> ORGANISM: Homo sapiens

<400> SEQUENCE: 258
ggcacgaggg gtcgcgctgc cgccgtttta tttgaagaca tcgtccagtt ctgaccatgg 60
actcgcagcc atcggccctt agtttccatc ccctctagtg ggccttcggg ggctctactg 120
acgtccctcc ttcccttggt accgggccgg ggaagtgttc tcgggcgcgg gaggttccgc 180
atgcccaggc ctggccaggg gagatgaccg atccgtcgct ggggctgaca gtccccatgg 240
cgccgcctct ggccccgctc cctccccggg acccaaacgg ggcgggatcc gagtggagaa 300
agcccggggc cgtgagcttc gccgacgtgg ccgtgtactt ctcccgggag gagtggggct 360
gcctgcggcc cgcgcagagg gccctgtacc gggacgtgat gcgggagacc tacggccacc 420
tgggcgcgct cggtgagagc cccacctgct tgcctgggcc ctgcgcctcc acaggccctg 480
ccgcgcctct gggagctgcg tgtggagttg ggggccccgg ggccgggcag gcggcctcct 540
cgcagcgtgg ggtttgcgtt cttctccccc aggagtcgga ggcagcaagc cggcgctcat 600
ctcctgggtg gaggagaagg ccgaactgtg ggatccggct gcccaggatc cggaggtggc 660
gaagtgtccg acagaagcgg acccagcaga ttccagaaac aaggaagagg aaagacaaag 720
ggaagggacg ggagccctgg agaagcccga ccctgtggcc gccgggtctc ctgggctgaa 780
ggctccccaa gccccctttg ccgggttgga gcagctgtcc aaggcccggc gccggagtcg 840
cccccgcttt tttgcccacc cccctgtccc ccgagctgac cagcgtcacg gctgctacgt 900
gtgcgggaag agcttcgcct ggcgctccac actggtggag cacatttaca gccacagggg 960
cgagaagccc ttccactgcg cagactgcgg caagggcttc ggccacgctt cctccctgag 1020
caaacaccgg gccatccatc gtggggagcg gccccaccgc tgtcccgagt gtggtcgggc 1080
cttcatgcgc cgcacggcgc tgacttctca cctgcgcgtt cacactggcg agaagcccta 1140
ccgctgcccg cagtgtggcc gctgcttcgg cctgaagacc ggcatggcca agcaccaatg 1200
ggtccatcgg cccgggggcg aggggcgtag ggccggcgcc cctgggggc tgtctgtgac 1260 cctgactcct gtccgcgggg acctggaccc gcctgtgggc ttccagctgt atccagagat 1320
attccaggaa tgtgggtgac ggcctaaaaa gtgaccatct agacattgtg ggcggcccga 1380
gatgggctca ggggcccgaa cctctgcagc ggcctgcagg gaggtcccag aatccaccgc 1440
aagagctggc ctggggtgcg gacagtctga tcttgggctc tcagcagcct cttctgccag 1500
caccttgctc cccgctgccc tgggctctcc aaggccccct ttgctgaggc agggctgagg 1560
tgagaacccc ccagacctcc atacagggaa gcaaaagctg tttctcctcc cagagatgct 1620
aagaggattg aggtagagaa gaaccttgtt ttctctgttg tctttttctt tttactttt 1680 taattttttg agacggagtt ttgctcttgt tgcccaggct ggagtgcaat ggtgcgatct 1740
cgactcactg caacttccac ctcctggagt caagcgattc tcctgcctca gccacccaag 1800

```
tagctggaat tacaggcacc tgccactatg cccggctaac tttttgtatt tttagtagag   1860

atggggtttc accatgttgg ctaggctggt ctcgaactcc tgccctcagg tgatccaccc   1920

acctctgcct cccaaagtgc tgggattaca ggcgtgagcc acctcacctg gccttttctt   1980

ttttattctt tgaccttccc acaagacaat acccattgtc tgtttttttt gtttatttat   2040

ttacttatta agacagcatc ttgctcctca cccaggctgg aatgcagtgg tgtgaactgg   2100

gctcactgca gcctagacct gctgggctca aggaatcctc ctgcccccagc ctctcagatg   2160

gctgtgacta caggtgggca acactatgcc tggttaattt ttaaattttt ttgcagagat   2220

ggggttccca ctatgttgat caggctggtc tcaaactcct cggttcaagc aattcgccca   2280

ccttggcctc ccaaagtgct gggattacag gggagccact gcactggcct tcattgtctt   2340

tttgctgcac aacctaaaaa accagtgacc ctgtattgga aaaaaaaaaa aaaaaaaaaa   2400

a                                                                   2401


<210> SEQ ID NO 259
<211> LENGTH: 2384
<212> TYPE: DNA
<213> ORGANISM: Homo sapiens

<400> SEQUENCE: 259

gccatggccg ccggccccgc gccgcccccc ggccgccccc gggcgcagat gccgcatctg     60

aggaaggtgc gaggcggatg gagcgggtgg tcgtgagcat gcaggacccc gaccagggcg    120

tgaagatgcg gagccagcgc ctgctggtca ccgtcattcc ccacgcggtg acaggcagcg    180

acgtcgtgca gtggttggcc cagaagttct gcgtctcgga ggaggaggcc ctgcacctgg    240

gcgccgtcct ggtgcagcat ggctacatct acccgctgcg cgacccccgt agcctcatgc    300

tccggccaga cgagacgccc tacaggttcc agaccccgta cttctggaca agtaccctga    360

ggccggctgc agagctggac tatgccatct acctggccaa gaagaacatc cgaaaacggg    420

ggaccctggt ggattatgag aaggactgct atgaccggct acacaagaag atcaaccacg    480

catgggacct ggtgctgatg caggcgaggg agcagctgag ggcagccaag cagcgcagca    540

agggggacag gctggtcatt gcgtgccagg agcagaccta ctggctggtg aacaggcccc    600

cgcccggggc cccgatgtg ctggagcagg gtccagggcg gggatcctgc gctgccagcc    660

gtgtgctcat gaccaagagt gcagatttcc ataagcggga gatcgagtac ttcaggaaag    720

cgctgggcag gacccgagtg aagtcctccg tctgccttga ggcgtacctg agtttctgcg    780

gccagcgtgg accccacgat cccctcgtgt cggggtgcct gcccagcaat ccctggatct    840

cagacaatga cgcctactgg gtcatgaatg cccccacggt ggctgccccc acgaagctcc    900

gtgtggagag atggggcttc agcttccggg agctcctgga ggaccccgtg gggcgggccc    960

acttcatgga ctttctggga aaggagttca gtggagaaaa cctcagcttc tgggaggcat   1020

gtgaggagct tcgatatgga gcgcaggccc aggtccccac cctggtggat gccgtgtacg   1080

agcagttcct ggcccccgga gctgcccact gggtcaacat cgacagccgg accatggagc   1140

agaccctgga ggggctgcgc cagccccacc gctatgtcct ggatgacgcc cagctgcaca   1200

tatacatgct catgaagaag gactcctacc caaggttcct gaagtctgac atgtacaagg   1260

ccctcctggc agaggctggg atcccgctgg agatgaagag acgcgtgttc ccgtttacgt   1320

ggaggccacg gcactcgagc cccagccctg cactccttcc cacccctgtg gagcccacag   1380

cggcttgtgg ccctgggggt ggagatgggg tggcctagtg gacctggccc atctgccact   1440

ctagtccctg cagctcaacg tcctgcgtga atgcagcagc cacccccgtc ttggcccagg   1500
```

tcctgggggc tgctgaaccc agcaccagtg tccccttgtg cccagggggc ccagtcttct 1560
gtggggtgca cagcctccct ccctccagca agccctccct gcccagaagg aatgggtcca 1620
ggtgtggatt cccagggagg gggttcattg gctcagcttg ggtcagggca gagcctgtta 1680
cctgaagaga ggtgagacca aggccacagg gagctccacc ttctctggtc ttcagtccag 1740
cactgggtgc ccatccccat ctctaaaacc agtaaatcag ccagcgaata cccggaagca 1800
agatgcacag gcgggcggct tcccacacac ccgtcacaag acgcggacat gcaggtctcg 1860
gcgcgagctc tgccccgtcc aagagcctct ccgctgtcgc ccagtgtgag cctggaagag 1920
gacccaagag agtgccgtgc tgaggctgcc tcgaggtcac tgccttccgg agctgcgcct 1980
attcctccct cgccaaacgc gttccagaat ttgtccacag gtgcgccggc acctgctttc 2040
ccacctcgag gccgcggcct ccccccgat ttatagacaa ctctgacatt gtcaccccac 2100
tgacgaggcc cgattccata gggtggatcc ttgccaggcg tccctgatcc tccctgccca 2160
agtcttcctt cgtgagctgg ccttgctccc catcccccaa gtgcctcacc agtcccccag 2220
actgggtgaa ggtacagctg gctcctttcg ggggtgcagc ttcaactctc tcggcggtag 2280
ggcggtgcca tccccaccca tagggctggc tcacatccag tcactcccaa cagcgtccag 2340
cacacaaata aaagaccctt gggccctggc tctgagaaaa aaaa 2384

<210> SEQ ID NO 260
<211> LENGTH: 1500
<212> TYPE: DNA
<213> ORGANISM: Homo sapiens

<400> SEQUENCE: 260
agactgccga gcagccttga gccgttgagc agctgaacag aggccatgcc ggggcactcc 60
gaggcctgag acgaccacgc ctgtgccgct gaggaccttc atcagggctc cgtccacttg 120
gcccgcttgg ctgtccaatc acactccagt gtcaaccact ggcacccagc agccaagaga 180
ggtgtggcgt ggccctgggg acgcatggct gaggcaggaa caggtgagcc gtcccccagc 240
gtggagggcg aacacgggac ggagtatgac acgctgcctt ccgacacagt ctccctcagt 300
gactcggact ctgacctcag cttgcccggt ggtgctgaag tggaagcact gtccccgatg 360
gggctgcctg gggaggagga ttcaggtcct gatgagccgc cctcaccccc gtcaggcctc 420
ctcccagcca cggtgcagcc attccatctg agaggcatga gctccacctt ctcccagcgc 480
agccgtgaca tctttgactg cctggagggg gcggccagac gggctccatc ctctgtggcc 540
cacaccagca tgagtgacaa cggaggcttc aagcggcccc tagcgccctc aggccggtct 600
ccagtggaag gcctgggcag ggcccatcgg agccctgcct caccaagggt gcctccggtc 660
cccgactacg tggcacaccc cgagcgctgg accaagtaca gcctggaaga tgtgaccgag 720
gtcagcgagc agagcaatca ggccaccgcc ctggccttcc tgggctccca gagcctggct 780
gcccccactg actgcgtgtc ctccttcaac caggatccct ccagctgtgg ggaggggagg 840
gtcatcttca ccaaaccagt ccgaggggtc gaagccagac acgagaggaa gagggtcctg 900
gggaaggtgg gagagccagg caggggcggc cttgggaatc ctgccacaga caggggcgag 960
ggccctgtgg agctggccca tctggccggg cccgggagcc cagaggctga ggagtggggc 1020
agcccccatg gaggcctgca ggaggtggag gcactgtcag ggtctgtcca cagtgggtct 1080
gtgccaggtc tcccgccggt ggaaactgtt ggcttccatg gcagcaggaa gcggagtcga 1140
gaccacttcc ggaacaagag cagcagcccc gaggacccag gtgctgaggt ctgagaggga 1200

-continued gatggcccag cctgacccca ctggccactg ccatcctgct gccttcccag tggggctggt 1260 caggggggcag cctggccact gcctagctgg aatgggagga agcctgcagg tggcaccggt 1320
ggccctggct gcagttctgg gcagcatcct cccaagcaga gaccttgctg aagctcctgg 1380
ggtgtggggt gtgggctgga agcactggct ccctggtagg gacaataaag gttttgggtc 1440
tttcaaaaaa aaaaaaaaaa aaaaaaaaaa aaaaaaaaaa aaaaaaaaaa aaaaaaaaac 1500

<210> SEQ ID NO 261
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 261
tcatcttcac caaaccagtc cgaggggtcg aagccagaca cgagaggaag agggtcctgg 60

<210> SEQ ID NO 262
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 262
ctctgctcct gctcctgcct gcatgttctc tctgttgttg gagcctggag ccttgctctc 60

<210> SEQ ID NO 263
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 263
tgctcccggc tgtcctcctc tcctcttccc tagtgagtgg ttaatgagtg ttaatgccta 60

<210> SEQ ID NO 264
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 264
ccccatctct aaaaccagta aatcagccag cgaatacccg gaagcaagat gcacaggcgg 60

<210> SEQ ID NO 265
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 265
ccagaaacaa ggaagaggaa agacaaaggg aagggacggg agccctggag aagcccgacc 60

<210> SEQ ID NO 266
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 266

```
aagtacaacc catgctgcta agatgcgagc aggaagaggc atcctttgct aaatcctgtt     60


<210> SEQ ID NO 267
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 267

acctcacccc tgcccggccc aagctctact tgtgtacagt gtatattgta taatagacaa     60


<210> SEQ ID NO 268
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 268

ttcccttaat tcctcctccc gaccttttt acccccccag ttgcagtatt taactgggct     60
```